US007820803B2

(12) United States Patent
Stephens et al.

(10) Patent No.: US 7,820,803 B2
(45) Date of Patent: Oct. 26, 2010

(54) IMMOBILIZED PHOSPHATIDIC ACID PROBE

(75) Inventors: Len Stephens, Cambridgeshire (GB); Phillip Thomas Hawkins, Cambridgeshire (GB); Andrew Bruce Holmes, c/o Bio21 Institute, University of Melbourne, Victoria, Parkville (AU) 3010; Maria Manifava, Cambridge (GB); Ze-Yi Lim, Blk 411 #04-3081, Commonwealth Avenue West, Singapore (SG) 120411; Nicholas Ktistakis, Cambridge (GB); Johannes Wilhelmus John Fitzgerald Thuring, Antwerp (BE)

(73) Assignees: Andrew Bruce Holmes, London (GB); Ze-Yi Lim, Singapore (SG); Johannes Wilhelmus John Fitzgerald, Antwerp (BE)

( * ) Notice: Subject to any disclaimer, the term of this patent is extended or adjusted under 35 U.S.C. 154(b) by 249 days.

(21) Appl. No.: 10/362,571

(22) PCT Filed: Aug. 23, 2001

(86) PCT No.: PCT/GB01/03791
§ 371 (c)(1),
(2), (4) Date: Aug. 28, 2003

(87) PCT Pub. No.: WO02/18946
PCT Pub. Date: Mar. 7, 2002

(65) Prior Publication Data
US 2004/0072244 A1 Apr. 15, 2004

(30) Foreign Application Priority Data
Aug. 23, 2000 (GB) ................................. 0020833.0
Dec. 15, 2000 (GB) ................................. 0030637.3

(51) Int. Cl.
*C07H 23/00* (2006.01)
(52) U.S. Cl. ..................................... 536/17.1; 536/24.3

(58) Field of Classification Search ................. 536/17.1, 536/24.3, 24.31, 24.32; 554/79, 80, 81, 82
See application file for complete search history.

(56) References Cited

FOREIGN PATENT DOCUMENTS

WO    WO00/00584    1/2000
WO    WO02/18946    3/2002

OTHER PUBLICATIONS

Anderson et al., Current Biology 10(22): 1403-1412 (2000).
Delon et al., The Journal of Biological Chemistry 279(43) 44763-44774 (2004).
Gleim, Medical News Today, Sep. 15, 2003.
Krugmann et al., Molecular Cell 9: 95-108 (2002).
Manifava et al., The Journal of Biological Chemistry 276(12): 8987-8994 (2001).
Prestwich, Chemistry and Biology 11: 619-637 (2004).
Frank et al., Biochemistry 38:11993-12002 (1999).
Holmes, Phosphoinositides As Probes for Protein Kinases (Slide Presentation)—Meeting in Boston (Dec. 1999).
Manifava et al., Journal of Biological Chemistry 276(12): 8987-8994 (2001).
Moria et al., Tennen Yuki Kagobutsu Toronkai Koen Yashishu, pp. 43-48 (1997) Abstract No. 130:338312.
Ohlsson et al., Tetrahedron Letters 40: 2011-2014 (1999).
Painter et al., Chem. Commun., pp. 645-646 (2001).
Prestwich et al., J. Am. Chem. Soc. 113: 1822-1825 (1991).
Rao et al., Journal of Biological Chemistry 274(53): 37893-37900 (1999).
Shirai et al., Tetrahedron Letters 39: 9485-9488 (1998).
Shirai et al., Biochimica et Biophysica Acta 1402: 292-302 (1998).
Tanaka et al., Boisci. Biotechnol. Biochem. 63(2): 368-372 (1999).
Wang et al., Analytical Biochemistry 280: 301-307 (2000).
Watanabe et al., Tetrahedron Letters 41: 8509-8512 (2000).
Echelon Research Laboratories Inc.'s Online Catalog, Jul. 3, 2001.
Nimbus Biotechnology's Product Catalog, Jul. 10, 2001.
Transil—A Completely New Chromatography Material, 2001.

*Primary Examiner*—Elli Peselev
(74) *Attorney, Agent, or Firm*—Perkins Coie LLP

(57) ABSTRACT

The invention relates to immobilized phosphatidic acid probes which can be used to identify important proteins for signal transduction, housekeeping and diagnosis.

38 Claims, 12 Drawing Sheets 1  2  3  4  5

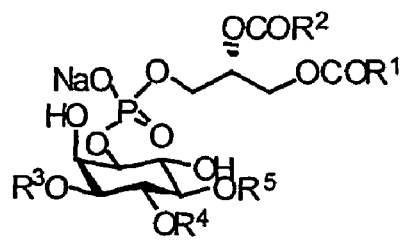
R¹= arachidonyl, R²= stearoyl
PtdIns(3)P: R³= PO(ONa)₂ R⁴= H, R⁵= H
PtdIns(3,4)P₂: R³= PO(ONa)₂, R⁴= PO(ONa)₂, R⁵= H
PtdIns(3,4,5)P₃ R³= PO(ONa)₂, R⁴= PO(ONa)₂, R⁵= PO(ONa)
PtdIns(4,5)P₂: R³= H, R⁴= PO(ONa)₂, R⁵ = PO(ONa)₂
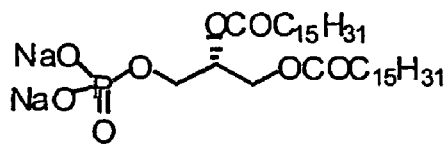
dipalmitoyl phosphatidic acid
Figure 3 Phosphoinositides and dipalmitoyl PA

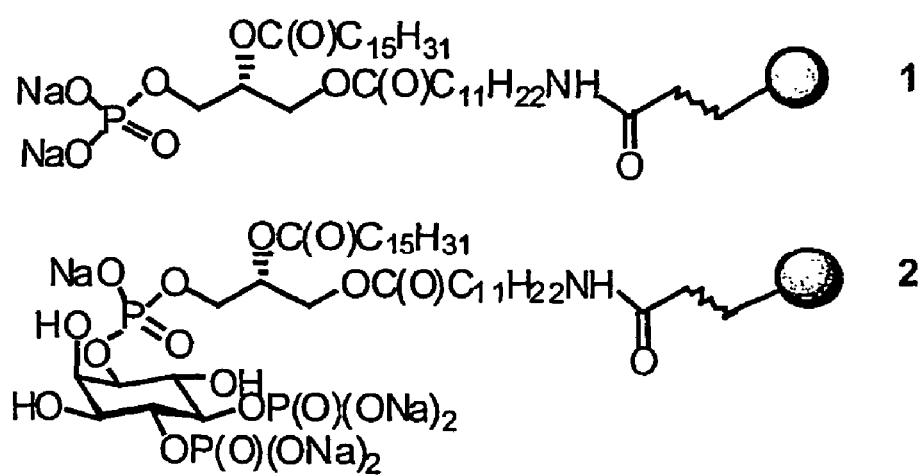
Figure 4 Immobilised PA 1 and PtdIns(4,5)P$_2$ 2

With PH domains
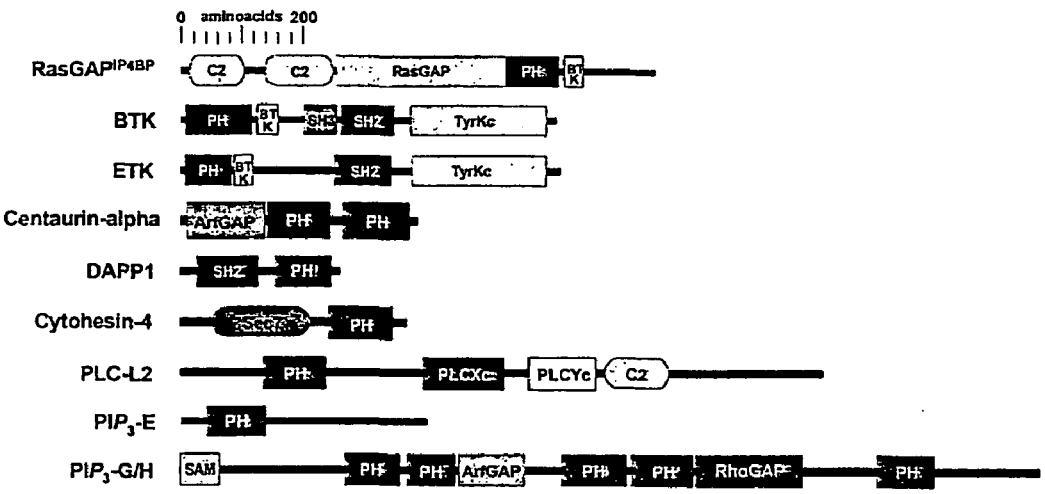
With FYVE domains
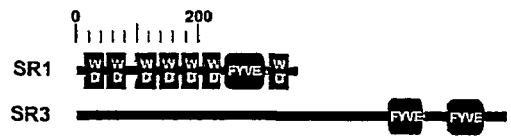
With SEC14 homology domains
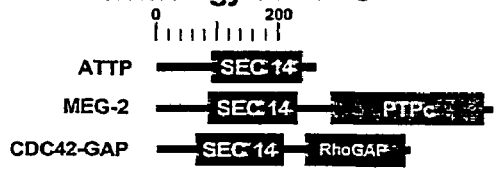
Miscellaneous
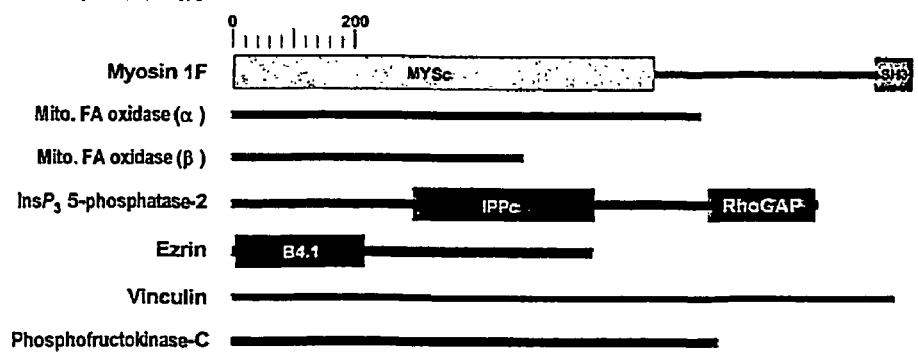
Figure 10

SEQUENCE LISTING

<160> NUMBER OF SEQ ID NOS: 10

<210> SEQ ID NO 1
<211> LENGTH: 1622
<212> TYPE: DNA
<213> ORGANISM: Homo sapiens
<220> FEATURE:
<221> NAME/KEY: CDS
<222> LOCATION: (158)..(1471)
<223> OTHER INFORMATION:

<400> SEQUENCE: 1

```
gtttaagtag aatcctcaag cttggcctca gagtactatg aggcttctga atccaggaat    60
aagactgctc ttggatttac tctctttgta ttgcatgtca aaggcaacag aactggacca   120
```

-continued

```
agaaaattca taactttttg cgtttgtttc tactaag atg aca tca tac atg gct        175
                                        Met Thr Ser Tyr Met Ala
                                        1               5 att gat ggc agt gct ctt gtt ccc ttg cgt cag aag ccc agg agg aaa         223
Ile Asp Gly Ser Ala Leu Val Pro Leu Arg Gln Lys Pro Arg Arg Lys
        10              15                  20 act caa ggt ttt ctc acg atg agt cgg agg agg ata tcg tgt aaa gat         271
Thr Gln Gly Phe Leu Thr Met Ser Arg Arg Arg Ile Ser Cys Lys Asp
            25              30                  35 ctg ggc cat gct gac tgc caa ggg tgg ctg tat aag aaa aag gaa aag         319
Leu Gly His Ala Asp Cys Gln Gly Trp Leu Tyr Lys Lys Lys Glu Lys
        40              45                  50 gga agt ttc cta agc aac aaa tgg aaa aag ttc tgg gtg ata ctg aag         367
Gly Ser Phe Leu Ser Asn Lys Trp Lys Lys Phe Trp Val Ile Leu Lys
55              60                  65                  70 ggg tcg tca ctg tac tgg tat agc aat caa atg gca gag aaa gct gat         415
Gly Ser Ser Leu Tyr Trp Tyr Ser Asn Gln Met Ala Glu Lys Ala Asp
                75                  80                  85 gga ttt gtc aac ctg cct gat ttc act gtg gaa aga gca tct gaa tgc         463
Gly Phe Val Asn Leu Pro Asp Phe Thr Val Glu Arg Ala Ser Glu Cys
            90                  95                  100 aag aaa aag cat gct ttt aag atc agc cat cca cag atc aag acc ttt         511
Lys Lys Lys His Ala Phe Lys Ile Ser His Pro Gln Ile Lys Thr Phe
        105                 110                 115 tat ttt gca gct gag aat gtg cag gaa atg aac gtg tgg tta aat aaa         559
Tyr Phe Ala Ala Glu Asn Val Gln Glu Met Asn Val Trp Leu Asn Lys
    120                 125                 130 ctt gga tcg gct gta atc cat cag gaa tcc act aca aag gat gaa gaa         607
Leu Gly Ser Ala Val Ile His Gln Glu Ser Thr Thr Lys Asp Glu Glu
135             140                 145                 150 tgt tac agt gaa agt gaa cag gaa gat cca gaa ata gct gcg gag aca         655
Cys Tyr Ser Glu Ser Glu Gln Glu Asp Pro Glu Ile Ala Ala Glu Thr
                155                 160                 165 cca ccc cct cct cac gct tcc cag act cag tct ttg act gca cag cag         703
Pro Pro Pro Pro His Ala Ser Gln Thr Gln Ser Leu Thr Ala Gln Gln
            170                 175                 180 gca tct tca tcc tca ccc agc ctg agt gga acg tcg tat tct ttc tct         751
Ala Ser Ser Ser Ser Pro Ser Leu Ser Gly Thr Ser Tyr Ser Phe Ser
        185                 190                 195 tcc ctg gaa aat aca gtg aag aca ccc agc agt ttt cct tcc tcc tta         799
Ser Leu Glu Asn Thr Val Lys Thr Pro Ser Ser Phe Pro Ser Ser Leu
    200                 205                 210 tct aaa gag aga caa tcc ttg cct gac aca gtt aac agt ttg tct gct         847
Ser Lys Glu Arg Gln Ser Leu Pro Asp Thr Val Asn Ser Leu Ser Ala
215             220                 225                 230 gct gaa gat gag gga caa cca ata acg ttt gct gtg caa gtt cat tca         895
Ala Glu Asp Glu Gly Gln Pro Ile Thr Phe Ala Val Gln Val His Ser
                235                 240                 245 cct gta ccc tca gag gca ggc atc cac aag gcc ctg gaa aac agt ttt         943
Pro Val Pro Ser Glu Ala Gly Ile His Lys Ala Leu Glu Asn Ser Phe
            250                 255                 260 gtc aca tca gaa agt gga ttt ttg aac tct tta tct agt gat gat act         991
Val Thr Ser Glu Ser Gly Phe Leu Asn Ser Leu Ser Ser Asp Asp Thr
        265                 270                 275 tct tca ttg agt agc aat cat gac cat ctt act gtc cca gat aag cct        1039
Ser Ser Leu Ser Ser Asn His Asp His Leu Thr Val Pro Asp Lys Pro
    280                 285                 290 gct gga tca aag atc atg gac aaa gaa gag aca aaa gtg tct gaa gat        1087
Ala Gly Ser Lys Ile Met Asp Lys Glu Glu Thr Lys Val Ser Glu Asp
```

-continued

```
                                    295                 300                 305                 310
gat gaa atg gag aag ctg tac aaa tca tta gag caa gct agt cta tct    1135
Asp Glu Met Glu Lys Leu Tyr Lys Ser Leu Glu Gln Ala Ser Leu Ser
                315                 320                 325 cct ctt ggg gac cga cga cct tcg act aaa aag gag ttg aga aaa tcc    1183
Pro Leu Gly Asp Arg Arg Pro Ser Thr Lys Lys Glu Leu Arg Lys Ser
            330                 335                 340 ttt gtt aag cgg tgt aaa aat cca tct ata aac gag aaa ctc cac aaa    1231
Phe Val Lys Arg Cys Lys Asn Pro Ser Ile Asn Glu Lys Leu His Lys
        345                 350                 355 atc cga aca ttg aat agc aca tta aag tgt aaa gaa cat gat ctg gcc    1279
Ile Arg Thr Leu Asn Ser Thr Leu Lys Cys Lys Glu His Asp Leu Ala
    360                 365                 370 atg att aac cag ttg ctg gat gac ccg aag ctg aca gcc agg aaa tac    1327
Met Ile Asn Gln Leu Leu Asp Asp Pro Lys Leu Thr Ala Arg Lys Tyr
375                 380                 385                 390 aga gag tgg aaa gtc atg aac acc ctg ctg atc cag gac atc tat cag    1375
Arg Glu Trp Lys Val Met Asn Thr Leu Leu Ile Gln Asp Ile Tyr Gln
                395                 400                 405 cag cag cgg gct tcg cct gcc cct gat gac act gat gac acc ccc cag    1423
Gln Gln Arg Ala Ser Pro Ala Pro Asp Asp Thr Asp Asp Thr Pro Gln
            410                 415                 420 gaa ctc aag aaa tca cct tct tct ccc tct gtt gaa aat tcc att tga    1471
Glu Leu Lys Lys Ser Pro Ser Ser Pro Ser Val Glu Asn Ser Ile
        425                 430                 435 gacaaagtca gggttttctc ctcttatatt ttatcacaag caactcttca agatgttgca    1531
aaagcttaca ttttttcctta aaaggaaaac tgaaacccag tccttcaagc atcagcttcc    1591
catctaaaga tgcacgttag atgaagataa t                                    1622

<210> SEQ ID NO 2
<211> LENGTH: 437
<212> TYPE: PRT
<213> ORGANISM: Homo sapiens

<400> SEQUENCE: 2

Met Thr Ser Tyr Met Ala Ile Asp Gly Ser Ala Leu Val Pro Leu Arg
1               5                   10                  15

Gln Lys Pro Arg Arg Lys Thr Gln Gly Phe Leu Thr Met Ser Arg Arg
            20                  25                  30

Arg Ile Ser Cys Lys Asp Leu Gly His Ala Asp Cys Gln Gly Trp Leu
        35                  40                  45

Tyr Lys Lys Lys Glu Lys Gly Ser Phe Leu Ser Asn Lys Trp Lys Lys
    50                  55                  60

Phe Trp Val Ile Leu Lys Gly Ser Ser Leu Tyr Trp Tyr Ser Asn Gln
65                  70                  75                  80

Met Ala Glu Lys Ala Asp Gly Phe Val Asn Leu Pro Asp Phe Thr Val
                85                  90                  95

Glu Arg Ala Ser Glu Cys Lys Lys Lys His Ala Phe Lys Ile Ser His
            100                 105                 110

Pro Gln Ile Lys Thr Phe Tyr Phe Ala Ala Glu Asn Val Gln Glu Met
        115                 120                 125

Asn Val Trp Leu Asn Lys Leu Gly Ser Ala Val Ile His Gln Glu Ser
    130                 135                 140

Thr Thr Lys Asp Glu Glu Cys Tyr Ser Glu Ser Glu Gln Glu Asp Pro
145                 150                 155                 160

Glu Ile Ala Ala Glu Thr Pro Pro Pro His Ala Ser Gln Thr Gln
```

```
                    165                 170                 175
Ser Leu Thr Ala Gln Gln Ala Ser Ser Ser Pro Ser Leu Ser Gly
            180                 185                 190

Thr Ser Tyr Ser Phe Ser Ser Leu Glu Asn Thr Val Lys Thr Pro Ser
        195                 200                 205

Ser Phe Pro Ser Ser Leu Ser Lys Glu Arg Gln Ser Leu Pro Asp Thr
    210                 215                 220

Val Asn Ser Leu Ser Ala Ala Glu Asp Glu Gly Gln Pro Ile Thr Phe
225                 230                 235                 240

Ala Val Gln Val His Ser Pro Val Pro Ser Glu Ala Gly Ile His Lys
            245                 250                 255

Ala Leu Glu Asn Ser Phe Val Thr Ser Glu Ser Gly Phe Leu Asn Ser
        260                 265                 270

Leu Ser Ser Asp Asp Thr Ser Ser Leu Ser Ser Asn His Asp His Leu
    275                 280                 285

Thr Val Pro Asp Lys Pro Ala Gly Ser Lys Ile Met Asp Lys Glu Glu
            290                 295                 300

Thr Lys Val Ser Glu Asp Asp Glu Met Glu Lys Leu Tyr Lys Ser Leu
305                 310                 315                 320

Glu Gln Ala Ser Leu Ser Pro Leu Gly Asp Arg Arg Pro Ser Thr Lys
            325                 330                 335

Lys Glu Leu Arg Lys Ser Phe Val Lys Arg Cys Lys Asn Pro Ser Ile
        340                 345                 350

Asn Glu Lys Leu His Lys Ile Arg Thr Leu Asn Ser Thr Leu Lys Cys
    355                 360                 365

Lys Glu His Asp Leu Ala Met Ile Asn Gln Leu Leu Asp Asp Pro Lys
            370                 375                 380

Leu Thr Ala Arg Lys Tyr Arg Glu Trp Lys Val Met Asn Thr Leu Leu
385                 390                 395                 400

Ile Gln Asp Ile Tyr Gln Gln Arg Ala Ser Pro Ala Pro Asp Asp
            405                 410                 415

Thr Asp Asp Thr Pro Gln Glu Leu Lys Lys Ser Pro Ser Ser Pro Ser
            420                 425                 430

Val Glu Asn Ser Ile
            435

<210> SEQ ID NO 3
<211> LENGTH: 5210
<212> TYPE: DNA
<213> ORGANISM: Homo sapiens
<220> FEATURE:
<221> NAME/KEY: CDS
<222> LOCATION: (29)..(4663)
<223> OTHER INFORMATION:

<400> SEQUENCE: 3
cgcgtagtga gcaatggcct gagccccc atg gct gcc cct cag gac ctg gac         52
                              Met Ala Ala Pro Gln Asp Leu Asp
                                1               5 atc gct gtg tgg ctg gcc acg gtg cac ctg gag cag tat gca gac acg       100
Ile Ala Val Trp Leu Ala Thr Val His Leu Glu Gln Tyr Ala Asp Thr
        10                  15                  20 ttc cga cgg cat ggc ctg gct aca gca ggt gca gcc cgg ggc ctg ggc       148
Phe Arg Arg His Gly Leu Ala Thr Ala Gly Ala Ala Arg Gly Leu Gly
25                  30                  35                  40 cac gag gag ttg aag cag ttg ggc atc agc gcc aca ggg cac cgg aaa       196
His Glu Glu Leu Lys Gln Leu Gly Ile Ser Ala Thr Gly His Arg Lys
```

-continued

|  |  |  |  |  |  |  |  |  |  |  |  |
|---|---|---|---|---|---|---|---|---|---|---|---|
|  | 45 |  |  |  | 50 |  |  |  | 55 |  |  | cgc att cta cgc ctg ctg cag aca ggc acc gaa gag ggc tcc ctg gat    244
Arg Ile Leu Arg Leu Leu Gln Thr Gly Thr Glu Glu Gly Ser Leu Asp
         60                  65                  70 ccc aaa tca gat agt gcc atg gaa cca tcc ccc agc cca gcc ccg caa    292
Pro Lys Ser Asp Ser Ala Met Glu Pro Ser Pro Ser Pro Ala Pro Gln
     75                  80                  85 gcc cag ccc cct aag ccc gtg ccg aag ccc agg acc gtg ttt ggt gga    340
Ala Gln Pro Pro Lys Pro Val Pro Lys Pro Arg Thr Val Phe Gly Gly
 90                  95                 100 ctc agt ggc cct gcc acc act cag aga cct ggg ctg agc cca gcc ctc    388
Leu Ser Gly Pro Ala Thr Thr Gln Arg Pro Gly Leu Ser Pro Ala Leu
105                 110                 115                 120 ggg gga cca gga gtg tcc agg agc cca gag ccc agc cca agg ccc cct    436
Gly Gly Pro Gly Val Ser Arg Ser Pro Glu Pro Ser Pro Arg Pro Pro
                125                 130                 135 cct ctc ccc act tcc tcc tct gag cag tct tca gcc cta aat act gtg    484
Pro Leu Pro Thr Ser Ser Ser Glu Gln Ser Ser Ala Leu Asn Thr Val
                140                 145                 150 gag atg atg cct aat tcc atc tac ttc ggc ctg gac tca aga ggc agg    532
Glu Met Met Pro Asn Ser Ile Tyr Phe Gly Leu Asp Ser Arg Gly Arg
                155                 160                 165 gca cag gca gct cag gac aag gcc cca gac agc tcc caa atc tct gcc    580
Ala Gln Ala Ala Gln Asp Lys Ala Pro Asp Ser Ser Gln Ile Ser Ala
            170                 175                 180 ccc acc cct gcc ctc agg ccc aca aca ggc aca gtg cac atc atg gat    628
Pro Thr Pro Ala Leu Arg Pro Thr Thr Gly Thr Val His Ile Met Asp
185                 190                 195                 200 cct ggt tgc ctg tac tat ggt gtc caa cct gtg ggg act cca gga gcc    676
Pro Gly Cys Leu Tyr Tyr Gly Val Gln Pro Val Gly Thr Pro Gly Ala
                205                 210                 215 ccc gac aga aga gag agc aga ggt gtt tgt cag ggc agg gct gaa cac    724
Pro Asp Arg Arg Glu Ser Arg Gly Val Cys Gln Gly Arg Ala Glu His
            220                 225                 230 agg ctc agc aga cag gat ctg gag gca cgg gag gat gct ggc tat gcc    772
Arg Leu Ser Arg Gln Asp Leu Glu Ala Arg Glu Asp Ala Gly Tyr Ala
                235                 240                 245 agc ctt gag cta cct gga gac tcc acc ctc tta tcg ccc acc ctg gaa    820
Ser Leu Glu Leu Pro Gly Asp Ser Thr Leu Leu Ser Pro Thr Leu Glu
            250                 255                 260 aca gag gag acc agt gat gac ctc att tca ccc tat gcc agc ttc tcc    868
Thr Glu Glu Thr Ser Asp Asp Leu Ile Ser Pro Tyr Ala Ser Phe Ser
265                 270                 275                 280 ttc acg gca gac cgc ctc acg ccc ctg ctc agt ggc tgg cta gac aag    916
Phe Thr Ala Asp Arg Leu Thr Pro Leu Leu Ser Gly Trp Leu Asp Lys
                285                 290                 295 ctc tcc cct cag gga aac tat gtc ttc cag aga cgc ttt gtg cag ttc    964
Leu Ser Pro Gln Gly Asn Tyr Val Phe Gln Arg Arg Phe Val Gln Phe
            300                 305                 310 aat ggg agg agt ctg atg tac ttt ggc agt gac aag gac ccc ttc cct   1012
Asn Gly Arg Ser Leu Met Tyr Phe Gly Ser Asp Lys Asp Pro Phe Pro
                315                 320                 325 aag ggt gtg ata cct ttg act gcc att gag atg acc cgc agc agc aag   1060
Lys Gly Val Ile Pro Leu Thr Ala Ile Glu Met Thr Arg Ser Ser Lys
            330                 335                 340 gac aac aag ttc cag gtc atc acc ggc cag agg gtg ttc gtg ttc cgc   1108
Asp Asn Lys Phe Gln Val Ile Thr Gly Gln Arg Val Phe Val Phe Arg
345                 350                 355                 360 aca gag agc gag gct cag cgg gac atg tgg tgc tcc acg ctg cag tcc   1156

```
                Thr Glu Ser Glu Ala Gln Arg Asp Met Trp Cys Ser Thr Leu Gln Ser
                                365                 370                 375 tgt ctg aag gag cag cgc ctc ctg ggc cac ccc cgg ccc cca caa cca                1204
Cys Leu Lys Glu Gln Arg Leu Leu Gly His Pro Arg Pro Pro Gln Pro
            380                 385                 390 ccc cga ccc ctc cgc acg ggc atg ctg gag ctg cgt gga cac aag gcc                1252
Pro Arg Pro Leu Arg Thr Gly Met Leu Glu Leu Arg Gly His Lys Ala
        395                 400                 405 aag gtg ttt gct gcc ttg agc cct gga gag ctg gca ctg tac aag agt                1300
Lys Val Phe Ala Ala Leu Ser Pro Gly Glu Leu Ala Leu Tyr Lys Ser
    410                 415                 420 gag cag gcc ttc tct ctg ggc atc ggg atc tgc ttc atc gaa ctg cag                1348
Glu Gln Ala Phe Ser Leu Gly Ile Gly Ile Cys Phe Ile Glu Leu Gln
425                 430                 435                 440 ggc tgc agc gtc cgg gag acc aag agt cga agc ttt gac ctg ctc aca                1396
Gly Cys Ser Val Arg Glu Thr Lys Ser Arg Ser Phe Asp Leu Leu Thr
                445                 450                 455 ccc cat cgc tgc ttc agc ttc aca gcc gag tct ggg ggt gct cgg cag                1444
Pro His Arg Cys Phe Ser Phe Thr Ala Glu Ser Gly Gly Ala Arg Gln
            460                 465                 470 agc tgg gcg gcc gct ctg cag gaa gca gta acc gag acc ctg tct gac                1492
Ser Trp Ala Ala Ala Leu Gln Glu Ala Val Thr Glu Thr Leu Ser Asp
        475                 480                 485 tac gag gtg gct gag aag atc tgg tct aat cgg gcc aac cgg cag tgt                1540
Tyr Glu Val Ala Glu Lys Ile Trp Ser Asn Arg Ala Asn Arg Gln Cys
    490                 495                 500 gcg gac tgt ggg tcc tcc cgc cca gat tgg gct gct gtc aat ttg ggg                1588
Ala Asp Cys Gly Ser Ser Arg Pro Asp Trp Ala Ala Val Asn Leu Gly
505                 510                 515                 520 gtg gtc atc tgc aag cag tgt gca ggt cag cac cgg gcc ctg ggt tct                1636
Val Val Ile Cys Lys Gln Cys Ala Gly Gln His Arg Ala Leu Gly Ser
                525                 530                 535 ggg atc tcc aag gtg cag agc ctg aag ctg gac acg agt gtc tgg agt                1684
Gly Ile Ser Lys Val Gln Ser Leu Lys Leu Asp Thr Ser Val Trp Ser
            540                 545                 550 aat gag ata gta cag tta ttc att gtc ctg gga aat gat cgt gcc aac                1732
Asn Glu Ile Val Gln Leu Phe Ile Val Leu Gly Asn Asp Arg Ala Asn
        555                 560                 565 cgc ttc tgg gca ggg acc cta ccc cca ggt gag gga cta cat cca gat                1780
Arg Phe Trp Ala Gly Thr Leu Pro Pro Gly Glu Gly Leu His Pro Asp
    570                 575                 580 gcg acc cct ggc ccc cgg gga gag ttc atc tcc cga aag tac cgt ctg                1828
Ala Thr Pro Gly Pro Arg Gly Glu Phe Ile Ser Arg Lys Tyr Arg Leu
585                 590                 595                 600 ggt ctc ttc cgg aag ccc cac cct cag tac cca gat cat agc cag ctt                1876
Gly Leu Phe Arg Lys Pro His Pro Gln Tyr Pro Asp His Ser Gln Leu
                605                 610                 615 ctc cag gca ctg tgt gca gct gtg gca aga ccc aac ctg ctg aag aac                1924
Leu Gln Ala Leu Cys Ala Ala Val Ala Arg Pro Asn Leu Leu Lys Asn
            620                 625                 630 atg acc cag ctc ctc tgt gtt gag gcc ttt gaa ggc gag gag ccc tgg                1972
Met Thr Gln Leu Leu Cys Val Glu Ala Phe Glu Gly Glu Glu Pro Trp
        635                 640                 645 ttc ccc cca gcc cct gat ggc agc tgc cct ggc ctc ttg ccc tca gac                2020
Phe Pro Pro Ala Pro Asp Gly Ser Cys Pro Gly Leu Leu Pro Ser Asp
    650                 655                 660 ccc tcc cct ggt gtg tac aat gag gtg gtg gtg cgt gct act tac agc                2068
Pro Ser Pro Gly Val Tyr Asn Glu Val Val Val Arg Ala Thr Tyr Ser
665                 670                 675                 680
```

```
                                                    -continued ggc ttc ctg tac tgc agt ccc gtc agc aac aaa gct gga ccc tca ccc      2116
Gly Phe Leu Tyr Cys Ser Pro Val Ser Asn Lys Ala Gly Pro Ser Pro
            685                 690                 695 cct cgc agg ggc cgg gat gct ccc ccg cgc ctt tgg tgt gtg ctg gga      2164
Pro Arg Arg Gly Arg Asp Ala Pro Pro Arg Leu Trp Cys Val Leu Gly
        700                 705                 710 gca gct ctg gaa atg ttt gca tcg gaa aac agc cct gaa ccc ctc agc      2212
Ala Ala Leu Glu Met Phe Ala Ser Glu Asn Ser Pro Glu Pro Leu Ser
    715                 720                 725 ctc ata cag ccc cag gat att gta tgt ctg ggt gtg agc ccc cca ccc      2260
Leu Ile Gln Pro Gln Asp Ile Val Cys Leu Gly Val Ser Pro Pro Pro
730                 735                 740 act gac cca ggt gac agg ttc ccc ttt tcc ttt gag ctc atc ctc gct      2308
Thr Asp Pro Gly Asp Arg Phe Pro Phe Ser Phe Glu Leu Ile Leu Ala
745                 750                 755                 760 ggg ggg agg atc cag cat ttt ggc aca gat gga gct gac agt ctg gag      2356
Gly Gly Arg Ile Gln His Phe Gly Thr Asp Gly Ala Asp Ser Leu Glu
                765                 770                 775 gcc tgg act agt gct gtg ggc aag tgg ttc tcc ccg ctg agc tgc cac      2404
Ala Trp Thr Ser Ala Val Gly Lys Trp Phe Ser Pro Leu Ser Cys His
            780                 785                 790 cag ctg ctg ggc ccc ggg ctg ctg cgg ctg ggc cgc cta tgg ctg cgg      2452
Gln Leu Leu Gly Pro Gly Leu Leu Arg Leu Gly Arg Leu Trp Leu Arg
        795                 800                 805 tcc ccc tcc cat aca gcc ccg gcc cct ggt ctc tgg ctg tca ggg ttt      2500
Ser Pro Ser His Thr Ala Pro Ala Pro Gly Leu Trp Leu Ser Gly Phe
    810                 815                 820 ggc ctc ctt cgt ggt gac cac ctc ttc ctg tgc tca gcg ccg ggc cca      2548
Gly Leu Leu Arg Gly Asp His Leu Phe Leu Cys Ser Ala Pro Gly Pro
825                 830                 835                 840 ggc ccc cca gcc cct gag gac atg gtg cat ctg cgg cgg cta cag gag      2596
Gly Pro Pro Ala Pro Glu Asp Met Val His Leu Arg Arg Leu Gln Glu
                845                 850                 855 atc agt gtg gtt tct gca gct gac acc cca gat aag aaa gag cat ttg      2644
Ile Ser Val Val Ser Ala Ala Asp Thr Pro Asp Lys Lys Glu His Leu
            860                 865                 870 gtc ctg gtg gag aca gga agg acc ctg tat ctg caa gga gag ggc cgg      2692
Val Leu Val Glu Thr Gly Arg Thr Leu Tyr Leu Gln Gly Glu Gly Arg
        875                 880                 885 ctg gac ttc acg gca tgg aac gca gcc att ggg ggc gcg gct ggt ggg      2740
Leu Asp Phe Thr Ala Trp Asn Ala Ala Ile Gly Gly Ala Ala Gly Gly
    890                 895                 900 ggc ggc aca ggg ctg cag gag cag cag atg agc cgg ggt gac atc ccc      2788
Gly Gly Thr Gly Leu Gln Glu Gln Gln Met Ser Arg Gly Asp Ile Pro
905                 910                 915                 920 atc atc gtg gat gcc tgc atc agt ttt gtt acc cag cat ggg ctc cgg      2836
Ile Ile Val Asp Ala Cys Ile Ser Phe Val Thr Gln His Gly Leu Arg
                925                 930                 935 ctg gaa ggt gta tac cgg aaa ggg ggc gct cgt gcc cgc agc ctg aga      2884
Leu Glu Gly Val Tyr Arg Lys Gly Gly Ala Arg Ala Arg Ser Leu Arg
            940                 945                 950 ctc ctg gct gag ttc cgt cgg gat gcc cgg tcg gtg aag ctc cga cca      2932
Leu Leu Ala Glu Phe Arg Arg Asp Ala Arg Ser Val Lys Leu Arg Pro
        955                 960                 965 ggg gag cac ttt gtg gag gat gtc act gac aca ctc aaa cgc ttc ttt      2980
Gly Glu His Phe Val Glu Asp Val Thr Asp Thr Leu Lys Arg Phe Phe
    970                 975                 980 cgt gag ctc gat gac cct gtg acc tct gca cgg ttg ctg cct cgc tgg      3028
Arg Glu Leu Asp Asp Pro Val Thr Ser Ala Arg Leu Leu Pro Arg Trp
985                 990                 995                 1000
```

-continued

```
agg gag gct gct gag ctg ccc cag aag aat cag cgc ctg gag aaa      3073
Arg Glu Ala Ala Glu Leu Pro Gln Lys Asn Gln Arg Leu Glu Lys
            1005                1010                1015 tat aaa gat gtg att ggc tgc ctg ccg cgg gtc aac cgc cgc aca      3118
Tyr Lys Asp Val Ile Gly Cys Leu Pro Arg Val Asn Arg Arg Thr
                1020                1025                1030 ctg gcc acc ctc att ggg cat ctc tat cgg gtg cag aaa tgt gcg      3163
Leu Ala Thr Leu Ile Gly His Leu Tyr Arg Val Gln Lys Cys Ala
            1035                1040                1045 gct cta aac cag atg tgc acg cgg aac ttg gct ctg ctg ttt gca      3208
Ala Leu Asn Gln Met Cys Thr Arg Asn Leu Ala Leu Leu Phe Ala
                1050                1055                1060 ccc agc gtg ttc cag acg gat ggg cga ggg gag cac gag gtg cga      3253
Pro Ser Val Phe Gln Thr Asp Gly Arg Gly Glu His Glu Val Arg
            1065                1070                1075 gtg ctg caa gag ctc att gat ggc tac atc tct gtc ttt gat atc      3298
Val Leu Gln Glu Leu Ile Asp Gly Tyr Ile Ser Val Phe Asp Ile
                1080                1085                1090 gat tct gac cag gta gct cag att gac ttg gag gtc agt ctt atc      3343
Asp Ser Asp Gln Val Ala Gln Ile Asp Leu Glu Val Ser Leu Ile
            1095                1100                1105 acc acc tgg aag gac gtg cag ctg tct cag gct gga gac ctc atc      3388
Thr Thr Trp Lys Asp Val Gln Leu Ser Gln Ala Gly Asp Leu Ile
                1110                1115                1120 atg gaa gtt tat ata gag cag cag ctc cca gac aac tgt gtc acc      3433
Met Glu Val Tyr Ile Glu Gln Gln Leu Pro Asp Asn Cys Val Thr
            1125                1130                1135 ctg aag gtg tcc cca acc ctg act gct gag gag ctg act aac cag      3478
Leu Lys Val Ser Pro Thr Leu Thr Ala Glu Glu Leu Thr Asn Gln
                1140                1145                1150 gta ctg gag atg cgg ggg aca gca gct ggg atg gac ttg tgg gtg      3523
Val Leu Glu Met Arg Gly Thr Ala Ala Gly Met Asp Leu Trp Val
            1155                1160                1165 act ttt gag att cgc gag cat ggg gag ctg gag cgg cca ctg cat      3568
Thr Phe Glu Ile Arg Glu His Gly Glu Leu Glu Arg Pro Leu His
                1170                1175                1180 ccc aag gaa aag gtc tta gag cag gct tta caa tgg tgc cag ctc      3613
Pro Lys Glu Lys Val Leu Glu Gln Ala Leu Gln Trp Cys Gln Leu
            1185                1190                1195 cca gag ccc tgc tca gct tcc ctg ctc ttg aaa aaa gtc ccc ctg      3658
Pro Glu Pro Cys Ser Ala Ser Leu Leu Leu Lys Lys Val Pro Leu
                1200                1205                1210 gcc caa gct ggc tgc ctc ttc aca ggt atc cga cgt gag agc cca      3703
Ala Gln Ala Gly Cys Leu Phe Thr Gly Ile Arg Arg Glu Ser Pro
            1215                1220                1225 cgg gtg ggg ctg ttg cgg tgt cgt gag gag cca cct cgc ttg ctg      3748
Arg Val Gly Leu Leu Arg Cys Arg Glu Glu Pro Pro Arg Leu Leu
                1230                1235                1240 gga agc cgc ttc cag gag agg ttc ttt ctg ctc cgt ggc cgc tgc      3793
Gly Ser Arg Phe Gln Glu Arg Phe Phe Leu Leu Arg Gly Arg Cys
            1245                1250                1255 ctg ctg ctg ctc aag gag aag aaa agc tct aaa cca gaa cgg gag      3838
Leu Leu Leu Leu Lys Glu Lys Lys Ser Ser Lys Pro Glu Arg Glu
                1260                1265                1270 tgg cct ttg gaa ggt gcc aag gtc tac ctg gga atc cgc aag aag      3883
Trp Pro Leu Glu Gly Ala Lys Val Tyr Leu Gly Ile Arg Lys Lys
            1275                1280                1285 tta aag ccc cca aca ccg tgg ggc ttc aca ttg ata cta gag aag      3928
Leu Lys Pro Pro Thr Pro Trp Gly Phe Thr Leu Ile Leu Glu Lys
```

-continued

|  |  |
|---|---|
| atg cac ctc tac ttg tcc tgc act gac gag gat gaa atg tgg gat<br>Met His Leu Tyr Leu Ser Cys Thr Asp Glu Asp Glu Met Trp Asp<br>　　　　　　　　1305　　　　　　　　1310　　　　　　　　1315 | 3973 |
| tgg acc acc agc atc ctt aaa gcc cag cac gat gac cag cag cca<br>Trp Thr Thr Ser Ile Leu Lys Ala Gln His Asp Asp Gln Gln Pro<br>　　　　　　　　1320　　　　　　　　1325　　　　　　　　1330 | 4018 |
| gtg gtc tta cga cgc cat tcc tcc tct gac ctt gcc cgt cag aag<br>Val Val Leu Arg Arg His Ser Ser Ser Asp Leu Ala Arg Gln Lys<br>　　　　　　　　1335　　　　　　　　1340　　　　　　　　1345 | 4063 |
| ttt ggc act atg cct ttg ctg cct atc cgt ggg gat gac agt gga<br>Phe Gly Thr Met Pro Leu Leu Pro Ile Arg Gly Asp Asp Ser Gly<br>　　　　　　　　1350　　　　　　　　1355　　　　　　　　1360 | 4108 |
| gcc acc ctc ctc tct gcc aat cag acc ctg cgg cga cta cac aac<br>Ala Thr Leu Leu Ser Ala Asn Gln Thr Leu Arg Arg Leu His Asn<br>　　　　　　　　1365　　　　　　　　1370　　　　　　　　1375 | 4153 |
| cgg agg acc ctg tcc atg ttc ttt cca atg aag tca tcc cag ggg<br>Arg Arg Thr Leu Ser Met Phe Phe Pro Met Lys Ser Ser Gln Gly<br>　　　　　　　　1380　　　　　　　　1385　　　　　　　　1390 | 4198 |
| tct gtg gag gag caa gag gag ctg gag gag cct gtg tac gag gag<br>Ser Val Glu Glu Gln Glu Glu Leu Glu Glu Pro Val Tyr Glu Glu<br>　　　　　　　　1395　　　　　　　　1400　　　　　　　　1405 | 4243 |
| cca gtg tat gag gaa gta ggg gcc ttc cct gag ttg atc cag gac<br>Pro Val Tyr Glu Glu Val Gly Ala Phe Pro Glu Leu Ile Gln Asp<br>　　　　　　　　1410　　　　　　　　1415　　　　　　　　1420 | 4288 |
| act tct acc tcc ttc tcc acc aca cgg gag tgg aca gtg aag cca<br>Thr Ser Thr Ser Phe Ser Thr Thr Arg Glu Trp Thr Val Lys Pro<br>　　　　　　　　1425　　　　　　　　1430　　　　　　　　1435 | 4333 |
| gag aac ccc ctc acc agc cag aag tca ttg gat caa ccc ttt ctc<br>Glu Asn Pro Leu Thr Ser Gln Lys Ser Leu Asp Gln Pro Phe Leu<br>　　　　　　　　1440　　　　　　　　1445　　　　　　　　1450 | 4378 |
| tcc aag tca agc acc ctt ggc cag gag gag agg cca cct gag ccc<br>Ser Lys Ser Ser Thr Leu Gly Gln Glu Glu Arg Pro Pro Glu Pro<br>　　　　　　　　1455　　　　　　　　1460　　　　　　　　1465 | 4423 |
| cct cca ggc ccc cct tca aag agc agt ccc cag gca cgg ggg tcc<br>Pro Pro Gly Pro Pro Ser Lys Ser Ser Pro Gln Ala Arg Gly Ser<br>　　　　　　　　1470　　　　　　　　1475　　　　　　　　1480 | 4468 |
| cta gag gaa cag ctg ctc cag gag ctc agc agc ctc atc ctg agg<br>Leu Glu Glu Gln Leu Leu Gln Glu Leu Ser Ser Leu Ile Leu Arg<br>　　　　　　　　1485　　　　　　　　1490　　　　　　　　1495 | 4513 |
| aaa gga gag acc act gca ggc ctg gga agt cct tcc cag cca tcc<br>Lys Gly Glu Thr Thr Ala Gly Leu Gly Ser Pro Ser Gln Pro Ser<br>　　　　　　　　1500　　　　　　　　1505　　　　　　　　1510 | 4558 |
| agc ccc caa tcc ccc agc ccc act ggc ctt cca aca cag aca cct<br>Ser Pro Gln Ser Pro Ser Pro Thr Gly Leu Pro Thr Gln Thr Pro<br>　　　　　　　　1515　　　　　　　　1520　　　　　　　　1525 | 4603 |
| ggc ttc ccc acc caa ccc cca tgc act tcc agt cca ccc tcc agc<br>Gly Phe Pro Thr Gln Pro Pro Cys Thr Ser Ser Pro Pro Ser Ser<br>　　　　　　　　1530　　　　　　　　1535　　　　　　　　1540 | 4648 |
| cag ccc ctc aca tga ccctaggacc agcagtctga gagggtaggt accagaagac<br>Gln Pro Leu Thr | 4703 |
| ccagaaactc ttatcgtggc actgttgcag cttcctctgc cctggctgga aagactccag | 4763 |
| aatccagtgt ggtgctgtgg aaggagcact ggactaaagg cttcagtggc tgcgtgtccc | 4823 |
| aggacaggtc atggccctc tctgggccca gcccatttat ctataccatg aggtaactga | 4883 |
| agtaaggaga gcagtgaatg tcaaactgtg tttcttagag ccataagccc cacatattat | 4943 |
| ccctgaacaa gggcagctcc tgctttatat atttgatacg taggggttcc atgagagatt | 5003 |

-continued

```
ttgggtttta aaggaatggt tttactgcat taaagaaaaa aaatgctttg gaaaccagag      5063
gcctgggtga tgttaaagtc tatcctgtcc cacttcctac attctgggac taccgtgaag      5123
cctggagtag ggagagcgag tttgggagct gggactcggg gagtcaaaaa tagatgagta      5183
attgtcaata aacctgggaa ccaaaag                                           5210
```

<210> SEQ ID NO 4
<211> LENGTH: 1544
<212> TYPE: PRT
<213> ORGANISM: Homo sapiens

<400> SEQUENCE: 4

```
Met Ala Ala Pro Gln Asp Leu Asp Ile Ala Val Trp Leu Ala Thr Val
1               5                   10                  15

His Leu Glu Gln Tyr Ala Asp Thr Phe Arg Arg His Gly Leu Ala Thr
            20                  25                  30

Ala Gly Ala Ala Arg Gly Leu Gly His Glu Glu Leu Lys Gln Leu Gly
        35                  40                  45

Ile Ser Ala Thr Gly His Arg Lys Arg Ile Leu Arg Leu Leu Gln Thr
    50                  55                  60

Gly Thr Glu Glu Gly Ser Leu Asp Pro Lys Ser Asp Ser Ala Met Glu
65                  70                  75                  80

Pro Ser Pro Ser Pro Ala Pro Gln Ala Gln Pro Lys Pro Val Pro
            85                  90                  95

Lys Pro Arg Thr Val Phe Gly Gly Leu Ser Gly Pro Ala Thr Thr Gln
            100                 105                 110

Arg Pro Gly Leu Ser Pro Ala Leu Gly Gly Pro Gly Val Ser Arg Ser
        115                 120                 125

Pro Glu Pro Ser Pro Arg Pro Pro Leu Pro Thr Ser Ser Ser Glu
    130                 135                 140

Gln Ser Ser Ala Leu Asn Thr Val Glu Met Met Pro Asn Ser Ile Tyr
145                 150                 155                 160

Phe Gly Leu Asp Ser Arg Gly Arg Ala Gln Ala Ala Gln Asp Lys Ala
            165                 170                 175

Pro Asp Ser Ser Gln Ile Ser Ala Pro Thr Pro Ala Leu Arg Pro Thr
            180                 185                 190

Thr Gly Thr Val His Ile Met Asp Pro Gly Cys Leu Tyr Tyr Gly Val
        195                 200                 205

Gln Pro Val Gly Thr Pro Gly Ala Pro Asp Arg Arg Glu Ser Arg Gly
    210                 215                 220

Val Cys Gln Gly Arg Ala Glu His Arg Leu Ser Arg Gln Asp Leu Glu
225                 230                 235                 240

Ala Arg Glu Asp Ala Gly Tyr Ala Ser Leu Glu Leu Pro Gly Asp Ser
            245                 250                 255

Thr Leu Leu Ser Pro Thr Leu Glu Thr Glu Glu Thr Ser Asp Asp Leu
            260                 265                 270

Ile Ser Pro Tyr Ala Ser Phe Ser Phe Thr Ala Asp Arg Leu Thr Pro
        275                 280                 285

Leu Leu Ser Gly Trp Leu Asp Lys Leu Ser Pro Gln Gly Asn Tyr Val
    290                 295                 300

Phe Gln Arg Arg Phe Val Gln Phe Asn Gly Arg Ser Leu Met Tyr Phe
305                 310                 315                 320

Gly Ser Asp Lys Asp Pro Phe Pro Lys Gly Val Ile Pro Leu Thr Ala
            325                 330                 335
```

```
Ile Glu Met Thr Arg Ser Ser Lys Asp Asn Lys Phe Gln Val Ile Thr
            340                 345                 350
Gly Gln Arg Val Phe Val Phe Arg Thr Glu Ser Glu Ala Gln Arg Asp
        355                 360                 365
Met Trp Cys Ser Thr Leu Gln Ser Cys Leu Lys Glu Gln Arg Leu Leu
370                 375                 380
Gly His Pro Arg Pro Pro Gln Pro Pro Arg Pro Leu Arg Thr Gly Met
385                 390                 395                 400
Leu Glu Leu Arg Gly His Lys Ala Lys Val Phe Ala Ala Leu Ser Pro
                405                 410                 415
Gly Glu Leu Ala Leu Tyr Lys Ser Glu Gln Ala Phe Ser Leu Gly Ile
                420                 425                 430
Gly Ile Cys Phe Ile Glu Leu Gln Gly Cys Ser Val Arg Glu Thr Lys
            435                 440                 445
Ser Arg Ser Phe Asp Leu Leu Thr Pro His Arg Cys Phe Ser Phe Thr
        450                 455                 460
Ala Glu Ser Gly Gly Ala Arg Gln Ser Trp Ala Ala Ala Leu Gln Glu
465                 470                 475                 480
Ala Val Thr Glu Thr Leu Ser Asp Tyr Glu Val Ala Glu Lys Ile Trp
                485                 490                 495
Ser Asn Arg Ala Asn Arg Gln Cys Ala Asp Cys Gly Ser Ser Arg Pro
                500                 505                 510
Asp Trp Ala Ala Val Asn Leu Gly Val Val Ile Cys Lys Gln Cys Ala
            515                 520                 525
Gly Gln His Arg Ala Leu Gly Ser Gly Ile Ser Lys Val Gln Ser Leu
        530                 535                 540
Lys Leu Asp Thr Ser Val Trp Ser Asn Glu Ile Val Gln Leu Phe Ile
545                 550                 555                 560
Val Leu Gly Asn Asp Arg Ala Asn Arg Phe Trp Ala Gly Thr Leu Pro
                565                 570                 575
Pro Gly Glu Gly Leu His Pro Asp Ala Thr Pro Gly Pro Arg Gly Glu
                580                 585                 590
Phe Ile Ser Arg Lys Tyr Arg Leu Gly Leu Phe Arg Lys Pro His Pro
            595                 600                 605
Gln Tyr Pro Asp His Ser Gln Leu Leu Gln Ala Leu Cys Ala Ala Val
        610                 615                 620
Ala Arg Pro Asn Leu Leu Lys Asn Met Thr Gln Leu Leu Cys Val Glu
625                 630                 635                 640
Ala Phe Glu Gly Glu Glu Pro Trp Phe Pro Pro Ala Pro Asp Gly Ser
                645                 650                 655
Cys Pro Gly Leu Leu Pro Ser Asp Pro Ser Pro Gly Val Tyr Asn Glu
                660                 665                 670
Val Val Val Arg Ala Thr Tyr Ser Gly Phe Leu Tyr Cys Ser Pro Val
            675                 680                 685
Ser Asn Lys Ala Gly Pro Ser Pro Arg Arg Gly Arg Asp Ala Pro
        690                 695                 700
Pro Arg Leu Trp Cys Val Leu Gly Ala Ala Leu Glu Met Phe Ala Ser
705                 710                 715                 720
Glu Asn Ser Pro Glu Pro Leu Ser Leu Ile Gln Pro Gln Asp Ile Val
                725                 730                 735
Cys Leu Gly Val Ser Pro Pro Thr Asp Pro Gly Asp Arg Phe Pro
                740                 745                 750
Phe Ser Phe Glu Leu Ile Leu Ala Gly Gly Arg Ile Gln His Phe Gly
```

-continued

```
              755                 760                 765
Thr Asp Gly Ala Asp Ser Leu Glu Ala Trp Thr Ser Ala Val Gly Lys
770                 775                 780

Trp Phe Ser Pro Leu Ser Cys His Gln Leu Leu Gly Pro Gly Leu Leu
785                 790                 795                 800

Arg Leu Gly Arg Leu Trp Leu Arg Ser Pro Ser His Thr Ala Pro Ala
                805                 810                 815

Pro Gly Leu Trp Leu Ser Gly Phe Gly Leu Leu Arg Gly Asp His Leu
                    820                 825                 830

Phe Leu Cys Ser Ala Pro Gly Pro Gly Pro Ala Pro Glu Asp Met
                    835                 840                 845

Val His Leu Arg Arg Leu Gln Glu Ile Ser Val Val Ser Ala Ala Asp
850                 855                 860

Thr Pro Asp Lys Lys Glu His Leu Val Leu Val Glu Thr Gly Arg Thr
865                 870                 875                 880

Leu Tyr Leu Gln Gly Glu Gly Arg Leu Asp Phe Thr Ala Trp Asn Ala
                    885                 890                 895

Ala Ile Gly Gly Ala Ala Gly Gly Gly Thr Gly Leu Gln Glu Gln
                    900                 905                 910

Gln Met Ser Arg Gly Asp Ile Pro Ile Ile Val Asp Ala Cys Ile Ser
                    915                 920                 925

Phe Val Thr Gln His Gly Leu Arg Leu Glu Gly Val Tyr Arg Lys Gly
                    930                 935                 940

Gly Ala Arg Ala Arg Ser Leu Arg Leu Leu Ala Glu Phe Arg Arg Asp
945                 950                 955                 960

Ala Arg Ser Val Lys Leu Arg Pro Gly Glu His Phe Val Glu Asp Val
                    965                 970                 975

Thr Asp Thr Leu Lys Arg Phe Phe Arg Glu Leu Asp Asp Pro Val Thr
                980                 985                 990

Ser Ala Arg Leu Leu Pro Arg Trp Arg Glu Ala Ala Glu Leu Pro Gln
                    995                1000                1005

Lys Asn Gln Arg Leu Glu Lys Tyr Lys Asp Val Ile Gly Cys Leu
            1010                1015                1020

Pro Arg Val Asn Arg Arg Thr Leu Ala Thr Leu Ile Gly His Leu
            1025                1030                1035

Tyr Arg Val Gln Lys Cys Ala Ala Leu Asn Gln Met Cys Thr Arg
            1040                1045                1050

Asn Leu Ala Leu Leu Phe Ala Pro Ser Val Phe Gln Thr Asp Gly
            1055                1060                1065

Arg Gly Glu His Glu Val Arg Val Leu Gln Glu Leu Ile Asp Gly
            1070                1075                1080

Tyr Ile Ser Val Phe Asp Ile Asp Ser Asp Gln Val Ala Gln Ile
            1085                1090                1095

Asp Leu Glu Val Ser Leu Ile Thr Thr Trp Lys Asp Val Gln Leu
            1100                1105                1110

Ser Gln Ala Gly Asp Leu Ile Met Glu Val Tyr Ile Glu Gln Gln
            1115                1120                1125

Leu Pro Asp Asn Cys Val Thr Leu Lys Val Ser Pro Thr Leu Thr
            1130                1135                1140

Ala Glu Glu Leu Thr Asn Gln Val Leu Glu Met Arg Gly Thr Ala
            1145                1150                1155

Ala Gly Met Asp Leu Trp Val Thr Phe Glu Ile Arg Glu His Gly
            1160                1165                1170
```

```
Glu Leu Glu Arg Pro Leu His Pro Lys Glu Lys Val Leu Glu Gln
    1175                1180                1185

Ala Leu Gln Trp Cys Gln Leu Pro Glu Pro Cys Ser Ala Ser Leu
    1190                1195                1200

Leu Leu Lys Lys Val Pro Leu Ala Gln Ala Gly Cys Leu Phe Thr
    1205                1210                1215

Gly Ile Arg Arg Glu Ser Pro Arg Val Gly Leu Leu Arg Cys Arg
    1220                1225                1230

Glu Glu Pro Pro Arg Leu Leu Gly Ser Arg Phe Gln Glu Arg Phe
    1235                1240                1245

Phe Leu Leu Arg Gly Arg Cys Leu Leu Leu Lys Glu Lys Lys
    1250                1255                1260

Ser Ser Lys Pro Glu Arg Glu Trp Pro Leu Glu Gly Ala Lys Val
    1265                1270                1275

Tyr Leu Gly Ile Arg Lys Lys Leu Lys Pro Pro Thr Pro Trp Gly
    1280                1285                1290

Phe Thr Leu Ile Leu Glu Lys Met His Leu Tyr Leu Ser Cys Thr
    1295                1300                1305

Asp Glu Asp Glu Met Trp Asp Trp Thr Thr Ser Ile Leu Lys Ala
    1310                1315                1320

Gln His Asp Asp Gln Gln Pro Val Val Leu Arg Arg His Ser Ser
    1325                1330                1335

Ser Asp Leu Ala Arg Gln Lys Phe Gly Thr Met Pro Leu Leu Pro
    1340                1345                1350

Ile Arg Gly Asp Asp Ser Gly Ala Thr Leu Leu Ser Ala Asn Gln
    1355                1360                1365

Thr Leu Arg Arg Leu His Asn Arg Arg Thr Leu Ser Met Phe Phe
    1370                1375                1380

Pro Met Lys Ser Ser Gln Gly Ser Val Glu Glu Gln Glu Glu Leu
    1385                1390                1395

Glu Glu Pro Val Tyr Glu Glu Pro Val Tyr Glu Glu Val Gly Ala
    1400                1405                1410

Phe Pro Glu Leu Ile Gln Asp Thr Ser Thr Ser Phe Ser Thr Thr
    1415                1420                1425

Arg Glu Trp Thr Val Lys Pro Glu Asn Pro Leu Thr Ser Gln Lys
    1430                1435                1440

Ser Leu Asp Gln Pro Phe Leu Ser Lys Ser Ser Thr Leu Gly Gln
    1445                1450                1455

Glu Glu Arg Pro Pro Glu Pro Pro Gly Pro Pro Ser Lys Ser
    1460                1465                1470

Ser Pro Gln Ala Arg Gly Ser Leu Glu Gln Leu Leu Gln Glu
    1475                1480                1485

Leu Ser Ser Leu Ile Leu Arg Lys Gly Glu Thr Thr Ala Gly Leu
    1490                1495                1500

Gly Ser Pro Ser Gln Pro Ser Ser Pro Gln Ser Pro Ser Pro Thr
    1505                1510                1515

Gly Leu Pro Thr Gln Thr Pro Gly Phe Pro Thr Gln Pro Pro Cys
    1520                1525                1530

Thr Ser Ser Pro Pro Ser Ser Gln Pro Leu Thr
    1535                1540

<210> SEQ ID NO 5
<211> LENGTH: 1821
```

```
<212> TYPE: DNA
<213> ORGANISM: Homo sapiens
<220> FEATURE:
<221> NAME/KEY: CDS
<222> LOCATION: (91)..(1323)
<223> OTHER INFORMATION:

<400> SEQUENCE: 5
```

| | | |
|---|---|---|
| ggccgaaggg aaaccggcgc gtccccgcc cgcccaggcg tcagctgatg ggctgcctgc | 60 |
| cgaggaggcc gcagcagtcg ccgcgcgaac atg gcg gcc gaa atc cac tcc agg<br>                                               Met Ala Ala Glu Ile His Ser Arg<br>                                               1             5 | 114 |

```
ccg cag agc agc cgc ccg gtg ctg ctg agc aag atc gag ggg cac cag      162
Pro Gln Ser Ser Arg Pro Val Leu Leu Ser Lys Ile Glu Gly His Gln
 10              15                  20 gac gcc gtc acg gcc gcg ctg ctc atc ccc aag gag gac ggc gtg atc      210
Asp Ala Val Thr Ala Ala Leu Leu Ile Pro Lys Glu Asp Gly Val Ile
 25                  30                  35                  40 acg gcc agc gag gac aga acc atc cgg gta tgg ctg aaa aga gac agt      258
Thr Ala Ser Glu Asp Arg Thr Ile Arg Val Trp Leu Lys Arg Asp Ser
                 45                  50                  55 ggt caa tac tgg ccc agc att tac cac aca atg gcc tct cct tgc tct      306
Gly Gln Tyr Trp Pro Ser Ile Tyr His Thr Met Ala Ser Pro Cys Ser
             60                  65                  70 gct atg gct tac cat cat gac agc aga cgg ata ttt gtg ggc cag gat      354
Ala Met Ala Tyr His His Asp Ser Arg Arg Ile Phe Val Gly Gln Asp
         75                  80                  85 aat gga gct gta atg gaa ttt cac gtt tct gaa gat ttt aat aaa atg      402
Asn Gly Ala Val Met Glu Phe His Val Ser Glu Asp Phe Asn Lys Met
 90                  95                 100 aac ttt atc aag acc tac cca gct cat cag aac cgg gtg tct gcg att      450
Asn Phe Ile Lys Thr Tyr Pro Ala His Gln Asn Arg Val Ser Ala Ile
105                 110                 115                 120 atc ttc agc ttg gcc aca gag tgg gtg atc agt acc ggc cac gac aag      498
Ile Phe Ser Leu Ala Thr Glu Trp Val Ile Ser Thr Gly His Asp Lys
                125                 130                 135 tgt gtg agc tgg atg tgc acg cgg agc ggg aac atg ctc ggg agg cac      546
Cys Val Ser Trp Met Cys Thr Arg Ser Gly Asn Met Leu Gly Arg His
            140                 145                 150 ttc ttc acg tcc tgg gct tcg tgt ctg caa tat gac ttt gac act cag      594
Phe Phe Thr Ser Trp Ala Ser Cys Leu Gln Tyr Asp Phe Asp Thr Gln
        155                 160                 165 tat gct ttc gtt ggt gat tat tct ggg cag atc acc ctg ctg aag ctt      642
Tyr Ala Phe Val Gly Asp Tyr Ser Gly Gln Ile Thr Leu Leu Lys Leu
    170                 175                 180 gaa cag aac acg tgt tca gtc atc aca acc ctc aaa gga cat gaa ggt      690
Glu Gln Asn Thr Cys Ser Val Ile Thr Thr Leu Lys Gly His Glu Gly
185                 190                 195                 200 agt gtc gcc tgc ctc tgg tgg gac cct att cag cgg tta ctc ttc tca      738
Ser Val Ala Cys Leu Trp Trp Asp Pro Ile Gln Arg Leu Leu Phe Ser
                205                 210                 215 gga gca tct gac aac agc atc atc atg tgg gac atc gga gga agg aaa      786
Gly Ala Ser Asp Asn Ser Ile Ile Met Trp Asp Ile Gly Gly Arg Lys
            220                 225                 230 ggc cgg acg ctg tta ctt cag ggc cat cat gac aag gtg cag tcg ctg      834
Gly Arg Thr Leu Leu Leu Gln Gly His His Asp Lys Val Gln Ser Leu
        235                 240                 245 tgc tac ctt cag ctc acc agg cag ctc gtc tcc tgt tcc tcg gac ggc      882
Cys Tyr Leu Gln Leu Thr Arg Gln Leu Val Ser Cys Ser Ser Asp Gly
    250                 255                 260
```

```
gga att gca gtg tgg aac atg gat gtt agc aga gaa gag gct cct cag      930
Gly Ile Ala Val Trp Asn Met Asp Val Ser Arg Glu Glu Ala Pro Gln
265                 270                 275                 280 tgg ttg gaa agt gat tct tgt cag aaa tgt gag cag cca ttt ttc tgg      978
Trp Leu Glu Ser Asp Ser Cys Gln Lys Cys Glu Gln Pro Phe Phe Trp
                285                 290                 295 aac ata aag cag atg tgg gac acc aag acg ctg ggg cta aga caa cat     1026
Asn Ile Lys Gln Met Trp Asp Thr Lys Thr Leu Gly Leu Arg Gln His
                300                 305                 310 cac tgc agg aaa tgc ggg cag gct gtc tgc ggg aag tgc agc agc aag     1074
His Cys Arg Lys Cys Gly Gln Ala Val Cys Gly Lys Cys Ser Ser Lys
                315                 320                 325 cgc tca agt tac cca gtc atg ggc ttc gag ttc caa gtc cgg gtt tgt     1122
Arg Ser Ser Tyr Pro Val Met Gly Phe Glu Phe Gln Val Arg Val Cys
330                 335                 340 gat tct tgt tac gac tcc atc aaa gat gaa gat cgg act tct cta gcg     1170
Asp Ser Cys Tyr Asp Ser Ile Lys Asp Glu Asp Arg Thr Ser Leu Ala
345                 350                 355                 360 acc ttt cat gaa gga aaa cat aac att tcc cac atg tcc atg gac att     1218
Thr Phe His Glu Gly Lys His Asn Ile Ser His Met Ser Met Asp Ile
                365                 370                 375 gcc agg gga ctg atg gtg acc tgt ggg acc gac cgc att gta aag atc     1266
Ala Arg Gly Leu Met Val Thr Cys Gly Thr Asp Arg Ile Val Lys Ile
                380                 385                 390 tgg gac atg aca cct gtg gtg ggc tgc agt ctg gcg act ggg ttt tct     1314
Trp Asp Met Thr Pro Val Val Gly Cys Ser Leu Ala Thr Gly Phe Ser
                395                 400                 405 ccg cac tga tctgagagct gggcagcgtc cacacctaag aacagcagct             1363
Pro His
    410 ccaccaaatg aagtccctct cacgcagctc cacagcgctg tctcgtgaat ggacagtagc   1423 cacttacaaa caaatcaaca ttttttaaaaa gaaaatgtaa aggtgtgttt tggggcattt   1483 gtggaactta cccatgggga ctaatatgga aaaggtctgt ccatagtggt tccctgaaga   1543 ctggaattac ttcagcaaaa cttccccatg aacagctaat gtgtagtgaa agaatgagct   1603 agcaaatgag ttttagcggg gacaaaaaat caaacaaaaa agtgaatgct tagaaccttc   1663 tcaaagcagt cacaagtaca gacacttcac ttagcctagg gggccttcca gggttcttgt   1723 ggctgttgtc agagcaggag ctgggggagg gaagacttgt tctctctttc ttgaggggtg   1783 gcattaggaa cttacgaaac cagagacctt tccctatg                          1821
```

<210> SEQ ID NO 6
<211> LENGTH: 410
<212> TYPE: PRT
<213> ORGANISM: Homo sapiens

<400> SEQUENCE: 6

```
Met Ala Ala Glu Ile His Ser Arg Pro Gln Ser Ser Arg Pro Val Leu
1               5                   10                  15

Leu Ser Lys Ile Glu Gly His Gln Asp Ala Val Thr Ala Ala Leu Leu
            20                  25                  30

Ile Pro Lys Glu Asp Gly Val Ile Thr Ala Ser Glu Asp Arg Thr Ile
        35                  40                  45

Arg Val Trp Leu Lys Arg Asp Ser Gly Gln Tyr Trp Pro Ser Ile Tyr
    50                  55                  60

His Thr Met Ala Ser Pro Cys Ser Ala Met Ala Tyr His His Asp Ser
65                  70                  75                  80
```

```
Arg Arg Ile Phe Val Gly Gln Asp Asn Gly Ala Val Met Glu Phe His
                85                  90                  95
Val Ser Glu Asp Phe Asn Lys Met Asn Phe Ile Lys Thr Tyr Pro Ala
            100                 105                 110
His Gln Asn Arg Val Ser Ala Ile Ile Phe Ser Leu Ala Thr Glu Trp
        115                 120                 125
Val Ile Ser Thr Gly His Asp Lys Cys Val Ser Trp Met Cys Thr Arg
    130                 135                 140
Ser Gly Asn Met Leu Gly Arg His Phe Phe Thr Ser Trp Ala Ser Cys
145                 150                 155                 160
Leu Gln Tyr Asp Phe Asp Thr Gln Tyr Ala Phe Val Gly Asp Tyr Ser
                165                 170                 175
Gly Gln Ile Thr Leu Leu Lys Leu Glu Gln Asn Thr Cys Ser Val Ile
            180                 185                 190
Thr Thr Leu Lys Gly His Glu Gly Ser Val Ala Cys Leu Trp Trp Asp
        195                 200                 205
Pro Ile Gln Arg Leu Leu Phe Ser Gly Ala Ser Asp Asn Ser Ile Ile
    210                 215                 220
Met Trp Asp Ile Gly Gly Arg Lys Gly Arg Thr Leu Leu Leu Gln Gly
225                 230                 235                 240
His His Asp Lys Val Gln Ser Leu Cys Tyr Leu Gln Leu Thr Arg Gln
                245                 250                 255
Leu Val Ser Cys Ser Ser Asp Gly Gly Ile Ala Val Trp Asn Met Asp
            260                 265                 270
Val Ser Arg Glu Glu Ala Pro Gln Trp Leu Glu Ser Asp Ser Cys Gln
        275                 280                 285
Lys Cys Glu Gln Pro Phe Phe Trp Asn Ile Lys Gln Met Trp Asp Thr
    290                 295                 300
Lys Thr Leu Gly Leu Arg Gln His His Cys Arg Lys Cys Gly Gln Ala
305                 310                 315                 320
Val Cys Gly Lys Cys Ser Ser Lys Arg Ser Ser Tyr Pro Val Met Gly
                325                 330                 335
Phe Glu Phe Gln Val Arg Val Cys Asp Ser Cys Tyr Asp Ser Ile Lys
            340                 345                 350
Asp Glu Asp Arg Thr Ser Leu Ala Thr Phe His Glu Gly Lys His Asn
        355                 360                 365
Ile Ser His Met Ser Met Asp Ile Ala Arg Gly Leu Met Val Thr Cys
    370                 375                 380
Gly Thr Asp Arg Ile Val Lys Ile Trp Asp Met Thr Pro Val Val Gly
385                 390                 395                 400
Cys Ser Leu Ala Thr Gly Phe Ser Pro His
                405                 410

<210> SEQ ID NO 7
<211> LENGTH: 3699
<212> TYPE: DNA
<213> ORGANISM: Homo sapiens
<220> FEATURE:
<221> NAME/KEY: CDS
<222> LOCATION: (573)..(2906)
<223> OTHER INFORMATION:

<400> SEQUENCE: 7
cccgggaggc aacgaaggag gagggtggcg gagatggaga tgaggatgga tctgccggtg      60
tcctgaggaa tagcctctgc ccccactggc gccctgcggc cccccgacgc cgccttgctg     120
```

-continued

```
cggccgagct tctcagtggt atcccctgaa atactgactt caggtcgaat tatattgaaa      180
agctcctgac cactttcttt cattaccaaa actttgtagc tgatgtccaa ccgatgaacc      240
caccaccgtg aacccatcag acctctctca gatagccata aaagacccct ccaagtcaat      300
tttgaccaca tctttgcttg cactttatgg aggatgaaac catcaaacca aatcaacgtt      360
gctgctaata caagagtctt agaggcagca aattaaaaat ttgaacattt gtttgtgaag      420
aactataaca ggacatgaaa ggtgttcttt tttaaagtgt tcagaaccct gtggaagttt      480
cgtgcagtct tcagactcaa atcttcgtct tcaccccggg ggcaagctca gtgactatta      540
tatggtgggt gtgtttcctt accagcgtga gt atg agt gcc cag act tcc cca       593
                                    Met Ser Ala Gln Thr Ser Pro
                                    1               5
```

```
gca gag aag ggc ctg aat ccg ggg ctg atg tgc cag gaa agt tac gct       641
Ala Glu Lys Gly Leu Asn Pro Gly Leu Met Cys Gln Glu Ser Tyr Ala
            10                  15                  20 tgc agc ggg act gat gaa gct atc ttt gag tgt gat gag tgc tgc agt       689
Cys Ser Gly Thr Asp Glu Ala Ile Phe Glu Cys Asp Glu Cys Cys Ser
25                  30                  35 ctg cag tgt ctc cgc tgc gag gag gag ctc cat cgg cag gag cgc ctg       737
Leu Gln Cys Leu Arg Cys Glu Glu Glu Leu His Arg Gln Glu Arg Leu
40                  45                  50                  55 aga aac cat gag cgg ata aga ctc aaa cct ggc cat gtc cct tac tgt       785
Arg Asn His Glu Arg Ile Arg Leu Lys Pro Gly His Val Pro Tyr Cys
                60                  65                  70 gac ctc tgc aag ggt ctc agt ggg cat tta cca ggt gtt agg cag agg       833
Asp Leu Cys Lys Gly Leu Ser Gly His Leu Pro Gly Val Arg Gln Arg
                75                  80                  85 gca ata gtg agg tgc cag acc tgc aaa att aac ttg tgc ctg gag tgc       881
Ala Ile Val Arg Cys Gln Thr Cys Lys Ile Asn Leu Cys Leu Glu Cys
                90                  95                  100 cag aag agg act cat tct ggg ggt aac aaa agg aga cac cct gtt act       929
Gln Lys Arg Thr His Ser Gly Gly Asn Lys Arg Arg His Pro Val Thr
            105                 110                 115 gtg tac aat gtc agt aat ctc cag gag tca ctg gag gca gaa gag atg       977
Val Tyr Asn Val Ser Asn Leu Gln Glu Ser Leu Glu Ala Glu Glu Met
120                 125                 130                 135 gat gag gag acc aag agg aag aag atg act gag aag gtt gtg agt ttc      1025
Asp Glu Glu Thr Lys Arg Lys Lys Met Thr Glu Lys Val Val Ser Phe
                140                 145                 150 ctc cta gta gac gaa aat gaa gaa att cag gta aca aat gaa gaa gac      1073
Leu Leu Val Asp Glu Asn Glu Glu Ile Gln Val Thr Asn Glu Glu Asp
            155                 160                 165 ttt att aga aaa ttg gac tgc aaa cct gat cag cat ctg aaa gtg gtt      1121
Phe Ile Arg Lys Leu Asp Cys Lys Pro Asp Gln His Leu Lys Val Val
            170                 175                 180 tcc att ttt gga aat act ggt gat gga aag tct cat act ctc aac cac      1169
Ser Ile Phe Gly Asn Thr Gly Asp Gly Lys Ser His Thr Leu Asn His
            185                 190                 195 act ttc ttt tat ggt cgt gaa gtc ttt aaa acc tcc ccg acc cag gag      1217
Thr Phe Phe Tyr Gly Arg Glu Val Phe Lys Thr Ser Pro Thr Gln Glu
200                 205                 210                 215 tcc tgc act gtg gga gtg tgg gca gcc tat gac cca gtt cac aaa gta      1265
Ser Cys Thr Val Gly Val Trp Ala Ala Tyr Asp Pro Val His Lys Val
                220                 225                 230 gca gtg atc gat acg gaa ggg ctc ctg ggg gcc acc gtg aat cta agc      1313
Ala Val Ile Asp Thr Glu Gly Leu Leu Gly Ala Thr Val Asn Leu Ser
            235                 240                 245 cag aga aca cgg ctg ctg ctt aag gtc ctg gcc atc tca gac ctc gtc      1361
```

-continued

```
        Gln Arg Thr Arg Leu Leu Leu Lys Val Leu Ala Ile Ser Asp Leu Val
                    250                 255                 260 atc tat cga act cat gca gac cgg ctg cat aac gac ctc ttc aaa ttc          1409
Ile Tyr Arg Thr His Ala Asp Arg Leu His Asn Asp Leu Phe Lys Phe
            265                 270                 275 ctt ggg gat gcc tca gaa gct tat ctg aag cac ttc acc aag gag ctc          1457
Leu Gly Asp Ala Ser Glu Ala Tyr Leu Lys His Phe Thr Lys Glu Leu
280                 285                 290                 295 aag gcc acc act gct cgc tgt ggc ctg gat gtc cct tta tcc aca ctg          1505
Lys Ala Thr Thr Ala Arg Cys Gly Leu Asp Val Pro Leu Ser Thr Leu
                300                 305                 310 ggc cct gca gtt atc atc ttc cat gag acc gtg cac acc cag cta ctg          1553
Gly Pro Ala Val Ile Ile Phe His Glu Thr Val His Thr Gln Leu Leu
            315                 320                 325 ggc tct gat cat ccc tca gag gtg cca gag aag ctc atc cag gac cgg          1601
Gly Ser Asp His Pro Ser Glu Val Pro Glu Lys Leu Ile Gln Asp Arg
        330                 335                 340 ttc cgg aag ctg ggc cgt ttc cct gaa gcc ttt agt tcc att cac tac          1649
Phe Arg Lys Leu Gly Arg Phe Pro Glu Ala Phe Ser Ser Ile His Tyr
    345                 350                 355 aag gga acg agg act tac aac cct ccc acg gac ttt tct ggg ctt cgg          1697
Lys Gly Thr Arg Thr Tyr Asn Pro Pro Thr Asp Phe Ser Gly Leu Arg
360                 365                 370                 375 cgt gct ttg gag cag cta cta gag aat aac acc acc cgt tct ccc cgg          1745
Arg Ala Leu Glu Gln Leu Leu Glu Asn Asn Thr Thr Arg Ser Pro Arg
                380                 385                 390 cac ccg gga gtc atc ttc aaa gcc ctg aag gca cta agt gac cgc ttc          1793
His Pro Gly Val Ile Phe Lys Ala Leu Lys Ala Leu Ser Asp Arg Phe
            395                 400                 405 agc ggt gag atc ccc gat gac cag atg gcg cac agc tcc ttt ttt cca          1841
Ser Gly Glu Ile Pro Asp Asp Gln Met Ala His Ser Ser Phe Phe Pro
        410                 415                 420 gat gag tat ttc acc tgc tcc tcc ttg tgc ctc agc tgt ggg gtt gga          1889
Asp Glu Tyr Phe Thr Cys Ser Ser Leu Cys Leu Ser Cys Gly Val Gly
    425                 430                 435 tgt aag aaa agc atg aat cat ggg aag gaa gga gtg cct cat gaa gcc          1937
Cys Lys Lys Ser Met Asn His Gly Lys Glu Gly Val Pro His Glu Ala
440                 445                 450                 455 aag agc cgc tgc aga tac tcc cac cag tat gac aac cga gtg tat acc          1985
Lys Ser Arg Cys Arg Tyr Ser His Gln Tyr Asp Asn Arg Val Tyr Thr
                460                 465                 470 tgc aag gcc tgc tat gag aga ggc gag gaa gtc agt gta gtg ccc aaa          2033
Cys Lys Ala Cys Tyr Glu Arg Gly Glu Glu Val Ser Val Val Pro Lys
            475                 480                 485 aca tct gct tcc act gac tcc ccc tgg atg ggt ctc gca aaa tat gcc          2081
Thr Ser Ala Ser Thr Asp Ser Pro Trp Met Gly Leu Ala Lys Tyr Ala
        490                 495                 500 tgg tct ggg tat gtg atc gaa tgt cct aac tgt ggc gtg gtc tat cgt          2129
Trp Ser Gly Tyr Val Ile Glu Cys Pro Asn Cys Gly Val Val Tyr Arg
    505                 510                 515 agt cgg cag tac tgg ttt gga aac caa gat cct gtg gat acg gtg gtg          2177
Ser Arg Gln Tyr Trp Phe Gly Asn Gln Asp Pro Val Asp Thr Val Val
520                 525                 530                 535 cgg aca gag att gtg cat gtg tgg cct gga act gat ggg ttt ctg aag          2225
Arg Thr Glu Ile Val His Val Trp Pro Gly Thr Asp Gly Phe Leu Lys
                540                 545                 550 gac aac aac aat gct gcc cag cgc ctg ttg gac ggg atg aac ttc atg          2273
Asp Asn Asn Asn Ala Ala Gln Arg Leu Leu Asp Gly Met Asn Phe Met
            555                 560                 565
```

```
                                                          -continued
gct cag tcg gtg tcc gag ctt agc ctt gga ccc acc aag gct gtg act        2321
Ala Gln Ser Val Ser Glu Leu Ser Leu Gly Pro Thr Lys Ala Val Thr
        570                 575                 580 tcc tgg ctg aca gac cag atc gcc cct gcc tac tgg agg ccc aac tcc        2369
Ser Trp Leu Thr Asp Gln Ile Ala Pro Ala Tyr Trp Arg Pro Asn Ser
585                 590                 595 cag att ctg agc tgc aac aag tgt gcg acg tcc ttt aaa gat aac gac        2417
Gln Ile Leu Ser Cys Asn Lys Cys Ala Thr Ser Phe Lys Asp Asn Asp
600                 605                 610                 615 act aag cat cac tgc cga gcc tgt ggg gag ggc ttc tgt gac agc tgt        2465
Thr Lys His His Cys Arg Ala Cys Gly Glu Gly Phe Cys Asp Ser Cys
                620                 625                 630 tca tca aag act cgg cca gtg cct gag cgg ggc tgg ggc cct gcg cca        2513
Ser Ser Lys Thr Arg Pro Val Pro Glu Arg Gly Trp Gly Pro Ala Pro
        635                 640                 645 gtg cgg gtc tgt gac aac tgc tac gaa gcc agg aac gtc cag tta gct        2561
Val Arg Val Cys Asp Asn Cys Tyr Glu Ala Arg Asn Val Gln Leu Ala
            650                 655                 660 gtt acc gag gca caa gtg gac gat gaa ggt gga acg ctc att gct cgg        2609
Val Thr Glu Ala Gln Val Asp Asp Glu Gly Gly Thr Leu Ile Ala Arg
665                 670                 675 aag gtg ggc gag gcc gtg cag aac act ctg gga gcc gtg gtg aca gcc        2657
Lys Val Gly Glu Ala Val Gln Asn Thr Leu Gly Ala Val Val Thr Ala
680                 685                 690                 695 att gac ata cca cta ggt ctg gta aag gac gcg gcc agg cct gcg tac        2705
Ile Asp Ile Pro Leu Gly Leu Val Lys Asp Ala Ala Arg Pro Ala Tyr
                700                 705                 710 tgg gtg cct gac cac gaa atc ctc cac tgc cac aac tgc cgg aag gag        2753
Trp Val Pro Asp His Glu Ile Leu His Cys His Asn Cys Arg Lys Glu
        715                 720                 725 ttc agc atc aag ctc tcc aag cac cac tgc cgg gcc tgc gga cag ggc        2801
Phe Ser Ile Lys Leu Ser Lys His His Cys Arg Ala Cys Gly Gln Gly
            730                 735                 740 ttc tgt gat gag tgc tcc cat gac cgc cgg gct gtt cct tct cgt ggc        2849
Phe Cys Asp Glu Cys Ser His Asp Arg Arg Ala Val Pro Ser Arg Gly
745                 750                 755 tgg gac cat ccc gtc cga gtc tgc ttc aac tgc aat aaa aag ccc ggt        2897
Trp Asp His Pro Val Arg Val Cys Phe Asn Cys Asn Lys Lys Pro Gly
760                 765                 770                 775 gac ctt taa ccccagcccc ctctccgagt ccttcacaat tccttaggtt               2946
Asp Leu ctcagggtta gaaacagtct tgcgaggtag gccctcctcc cagtcacctg ctgtggtgtg     3006
tgtcctctcc tctccgcatc cagggccact ttccctcagt gggggtgagc ctggcggcag     3066
gcccgaaggt gtggacccct cagggcaggg gaccttgcaa cttatcgcaa aggggaatga     3126
acctgaatcc gttgcattta tttcagttaa aaataatgaa tatatatgtg tatatctctc     3186
tctcatatat acatatgaaa ggcactcggg gcgtatcgag gctgctgctg gctgtgaaga     3246
cttcgcacag tctcctccgc acagggtgag gtggcagtgg cagcacgtct tcctcatgag     3306
ccgagccagg tccatggcca ccacgtggct ggcccctttcc tctgctgctc ttggagcctt    3366
ggaagcctct cctgtccttg gctcttccct ccatgcctgt cagctgcctg gggagtgagc     3426
ctccctggtc cttcctgcct gaaacagcct gaagggaatt ctccctaggt ctcctgggag    3486
tcgagtccca attcttggct taagcctgtt ttagtcagag accacccaac ttagcgtgca     3546
ggtcaccgga gtgggtggag ggtcagaggt cgggtcttcg gccctgagaa gtagaaatgc     3606
aggggccgtg ctgtccctgg tcccccaggg aacagcaagg aaggaactga gccttctcca     3666
```

```
gcagggcttc ctgtcccgat gcttgtgtct cca                    3699
```

<210> SEQ ID NO 8
<211> LENGTH: 777
<212> TYPE: PRT
<213> ORGANISM: Homo sapiens

<400> SEQUENCE: 8

```
Met Ser Ala Gln Thr Ser Pro Ala Glu Lys Gly Leu Asn Pro Gly Leu
1               5                   10                  15

Met Cys Gln Glu Ser Tyr Ala Cys Ser Gly Thr Asp Glu Ala Ile Phe
            20                  25                  30

Glu Cys Asp Glu Cys Cys Ser Leu Gln Cys Leu Arg Cys Glu Glu Glu
        35                  40                  45

Leu His Arg Gln Glu Arg Leu Arg Asn His Glu Arg Ile Arg Leu Lys
    50                  55                  60

Pro Gly His Val Pro Tyr Cys Asp Leu Cys Lys Gly Leu Ser Gly His
65                  70                  75                  80

Leu Pro Gly Val Arg Gln Arg Ala Ile Val Arg Cys Gln Thr Cys Lys
                85                  90                  95

Ile Asn Leu Cys Leu Glu Cys Gln Lys Arg Thr His Ser Gly Gly Asn
            100                 105                 110

Lys Arg Arg His Pro Val Thr Val Tyr Asn Val Ser Asn Leu Gln Glu
        115                 120                 125

Ser Leu Glu Ala Glu Glu Met Asp Glu Glu Thr Lys Arg Lys Lys Met
    130                 135                 140

Thr Glu Lys Val Val Ser Phe Leu Leu Val Asp Glu Asn Glu Glu Ile
145                 150                 155                 160

Gln Val Thr Asn Glu Glu Asp Phe Ile Arg Lys Leu Asp Cys Lys Pro
                165                 170                 175

Asp Gln His Leu Lys Val Val Ser Ile Phe Gly Asn Thr Gly Asp Gly
            180                 185                 190

Lys Ser His Thr Leu Asn His Thr Phe Phe Tyr Gly Arg Glu Val Phe
        195                 200                 205

Lys Thr Ser Pro Thr Gln Glu Ser Cys Thr Val Gly Val Trp Ala Ala
    210                 215                 220

Tyr Asp Pro Val His Lys Val Ala Val Ile Asp Thr Glu Gly Leu Leu
225                 230                 235                 240

Gly Ala Thr Val Asn Leu Ser Gln Arg Thr Arg Leu Leu Leu Lys Val
                245                 250                 255

Leu Ala Ile Ser Asp Leu Val Ile Tyr Arg Thr His Ala Asp Arg Leu
            260                 265                 270

His Asn Asp Leu Phe Lys Phe Leu Gly Asp Ala Ser Glu Ala Tyr Leu
        275                 280                 285

Lys His Phe Thr Lys Glu Leu Lys Ala Thr Thr Ala Arg Cys Gly Leu
    290                 295                 300

Asp Val Pro Leu Ser Thr Leu Gly Pro Ala Val Ile Ile Phe His Glu
305                 310                 315                 320

Thr Val His Thr Gln Leu Leu Gly Ser Asp His Pro Ser Glu Val Pro
                325                 330                 335

Glu Lys Leu Ile Gln Asp Arg Phe Arg Lys Leu Gly Arg Phe Pro Glu
            340                 345                 350

Ala Phe Ser Ser Ile His Tyr Lys Gly Thr Arg Thr Tyr Asn Pro Pro
        355                 360                 365
```

-continued

```
Thr Asp Phe Ser Gly Leu Arg Arg Ala Leu Glu Gln Leu Leu Glu Asn
    370                 375                 380
Asn Thr Thr Arg Ser Pro Arg His Pro Gly Val Ile Phe Lys Ala Leu
385                 390                 395                 400
Lys Ala Leu Ser Asp Arg Phe Ser Gly Glu Ile Pro Asp Asp Gln Met
                405                 410                 415
Ala His Ser Ser Phe Phe Pro Asp Glu Tyr Phe Thr Cys Ser Ser Leu
                420                 425                 430
Cys Leu Ser Cys Gly Val Gly Cys Lys Lys Ser Met Asn His Gly Lys
                435                 440                 445
Glu Gly Val Pro His Glu Ala Lys Ser Arg Cys Arg Tyr Ser His Gln
                450                 455                 460
Tyr Asp Asn Arg Val Tyr Thr Cys Lys Ala Cys Tyr Glu Arg Gly Glu
465                 470                 475                 480
Glu Val Ser Val Val Pro Lys Thr Ser Ala Ser Thr Asp Ser Pro Trp
                485                 490                 495
Met Gly Leu Ala Lys Tyr Ala Trp Ser Gly Tyr Val Ile Glu Cys Pro
                500                 505                 510
Asn Cys Gly Val Val Tyr Arg Ser Arg Gln Tyr Trp Phe Gly Asn Gln
    515                 520                 525
Asp Pro Val Asp Thr Val Val Arg Thr Glu Ile Val His Val Trp Pro
530                 535                 540
Gly Thr Asp Gly Phe Leu Lys Asp Asn Asn Asn Ala Ala Gln Arg Leu
545                 550                 555                 560
Leu Asp Gly Met Asn Phe Met Ala Gln Ser Val Ser Glu Leu Ser Leu
                565                 570                 575
Gly Pro Thr Lys Ala Val Thr Ser Trp Leu Thr Asp Gln Ile Ala Pro
                580                 585                 590
Ala Tyr Trp Arg Pro Asn Ser Gln Ile Leu Ser Cys Asn Lys Cys Ala
                595                 600                 605
Thr Ser Phe Lys Asp Asn Asp Thr Lys His His Cys Arg Ala Cys Gly
    610                 615                 620
Glu Gly Phe Cys Asp Ser Cys Ser Ser Lys Thr Arg Pro Val Pro Glu
625                 630                 635                 640
Arg Gly Trp Gly Pro Ala Pro Val Arg Val Cys Asp Asn Cys Tyr Glu
                645                 650                 655
Ala Arg Asn Val Gln Leu Ala Val Thr Glu Ala Gln Val Asp Asp Glu
                660                 665                 670
Gly Gly Thr Leu Ile Ala Arg Lys Val Gly Glu Ala Val Gln Asn Thr
                675                 680                 685
Leu Gly Ala Val Val Thr Ala Ile Asp Ile Pro Leu Gly Leu Val Lys
                690                 695                 700
Asp Ala Ala Arg Pro Ala Tyr Trp Val Pro Asp His Glu Ile Leu His
705                 710                 715                 720
Cys His Asn Cys Arg Lys Glu Phe Ser Ile Lys Leu Ser Lys His His
                725                 730                 735
Cys Arg Ala Cys Gly Gln Gly Phe Cys Asp Glu Cys Ser His Asp Arg
                740                 745                 750
Arg Ala Val Pro Ser Arg Gly Trp Asp His Pro Val Arg Val Cys Phe
                755                 760                 765
Asn Cys Asn Lys Lys Pro Gly Asp Leu
770                 775
```

```
<210> SEQ ID NO 9
<211> LENGTH: 3617
<212> TYPE: DNA
<213> ORGANISM: Homo sapiens
<220> FEATURE:
<221> NAME/KEY: CDS
<222> LOCATION: (41)..(3337)
<223> OTHER INFORMATION:

<400> SEQUENCE: 9
attcaggagc ctccaggagc ccagacacca gccccccacc atg ggc agc aag gag        55
                                            Met Gly Ser Lys Glu
                                            1               5 cgc ttc cac tgg cag agc cac aac gtg aag cag agc ggc gtg gat gac       103
Arg Phe His Trp Gln Ser His Asn Val Lys Gln Ser Gly Val Asp Asp
                10                  15                  20 atg gtg ctt ctt ccc cag atc acc gaa gac gcc att gcc gcc aac ctc       151
Met Val Leu Leu Pro Gln Ile Thr Glu Asp Ala Ile Ala Ala Asn Leu
            25                  30                  35 cgg aag cgc ttc atg gac gac tac atc ttc acc tac atc ggc tct gtg       199
Arg Lys Arg Phe Met Asp Asp Tyr Ile Phe Thr Tyr Ile Gly Ser Val
        40                  45                  50 ctc atc tct gta aac ccc ttc aag cag atg ccc tac ttc acc gac cgt       247
Leu Ile Ser Val Asn Pro Phe Lys Gln Met Pro Tyr Phe Thr Asp Arg
    55                  60                  65 gag atc gac ctc tat cag ggc gcg gcc cag tat gag aat cct ccg cac       295
Glu Ile Asp Leu Tyr Gln Gly Ala Ala Gln Tyr Glu Asn Pro Pro His
70                  75                  80                  85 atc tac gcc ctc acg gac aac atg tac cgg aac atg ctt atc gac tgt       343
Ile Tyr Ala Leu Thr Asp Asn Met Tyr Arg Asn Met Leu Ile Asp Cys
                90                  95                 100 gag aac cag tgt gtc atc att agt gga gag agt gga gct ggg aag aca       391
Glu Asn Gln Cys Val Ile Ile Ser Gly Glu Ser Gly Ala Gly Lys Thr
            105                 110                 115 gtg gca gcc aaa tat atc atg ggc tac atc tcc aag gtg tct ggc gga       439
Val Ala Ala Lys Tyr Ile Met Gly Tyr Ile Ser Lys Val Ser Gly Gly
        120                 125                 130 ggc gag aag gtc cag cac gtc aaa gat atc atc ctg cag tcc aac ccg       487
Gly Glu Lys Val Gln His Val Lys Asp Ile Ile Leu Gln Ser Asn Pro
    135                 140                 145 ctg ctc gag gcc ttc ggc aac gcc aag act gtg cgc aac aac aat tcc       535
Leu Leu Glu Ala Phe Gly Asn Ala Lys Thr Val Arg Asn Asn Asn Ser
150                 155                 160                 165 agc cgc ttt ggc aag tac ttt gag atc cag ttc agc cga ggt ggg gag       583
Ser Arg Phe Gly Lys Tyr Phe Glu Ile Gln Phe Ser Arg Gly Gly Glu
                170                 175                 180 cca gat ggg ggc aag atc tcc aac ttc ttg ctg gag aag tcc cgc gtg       631
Pro Asp Gly Gly Lys Ile Ser Asn Phe Leu Leu Glu Lys Ser Arg Val
            185                 190                 195 gtc atg caa aat gaa aat gag agg aac ttc cac atc tac tac cag ctg       679
Val Met Gln Asn Glu Asn Glu Arg Asn Phe His Ile Tyr Tyr Gln Leu
        200                 205                 210 ctg gaa ggg gcc tcc cag gag caa agg cag aac ctg ggc ctc atg aca       727
Leu Glu Gly Ala Ser Gln Glu Gln Arg Gln Asn Leu Gly Leu Met Thr
    215                 220                 225 ccg gac tac tat tac tac ctc aac caa tcg gac acc tac cag gtg gac       775
Pro Asp Tyr Tyr Tyr Tyr Leu Asn Gln Ser Asp Thr Tyr Gln Val Asp
230                 235                 240                 245 ggc acg gac gac aga agc gac ttt ggt gag act ctg agt gct atg cag       823
Gly Thr Asp Asp Arg Ser Asp Phe Gly Glu Thr Leu Ser Ala Met Gln
                250                 255                 260
```

```
gtt att ggg atc ccg ccc agc atc cag cag ctg gtc ctg cag ctc gtg    871
Val Ile Gly Ile Pro Pro Ser Ile Gln Gln Leu Val Leu Gln Leu Val
            265                 270                 275 gcg ggg atc ttg cac ctg ggg aac atc agt ttc tgt gaa gac ggg aat    919
Ala Gly Ile Leu His Leu Gly Asn Ile Ser Phe Cys Glu Asp Gly Asn
        280                 285                 290 tac gcc cga gtg gag agt gtg gac ctc ctg gcc ttt ccc gcc tac ctg    967
Tyr Ala Arg Val Glu Ser Val Asp Leu Leu Ala Phe Pro Ala Tyr Leu
    295                 300                 305 ctg ggc att gac agc ggg cga ctg cag gag aag ctg acc agc cgc aag   1015
Leu Gly Ile Asp Ser Gly Arg Leu Gln Glu Lys Leu Thr Ser Arg Lys
310                 315                 320                 325 atg gac agc cgc tgg ggc ggg cgc agc gag tcc atc aat gtg acc ctc   1063
Met Asp Ser Arg Trp Gly Gly Arg Ser Glu Ser Ile Asn Val Thr Leu
                330                 335                 340 aac gtg gag cag gca gcc tac acc cgt gat gcc ctg gcc aag ggg ctc   1111
Asn Val Glu Gln Ala Ala Tyr Thr Arg Asp Ala Leu Ala Lys Gly Leu
            345                 350                 355 tat gcc cgc ctc ttc gac ttc ctc gtg gag gcc atc aac cgt gct atg   1159
Tyr Ala Arg Leu Phe Asp Phe Leu Val Glu Ala Ile Asn Arg Ala Met
        360                 365                 370 cag aaa ccc cag gaa gag tac agc atc ggt gtg ctg gac att tac ggc   1207
Gln Lys Pro Gln Glu Glu Tyr Ser Ile Gly Val Leu Asp Ile Tyr Gly
    375                 380                 385 ttc gag atc ttc cag aaa aat ggc ttc gag cag ttt tgc atc aac ttc   1255
Phe Glu Ile Phe Gln Lys Asn Gly Phe Glu Gln Phe Cys Ile Asn Phe
390                 395                 400                 405 gtc aat gag aag ctg cag caa atc ttt atc gaa ctt acc ctg aag gcc   1303
Val Asn Glu Lys Leu Gln Gln Ile Phe Ile Glu Leu Thr Leu Lys Ala
                410                 415                 420 gag cag gag gag tat gtg cag gaa ggc att cgc tgg act cca atc cag   1351
Glu Gln Glu Glu Tyr Val Gln Glu Gly Ile Arg Trp Thr Pro Ile Gln
            425                 430                 435 tac ttc aac aac aag gtc gtc tgt gac ctc atc gaa aac aag ctg agc   1399
Tyr Phe Asn Asn Lys Val Val Cys Asp Leu Ile Glu Asn Lys Leu Ser
        440                 445                 450 ccc cca ggc atc atg agc gtc ttg gac gac gtg tgc gcc acc atg cac   1447
Pro Pro Gly Ile Met Ser Val Leu Asp Asp Val Cys Ala Thr Met His
    455                 460                 465 gcc acg ggc ggg gga gca gac cag aca ctg ctg cag aag ctg cag gcg   1495
Ala Thr Gly Gly Gly Ala Asp Gln Thr Leu Leu Gln Lys Leu Gln Ala
470                 475                 480                 485 gct gtg ggg acc cac gag cat ttc aac agc tgg agc gcc ggc ttc gtc   1543
Ala Val Gly Thr His Glu His Phe Asn Ser Trp Ser Ala Gly Phe Val
                490                 495                 500 atc cac cac tac gct ggc aag gtc tcc tac gac gtc agc ggc ttc tgc   1591
Ile His His Tyr Ala Gly Lys Val Ser Tyr Asp Val Ser Gly Phe Cys
            505                 510                 515 gag agg aac cga gac gtt ctc ttc tcc gac ctc ata gag ctg atg cag   1639
Glu Arg Asn Arg Asp Val Leu Phe Ser Asp Leu Ile Glu Leu Met Gln
        520                 525                 530 acc agt gag cag gcc ttc ctc cgg atg ctc ttc ccc gag aag ctg gat   1687
Thr Ser Glu Gln Ala Phe Leu Arg Met Leu Phe Pro Glu Lys Leu Asp
    535                 540                 545 gga gac aag aag ggg cgc ccc agc acc gcc ggc tcc aag atc aag aaa   1735
Gly Asp Lys Lys Gly Arg Pro Ser Thr Ala Gly Ser Lys Ile Lys Lys
550                 555                 560                 565 caa gcc aac gac ctg gtg gcc aca ctg atg agg tgc aca ccc cac tac   1783
Gln Ala Asn Asp Leu Val Ala Thr Leu Met Arg Cys Thr Pro His Tyr
                570                 575                 580
```

```
atc cgc tgc atc aaa ccc aac gag acc aag cac gcc cga gac tgg gag    1831
Ile Arg Cys Ile Lys Pro Asn Glu Thr Lys His Ala Arg Asp Trp Glu
            585                 590                 595 gag aac aga gtc aag cac cag gtg gaa tac ctg ggc ctg aag gag aac    1879
Glu Asn Arg Val Lys His Gln Val Glu Tyr Leu Gly Leu Lys Glu Asn
        600                 605                 610 atc agg gtg cgc aga gcc ggc ttc gcc tac cgc cgc cag ttc gcc aaa    1927
Ile Arg Val Arg Arg Ala Gly Phe Ala Tyr Arg Arg Gln Phe Ala Lys
    615                 620                 625 ttc ctg cag agg tat gcc att ctg acc ccc gag acg tgg ccg cgg tgg    1975
Phe Leu Gln Arg Tyr Ala Ile Leu Thr Pro Glu Thr Trp Pro Arg Trp
630                 635                 640                 645 cgt ggg gac gaa cgc cag ggc gtc cag cac ctg ctt cgg gcg gtc aac    2023
Arg Gly Asp Glu Arg Gln Gly Val Gln His Leu Leu Arg Ala Val Asn
                650                 655                 660 atg gag ccc gac cag tac cag atg ggg agc acc aag gtc ttt gtc aag    2071
Met Glu Pro Asp Gln Tyr Gln Met Gly Ser Thr Lys Val Phe Val Lys
            665                 670                 675 aac cca gag tcg ctt ttc ctc ctg gag gag gtg cga gag cga aag ttc    2119
Asn Pro Glu Ser Leu Phe Leu Leu Glu Glu Val Arg Glu Arg Lys Phe
        680                 685                 690 gat ggc ttt gcc cga acc atc cag aag gcc tgg cgg cgc cac gtg gct    2167
Asp Gly Phe Ala Arg Thr Ile Gln Lys Ala Trp Arg Arg His Val Ala
    695                 700                 705 gtc cgg aag tac gag gag atg cgg gag gaa gct tcc aac atc ctg ctg    2215
Val Arg Lys Tyr Glu Glu Met Arg Glu Glu Ala Ser Asn Ile Leu Leu
710                 715                 720                 725 aac aag aag gag cgg agg cgc aac agc atc aat cgg aac ttc gtc ggg    2263
Asn Lys Lys Glu Arg Arg Arg Asn Ser Ile Asn Arg Asn Phe Val Gly
                730                 735                 740 gac tac ctg ggg ctg gag gag cgg ccc gag ctg cgt cag ttc ctg ggc    2311
Asp Tyr Leu Gly Leu Glu Glu Arg Pro Glu Leu Arg Gln Phe Leu Gly
            745                 750                 755 aag aag gag cgg gtg gac ttc gcc gat tcg gtc acc aag tac gac cgc    2359
Lys Lys Glu Arg Val Asp Phe Ala Asp Ser Val Thr Lys Tyr Asp Arg
        760                 765                 770 cgc ttc aag ccc atc aag cgg gac ttg atc ctg acg ccc aag tgt gtg    2407
Arg Phe Lys Pro Ile Lys Arg Asp Leu Ile Leu Thr Pro Lys Cys Val
    775                 780                 785 tat gtg att ggg cga gag aaa atg aag aag gga cct gag aag ggc cag    2455
Tyr Val Ile Gly Arg Glu Lys Met Lys Lys Gly Pro Glu Lys Gly Gln
790                 795                 800                 805 gtg tgt gaa gtc ttg aag aag aaa gtg gac atc cag gct ctg cgg gga    2503
Val Cys Glu Val Leu Lys Lys Lys Val Asp Ile Gln Ala Leu Arg Gly
                810                 815                 820 gtc tcc ctc agc acg cga cag gac gac ttc ttc atc ctc caa gag gat    2551
Val Ser Leu Ser Thr Arg Gln Asp Asp Phe Phe Ile Leu Gln Glu Asp
            825                 830                 835 gcc gcc gac agc ttc ctg gag agc gtc ttc aag acc gag ttt gtc agc    2599
Ala Ala Asp Ser Phe Leu Glu Ser Val Phe Lys Thr Glu Phe Val Ser
        840                 845                 850 ctt ctg tgc aag cgc ttc gag gag gcg acg cgg agg ccc ctg ccc ctc    2647
Leu Leu Cys Lys Arg Phe Glu Glu Ala Thr Arg Arg Pro Leu Pro Leu
    855                 860                 865 acc ttc agc gac aca cta cag ttt cgg gtg aag aag gag ggc tgg ggc    2695
Thr Phe Ser Asp Thr Leu Gln Phe Arg Val Lys Lys Glu Gly Trp Gly
870                 875                 880                 885 ggt ggc ggc acc cgc agc gtc acc ttc tcc cgc ggc ttc ggc gac ttg    2743
Gly Gly Gly Thr Arg Ser Val Thr Phe Ser Arg Gly Phe Gly Asp Leu
```

```
                    890                895                900
gca gtg ctc aag gtt ggc ggt cgg acc ctc acg gtc agc gtg ggc gat              2791
Ala Val Leu Lys Val Gly Gly Arg Thr Leu Thr Val Ser Val Gly Asp
                    905                910                915 ggg ctg ccc aag agc tcc aag cct acg cgg aag gga atg gcc aag gga              2839
Gly Leu Pro Lys Ser Ser Lys Pro Thr Arg Lys Gly Met Ala Lys Gly
                920                925                930 aaa cct cgg agg tcg tcc caa gcc cct acc cgg gcg gcc cct gcg ccc              2887
Lys Pro Arg Arg Ser Ser Gln Ala Pro Thr Arg Ala Ala Pro Ala Pro
        935                940                945 ccc aga ggc atg gat cgc aat ggg gtg ccc ccc tct gcc aga ggg ggc              2935
Pro Arg Gly Met Asp Arg Asn Gly Val Pro Pro Ser Ala Arg Gly Gly
950                955                960                965 ccc ctg ccc ctg gag atc atg tct gga ggg ggc acc cac agg cct ccc              2983
Pro Leu Pro Leu Glu Ile Met Ser Gly Gly Gly Thr His Arg Pro Pro
                    970                975                980 cgg ggc cct ccg tcc aca tcc ctg gga gcc agc aga cga ccc cgg gca              3031
Arg Gly Pro Pro Ser Thr Ser Leu Gly Ala Ser Arg Arg Pro Arg Ala
                985                990                995 cgt ccg ccc tca gag cac aac aca gaa ttc ctc aac gtg cct gac                  3076
Arg Pro Pro Ser Glu His Asn Thr Glu Phe Leu Asn Val Pro Asp
            1000                1005                1010 cag ggc atg gcc ggc atg cag agg aag cgc agc gtg ggg caa cgg                  3121
Gln Gly Met Ala Gly Met Gln Arg Lys Arg Ser Val Gly Gln Arg
        1015                1020                1025 cca gtg cct ggt gtg ggc cga ccc aag ccc cag cct cgg aca cat                  3166
Pro Val Pro Gly Val Gly Arg Pro Lys Pro Gln Pro Arg Thr His
    1030                1035                1040 ggt ccc agg tgc cgg gcc cta tac cag tac gtg ggc caa gat gtg                  3211
Gly Pro Arg Cys Arg Ala Leu Tyr Gln Tyr Val Gly Gln Asp Val
    1045                1050                1055 gac gag ctg agc ttc aac gtg aac gag gtc att gag atc ctc atg                  3256
Asp Glu Leu Ser Phe Asn Val Asn Glu Val Ile Glu Ile Leu Met
    1060                1065                1070 gaa gat ccc tcg ggc tgg tgg aag ggc cgg ctt cac ggc cag gag                  3301
Glu Asp Pro Ser Gly Trp Trp Lys Gly Arg Leu His Gly Gln Glu
    1075                1080                1085 ggc ctt ttc cca ggr aac tac gtg gag aag atc tga gctgggcct                    3347
Gly Leu Phe Pro Xaa Asn Tyr Val Glu Lys Ile
    1090                1095 gggatactgc cttctctttc gcccgcctat ctgcctgccg gcctggtggg gagccaggcc            3407
ctgccaatga gagcctcgtt tacctgggct gcaatagcct aaaagtccag tcctttggcc            3467
tccagtcctg cccaggccct gggtcaccag gtcactgctg cagcccccgc ccctgggccc            3527
tggtcttcct ccaacatcac acctgctgcc cattctccat ttctgtgtgt gtcaaagggg            3587
actaacagca gaatctacct cccaactgcc                                             3617

<210> SEQ ID NO 10
<211> LENGTH: 1098
<212> TYPE: PRT
<213> ORGANISM: Homo sapiens
<220> FEATURE:
<221> NAME/KEY: misc_feature
<222> LOCATION: (1092)..(1092)
<223> OTHER INFORMATION: The 'Xaa' at location 1092 stands for Gly.

<400> SEQUENCE: 10

Met Gly Ser Lys Glu Arg Phe His Trp Gln Ser His Asn Val Lys Gln
1               5                   10                  15
```

-continued

```
Ser Gly Val Asp Asp Met Val Leu Leu Pro Gln Ile Thr Glu Asp Ala
         20                  25                  30

Ile Ala Ala Asn Leu Arg Lys Arg Phe Met Asp Asp Tyr Ile Phe Thr
     35                  40                  45

Tyr Ile Gly Ser Val Leu Ile Ser Val Asn Pro Phe Lys Gln Met Pro
 50                  55                  60

Tyr Phe Thr Asp Arg Glu Ile Asp Leu Tyr Gln Gly Ala Ala Gln Tyr
 65                  70                  75                  80

Glu Asn Pro Pro His Ile Tyr Ala Leu Thr Asp Asn Met Tyr Arg Asn
                 85                  90                  95

Met Leu Ile Asp Cys Glu Asn Gln Cys Val Ile Ile Ser Gly Glu Ser
             100                 105                 110

Gly Ala Gly Lys Thr Val Ala Ala Lys Tyr Ile Met Gly Tyr Ile Ser
             115                 120                 125

Lys Val Ser Gly Gly Gly Glu Lys Val Gln His Val Lys Asp Ile Ile
130                 135                 140

Leu Gln Ser Asn Pro Leu Leu Glu Ala Phe Gly Asn Ala Lys Thr Val
145                 150                 155                 160

Arg Asn Asn Asn Ser Ser Arg Phe Gly Lys Tyr Phe Glu Ile Gln Phe
                 165                 170                 175

Ser Arg Gly Gly Glu Pro Asp Gly Gly Lys Ile Ser Asn Phe Leu Leu
             180                 185                 190

Glu Lys Ser Arg Val Val Met Gln Asn Glu Asn Glu Arg Asn Phe His
         195                 200                 205

Ile Tyr Tyr Gln Leu Leu Glu Gly Ala Ser Gln Glu Gln Arg Gln Asn
210                 215                 220

Leu Gly Leu Met Thr Pro Asp Tyr Tyr Tyr Leu Asn Gln Ser Asp
225                 230                 235                 240

Thr Tyr Gln Val Asp Gly Thr Asp Asp Arg Ser Asp Phe Gly Glu Thr
             245                 250                 255

Leu Ser Ala Met Gln Val Ile Gly Ile Pro Pro Ser Ile Gln Gln Leu
         260                 265                 270

Val Leu Gln Leu Val Ala Gly Ile Leu His Leu Gly Asn Ile Ser Phe
     275                 280                 285

Cys Glu Asp Gly Asn Tyr Ala Arg Val Glu Ser Val Asp Leu Leu Ala
 290                 295                 300

Phe Pro Ala Tyr Leu Leu Gly Ile Asp Ser Gly Arg Leu Gln Glu Lys
305                 310                 315                 320

Leu Thr Ser Arg Lys Met Asp Ser Arg Trp Gly Gly Arg Ser Glu Ser
                 325                 330                 335

Ile Asn Val Thr Leu Asn Val Glu Gln Ala Ala Tyr Thr Arg Asp Ala
             340                 345                 350

Leu Ala Lys Gly Leu Tyr Ala Arg Leu Phe Asp Phe Leu Val Glu Ala
         355                 360                 365

Ile Asn Arg Ala Met Gln Lys Pro Gln Glu Glu Tyr Ser Ile Gly Val
     370                 375                 380

Leu Asp Ile Tyr Gly Phe Glu Ile Phe Gln Lys Asn Gly Phe Glu Gln
385                 390                 395                 400

Phe Cys Ile Asn Phe Val Asn Glu Lys Leu Gln Gln Ile Phe Ile Glu
                 405                 410                 415

Leu Thr Leu Lys Ala Glu Gln Glu Glu Tyr Val Gln Glu Gly Ile Arg
             420                 425                 430

Trp Thr Pro Ile Gln Tyr Phe Asn Asn Lys Val Val Cys Asp Leu Ile
```

-continued

```
            435                 440                 445
Glu Asn Lys Leu Ser Pro Pro Gly Ile Met Ser Val Leu Asp Asp Val
450                 455                 460

Cys Ala Thr Met His Ala Thr Gly Gly Gly Ala Asp Gln Thr Leu Leu
465                 470                 475                 480

Gln Lys Leu Gln Ala Ala Val Gly Thr His Glu His Phe Asn Ser Trp
                485                 490                 495

Ser Ala Gly Phe Val Ile His His Tyr Ala Gly Lys Val Ser Tyr Asp
                500                 505                 510

Val Ser Gly Phe Cys Glu Arg Asn Arg Asp Val Leu Phe Ser Asp Leu
                515                 520                 525

Ile Glu Leu Met Gln Thr Ser Glu Gln Ala Phe Leu Arg Met Leu Phe
530                 535                 540

Pro Glu Lys Leu Asp Gly Asp Lys Lys Gly Arg Pro Ser Thr Ala Gly
545                 550                 555                 560

Ser Lys Ile Lys Lys Gln Ala Asn Asp Leu Val Ala Thr Leu Met Arg
                565                 570                 575

Cys Thr Pro His Tyr Ile Arg Cys Ile Lys Pro Asn Glu Thr Lys His
                580                 585                 590

Ala Arg Asp Trp Glu Glu Asn Arg Val Lys His Gln Val Glu Tyr Leu
595                 600                 605

Gly Leu Lys Glu Asn Ile Arg Val Arg Arg Ala Gly Phe Ala Tyr Arg
610                 615                 620

Arg Gln Phe Ala Lys Phe Leu Gln Arg Tyr Ala Ile Leu Thr Pro Glu
625                 630                 635                 640

Thr Trp Pro Arg Trp Arg Gly Asp Glu Arg Gln Gly Val Gln His Leu
                645                 650                 655

Leu Arg Ala Val Asn Met Glu Pro Asp Gln Tyr Gln Met Gly Ser Thr
                660                 665                 670

Lys Val Phe Val Lys Asn Pro Glu Ser Leu Phe Leu Leu Glu Glu Val
                675                 680                 685

Arg Glu Arg Lys Phe Asp Gly Phe Ala Arg Thr Ile Gln Lys Ala Trp
690                 695                 700

Arg Arg His Val Ala Val Arg Lys Tyr Glu Glu Met Arg Glu Glu Ala
705                 710                 715                 720

Ser Asn Ile Leu Leu Asn Lys Lys Glu Arg Arg Asn Ser Ile Asn
                725                 730                 735

Arg Asn Phe Val Gly Asp Tyr Leu Gly Leu Glu Glu Arg Pro Glu Leu
                740                 745                 750

Arg Gln Phe Leu Gly Lys Lys Glu Arg Val Asp Phe Ala Asp Ser Val
                755                 760                 765

Thr Lys Tyr Asp Arg Arg Phe Lys Pro Ile Lys Arg Asp Leu Ile Leu
770                 775                 780

Thr Pro Lys Cys Val Tyr Val Ile Gly Arg Glu Lys Met Lys Lys Gly
785                 790                 795                 800

Pro Glu Lys Gly Gln Val Cys Glu Val Leu Lys Lys Val Asp Ile
                805                 810                 815

Gln Ala Leu Arg Gly Val Ser Leu Ser Thr Arg Gln Asp Asp Phe Phe
                820                 825                 830

Ile Leu Gln Glu Asp Ala Ala Asp Ser Phe Leu Glu Ser Val Phe Lys
                835                 840                 845

Thr Glu Phe Val Ser Leu Leu Cys Lys Arg Phe Glu Glu Ala Thr Arg
850                 855                 860
```

```
Arg Pro Leu Pro Leu Thr Phe Ser Asp Thr Leu Gln Phe Arg Val Lys
865             870                 875                 880

Lys Glu Gly Trp Gly Gly Gly Thr Arg Ser Val Thr Phe Ser Arg
            885                 890                 895

Gly Phe Gly Asp Leu Ala Val Leu Lys Val Gly Gly Arg Thr Leu Thr
                900             905                 910

Val Ser Val Gly Asp Gly Leu Pro Lys Ser Ser Lys Pro Thr Arg Lys
            915                 920             925

Gly Met Ala Lys Gly Lys Pro Arg Arg Ser Ser Gln Ala Pro Thr Arg
        930             935             940

Ala Ala Pro Ala Pro Pro Arg Gly Met Asp Arg Asn Gly Val Pro Pro
945             950             955                 960

Ser Ala Arg Gly Gly Pro Leu Pro Leu Glu Ile Met Ser Gly Gly Gly
                965             970                 975

Thr His Arg Pro Pro Arg Gly Pro Pro Ser Thr Ser Leu Gly Ala Ser
            980             985                 990

Arg Arg Pro Arg Ala Arg Pro Pro  Ser Glu His Asn Thr  Glu Phe Leu
        995             1000                 1005

Asn Val  Pro Asp Gln Gly Met  Ala Gly Met Gln Arg  Lys Arg Ser
    1010                 1015                 1020

Val Gly  Gln Arg Pro Val Pro  Gly Val Gly Arg Pro  Lys Pro Gln
    1025                 1030                 1035

Pro Arg  Thr His Gly Pro Arg  Cys Arg Ala Leu Tyr  Gln Tyr Val
    1040                 1045                 1050

Gly Gln  Asp Val Asp Glu Leu  Ser Phe Asn Val Asn  Glu Val Ile
    1055                 1060                 1065

Glu Ile  Leu Met Glu Asp Pro  Ser Gly Trp Trp Lys  Gly Arg Leu
    1070                 1075                 1080

His Gly  Gln Glu Gly Leu Phe  Pro Xaa Asn Tyr Val  Glu Lys Ile
    1085                 1090                 1095
```

IMMOBILIZED PHOSPHATIDIC ACID PROBE

This application is a 371 of PCT/GB01/03791 on Aug. 23, 2001, which is hereby incorporated by reference.

FIELD OF THE INVENTION

The invention relates to a solid support reagent to detect the presence or expression level of proteins in biomedical research. The invention relates to probes which can be used to identify important proteins for signal transduction, housekeeping and diagnosis.

BACKGROUND TO THE INVENTION

Phosphatidic acid (PA) synthesised via the glycerol-3-phosphate or the dihydroxyacetone phosphate pathway is an important intermediate in the biosynthesis of glycerophospholipids and triacylglycerols [Athenstaedt and Daum, Eur. J. Biochem. 266: 1-16 (1999)]. In addition, because PA can be produced from hydrolysis of phosphatidylcholine (PC) by phospholipase D (PLD), it is recently attracting considerable interest as a potential second messenger. This hypothesis is based on the observation that many agonists cause PLD-activation (and thus PA formation) in a variety of cell types and tissues to regulate many cellular pathways including secretion, respiratory burst, calcium influx, mitosis, etc [Exton, Biochimica et Biophysica Acta 1439: 121-133 (1999)]. If PA is indeed a second messenger, it would be expected to interact specifically with a certain class of cellular proteins. However, the identification of such proteins has not been achieved to date in a systematic approach, and would be extremely complicated by conventional methods for the following reasons:

1. PA is unstable in cells since it is rapidly dephosphorylated to give diacylglycerol [Hodgin et al. TIBS 23: 200-204 (1998)].
2. Free PA (both synthetic or from biological origin) is difficult to handle due to its poor solublity in aqueous media. Extensive sonication to obtain liposomes is hence required. (Pure naturally-occurring or synthetic PA is difficult to solubilise in vitro, requiring either organic solvents or extensive sonication to produce liposomes).
3. Even if PA were reconstituted into liposomes, it would be impossible to identify detergent-extracted PA-binding proteins (vide infra) since the detergent used would destroy the integrity of the liposome structure.

SUMMARY OF THE INVENTION

To overcome the above problems, and to identify the class of proteins which bind PA, we have invented an immobilised PA derivative attached onto a solid support. An example is illustrated in Formula I. The preferred stereochemistry is shown in Formula II. Our invention can become an important research tool in fundamental research and it will provide unique opportunities in the fields of diagnostics and drug discovery. In the following description we use the terms "PA resin" and "PA bead" to refer to the immobilised phosphatidic acid derivative probes of this invention.

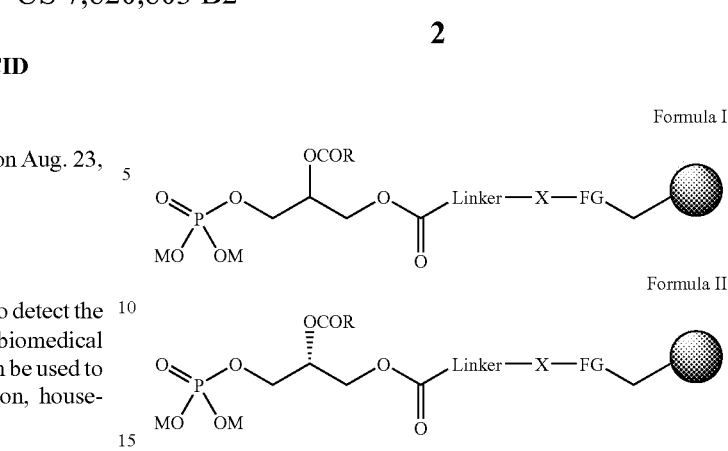

A further embodiment is illustrated in Formula III. The preferred stereochemistry is shown in Formula IV.

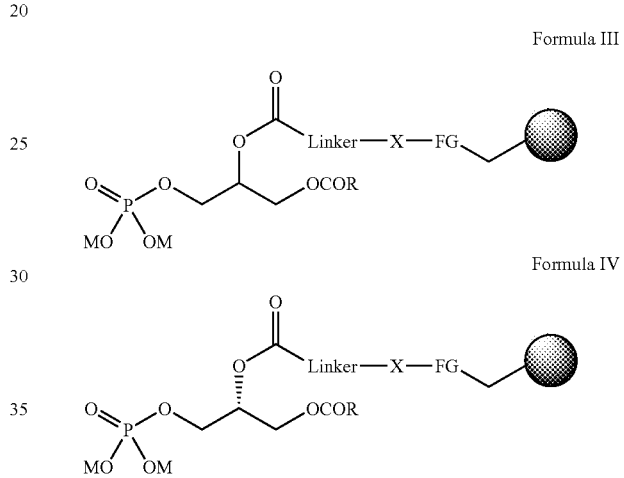

The invention covers phosphatidic acid functionalised solid supports of the general formula as is depicted in Formulae I, II, III and IV and includes the following characteristics:

The linker consists of aryl, heteroaryl, alkyl with possible heteroatoms and/or unsaturations, preferably chains of $(CH_2)_n$, with n=8-20, most preferably n=11. The heteroatom X maybe O, S, or, most preferably NH. The functional group (FG) is a carbonyl from a carboxylate (thiolo)ester, or, most preferably an amide. The R-substituent at the sn2-position or sn-position of the sn-glycerol-3-phosphate derivative carries an aryl, alkyl group, or a combination, preferably $R=C_mH_{2m+1}$, m=8-20, m=16 is optimal. Unsaturations are allowed, such as in an arachidonyl side chain. It is preferred that the diacyl glycerol is based on the sn-glycerol-3-phosphate family, as in the natural series. Alternatively, the diacyl glycerol may be based on the enantiomeric sn-glycerol-1-phosphate family, or a racemic mixture may be used. The phosphate head groups maybe substituted by phosphonic acid or thiono phosphate. The ion M represents any cation, preferably $Na^+$, $NH_4^+$. The solid support with the attachment to the functional group is illustrated as:

Any suitable covalent attachment may link the solid support to the functional group. It is to be noted that this symbolic illustration is not to be interpreted as representing solely a —$CH_2$— linkage between the functional group and the solid support. The nature of the solid supports is limited to those which swell in water, such as agarose, sepharose, PEG based resins.

Examples of probes covered by these general formulae are shown in Table 2.

In a further embodiment the PA-functionalised solid support maybe modified to carry photoaffinity labels such as aryl azides, α-halo-carbonyl compounds, diaryl ketones, etc. for mapping the binding pocket. Specifically, a $^{125}$I-labeled azido salicylate (Pierce product catalogue, 2000) could be attached through an α-amide linkage at the sn2-position of the sn-glycerol-3-phosphate derivative. After incubation with a specific PA-binding protein, photolysis, hydrolysis of the acyl glycerol bonds, and PAGE analysis of the tryptic digests, information about the radio-labelled binding sequence may be obtained.

Yet another embodiment involves attachment of fluorescent reporter groups in the carboxyl side chain ester attached to the sn2-alkoxy substituent of the sn-glycerol-3-phosphate derivative (Formulae I or II) or to the carboxyl side chain ester attached to the sn-1 position of the sn-glycerol-3-phosphate derivative (Formulae III or IV) to obtain binding affinities.

The specificity of the PA resin for tissue culture extracts may be influenced by the nature of detergent used.

Currently, our preferred surfactant is a non-ionic surfactant NP-40, which is commercially available and is similar to TRITON (RTM) X-100 (which is polyoxyethylene (9.5 average) p-t-octylphenol). We believe that the inclusion of a non-ionic surfactant aids and/or maintains the specificity of the probe for PA.

The linker has the function of affecting the way that the phosphatidic "head group" is presented (e.g. for recognition and binding by a specific protein). The choice of linker may be made so as either to mimic the "natural" presentation of the head group as it would occur at a lipid membrane surface, or alternatively the linker may be chosen deliberately so as to result in a non-natural presentation. Those skilled in the art will recognise that since there are many (about 50) possible different types of PA in a cell, the ability to manipulate the linker of the PA resin of the invention can provide useful benefit.

With regard to the stereocentre of the diacyl glycerol, it is to be noted that the stereochemistry in the natural series is based on sn-glycerol-3-phosphate (Formula II, IV). Under certain circumstances it might be desirable to have the chiral carbon in a non-natural stereochemistry (or enantiomeric, as allowed by Formla I or III, based on sn-glycerol-1-phosphate) as this might give interesting/useful effects on the binding and/or specificity of PA.

With regard to the phosphate head group, it may be desirable to make a substitution (as described, above), for example in order to protect the group from hydrolysis. It is to be noted that substitution by e.g. phosphoric acid or thiono phosphate would render the head group resistant to hydrolysis by endogenous or added hydrolase.

In other embodiments of the invention, other derivatives of phosphatidic acid are attached onto a solid support to provide probes of the invention. Such derivatives include phosphoinositides such as (D)-Ptd Ins (3,4,5) $P_3$ ($PIP_3$), (D)-Ptd Ins (3,4) $P_2$ ($PIP_2$), (D)-Ptd Ins (3,5) $P_2$ ($PIP_2$), (D)-Ptd Ins (4,5) $P_2$ ($PIP_2$), and (D)-Ptd Ins (3) P (PIP) (collectively referred to as $PIP_n$'s,—see FIG. 3), or analogues thereof. Examples are shown in Table 3. Immobilised $PIP_n$'s or their analogues can be used to identify $PIP_n$ binding proteins.

The immobilised PA-derivative or phosphoinositide may be non-covalently or covalently attached onto the solid support. Where the PA-derivative or phosphoinositide is non-covalently attached it is preferred that the strength of the non-covalent attachment is such that it is not disrupted under conditions in which a protein may be bound specifically to the probe. A suitable binding energy is greater than that of thiol for gold (i.e. greater than about 200 KJ/mole).

Rao et al (*JBC* 1999, 274 (53), 37893-37900) reports avidin-coated beads pre-bound to biotinylated PtdIns-3,4-$P_2$ and PtdIns-3,4,5-$P_3$, as shown in FIG. 1 on page 37894 of that document.

We have appreciated that phosphoinositides other than PtdIns-3,4-$P_2$ and PtdIns-3,4,5-$P_3$ may be non-covalently immobilised onto a solid support to provide probes for use in identifying binding proteins for those phosphoinositides. For example, any of the free phosphoinositides shown in Table 3, or functional analogues thereof may be non covalently attached onto a solid support.

It is preferred, however, that a PA-derivative or phosphoinositide is covalently attached onto the solid support. A disadvantage of non covalent attachment is that the non covalent interaction is disrupted under conditions required to remove proteins bound to the solid support. Thus, the solid support cannot be reused after an analysis of protein binding has been performed. This can add significantly to the cost of performing experiments, particularly where more expensive solid supports are used, such as agarose beads.

Covalent attachment of inositol 1,4,5-trisphosphate ($IP_3$) to Affi-Gel 10 resin has been described by Prestwich et al 1991 (*Am. Chem. Soc.* 1991, 113, 1822-1825). This document discloses attachment of the 1-O-(3-aminopropyl)ester of inositol 1,4,5-trisphosphate ($IP_3$) to resin (as shown in Scheme I, compound 1c, on page 1823 of the document) and use of the resulting bioaffinity matrix to purity the known $IP_3$ receptor ($IP_3R$). Note that $IP_3$ is not a "phosphoinositide".

Shirai et al (Biochim. Biophys. Acta 1998, 1402, 292-302) discloses attachment of a PI 3,4,5-$P_3$ analogue ($PIP_3$-APB, as shown in FIG. 1 on page 294 of the document) to Affi-Gel 10 beads and their use to purify $PIP_3$ binding proteins.

In one aspect of the invention phosphoinositides other than $PIP_3$-APB may be attached onto a solid support. Preferably the attachment is covalent. Suitable examples are shown in Table 3.

Probes of the invention may be used to identify PA binding proteins or phosphoinositide binding proteins. In order to efficiently identify such proteins, it is advantageous if the probes can bind proteins which are present in relatively low abundance and/or proteins which have relatively low PA or phosphoinositide affinity. We believe that key factors in binding of relatively low abundance and/or low affinity proteins are: the part of the PA-derivative or phosphoinositide which is covalently linked to the solid support; the physical characteristics of the linkage; and the nature of the groups at the sn1-, and sn2-positions of the sn-glycerol-3-phosphate derivative.

In particular, it is thought that attachment of the PA-derivative or phosphoinositide via a long-chain fatty acid side chain of the molecule to the solid support ensures that the head group of the PA-derivative or phosphoinositol is available for binding by a PA-binding or phosphoinositide-binding protein. It is believed that this arrangement mimics cellular PA or phosphoinositide. It is thought that the length of the linkage between the head group and the solid support should not be too short, otherwise the solid support may sterically interfere with binding. The presence of a fatty acid side chain, and especially a long-chain fatty acid, at the sn1-position and/or the sn2-position position of the sn-glycerol-3-phosphate derivative is thought to be required for optimal binding by PA/phosphoinositide binding proteins. Suitable length fatty acid side chains are 8-20 carbon atoms in length, unsaturations being allowed. Fatty acid side chains with 17 carbon atoms (including the ester carbon) are preferred at the sn2-position of the sit-glycerol-3-phosphate derivative, and fatty acid side chains with 12 carbon atoms (including the ester carbon) are preferred at the sn1-position of the sn-glycerol-3-phosphate derivative, as these lengths are thought to best mimic cellular PA/phosphoinositide.

Our results show that probes of the invention with suitable length fatty acid side chains specifically bind several proteins (see for example Table 1). It is believed that such probes can be used to detect many more phosphoinositide binding proteins than the $PIP_3$-APB beads described by Shirai et al.

Examples of embodiments of the invention in which a phosphoinositide is covalently attached onto a solid support are shown in general Formulae V and VI:

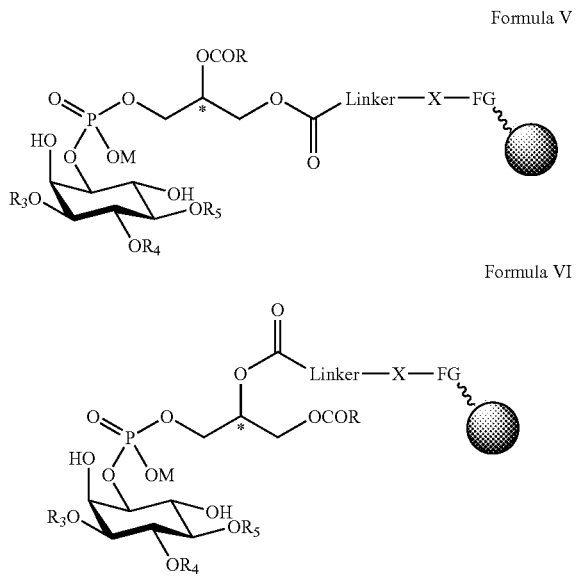

Formula V

Formula VI where:
R=aryl, alkyl group, or a combination, preferably $R=C_mH_{2m+1}$,
m=8-20, m=16 is optimal.
$R_3=P(O)(OM)_2$; $R_4=H$; $R_5=H$ (PI(3)P);
$R_3=H$; $R_4=P(O)(OM)_2$; $R_5=H$ (PI(4)P);
$R_3=H$; $R_4=H$; $R_5=P(O)(OM)_2$ (PI(5)P);
$R_3=P(O)(OM)_2$; $R_4=P(O)(OM)_2$; $R_5=H$ (PI(3,4)$P_2$);
$R_3=P(O)(OM)_2$; $R_4=H$; $R_5=P(O)(OM)_2$ (PI(3,5)$P_2$);
$R_3=H$; $R_4=P(O)(OM)_2$; $R_5=P(O)(OM)_2$ (PI(4,5)$P_2$); or
$R_3=P(O)(OM)_2$; $R_4=P(O)(OM)_2$; $R_5=P(O)(OM)_2$ (PI(3,4,5)$P_3$).

M=any cation, preferably $Na^+$, $NH4^+$
*Denotes a stereogenic centre. More preferably a stereogenic centre with an R absolute configuration.
Linker=aryl, heteroaryl, alkyl with possible heteroatoms and/or unsaturations. Preferably chains of $(CH_2)_n$ with n=8-20, most preferably n=11.
X=O, S, or, most preferably NH.
FG=Carbonyl from a carboxylate, thiolo(ester), or, most preferably an amide.
Unsaturations are allowed, such as in an arachidonyl side chain.

=solid support with attachment to functional group. Any suitable covalent attachment may link the solid support to the functional group. Suitable solid supports are organic polymeric supports. Preferred solid supports are those which swell in water, such as agarose, sepharose, PEG based resins. Affi-Gel 10 and Affi-Gel 15 (Bio-Rad) are preferred examples.

Examples of probes covered by these general formulae are shown in Table 3.

It is to be noted that one or more of the free OH groups on the inositol ring of formulae V, VI, VII, VIII (and formulae V', VI', VII', VIII', V''', VI''', VII''', VIII''', see below) could be O-alkyl, or O-aryl derivatives or heteroatom analogues (examples of heteroatoms being S, N, P). One or more of the phosphate esters in formulae V, VI, VII, VIII (and formulae V', VI', VII', VIII', V''', VI''', VII''', VIII''', see below) could be replaced by a thionophosphate, or a phosphinic acid derivative or a phosphonic acid derivative.

It may be that effective protein binding to probes of the invention may be achieved where the optimum length of the linker attached to the sn1-, or sn-2position of the sn-glycerol-3-phosphate derivative is reduced, but a longer attachment to the solid support is used. This is expected to occur in cases where a protein recognises the head group of the PA-derivative or phosphoinositide, substantially independently of the identity of the fatty acid side chains (or other groups attached to the sn1-, and sn2-positions of the sn-glycerol-3-phosphate derivative), but is sterically inhibited from binding unless the head group is at least a certain distance from the solid support. Suitable probes are provided according to General formulae VII and VIII:

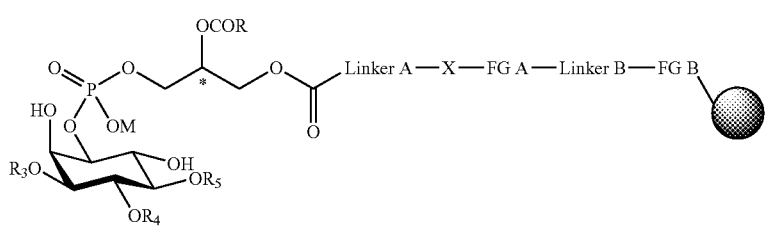

Formula VII

-continued

Formula VIII

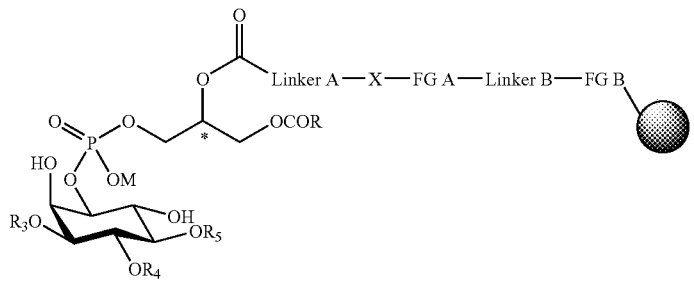

Where:
R=aryl, alkyl group, or a combination, preferably R=$C_mH_{2m+1}$, m=8-20, m=16 is optimal.
$R_3$=P(O)(OM)$_2$; $R_4$=H; $R_5$=H (PI(3)P);
$R_3$=H; $R_4$=P(O)(OM)$_2$; $R_5$=H (PI(4)P);
$R_3$=H; $R_4$=H; $R_5$=P(O)(OM)$_2$ (PI(5)P);
$R_3$=P(O)(OM)$_2$; $R_4$=P(O)(OM)$_2$; $R_5$=H (PI(3,4)P$_2$);
$R_3$=P(O)(OM)$_2$; $R_4$=H; $R_5$=P(O)(OM)$_2$ (PI(3,5)P$_2$);
$R_3$=H; $R_4$=P(O)(OM)$_2$; $R_5$=P(O)(OM)$_2$ (PI(4,5)P$_2$); or
$R_3$=P(O)(OM)$_2$; $R_4$=P(O)(OM)$_2$; $R_5$=P(O)(OM)$_2$ (PI(3,4,5)P$_3$).
M=any cation, preferably Na$^+$, NH4$^+$
*Denotes a stereogenic centre. More preferably a stereogenic centre with an R absolute configuration.
X=O, S, or, most preferably NH.
FG A=Carbonyl from a carboxylate, thiolo(ester), or, most preferably an amide.
Linker A=aryl, heteroaryl, alkyl with possible heteroatoms and/or unsaturations. Preferably chains of (CH$_2$)$_n$.
Linker B=aryl, heteroaryl, alkyl with possible heteroatoms and/or saturations.
These could be any atoms, more preferably C, N, O, S, more preferably still methylene groups linked via amide and ester bonds.
Preferably the total length of linker A and linker B is 8-60 atoms, more preferably 19-31 atoms, most preferably 22 atoms.
FG B=Amide, thiolo(ester), or, most preferably ester.
Unsaturations are allowed, such as in an arachidonyl side chain.

=solid support with attachment to functional group.

It will be appreciated that equivalent structures may be provided for general formulae I-IV.

There is also provided according to the invention use of a probe of the invention to bind a binding partner of the Phosphatidic Acid derivative or phosphoinositide attached onto the solid support. Preferably the binding partner is a protein.

A probe of the invention may be used for testing the PA/PIPn-binding and/or affinity of a protein.

The invention provides an assay method which involves the step of detecting and/or measuring the binding of a probe of the invention when said probe is exposed to a protein in a test sample. Such an assay may involve the steps of identifying and/or isolating said protein by binding to said probe. Said probe may be used to detect/measure/identify and/or isolate more than one type of PA and/or PIPn binding protein from a test sample containing many proteins. More than one type of probe may be used to detect/measure/identifying and/or isolate more than one type of PA and/or PIPn binding protein. The test sample may be a tissue or tissue culture extract, preferably a lysed extract. The test sample may be obtained by lysis of cells in a buffer containing at least one non-ionic surfactant, such as TRITON (RTM) X-100 or NP-40. The probe may be exposed to said test sample in the presence or absence of soluble PA and/or PIPn. Protein-probe binding may be compared between more than one test sample to determine PA-binding protein and/or PIPn binding protein variation between said samples.

There is also provided: use of an assay method of the invention to detect/measure/identify and/or isolate a PA-binding protein and/or a PIPn-binding protein in a test sample; use of an assay method of the invention to detect and/or measure the ability of an agent, applied to said PA-binding protein-containing and/or PIPn-binding protein-containing test sample, to agonise or antagonise protein-probe binding; use of an assay method of the invention to detect and/or measure the ability of an agent, applied to said probe, to agonise or antagonise protein-probe binding.

The invention further provides a PA-binding protein or a PIPn-binding protein detected/measured/identified and/or isolated by an assay method of the invention, and an agent capable of agonising or antagonising protein-probe binding detected and/or measured by use of an assay method of the invention.

In a further aspect of the invention, a probe of the invention coupled to scintillant may be used to identify an agonist or antagonist of the interaction of a PA/PIPn-binding protein with PA or PIPn. Such uses are particularly suited for high throughput screening of candidate agonists/antagonists, especially single step high throughput screening. A radiolabelled protein (radiolabelled for example with tritiated leucine, or $^{35}$S-methionine) known to bind PA or PIPn is tested for binding to a probe of the invention coupled to scintillant in the presence and absence of one or more candidate agonists and/or antagonists. The advantage of using probe coupled to scintillant is that the difference in signal obtained between normal binding (i.e. in a control sample without any candidate antagonist or agonist) of PA or PIPn binding protein to the probe and reduced or enhanced binding (i.e. in samples with agonist or antagonist) is much greater than can be obtained without the scintillant. Consequently, agonists and antagonists can be more readily identified. A similar strategy but using fluorescence detection can be envisaged, with the probe and the protein containing fluorophores of different excitation.

There is also provided according to the invention a method of making a probe which comprises attaching a Phosphatidic Acid derivative onto a solid support. A suitable comprises reacting a compound of formula I', II', III', or IV':

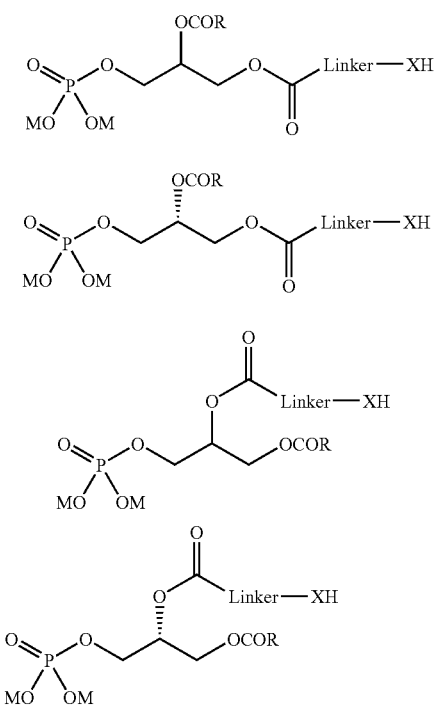

Formula I'

Formula II'

Formula III'

Formula IV' with

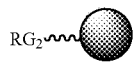

in which:
(a) the linker consists of aryl, heteroaryl, alkyl with possible heteroatoms and/or unsaturations, preferably chains of $(CH_2)_n$, with n=8-20, most preferably n=11;
(b) the R-substituent carries an aryl, alkyl group, or a combination, preferably $R=C_mH_{2m+1}$, m=8-20, m=16 is optimal;
(c) the ion M represents any cation, preferably $Na^+$, $NH4^+$;
(d) unsaturations are allowed, such as in an arachidonyl side chain;
X=NH,O,S
$RG_2$=a reactive group capable of reaction with XH, e.g. N-hydroxy-succinimide-activated carboxylate

=solid support with attachment to $RG_2$.

Such methods may further comprises deprotecting a compound of formula I'', II'', III'', or IV''' to form the compound of formula I', II', III', or IV':

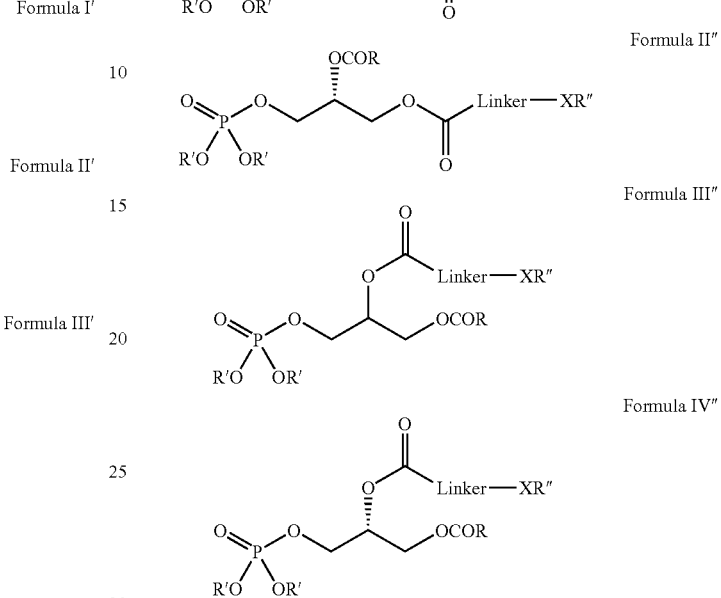

Formula I''

Formula II''

Formula III''

Formula IV'' where:
(a) the linker consists of aryl, heteroaryl, alkyl with possible heteroatoms and/or unsaturations, preferably chains of $(CH_2)_n$, with n=8-20, most preferably n=11;
(b) the heteroatom X maybe O, S, or, most preferably NH;
(c) the R-substituent carries an aryl, alkyl group, or a combination, preferably $R=C_mH_{2m+1}$, m=8-20, m=16 is optimal;
(d) unsaturations are allowed, such as in an arachidonyl side chain;
(e) R'=any suitable protecting group, preferably Bn; trialkyl silyl; $CNCH_2CH_2$—
(f) R''=any suitable protecting group, preferably Fmoc; CBz, when X is NH Examples of compounds of formulae I' or II' are shown in Table 2.

There is also provided a method of making a probe which comprises attaching a phosphoinositide onto a solid support. A suitable method comprises reacting a compound of formula V' or VI':

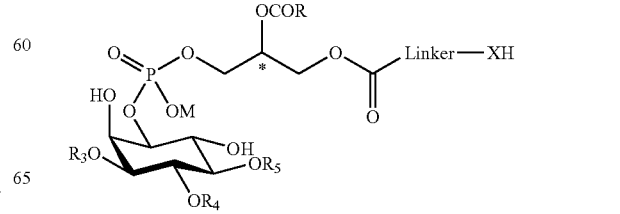

Formula V'

-continued

Formula VI'

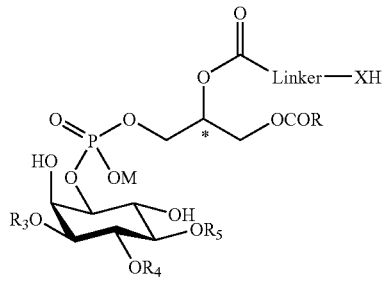

where: R=aryl, alkyl group, or a combination, preferably R=$C_mH_{2m+1}$,
  m=8-20, most preferably m=16 is optimal.
  $R_3$=P(O)(OM)$_2$; $R_4$=H; $R_5$=H (PI(3)P);
  $R_3$=H; $R_4$=P(O)(OM)$_2$; $R_5$=H (PI(4)P);
  $R_3$=H; $R_4$=H; $R_5$=P(O)(OM)$_2$ (PI(5)P);
  $R_3$=P(O)(OM)$_2$; $R_4$=P(O)(OM)$_2$; $R_5$=H (PI(3,4)P$_2$);
  $R_3$=P(O)(OM)$_2$; $R_4$=H; $R_5$=P(O)(OM)$_2$ (PI(3,5)P$_2$);
  $R_3$=H; $R_4$=P(O)(OM)$_2$; $R_5$=P(O)(OM)$_2$ (PI(4,5)P$_2$); or
  $R_3$=P(O)(OM)$_2$; $R_4$=P(O)(OM)$_2$; $R_5$=P(O)(OM)$_2$ (PI(3,4,5)P$_3$).
M=any cation, preferably Na$^+$, NH4$^+$
*Denotes a stereogenic centre. More preferably a stereogenic centre with an R absolute configuration.
Linker=aryl, heteroaryl, alkyl with possible heteroatoms and/or unsaturations. Preferably chains of (CH$_2$)$_n$ with n=8-20, most preferably n=11.
X=NH, O, S
Unsaturations are allowed, such as in an arachidonyl side chain.
  with

where

=solid support with attachment to RG$_2$.
RG$_2$=a reactive group capable of reaction with XH, e.g. N-hydroxy-succinimide-activated carboxylate
A further suitable method comprises reacting a compound of formula VII' or VIII':

Formula VII'

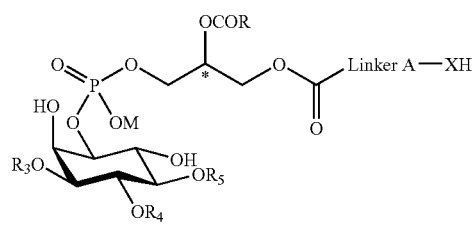

-continued

Formula VIII'

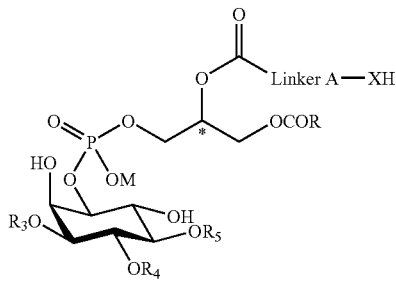

Where:
  R=aryl, alkyl group, or a combination, preferably R=$C_mH_{2m+1}$,
  m=8-20, most preferably m=16 is optimal.
  $R_3$=P(O)(OM)$_2$; $R_4$=H; $R_5$=H (PI(3)P);
  $R_3$=H; $R_4$=P(O)(OM)$_2$; $R_5$=H (PI(4)P);
  $R_3$=H; $R_4$=H; $R_5$=P(O)(OM)$_2$ (PI(5)P);
  $R_3$=P(O)(OM)$_2$; $R_4$=P(O)(OM)$_2$; $R_5$=H (PI(3,4)P$_2$);
  $R_3$=P(O)(OM)$_2$; $R_4$=H; $R_5$=P(O)(OM)$_2$ (PI(3,5)P$_2$);
  $R_3$=H; $R_4$=P(O)(OM)$_2$; $R_5$=P(O)(OM)$_2$ (PI(4,5)P$_2$); or
  $R_3$=P(O)(OM)$_2$; $R_4$=P(O)(OM)$_2$; $R_5$=P(O)(OM)$_2$ (PI(3,4,5)P$_3$).
M=any cation, preferably Na$^+$, NH4$^+$
*Denotes a stereogenic centre. More preferably a stereogenic centre with an R absolute configuration.
Linker A=aryl, heteroaryl, alkyl with possible heteroatoms and/or unsaturations. Preferably chains of (CH$_2$)$_n$.
X=NH, O, S
Unsaturations are allowed, such as in an arachidonyl side chain.
  with RG$_2$
|
Linker B—FG B Linker B=Aryl, heteroaryl, alkyl with possible heteroatoms and/or unsaturations. These could be any atoms, more preferably C, N, O, S, more preferably still methylene groups linked via amide ester bonds.
Preferably the total length of linker A and linker B is 8-60 atoms, more preferably 19-31 atoms, most preferably 22 atoms.
FG B=Amide, thiolo(ester), or most preferably ester

=solid support with attachment to FG B
RG$_2$=a reactive group capable of reaction with XH, e.g. N-hydroxy-succinimide-activated carboxylate
Such methods may further comprise deprotecting a compound or formula V", VI", VII", or VIII" to form the compound of formula V', VI', VII' or VIII':

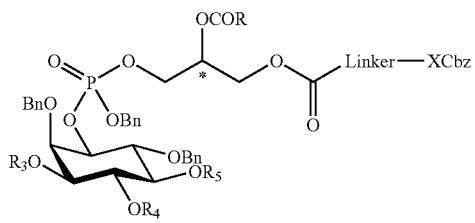

Formula V″

Formula VI″ where:

R=aryl, alkyl group, or a combination, preferably R=$C_mH_{2m+1}$, m=8-20, most preferably m=16 is optimal.

$R_3$=P(O)(OBn)$_2$; $R_4$=H; $R_5$=H (PI(3)P);

$R_3$=H; $R_4$=P(O)(OBn)$_2$; $R_5$=H (PI(4)P);

$R_3$=H; $R_4$=H; $R_5$=P(O)(OBn)$_2$ (PI(5)P);

$R_3$=P(O)(OBn)$_2$; $R_4$=P(O)(OBn)$_2$; $R_5$=H (PI(3,4)P$_2$);

$R_3$=P(O)(OBn)$_2$; $R_4$=H; $R_5$=P(O)(OBn)$_2$ (PI(3,5)P$_2$);

$R_3$=H; $R_4$=P(O)(OBn)$_2$; $R_5$=P(O)(OBn)$_2$ (PI(4,5)P$_2$); or $R_3$=P(O)(OBn)2; $R_4$=P(O)(OBn)$_2$; $R_5$=P(O)(OBn)$_2$ (PI(3,4,5)P$_3$).

*Denotes a stereogenic centre. More preferably a stereogenic centre with an R absolute configuration.

Linker=Aryl, heteroaryl, alkyl with possible heteroatoms and/or unsaturations. Preferably chains of (CH$_2$)$_n$ with n=8-20, most preferably n=11.

X=O, S, or, most preferably NH.

Unsaturations are allowed, such as in an arachidonyl side chain.

Formula VII″

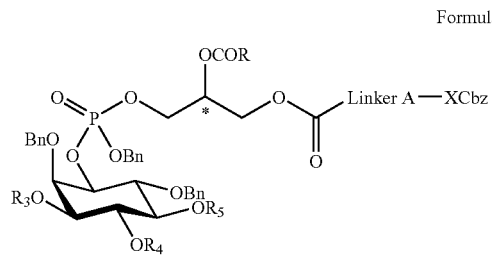

-continued

Formula VIII″

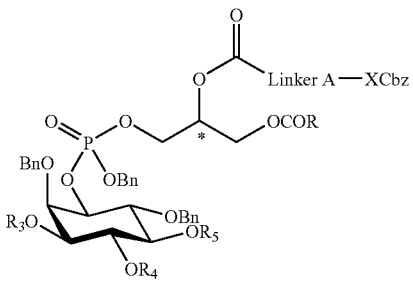

Where:

R=aryl, alkyl group, or a combination, preferably R=$C_mH_{2m+1}$, m=8-20, most preferably m=16 is optimal.

$R_3$=P(O)(OBn)$_2$; $R_4$=H; $R_5$=H (PI(3)P);

$R_3$=H; $R_4$=P(O)(OBn)$_2$; $R_5$=H (PI(4)P);

$R_3$=H; $R_4$=H; $R_5$=P(O)(OBn)$_2$ (PI(5)P);

$R_3$=P(O)(OBn)$_2$; $R_4$=P(O)(OBn)$_2$; $R_5$=H (PI(3,4)P$_2$);

$R_3$=P(O)(OBn)$_2$; $R_4$=H; $R_5$=P(O)(OBn)$_2$ (PI(3,5)P$_2$);

$R_3$=H; $R_4$=P(O)(OBn)$_2$; $R_5$=P(O)(OBn)$_2$ (PI(4,5)P$_2$); or $R_3$=P(O)(OBn)$_2$; $R_4$=P(O)(OBn)$_2$; $R_5$=P(O)(OBn)$_2$ (PI(3,4,5)P$_3$).

*Denotes a stereogenic centre. More preferably a stereogenic centre with an R absolute configuration.

Linker A=aryl, heteroaryl, alkyl with possible heteroatoms and/or unsaturations. Preferably chains of (CH$_2$)$_n$.

X=O, S, or, most preferably NH.

Unsaturations are allowed, such as in an arachidonyl side chain

Examples of compounds of formula V′, VI′, VII′, or VIII′ are shown in Table 3.

There is further provided according to the invention a compound having a formula according to any of formulae I′, II′, III′, IV′, V′, VI′, VII′, VIII′, I″, II″, III″, IV″, V″, VI″, VII″, VIII″, and use of such compounds to make a probe of the invention.

There is also provided according to the invention a method of making a compound of Formula I′, II′, III′, or IV′ which method comprises removal of the protecting groups of a compound of Formula I″, II″, III″, or IV″, respectively, preferably by reductive debenzylation.

There is further provided according to the invention a method of making a compound of Formula V′, VI′, VII′, or VIII′ which method includes reductive debenzylation of a compound of Formula V″, VI″, VII″, or VIII″, respectively.

The invention also provides a method of making a compound of Formula I″, II″, III″, or IV″ by phosphitylation of alcohol:

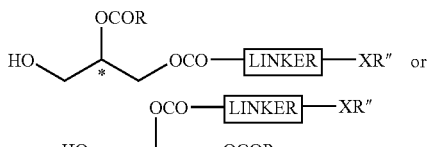

Preferably the * position is in the R configuration with $(R'''O)_2 PN^iPr_2$ and oxidation of the phosphitylated product, where $R'''=Bn$; $CNCH_2CH_2—$; trialkyl silyl.

A method of making a compound of Formula V", VI", VII", or VIII" is also provided by coupling a first alcohol of formula:

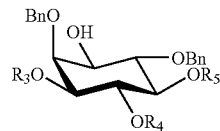

with a second alcohol of formula:

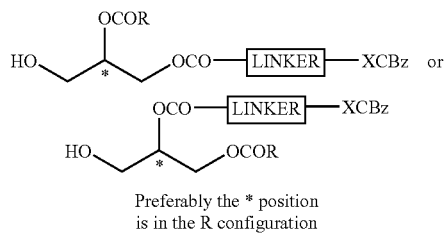

Preferably the * position is in the R configuration through a phosphodiester linkage.

Preferably the second alcohol is phosphitylated with BnOP$(N^iPr_2)_2$ to produce a phosphoramidite of formula:

BnO\P/$N^iPr_2$
    O\     OCOR
         \\\\OCO—[LINKER]—XCBz   or
              *

BnO\P/$N^iPr_2$
    O\     OCO—[LINKER]—XCBz
         \\\\OCOR
              *

Preferably the * position is in the R configuration which is then coupled to the first alcohol above to make the compound of Formula V", VI", VIII", or VIII".

There is further provided a method of making a compound of Formula I', II', III>, or IV' which comprises making a compound of Formula I", II", III" or IV" by the above method followed by removal of the protecting groups of the compound of Formula I", II", III', or IV", preferably by reductive debenzylation.

There is also provided a method of making a compound of Formula V', VI', VII', or VIII', which comprises making a compound of Formula V", VI", VII", or VIII" by a method above followed by reductive debenzylation of the compound of Formula V", VI", VII", VIII".

There is further provided a method of making a probe of the invention which comprises coupling a compound of Formula I', II', III', IV', V', VI', VII', or VIII', made by an above method, to the solid support.

The compound may be coupled to an N-hydroxy-succinimide-activated carboxylate of the solid support.

The alcohol of Formula:

BnO  OH
  \  |
$R_3O$\ /\_OBn
       \/  $OR_5$
       |
       $OR_4$ may be made from a compound of Formula 44:

Formula 44

BnO  OH
  \  |
   O\ /\_OBn
     \/  OAll
     |
     O for example as described in Example 3.

Further Definition of the Linker of Formulae I-IV, V, VI, I'-IV', V', VI', I"-IV", V", VI"

As an alternative to the linker definitions given above for these formulae, the linker may comprise or consist of carbon chains, for example made up of aryl, heteroaryl, alkyl, or combinations of these. An example of such a linker is —$(CH_2)_n$-aryl-. Preferably the linker comprises or consits of chains of $(CH_2)_n$, with n=8-20, most preferably n=11. Where the linker comprises a chain of $(CH_2)_n$, preferably the chain is attached directly to the ester carbon attached to the linker.

Further Definition of the R-Substituent of Formulae I-IV, V, VI, I'-IV', V', VI', I"-IV", V", VI"

As an alternative to the definitions of the R-substituent given above for these formulae, the R-substituent may comprise or consist of carbon chains, for example made up of aryl, alkyl, or a combination. Preferably the R-substituent comprises or consits of chains of $R=C_mH_{2m+1}$, m=16 is optimal. Where the R-substituent comprises $C_mH_{2m+1}$, preferably this is attached directly to the ester carbon attached to the R-substituent.

DESCRIPTION OF FIGURES

FIG. 3. Phosphoinositides and dipalmitoyl PA;

FIG. 4. Immobilised PA and Ptd Ins (4.5) P2;

FIG. 10. Domain structures of proteins isolated on phosphoinositide beads. The SMART programme was used to identify domains.

EXAMPLE 1

The immobilised PA [1] was prepared by coupling of the ω-amino phosphatidic acid (−) [2], which was synthesised in 7 steps starting from the optically pure protected glycerol derivative (−) [3], with the N-hydroxysuccinimide (NHS) activated ester agarose resin, Affi-Gel 10, as is depicted in Scheme 1. The poor solubility of [2] in a range of solvents neccesitated the use of the solvent combination chloroform-methanol-water (0.8:1:0.2). Excess resin (ca. 5 equiv. of NHS-groups) was used, resulting in a loading of 80% [2] onto the beads, as determined by the quantification of recovered [2] by 1H-NMR in the presence of an internal standard.

Figure 1:
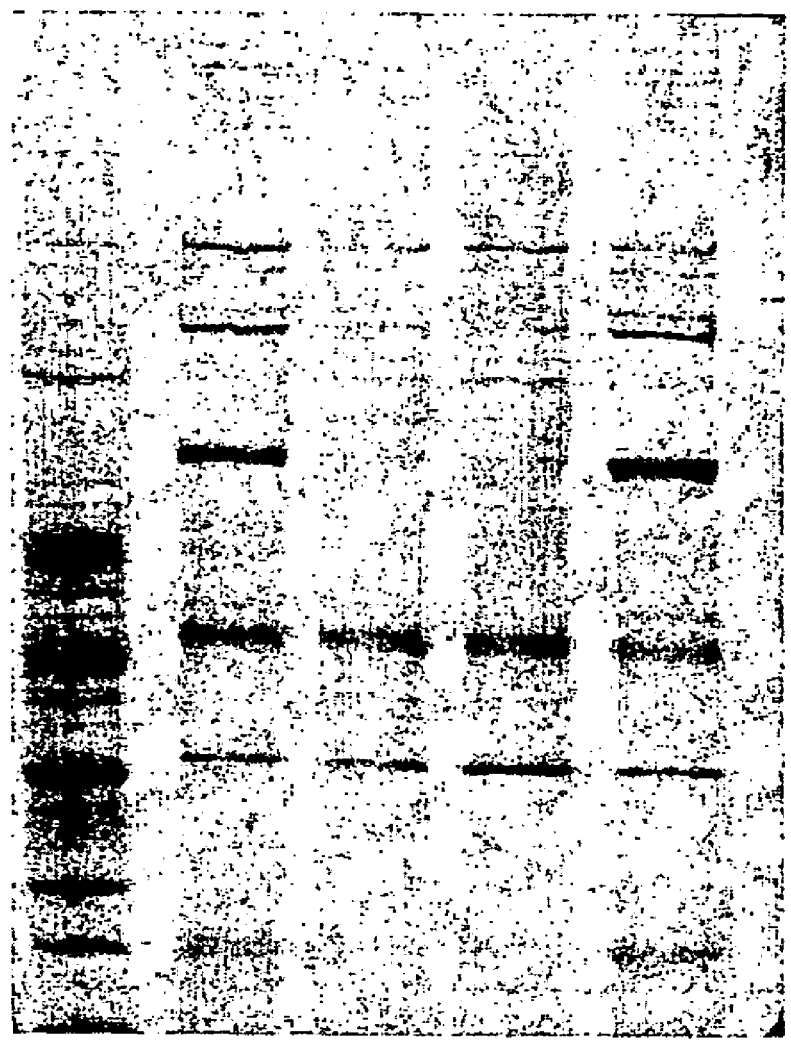
FIG. 1. Identification of PA-binding proteins from brain cytosol. Brain cytosol (lane 1) was mixed with PA resin (lanes 2-4) without (lanes 2, 5) or with (lanes 3, 4) preaddition of soluble C:12 PA at 75 µM. After incubation for 2 hr at 4° C. and three washes, polypeptides bound to the resin were analysed by SDS-PAGE and stained with silver. The molecular weight range of this gel is 200-20 kD. Notice that several bands are reduced in intensity after pretretament with soluble PA.

When a brain cytosolic extract was treated with the PA-resin [1], both in the presence and absence of soluble PA, and the resin-bound fraction subsequently analysed by SDS-PAGE, a number of bands appeared representing proteins with the desired characteristics. They had relatively high intensity when incubated in the absence of soluble PA, but their appearance was dramatically reduced when soluble PA was present, as is illustrated in FIG. 1.

The Synthesis of the Reagent [1] is as Follows (Numbers in Brackets Refer to the Structures Shown in Scheme 1)

1-O-[12-(N-benzyloxycarbonyl-amino)dodecanoyl]-3-O-(4-methoxybenzyl-sn-glycerol [6]: The diol [5] (2.47 g, 12 mmol) [see Chen, Profit and Prestwich: J. Org. Chem. 61: 6305-6312 (1996)], DCC (2.64 g, 13 mmol) and DMAP (1.56 g, 13 mmol) was added to dry $CH_2Cl_2$ (100 mL) under nitrogen and the reaction was stirred for 30 mins at 0° C. 12-(Benzyloxycarbonyl)-amino-dodecanoic acid (2.27 g, 6.5 mmol) in dry $CH_2Cl_2$ (5 mL) was transferred via cannula into the reaction mixture under nitrogen and stirred at room temperature overnight. The reaction was quenched by addition of water (50 mL) and the aqueous phase was extracted with $CH_2Cl_2$ (3×40 mL). The combined organic extracts were washed with brine (20 mL) and dried over $MgSO_4$. Flash chromatography (50% EtOAc in hexane) of the residue gave alcohol [6] (3.15 g, 5.8 mmol, 89%) as a white solid: m.p. 51-53° C. (from EtOAc); $[\alpha]_D^{20}$=+1.7 (c 0.52 in $CHCl_3$); Rf=0.48 (50% EtOAc/hexane); γmax($CHCl_3$)/cm$^{-1}$ 3689, 3585, 3450, 3004, 2931, 2856, 1720, 1655, 1612, 1514, 1463, 1454, 1252, 1234, 1174, 1132, 1101, 1035; δH (400 MHz; $CDCl_3$) 7.35-7.28 (5 H, m, Bn), 7.24 (2 H, d, J 8.6, PMB), 6.87 (2 H, d, J 8.6, PMB), 5.08 (2 H, s, $OCH_2$), 4.84 (1 H, bs, NH), 4.50-4.42 (2 H, m, $OCH_2$), 4.16 (1 H, dd, J 11.5, 4.5, $CH_2CHCH_2$), 4.11 (1 H, dd, J 11.5, 6.0, $CH_2CHCH_2$), 3.99-3.97 (1 H, m, $CH_2CHCH_2$), 3.79 (3 H, s, $OCH_3$), 3.51 (1 H, dd, J 9.6, 4.4 $CH_2CHCH_2$), 3.44 (1 H, J 9.6, 6.0, $CH_2CHCH_2$), 3.16 (2 H, q, J 6.7, $CH_2NH$), 2.70 (1 H, bs, OH), 2.30 (2 H, t, J 7.6, $OCOCH_2$), 1.59 (2 H, qn, J 6.7, $CH_2CH_2NH$), 1.47-1.37 (2 H, m, $OCOCH_2CH_2$), 1.25 (16 H, bs, $C_{11}H_{22}NH$); δC (100 MHz; $CDCl_3$) 173.9 (OCO), 159.4 (NHCO), 156.4 ($CH_3OC$), 136.7, 129.8, 129.4, 129.2, 128.4, 128.1, 113.9 (7×Bn and PMB), 73.1 (CH), 70.6, 68.9, 66.5, 65.4 (4×$CH_2$), 55.2 ($OCH_3$), 41.1 ($CH_2NH$), 34.1, 29.9, 29.5, 29.4, 29.3, 29.2, 29.1, 29.0, 26.7, 24.5 (10×$CH_2$); m/z (CI) [Found (M+H)$^+$544.3302. $C_{31}H_{46}O_7N$ requires M, 544.3274].

1-O-[12-(N-benzyloxycarbony-amino)dodecanoyl]-2-O-hexadecanoyl-3-O-(4-methoxybenzyl)sn-glycerol [7]: To a solution of alcohol [6] (3.14 g, 5.7 mmol) in dry $CH_2Cl_2$ (20 mL) under nitrogen was added DMAP (0.035 g, 0.29 mmol). The resulting solution was cooled to 0° C. and dry pyridine (0.68 g, 0.70 mL, 8.68 mmol) was added dropwise. After stirring for 30 mins, palmitoyl chloride (1.75 g, 1.93 mL, 6.37 mmol) was added dropwise under nitrogen and the reaction mixture was stirred overnight. Water (50 mL) was added to quench the reaction. The aqueous phase was extracted with ether (3×50 mL) and the ethereal layers were washed with 2 M HCl (20 mL). The acid phase was back extracted with ether (50 mL) and the combined ethereal layers were washed with brine (20 mL) and dried over $MgSO_4$. Flash chromatography eluting with 50% EtOAc in hexane gave the ester [7] (3.17 g, 4.1 mmol, 70%) as a white solid: (Found: C, 72.6; H, 9.85; N, 1.8. $C_{47}H_{75}O_8N$ requires C, 72.2; H, 9.7; N, 1.8%); m.p. 44-47° C. (from EtOAc); $[\alpha]_D^{20}$=+5.5 (c 0.59 in $CHCl_3$); Rf=0.20 (20% EtOAc/hexane); γmax($CHCl_3$)/cm$^{-1}$ 3451, 2926, 2854, 1728, 1612, 1514, 1465, 1366, 1302, 1252, 1173, 1110; δH (400 MHz; $CDCl_3$) 7.35-7.30 (5 H, m, Bn), 7.23 (2 H, d, J 11.5, PMB), 6.87 (2 H, d, J 8.7, PMB), 5.22 (1 H, qn, J 5.1, $CH_2CHCH_2$), 5.09 (2 H, s, $OCH_2$), 4.74 (1 H, bs, NH), 4.48 (1 H, d, J 12.0, $OCH_2$), 4.44 (1 H, d, J 12.0, $OCH_2$), 4.32 (1 H, dd, J 11.8, 3.8, $CH_2CHCH_2$), 4.17 (1 H, dd, J 11.8, 6.4, $CH_2CHCH_2$), 3.80 (3 H, s, $OCH_3$), 3.55 (2 H, dd, J 5.1, 1.1, CH2CHCH2), 3.18 (2 H, q, J 6.6, $CH_2NH$), 2.31 (2 H, t, J 7.4, $OCOCH_2$), 2.27 (2 H, t, J 8.1, $OCOCH_2$), 1.66-1.56 (6 H, m, $OCOCH_2CH_2$, $CH_2CH_2NH$), 1.55-1.47 (2 H, m, $CH_2CH_2CH_2NH$), 1.25 (36 H, bs, $COC_{15}H_{31}$, $C_{11}H_{22}NH$), 0.88 (3 H, t, J 6.6 $CH_3$); δC (100 MHz; CDCl3) 173.4, 173.1 (2×OCO), 159.3 (NHCO), 156.4 ($CH_3OC$), 136.7, 129.8, 129.3, 129.0, 128.5, 128.06, 113.81 (7×Bn and PMB), 72.9 ($CH_2$), 70.1 (CH), 70.0, 67.9, 66.5 (3×$CH_2$), 55.8 ($OCH_3$), 41.1 ($CH_2NH$), 34.3, 34.1 31.9, 29.9, 29.7, 29.5, 29.4, 29.3, 29.2, 29.1, 24.9, 24.8, 22.6 (13×$CH_2$), 14.1 ($CH_3$); m/z (CI) [Found (M+H)$^+$ 782.56140. $C_{47}H_{76}O_8N$ requires M, 782.55707].

1-O-[12-(N-benzyloxycarbony-amino)dodecanoy]-2-O-hexadecanoyl-sn-glycerol [8]: To a solution of $CH_2Cl_2$ (50 mL) and $H_2O$ (5 mL) under air was added the diacylglycerol [7] (3.12 g, 4.00 mmol). DDQ (1.81 g, 8.00 mmol) was added and the reaction was stirred overnight at room temperature. The reaction was diluted with $CH_2Cl_2$ (50 mL) and washed with saturated $NaHCO_3$ solution (20 mL), brine (20 mL) and dried over $MgSO_4$. Flash chromatography eluting with 40-50% EtOAc in hexane gave the alcohol [8] (2.40 g, 3.62 mmol, 91%) as an off white solid: (Found: C, 70.7; H, 10.1; N, 2.1. $C_{39}H_{67}O_7N$ requires C, 70.7; H, 10.2; N, 2.1%); m.p. 56-58° C. $[\alpha]_D^{20}$=−3.2 (c 1.02 in $CHCl_3$); Rf=0.20 (30% EtOAc/hexane); γmax($CHCl_3$)/cm$^{-1}$ 3450, 2924, 2854, 1724, 1602, 1517, 1465, 1413, 1372, 1251, 1164; δH (400 MHz; $CDCl_3$) 7.34-7.25 (5 H, m, Bn), 5.10-5.05 (3 H, m, $CH_2CHCH_2$, $OCH_2C_6H_5$), 4.81 (1 H, bs, NH), 4.31 (1 H, dd, J 11.9, 4.4, $CH_2CHCH_2$), 4.20 (1 H, dd, J 11.9, 5.8, $CH_2CHCH_2$), 3.71 (2 H, d, J 5.8, $CH_2CHCH_2$), 3.16 (2 H, q, J 6.6, $CH_2NH$), 2.32 (2 H, t, J 7.5, $OCOCH_2$), 2.30 (2 H, t, J 7.8, $OCOCH_2$), 1.63-1.59 (4 H, m, $OCOCH_2CH_2$, $CH_2CH_2NH$), 1.58-1.45 (2 H, m, $CH_2CH_2CH_2NH$), 1.25 (36 H, bs, $COC_{15}H_{31}$, $C_{11}H_{22}NH$), 0.87 (3 H, t, J 6.6, $CH_2CH3$); δC (63.5 MHz; $CDCl_3$) 173.7, 173.4 (OCO), 156.4 (NHCO), 136.7, 128.5, 128.0, 112.6 (4×Bn), 72.1 (CH), 66.6, 62.1, 61.4 (3×$CH_2$), 41.1 ($NHCH_2$), 34.3, 34.1, 31.9, 30.0, 29.7, 29.6, 29.5, 29.3, 29.2, 29.1, 26.7, 24.9, 22.7 (12×$CH_2$), 14.1 ($CH_3$); m/z (CI) [Found (M+Na)$^+$ 684.4828. $C_{39}H_{67}O_7NNa$ requires M, 684.4816].

1-O-[(12-N-benzyloxycarbonyl-amino)dodecanoyl]-2-O-hexadecanoyl-sn-glycer-3-yl bis-O-benzylphosphate [9]: Dry $CH_2Cl_2$ (10 mL) was added into a mixture of alcohol [8] (1.00 g, 1.51 mmol), 1H-tetrazole (1.04 g, 3.02 mmol) and bisbenzyl(N,N,-diisopropylamino)phosphine (0.31 g, 4.54 mmol) under nitrogen. The reaction mixture was stirred at room temperature for 2 h until tlc indicated no starting material was left. The reaction mixture was cooled to −78° C. and mCPBA (1.43 g, 8.3 mmol) was added in one portion. The reaction mixture was warmed to room temperature over 2 h and stirred overnight. The reaction mixture was diluted with $CH_2Cl_2$ (30 mL) and washed with 10% $NaHSO_3$ solution (50 mL). The aqueous phase was back extracted with $CH_2Cl_2$ (2×50 mL). The combined organic extracts were washed with saturated $NaHCO_3$ solution (20 mL), brine (20 mL) and dried over $MgSO_4$. The residue was chromatographed (40% EtOAc in hexane) affording phosphate [9] (1.14 g, 1.24 mmol, 82%) as an off white gum: (Found: C, 69.2; H, 8.8; N, 1.5; P, 3.4. $C_{53}H_{80}O_{10}NP$ requires C, 69.0; H, 8.75; N, 1.5; P, 3.4%); m.p. 40-42° C. (from EtOAc/hexane); $[\alpha]_D^{20}$=+1.8 (c 0.23 in $CHCl_3$); Rf=0.11 (30% EtOAc/hexane); γmax($CHCl_3$)/cm$^{-1}$ 3542, 3022, 2853, 1733, 1601, 1512, 1433, 1222, 1217, 1032; δP (101.3 MHz; $CDCl_3$) −0.64; δH (400 MHz; $CDCl_3$) 7.37-7.27 (15 H, m, Bn), 5.16 (1 H, qn, J 5.0, $CH_2CHCH_2$), 5.08 (H, s, $OCH_2$), 5.05-5.00 (4 H, m, $OCH_2$), 4.85 (1 H, bs, NH), 4.25 (1 H, dd J 11.9, 4.4, $CH_2CHCH_2$), 4.13-4.05 (3 H, m, $CH_2CHCH_2$), 3.16 (2 H, q, J 6.5, $CH_2NH$), 2.26 (2 H, t, J 7.2, $OCOCH_2$), 2.24 (2 H, t, J 7.6, $OCOCH_2$), 1.58-1.57 (4 H, m, $OCOCH_2CH_2$), 1.48-1.46 (2 H, m, $CH_2CH_2NH$), 1.25 (39 H, bs, $COC_{15}H_{31}$, $C_{11}H_{22}NH$), 0.87 (3 H, t, J 6.6 $CH_3$); δC (100 MHz; $CDCl_3$) 173.1, 172.7 (OCO), 156.4 (NHCO), 136.7, 135.6, 135.5 (3×$CH_2C$), 128.6, 128.5, 128.1, 128.0, 127.9, 127.8, (6×Bn), 69.5 (CH), 69.4, 69.3, 66.5, 65.4, 61.6 (5×$CH_2$), 41.10 ($CH_2NH$), 34.1, 33.9, 31.9, 29.68, 29.7, 29.6, 29.5, 29.4, 29.3, 29.2, 29.1, 29.0, 26.7, 24.8, 22.7 (15×$CH_2$), 14.11 ($CH_3$); m/z (+FAB) [Found (M+Na)$^+$ 944.5417. $C_{53}H_{80}O_{10}NPNa$ requires M, 944.5427].

1-O-(12-Amino)dodecanoyl-2-O-hexadecanoyl-sn-glycer-3-ylphosphate [2]: To a solution of $^tBuOH$ (18 mL) and $H_2O$ (3 mL) in a steel tube was added the benzyl phosphate [9] (0.1 g, 0.11 mmol). The reaction mixture was placed in an autoclave and the steel tube and autoclave was vented with $H_2$ four and five times respectively. The autoclave was finally pressurised to 15 bar and stirred for 18 h. The pressure was slowly released and the reaction mixture was centrifuged. The $^tBuOH/H_2O$ layer was discarded and the residue was washed with $MeOH/CHCl_3$ (1:1 v/v). The suspension was centrifuged and the organic layer was collected and passed through a pad of celite. The filtrate was centrifuged to remove traces of celite and the organic layer was collected and concentrated in vacuo affording phosphate [2] (0.052 g, 0.084 mmol, 78%) as a white solid: $[\alpha]_D^{20}$=−8.9 (c 0.09 in $CHCl_3/H_2O$ 1:1); γmax(KBr)/cm$^{-1}$ 3838, 2918, 2849, 1732, 1684, 1469, 1417, 1382, 1242, 1166, 1044, 937; δp [101 MHz; $CD_3OD/CDCl_3$ (1:1)] 1.31; δH [500 MHz; $CD_3OD/CDCl_3$ (1:1)] 4.88 (1 H, bs, $CH_2CHCH_2$), 4.13 (1 H, dd, J 12.0, 3.0, $CCH_2CHCH_2$), 3.83 (1 H, dd, J 12.0, 3.0, $CH_2CHCH_2$), 3.66-3.64 (2 H, m, $CH_2CHCH_2$), 2.55 (2H, t, J 7.6, $CH_2NH_2$), 2.01-1.98 (4 H, m, $COCH_2$), 1.33-1.28 (6 H, m, $COCH_2CH_2$, $CH_2CH_2NH_2$), 0.98-0.92 (38 H, m, $C_{15}H_{31}$, $C_{11}H_{22}$), 0.54 (3 H, t, J 6.5 ($CH_3$); oH [500 MHz; $CD_3OD/CDCl_3$ (1:1)] 173.5, 173.1 (2×OC=O), 70.2, 62.0 (CH and $CH_2$), 39.0, 33.6, 33.6, 33.3, 31.3, 29.0, 28.8, 28.7, 28.5, 27.7, 27.6, 27.4, 27.2, 26.7, 25.3, 24.2, 23.8, 22.0, 13.1 (19× $C_{15}H_{31}$, $C_{11}H_{22}$).

1-O-[(12-N-affigel-10-amino)dodecanoyl]-2-O-hexadecanoyl-sn-glycer-3-yl phosphate [1]: Affigel-10 (2 mL slurry, 30.00 µmol) was filtered and washed with $CHCl_3/MeOH/H_2O$ (0.8:1:0.2, 15 mL). It was transferred to a stirred solution of the acid [2] (4.0 mg, 6.14 µmol) and $NaHCO_3$ (0.025 g, 0.30 mmol) in $CHCl_3/MeOH/H_2O$ (0.8:1:0.2, 2 mL). The reaction mixture was stirred at room temperature for 18 h. The reaction mixture was filtered and washed with $H_2O$ (5 mL), $CHCl_3/MeOH/H_2O$ (0.8:1:0.2, 10 mL) and $H_2O$ (5 mL) again. The gel was stored in $H_2O$ at 0° C. The filtrates were combined and 4.83 mmol of the internal standard was added. The solvent was removed in vacuo and the white residue was taken up in $CDCl_3/CD_3OD$ (1:1 v/v) for proton NMR. The orthoformate:amine ratio was estimated to be 1:0.22 which implied that 5.33 µmol of the amine was loaded on to the beads.

Use of the Invention for Identification of PA Binding Proteins

In this document we disclose that resin-bound PA, illustrated as [1]. in Scheme 1, shows surprisingly a high affinity for a family of proteins which are expected to play important roles in both housekeeping cellular functions and in signal transduction. The observed affinity of the proteins for PA allows important substances in the MW range 60250 kD, and preferably in the range 60-160 kD to be identified.

Using this PA derivative we have identified a family of cytosolic brain proteins that showed strong and specific binding to PA. An unexpected common characteristic among some of the known proteins identified is their involvement in distinct stages of intracellular transport, from coated vesicle formation (coatomer and ADP ribosylation factor, Arf), to fusion (N ethylmaleimide sensitive factor NSF) and vesicle movement along microtubules (kinesin). Surprisingly, the resin-bound PA was much more stable than the cellular counterpart, and could be advantageously re-used a number of times (e.g. 5 times) without noticeable degradation or loss of activity. This is of crucial importance for any practical application.

A general approach for identifying PA binding proteins from tissue extracts is as follows: The tissue is homogenised using standard methods, and two fractions are produced, cysosol and membranes. The cytosol fraction is mixed 1:1 with buffer A (50 mM Tris-HCl pH 8.0, 150 mM NaCl, 10 mM EDTA, 1% NP-40, protease inhibitors) and then incubated with the PA resin equilibrated for 30 min in buffer B (50 mM Tris-HCl pH 7.5, 150 mM NaCl, 5 mM EDTA, 0.1% Tween-20, 0.02% Na azide). The membrane fraction is mixed 1:3 with buffer A but containing 2% NP-40 for 30 min on ice. The sample is then spun at 100,000×g for one hr to produce a soluble membrane extract. This extract is mixed with PA beads equilibrated as described above and processed similarly as above.

The sample is put in a rotator at 4° C. for 2 hr, and then washed three times with buffer B in the cold. These washes are very important since they remove non-specifically bound proteins. To provide an extra level of specificity we do the following modification. To one of duplicate samples excess soluble PA is added before the beads are introduced (the soluble PA solution is made by drying C:12 or C:8 PA dissolved in chloroform, resuspending in buffer A and sonicating for 5 min to make a stock solution of 250 mM). The assumption is that excess soluble PA will compete with the PA on the resin thus reducing the amount of protein that is recovered bound to the resin (see FIG. 1). Bands of interest are excised from the gel and treated with trypsin. The tryptic digests produced from the various bands are analysed by mass spectroscopy.

The catalogue of PA binding proteins obtainable using the invention is not complete. Nevertheless, such proteins are expected to fall into three embodiments:

The First Embodiment

Proteins of known identity and function but whose exact mechanism of action is not well understood. Kinesin, N-ethylmaleimide-sensitive factor (NSF), coatomer and ADP ribosylation factor (Arf) of the PA binding proteins identified so far using the PA resin fall into this category. We will briefly discuss kinesin as an example but similar arguments can be made for the rest of the known proteins. Membrane vesicle and organelle movement in eucaryotic cells is driven along microtubules by motor proteins [Rogers and Gelfand, Current Opinion in Cell Biology 12: 57-62 (2000)]. Kinesins, which are among the best understood of those motor proteins, hydrolyse ATP to generate movement along microtubules [Sablin, Current Opinion in Cell Biology 12: 3541 (2000)]. Part of the kinesin molecule has been crystalised, and mice carrying targeted knockouts for conventional kinesin have been generated. Thus the kinesin field is very advanced. However, the exact mechanism by which kinesins bind the membrane of the organelles or vesicles that they help transport is unknown [Bloom and Goldstein, J. Cell Biology 140: 1277-1280 (1998)]. Our identification of kinesin among the PA binding proteins suggests that PA may play a role in the recognition of the membrane by kinesins and may help solve this long-standing problem. Kinesin, in addition, has been implicated as an important target for the treatment of cancer [Cytokinetics, Inc., Chemistry & Biology 6: R225-R226 (1999)]; any discovery leading to a better understanding of the function of this protein may lead to the discovery of novel, or the design of more rational, drug therapies.

The Second Embodiment

Proteins of known identity but whose function is not understood. Neurochondrininorbin, a PA binding protein identified using the PA resin falls into this category. The gene for this protein was found to be upregulated following treatment of rat hippocampal slices with tetraethylammonium, a compound that induces long-term potentiation-like synaptic enhancement [Shinozaki et al. Biochem. Biophys. Res. Comm. 240: 766-771 (1997)]. Subsequent work has shown that norbin is present in dendrites of neural outgrowth [Shinozaki et al. Molecular Brain Research 71: 364-368 (1999)] whereas independent work based on expression cloning has indicated an additional role for this protein in bone metastasis [Ishizuka et al. Biochim. Biophys. Acta 1450: 92-98 (1999)]. For such a protein and others to be identified, discovery of their PA binding property may provide important clues as to their function and should help to design experiments to elucidate this function. For those that appear to have medical relevance, this approach may also help design strategies that control their function.

The Third Embodiment

Totally Novel Proteins.

Scope of the Invention

The PA resin described above and the PIPn resins described below are general analytical tools for identification of additional PA-binding or PIPn-binding proteins from different tissues and biological fluids. We envisage that the cytosolic and membrane contents of any cell type can be screened for PA/PIPn binding proteins using these resins. (In addition to brain, a partial list includes liver, kidney, heart, pancreas, macrophages, neutrophils.) In all cases, cytosolic or membrane fractions could be subjected to assays as described above. Once a series of proteins, which bind directly to PA or PIPn, have been identified, they could be examined as to which amino acids are involved in the binding, using a photoaffinity labeled PA-analogue (see above) or PIPn analogue. Comparison among those proteins should result in a common motif which may define the PA binding motif or a PIPn binding motif. Once the motif is identified, it can be used as a search tool to identify most proteins, that are expected to bind PA or PIPn and that are described in the databases. Thus the PA and PIPn resins are expected to reveal the majority of the members of the PA and PIPn binding protein families.

Figure 2:
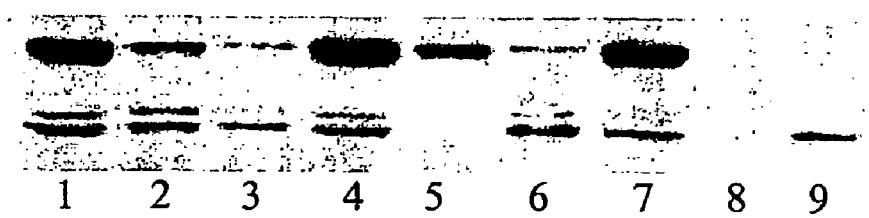
FIG. 2. Simian COS-7 cells were grown on plastic plates to 80% confluency. Following removal of the culture medium and three washes in PBS, the cells were lysed in buffer containing 50 mM Tris-HCl pH 8.0, 150 mM NaCl, 10 mM EDTA and 0.2% of Na deoxycholate (lanes 1-3), 0.4% NP-40 (lanes 4-6) or 0.4% CHAPS (lanes 7-9). The lysates were centrifuged at 12,000×g for 10 min and insoluble material was discarded. The supernatant from each lysate (shown in lanes 1, 4, 7) was mixed with PA resin (lanes 2, 5, 8) or $PIP_2$ resin (lanes 3, 6, 9) for 2 hr at 4° C. After three washes, polypeptides bound to the resin were resolved by SDS-PAGE followed by electroblotting onto nitrocellulose. The blot was probed with antibodies to coatomer subunit β-cop (upper band) and to PLCó (lower band). Notice that the specificity of the PA resin for coatomer and of the $PIP_2$ resin for PLCó is maintained only for samples lysed with NP-40.

We foresee important applications of the PA and PIPn resins in diagnostics, Extracts from healthy or pathological tissues could be compared side by side and their fall complement of PA or PIPn binding proteins may hence be established. Any protein whose amount and/or electrophoretic mobility changes in the pathological tissue in comparison to the healthy tissue could be identified by mass spectroscopy. Such proteins will be candidates both as markers for the disease and as therapeutic targets (see below). Additionally, to identify key PA-binding or PIPn-binding proteins involved in cell differentiation, similar assays may be done in matched samples of tissue culture cells that differ in some important physiological parameter. Examples include cell lines before and after differentiation into a neuronal phenotype (e.g. PC12 cells with and without treatment with nerve growth factor) or endothelial cell lines induced to mimic angiogenesis with vascular permeability factor [Hanahan and Folkman, Cell 86: 353-364 (1996)]. Since this assay involves extracts from whole cells grown on plastic as opposed to tissue sources, we have tested extraction conditions that maintain the specificity of the PA resin. Surprisingly, specificity is maintained with low concentrations of non ionic detergents (FIG. 2).

The approach of identifying candidate proteins by comparing their expression level and pattern between "normal" and "altered" tissues or cell lines has similarity to current proteomics strategies that are in use by many pharmaceutical companies whereby total cellular proteins from such tissues are analysed with a view to identify potentially interesting changes in expression profiles. We point out two essential differences with the approach proposed here: (a) The PA (or PIPn) resin acts as a concentration/enrichment reagent thus allowing small differences, or differences in rare proteins to be more readily detectable. (b) Since a functional requirement is built into the screening process (i.e. PA, or PIPn, binding), the resulting proteins from our approach can be studied with some prior knowledge of their potential function.

We foresee important applications of the PA and PIPn resins in therapeutics. The PA and PIPn resins provide unique tools for identification of small molecule compounds that interfere with or enhance PA (or PIPn) binding of proteins identified using the schemes above since it is essentially a solid phase reagent amenable to automated assays. Following identification of a candidate target protein, specific monoclonal antibodies against this protein could be raised and the protein itself may then be produced in miligram amounts. The preferred binding assay is based on detection by ELISA using the specific antibodies raised. Other configurations of the binding assay include the use of PA or PIPn functionalised with a fluorescent reporter group (detection of binding will be done by fluorometry) or the use of radioactive protein (detection of binding will be done by scintillation counting). Candidate compounds (obtained from commercial sources) can be introduced in the binding assay prior to adding the PA resin. If a compound interferes with binding, detection of the protein is expected to be reduced. If it enhances binding, detection should be higher. Compounds identified using this screen might become interesting drug lead candidates.

An Experimental Protocol for Obtaining Lead Compound

Isogeneic healthy rats are treated with streptozotocin (65 mg/kg i.v.) to render them diabetic. After sacrification of animals at different stages of disease progression (0, 1, 2, 3, 4, 6, 8 week), several organs (liver, kidney, heart, brain) are dissected for further study. Extracts from each organ at various stages of diabetes are assayed for PA-binding proteins (or PIPn-binding proteins) using the PA resin or PIPn resin) described here. Assume that protein $\Omega$ is identified to be present at higher levels in the liver as a function of disease progression. Antibodies against $\Omega$ are then raised, thus allowing a screen for interfering compounds to be initiated. The antibodies can be used for diagnosis of disease progression. In addition, since $\Omega$ was identified by its ability to differentially bind to PA (or PIPn) as the disease progresses, molecules that interfere with this binding maybe of relevance as a therapeutic compound.

One specific example of the use of the PA resin to identify subtle changes in the pattern of protein expression is concerned with the binding of Arf6 to PA. We have found that the active form of Arf6 (i.e. bound to GTP) binds with 50-fold higher affinity to the PA beads in comparison to the inactive form (i.e. bound to GDP). Thus, when cellular samples containing equal amounts of Arf(GDP) or Arf6(GTP) were analysed for PA binding side by side, 50 times more Arf6 (GTP) than Arf6(GDP) was bound to the PA resin. The implications for this are significant since, if an altered cell line or tissue contains "activated" Arf6 in comparison to its normal counterpart, analysis of the two samples with the PA beads will detect this potentially important difference.

Scheme 1

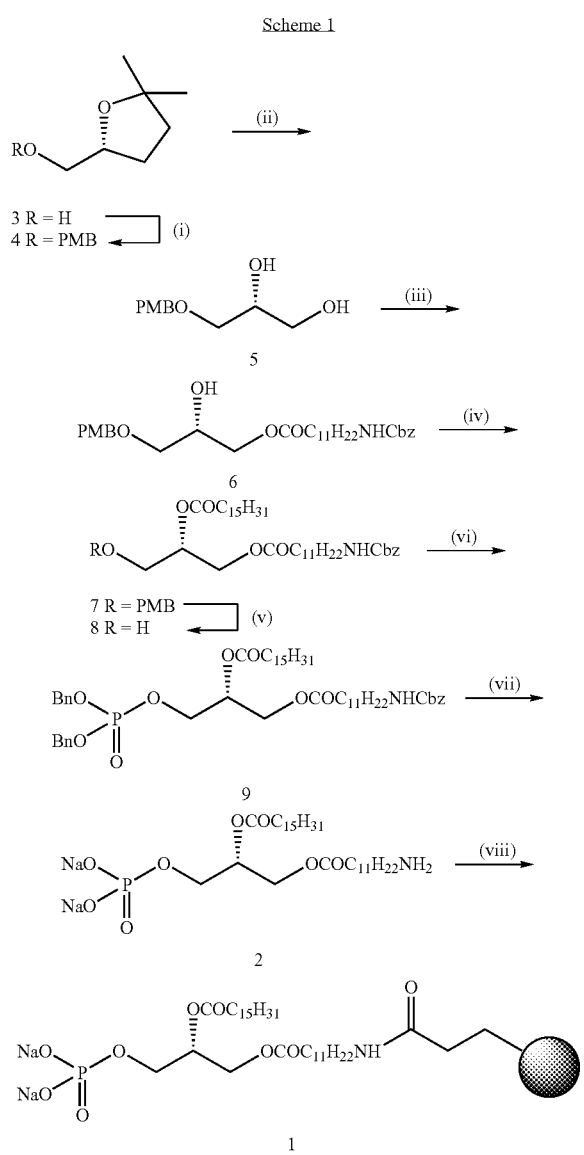

Reagents and Conditions
(i) PMBCl, NaH, DMF, 0° C. - r.t., 90%
(ii) conc. HCl, MeOH, reflux, 73%
(iii) 12-amino-(benzyloxycarbonyl)-dodecanoic acid, DCC, DMAP, $CH_2Cl_2$, 0° C. - r.t., 89%
(iv) palmitoyl chloride, pyridine, DMAP, $CH_2Cl_2$, 0° C. - r.t., 70%
(v) DDQ, "wet" $CH_2Cl_2$, 91%
(vi) $(OBn)_2PN^iPr_2$, 1H-tetrazole, r.t, then mCPA, -78° C. - r.t., 82%
(vii) Pd black, $NaHCO_3$, $^tBuOH/H_2O$, $H_2$, 15 bar, 18 h, r.t., 78%
(viii) Affigel-10, $CHCl_3/MeOH/H_2O$ (0.8:1:0.2), $NaHCO_3$, 18 h, 18% loading

EXAMPLE 2

Synthesis and Biological Evaluation of a PtdIns(3,4,5)$P_3$ Affinity Matrix

New PtdIns(3,4,5)$P_3$ binding proteins have been identified utilising PtdIns(3,4,5)$P_3$ modified affinity matrix 11 which was synthesised from myo-inositol derivative 12, phosphoramidite 19 and an agarose based solid support.

The role of myo-inositol phospholipids in cell signalling systems is well established.[1-4] One such signal transduction mechanism involves the in vivo production of PtdIns(3,4,5)$P_3$ via phosphorylation of PtdIns(4,5)$P_2$ mediated by PI3K.[5] Although PtdIns(3,4,5)$P_3$ binding proteins are known,[6] many of the cellular processes downstream of PI3K activation do not yet have a defined lipid binding protein mapped above them. For this reason we embarked on the preparation and evaluation of an affinity matrix based on PtdIns(3,4,5)$P_3$.

The phospholipid was attached to an agarose matrix by an amide linkage formed between a carboxylic acid-terminated side chain on the agarose and a 3-(ω-aminoacyl) glycerol derivative on the phospholipid (Scheme 2). The phospholipid 21 was prepared by coupling the alcohols 12[7] and 13 (from the commercially available (S)-(+)-1,2-O-isopropylideneglycerol 14) through a phosphodiester linkage.

Scheme 2

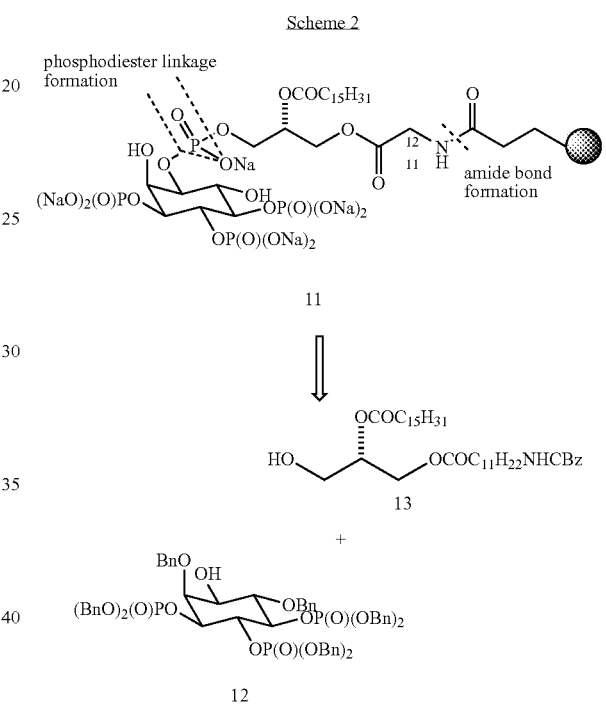

We initially protected the primary alcohol 14 as the t-butyldiphenylsilyl ether, but encountered difficulties in its removal at a later stage of the synthesis. A more efficient process involved 4-methoxybenzylation of the primary alcohol 14 (Scheme 3),[8] followed by acetonide removal to give the PMB-ether 15. Selective esterification of the primary alcohol in 15 with the Cbz-protected ω-amino acid 16, followed by palmitoylation of the secondary alcohol 17 gave the diester 18. Oxidative removal (CAN) of the PMB protecting group and phosphitylation of 13 with $BnOP(N^iPr_2)_2$[9] gave the phosphoramidite 19.†

Scheme 3

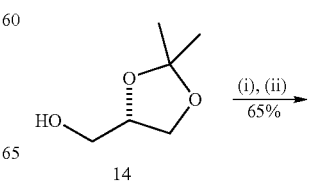

-continued

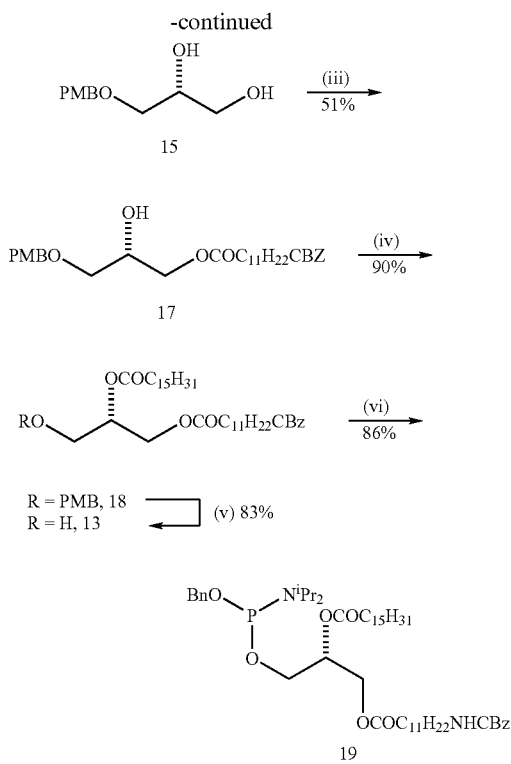

Reagents and conditions:
i, NaH, p-MeOC₆H₄CH₂Cl (PMBCl), DMF;
ii, PTSA, MeOH;
iii, HOOCC₁₁H₂₂NHCBz 16, DCC, DMAP, CH₂Cl₂;
iv, Palmitoyl chloride, DMAP, pyridine, CH₂Cl₂;
v, CAN, MeCN
vi, BnOP(NⁱPr₂)₂, 1H-tetrazole, CH₂Cl₂.

The lipid side chain, in the form of the phosphoramidite 19, was then coupled with the enantiomerically pure alcohol (−)-12 to afford the perbenzylated compound 20 (Scheme 4). Reductive debenzylation was readily effected using H₂ (50 psi) in the presence of Pd-black and NaHCO₃ in Bu$^t$OH—H₂O (6:1) as the solvent, to afford the amine 21 in good yield.† This was then coupled with the N-hydroxysuccinimide (NHS) activated ester resin, Affi-Gel 10,§ to afford the PtdIns(3,4,5)P₃ modified matrix 11. Excess resin (ca 5 equivalents) was required to ensure the complete consumption of the amine which was determined by a negative Kaiser test.‡

Scheme 4

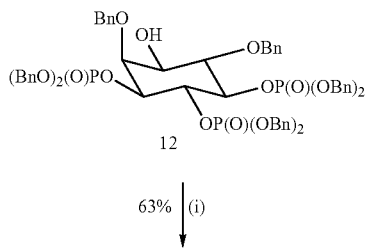

-continued

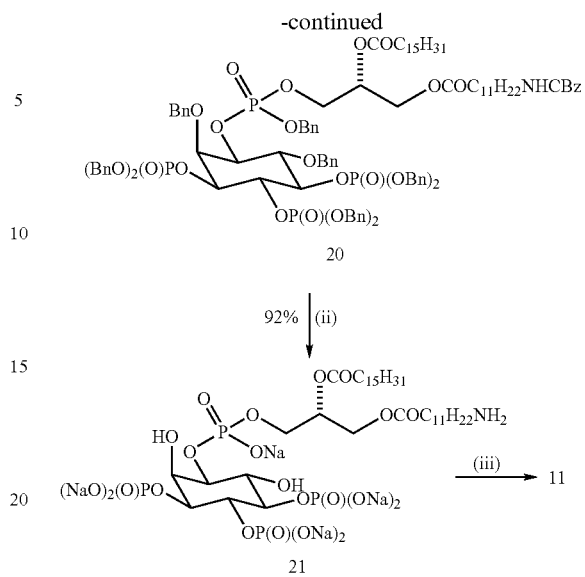

Reagents and conditions:
i, 1H-tetrazole, 19, CH₂Cl₂, then MCPBA;
ii, Pd-black, H₂ (50 psi), Bu$^t$OH—H₂O (6:1), NaHCO₃;
(iii), Affi-Gel-10, NaHCO₃, H₂O.

Pilot experiments showed that PKB (25 mM) [a known[6,10] PtdIns(3,4,5)P₃ binding protein] would bind to the matrix 11 and could be completely displaced by 10 mM D,D-PtdIns(3,4,5)P₃†† but not at all by 10 mM LL-PtdIns(3,4,5)P₃, thus establishing the potential specificity of the matrix. When applied to a pig neutrophil cytosol a number of proteins have been identified that bind to the resin 11 in a PtdIns(3,4,5)P₃ sensitive manner. Several novel proteins were identified and the full biological results are discussed below in Example 4. One of these proteins was subsequently shown to be identical to the recently characterised protein, DAPP1, possessing a Src homology (SH2) domain and a pleckstrin homology (PH) domain. This novel protein had been independently identified from a data base search by comparison of the PH domain sequences with known PtdIns(3,4,5)P₃ binding proteins.[11] The fact that the 'functional screen assay' identified several proteins including DAPP1, which is involved in endosomal trafficking or sorting,[12] is noteworthy and exemplifies the strength of the approach. Very recently biotinylated PtdIns(3,4,5)P₃ has been used as an affinity ligand for the purification of recombinant PtdIns(3,4,5)P₃ binding proteins.[13]

In summary we have demonstrated a synthesis of a PtdIns(3,4,5)P₃-modified matrix and demonstrated its use as a tool for the identification of proteins binding to PtdIns(3,4,5)P₃. The flexible nature of the methodology and the biological success of resin 11 warrants further investigation into the preparation and biological evaluation of other D-3 phosphorylated myo-inositol phospholipid modified matrixes.[14]

FOOTNOTES AND REFERENCES FOR EXAMPLE 2

† All new compounds exhibited spectroscopic and analytical data in accord with the assigned structure. Selected data (J values in Hz) for 19:[α]$_D^{22}$+7.0 (c 1.9 in CHCl₃); δH (250 MHz, CDCl₃), 7.38-7.28 (10 H, m, Ph), 5.20-5.10 (1 H, m), 5.10 (2 H, bs, OCH₂Ph), 4.80-4.60 (3 H, m), 4.36 (1 H, m), 4.12 (1 H, m), 3.85-3.55 (4 H, m), 3.18 (2 H, aq, J 6.7, CH₂NH), 2.29 (4 H, at, J 7.3), 1.64-1.40 (6 H, m), 1.30-1.20

(38 H, m), 1.17 (12 H, 2xd, J 6.8, 4×Me), 0.97 (3 H, t, J 6.9, Me); δP (101.25 MHz, CDCl$_3$), 149.2, 149.1; m/z (FIB) [Found: (M+Na)$^+$ 921.6022. C$_{52}$H$_{87}$N$_2$O$_8$Pna requires 921.6098]. For 21: [α]$_D^{22}$+3.0 (c0.1 in H20); vmax (KBr/cm$^{-1}$) 3403, 2920, 2850, 1742, 1238, 1094; δH (250 MHz, D$_2$O), 5.25 (1 H, bs), 4.45-3.80 (10H, m), 2.95-2.85 (2 H, m), 2.40-2.25 (4 H, m), 1.65-1.05 (44 H, m), 0.85-0.70 (3 H, m); δP (101.25 MHz, D$_2$O), 5.81, 4.79, 3.55, 0.80; m/z (-ve FAB) 1142 [(M−Na)$^-$, 25%], 1119 (50), 1098 (100), 1076 (90).

§ Affigel 10 was Purchased From BioRad.

‡ The matrix 11 was constructed by reacting 60 mole of N-hydroxysuccinimide activated resin (4 mL) with 12.2 mmole of the amine 21 in the presence of 122 mmole NaHCO$_3$ at 0° C. overnight. †† D,D-PtdIns(3,4,5)P$_3$ refers to the dipalmitoyl analogue of PtdIns(3,4,5)P$_3$ containing the 1(D)-myo-inositol ring stereochemistry and sn-2-diacylglycerol side chain; L,L-PtdIns(3,4,5)P$_3$ refers to the enantiomer.

1. C. L. Carpenter and L. C. Cantley, *Curr. Opin. Cell Biol.*, 1996, 8, 153.
2. A. Toker, M. Meyer, K. K. Reddy, J. R. Falck, R. Aneja, S. Aneja, A. Parra, D. J. Burns, L. M. Ballas and L. C. Cantley, *J. Biol. Chem.*, 1994, 269, 32358.
3. M. J. Berridge, *Nature*, 1993, 361, 315.
4. L. R. Stephens, T. R. Jackson and P. T. Hawkins, *Biochem. Biophys. Acta*, 1993, 1179, 27.
5. C. P. Downes and A. N. Carter, *Cellular Signalling*, 1991, 3, 501.
6. P. R. Shepherd, D. J. Withers and K. Siddle, *Biochemical J.*, 1998, 333, 471.
7. G. F. Painter, S. J. A. Grove, I. H. Gilbert, A. B. Holmes, P. R. Raithby, M. L. Hill, P. T. Hawkins and L. R. Stephens, *J. Chem. Soc., Perkin Trans.* 1, 1999, 923.
8. J. Chen, A. A. Profit and G. D. Prestwich, *J. Org. Chem.*, 1996, 61, 6305.
9. E. Dreef, C. J. J. Elie, P. Hoogerhout, G. A. van der Marel and J. H. van Boom, *Tetrahedron Lett.*, 1988, 29, 6513.
10. S. R. James, C. P. Downes, R. Gigg, S. J. A. Grove, A. B. Holmes and D. R. Alessi, *Biochemical J.*, 1996, 315, 709.
11. S. Dowler, R A. Currie, C. P. Downes and D. R. Alessi, *Biochein. J.*, 1999, 342, 7
12. K. Anderson, P. Lipp, M. Bootman, S. H. Ridley, J. Coadwell, L. Ronnstrand, J. Lennartsson, A. B. Holmes, G. F. Painter, J. Thuring, Z.-Y. Lim, H. Erdjument-Bromage, A. Grewal, P. Temspt, L. R. Stephens and P. T. Hawkins, *Curr. Biol.*, 2000, 10, 1403.
13. D. S. Wang, T. T. Ching, J. St Pyrek and C. S. Chen, *Anal. Biochem.*, 2000, 208, 301.
14. P. T. Hawkins et al., *Nature Biotechnol.*, manuscript in preparation.

EXAMPLE 3

Synthesis and Biological Evaluation of a PtdIns(4,5)P$_2$ and Phosphatidic Acid Affinity Matrix

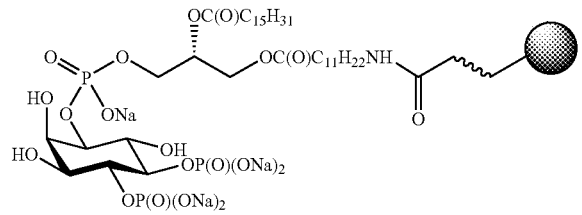

Ptd Ins(4,5)P$_2$ and dipalmitoyl PA were synthesised. In order to identify the direct downstream effectors of these molecules, dipalmitoyl PA and PtdIns(4,5)P$_2$ were immobilised onto a solid support, Affi Gel-10 giving 31 and 32. Using 31 and 32 as affinity matrices, a number of known proteins as well as a set of novel proteins were found to bind specifically to PA.

Phosphoinositides (PIP$_n$'s) (FIG. 3) represent a class of membrane phospholipids, which exhibit a wide range of activities in cell signaling cascades.[15] The 3-phosphorylated lipid products of phosphatidylinositol-3-kinase (PI$_3$K), viz. PtdIns(3)P, PtdIns(3,4)P$_2$ and PtdIns(3,4,5)P$_3$, mediate cell functions as diverse as cell movement, division and survival as well as glucose transport and many other functions, upon cell surface receptor stimulation by hormones and growth factors.[16-18] The PtdIns(3,4,5)P$_3$ is the product of 3-phosphorylation of the relatively abundant PtdIns(4,5)P$_2$. Another well established function of PtdIns(4,5)P$_2$ is phospholipase C (PLC)-promoted hydrolysis to give diacylglycerol and inositol(1,4,5)P$_3$; the former activates protein kinase C (PKC) where the latter releases Ca$^{2+}$ from internal stores.[19] Recent work has shown that PtdIns(4,5)P$_2$ is a highly versatile signaling molecule in its own right, and is involved in fundamental processes in membrane trafficking and plasma membrane-cytoskeleton linkages.[20] As such PtdIns(4,5)P$_2$ serves as an effector of many multiple downstream proteins, many of which remain to be identified. The biosynthesis of PtdIns(4,5)P$_2$ involves mainly 5-phosphorylation of PtdIns(4)P by PI4P-5-kinase,[19] which is activated by phosphatidic acid (PA), a product of phospholipase D (PLD)-catalyzed hydrolysis of phosphatidyl choline.[21] It is suspected that PA, besides being an important intermediate in the biosynthesis of glycerophospholipids, fulfills crucial roles in lipid based signaling and intracellular trafficking, because PLD activation is associated with the regulation of those processes.[22,23] This would imply the existence of PA-interacting proteins that operate downstream of PLD activation.

To identify the direct downstream effectors of PtdIns(4,5) P$_2$ and PA, and hence to gain more insight in their roles in signaling and house-keeping, we embarked on the synthesis of immobilized analogs of PA 31 and PtdIns(4,5)P$_2$ 32, having saturated fatty acid chains, as illustrated in FIG. 4.

These affinity reagents were prepared by attaching a terminal fatty acid amino function at the sn-1 position of the glycerol moiety, as in 33 and 34, to an agarose solid support.

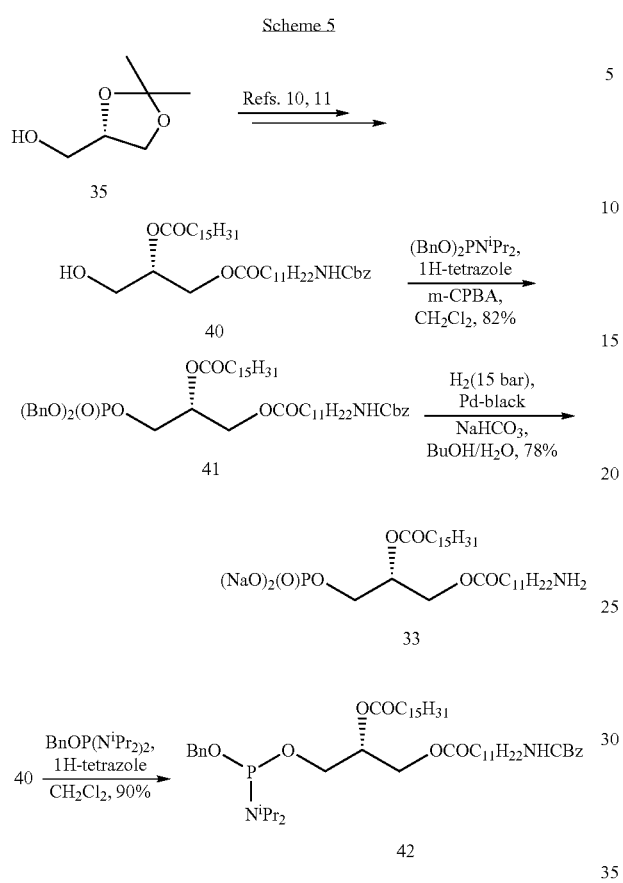

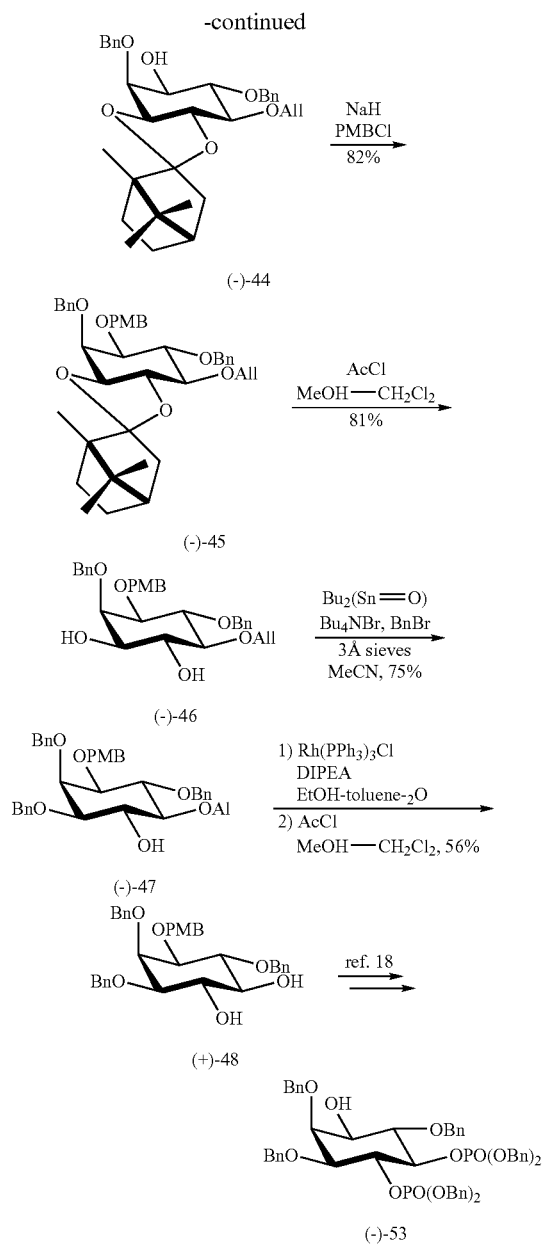

The soluble PA analog 33 was prepared by extension of methodology previously developed in our group and by others (Scheme 5).[24,25] The commercially available (S)-(+)-1,2-O-isopropylidene glycerol 35 was converted to the alcohol 40 in 5 steps, followed by phosphitylation with $BnO_2P(N^iPr_2)$ and in situ oxidation with mCPBA to give 41. Reductive debenzylation was readily effected using $H_2$ (15 bar) in the presence of Pd-black and $NaHCO_3$ in $^tBuOH-H_2O$ (6:1) as the solvent, to afford the amine 33, isolated as the sodium salt, in good yield. Alternatively, 40 was phosphitylated with $BnOP(N^iPr_2)_2$ to give the phosphoramidite 42, which is the lipid synthon in the preparation of the ω-amino PtdIns(4,5)P$_2$ 34 (vide infra).[25,26]

Scheme 6

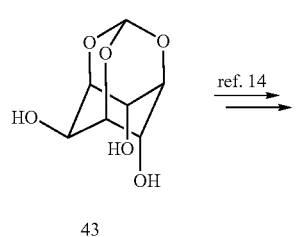

43

The synthesis of 34[27] (Scheme 6) started from the readily available myo-inositol orthoformate 43, that was converted in 6 steps to the optically pure camphor acetal (−)-44, derived from (−)-camphor. The intermediate (−)-44, in which the resolving camphor fragment also served to protect the 3- and 4-positions of the myo-inositol ring, has previously been utilized by us in the synthesis of dipalmitoyl PtdIns(3,4,5)P$_3$.[28] Subsequent p-methoxybenzylation followed by acetal deprotection afforded the 3,4-diol (−)-46.[29] Chemoselective benzylation of the 3-position was readily effected via the in situ generated stannane acetal in the presence of tetrabutylammonium bromide and benzyl bromide in refluxing acetonitrile. Using these conditions developed by Gigg et al.,[30] the ratio of 3-benzyl:4benzyl was approximately 4:1 as judged by $^1$H-NMR analysis. It should be noted that preformation of the cyclic stannane acetal, followed by benzylation in the presence of CsF in DMF,[31]

resulted in a lower yield and selectivity. The required 3-benzylated product (−)-47 was purified by flash chromatography and trituration. Deprotection of the 5-O-allyl ether using Wilknson's catalyst followed by acid treatment furnished the known diol (+)-48.

Scheme 7

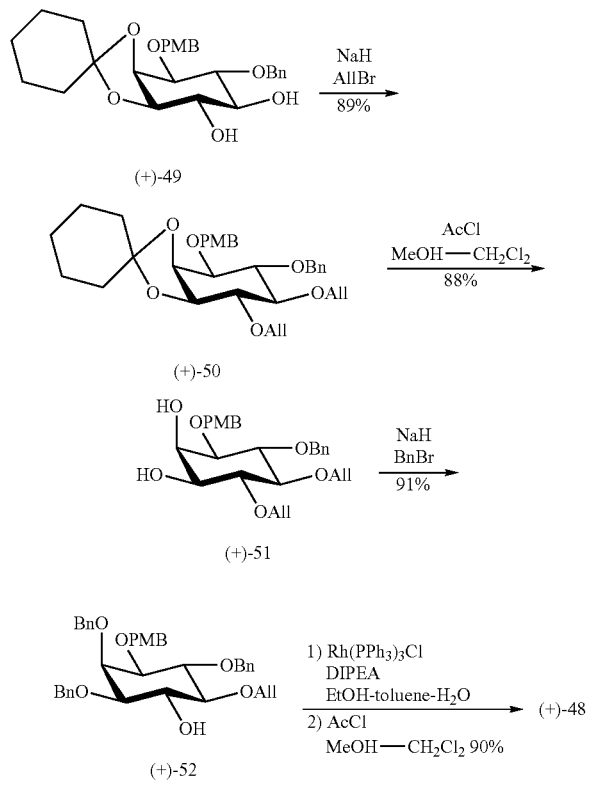

Definite proof for the observed regioselectivity of the stannylation-benzylation process was obtained by an independent synthesis of the diol (+)-48,[32] starting from the known optically pure diol (+)-49.[31] A four step sequence (Scheme 7) yielded (+)-48, which had identical optical rotatory and ¹H-NMR data as compared with the material prepared via Scheme 6. The diol (+)-48 was phosphorylated and PMB-deprotected under standard conditions to afford the known alcohol (−)-53, which was then coupled with the phosphoramidite 42 in the presence of 1H-tetrazole, followed by in situ mCPBA oxidation to give the fully protected phosphoinositide (−)-54. Global deprotection was carried out using similar conditions to those discussed to give the ω-amino PtdIns(4,5)P₂ analog 34.

Scheme 8

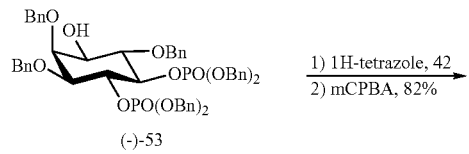

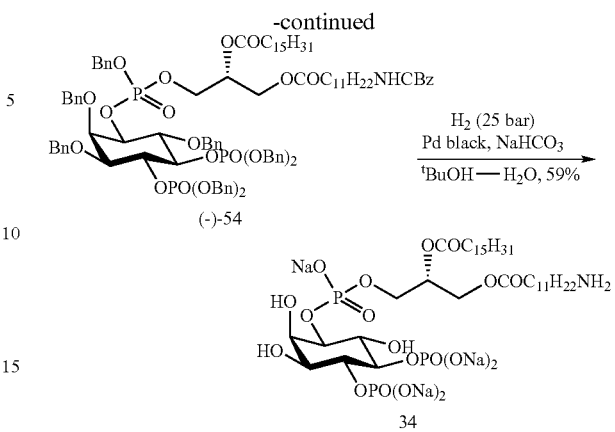

Finally, the PA amine 33 and PtdIns(4,5)P₂ amine 34 were coupled to the N-hydroxysuccinimide (NHS)-activated ester resin, Affi-Gel 10, to afford the corresponding affinity matrices 31 and 32. The PtdIns(4,5)P₂ modified matrix was prepared in water using excess NaHCO₃, by reacting the activated Affi Gel 10 [resin 60 mmol (4 mL)] with the amine 34 (14.3 mmol) to give a loading of 4.5 mmol as judged from the recovery of the amino phospholipid 34, that was quantified by 500 MHz ¹H-NMR spectroscopy in the presence of myo-inositol orthoformate 43 as the internal standard. The poor solubility of the amino-terminated PA 31 necessitated the use of the solvent combination chloroform-methanol-water 4:5:1 to yield material with a loading of 5.3 mmol starting from 30 mmol activated ester resin.

Figure 5:
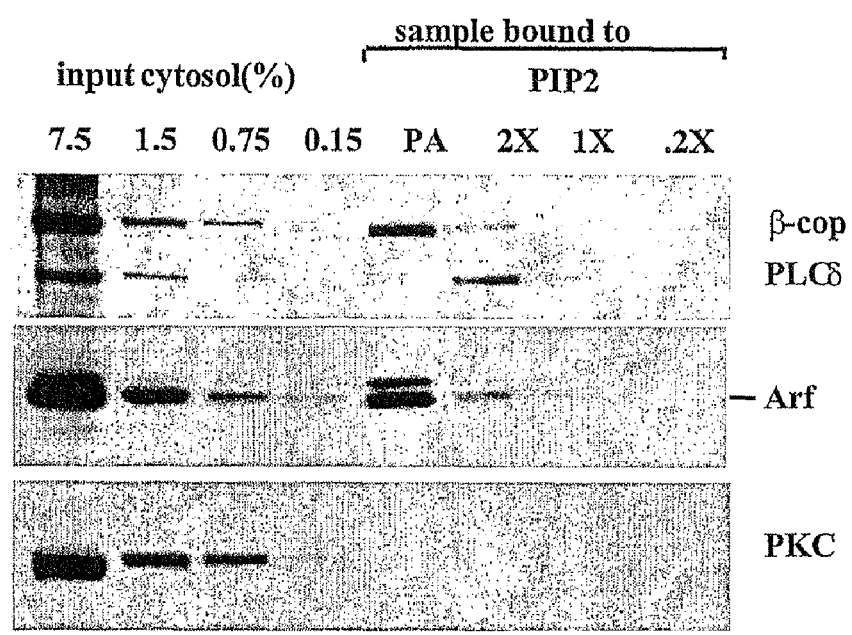
FIG. 5. Specificity of PA and Ptd Ins (4,5) P2 beads.

By treating the PA-modified affinity resin 31 with a brain cytosol extract in the presence of a non-ionic detergent, we found that a number of proteins bind specifically to those beads, i.e. their binding was inhibited by soluble dilauroyl PA. Amongst the PA-binding proteins identified were the b-cop subunit of coatomer, ADP ribosylation factor (Arf), N'-ethylmaleimide-sensitive factor (NSF) and kinesin, all of which are involved in intracellular traffic. In addition a set of 5 novel proteins was found. To further emphasize the observed binding specificity and the strength of the affinity reagents PA 31 and PtdIns(4,5)P₂ 32 to identify (detect) phospholipid-protein interactions, we treated in parallel brain cytosol with PA-resin 31 and various amounts of immobilized PtdIns(4,5)P₂ 32 (FIG. 5). Cytosol was mixed for 1 h with PA beads (150 nmol) or three different concentration of PtdIns (4,5)P₂ beads (120 nmol maximum) as shown. Following washes, the proteins bound to the beads were analysed by SDS-PAGE probed with antibodies to b-cop, Arf, PLCd (a known effector of PtdIns(4,5)P₂, vide supra) and PKC (an abundant cytosolic protein that binds acidic phospholipids and diacyl glycerol). We were pleased to see that b-cop and Arf bound strongly to the PA-beads 31, and only weakly to PtdIns(4,5)P₂ beads. Conversely, under the same conditions PLCd had a strong interaction with the PtdIns(4,5)P₂ beads, wheareas its binding to PA-resin 31 was undetectable. Finally, the negative control PKC did not bind to any of the beads.

In conclusion, we have synthesized a PA-functionalized solid support 31 and the corresponding 4,5-phosphoinositide 32 involving the key synthon 44. The observed binding profiles with several cytosolic proteins and the high degree of specificity warrant the further use of these materials in cellular biology.

We have covalently-coupled several inositol phospholipid (phosphoinositide) species to sepharose beads to provide novel affinity-capture tools. Initial use of these beads to capture proteins in leucocyte, platelet, brain and liver cytosol resulted in the identification of some 21 proteins which specifically bound to the phosphoinositide moeity attached to the beads. 11 of these proteins (4 of which remain undescribed in the literature) possess established phosphoinositide binding domains (9 have one or more PH domains; 2 have one or more FYVE domains) establishing the effectiveness of this approach and pointing to the possibility that novel domains may exist in the other proteins identified. Phosphoinositide binding proteins are known to be key components of intracellular signalling pathways used by growth factor receptors and inflammatory stimuli and also of intracellular vesicle trafficking pathways and thus it is anticipated that high-throughput use of the matrices we have created here could be used as a discovery tool for new proteins involved in these pathways and also as a probe for functional expression of established members of these families.

REFERENCES FOR EXAMPLE 3

(15) Toker, A; Cantley, L. C. *Nature* 1997, 387, 673-676.
(16) Rameh, L. E.; Cantley, L. C. *J. Biol. Chem.* 1999, 274, 8347-8350.
(17) Dekker, L. V.; Segal, A. W. *Science* 2000, 287, 982-985.
(18) Corvera, S.; Czech, M. P. *Trends Cell Biol.* 1998, 8, 442-446.
(19) Toker, A. *Curr. Opin. Cell Biol.* 1998, 10, 254-261.
(20) Czech, M. P. *Cell* 2000, 100, 603-606.
(21) Frohman, M. A.; Sung, T. C.; Morris, A. J. *Biochim. Biophys. Acta* 1999, 1439, 175-186.
(22) Exton, J. H. Biochim. Biophys. Acta 1999, 1439, 121-133.
(23) Liscovitch, M.; Czarny, M.; Fiucci, G.; Tang, X. *Biochem. J.* 2000, 345, 401-415.
(24) Painter, G. F.; Thuring, J. W. J. F.; Lim, Z.-Y.; Holmes, A. B.; Hawkins, P. T.; Stephens, L. R. *Chem. Commum.*, submitted.
(25) Chen, J.; Profit, A. A.; Prestwich, G. D. *J. Org. Chem.* 1996, 61, 6305-6312.
(26) For other syntheses of sn-1-aminoacyl PIPn analogues, see: Prestwich, G. D. *Acc. Chem. Res.* 1996, 29, 503-513 and refs. cited therein. Falck, J. R.; Krishna, U. M.; Reddy Katipally, K.; Capdevila, J. H.; Ulug, E. T. *Tetrahedron Lett.* 2000, 41, 4271-4275. Falck, J. R.; Krishna, U. M.; Capdevila, J. H. *Bioorg. Med. Chem. Lett.*, 2000, 10, 1711-1713.
(27) For some recent syntheses of PtdIns(4,5)$P_2$ analogues see: Gu, Q.-M.; Prestwich, G. D. *J. Org. Chem.* 1996, 61, 8642-8647. Falck, J. R.; Krishna, U. M.; Capdevila, J. H. *Tetrahedron Lett.* 1999, 40, 8771-8774.
(28) Painter, G. F.; Grove, S. J. A.; Gilbert, I. H.; Holmes, A. B.; Raithby, P. R.; Hill, M. L.; Hawkins, P. T.; Stephens, L. R., *J. Chem. Soc. Perkin Trans.* 1 1999, 923.
(29) Grove, S. J. A.; Gilbert, I. H.; Holmes, A. B.; Painter, G. F.; Hill, M. L. *Chem. Commun.* 1997,1633-1634.
(30) Desai, J.; Gigg, R.; Gigg, R.; Payne, S. *Carbohydr. Res.* 1992, 225, 209-228.
(31) Wang, D.-S.; Chen, C.-S. *J. Org. Chem.* 1996, 61, 5905-5910.
(32) Desai, J.; Gigg, R.; Gigg, R.; Martin-Zamora, E. *Carbohydr. Res.* 1994, 262, 59-77.

EXAMPLE 4

Identification of Phosphoinositide-Binding Proteins by Targetted Proteomics Using Selective Affinity Matrices Summary Phosphoinositides play a critical role in many cellular regulatory processes and there is a need for a systematic approach to identifying their target proteins. We show that matrices displaying tethered homologues of natural phosphoinositides can be used to capture many phosphoinositide binding proteins in cell and tissue extracts simultaneously and that these proteins can be effectively identified by coupling a simple functional display (based on competition for binding to free phosphoinositides and gel electrophoresis) with mass-spectrometric fingerprinting and/or sequencing. We present the identification of over 20 proteins isolated by this method, mostly from leukocyte extracts: they include known and novel proteins with established phosphoinositide binding domains and also known proteins with surprising and unusual phosphoinositide-binding properties. We also describe the use of these matrices to construct simple and very effective phosphoinositide-binding assays for recombinant proteins expressed in cell lysates or in purified form.

Introduction

Phosphoinositides (PtdIns and its phosphorylated derivatives) are membrane phospholipids that dictate the localisation and function of many intracellular target proteins. These target proteins influence many critical processes in eukaryote cells, including signalling by cell-surface receptors, vesicle trafficking and cytoskeletal assembly and disassembly, and novel phosphoinositide functions continue to emerge (reviewed in Martin, 1998; Toker, 1998; Leevers et al., 1999; Rameh and Cantley, 1999; Cockcroft, 2000). Recent years have seen an increase in the number of known phosphoinositides to eight (PtdIns, PtdIns3P, PtdIns4P, PtdIns5P, PtdIns(3,4)$P_2$, PtdIns(4,5)$P_2$, PtdIns(3,5)$P_2$ and PtdIns(3,4,5)$P_3$), making the analysis of their functions ever more complex.

Some selective interaction between a particular phosphoinositide and a discriminatory phosphoinositide-binding domain(s) in an involved protein is central to most phosphoinositide-regulated events. Some pleckstrin homology (PH) domains selectively bind PtdIns(4,5)$P_2$, some have a particular affinity for PtdIns(3,4,5)$P_3$ and/or PtdIns(3,4)$P_2$, and others bind anionic phospholipids non-selectively (Lemmon and Ferguson, 2000). Some C2B domains bind PtdIns(3,4,5)$P_3$ and PtdIns(4,5)$P_2$ (e.g. Schiavo et al., 1996) and some FYVE domains selectively bind PtdIns3P (e.g. Stenmark and Aasland, 1999; Burd and Emr, 1998).

Once the phosphoinositide-binding properties of particular domain types were recognised, additional phosphoinositide-binding proteins were speedily identified by cloning novel molecules found in genome databases (e.g. Isakoff et al., 1998; Dowler et al., 2000). However, a major limitation of this approach is that it cannot identify phosphoinositide-binding sites that do not belong to one of these recognised domain families. There are now many proteins that have been established to bind phosphoinositides, mainly by various ad hoc strategies, but within which primary sequence determinants have not yet been defined: e.g. several cytoskeletal/focal adhesion proteins (Flanagan and Janmey, 2000), signalling proteins (e.g. the MARCKS-protein, Wang et al., 2000) or proteins involved in vesicle trafficking (e.g. the AP2 adaptor, Gaidarov and Keen, 1999). The problem of identifying protein targets is most severe when studying recently discovered phosphoinositides (e.g. PtdIns5P, PtdIns(3,5)P$_2$; Rameh et al., 1997; Dove et al., 1997) for which there is no paradigmatic information.

An ideal way to get an overview of the constellation of proteins that interact specifically with one or more of the phosphoinositides would be by screening protein mixtures from cells or tissues with an assumption-free proteomic method. 'Proteomnics' is often taken to mean mapping of the expression of all proteins (e.g. by 2-D gels followed by high-throughput mass spectrometry) in a manner akin to microarray analysis of a cell's entire mRNA complement—but this cannot yield information on protein interactions with other proteins, with nucleic acids or with small molecules. To learn about these, targetted analyses of macromolecular interactions must be used to define function-critical subsets of the proteome.

Affinity matrices derivatised with synthetic phosphoinositides offer one such approach. Previous studies using matrices carrying Ins(1,3,4,5)P$_4$-like structures [isosteric with the PtdIns(3,4,5)P$_3$ headgroup; Hammonds-Odie et al., 1996; Stricker et al. 1997; Shirai et al. 1998; Tanaka et al. 1997] or linked to biotinylated diC$_8$-PtdIns(3,4,5)P$_3$ (Rao et al. 1999) have identified a few novel PtdIns(3,4,5)P$_3$-binding proteins. This encouraged us to think that we might efficiently identify multiple phosphoinositide-binding proteins from a single tissue by combining protein isolation on new affinity matrices carrying the tethered homologues of natural phosphoinositides with protein identification by state-of-the-art technologies. To avoid false positives, we would target proteins whose binding was competitively inhibited by free phosphoinositides.

In this example, we report such surveys of the phosphoinositide-binding proteins of several tissues, particularly neutrophils. Not only have we isolated many proteins with established phosphoinositide-binding domains, including two novel proteins with PH domains and two novel proteins with FYVE domains, but we also identified members of previously untargetted protein families which reveal unexpected phosphoinositide-binding properties.

Results

Figure 6:
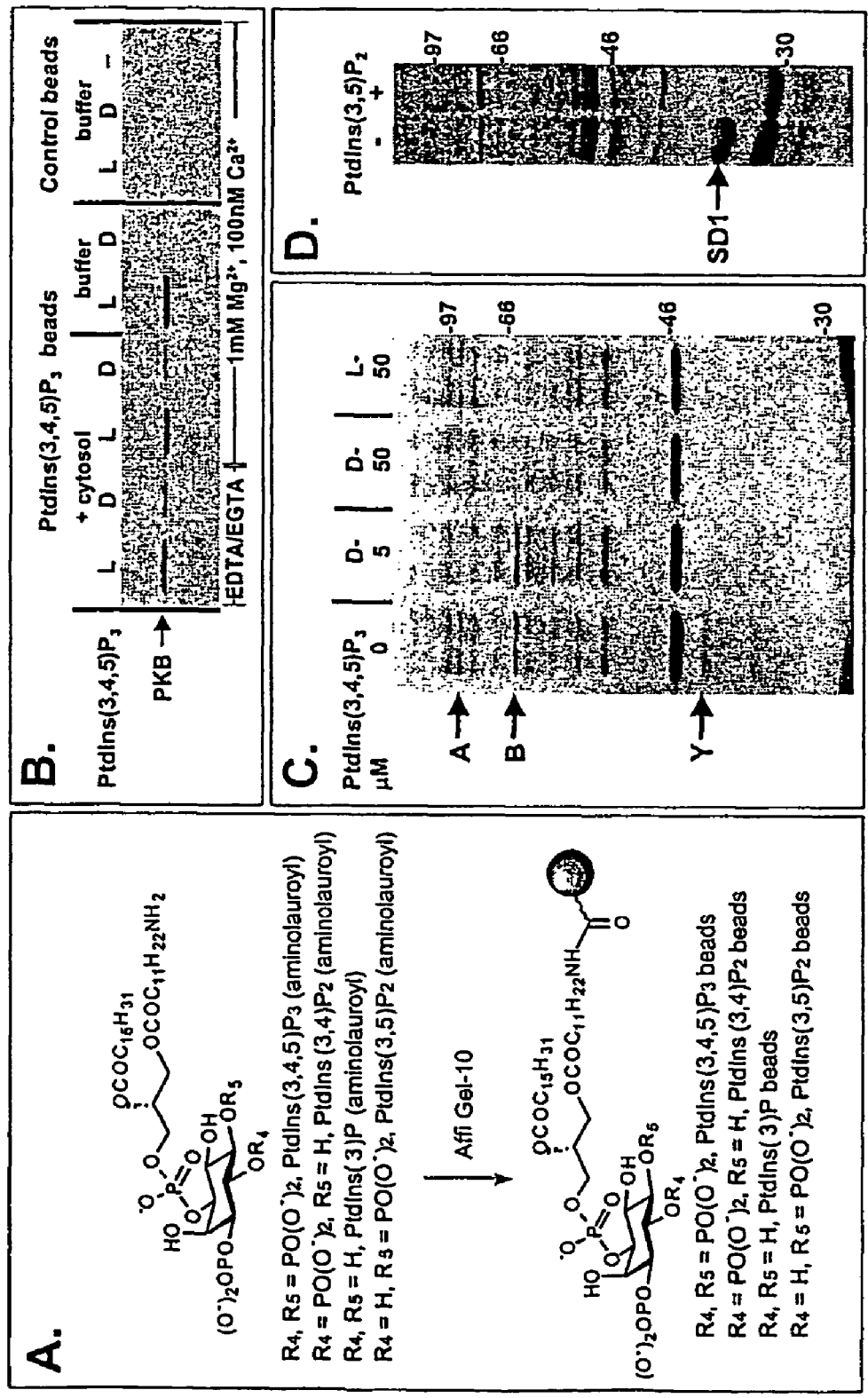
FIG. 6. Phosphoinositide-derivatised beads: structures and protein-binding properties. Structures of the beads. B. Binding of recombinant protein kinase B to $PtdIns(3,4,5)P_3$ beads. Purified N-terminally EE-tagged PKB (100 nM) was incubated with leukocyte cytosol (~4 mg ml$^{-1}$ protein) or buffer, in the presence of the indicated $PtdIns(3,4,5)P_3$ stereoisomer (20 μM). In some samples, EDTA was replaced with 1 mM $MgCl_2$ and EGTA by a $Ca^{2+}$/EGTA buffer ($[Ca^{2+}]$=100 nM). Samples (1 ml) were mixed with $PtdIns(3,4,5)P_3$-derivatised or ethanolamine-derivatised (control) Affigel-10 (10l) for 45 min. Bead-bound PKB was detected after washing by SDS-PAGE and an anti-EE immunoblot. In the absence of PtdIns $(3,4,5)P_3$, ~1% of the added PKB was bead-bound. C, D. Examples of the binding of phosphoinositide-binding proteins in total cytosol extracts to the derivatised beads. In C, Pig leukocyte cytosol (4.5 ml; 8 mg ml$^{-1}$ protein) was incubated with free D- or L-$PtdIns(3,4,5)P_3$, and aliquots were mixed with $PtdIns(3,4,5)P_3$ beads (20 l; see Methods). In D, Rat liver cytosol (1 ml; 7.5 mg ml$^{-1}$ protein) was, incubated with $PtdIns(3,5)P_2$ beads (10 l), with or without 20 μM free $PtdIns(3,5)P_2$ (see Methods). Proteins that remained bound after washing were separated by SDS-PAGE and silver-stained: the positions of m.w. markers are shown. Arrows identify abundant proteins whose binding was competed effectively by free phosphoinositides (these are labelled according to the identities that were later given to them after ion-exchange separations of similar extracts, see FIGS. 7, 8 and Table1).

The Use of PtdIns(3,4,5)P$_3$-delivatised Beads to Isolate PtdIns(3,4,5)P$_3$-binding Proteins From Leukocytes FIG. 6a shows the nature of the derivatised beads used in this study. Initial experiments defined conditions for identifying proteins that bound specifically to the PtdIns(3,4,5)P$_3$ moiety on the PtdIns(3,4,5)P$_3$-derivatised beads. In the adopted assay, tissue samples were pre-incubated, with or without a competing phosphoinositide (usually PtdIns(3,4,5)P$_3$), at near-physiological salt concentration ($\geq$0.1 M NaCl) and with a non-ionic detergent ($\geq$0.1% NP40) and reagents likely to inhibit PtdIns(3,4,5)P$_3$ hydrolysis ($\beta$-glycerophosphate, F$^-$, orthovanadate, divalent cations chelated). They were then incubated with PtdIns(3,4,5)P$_3$ beads, and proteins that were retained by the beads were identified by SDS-PAGE. FIG. 6b demonstrates that D-PtdIns(3,4,5)P$_3$ stereospecifically inhibited the binding of recombinant protein kinase B (PKB), an established PtdIns(3,4,5)P$_3$ target (e.g. Stephens et al., 1998), to bead-bound D-PtdIns(3,4,5)P$_3$, and that leukocyte cytosol had little effect on its binding. These results suggested that the PtdIns(3,4,5)P$_3$ on the beads was displayed effectively and that the derivatised beads might provide a facile route for isolating phosphoinositide target proteins.

Figure 7:
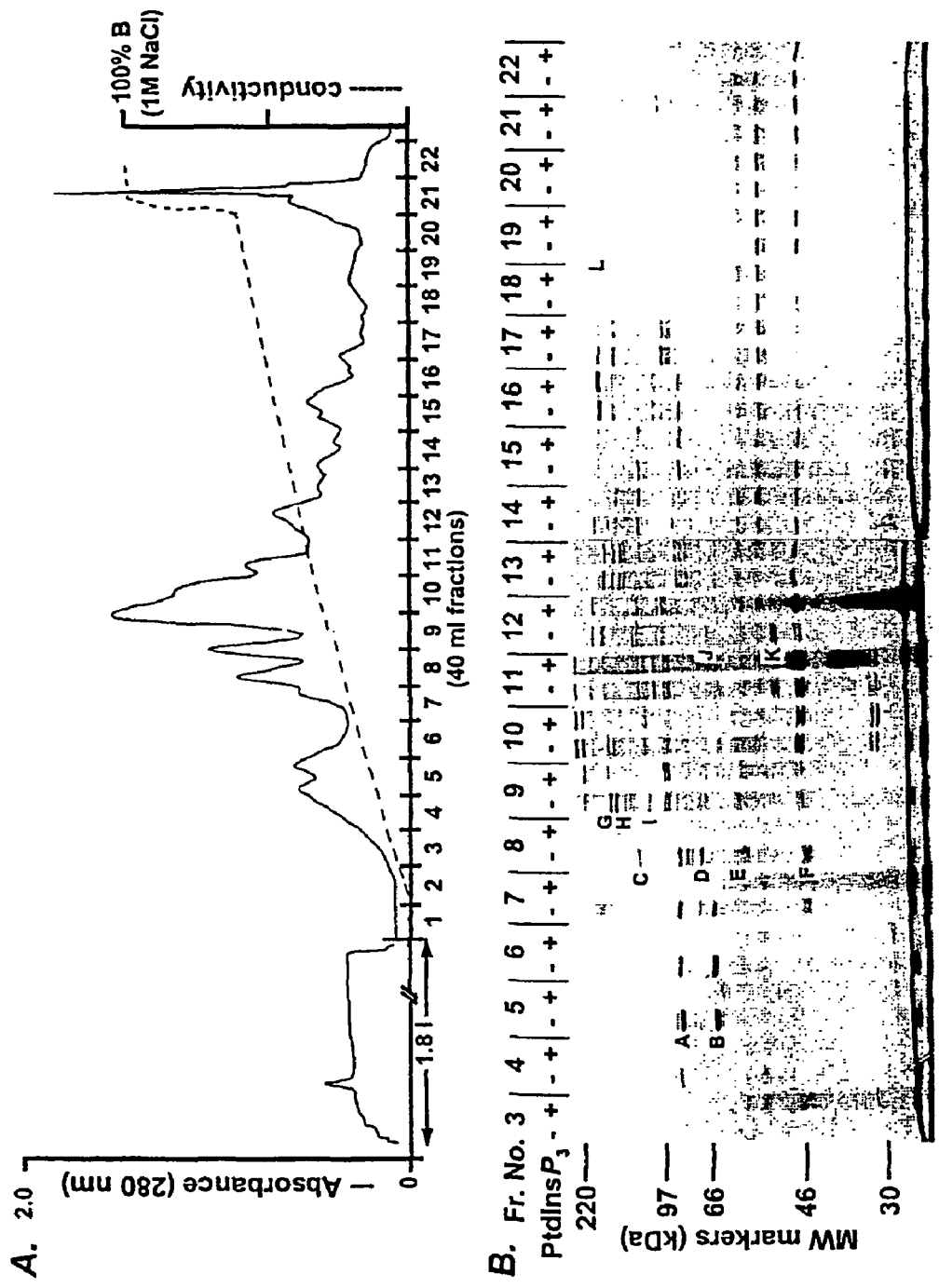
FIG. 7. Anion-exchange chromatography of pig leukocyte cytosol proteins that bind $PtdIns(3,4,5)P_3$. Cytosolic protein (~3 g) was fractionated by anion-exchange chromatography (Q-Sepharose HR; see Methods). A. Conductivity and absorbance traces. B. Silver-stained SDS-PAGE gel of proteins that bound to $PtdIns(3,4,5)P_3$ beads, with and without 50 μM $PtdInS(3,4,5)P_3$. Bands A-L, whose binding was inhibited by $PtdIns(3,4,5)P_3$, were isolated from a scaled-up separation (see Methods). Table 1 lists proteins that have been identified.
Figure 8:
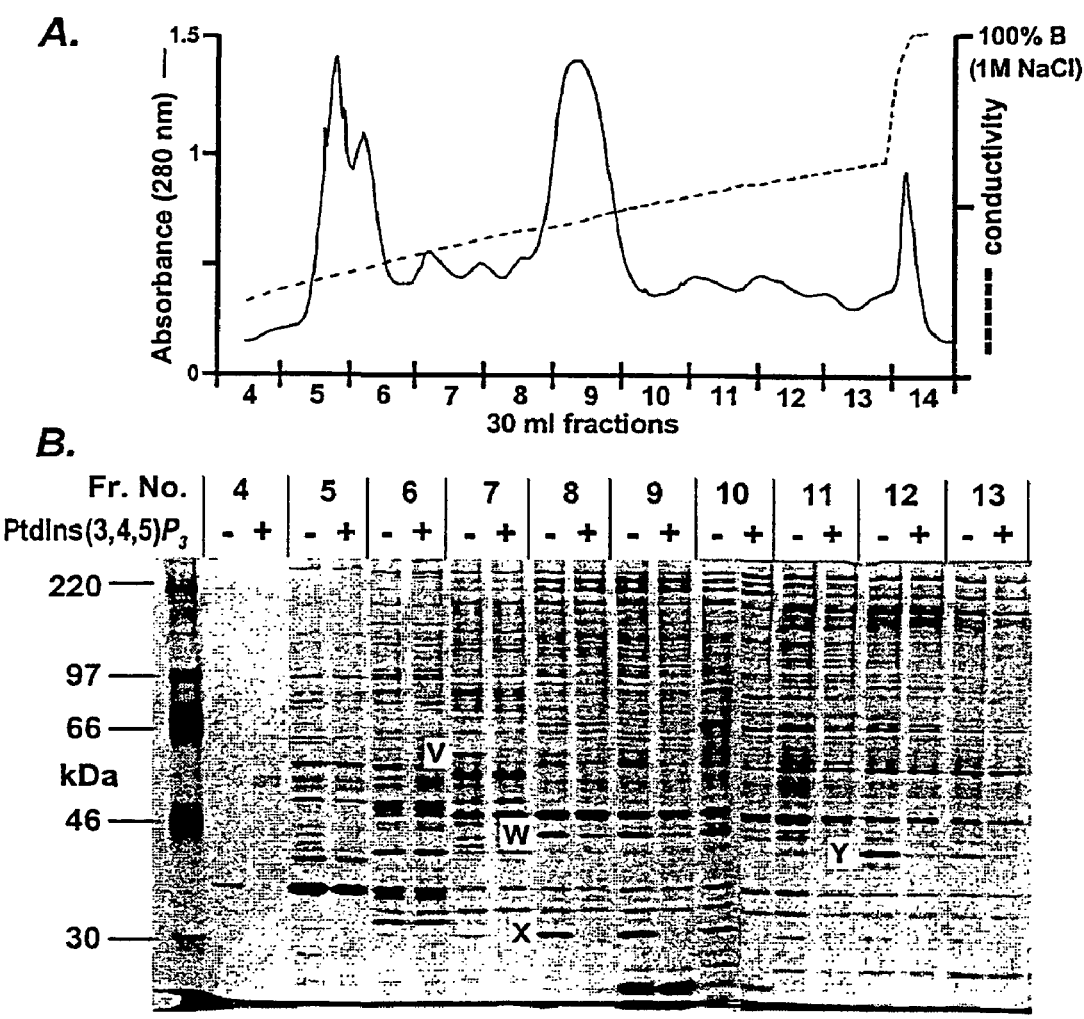
FIG. 8. Cation-exchange chromatography of pig leukocyte cytosol proteins that bind $PtdIns(3,4,5)P_3$. Pig leukocyte cytosol (~2.4 g protein) was separated by cation-exchange chromatography (S-Sepharose HP; see Methods). A. Conductivity and absorbance traces. B. Silver-stained SDS-PAGE gel showing proteins recovered on $PtdIns(3,4,5)P_3$ beads after incubation with or without 25 μM $PtdIns(3,4,5)P_3$. $PtdIns(3,4,5)P_3$ inhibited the binding of bands V-Y, which were isolated from a scaled-up separation (see Methods). Table 1 identifies some of these proteins.
Figure 9:
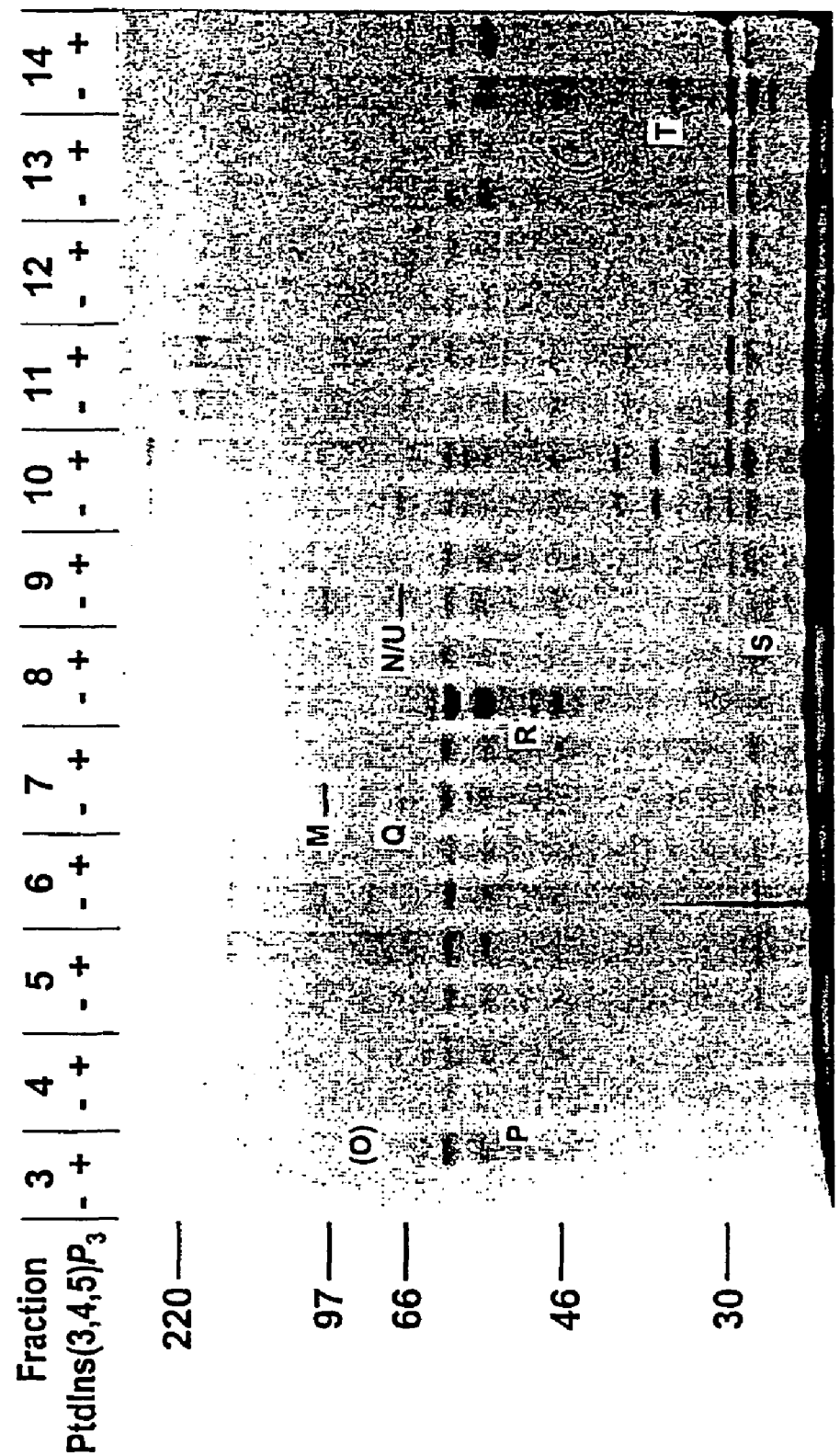
FIG. 9. Anion-exchange chromatography of NP-40-solubilised pig leukocytemembrane $PtdIns(3,4,5)P_3$ binding proteins. NP-40-solubilised pig leukocyte membranes (~90 mg protein) were separated by anion-exchange chromatography on Q-Sepharose HR (see Methods). A silver-stained SDS-PAGE gel shows the proteins recovered from $PtdIns(3,4,5)P_3$ beads after incubation with or without 27 μM $PtdIns(3,4,5)P_3$. The major bands whose binding was inhibited by $PtdIns(3,4,$ $5)P_3$ are designated M-U and were isolated by scaled-up assays (see Methods). The identities of some of these are in Table 1.

We are currently trying to understand the function of the phosphoinositide 3-kinase signalling system in neutrophils, so much of the work employed pig leukocyte cytosol as an abundant source of relevant PtdIns(3,4,5)P$_3$-binding proteins. The binding of several cytosolic proteins to the PtdIns(3,4,5)P$_3$-beads was inhibited by free PtdIns(3,4,5)P$_3$ (D- or L-isomer, or both), but many other proteins interacted with the beads in a PtdIns(3,4,5)P$_3$-independent way (FIG. 6c), making it difficult to recover proteins of interest in sufficient purity for unambiguous identification. We reduced the protein complexity of the samples applied to the beads by first fractionating them by ion-exchange chromatography. Using this approach we were able to isolate several proteins in sufficient yield and purity to attempt their identification (A-L, FIG. 7; V-Y, FIG. 8). We also screened various detergent and high salt (1 M NaCl) extracts of leukocyte membranes for PtdIns(3,4,5)P$_3$-binding proteins, and proteins M-U were isolated from chromatographically fractionated NP40 extracts (FIG. 9).

Identification of PtdIns(3,4,5)P$_3$-Binding Proteins

Some of the proteins isolated were digested with trypsin and identified by mass fingerprinting and sequencing (see Methods and Table 1). This identified: porcine orthologues of four characterised PtdIns(3,4,5)P$_3$-binding proteins (rasGAP$^{IP4BP}$, BTK, ETK and centaurin-$\alpha$); five proteins (C, E, F, G/H, and X) that were novel at the time of isolation; and porcine orthologues of seven proteins that were not known to bind PtdIns(3,4,5)P$_3$-rho/CDC42 GTPase-activating protein (CDC42-GAP), myosin 1F, megakaryocyte protein-tyrosine phosphatase (MEG2), Type II inositol polyphosphate 5-phosphatase and/or ezrin (both present in band D), and the $\alpha$ and $\beta$ subunits of mitochondrial fatty acid oxidase.

We cloned the human orthologues of proteins C, E, F, G/H, and X: near-identical ORFs have been independently described for F (cytohesin-4; Ogasawara et al., 2000), X (DAPP1, Dowler et al., 1999; also termed PHISH, Rao et al., 1999; or Bam32, Marshall et al., 2000) and C (PLC-L2, Otsuki et al., 1999). Schematic "domain profiles" for these proteins are in FIG. 10.

Proteins Isolated on PtdIns(3,4)P$_2$, PtdIns(3,5)P$_2$ and PtdIns3P Matrices

We also analysed cytosol from pig platelet, sheep brain, sheep liver and rat liver for proteins that bound to beads derivatised with PtdIns(3,4)P$_2$, PtdIns(3,5)P$_2$ or PtdIns3P, particularly focussing on proteins that were not readily displaced by PtdIns(3,4,5)P$_3$ and so might selectively bind other phosphoinositide(s). The PtdIns(3,4)P$_2$ and PtdIns(3,5)P$_2$ beads showed a limited degree of non-phosphoinositide-dependent protein binding (an example of using the PtdIns(3,5)P$_2$ beads to isolate proteins from rat liver cytosol is given in FIG. 6d), but there was a high background of non-specific protein adsorption to PtdIns3P beads, so it was hard to characterise genuine PtdIns3P-dependent binding (not shown).

Several proteins were isolated from the fractionated cytosols (SR1-SR7 and SD1: Table 1 gives their tissue and bead origins). Type C 6-phosphofructokinase (PFK-C) was isolated on PtdIns3P beads, vinculin on PtdIns(3,4)P$_2$ beads and -tocopherol trasfer protein (ATTP) on PtdIns(3,5)P$_2$ and PtdIns(3,4)P$_2$ beads. The PtdIns3P and PtdIns(3,4)P$_2$ beads also yielded two proteins that were novel at the time of isolation (SR1 and SR$_3$; Table 1). The human orthologues of SR1 and SR3 were cloned (FIG. 10) and very recently a near identical ORF has been described for SR3 (DFCP-1; Derubeis et al 2000).

The Phosphoinositide-Binding Specificities of Recombinant Proteins

Several of the proteins were made in recombinant form in Cos-7 cells, E. coli or baculovirus-infected Sf9 cells. We purified CT-EE-tagged $PIP_3$-G/H, NT-EE-SR1, NT-EE-SR3 and NT-EE-myosin IF from Sf9 cells; and GST-CDC42GAP, GST-cytohesin-4, GST-MEG2, GST-DAPP1 and HIS-ATTP from E. coli. We could not purify full-length $PIP_3$-E, but obtained an N-terminal truncation containing its PH domain (residues 40-437).

We investigated the relative abilities of various phosphoinositides to compete with the binding to $PtdIns(3,4,5)P_3$ or $PtdIns(3,4)P_2$ beads of tagged and purified proteins (EE-, GST- or His-; some tags were removed by thrombin cleavage; see Methods) and of proteins heterologously expressed in Cos-7-cell lysates (N-terminally myc- or GFP-tagged). With lysates, assays were run under conditions similar to those used to isolate the proteins—with micellar NP40, physiological salt, EDTA and other reagents to minimise phosphoinositide metabolism (see Methods). Assays on purified proteins used micellar NP40 in PBS, with 1 mM $MgCl_2$ to approximate to the physiological divalent cation environment and minimise the stripping of $Zn^{2+}$ from FYVE domains.

Figure 11:
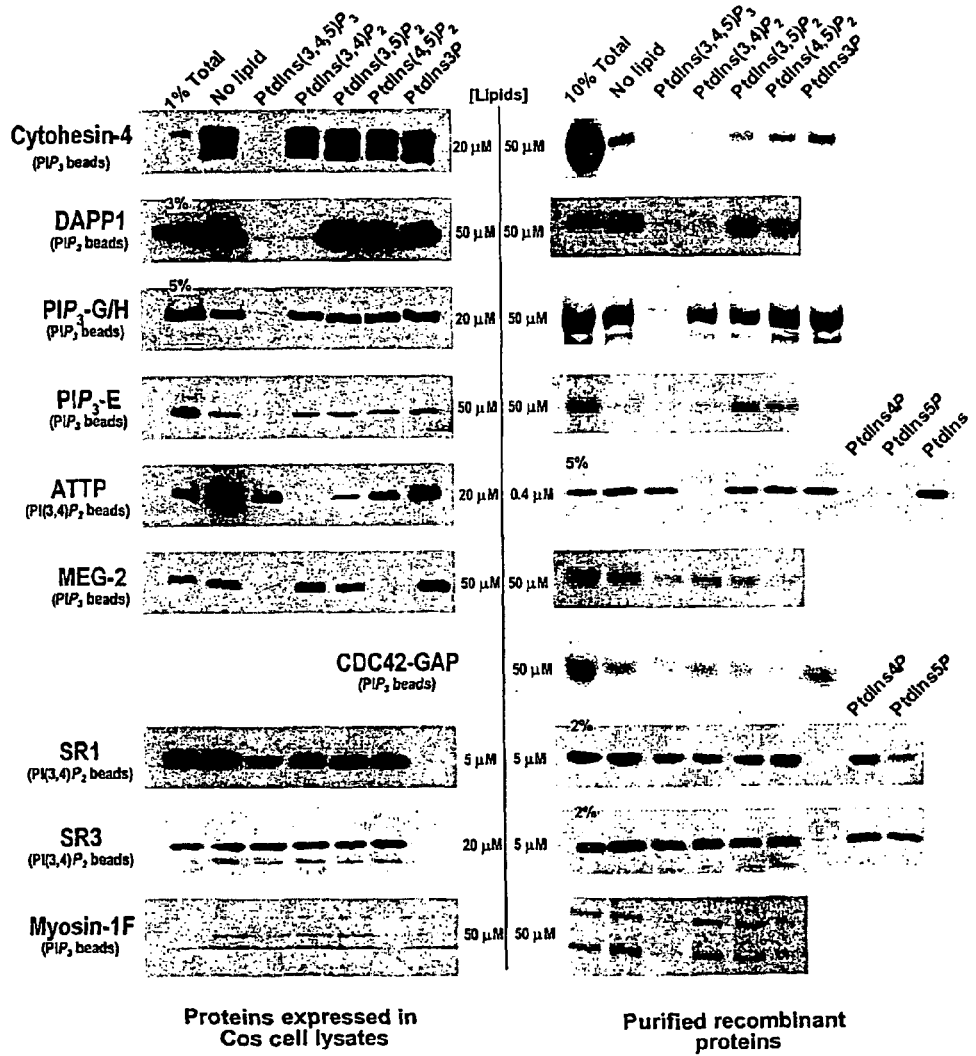
FIG. 11. Protein binding to derivatised beads: inhibition by free phosphoinositides. Recombinant proteins (in Cos cell lysates or expressed and purified) were bound to $PtdIns(3,4,$ $5)P_3$ or $PtdIns(3,4)P_2$ beads in the presence of various free phosphoinositides (for details, see Methods). For $PIP_3$-E, a full length construct was expressed in Cos cells while a truncated version (residues 40-437) was purified from *E.Coli*. In the examples shown, all lipids were presented to a particular protein at the same concentration—this was chosen as a concentration at which the most effective lipid showed just-maximal competition. Unless otherwise indicated, the first lane was loaded with a sample equivalent to 1% (Cos cell lysates) or 10% (purified recombinant proteins) of the protein sample that was incubated with beads. As appropriate, tagged proteins were detected with antibodies (anti-myc, anti-GFP, anti-HIS, or anti-EE; see Methods) or by silver-staining ($PIP_3$-G/H-EE, EE-myosin 1F, GST-cytohesin-4, DAPP1, $PIP_3$-E, MEG-2 and CDC42-GAP). For each protein, the data shown are representative of information collected in 4 independent experiments.

FIG. 11 shows examples of the results obtained: for each protein the competing phosphoinositides were all at one concentration, chosen to achieve just maximal inhibition by the most effectively competing lipid. Since the surface lipid concentrations on the derivatised beads are unknown, and may vary between batches and during multiple rounds of bead re-use, the results indicate only the relative affinities of the relevant binding sites on the proteins for various phosphoinositides. Several of the relative affinity screens were replicated with pure proteins and Cos-7 cell lysates, so the results are likely to reflect the intrinsic phosphoinositide-binding properties of the proteins. The PH domain-containing proteins all bound to $PtdIns(3,4,5)P_3$ beads and were displaced most effectively by $PtdIns(3,4,5)P_3$ (cytohesin-4, $PIP_3$-G/H, $PIP_3$-E) or equally by $PtdIns(3,4,5)P_3$ and $PtdIns(3,4)P_2$ (DAPP1). By contrast, the FYVE domain-containing proteins (SR1 and SR3) were harvested with $PtdIns(3,4)P_2$ beads, and PtdIns3P displaced them most effectively. SR3 bound better to $PtdIns(3,4)P_2$ beads that were being re-used, maybe because of their partial conversion to PtdIns3P (not shown).

Our isolation of three proteins containing Sec14 domains was unexpected, and they had different and unusual binding specificities. α-tocopherol-transfer protein (ATTP) was displaced most effectively from $PtdIns(3,4)P_2$ beads by $PtdIns(3,4)P_2$, PtdIns4P or PtdIns5P. MEG2 was displaced most effectively from $PtdIns(3,4,5)P_3$ beads by $PtdIns(3,4,5)P_3$ or $PtdIns(4,5)P_2$. CDC42GAP bound weakly to $PtdIns(3,4,5)P_3$ or $PtdIns(4,5)P_2$ beads (data not shown), and was poorly displaced by the phosphoinositides tested ($PtdIns(4,5)P_2$ and $PtdIns(3,4,5)P_3$ were the most effective). Myosin IF bound to $PtdIns(3,4,5)P_3$ beads and was displaced best by $PtdIns(3,4,5)P_3$ or $PtdIns(4,5)P_2$.

Figure 12:
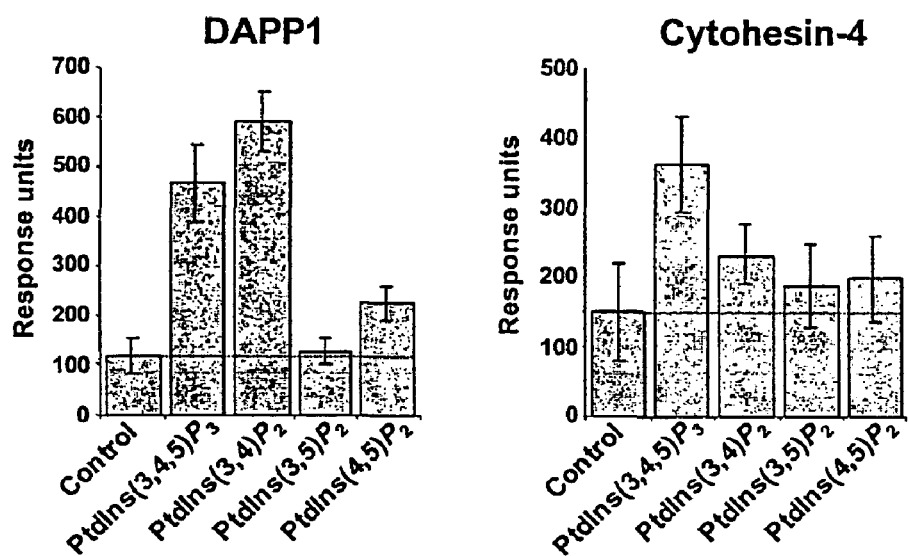
FIG. 12. Binding of DAPP1 and GST ytohesin4 to phosphoinositide-containing PtdEtn/PtdCho/PtdSer (1:1:1) surfaces on an HPA sensor-chip (see Methods). The data represent the mean±S.E.M. (n=36 independent determination) of the mass of protein binding at equilibrium to the chip surface after flowing 100 nM recombinant $DAPP_1$ or GST-cytohesin-4 over the chip.

Surface Plasmon Resonance Analysis of Binding to Phosphoinositide-doped Lipid Monolayers We used a surface plasmon resonance (SPR) biosensor to analyse and characterise the binding of some proteins to lipid surfaces of defined composition. FIG. 12 shows the binding of DAPP1 and cytohesin-4 to self-assembled PtdEtn/PtdSer/PtdCho (1:1:1) monolayers on alkane-coated HPA chips. Both proteins bound weakly to this surface, and binding was promoted by small proportions of phosphoinositides (usually 3-10 mole percent). In accord with the specificities from the bead displacement assays, cytohesin-4 bound best to surfaces containing $PtdIns(3,4,5)P_3$ and DAPP1 to surfaces containing $PtdIns(3,4,5)P_3$ or $PtdIns(3,4)P_2$. These results are consistent with the receptor-driven, and phosphoinositide 3-kinase-dependent, recruitment of DAPP1 (Anderson et al., 2000; Marshall et al., 2000) and cytohesin-4 (A. McGregor, data not shown) from the cytosol to the plasma membranes of stimulated cells.

We also examined $PIP_3$-G/H, SR3, ATTP, MEG2 and CDC42GAP, but it was difficult to assess their phosphoinositide affinities because they all bound strongly to the PtdEtn/PtdSer/PtdCho surface.

Discussion

The affinity matrix-based approach that we used to capture, display and identify a substantial number of phosphoinositide-binding proteins makes no prior assumptions about the nature of such binding proteins, such as the possession of a particular domain(s). It rapidly identifies multiple proteins by a three-step protocol—a cell fraction is chromatographically sub-fractionated, fractions are screened for proteins that bind to phosphoinositides, and proteins are identified by mass spectrophotometric fingerprinting and/or sequencing. We re-isolated 14 previously known proteins and identified, cloned and characterised seven new phosphoinositide-binding gene products, the ORFs for three of which remain undefined in the databases (SR1, $PIP_3$-E and $PIP_3$-G/H). The sequences of these ORFs are given below. The retrieval of several, now authenticated $PtdIns(3,4,5)P_3$-binding proteins validates this method ie. BTK, ETK, centaurin-α and DAPP1 (Li et al., 1997; Qiu et al., 1998; Jackson et al., 2000; Anderson et al., 2000; Dowler et al., 1999; Marshall et at., 2000). In addition, we isolated cytohesin-4, which is the newest member of a family of Arf GTP-exchangers with established credentials as $PtdIns(3,4,5)P_3$ effectors (e.g. Jackson et al., 2000).

We also identified several phosphoinositide-binding proteins that earlier screens did not detect. Some are novel ($PIP_3$-E; $PIP_3$-G/H; SR1), whilst others are previously known proteins whose phosphoinositide affinities were not previously recognised (ATTP; MEG2; CDC42GAP; mitochondrial fatty acid oxidase; Type C phosphofructokinase). It was also clear from inspection of the original gels of fractionated cytosol and membrane extracts that many more phosphoinositide-binding proteins were present than we have identified (we estimate more than 30 proteins in leukocyte cytosol alone). We note, for example, that some important $PtdIns(3,4,5)P_3$ targets (e.g. PKB and PDK-1) have not yet emerged from this screen.

We identified many more proteins that interact specifically with acutely regulated phosphoinositide messengers, particularly $PtdIns(3,4,5)P_3$, than with phosphoinositides implicated in intracellular processes such as membrane trafficking (e.g. PtdIns3P). $PtdIns(3,4,5)P_3$ may genuinely have many more target proteins than other phosphoinositides, but it is also possible that our harvest retrieved fewer protein targets of the less highly charged phosphoinositides because these are harder to identify. $PtdIns(3,4,5)P_3$ may tend to have a higher affinity for its effectors than PtdIns3P, making it easy to discriminate between specific and non-specific binding. Moreover, phosphoinositide-binding proteins that are involved in membrane trafficking often require multiple functional interactions with membranes. For instance, EEA1 only associates with early endosomes whose membranes simultaneously contain both PtdIns3P and rab5 (Lawe et al., 2000). In such situations, proteins that recognise phosphoinositides need a fairly low phosphoinositide affinity, so that functional association with a membrane will require both interactions. In this regard, it will be interesting to examine the role of PtdIns3P binding in the localisation of our novel FYVE domain-containing proteins (SR1 and SR3). The sequence of the SR3 ORF is given below.

Our identification of a trio of polyphosphoinositide-binding proteins that contain SEC14-like domains (ATTP, MEG2, and CDC42GAP) was unexpected. Designation of a SEC14 domain relies on sequence homology with the canonical yeast PtdIns transfer protein Sec14p (Bankaitis et al., 1990; Alb et al., 1995). Eukaryote databases currently contain more than one hundred SEC14 domain-containing proteins, but with no consensus on any shared common function. It has been reported that several other SEC14 domain-containing yeast proteins catalyse inter-membrane PtdIns transfer (Li et al., 2000), and that two SEC14 domain-containing proteins from soybean, Ssh1p and Ssh2p, bind PtdIns(4,5)$P_2$ (Ssh2p) and either PtdIns(4,5)$P_2$ or PtdIns(3,5)$P_2$ (Ssh1p) (Kearns et al., 1998).

Even with this background, polyphosphoinositide binding by ATTP, MEG2, and CDC42GAP, which have no obvious links to phosphoinositide function, was a surprise. These proteins are thought to have very different functions: ATTP is involved in intracellular-tocopherol trafficking (Arita et al., 1995), CDC42GAP stimulates GTP hydrolysis by the small GTPase CDC42 (Lancaster et al., 1994; Barfod et al., 1993), and MEG2 is a haemopoietic protein-tyrosine phosphatase (Gu et al., 1992). They show no sequence similarity outside the SEC14 domain, so their SEC14 domains probably bind polyphosphoinositides—but why remains to be determined. These results make it likely that a subset of the many SEC14 domain-containing proteins constitutes an unrecognised class of proteins with a propensity for binding PtdIns and/or phosphorylated PtdIns derivatives. This idea is intriguing, given that SEC14 domains often occur in proteins involved in signalling: for example, additional protein-tyrosine phosphatases; GEFs and GAPs that regulate the guanine nucleotides status of Rho and Ras (including neurofibromin-related protein NF-1); and a diacyglycerol kinase-related protein from Drosophila.

A striking feature was how many of the proteins that we harvested are involved, directly (myosin 1F, ezrin, vinculin) or indirectly (via the control of rho family GTPases; cytohesin-4, α-centaurin, $PIP_3$-G/H), in control of the cytoskeleton. The sequence of the myosin-1F ORF is shown below. It is becoming ever clearer that phosphoinositides have essential roles in coordinating the complex spatial and temporal events underlying cell adhesion and movement (see Martin, 1998; Flanagan and Jamney, 2000), and relating the phosphoinositide-binding properties of individual proteins to an understanding of these processes is a major challenge.

We do not understand why phosphofructokinase type C and mitochondrial fatty acid oxidase were recovered on our phosphoinositide-beads: evidence for any physiological significance of these interactions can only come from further work.

We not only used the derivatised beads to isolate the above proteins, but also showed that they can be used to establish the phosphoinositide-binding selectivities of proteins: we provide data on nine proteins that are either novel or previously uncharacterised in this respect. This method is quick and avoids many of the presentational and practical problems inherent in other methods, such as binding to phosphoinositides displayed on nitrocellulose or on Biacore chips. It would seem relatively straight forward to convert this method to a high-throughput format which could be used to screen for compounds which interfere with phosphoinositide binding to recombinant proteins. The phosphoinositide selectivities that were determined using these beads confirmed the conclusions from earlier studies of the same proteins by other methods. For example, cytohesins are highly selective towards PtdIns(3,4,5)$P_3$ (Klarlund et al., 1998), but DAPP1/PHISH/Bam32 binds PtdIns(3,4,5)$P_3$ or PtdIns(3,4)$P_2$ (Kavran et al., 1998; Dowler et al., 1999). It is therefore likely that $PIP_3$-G/H and $PIP_3$-E, which are newly isolated and showed clear PtdIns(3,4,5)$P_3$ selectivity, are genuine PtdIns(3,4,5)$P_3$ targets.

In summary, we have used a targetted proteomic approach to screen cell and tissue extracts for proteins that bind with high specificity to phosphoinositides displayed on synthetic affinity matrices and to identify these proteins by mass spectrometry. These affinity matrices retrieved phosphoinositide-binding proteins even from quite complex protein mixtures, suggesting it will be possible to use this approach in conjunction with modern 2-D gel/high-throughput mass spectrometry technologies to rapidly screen for variations in the expression of phosphoinositide-binding proteins. In this regard, it is well established that some Bruton's tyrosine kinase PH domain mutations destroy BTK's ability to bind PtdIns(3,4,5)$P_3$ with high affinity and cause X-linked immunodeficiency (Vetrie et al., 1993); and mutations that disrupt ATTP cause a severe and progressive ataxia (Ben Hamida et al., 1993), apparently by disrupting α-tocopherol delivery to the brain. Both would prevent the proteins from being retrieved from the patients' cell extracts, raising the possibility of screening cell extracts from other patients with possible cell regulatory defects for changes in the their profiles of functional phosphoinositide-binding proteins.

Experimental Procedures

Isolation of Cells, Preparation of Cell Fractions and Protein Fractionation

Isolation procedures were at 0-4° C., using buffers adjusted at 4° C. Isolated preparations were used immediately or "snap-frozen" in liquid $N_2$ and stored at −80° C.

Pig Leukocytes

Isolation. Fresh blood was mixed with 0.146 volumes of ACD (80 mM trisodium citrate, 18 mM $NaH_2PO_4.H_2O$, 15.6 mM citric acid, 161 mM D-glucose). One fifth of a volume of 3% PVP/0.91% (w/v) NaCl was added, erythrocytes were allowed to settle, and the upper layer was centrifuged (500× $g_{av}$ 8 min). The leukocyte pellet was suspended in calcium-free Hanks medium and cells were collected by centrifugation and briefly shocked (20 sec; >20 volumes of ice-cold $H_2O$). The suspension was re-adjusted to the composition of Hanks' medium, and the cells were collected and washed in calcium-free Hanks. 30-40 l blood typically yielded 100-150 ml of packed cells.

Cytosol. Leukocytes were washed with 40 mM Tris-HCl (pH 7.5), 120 mM NaCl, 2.5 mM $MgCl_2$ (500×$g_{av}$, 10 min) and 1 volume of cells was suspended in 4 volumes of lysis buffer (100 mM NaCl, 40 mM Tris-HCl pH 7.5, 2 mM EGTA, 2.5 mM $MgCl_2$, 1 mM DTT, 0.1 mM PMSF and 10 µg.ml$^{-1}$ each of protease inhibitors (aprotinin, leupeptin, antipain and pepstatin A: ALAP). Cells were disrupted by sonication (4×12 sec; Heat systems probe sonicator, 1.2 cm tip), and the homogenate was centrifuged (900×$g_{av}$ for 10 min, then 160,000×$g_{av}$ for 60 min). 100 ml cell pellet gave ~250 ml cytosol containing ~2 g protein.

Anion-exchange chromatography of cytosol. Cytosol (3 g protein) was thawed and 0.1 mM PMSF and a protease inhibitor mixture (ALAP: see above) were added. After centrifugation (160,000×$g_{av}$; 30 min), the supernatant was filtered (0.2 µm cellulose acetate; glass microfibre prefilter, Whatman), diluted 4-fold with 30 mM Tris/HCl, pH 7.5, 0.04% Tween-20, 0.5 MM EGTA, 0.1 mM EDTA, 1% betaine, 0.01% azide, 1 mM DTT and 0.1 mM PMSF, and pumped at 5 ml min$^{-1}$ onto a 2.6×16 cm (~75 ml) Pharmacia Q-Sepharose HR column. Elution at 3.5 ml min$^{-1}$ used a linear NaCl gradient (750 ml, from 0 to 0.5 M; 22×40 ml fractions) in 30 mM Tris-HCl, pH 7.5, 0.5 mM EGTA, 0.1 mM EDTA, 0.03% Tween-20, 1% betaine, 1 mM DTT, 0.01% azide. 0.8 ml samples of the fractions were assayed for proteins binding to 10 µl PtdIns(3,4,5)P$_3$-beads in the presence or absence of 50 µM PtdIns(3,4,5)P$_3$ (see below). Fractions of interest were pooled and proteins A-L (see FIG. 7) were isolated by a scaled up procedure on 0.1-0.2 ml PtdIns(3,4,5)P$_3$-beads (see below).

Cation-exchange chromatography of cytosol. Cytosol (2.4 g protein) was thawed, protease inhibitors (ALAP, see above) were added, the mixture was centrifuged and filtered (see above), adjusted to pH 6.7 (Hepes), diluted 5-fold in 30 mM Hepes, pH 6.7, 0.0625% Tween-20, 1% betaine, 1 mM dithiothreitol and 0.0125% azide, and loaded (3.5 ml. min$^{-1}$) onto a 2.6×16 cm Pharmacia S-Sepharose HP cation-exchange column. Elution at 3.5 ml min$^{-1}$ used a linear NaCl gradient (400 ml; 3.5 ml. min$^{-1}$; 0 to 0.5 M; 15×30 ml fractions) in 30 mM Hepes pH 6.7, 0.5 mM EGTA, 0.05 mM EDTA, 1% betaine, 0.05% Tween-20, 0.01% azide, 1 mM DTT. Fractions were assayed for protein binding to PtdIns(3,4,5)P$_3$-beads, yielding proteins V-Y (see below and FIG. 8).

Membranes. PBS-washed leukocytes (~100 ml) were suspended in lysis buffer (3 volumes of 20 mM Hepes, pH 7.4, 0.1 M sucrose, 0.1 M KCl, 2 mM EGTA, 0.5 mM EDTA, 10 mM β-glycerophosphate, 0.1 mM PMSF and protease inhibitors (ALAP)), sonicated and a 'post-nuclear supernatant' obtained by centrifugation (900×$g_{av}$; 10 min). 15 ml samples were centrifuged (100,000×$g_{av}$; 60 min) into discontinuous sucrose gradients (12 ml 0.6 M sucrose over 12 ml 1.25 M sucrose, both in lysis buffer) in a swing-out rotor. The 0.6 M/1.25 M sucrose interface was collected, diluted >5-fold with lysis buffer and pelleted (160,000×$g_{av}$; 30 min). The plasma membrane-enriched pellet was suspended and stored in 20 mM Hepes pH 7.2, 0.125 M NaCl, 5 mM EDTA, 5 mM EGTA, 5 mM β-glycerophosphate, 10 mM NaF and stored. 100 ml cells typically yielded 30-40 mg membrane protein.

Anion-Exchange Chromatography of Detergent-Solubilised Membranes.

Membranes (90 mg) were solubilised on ice for 30 min in 85 ml of 40 mM Tris-HCl, 9 mM Hepes, 0.2 M NaCl, 2.2 mM EDTA, 2.2 mM EGTA, 4.5 mM NaF, 2.2 mM β-glycerophosphate, 1.5% NP40, 1 mM dithiothreitol, 0.1 mM PMSF and protease inhibitors (ALAP, see above) at pH 7.8. After centrifugation (250,000×$g_{av}$; 60 min), the supernatant was filtered, diluted ~7-fold and loaded onto a 1.6×7 cm Pharmacia Q-Sepharose H column: final concentrations were 0.4% NP40, 30 mM NaCl, 30 mM Tris, pH 7.8. Elution was with a linear NaCl gradient (0-0.5 M; 44×6 ml fractions) in 30 mM Tris, pH 7.8, 0.5 mM EGTA, 0.1 mM EDTA, 0.4% NP40, 0.01% azide. Fractions were assayed for proteins binding to PtdIns(3,4,5)P$_3$-beads, yielding proteins M and N (FIG. 9). A larger experiment (600 mg membrane protein) yielded proteins O-U. ps Other Cytosol Preparations Pig platelets. Blood/ACD (~35 l) was centrifuged (200×$g_{av}$, 15 min, room temperature). 5 mM EGTA was added to the supernatant, which was centrifuged (1,200×$g_{av}$; 20 min). The platelet pellets were: suspended in 2 l of 10 mM Hepes-NaOH, pH 7.2, 150 mM NaCl, 4 mM KCl, 4 mM EDTA, 2 mM EGTA; sedimented (1,200×$g_{av}$; 20 min); suspended in 250 ml ice-cold lysis buffer (30 mM Tris-HCl, pH 7.6, 80 mM NaCl, 2 mM EGTA, 0.5 mM EDTA, 1 mM DTT, 0.5 mM PMSF and protease inhibitors (ALAP)); sonicated (three 15 second bursts, with 30 seconds between bursts); and centrifuged (10$^6$×$g_{av}$; 45 min). Supernatants were stored at −80° C.

Sheep liver and brain. Tissues were quickly frozen and stored at −80° C. Samples were thawed, chopped in ice-cold lysis buffer (see above), disrupted (Polytron) and centrifuged (15,000 $g_{av}$, 30 min; then 150,000 $g_{av}$, 60 min). Floating fat was discarded, and the supernatant was used immediately for chromatography or stored frozen.

Rat liver. Livers were frozen in N$_2$ and stored at −80° C. They were homogenised (Waring blender, 4×20 sec, in 25 mM Hepes, 2 mM EDTA, 2 mM EDTA, 5 mM-glycerophosphate, 150 mM NaCl, 10 mM NaCl, 2 mM betaine, 10 mM DTT and protease inhibitors (ALAP; see above)), further disrupted with a tight Dounce homogeniser (10-20 strokes) and centrifuged (4000×$g_{av}$, 15 min; 100,000×$g_{av}$, 90 min). Floating fat was removed, and filtered supernatant were stored at −80° C.

Anion exchange chromatography. Cytosols were fractionated by anion-exchange chromatography by procedures analogous to those described above for leukocyte cytosol, leading to the isolation of proteins SR1-SR7 and SD1 (see Table 1).

Synthesis of Phosphoinositides and Phosphoinositide-Coupled Beads

Synthesis of the biological (D-) stereoisomers of the dipalmitoyl forms of PtdIns3P, PtdIns4P, PtdIns5P, PtdIns(3,5)P$_2$, PtdIns(3,4)P$_2$, PtdIns(4,5)P$_2$ and PtdIns(3,4,5)P$_3$, and of the biologically inactive reference compound L-PtdIns(3,4,5)$_3$, are described elsewhere (Painter et al., 1999). Lipid stocks were stored as dry films at −80° C.: the sodium salts of PtdIns(3,4,5)P$_3$, PtdIns(3,4)P$_2$. PtdIns(3,5)P$_2$ and PtdIns(4,5)P$_2$ were adjusted to pH 7.0 and dried under vacuum; PtdIns3P, PtdIns4P and PtdIns5P were converted to the free acids through a CHCl$_3$/MeOH/0.1M HCl (1:1:0.9) phase partition and the lower phases dried. Stocks (4-10 mM) were prepared by bath-sonicating dry lipid in H$_2$O (PtdIns(3,4,5)P$_3$, PtdIns(3,4)P$_2$, PtdIns(3,5)P$_2$, PtdIns(4,5)P$_2$) or DMSO (PtdIns3P, PtdIns4P, PtdIns5P): concentrations were determined by organic phosphorus assay.

Coupling of phosphoinositides to Affigel-10 beads is described in Examples 2 and 3. Derivatised and washed beads were stored at 4° C. in 0.1 M sodium phosphate buffer, pH 7.0, 0.01% azide. They were equilibrated for ≧30 min in assay buffer (typically 20 mM Hepes, pH 7.2 at 4° C., 0.2 M NaCl, 5 mM EDTA, 5 mM EGTA, 5 mM β-glycerophosphate, 10 mM NaF, 0.1% NP40) before use.

Identification of Phosphoinositide-binding Proteins

Before samples were subjected to binding studies, they were generally adjusted to: 20-30 mM Hepes/Na or Tris/HCl, pH 7.2-7.5, 5 mM β-glycerophosphate, ≧0.1 mM EDTA (in excess of the free Mg$^{2+}$), ≧0.1 M NaCl, 10 mM NaF, 0.1% NP-40, 1 mM sodium orthovanadate. They were kept on ice for 15 min, with or without free phosphoinositides (typically 5-50 µM), and then transferred onto phosphoinositide-derivatised beads [typically 1 ml onto 10 µl beads (analytical); or 30-100 ml onto 0.1-0.3 ml beads (preparative)], mixed and returned to ice (45 min). Beads were washed (3 times; <8 min) with 20 mM Hepes pH 7.2, 0.2 M NaCl, 5 mM EDTA, 5 mM EGTA, 5 mM β-glycerophosphate, 10 mM NaF, 0.1% NP-40, and then once in 5 mM Hepes, pH 7.2. Proteins were eluted with SDS-PAGE sample buffer (95° C. for 5 min), separated by SDS-PAGE and silver-stained (analytical experiments) or transferred to nitrocellulose (preparative). Beads, recycled by washing in SDS-PAGE buffer followed by 0.1 M sodium phosphate buffer, pH 7.0, were used up to five times.

Proteins that showed specific binding to phosphoinositide beads were digested with trypsin and processed for mass spectrometric fingerprinting (Erdjument-Bromage et al., 1998). Briefly, peptide mixtures were partially fractionated on Poros 50 R2 RP micro-tips, and resulting peptide pools were analysed by matrix-assisted laser-desorption/ionisation reflectron time-of-flight mass spectrometry (MALDI-reTOF MS) using a Reflex III instrument (Bruker Franzen; Bremen, Germany). Some samples were also analysed by electrospray ionisation (ESI) tandem MS on an API 300 triple quadrupole instrument (PE-SCIEX; Thornhill, Canada) with a custom-made fine ionization source (Geromanos et al., 2000). Mass values from the MALDI-TOF experiments were used to search a non-redundant protein database ('NR', NCBI, Bethesda, Md.), using the PeptideSearch algorithm (Mann et al., 1993). MS/MS spectra from the ESI triple quadrupole analyses were inspected for y" ion series, and the output was used as a search string in the SequenceTag (Mann and Wilm, 1994) and PepFrag (Fenyö et al., 1998) programs. Identifications were verified by comparing the computer-generated fragment ion series of predicted tryptic peptides with experimental MS/MS data. Sometimes, peptides were fractionated by reversed-phase HPLC (0.8 mm Vydac C18 column; LC-Packings, San Francisco, Calif.) (Elicone et al., 1994). Peak fractions were analysed by MALDI-TOF MS and automated Edman sequencing (477A; Applied Biosystems, Foster City, Calif.) (Tempst et al., 1994).

Cloning and Expression of Phosphoinositide-Binding Proteins

The resulting sequences revealed that complete mRNAs had not been described for five of the PtdIns(3,4,5)$P_3$-binding proteins (C, E, F, G/H and X) or two PtdIns(3,4)$P_2$-binding proteins (SR1 and SR3), but databases included fragment ESTs for each. Image ESTs were used to prepare $^{32}$P-labelled probes to screen cDNA libraries for C, E, G/H, SR1 and SR3. Useful clones were mainly from random-primed and oligodT-primed human U937 cell libraries in the λZAPII vector (Stratagene), and useful G/H clones came from a human spleen oligodT/random-primed library in λgtII (Clontech). SR3 clones were recovered from a mixed oligodT/random-primed rat brain library in λZAPII (Stratagene). Multiple overlapping clones allowed prediction of full-length human ORFs for each protein (rat brain sequence was used to PCR SR3 from human liver and brain cDNA (Clontech)). For F, peptide sequences allowed overlapping ESTs to be compiled into a predicted ORF, and this was obtained by nested PCR from human leukocyte cDNA (Clontech). For X, 5'-RACE-PCR from leukocyte cDNA (Clontech) allowed 5'-extension of EST 684797 to a full-length ORF, and gene-specific primers were used to recover a full-length clone.

Peptide sequences from other proteins indicated that they were porcine orthologues of an unconventional type I myosin (I: myosin 1F; X98411; Crozet et al., 1997), the protein tyrosine phosphatase MEG2 (V: Gu et al., 1992), CDC42GAP (K; Lancaster et al., 1994) and -tocopherol transfer protein (SR2; ATTP, Arita et al., 1995), respectively. Partial clones of human myosin 1F (C. Petit, Institut Pasteur, Paris, France) were used to screen U937 cell libraries: overlapping clones defined the full-length human cDNA. We obtained full-length cDNAs for human MEG2 (P. Majerus, University of Washington, St Louis, Mo., USA), and CDC42GAP (A. Hall, UCL, London, UK). Human ATTP cDNA was obtained by PCR from human liver cDNA (Clontech).

Recombinant Proteins

ORFs were subcloned into expression vectors by standard restriction enzyme cloning and PCR methods. When PCR was used, products were verified by sequencing. pGEX4T (Pharmacia) and pQE (Qiagen) vectors were used for bacterial expression of N-terminally GST- or His-tagged proteins, respectively. GST proteins were purified on glutathione-Sepharose-4B (Pharmacia) and His-tagged proteins on metal affinity resin (Talon, Clontech). Proteins were recovered from the elution buffers by gel filtration on PD10 columns (Pharmacia) in PBS, 1 mM EGTA, 0.01% azide. Thrombin cleavage of GST proteins was carried out on the glutathione-Sepharose beads in PBS, 1 mM DTT for 16 h at 4° C. Where needed, proteins were concentrated to $\geq 1$ mg ml$^{-1}$ using centrifugal filters (Centricon). They were stored at $-80°$ C. in 50% glycerol.

A modified pAcoGEE (Stephens et al., 1997) vector was used for baculovirus-driven expression of N-terminally EE-tagged SR1, SR3 and myo 1F, and for C-terminally EE-tagged PIP3-G/H proteins. Sf9 cells (ETCC) were grown in suspension culture (0.5-2.0×10$^6$ cells ml$^{-1}$) for up to 10 weeks in TNM-FH medium supplemented with 11% foetal bovine serum (heat-inactivated) and antibodies (penicillin/streptomycin). Transfer vectors were co-transfected with linearised baculovirus DNA (Baculo-Gold, PharMingen) into SF9 cells using cationic liposomes (Insectin, PharMingen). Recombinant viruses were plaque-purified and amplified via 3 cycles of infection to high titre ($>_{10}^8$ infectious particles ml$^{-1}$), and protein production was optimised for each construct. Typically, 2-4 litres of culture were infected at 10$^6$ cells ml$^{-1}$ with 10-40 ml of viral stock and cultured for 1.8-2.5 days, cells were harvested, washed in TNM-FH and snap-frozen. Pellets were thawed and sonicated into lysis buffer [1% (w/v) Triton X-100; 0.15 M NaCl; 40 mM HEPES, pH 7.4, 1 mM dithiothreitol, 0.1 mM PMSF and protease inhibitors (ALAP)] (and, for myosin 1F, 5 mM EGTA). Homogenates containing EE-tagged proteins were centrifuged (100, 000×g, 60 min) and mixed with EE-beads (anti-EE monoclonal antibody, dimethyl pimelimidate-crosslinked to Protein G-Sepharose; capacity ~2 mg of a 50 kD target protein ml$^{-1}$ beads). Immunoprecipitation (90 min, end-on-end at 4° C.) was followed by washing (4 times in 0.1% w/v Triton X-100; 0.3 M NaCl; 20 mM HEPES/Na, pH 7.4, 1 mM DTT; and 3× with PBS plus 1 mM DTT: plus, for SR1 and SR3, 10-20% ethylene glycol). Proteins were eluted with peptide EEYMPME (NH$_2$-terminus acetylated: 100 μg ml$^{-1}$). Loaded beads were incubated, 3-4 times for 20 mins on ice, with an equal volume of elution buffer, pooled supernatants were concentrated to $\leq 2.5$ ml (if necessary, with Centriplus concentrators, Amicon,) and passed through a PD-10 column (Pharmacia) (in elution buffer without peptide), and protein-containing fractions were concentrated and stored frozen. Concentrations were determined by SDS-PAGE followed by Coomasie staining and Bradford protein assay (BioRad) (with BSA standard, correcting for the 1.29-fold greater than average colour yield of BSA).

Use of Phosphoinositide-Deivatised Beads to Investigate the Specificities of Recombinant Proteins 10$^7$ Cos-7 cells were transfected by electroporation with 20 μg expression vector (usually Myc- or GFP-tagged), cells were allowed to recover in DMEM containing 10% FBS in 2×15 cm diameter dishes for 36-48 H, and were washed and lysed into 5 ml per dish of 1.0% NP-40, 20 mM Hepes, pH 7.5, 0.12 M NaCl, 5 mM EDTA, 5 mM EGTA, 5 mM β-glycerophosphate, 1 mM orthovanadate, 10 mM NaF. Lysates were centrifuged (190,000×g$_{av}$; 30 min).

Samples of the supernatants were diluted up to 4-fold in lysis buffer, depending on expression levels, and mixed with indicated concentrations of phosphoinositide in 1 ml (FIG. 11) for 10 min on ice. They were transferred to 5-20 µl phosphoinositide beads in lysis buffer and mixed gently for 45 min. Sedimented beads were washed (4×, ≦15 min) in modified lysis buffer (0.1% NP-40 rather than 1% NP-40). Proteins were eluted with SDS sample buffer, separated by SDS-PAGE and detected by immunoblotting [anti-myc (monoclonal 9E10) or anti-GFP (rabbit polyclonal): Clontech).

Assays with purified recombinant proteins (prepared via expression of EE, GST or His-tagged versions in $E.$ $coli$ or Sf9 cells—see above), were as just described, except that 0.2-2 µM proteins were incubated with indicated concentrations of phosphoinositides in PBS, 1 mM DTT, 1 mM $MgCl_2$, 0.1% NP-40, 0.5 mg $ml^{-1}$ BSA (omitted when bound protein was assessed by silver-staining). The beads were washed in PBS, 1 mM $MgCl_2$, 0.1% NP-40, 0.1 mg $ml^{-1}$ BSA (no BSA for silver-staining), and proteins were eluted in sample buffer, separated by SDS-PAGE and detected—either directly by silver-staining or after transfer to Immobilon by immunoblotting (anti-EE mouse ascites from Babco; anti-His-monoclonal from Clontech; anti-GST polyclonal from Amersham-Pharmacia).

Binding of Recombinant Proteins to Phosphoinositide-Containing Biacore Chips

Unilamellar phospholipid vesicles containing 2.5 mM natural phospholipids [PtdCho, PtdEtn and PtdSer (1:1:1); Avanti Polar Lipids Inc., Alabama] were prepared in PBS (pH 7.4), 1 mM $MgCl_2$, 1 mM EGTA, 0.01% azide by extrusion through 100 nm pores in polycarbonate filters. A lipid monolayer was formed on a hydrophobic affinity sensor-chip (HPA, Biacore AB) by first cleaning the chip with an 80 injection of 40 mM octyl D-glucoside (20 1 $min^{-1}$) then injecting 30 µl of the vesicle solution (2 µl $min^{-1}$) and washing with 40 µl of 10 mM NaOH (100 µl $min^{-1}$). Separate flow cells were then injected manually with $PtdIns(3,4)P_2$, $PtdIns(3,5)P_2$, $PtdIns(4,5)P_2$ or $PtdIns(3,4,5)P_3$. Measurements of binding levels at equilibrium were made using proteins at a concentration of 100 nM in a Biacore 3000 instrument.

REFERENCES FOR EXAMPLE 4

Alb, J. G., Gedvilaite, A., Cartee, R. T., Skinner, H. B. and Bankaitis, V. A. (1995). Mutant rat phosphatidylinositol/phosphatidylcholine transfer proteins specifically defective in phosphatidylinositol transfer: implications for the regulation of phosphatidylinositol transfer activity. Proc. Natl. Acad. Sci. 92, 8826-8830.

Anderson, K. E., Lipp, P., Bootman, M., Ridley, S. H., Coadwell, J., Ronnstrand, L., Lennartsson, J., Holmes, A. B., Painter, G. F., Thuring, J., Lim, Z., Erdjument-Bromage, H., Grewal, A., Tempst, P., Stephens, L. R. and Hawkins, P. T. (2000). DAPP1 undergoes a PI 3-kinase-dependent cycle of plasma membrane recruitment and endocytosis upon cell stimulation. Curr. Biol. 10, 1403-1412.

Arita, M., Sato, Y., Miyata, A., Tanabe, T., Takahashi, E., Kayden, H. J., Arai, H. and Inone, K. (1995). Human-tocopherol transfer protein: cDNA cloning, expression and chromosomal localization. Biochem. J. 306, 437-443.

Bankaitis, V. A., Aitken, J. R., Cleves, A. E. and Dowhan, W. (1990). An essential role for a phospholipid transfer protein in yeast Golgi function. Nature 347, 561-561.

Barfod, E. T., Zhang, Y., Kuang, W. J., Hart, M. J., Evans, T., Cerione, R. A. and Ashkenazi, A. (1993). Cloning and expression of a human CDC42 GTPase-activating protein reveals a functional SH3-binding domain. J. Biol. Chem. 268, 26059-26062.

Ben Hamida, C., Belal, D. S., Linder, C., Reutenauer, L., Dib, C., Gyapay, G., Vingal, A., Paslier, D. L., Cohen, D., Pandolfo, M., Mokini, V., Novelli, G., Hentati, F., Ben Hamida, M., Mandel, J-L. and Koenig, M. (1993). Localization of Friedreich ataxia phenotype with selective vitamin E deficiency to chromosome 8q by homozygosity mapping. Nature Genet. 5, 195-200.

Burd, C. G., and Emr, S. D. (1998). Phosphatidylinositol 3-phosphate signalling mediated by specific binding to RING FYVE domains. Mol. Cell 2, 157-162.

Cockcroft, S., ed. (2000) Biology of Phosphoinositides, Frontiers in Molecular Biology 27 (New York: Oxford University Press).

Crozet, F., el Amraoui, A., Blanchard, S., Lenoir, M., Ripoll, C., Vago, P., Hamel, C., Fizames, C., Levi-Acobas, F., Depetris, D., Mattei, M. G., Weil, D., Pujol, R. and Petit, C. (1997). Cloning of the genes encoding two murine and human cochlear unconventional type I myosins. Genomics 40, 332-341.

Derubeis, A. R., Young, M, F., Jia, L., Robey, P. G. and Fisher, L. W. (2000). Double FYVE-containing protein-1 (DFCP-1); isolation, cloning and characterisation of a novel FYVE finger protein from a bone marrow cDNA library. Gene 255, 195-203

Dove, S. K., Cooke, F. T., Douglas, M. R., Sayers, L. G., Parker, P. J. and Michell, R. H. (1997). Osmotic stress activates phosphatidylinositol 3,5-bisphosphate synthesis. Nature 390, 187-192.

Dowler, S., Currie, R. A., Campbell, D. G., Deak, M., Kular, G., Downes, C. P. and Alessi, D. R. (2000). Identification of pleckstrin-homology domain containing proteins with novel phosphoinositide-binding specificities. Biochem. J. 351, 19-31.

Dowler, S., Currie, R. A., Downes, C. P. and Alessi, D. R. (1999). DAPP1: a dual adaptor for phosphotyrosine and 3-phosphoinositides. Biochem. J. 342, 7-12.

Elicone, C., Lui, M., Geromanos, S., Erdjument-Bromage, H. and Tempst, P. (1994). Microbore reversed-phase high-performance liquid chromatographic purification of peptides for combined chemical sequencing-laser-desorption mass spectrometric analysis. J. Chromatogr. 676, 121-137.

Erdjument-Bromage, H., Lui, M., Lacornis, L., Grewal, A., Annan, R. S., MacNulty D. E., Carr, S. A. and Tempst, P. (1998). Micro-tip reversed-phase liquid chromatographic extraction of peptide pools for mass spectrometric analysis. J. Chromatogr. 826, 167-181.

Fenyo, D., Qin, J. and Chait, B. T. (1998). Protein identification using mass spectrometric information. Electrophoresis 19, 998-1005.

Flanagan, L. A. and Janmey, P. A. (2000). Regulation of cytoskeletal proteins by inositol lipids. In: Biology of Phosphoinositides, Frontiers in Molecular Biology 27, Cockcroft, S., ed. (New York: Oxford University Press), pp. 166-182.

Gaidarov, I. and Keen, J. H. (1999). Phosphoinositide-AP-2 interactions required for targeting to plasma membrane clathnn-coated pits. J. Cell. Biol. 146, 755-764.

Geromanos, S., Freckleton, G. and Tempst, P. (2000). Tuning of an electrospray ionization source for maximum peptide-ion transmission into a mass spectrometer. Anal. Chem. 72, 777-790.

Gu, M., Warshawsky, I. and Majerus, P. W. (1992). Cloning and expression of a cytosolic megakaryocyte protein-tyrosine-phosphatase with sequence homology to retinaldehyde-binding protein and yeast SEC 14p. Proc. Natl. Acad. Sci. USA. 89, 2980-2984.

Hammonds-Odie, L. P., Jackson, T. R., Profit, A. A., Blader, I. J., Turck, C. W., Prestwich, G. D. and Theibert, A. B. (1996). Identification and cloning of centaurin-α. J. Biol. Chem. 271, 18859-18868.

Isakoff, S., Cardozo, T., Andreev, J., Li, Z., Ferguson, K., Abagyan, R., Lemmon, M. A., Aronheim, A. and Skolnik, E. Y. (1998). Identification and analysis of PH domain-containing targets of phosphatidylinositol 3-kinase using a novel in vivo assay in yeast. EMBO J. 17, 5374-5387.

Jackson, T. R., Kearns, B. G. and Theibert, A. B. (2000). Cytohesins and centaurins: mediators of PI 3-kinase-regulated Arf signaling. Trends Biochem. Sci. 25, 489-495.

Kavran, J. M., Klein, D. E., Lee, A., Falasca, M., Isakoff, S. J., Skolnik, E. Y. and Lemmon, M. A. (1998) Specificity and promiscuity in phosphoinositide binding by pleckstrin homology domains. J. Biol. Chem. 273, 30497-30508

Kearns, M. A., Monks, D. E., Fang, M., Rivas, M. P., Courtney, P. D., Chen, J., Prestwich, G. D., Theibert, A. B., Dewey, R. E. and Bankaitis, V. A. (1998). Novel developmentally regulated phosphoinositide-binding proteins from soybean whose expression bypasses the requirement for an essential phosphatidylinositol transfer protein in yeast. EMBO J. 17, 4004-4017.

Klarlund, J. K., Rameh, L. E., Cantley, L. C., Buxton, J. M., Holik, J. J., Sakelis, C., Patki, V., Corvera, S., and Czech, M. P. (1998). Regulation of GRP1-catalysed ADP ribosylation factor guanine nucleotide exchange by phosphatidylinositol 3,4,5-trisphosphate. J. Biol. Chem. 273, 1859-1862.

Lancaster, C. A., Taylor-Harris, P. M., Self, A. J., Brill, S., Van Evp, H. E. and Hall, A. (1994). Characterization of rho GAP. J. Biol. Chem. 269, 1137-1142.

Lawe, D. C., Patki, V., Heller-Harrison, R., Lambright, D. and Corvera, S. (2000). The FYVE domain of early endosomal antigen 1 is required for both phosphatidylinositol 3-phosphate and Rab 5 binding. J. Biol. Chem. 275, 3699-3705.

Leevers, S. J., Vanhaesebroeck, B. and Waterfield, M. D. (1999). Signalling through phosphoinositide 3-kinases: the lipids take centre stage. Curr. Opinion Cell. Biol. 11, 219-225.

Lemmon, M. A. and Ferguson, K. M. (2000). Signal-dependent membrane targeting by pleckstrin homology (PH) domains. Biochem. J. 350, 1-18.

Li, Z., Wahl, M. I., Eguinoa, A., Stephens, L. R., Hawkins, P. T. and Whitte, O. N. (1997). Phosphatidylinositol 3-kinase-γ activates Bruton's tyrosine kinase in concert with src family kinases. Proc. Natl. Acad. Sci. 95, 13820-13825.

Li, X., Routt, S. M., xie, Z., Cui, X., Fang, M., Kearns, M. A., Bard, M., Kirsch, D. R. and Bankaitis, V. A. (2000) Identification of a novel famnily of nonclassic yeast phosphatidylinositol transfer proteins whose function modulates phospholipase d activity and sec14p-independent cell growth. Mol. Biol. Cell, 11, 1989-2005.

Mann, M. and Wilm, M. (1994). Error-tolerant identification of peptides in sequence databases by peptide Sequence tags. Anal. Chem. 66, 4390-4399.

Mann, M., Højrup, P. and Roepstorff, P. (1993). Use of mass spectrometric molecular weight information to identify proteins in databases. Biol. Mass Spectrom. 22, 338-345.

Marshall, A. J., Niiro, H., Lexner, C. G., Yun, T. J., Thomas, S., Disteche, C. M. et al. (2000). A novel B lymphocyte-associated adaptor protein, Bam32, regulates antigen receptor signalling downstream of phosphatidylinositol 3-kinase. J. Exp. Med. 191, 1319-1331.

Martin, T. F. (1998). Phosphoinositide lipids as signaling molecules: common themes for signal transduction, cytoskeletal regulation, and membrane trafficking. Ann. Rev. Cell. Dev. Biol. 14, 231-264.

Ogasawara, M., Kim, S-C., Adamik, R., Togawa, A., Ferrans, V. J., Takeda, K., Kirby, M., Moss, J. and Vaughan, M. (2000). Similarities in function and gene structure of cytohesin-4 and cytohesin-1, guanine nucleotide-exchange proteins for ADP-ribosylation factors. J. Biol. Chem. 275, 3331-3230.

Otsuki, M., Fukami, K., Kohno, T., Yokota, J. and Takenawa, T. (1999). Identification and characterization of a new phospholipase C-like protein, PLC-L (2). Biochem. Biophys. Res. Comm. 266, 97-103.

Painter, G. F., Grove, S. J. A., Gilbert, I. H., Holmes, A. B., Raithby, P. R., Hill, M. L., Hawkins, P. T. and Stephens, L. R. (1999). General synthesis of 3-phosphorylated myo-inositol phospholipids and derivatives. J. Chem. Soc. Perkin Trans. 1, 923-935.

Painter, G. F., Thuring, J. W., Lim, Z-Y., Holmes, A. B., Hawkins, P. T. and Stephens, L. R. (2001). Synthesis and biological evaluation of a PtdIns(3,4,5)$P_3$ affinity matrix. Chem. Commun. In Press.

Qui, Y., Robinson, D., Pretlow, T. G. and Kung, H. J. (1998). Etk/Bmx, a tyrosine kinase with a pleckstrin-homology domain, is an effector of phosphatidylinositol 3'-kinase and is involved in interleukin 6-induced neuroendocrine differentiation of prostate cancer cells. Proc. Natl. Acad. Sci. 95, 3644-3649.

Rameh, L. E. and Cantley, L. C. (1999). The role of phosphoinositide 3-kinase lipid products in cell function. J. Biol. Chem. 274, 8347-8350.

Rameh, L. E., Tolias, K. T., Duckworth, B. and Cantley, L. C. (1997). A new pathway for synthesis of phosphatidylinositol 4,5-bisphosphate. Nature 390, 192-196.

Rao, V. R., Corradetti, M. N., Chen, J., Peng, J., Yuan, J., Prestwick, E. D. et al. (1999). Expression cloning of protein targets for 3-phosphorylated phosphoinositides. J. Biol. Chem. 274:37893-37900.

Schiavo, G., Gu, Q-M., Prestwich, G. D., Sollner, T. H. and Rothman, J. E (1996). Calcium-dependent switching of the specificity of phosphoinositide binding to synaptotagmin. Proc. Natl. Acad. Sci 93, 13327-13332.

Shirai, T., Tanaka, K-I., Terada, Y., Sawada, T., Shirai, R., Hashimoto, Y., Nagata, S., Iwamatsu, A., Okawa, K., Li, S., Hattori, S., Mano, H. and Fukui, Y. (1998). Specific detection of phosphatidylinositol 3,4,5-trisphosphate binding proteins by the $PIP_3$ analogue beads: an application for rapid purification of the $PIP_3$ binding proteins. Biochim. et. Biophys. Acta 1402, 292-302.

Stenmark, H. and Aasland, R. (1999). FYVE-finger proteins-effectors of an inositol lipid. J. Cell. Sci. 112, 4175-4183.

Stephens, L., Anderson, K., Stokoe, D., Erdjument-Bromage, H., Painter, G. F., Holmes. A. B., Gaffney, P. R., Reese, C. B., McCormick, F., Tempst, P., Coadwell, J. and Hawkins, P. T. (1998). Protein kinase B kinases that mediate phosphatidylinositol 3,4,5-trisphosphate-dependent activation of protein kinase B. Science 279, 710-4.

Stephens, L. R., Eguinoa, A., Erdjument-Bromage, H., Lui, M., Cook, F. T. Coadwell, J. et al. (1997). The G sensitivity of a PI3K is dependent upon a tightly associated adaptor, p110. Cell 89, 105-114.

Stricker, R., Hulser, E., Fischer, J., Jarchau, T., Walter, U., Lottspeich, F. and Reiser, G. (1997). cDNA cloning of porcine $p42^{IP4}$, a membrane-associated and cytosolic 42Kd inositol (1,3,4,5) tetrakisphosphate receptor from pig brain with similar high affinity for PtdIns(3,4,5)P$_3$. FEBS Lett. 405, 229-236.

Tanaka, K., Imajoh-Ohmi, S., Sawada, T., Shirai, R., Hashimoto, Y., Iwasaki, S., Karbuchi, K., Kanaho, Y., Shirai, T., Terada, Y., Kimura, K., Nagata, S. and Fukui, Y. (1997). A target of phosphatidylinositol 3,4,5-trisphosphate with a zinc finger motif similar to that of the ADP-ribosylation-factor GTPase-activating protein and two pleckstrin homology domains. Eur. J. Biochem. 245, 512-519.

Tempst, P., Geromanos, S., Elicone, C. and Erdjument-Bromage, H. (1994). Improvements in microsequencer performance for low picomole sequence analysis. METHODS Companion Meth. Enzymol. 6, 248-261.

Toker, A. (1998). The synthesis and cellular roles of phosphatidylinositol 4,5-bisphosphate. Curr. Opin. Cell. Biol. 10, 254-261.

Vetrie, D., Vorechovsky, I., Sideras, P., Holland, J., Davies, A., Flinter, F., Hammarstrom, L., Kinnon, C., Levinsky, R., Bobrow, M., et al. (1993). The gene involved in X-linked agammaglobulinaemia is a member of the src family of protein tyrosine kinases. Nature 361, 226-233.

Wang, J., Arbuzora, A., Hangyás-Mihályné, G. and McLaughlin, S. (2000). The effector domain of myristoylated alanine-rich C kinase substrate (MARCKS) binds strongly to phosphatidylinositol 4,5-bisphosphate (PIP$_2$). J. Biol. Chem. In press.

TABLE 1

| Origin | Name | Size (kDa) | Identity | Acc. No. |
|---|---|---|---|---|
| PtdIns(3,4,S)P$_3$ beads | | | | |
| Pig leukocyte cytosol | PIP$_3$-A | 92 | RasGAP$^{IP4BP}$ | TR:Q14644 |
| Pig leukocyte cytosol | PIP$_3$-B | 65 | Bruton's Tyrosine Kinase (BTK) | SW:P35991 |
| Pig leukocyte cytosol | PIP$_3$-C | 145 | NOVEL [PLC-L2] | TR:Q9UPR0 |
| Pig leukocyte cytosol | PIP$_3$-D | 77 | Ezrin/Type II Ins(1,4,5)P$_3$ phosphatase (mixed) | SW:P31976/P3299 |
| Pig leukocyte cytosol | PIP$_3$-E | 61 | NOVEL | EM:XXXXX |
| Pig leukocyte cytosol | PIP$_3$-F | 45 | NOVEL [Cytohesin-4] | TR:Q9UIA0 |
| Pig leukocyte cytosol | PIP$_3$-G/H | 197/184 | NOVEL | EM:XXXXX |
| Pig leukocyte cytosol | PIP$_3$-I | 127 | Myosin 1F | EM:XIXXXX |
| Pig leukocyte cytosol | PIP$_3$-J | 73 | ETK | SW:P51813 |
| Pig leukocyte cytosol | PIP$_3$-K | 51 | CDC42-GAP | SW:Q07960 |
| Pig leukocyte cytosol | PIP$_3$-L | 200 | n.d. | |
| Pig leukocyte memb. | PIP$_3$-M | 94 | n.d. | |
| Pig leukocyte memb. | PIP$_3$-N | 65 | n.d. | |
| Pig leukocyte memb. | PIP$_3$-O | | n.d. (-subunit mitochondrial fatty acid oxidase?) | SW:Q29554 |
| Pig leukocyte memb. | PIP$_3$-P | | -subunit mitochondrial fatty acid oxidase | SW:046629 |
| Pig leukocyte memb. | PIP$_3$-Q | 64 | n.d. | |
| Pig leukocyte memb. | PIP$_3$-R | 56 | n.d. | |
| Pig leukocyte memb. | PIP$_3$-S | 28 | RasGAP$^{IP4BP}$ (fragment) | |
| Pig leukocyte memb. | PIP$_3$-T | 34 | n.d. | |
| Pig leukocyte memb. | PIP$_3$-U | 62 | n.d. | |
| Pig leukocyte cytosol | PIP$_3$-V | 59 | MEG2 | SW:P43378 |
| Pig leukocyte cytosol | PIP$_3$-W | 45 | PIP$_3$-F | TR:Q9UIA0 |
| Pig leukocyte cytosol | PIP$_3$-X | 31 | NOVEL [DAPP1] | TR:Q9UN19 |
| Pig leukocyte cytosol | PIP$_3$-Y | 42 | Centaurin- | TR:O02780 |
| PtdIns(3,4)P$_2$ beads | | | | |
| Sheep liver cytosol | SR1 | 46 | NOVEL | EM:XXXXX |
| Sheep liver cytosol | SR2 | | -tocopherol transfer protein (ATTP) | SW:P49638 |
| Sheep liver cytosol | SR3 | 80 | NOVEL [DFCP-1] | EM:XXXXX |
| Pig platelet cytosol | SR4 | 128 | Vinculin | SW:P18206 |
| Pig platelet cytosol | SR5 | 46 | SR1 | |
| PtdIns(3,5)P$_2$ beads | | | | |
| Rat liver cytosol | SD1 | 30 | ATTP | |
| PtdIns3P beads | | | | |
| Pig platelet cytosol | SR6 | 80 | 6-phosphofructokinase type C (PFK-C) | SW:K6PP_HUMN |
| Pig platelet cytosol | SR7 | 46 | SR1 | |

Proteins isolated on phosphoinositide-derivatised beads.

Proteins were excised on nitrocellulose, digested with trypsin and peptides identified by mass fingerprinting and aminoacid sequencing (see Methods).

Proteins that were unknown at the time of identification are described as NOVEL: independent ORFs encoding some of these proteins have since been described and their names are given in square brackets.

EMBL accession numbers are given for our ORFs where they remain undefined in the databases (PIP$_3$-E, PIP$_3$- G/H, SR1), they define new species orthologues (MYO1F) or add significantly to existing entries (SR3).

Protein O was tentatively identified on the basis of its size and co-chromatography with the -subunit of the mitochondrial fatty acid oxidase.

n.d. designates phosphoinositide-binding proteins that have not yet been identified.

SW: Swissprot.

TR: Trembl.

EM: Embl.

TABLE 2

Preferred Compounds and Probes of the Invention

Structure with OCOC$_7$H$_{15}$ at sn-2 and OCOC$_{11}$H$_{22}$NH$_2$
C8 at sn-2 position Structure with OCOC$_{11}$H$_{23}$ at sn-2 and OCOC$_{11}$H$_{22}$NH$_2$
C12 at sn-2 position Structure with OCOC$_{15}$H$_{31}$ at sn-2 and OCOC$_{11}$H$_{22}$NH$_2$
C16 at sn-2 position Structure with OCOC$_7$H$_{15}$ at sn-2 and OCOC$_{11}$H$_{22}$NH-bead
C8 at sn-2 position Structure with OCOC$_{11}$H$_{23}$ at sn-2 and OCOC$_{11}$H$_{22}$NH-bead
C12 at sn-2 position Structure with OCOC$_{15}$H$_{31}$ at sn-2 and OCOC$_{11}$H$_{22}$NH-bead
C16 at sn-2 position Changes in chain length at the sn-2 position Structure with OCOC$_8$H$_{17}$ at sn-2 and OCOC$_{11}$H$_{22}$NH$_2$
C9 at sn-2 position Structure with OCOC$_8$H$_{19}$ at sn-2 and OCOC$_{11}$H$_{22}$NH$_2$
C10 at sn-2 position Structure with OCOC$_{10}$H$_{21}$ at sn-2 and OCOC$_{11}$H$_{22}$NH$_2$
C11 at sn-2 position

TABLE 2-continued

Preferred Compounds and Probes of the Invention

Structure with OCOC$_{12}$H$_{25}$ at sn-2 and OCOC$_{11}$H$_{22}$NH$_2$
C13 at sn-2 position Structure with OCOC$_{13}$H$_{27}$ at sn-2 and OCOC$_{11}$H$_{22}$NH$_2$
C14 at sn-2 position Structure with OCOC$_{14}$H$_{29}$ at sn-2 and OCOC$_{11}$H$_{22}$NH$_2$
C15 at sn-2 position Structure with OCOC$_8$H$_{17}$ at sn-2 and OCOC$_{11}$H$_{22}$NH-bead
C9 at sn-2 position Structure with OCOC$_{18}$H$_{21}$ at sn-2 and OCOC$_{11}$H$_{22}$NH-bead
C11 at sn-2 position Structure with OCOC$_{12}$H$_{25}$ at sn-2 and OCOC$_{11}$H$_{22}$NH-bead
C13 at sn-2 position Structure with OCOC$_{13}$H$_{27}$ at sn-2 and OCOC$_{11}$H$_{22}$NH-bead
C14 at sn-2 position Structure with OCOC$_8$H$_{19}$ at sn-2 and OCOC$_{11}$H$_{22}$NH-bead
C10 at sn-2 position Structure with OCOC$_{14}$H$_{29}$ at sn-2 and OCOC$_{11}$H$_{22}$NH-bead
C15 at sn-2 position TABLE 2-continued
Preferred Compounds and Probes of the Invention
Changes in chain length at the sn-1 position
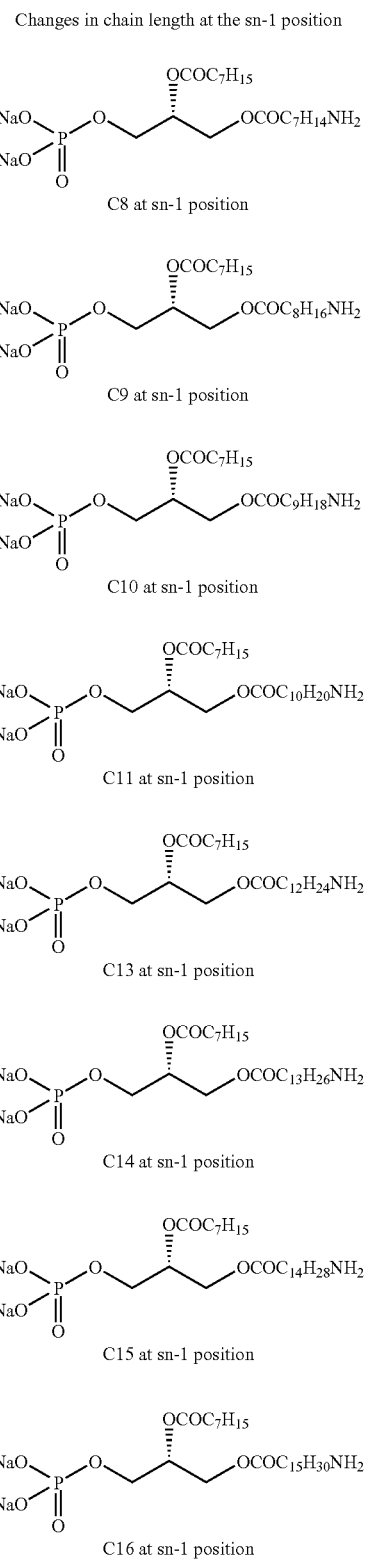
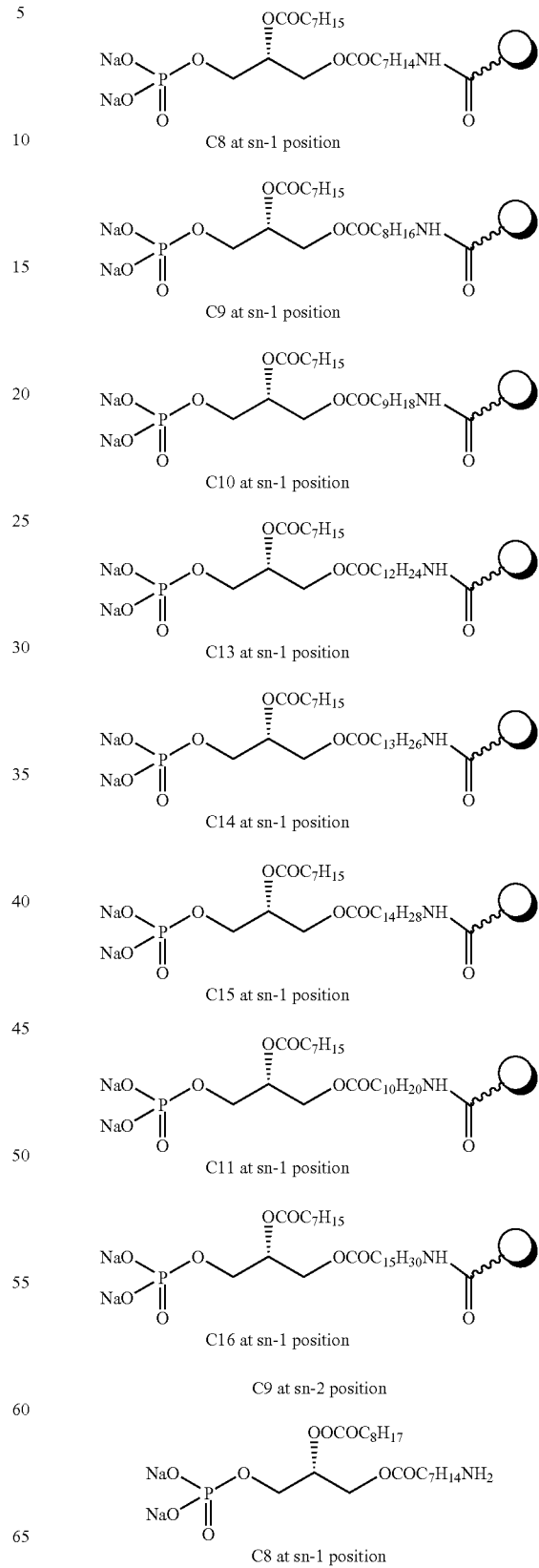

TABLE 2-continued

Preferred Compounds and Probes of the Invention $$\text{NaO}\diagdown\underset{\underset{O}{\|}}{P}\diagup O\diagdown\overset{OCOC_8H_{17}}{\diagup}\diagdown OCOC_8H_{15}NH_2$$
$$\text{NaO}\diagup$$

C9 at sn-1 position $$\text{NaO}\diagdown\underset{\underset{O}{\|}}{P}\diagup O\diagdown\overset{OCOC_8H_{17}}{\diagup}\diagdown OCOC_9H_{18}NH_2$$
$$\text{NaO}\diagup$$

C10 at sn-1 position $$\text{NaO}\diagdown\underset{\underset{O}{\|}}{P}\diagup O\diagdown\overset{OCOC_8H_{17}}{\diagup}\diagdown OCOC_{10}H_{20}NH_2$$
$$\text{NaO}\diagup$$

C11 at sn-1 position $$\text{NaO}\diagdown\underset{\underset{O}{\|}}{P}\diagup O\diagdown\overset{OCOC_8H_{17}}{\diagup}\diagdown OCOC_{12}H_{24}NH_2$$
$$\text{NaO}\diagup$$

C13 at sn-1 position $$\text{NaO}\diagdown\underset{\underset{O}{\|}}{P}\diagup O\diagdown\overset{OCOC_8H_{17}}{\diagup}\diagdown OCOC_{13}H_{25}NH_2$$
$$\text{NaO}\diagup$$

C14 at sn-1 position $$\text{NaO}\diagdown\underset{\underset{O}{\|}}{P}\diagup O\diagdown\overset{OCOC_8H_{17}}{\diagup}\diagdown OCOC_{14}H_{26}NH_2$$
$$\text{NaO}\diagup$$

C15 at sn-1 position $$\text{NaO}\diagdown\underset{\underset{O}{\|}}{P}\diagup O\diagdown\overset{OCOC_8H_{17}}{\diagup}\diagdown OCOC_{15}H_{30}NH_2$$
$$\text{NaO}\diagup$$

C16 at sn-1 position $$\text{NaO}\diagdown\underset{\underset{O}{\|}}{P}\diagup O\diagdown\overset{OCOC_8H_{17}}{\diagup}\diagdown OCOC_7H_{14}NH\text{—}\overset{\|}{\underset{O}{C}}\text{—}\bigcirc$$
$$\text{NaO}\diagup$$

C8 at sn-1 position $$\text{NaO}\diagdown\underset{\underset{O}{\|}}{P}\diagup O\diagdown\overset{OCOC_8H_{17}}{\diagup}\diagdown OCOC_9H_{18}NH\text{—}\overset{\|}{\underset{O}{C}}\text{—}\bigcirc$$
$$\text{NaO}\diagup$$

C9 at sn-1 position

TABLE 2-continued

Preferred Compounds and Probes of the Invention $$\text{NaO}\diagdown\underset{\underset{O}{\|}}{P}\diagup O\diagdown\overset{OCOC_8H_{17}}{\diagup}\diagdown OCOC_9H_{18}NH\text{—}\overset{\|}{\underset{O}{C}}\text{—}\bigcirc$$
$$\text{NaO}\diagup$$

C10 at sn-1 position $$\text{NaO}\diagdown\underset{\underset{O}{\|}}{P}\diagup O\diagdown\overset{OCOC_8H_{17}}{\diagup}\diagdown OCOC_{12}H_{24}NH\text{—}\overset{\|}{\underset{O}{C}}\text{—}\bigcirc$$
$$\text{NaO}\diagup$$

C13 at sn-1 position $$\text{NaO}\diagdown\underset{\underset{O}{\|}}{P}\diagup O\diagdown\overset{OCOC_8H_{17}}{\diagup}\diagdown OCOC_{13}H_{26}NH\text{—}\overset{\|}{\underset{O}{C}}\text{—}\bigcirc$$
$$\text{NaO}\diagup$$

C14 at sn-1 position $$\text{NaO}\diagdown\underset{\underset{O}{\|}}{P}\diagup O\diagdown\overset{OCOC_8H_{17}}{\diagup}\diagdown OCOC_{14}H_{28}NH\text{—}\overset{\|}{\underset{O}{C}}\text{—}\bigcirc$$
$$\text{NaO}\diagup$$

C15 at sn-1 position $$\text{NaO}\diagdown\underset{\underset{O}{\|}}{P}\diagup O\diagdown\overset{OCOC_8H_{17}}{\diagup}\diagdown OCOC_{10}H_{20}NH\text{—}\overset{\|}{\underset{O}{C}}\text{—}\bigcirc$$
$$\text{NaO}\diagup$$

C11 at sn-1 position $$\text{NaO}\diagdown\underset{\underset{O}{\|}}{P}\diagup O\diagdown\overset{OCOC_8H_{17}}{\diagup}\diagdown OCOC_{15}H_{30}NH\text{—}\overset{\|}{\underset{O}{C}}\text{—}\bigcirc$$
$$\text{NaO}\diagup$$

C16 at sn-1 position

C10 at sn-2 position $$\text{NaO}\diagdown\underset{\underset{O}{\|}}{P}\diagup O\diagdown\overset{OOCOC_8H_{19}}{\diagup}\diagdown OCOC_7H_{14}NH_2$$
$$\text{NaO}\diagup$$

C8 at sn-1 position $$\text{NaO}\diagdown\underset{\underset{O}{\|}}{P}\diagup O\diagdown\overset{OCOC_8H_{19}}{\diagup}\diagdown OCOC_8H_{16}NH_2$$
$$\text{NaO}\diagup$$

C9 at sn-1 position $$\text{NaO}\diagdown\underset{\underset{O}{\|}}{P}\diagup O\diagdown\overset{OCOC_8H_{19}}{\diagup}\diagdown OCOC_9H_{18}NH_2$$
$$\text{NaO}\diagup$$

C10 at sn-1 position

TABLE 2-continued

Preferred Compounds and Probes of the Invention

NaO−P(=O)(ONa)−O−CH(OCOC$_8$H$_{19}$)−CH$_2$−OCOC$_{10}$H$_{20}$NH$_2$
C11 at sn-1 position NaO−P(=O)(ONa)−O−CH(OCOC$_8$H$_{19}$)−CH$_2$−OCOC$_{12}$H$_{24}$NH$_2$
C13 at sn-1 position NaO−P(=O)(ONa)−O−CH(OCOC$_9$H$_{18}$)−CH$_2$−OCOC$_{13}$H$_{26}$NH$_2$
C14 at sn-1 position NaO−P(=O)(ONa)−O−CH(OCOC$_9$H$_{18}$)−CH$_2$−OCOC$_{14}$H$_{28}$NH$_2$
C15 at sn-1 position NaO−P(=O)(ONa)−O−CH(OCOC$_8$H$_{19}$)−CH$_2$−OCOC$_{15}$H$_{30}$NH$_2$
C16 at sn-1 position NaO−P(=O)(ONa)−O−CH(OCOC$_8$H$_{19}$)−CH$_2$−OCOC$_7$H$_{14}$NH−C(=O)−●
C8 at sn-1 position NaO−P(=O)(ONa)−O−CH(OCOC$_8$H$_{19}$)−CH$_2$−OCOC$_8$H$_{16}$NH−C(=O)−●
C9 at sn-1 position NaO−P(=O)(ONa)−O−CH(OCOC$_8$H$_{19}$)−CH$_2$−OCOC$_9$H$_{18}$NH−C(=O)−●
C10 at sn-1 position NaO−P(=O)(ONa)−O−CH(OCOC$_8$H$_{19}$)−CH$_2$−OCOC$_{12}$H$_{24}$NH−C(=O)−●
C13 at sn-1 position TABLE 2-continued Preferred Compounds and Probes of the Invention NaO−P(=O)(ONa)−O−CH(OCOC$_8$H$_{19}$)−CH$_2$−OCOC$_{13}$H$_{26}$NH−C(=O)−●
C14 at sn-1 position NaO−P(=O)(ONa)−O−CH(OCOC$_8$H$_{19}$)−CH$_2$−OCOC$_{14}$H$_{28}$NH−C(=O)−●
C15 at sn-1 position NaO−P(=O)(ONa)−O−CH(OCOC$_8$H$_{19}$)−CH$_2$−OCOC$_{10}$H$_{20}$NH−C(=O)−●
C11 at sn-1 position NaO−P(=O)(ONa)−O−CH(OCOC$_8$H$_{19}$)−CH$_2$−OCOC$_{15}$H$_{30}$NH−C(=O)−●
C16 at sn-1 position
C11 at sn-2 position NaO−P(=O)(ONa)−O−CH(OCOC$_{10}$H$_{21}$)−CH$_2$−OCOC$_7$H$_{14}$NH$_2$
C8 at sn-1 position NaO−P(=O)(ONa)−O−CH(OCOC$_{10}$H$_{21}$)−CH$_2$−OCOC$_9$H$_{18}$NH$_2$
C9 at sn-1 position NaO−P(=O)(ONa)−O−CH(OCOC$_{10}$H$_{21}$)−CH$_2$−OCOC$_9$H$_{18}$NH$_2$
C10 at sn-1 position NaO−P(=O)(ONa)−O−CH(OCOC$_{10}$H$_{21}$)−CH$_2$−OCOC$_{10}$H$_{20}$NH$_2$
C11 at sn-1 position NaO−P(=O)(ONa)−O−CH(OCOC$_{10}$H$_{21}$)−CH$_2$−OCOC$_{12}$H$_{24}$NH$_2$
C13 at sn-1 position TABLE 2-continued Preferred Compounds and Probes of the Invention

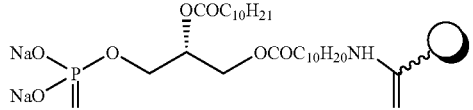
C14 at sn-1 position

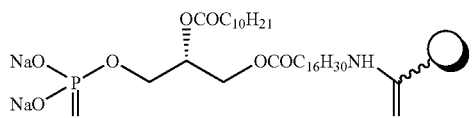
C15 at sn-1 position

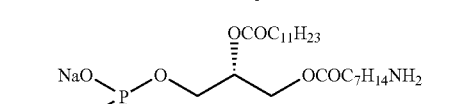
C16 at sn-1 position

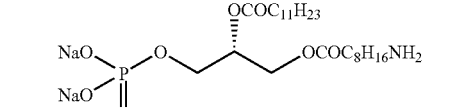
C8 at sn-1 position

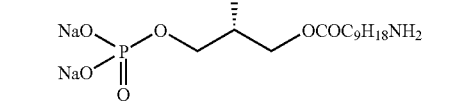
C9 at sn-1 position

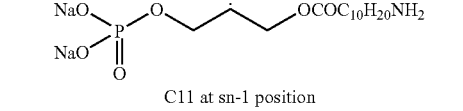
C10 at sn-1 position

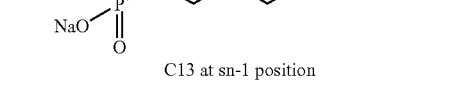
C13 at sn-1 position

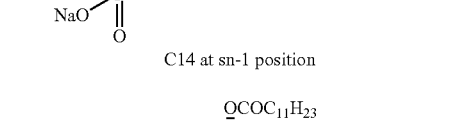
C13 at sn-1 position

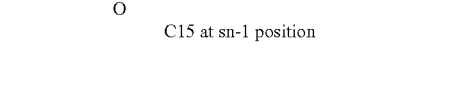
C15 at sn-1 position

TABLE 2-continued

Preferred Compounds and Probes of the Invention

C11 at sn-1 position

C12 at sn-2 position

C8 at sn-1 position

C9 at sn-1 position

C10 at sn-1 position

C11 at sn-1 position

C13 at sn-1 position

C14 at sn-1 position

C15 at sn-1 position

TABLE 2-continued

Preferred Compounds and Probes of the Invention (NaO)(NaO)P(=O)-O-CH2-CH(OCOC11H23)-CH2-OCOC15H30NH2
C16 at sn-1 position (NaO)(NaO)P(=O)-O-CH2-CH(OCOC11H23)-CH2-OCOC7H14NH-C(=O)-●
C8 at sn-1 position (NaO)(NaO)P(=O)-O-CH2-CH(OCOC11H23)-CH2-OCOC8H16NH-C(=O)-●
C8 at sn-1 position (NaO)(NaO)P(=O)-O-CH2-CH(OCOC11H23)-CH2-OCOC9H18NH-C(=O)-●
C10 at sn-1 position (NaO)(NaO)P(=O)-O-CH2-CH(OCOC11H23)-CH2-OCOC12H24NH-C(=O)-●
C13 at sn-1 position (NaO)(NaO)P(=O)-O-CH2-CH(OCOC11H23)-CH2-OCOC13H26NH-C(=O)-●
C14 at sn-1 position (NaO)(NaO)P(=O)-O-CH2-CH(OCOC11H23)-CH2-OCOC14H28NH-C(=O)-●
C15 at sn-1 position (NaO)(NaO)P(=O)-O-CH2-CH(OCOC11H23)-CH2-OCOC10H20NH-C(=O)-●
C11 at sn-1 position (NaO)(NaO)P(=O)-O-CH2-CH(OCOC11H23)-CH2-OCOC15H30NH-C(=O)-●
C16 at sn-1 position

TABLE 2-continued

Preferred Compounds and Probes of the Invention (NaO)(NaO)P(=O)-O-CH2-CH(OCOC12H25)-CH2-OCOC7H14NH2
C8 at sn-1 position (NaO)(NaO)P(=O)-O-CH2-CH(OCOC12H25)-CH2-OCOC9H18NH2
C9 at sn-1 position (NaO)(NaO)P(=O)-O-CH2-CH(OCOC12H25)-CH2-OCOC9H18NH2
C10 at sn-1 position (NaO)(NaO)P(=O)-O-CH2-CH(OCOC12H25)-CH2-OCOC10H20NH2
C11 at sn-1 position (NaO)(NaO)P(=O)-O-CH2-CH(OCOC12H25)-CH2-OCOC12H24NH2
C13 at sn-1 position (NaO)(NaO)P(=O)-O-CH2-CH(OCOC12H25)-CH2-OCOC13H26NH2
C14 at sn-1 position (NaO)(NaO)P(=O)-O-CH2-CH(OCOC12H25)-CH2-OCOC14H28NH2
C15 at sn-1 position (NaO)(NaO)P(=O)-O-CH2-CH(OCOC12H25)-CH2-OCOC15H30NH2
C16 at sn-1 position (NaO)(NaO)P(=O)-O-CH2-CH(OCOC12H25)-CH2-OCOC7H14NH-C(=O)-●
C8 at sn-1 position

TABLE 2-continued

Preferred Compounds and Probes of the Invention

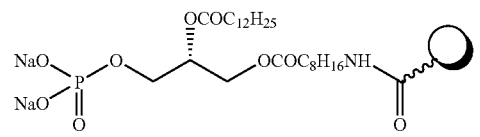

C9 at sn-1 position

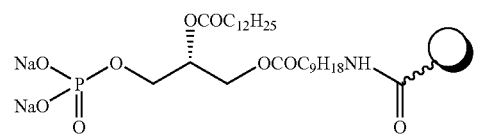

C10 at sn-1 position

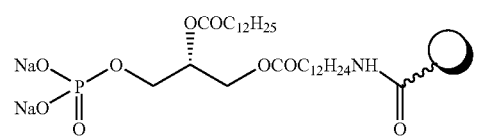

C13 at sn-1 position

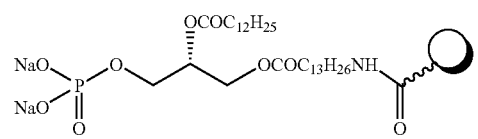

C14 at sn-1 position

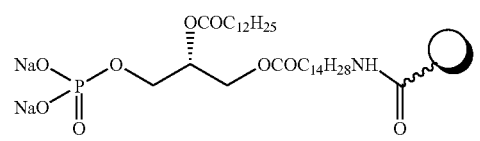

C15 at sn-1 position

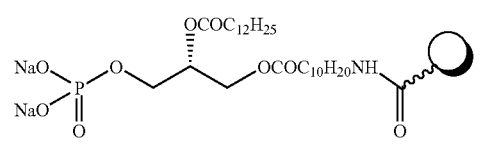

C11 at sn-1 position

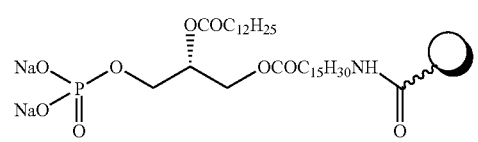

C16 at sn-1 position

C14 at sn-2 position

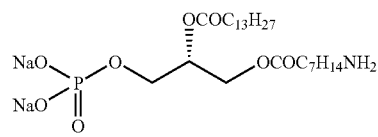

C8 at sn-1 position

TABLE 2-continued

Preferred Compounds and Probes of the Invention

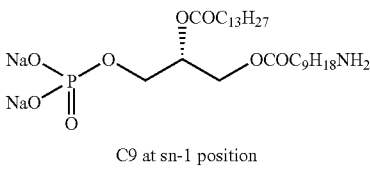

C9 at sn-1 position

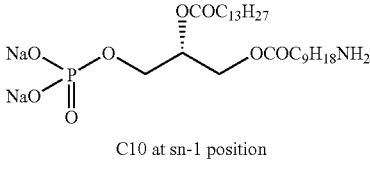

C10 at sn-1 position

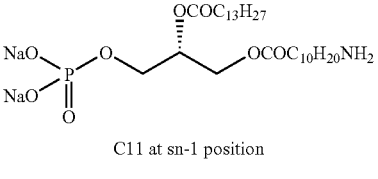

C11 at sn-1 position

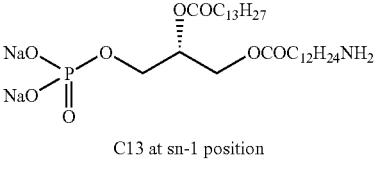

C13 at sn-1 position

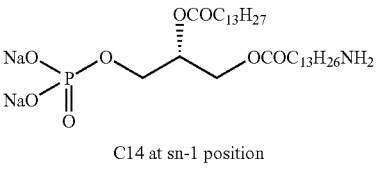

C14 at sn-1 position

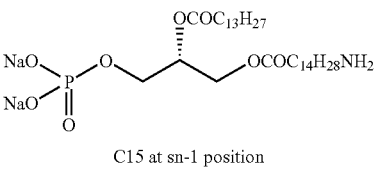

C15 at sn-1 position

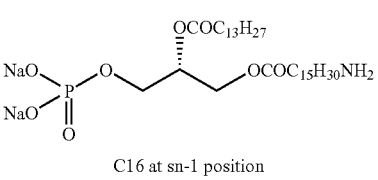

C16 at sn-1 position

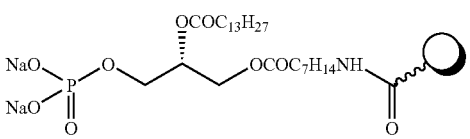

C8 at sn-1 position

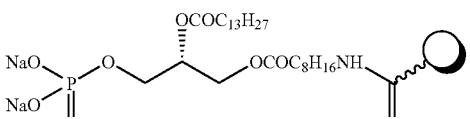

C9 at sn-1 position

TABLE 2-continued

Preferred Compounds and Probes of the Invention

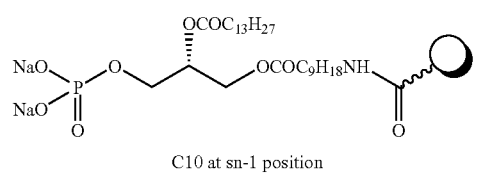

C10 at sn-1 position

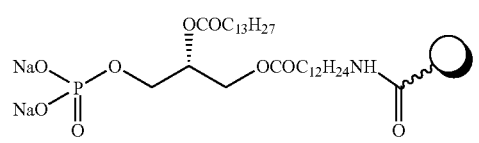

C13 at sn-1 position

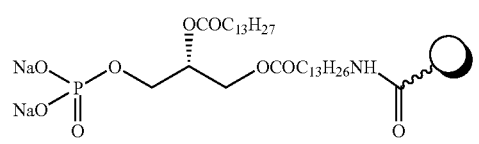

C14 at sn-1 position

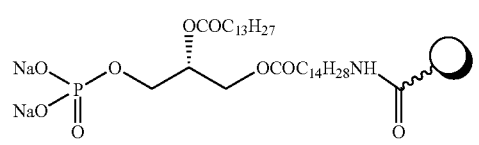

C15 at sn-1 position

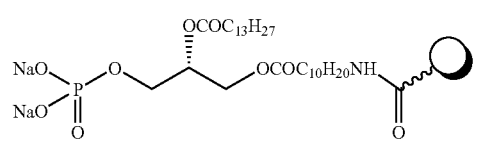

C11 at sn-1 position

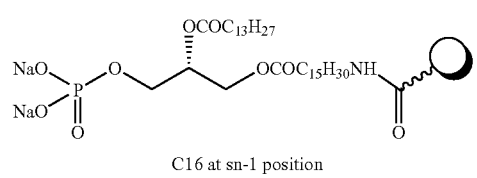

C16 at sn-1 position

C15 at sn-2 position

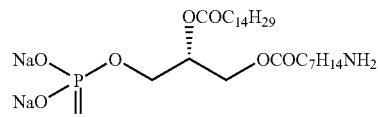

C8 at sn-1 position

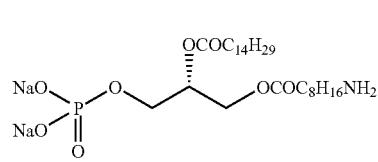

C9 at sn-1 position

TABLE 2-continued

Preferred Compounds and Probes of the Invention

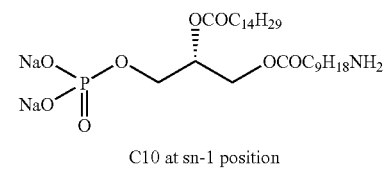

C10 at sn-1 position

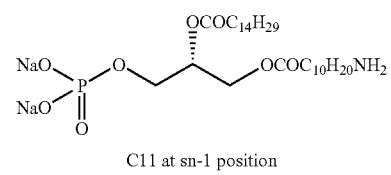

C11 at sn-1 position

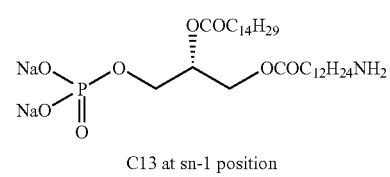

C13 at sn-1 position

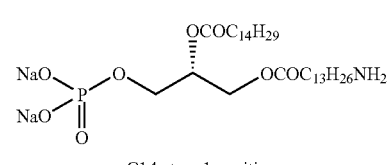

C14 at sn-1 position

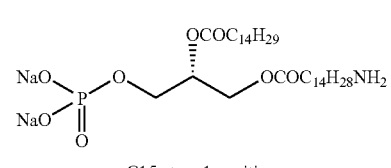

C15 at sn-1 position

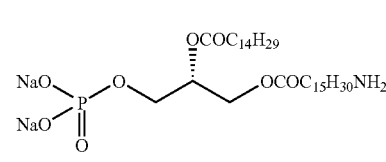

C16 at sn-1 position

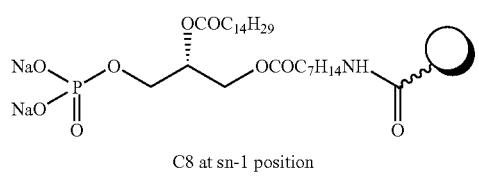

C8 at sn-1 position

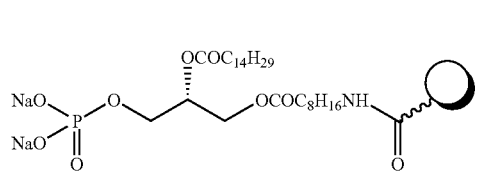

C9 at sn-1 position

TABLE 2-continued

Preferred Compounds and Probes of the Invention

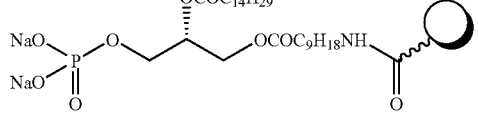

C10 at sn-1 position

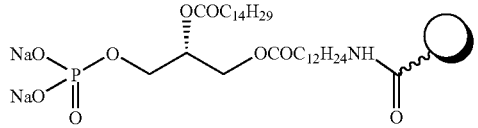

C13 at sn-1 position

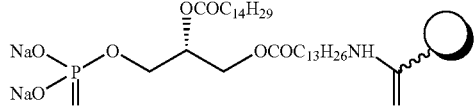

C14 at sn-1 position

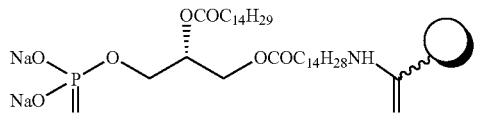

C15 at sn-1 position

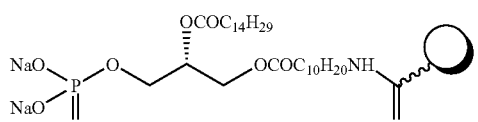

C11 at sn-1 position

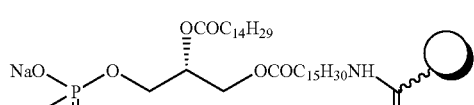

C16 at sn-2 position

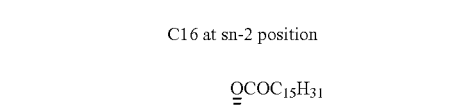

C8 at sn-1 position

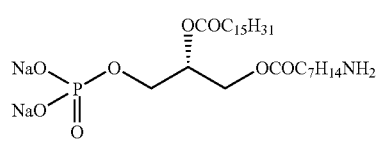

C9 at sn-1 position

TABLE 2-continued

Preferred Compounds and Probes of the Invention

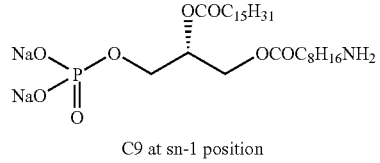

C10 at sn-1 position

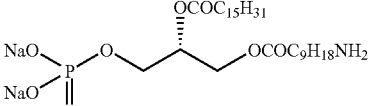

C11 at sn-1 position

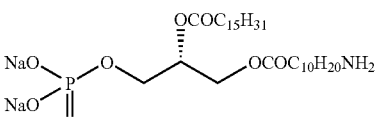

C13 at sn-1 position

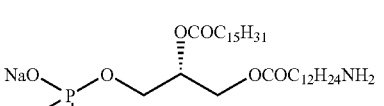

C14 at sn-1 position

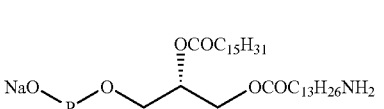

C15 at sn-1 position

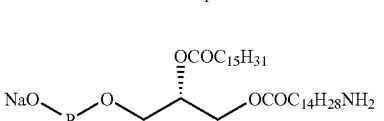

C16 at sn-1 position

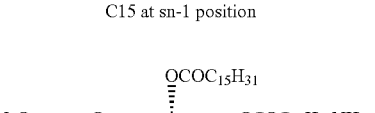

C8 at sn-1 position

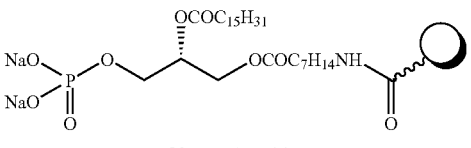

C9 at sn-1 position

TABLE 2-continued

Preferred Compounds and Probes of the Invention

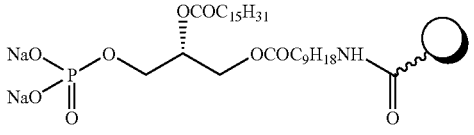

C10 at sn-1 position

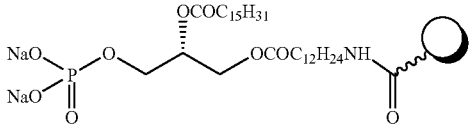

C13 at sn-1 position

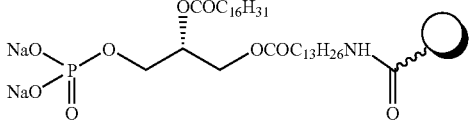

C14 at sn-1 position

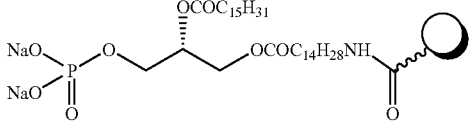

C15 at sn-1 position

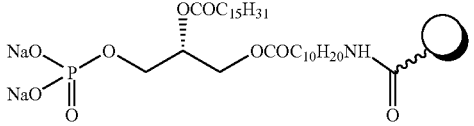

C11 at sn-1 position

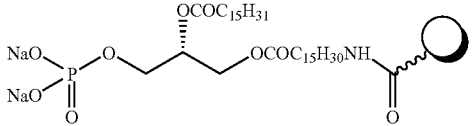

C16 at sn-1 position

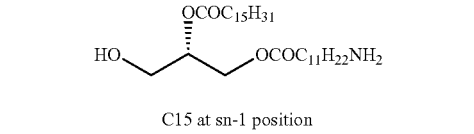

C15 at sn-1 position

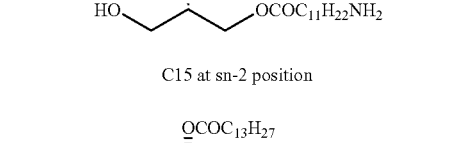

C15 at sn-2 position

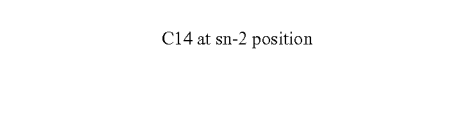

C14 at sn-2 position

TABLE 2-continued

Preferred Compounds and Probes of the Invention

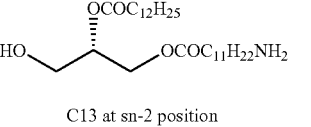

C13 at sn-2 position

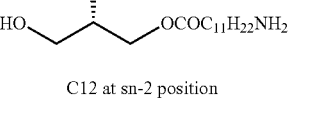

C12 at sn-2 position

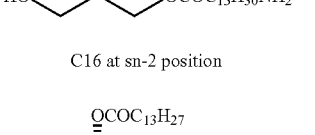

C16 at sn-2 position

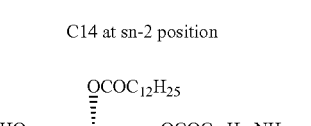

C14 at sn-2 position

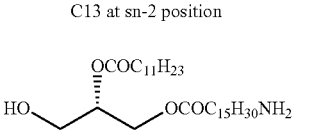

C13 at sn-2 position

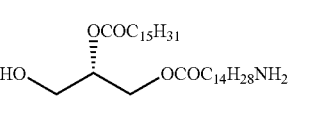

C12 at sn-2 position

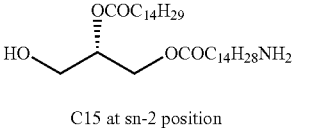

C16 at sn-2 position

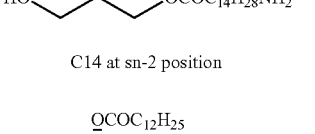

C15 at sn-2 position

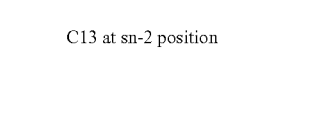

C14 at sn-2 position

OCOC$_{12}$H$_{25}$

HO OCOC$_{14}$H$_{28}$NH$_2$

C13 at sn-2 position

TABLE 2-continued

Preferred Compounds and Probes of the Invention

OCOC$_{11}$H$_{23}$
HO⌒⌒OCOC$_{14}$H$_{28}$NH$_2$

C12 at sn-2 position

OCOC$_{12}$H$_{25}$
HO⌒⌒OCOC$_{14}$H$_{28}$NH$_2$

C13 at sn-2 position

OCOC$_{15}$H$_{31}$
HO⌒⌒OCOC$_{13}$H$_{26}$NH$_2$

C16 at sn-2 position

OCOC$_{14}$H$_{29}$
HO⌒⌒OCOC$_{13}$H$_{26}$NH$_2$

C15 at sn-2 position

OCOC$_{13}$H$_{27}$
HO⌒⌒OCOC$_{13}$H$_{26}$NH$_2$

C14 at sn-2 position

OCOC$_{12}$H$_{25}$
HO⌒⌒OCOC$_{13}$H$_{26}$NH$_2$

C13 at sn-2 position

OCOC$_{11}$H$_{23}$
HO⌒⌒OCOC$_{13}$H$_{26}$NH$_2$

C12 at an-2 position

OCOC$_{15}$H$_{31}$
HO⌒⌒OCOC$_{12}$H$_{24}$NH$_2$

C16 at sn-2 position

OCOC$_{14}$H$_{29}$
HO⌒⌒OCOC$_{12}$H$_{24}$NH$_2$

C15 at sn-2 position

OCOC$_{13}$H$_{27}$
HO⌒⌒OCOC$_{12}$H$_{24}$NH$_2$

C14 at san-2 position

TABLE 2-continued

Preferred Compounds and Probes of the Invention

OCOC$_{12}$H$_{25}$
HO⌒⌒OCOC$_{12}$H$_{24}$NH$_2$

C13 at sn-2 position

OCOC$_{11}$H$_{23}$
HO⌒⌒OCOC$_{12}$H$_{24}$NH$_2$

C12 at sn-2 position

OCOC$_{15}$H$_{31}$
HO⌒⌒OCOC$_{11}$H$_{22}$NH—C(O)—⬤

C16 at sn-2 position

OCOC$_{14}$H$_{28}$
HO⌒⌒OCOC$_{11}$H$_{22}$NH—C(O)—⬤

C15 at sn-2 position

OCOC$_{13}$H$_{27}$
HO⌒⌒OCOC$_{11}$H$_{22}$NH—C(O)—⬤

C14 at sn-2 position

OCOC$_{12}$H$_{26}$
HO⌒⌒OCOC$_{11}$H$_{22}$NH—C(O)—⬤

C13 at sn-2 position

OCOC$_{11}$H$_{23}$
HO⌒⌒OCOC$_{11}$H$_{22}$NH—C(O)—⬤

C12 at sn-2 position

OCOC$_{15}$H$_{31}$
HO⌒⌒OCOC$_{15}$H$_{30}$NH—C(O)—⬤

C16 at sn-2 position

OCOC$_{14}$H$_{29}$
HO⌒⌒OCOC$_{15}$H$_{30}$NH—C(O)—⬤

C15 at sn-2 position

TABLE 2-continued

Preferred Compounds and Probes of the Invention

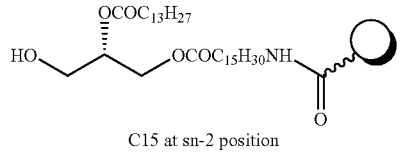

C15 at sn-2 position

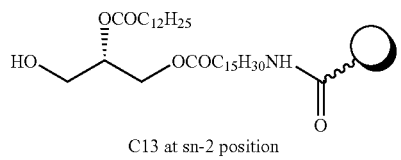

C13 at sn-2 position

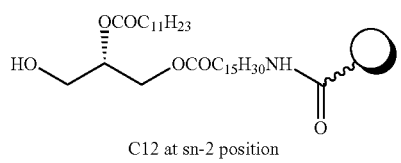

C12 at sn-2 position

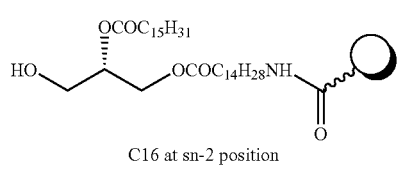

C16 at sn-2 position

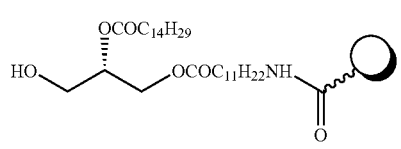

C15 at sn-2 position

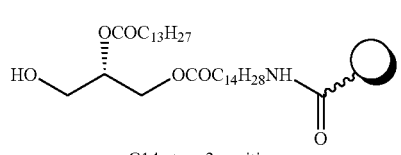

C14 at sn-2 position

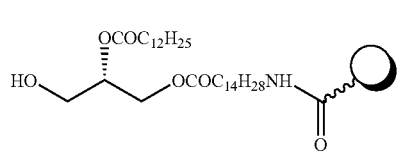

C13 at sn-2 position

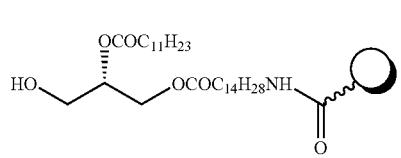

C12 at sn-2 position

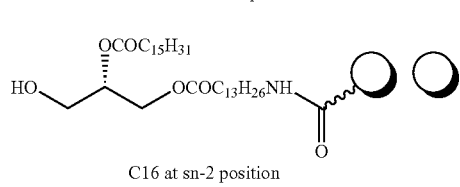

C16 at sn-2 position

TABLE 2-continued

Preferred Compounds and Probes of the Invention

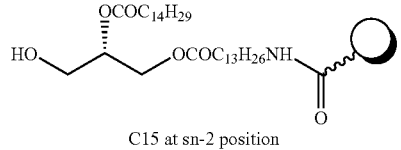

C15 at sn-2 position

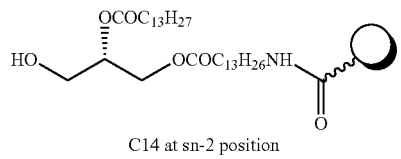

C14 at sn-2 position

C13 at sn-2 position

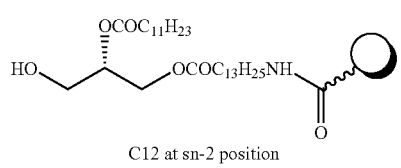

C12 at sn-2 position

C16 at sn-2 position

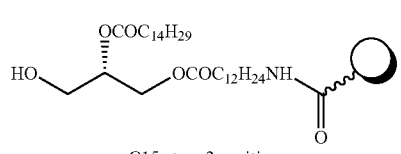

C15 at sn-2 position

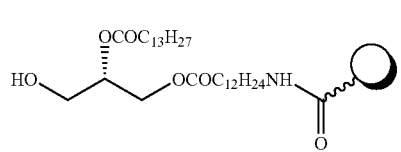

C14 at sn-2 position

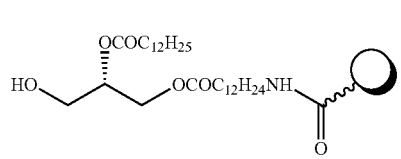

C13 at sn-2 position

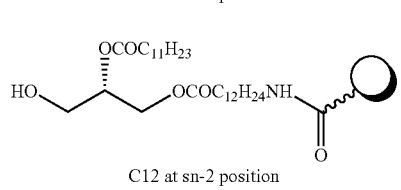

C12 at sn-2 position

TABLE 2-continued
Preferred Compounds and Probes of the Invention
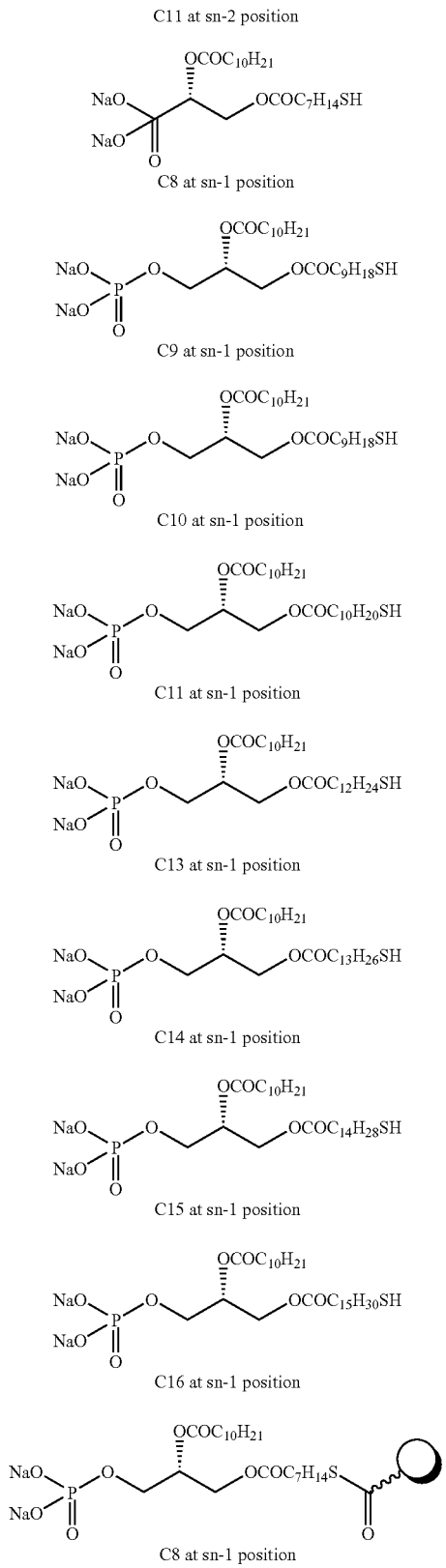
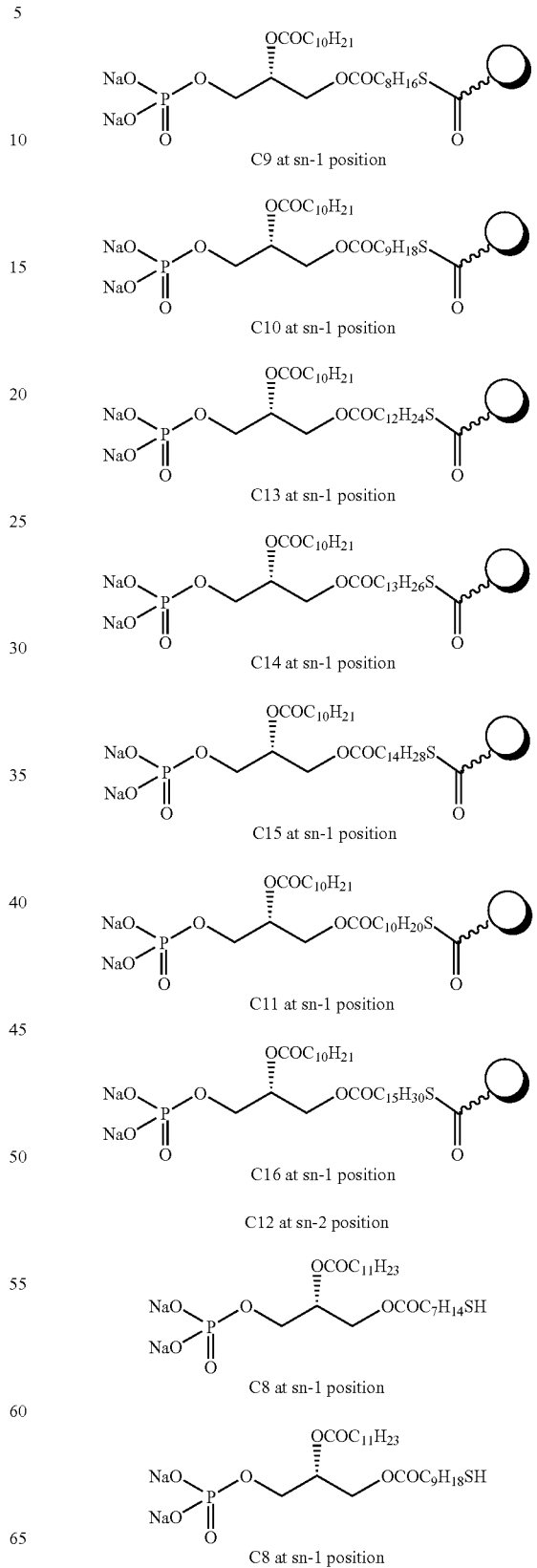

TABLE 2-continued

Preferred Compounds and Probes of the Invention

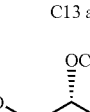

C10 at sn-1 position

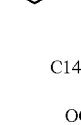

C11 at sn-1 position

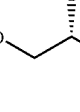

C13 at sn-1 position

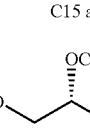

C14 at sn-1 position

C15 at sn-1 position

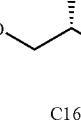

C16 at sn-1 position

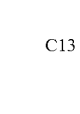

C8 at sn-1 position

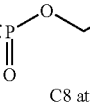

C9 at sn-1 position

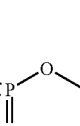

C10 at sn-1 position

TABLE 2-continued

Preferred Compounds and Probes of the Invention

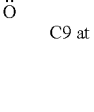

C13 at sn-1 position

C14 at sn-1 position

C15 at sn-1 position

C11 at sn-1 position

C16 at sn-1 position

C13 at sn-2 position

C8 at sn-1 position

C9 at sn-1 position

C10 at sn-1 position

C11 at sn-1 position

TABLE 2-continued

Preferred Compounds and Probes of the Invention

[Structure with $OCOC_{12}H_{25}$ and $OCOC_{12}H_{24}SH$, phosphate with NaO groups]
C13 at sn-1 position

[Structure with $OCOC_{12}H_{25}$ and $OCOC_{13}H_{26}SH$]
C14 at sn-1 position

[Structure with $OCOC_{12}H_{25}$ and $OCOC_{14}H_{28}SH$]
C15 at sn-1 position

[Structure with $OCOC_{12}H_{25}$ and $OCOC_{15}H_{30}SH$]
C18 at sn-1 position

[Structure with $OCOC_{12}H_{25}$ and $OCOC_7H_{14}S$—bead]
C8 at sn-1 position

[Structure with $OCOC_{12}H_{25}$ and $OCOC_8H_{16}S$—bead]
C9 at sn-1 position

[Structure with $OCOC_{12}H_{25}$ and $OCOC_9H_{18}S$—bead]
C10 at sn-1 position

[Structure with $OCOC_{12}H_{25}$ and $OCOC_{12}H_{24}S$—bead]
C13 at sn-1 position

[Structure with $OCOC_{12}H_{25}$ and $OCOC_{13}H_{26}S$—bead]
C14 at sn-1 position

[Structure with $OCOC_{12}H_{25}$ and $OCOC_{14}H_{28}S$—bead]
C15 at sn-1 position

[Structure with $OCOC_{12}H_{25}$ and $OCOC_{10}H_{20}S$—bead]
C11 at sn-1 position

[Structure with $OCOC_{12}H_{25}$ and $OCOC_{15}H_{30}S$—bead]
C18 at sn-1 position
C14 at sn-2 position

[Structure with $OCOC_{13}H_{27}$ and $OCOC_7H_{14}SH$]
C8 at sn-1 position

[Structure with $OCOC_{13}H_{27}$ and $OCOC_8H_{16}SH$]
C9 at sn-1 position

[Structure with $OCOC_{13}H_{27}$ and $OCOC_9H_{18}SH$]
C10 at sn-1 position

[Structure with $OCOC_{13}H_{27}$ and $OCOC_{10}H_{20}SH$]
C11 at sn-1 position

[Structure with $OCOC_{13}H_{27}$ and $OCOC_{12}H_{24}SH$]
C13 at sn-1 position

[Structure with $OCOC_{13}H_{27}$ and $OCOC_{13}H_{20}SH$]
C14 at sn-1 position

TABLE 2-continued

Preferred Compounds and Probes of the Invention

NaO-P(=O)(ONa)-O-CH₂-CH(OCOC₁₃H₂₇)-CH₂-OCOC₁₄H₂₈SH

C15 at sn-1 position

NaO-P(=O)(ONa)-O-CH₂-CH(OCOC₁₃H₂₇)-CH₂-OCOC₁₅H₂₀SH

C18 at sn-1 position

NaO-P(=O)(ONa)-O-CH₂-CH(OCOC₁₃H₂₇)-CH₂-OCOC₇H₁₄S-C(=O)-◯

C8 at sn-1 position

NaO-P(=O)(ONa)-O-CH₂-CH(OCOC₁₃H₂₇)-CH₂-OCOC₈H₁₆S-C(=O)-◯

C9 at sn-1 position

NaO-P(=O)(ONa)-O-CH₂-CH(OCOC₁₃H₂₇)-CH₂-OCOC₉H₁₈S-C(=O)-◯

C10 at sn-1 position

NaO-P(=O)(ONa)-O-CH₂-CH(OCOC₁₃H₂₇)-CH₂-OCOC₁₂H₂₄S-C(=O)-◯

C13 at sn-1 position

NaO-P(=O)(ONa)-O-CH₂-CH(OCOC₁₃H₂₇)-CH₂-OCOC₁₃H₂₆S-C(=O)-◯

C14 at sn-1 position

NaO-P(=O)(ONa)-O-CH₂-CH(OCOC₁₃H₂₇)-CH₂-OCOC₁₄H₂₈S-C(=O)-◯

C15 at sn-1 position

NaO-P(=O)(ONa)-O-CH₂-CH(OCOC₁₃H₂₇)-CH₂-OCOC₁₀H₂₀S-C(=O)-◯

C11 at sn-1 position

TABLE 2-continued

Preferred Compounds and Probes of the Invention

NaO-P(=O)(ONa)-O-CH₂-CH(OCOC₁₃H₂₇)-CH₂-OCOC₁₅H₃₀S-C(=O)-◯

C16 at sn-1 position

NaO-P(=O)(ONa)-O-CH₂-CH(OCOC₁₄H₂₉)-CH₂-OCOC₇H₁₄SH

C8 at sn-1 position

NaO-P(=O)(ONa)-O-CH₂-CH(OCOC₁₄H₂₉)-CH₂-OCOC₈H₁₆SH

C9 at sn-1 position

NaO-P(=O)(ONa)-O-CH₂-CH(OCOC₁₄H₂₉)-CH₂-OCOC₉H₁₈SH

C10 at sn-1 position

C15 at sn-2 position

NaO-P(=O)(ONa)-O-CH₂-CH(OCOC₁₄H₂₉)-CH₂-OCOC₁₀H₂₀S

C11 at sn-1 position

NaO-P(=O)(ONa)-O-CH₂-CH(OCOC₁₄H₂₉)-CH₂-OCOC₁₂H₂₄SH

C13 at sn-1 position

NaO-P(=O)(ONa)-O-CH₂-CH(OCOC₁₄H₂₉)-CH₂-OCOC₁₃H₂₆SH

C14 at sn-1 position

NaO-P(=O)(ONa)-O-CH₂-CH(OCOC₁₄H₂₉)-CH₂-OCOC₁₄H₂₈SH

C15 at sn-1 position

NaO-P(=O)(ONa)-O-CH₂-CH(OCOC₁₄H₂₉)-CH₂-OCOC₁₅H₃₀S

C16 at sn-1 position

TABLE 2-continued
Preferred Compounds and Probes of the Invention
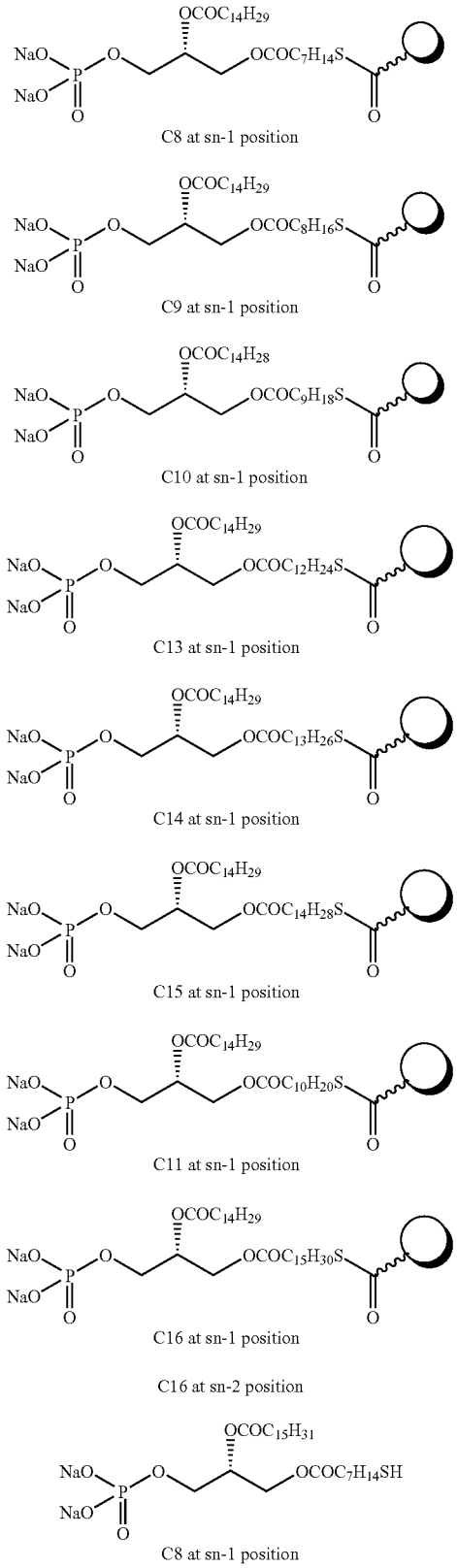
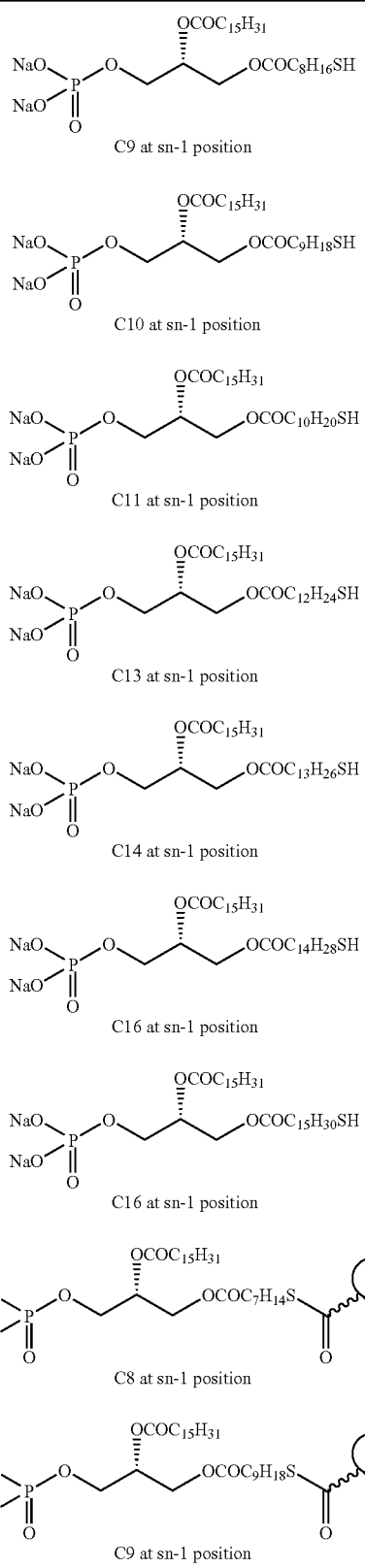

TABLE 2-continued

Preferred Compounds and Probes of the Invention

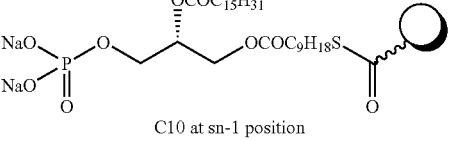

C10 at sn-1 position

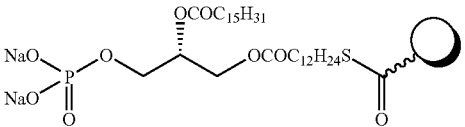

C13 at sn-1 position

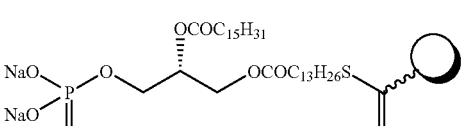

C14 at sn-1 position

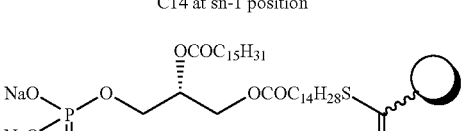

C15 at sn-1 position

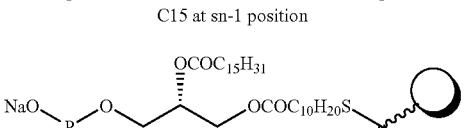

C11 at sn-1 position

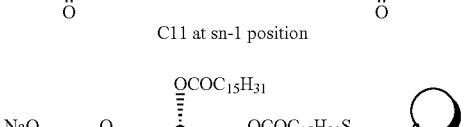

C15 at sn-1 position

Diacylglycerol

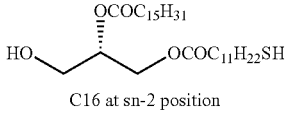

C16 at sn-2 position

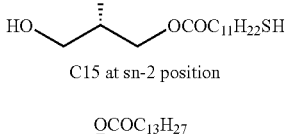

C15 at sn-2 position

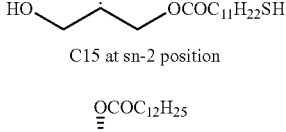

C15 at sn-2 position

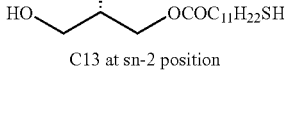

C13 at sn-2 position

TABLE 2-continued

Preferred Compounds and Probes of the Invention

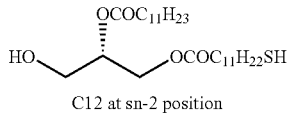

C12 at sn-2 position

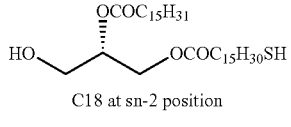

C18 at sn-2 position

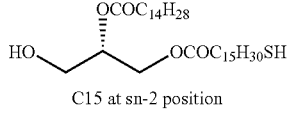

C15 at sn-2 position

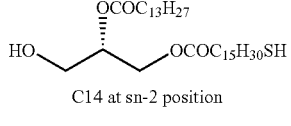

C14 at sn-2 position

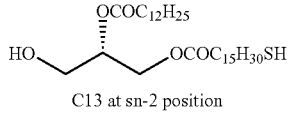

C13 at sn-2 position

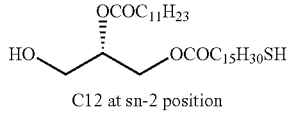

C12 at sn-2 position

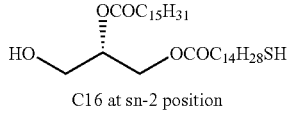

C16 at sn-2 position

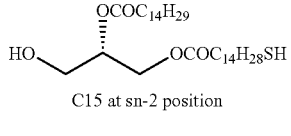

C15 at sn-2 position

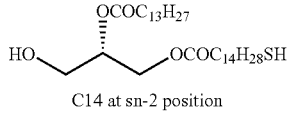

C14 at sn-2 position

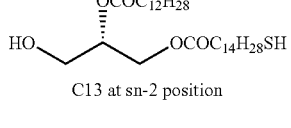

C13 at sn-2 position

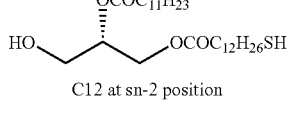

C12 at sn-2 position

TABLE 2-continued

Preferred Compounds and Probes of the Invention

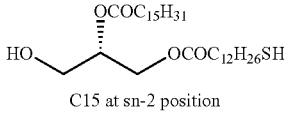

C15 at sn-2 position

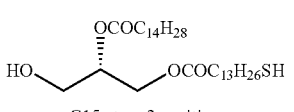

C15 at sn-2 position

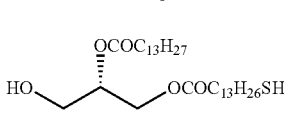

C14 at sn-2 position

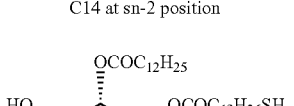

C13 at sn-2 position

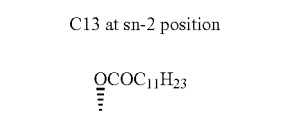

C12 at sn-2 position

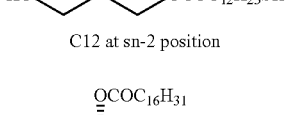

C16 at sn-2 position

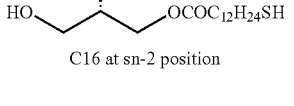

C15 at sn-2 position

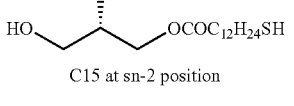

C14 at sn-2 position

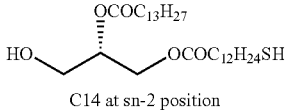

C13 at sn-2 position

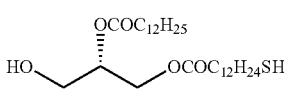

C12 at sn-2 position

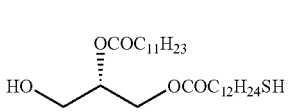

C16 at sn-2 position

TABLE 2-continued

Preferred Compounds and Probes of the Invention

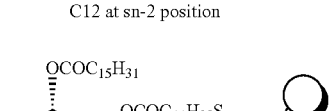

C15 at sn-2 position

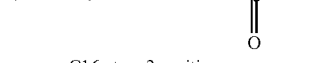

C14 at sn-2 position

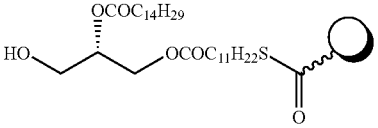

C13 at sn-2 position

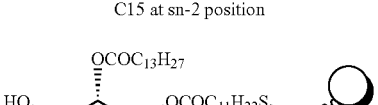

C12 at sn-2 position

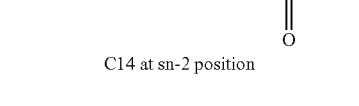

C16 at sn-2 position

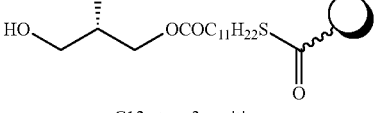

C15 at sn-2 position

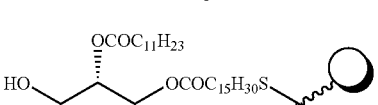

C14 at sn-2 position

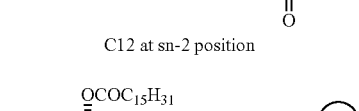

C13 at sn-2 position

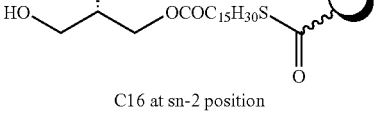

C12 at sn-2 position

TABLE 2-continued

Preferred Compounds and Probes of the Invention

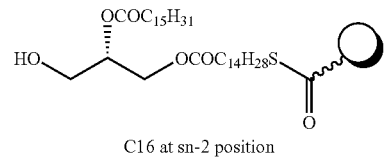

C16 at sn-2 position

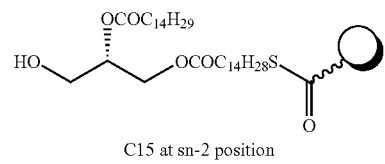

C15 at sn-2 position

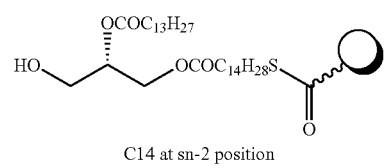

C14 at sn-2 position

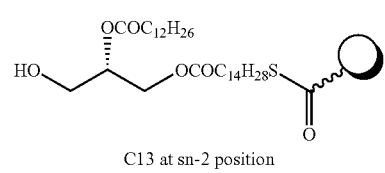

C13 at sn-2 position

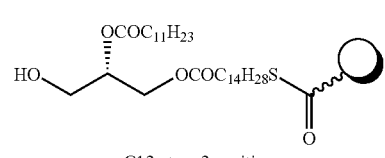

C12 at sn-2 position

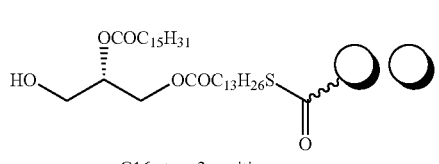

C16 at sn-2 position

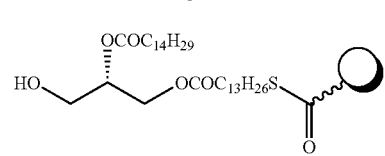

C15 at sn-2 position

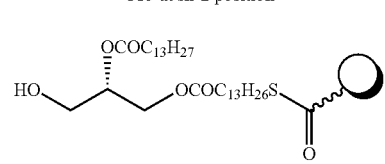

C14 at sn-2 position

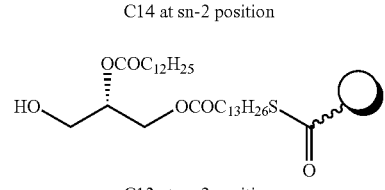

C13 at sn-2 position

TABLE 2-continued

Preferred Compounds and Probes of the Invention

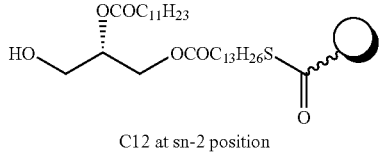

C12 at sn-2 position

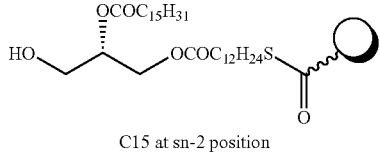

C15 at sn-2 position

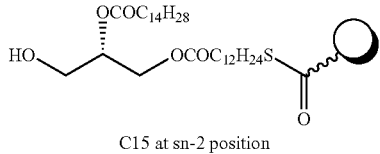

C15 at sn-2 position

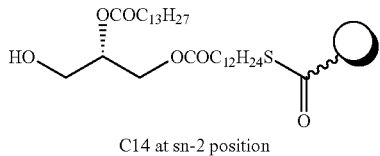

C14 at sn-2 position

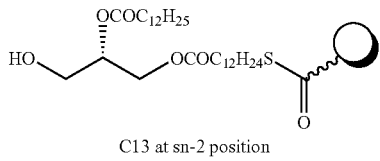

C13 at sn-2 position

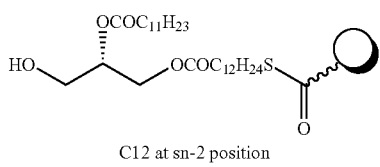

C12 at sn-2 position

Enantiomeric structures

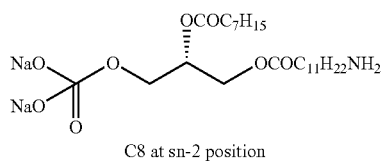

C8 at sn-2 position

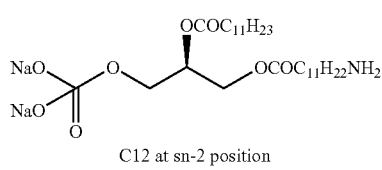

C12 at sn-2 position

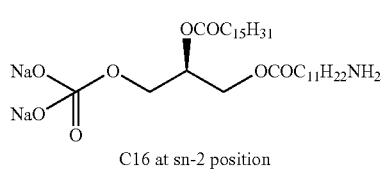

C16 at sn-2 position

TABLE 2-continued

Preferred Compounds and Probes of the Invention

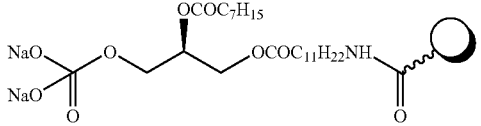

C8 at sn-2 position

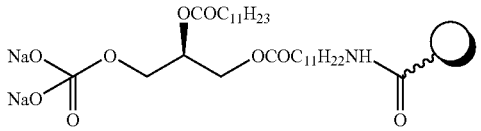

C12 at sn-2 position

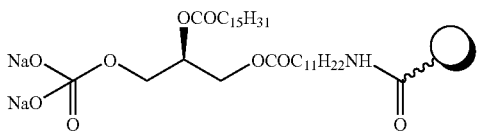

C16 at sn-2 position

Changes in chain length at the sn-2 position

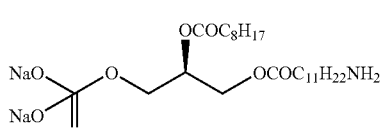

C9 at sn-2 position

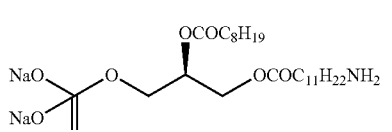

C10 at sn-2 position

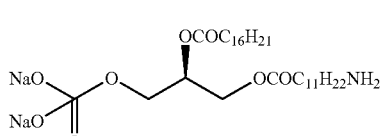

C11 at sn-2 position

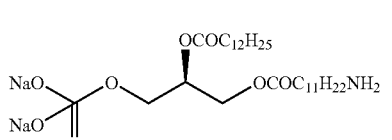

C13 at sn-2 position

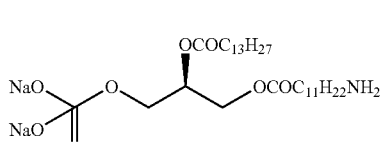

C14 at sn-2 position

C15 at sn-2 position

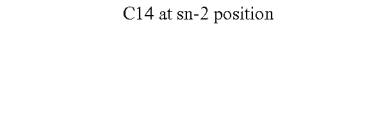

C9 at sn-2 position

C11 at sn-2 position

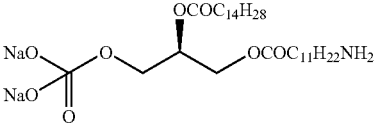

C13 at sn-2 position

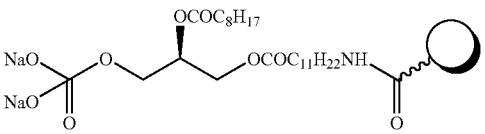

C14 at sn-2 position

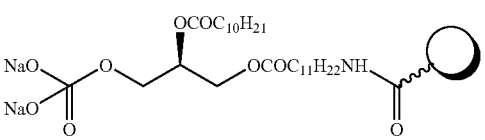

C10 at sn-2 position

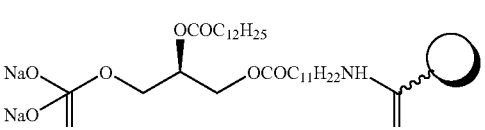

C15 at sn-2 position

Changes in chain at the sn-1 position

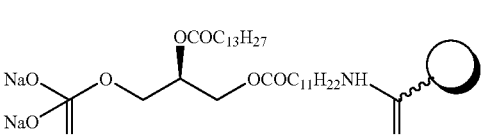

C8 at sn-1 position

TABLE 2-continued

Preferred Compounds and Probes of the Invention

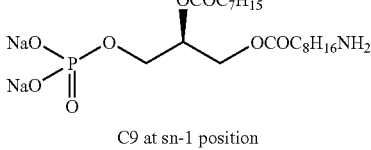

C9 at sn-1 position

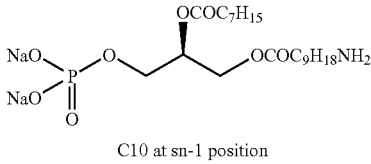

C10 at sn-1 position

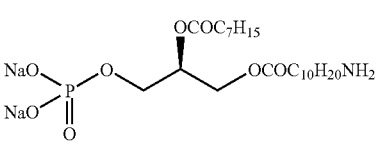

C11 at sn-1 position

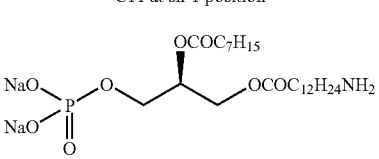

C13 at sn-1 position

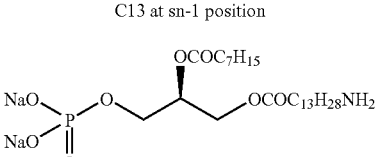

C14 at sn-1 position

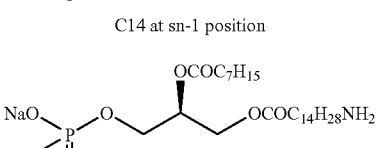

C15 at sn-1 position

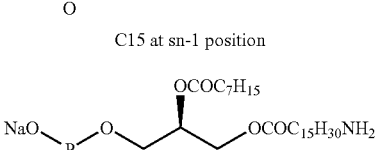

C16 at sn-1 position

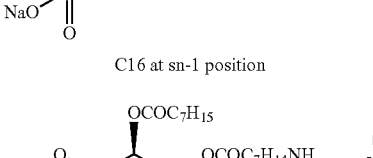

C8 at sn-1 position

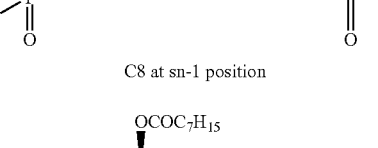

C9 at sn-1 position

TABLE 2-continued

Preferred Compounds and Probes of the Invention

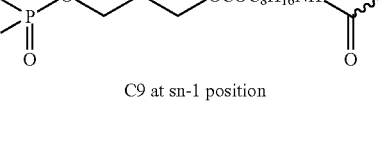

C10 at sn-1 position

C13 at sn-1 position

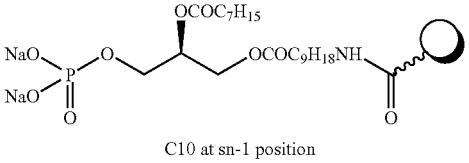

C14 at sn-1 position

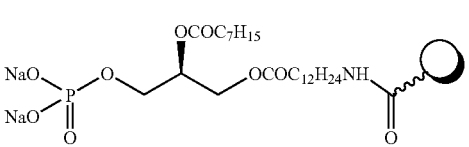

C15 at sn-1 position

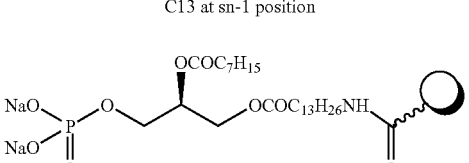

C11 at sn-2 position

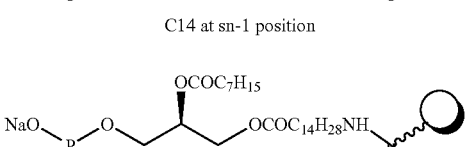

C16 at sn-2 position

C9 at sn-2 position

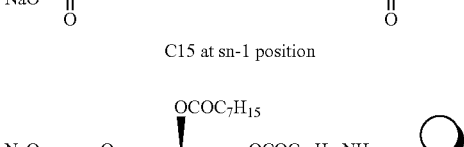

C8 at sn-2 position

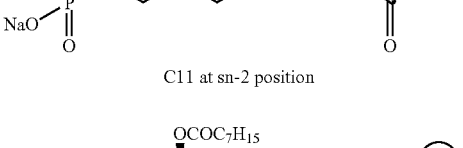

C9 at sn-2 position

TABLE 2-continued

Preferred Compounds and Probes of the Invention

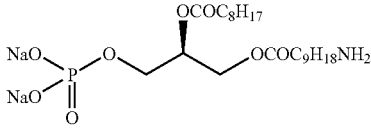

C10 at sn-2 position

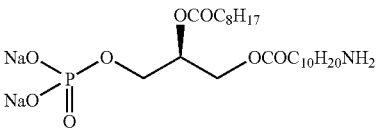

C11 at sn-2 position

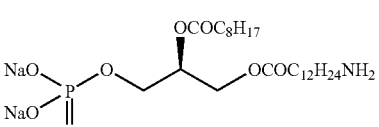

C13 at sn-2 position

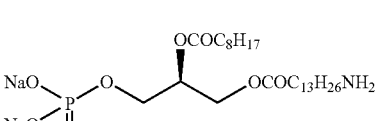

C14 at sn-2 position

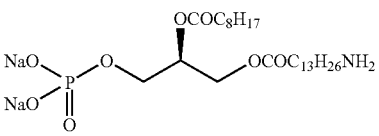

C15 at sn-2 position

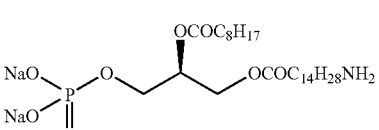

C16 at sn-2 position

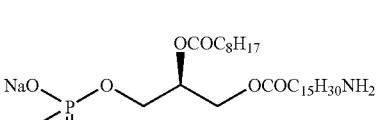

C8 at sn-2 position

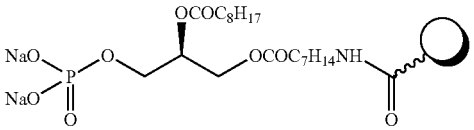

C9 at sn-2 position

TABLE 2-continued

Preferred Compounds and Probes of the Invention

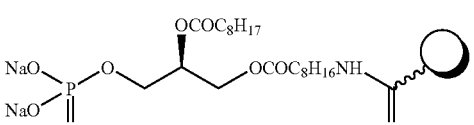

C10 at sn-2 position

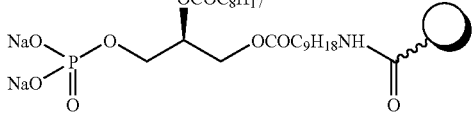

C13 at sn-2 position

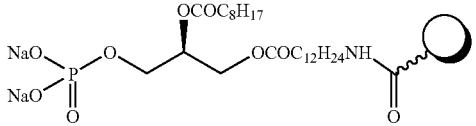

C14 at sn-2 position

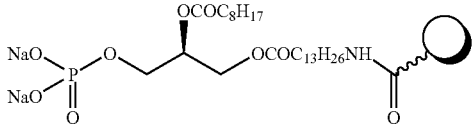

C15 at sn-2 position

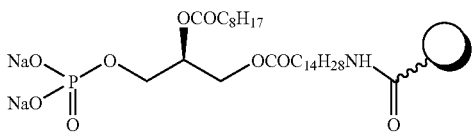

C11 at sn-1 position

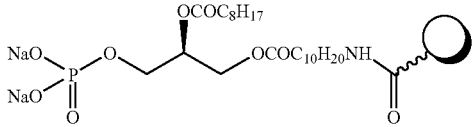

C16 at sn-1 position

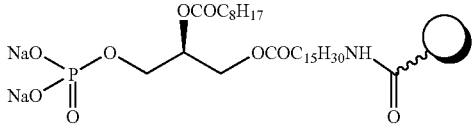

C10 at sn-2 position

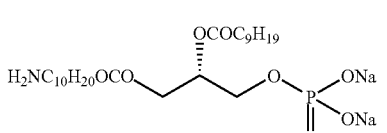

C11 at sn-1 position

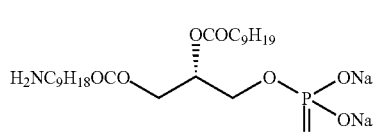

C10 at sn-1 position

TABLE 2-continued

Preferred Compounds and Probes of the Invention

H₂NC₉H₁₈OCO-CH(OCOC₉H₁₉)-CH₂-O-P(=O)(ONa)(ONa)
C9 at sn-1 position

H₂NC₇H₁₄OCO-CH(OCOC₉H₁₉)-CH₂-O-P(=O)(ONa)(ONa)
C8 at sn-1 position

H₂NC₁₄H₂₈OCO-CH(OCOC₉H₁₉)-CH₂-O-P(=O)(ONa)(ONa)
C15 at sn-1 position

H₂NC₁₄H₂₈OCO-CH(OCOC₉H₁₉)-CH₂-O-P(=O)(ONa)(ONa)
C15 at sn-1 position

H₂NC₁₃H₂₆OCO-CH(OCOC₉H₁₉)-CH₂-O-P(=O)(ONa)(ONa)
C14 at sn-1 position

H₂NC₁₂H₂₄OCO-CH(OCOC₉H₁₉)-CH₂-O-P(=O)(ONa)(ONa)
C13 at sn-1 position (Bead)-C(=O)-HNC₉H₁₈OCO-CH(OCOC₉H₁₉)-CH₂-O-P(=O)(ONa)(ONa)
C10 at sn-1 position (Bead)-C(=O)-HNC₉H₁₈OCO-CH(OCOC₉H₁₉)-CH₂-O-P(=O)(ONa)(ONa)
C9 at sn-1 position (Bead)-C(=O)-HNC₇H₁₄OCO-CH(OCOC₉H₁₉)-CH₂-O-P(=O)(ONa)(ONa)
C13 at sn-1 position (Bead)-C(=O)-HNC₁₄H₂₈OCO-CH(OCOC₉H₁₉)-CH₂-O-P(=O)(ONa)(ONa)
C15 at sn-1 position (Bead)-C(=O)-HNC₁₃H₂₆OCO-CH(OCOC₉H₁₉)-CH₂-O-P(=O)(ONa)(ONa)
C14 at sn-1 position (Bead)-C(=O)-HNC₁₂H₂₄OCO-CH(OCOC₉H₁₉)-CH₂-O-P(=O)(ONa)(ONa)
C13 at sn-1 position (Bead)-C(=O)-HNC₁₅H₂₀OCO-CH(OCOC₉H₁₉)-CH₂-O-P(=O)(ONa)(ONa)
C15 at sn-1 position (Bead)-C(=O)-HNC₁₀H₂₀OCO-CH(OCOC₉H₁₉)-CH₂-O-P(=O)(ONa)(ONa)
C11 at sn-1 position
C11 at sn-2 position H₂NC₁₀H₂₀OCO-CH(OCOC₁₀H₂₁)-CH₂-O-P(=O)(ONa)(ONa)
C11 at sn-1 position H₂NC₉H₁₈OCO-CH(OCOC₁₀H₂₁)-CH₂-O-P(=O)(ONa)(ONa)
C10 at sn-1 position H₂NC₈H₁₆OCO-CH(OCOC₁₀H₂₁)-CH₂-O-P(=O)(ONa)(ONa)
C9 at sn-1 position H₂NC₇H₁₄OCO-CH(OCOC₁₀H₂₁)-CH₂-O-P(=O)(ONa)(ONa)
C8 at sn-1 position TABLE 2-continued Preferred Compounds and Probes of the Invention

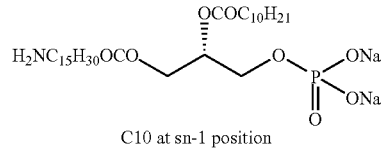

C10 at sn-1 position

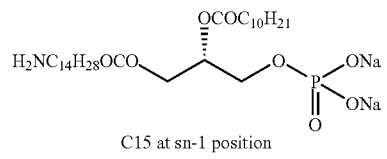

C15 at sn-1 position

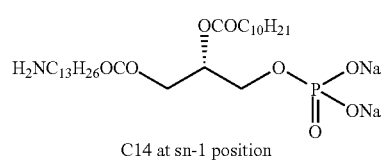

C14 at sn-1 position

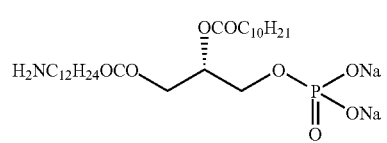

C13 at sn-1 position

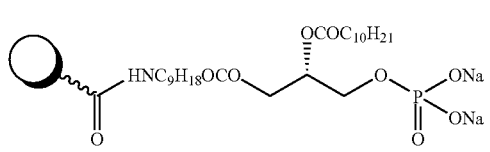

C9 at sn-1 position


C8 at sn-1 position


C15 at sn-1 position


C13 at sn-1 position

TABLE 2-continued

Preferred Compounds and Probes of the Invention

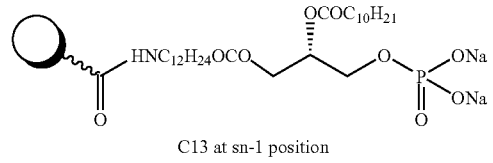

C13 at sn-1 position

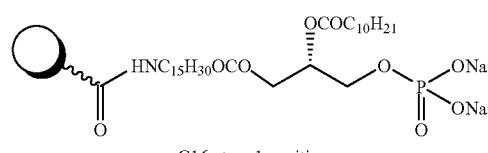

C16 at sn-1 position

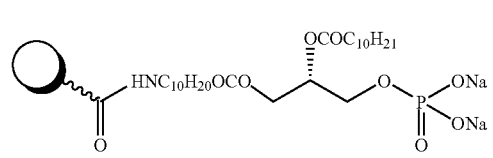

C11 at sn-1 position

C12 at sn-2 position

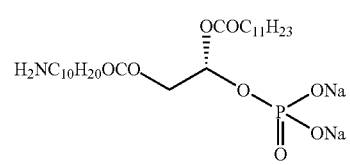

C11 at sn-1 position

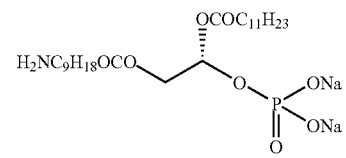

C10 at sn-1 position

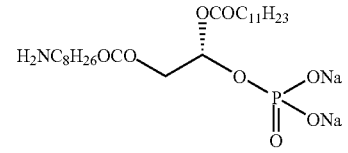

C9 at sn-1 position

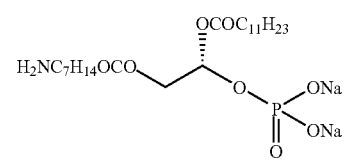

C8 at sn-1 position

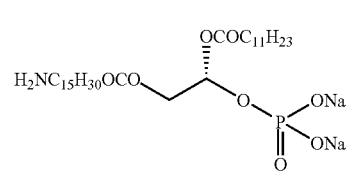

C16 at sn-1 position

TABLE 2-continued

Preferred Compounds and Probes of the Invention

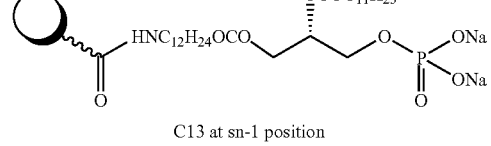

C15 at sn-1 position

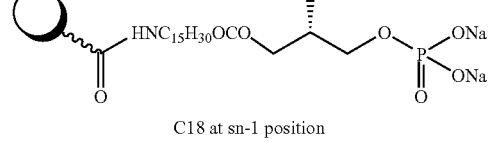

C14 at sn-1 position

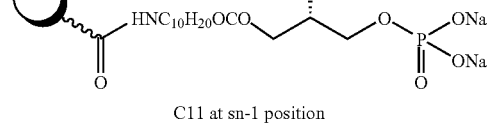

C13 at sn-1 position

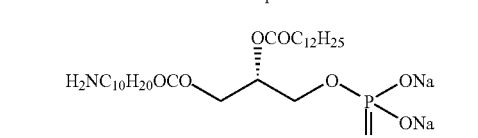

C10 at sn-1 position

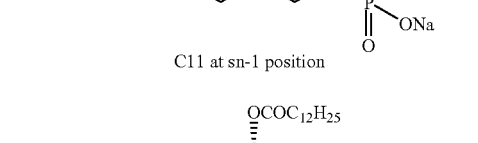

C9 at sn-1 position

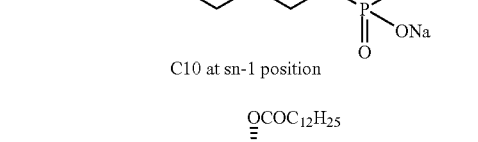

C8 at sn-1 position

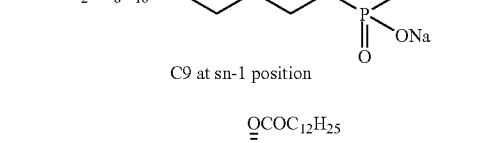

C15 at sn-1 position

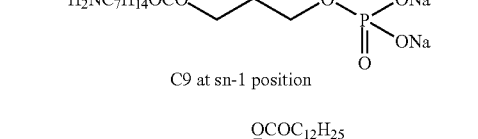

C14 at sn-1 position

TABLE 2-continued

Preferred Compounds and Probes of the Invention

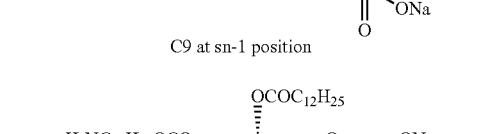

C13 at sn-1 position

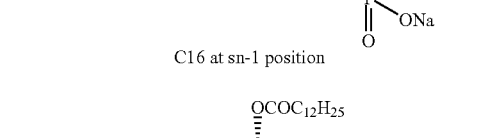

C18 at sn-1 position

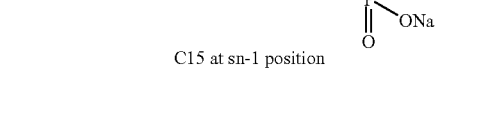

C11 at sn-1 position

C13 at sn-2 position

H$_2$NC$_{10}$H$_{20}$OCO—[structure]—OP(=O)(ONa)(ONa), OCOC$_{12}$H$_{25}$

C11 at sn-1 position

H$_2$NC$_9$H$_{18}$OCO—[structure]—OP(=O)(ONa)(ONa), OCOC$_{12}$H$_{25}$

C10 at sn-1 position

H$_2$NC$_8$H$_{16}$OCO—[structure]—OP(=O)(ONa)(ONa), OCOC$_{12}$H$_{25}$

C9 at sn-1 position

H$_2$NC$_7$H$_{14}$OCO—[structure]—OP(=O)(ONa)(ONa), OCOC$_{12}$H$_{25}$

C9 at sn-1 position

H$_2$NC$_{15}$H$_{30}$OCO—[structure]—OP(=O)(ONa)(ONa), OCOC$_{12}$H$_{25}$

C16 at sn-1 position

H$_2$NC$_{14}$H$_{28}$OCO—[structure]—OP(=O)(ONa)(ONa), OCOC$_{12}$H$_{25}$

C15 at sn-1 position

TABLE 2-continued

Preferred Compounds and Probes of the Invention

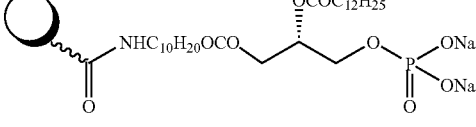

C14 at sn-1 position

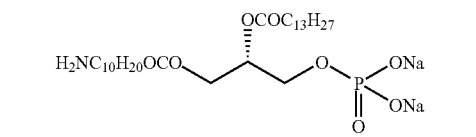

C13 at sn-1 position

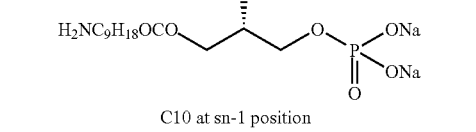

C9 at sn-1 position

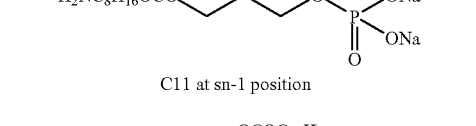

C8 at sn-1 position

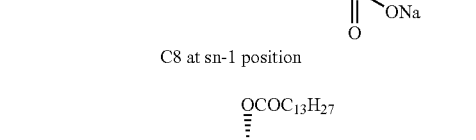

C8 at sn-1 position

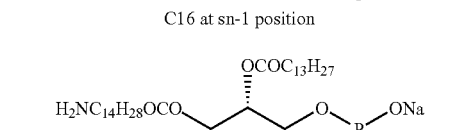

C15 at sn-1 position

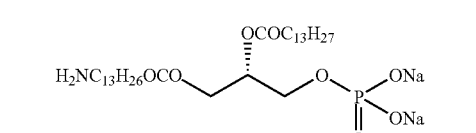

C14 at sn-1 position

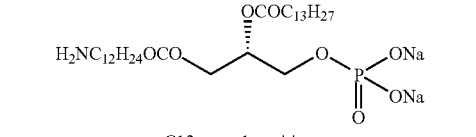

C13 at sn-1 position

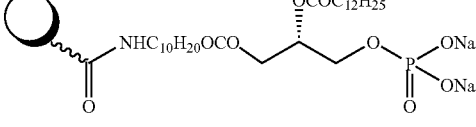

C16 at sn-1 position

TABLE 2-continued

Preferred Compounds and Probes of the Invention

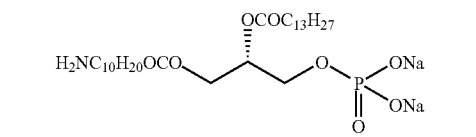

C11 at sn-1 position
C14 at sn-2 position

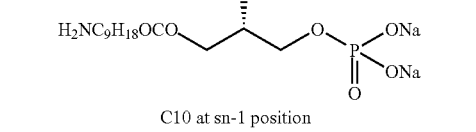

C11 at sn-1 position

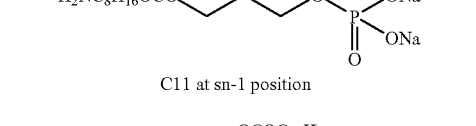

C10 at sn-1 position

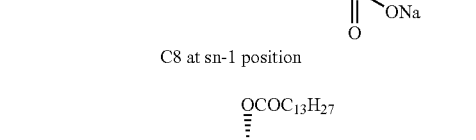

C11 at sn-1 position

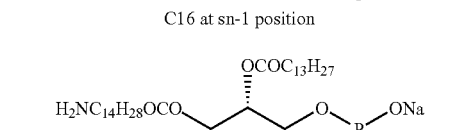

C8 at sn-1 position

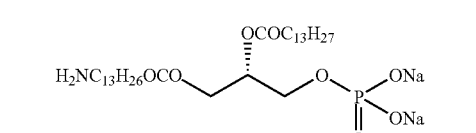

C16 at sn-1 position

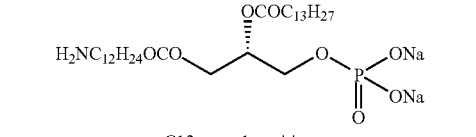

C16 at sn-1 position

C14 at sn-1 position

C13 at sn-1 position

TABLE 2-continued

Preferred Compounds and Probes of the Invention

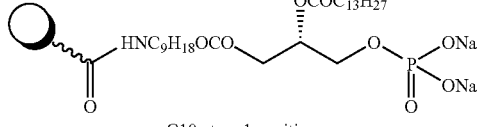
C10 at sn-1 position

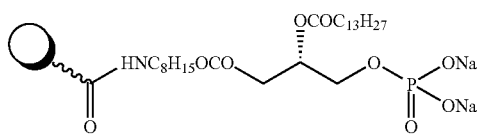
C9 at sn-1 position

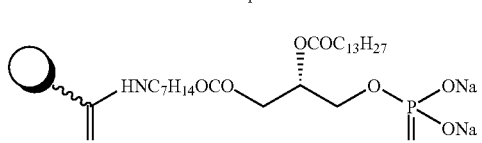
C8 at sn-1 position

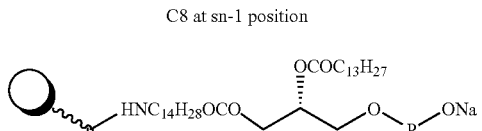
C15 at sn-1 position

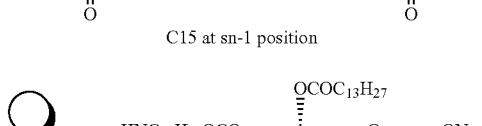
C14 at sn-1 position

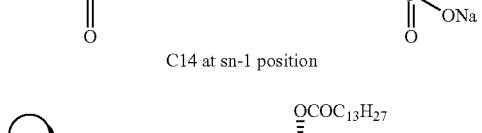
C13 at sn-1 position

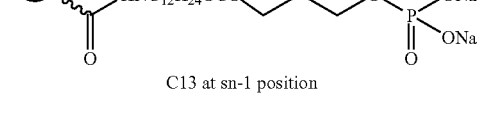
C18 at sn-1 position

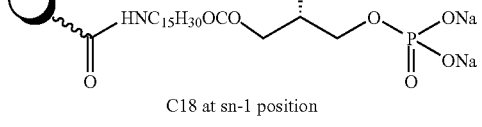
C11 at sn-1 position

Diacylglycerol

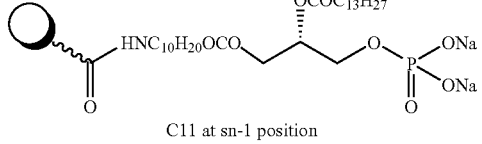
C12 at sn-2 position

TABLE 2-continued

Preferred Compounds and Probes of the Invention

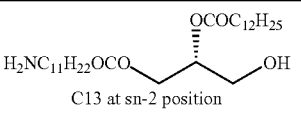
C13 at sn-2 position

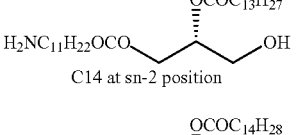
C14 at sn-2 position

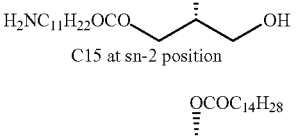
C15 at sn-2 position

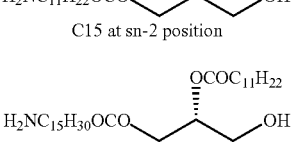
C15 at sn-2 position

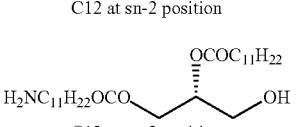
C12 at sn-2 position

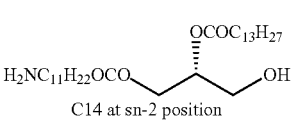
C13 at sn-2 position

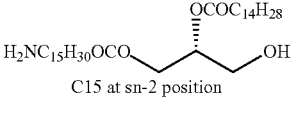
C14 at sn-2 position

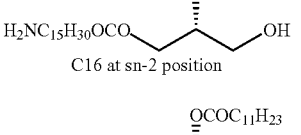
C15 at sn-2 position

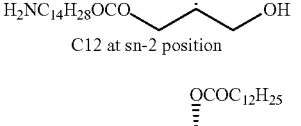
C16 at sn-2 position

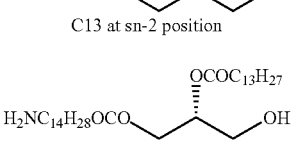
C12 at sn-2 position

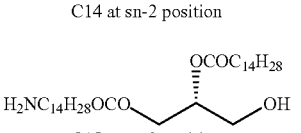
C13 at sn-2 position

C14 at sn-2 position

C15 at sn-2 position

TABLE 2-continued

Preferred Compounds and Probes of the Invention

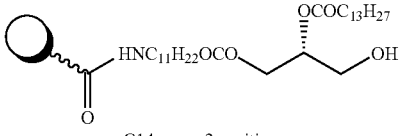
C16 at sn-2 position

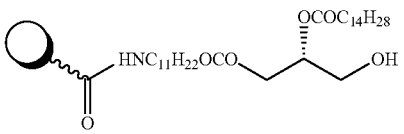
C12 at sn-2 position

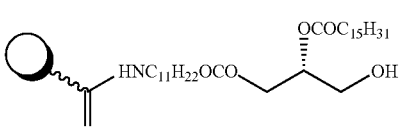
C13 at sn-2 position

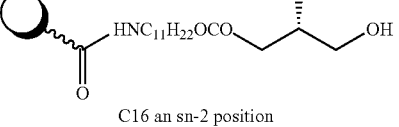
C14 at sn-2 position

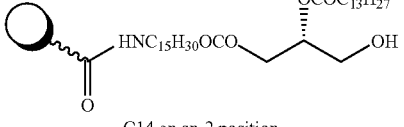
C15 at sn-2 position

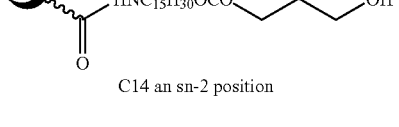
C16 at sn-2 position

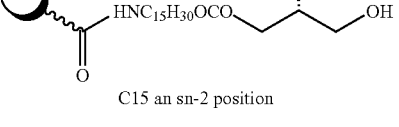
C12 at sn-2 position

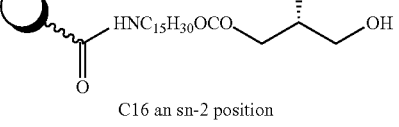
C13 at sn-2 position

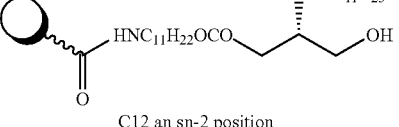
C14 at sn-2 position

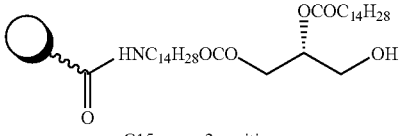
C15 at sn-2 position

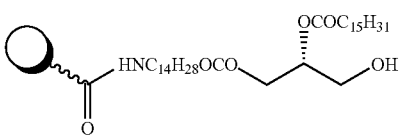
C16 at sn-2 position

C13 an sn-2 position

TABLE 2-continued

Preferred Compounds and Probes of the Invention

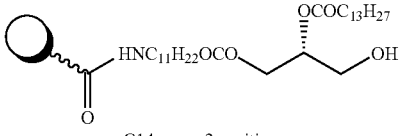
C14 an sn-2 position

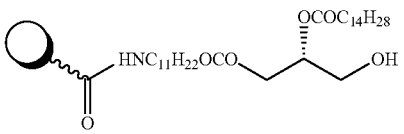
C15 an sn-2 position

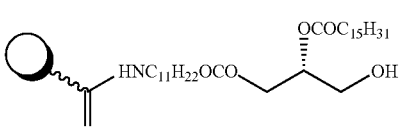
C16 an sn-2 position

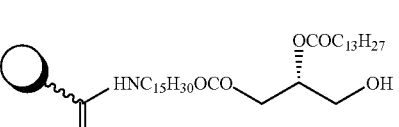
C14 an sn-2 position

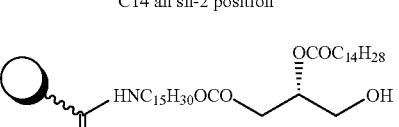
C15 an sn-2 position

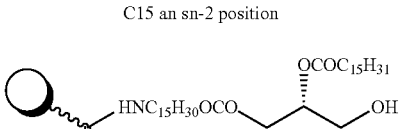
C16 an sn-2 position

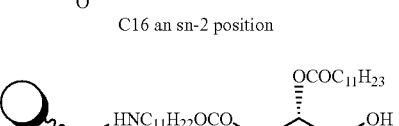
C12 an sn-2 position

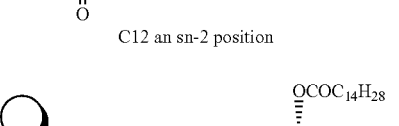
C15 an sn-2 position

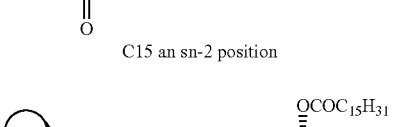
C16 an sn-2 position

TABLE 2-continued

Preferred Compounds and Probes of the Invention

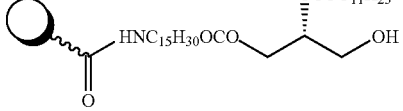

C12 an sn-2 position

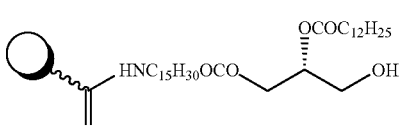

C13 an sn-2 position

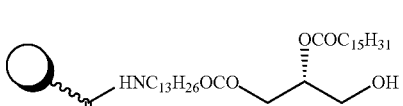

C15 an sn-2 position

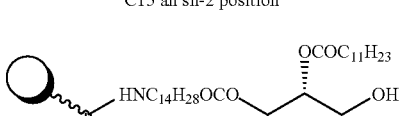

C12 an sn-2 position

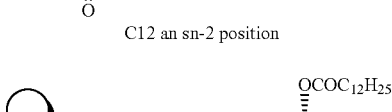

C13 an sn-2 position

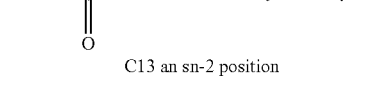

C14 an sn-2 position

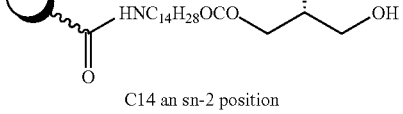

C12 an sn-2 position

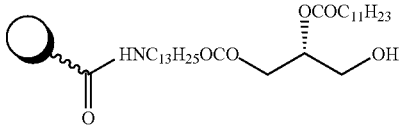

C13 an sn-2 position

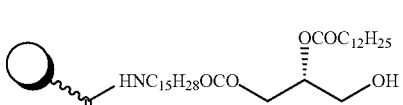

C14 an sn-2 position

TABLE 2-continued

Preferred Compounds and Probes of the Invention

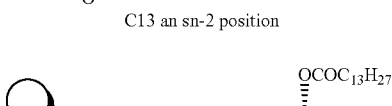

C15 an sn-2 position

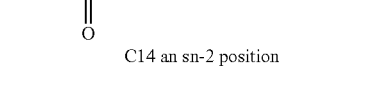

C13 an sn-2 position

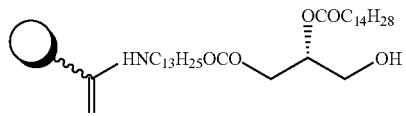

C14 an sn-2 position

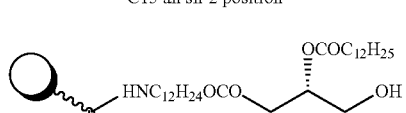

C15 an sn-2 position

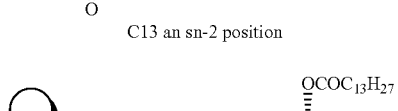

C16 an sn-2 position

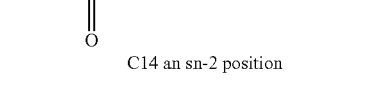

C12 an sn-2 position

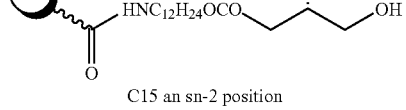

C8 at sn-2 position

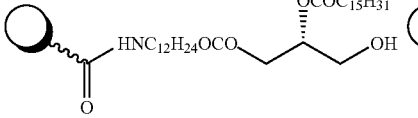

C12 at sn-2 position

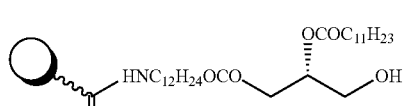

C16 at sn-2 position

TABLE 2-continued

Preferred Compounds and Probes of the Invention

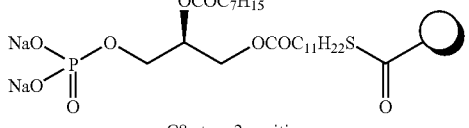

C8 at sn-2 position

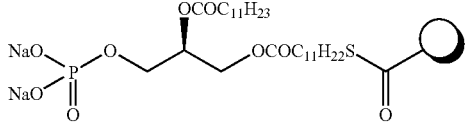

C12 at sn-2 position

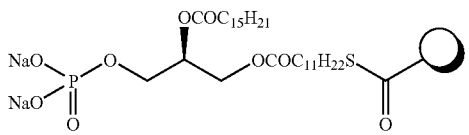

C16 at sn-2 position

Changes in chain length at the sn-2 position

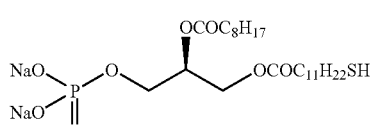

C9 at sn-2 position

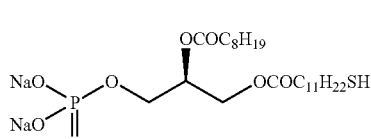

C10 at sn-2 position

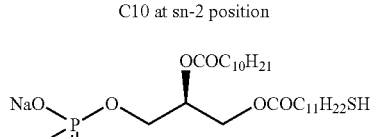

C11 at sn-2 position

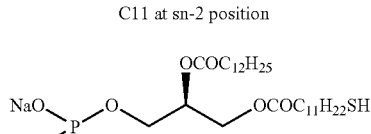

C13 at sn-2 position

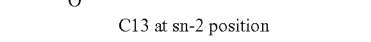

C14 at sn-2 position

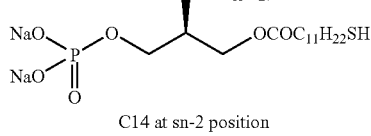

C15 at sn-2 position

TABLE 2-continued

Preferred Compounds and Probes of the Invention

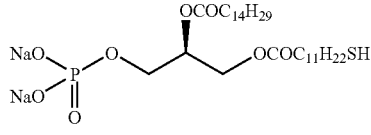

C9 at sn-2 position

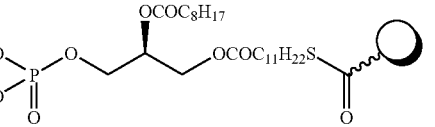

C11 at sn-2 position

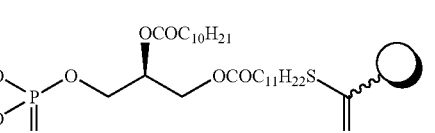

C13 at sn-2 position

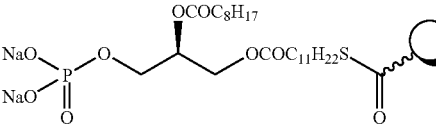

C14 at sn-2 position

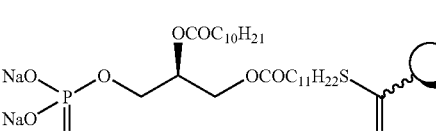

C10 at sn-2 position

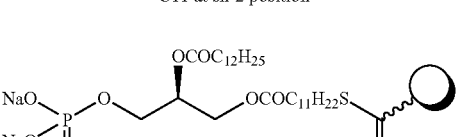

C15 at sn-2 position

Changes in chain length at the sn-1 position

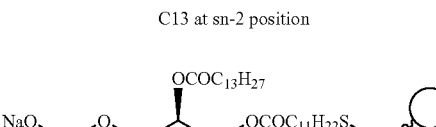

C8 at sn-2 position

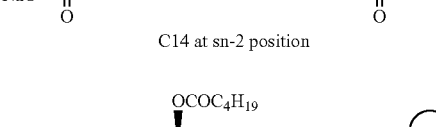

C9 at sn-1 position

TABLE 2-continued

Preferred Compounds and Probes of the Invention

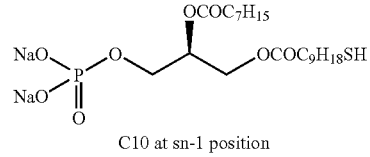

C10 at sn-1 position

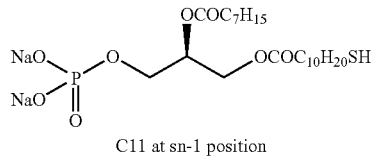

C11 at sn-1 position

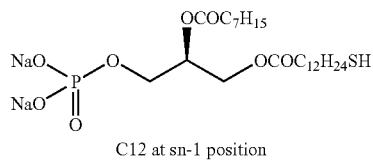

C12 at sn-1 position

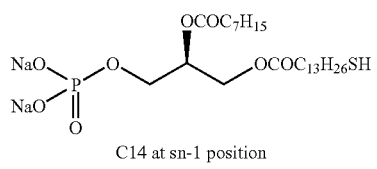

C14 at sn-1 position

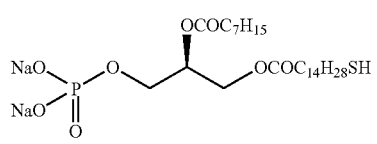

C15 at sn-1 position

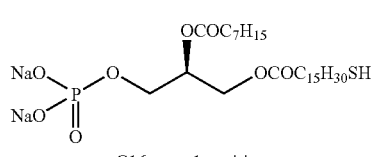

C16 at sn-1 position

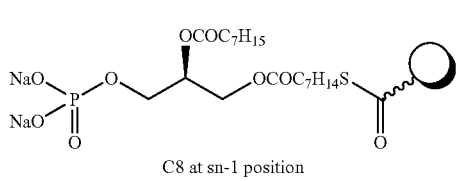

C8 at sn-1 position

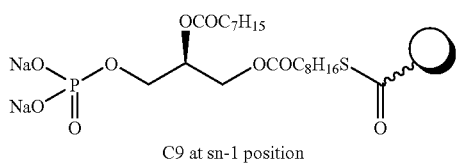

C9 at sn-1 position

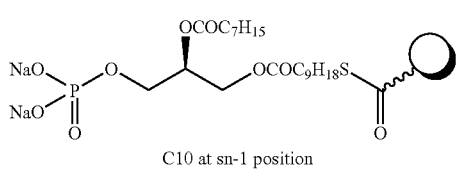

C10 at sn-1 position

TABLE 2-continued

Preferred Compounds and Probes of the Invention

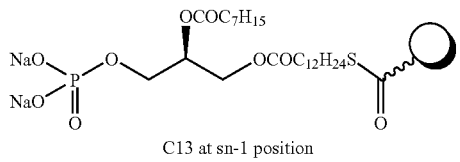

C13 at sn-1 position

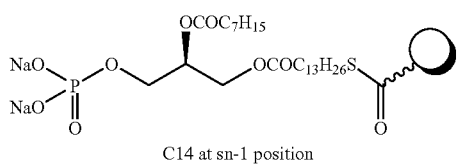

C14 at sn-1 position

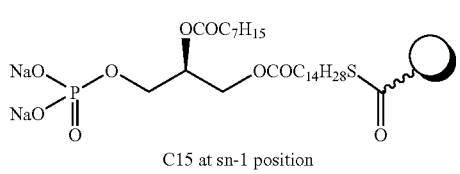

C15 at sn-1 position

C11 at sn-2 position

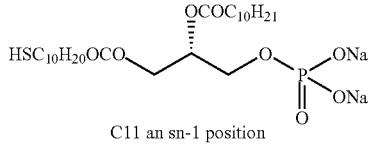

C11 an sn-1 position

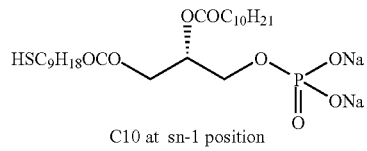

C10 at sn-1 position

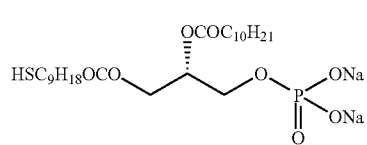

C8 at sn-1 position

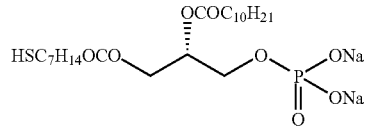

C8 at sn-1 position

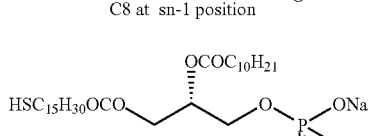

C18 at sn-1 position

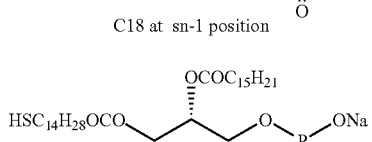

C15 at sn-1 position

TABLE 2-continued

Preferred Compounds and Probes of the Invention

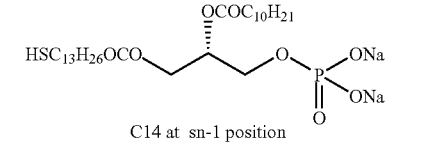

C14 at sn-1 position

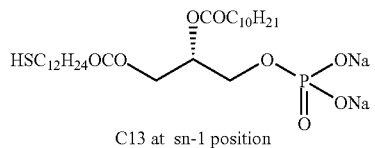

C13 at sn-1 position

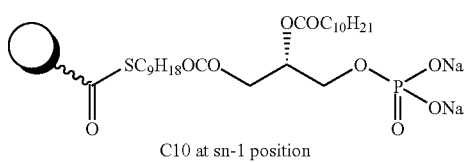

C10 at sn-1 position

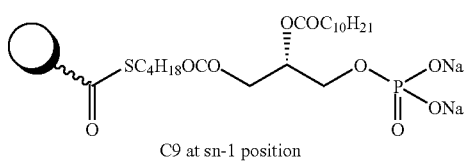

C9 at sn-1 position

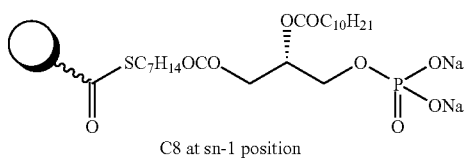

C8 at sn-1 position

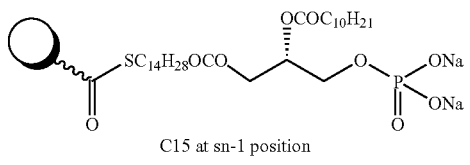

C15 at sn-1 position

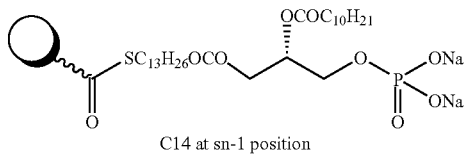

C14 at sn-1 position

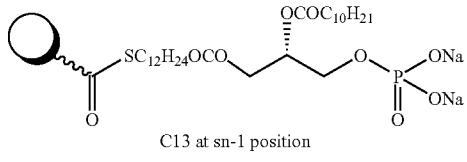

C13 at sn-1 position

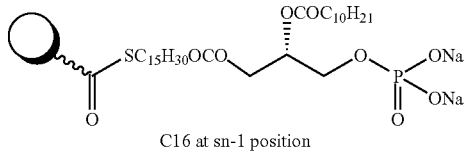

C16 at sn-1 position

TABLE 2-continued

Preferred Compounds and Probes of the Invention

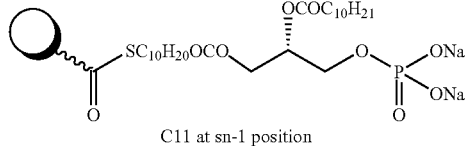

C11 at sn-1 position
C12 at sn-2 position

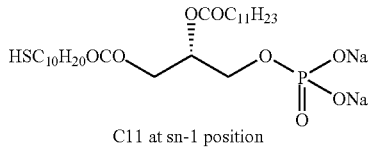

C11 at sn-1 position

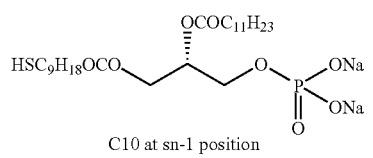

C10 at sn-1 position

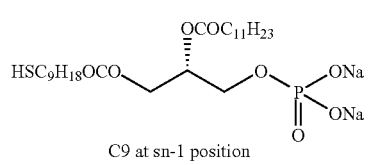

C9 at sn-1 position

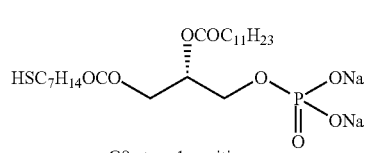

C8 at sn-1 position

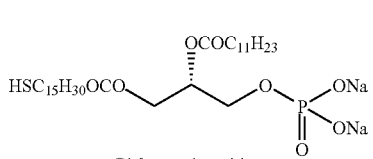

C16 at sn-1 position

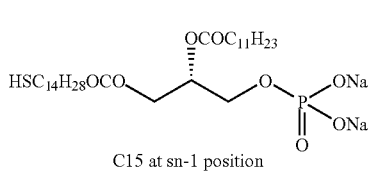

C15 at sn-1 position

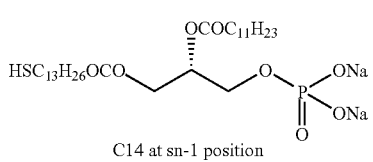

C14 at sn-1 position

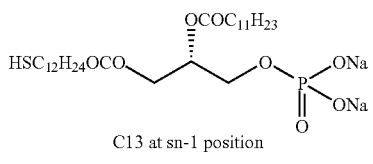

C13 at sn-1 position

TABLE 2-continued

Preferred Compounds and Probes of the Invention

⬤〰SC$_9$H$_{18}$OCO—CH(OCOC$_{11}$H$_{23}$)—O—P(=O)(ONA)(ONA)

C16 an sn-1 position

⬤〰SC$_4$H$_{15}$OCO—CH(OCOC$_{11}$H$_{23}$)—O—P(=O)(ONA)(ONA)

C9 an sn-1 position

⬤〰SC$_7$H$_{14}$OCO—CH(OCOC$_{11}$H$_{23}$)—O—P(=O)(ONA)(ONA)

C8 an sn-1 position

⬤〰SC$_{14}$H$_{28}$OCO—CH(OCOC$_{11}$H$_{23}$)—O—P(=O)(ONA)(ONA)

C15 an sn-1 position

⬤〰SC$_{13}$H$_{26}$OCO—CH(OCOC$_{11}$H$_{23}$)—O—P(=O)(ONA)(ONA)

C14 an sn-1 position

⬤〰SC$_{12}$H$_{24}$OCO—CH(OCOC$_{11}$H$_{23}$)—O—P(=O)(ONA)(ONA)

C13 an sn-1 position

⬤〰SC$_{15}$H$_{30}$OCO—CH(OCOC$_{11}$H$_{23}$)—O—P(=O)(ONA)(ONA)

C16 an sn-1 position

⬤〰SC$_{10}$H$_{20}$OCO—CH(OCOC$_{11}$H$_{23}$)—O—P(=O)(ONA)(ONA)

C11 an sn-1 position

C13 at sn-2 position

HSC$_{10}$H$_{20}$OCO—CH(OCOC$_{12}$H$_{25}$)—O—P(=O)(ONa)(ONa)

C11 an sn-1 position

TABLE 2-continued

Preferred Compounds and Probes of the Invention

HSC$_9$H$_{18}$OCO—CH(OCOC$_{12}$H$_{25}$)—O—P(=O)(ONa)(ONa)

C10 an sn-1 position

HSC$_8$H$_{15}$OCO—CH(OCOC$_{12}$H$_{25}$)—O—P(=O)(ONa)(ONa)

C9 an sn-1 position

HSC$_7$H$_{14}$OCO—CH(OCOC$_{12}$H$_{25}$)—O—P(=O)(ONa)(ONa)

C8 at sn-1 position

HSC$_{15}$H$_{30}$OCO—CH(OCOC$_{12}$H$_{25}$)—O—P(=O)(ONa)(ONa)

C18 at sn-1 position

HSC$_{14}$H$_{28}$OCO—CH(OCOC$_{12}$H$_{25}$)—O—P(=O)(ONa)(ONa)

C15 at sn-1 position

HSC$_{13}$H$_{26}$OCO—CH(OCOC$_{12}$H$_{25}$)—O—P(=O)(ONa)(ONa)

C14 at sn-1 position

HSC$_{12}$H$_{24}$OCO—CH(OCOC$_{12}$H$_{25}$)—O—P(=O)(ONa)(ONa)

C134 at sn-1 position

⬤〰SC$_9$H$_{18}$OCO—CH(OCOC$_{12}$H$_{26}$)—O—P(=O)(ONa)(ONa)

C10 at sn-1 position

⬤〰SC$_8$H$_{15}$OCO—CH(OCOC$_{12}$H$_{26}$)—O—P(=O)(ONa)(ONa)

C9 at sn-1 position

TABLE 2-continued

Preferred Compounds and Probes of the Invention

C8 at sn-1 position (sphere-SC7H14OCO-glycerol-OCOC12H25, phosphate-ONa,ONa)

C15 at sn-1 position (sphere-SC14H28OCO-, OCOC12H25)

C14 at sn-1 position (sphere-SC13H26OCO-, OCOC12H25)

C13 at sn-1 position (sphere-SC12H24OCO-, OCOC12H25)

C16 at sn-1 position (sphere-SC15H30OCO-, OCOC12H25)

C11 at sn-1 position (sphere-SC10H20OCO-, OCOC12H25)
C14 at sn-2 position

C11 at sn-1 position (HSC10H20OCO-, OCOC13H27)

C10 at sn-1 position (HSC9H18OCO-, OCOC13H27)

C9 at sn-1 position (HSC4H15OCO-, OCOC13H27)

TABLE 2-continued

Preferred Compounds and Probes of the Invention

C9 at sn-1 position (HSC7H14OCO-, OCOC13H27)

C16 at sn-1 position (HSC15H30OCO-, OCOC13H27)

C15 at sn-1 position (HSC14H28OCO-, OCOC13H27)

C14 at sn-1 position (HSC13H26OCO-, OCOC13H27)

C13 at sn-1 position (HSC12H24OCO-, OCOC13H27)

C10 at sn-1 position (sphere-SC9H18OCO-, OCOC13H27)

C9 at sn-1 position (sphere-SC8H16OCO-, OCOC13H27)

C8 at sn-1 position (sphere-SC7H14OCO-, OCOC13H27)

C10 at sn-1 position (sphere-SC14H28OCO-, OCOC13H27)

TABLE 2-continued

Preferred Compounds and Probes of the Invention

C9 at sn-1 position

C13 at sn-1 position

C16 at sn-1 position

C11 at sn-1 position
C15 at sn-2 position

C11 at sn-1 position

C10 at sn-1 position

C9 at sn-1 position

C8 at sn-1 position

C16 at sn-1 position

TABLE 2-continued

Preferred Compounds and Probes of the Invention

C15 at sn-1 position

C14 at sn-1 position

C13 at sn-1 position

C10 at sn-1 position

C9 at sn-1 position

C8 at sn-1 position

C15 at sn-1 position

C14 at sn-1 position

C13 at sn-1 position

TABLE 2-continued

Preferred Compounds and Probes of the Invention

C16 at sn-1 position

C11 at sn-1 position
C16 at sn-2 position

C11 at sn-1 position

C10 at sn-1 position

C9 at sn-1 position

C8 at sn-1 position

C16 at sn-1 position

C15 at sn-1 position

C14 at sn-1 position

TABLE 2-continued

Preferred Compounds and Probes of the Invention

C13 at sn-1 position

C10 at sn-1 position

C9 at sn-1 position

C8 at sn-1 position

C15 at sn-1 position

C14 at sn-1 position

C13 at sn-1 position

C18 at sn-1 position

C11 at sn-1 position

TABLE 2-continued

Preferred Compounds and Probes of the Invention

Diacylglycerol

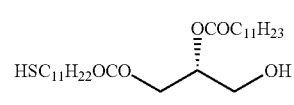

C12 at sn-2 position

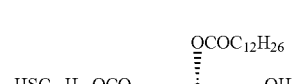

C13 at sn-2 position

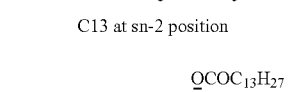

C14 at sn-2 position

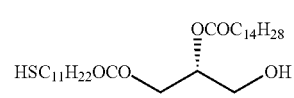

C15 at sn-2 position

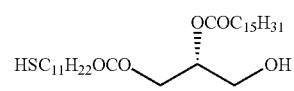

C16 at sn-2 position

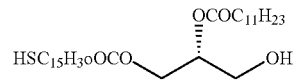

C12 at sn-2 position

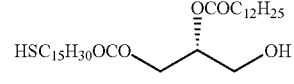

C13 at sn-2 position

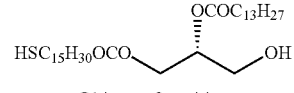

C14 at sn-2 position

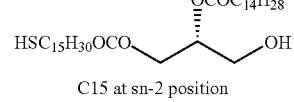

C15 at sn-2 position

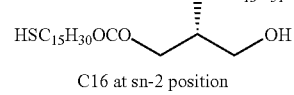

C16 at sn-2 position

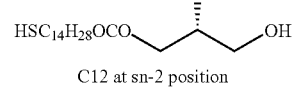

C12 at sn-2 position

TABLE 2-continued

Preferred Compounds and Probes of the Invention

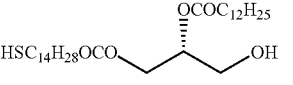

C13 at sn-2 position

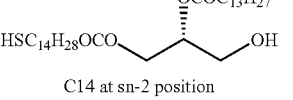

C14 at sn-2 position

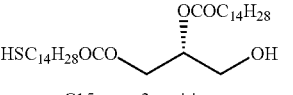

C15 at sn-2 position

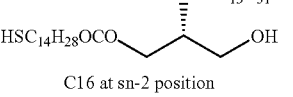

C16 at sn-2 position

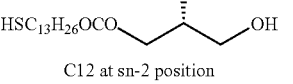

C12 at sn-2 position

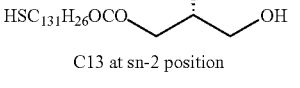

C13 at sn-2 position

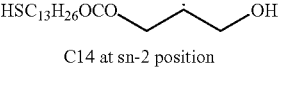

C14 at sn-2 position

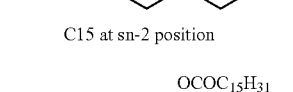

C15 at sn-2 position

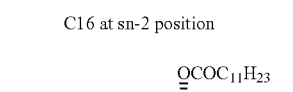

C16 at sn-2 position

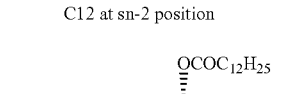

C12 at sn-2 position

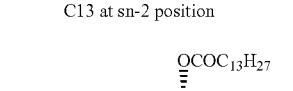

C13 at sn-2 position

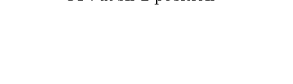

C14 at sn-2 position

TABLE 2-continued

Preferred Compounds and Probes of the Invention

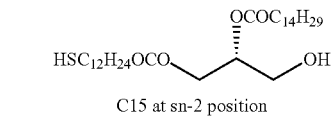

C15 at sn-2 position

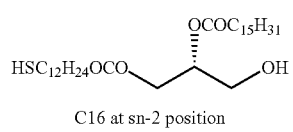

C16 at sn-2 position

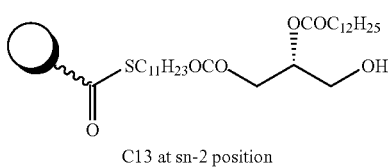

C13 at sn-2 position

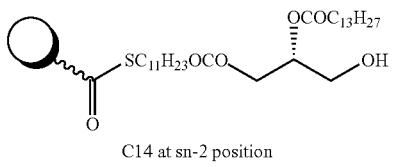

C14 at sn-2 position

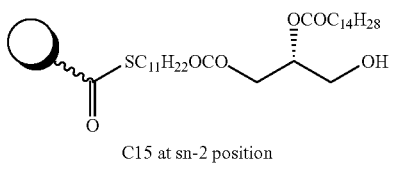

C15 at sn-2 position

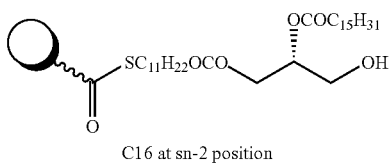

C16 at sn-2 position

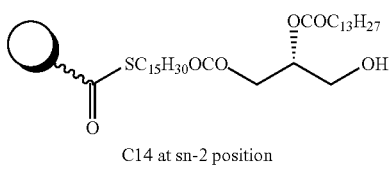

C14 at sn-2 position

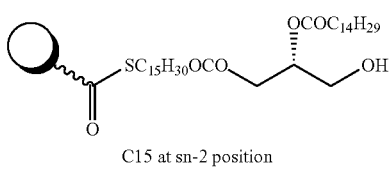

C15 at sn-2 position

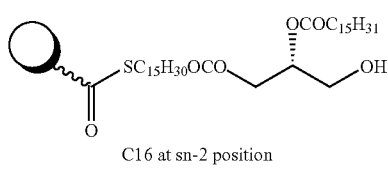

C16 at sn-2 position

TABLE 2-continued

Preferred Compounds and Probes of the Invention

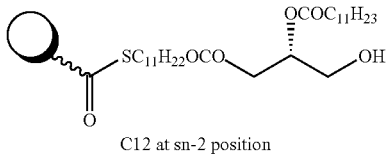

C12 at sn-2 position

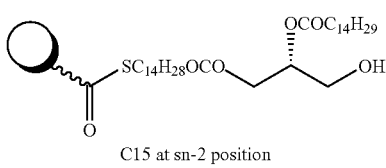

C15 at sn-2 position

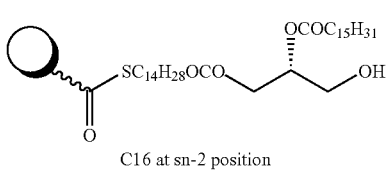

C16 at sn-2 position

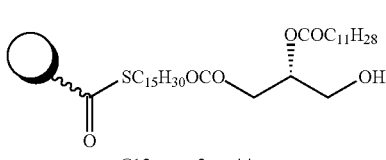

C12 at sn-2 position

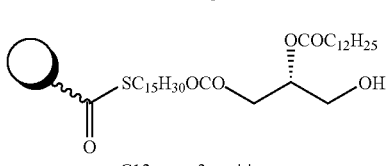

C13 at sn-2 position

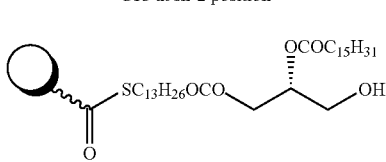

C16 at sn-2 position

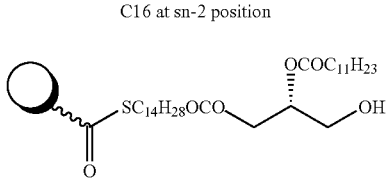

C12 at sn-2 position

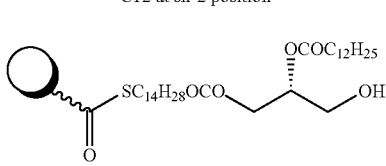

C13 at sn-2 position

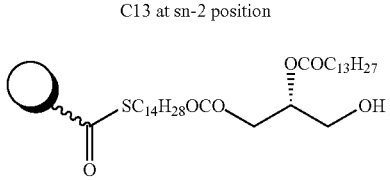

C14 at sn-2 position

TABLE 2-continued
Preferred Compounds and Probes of the Invention
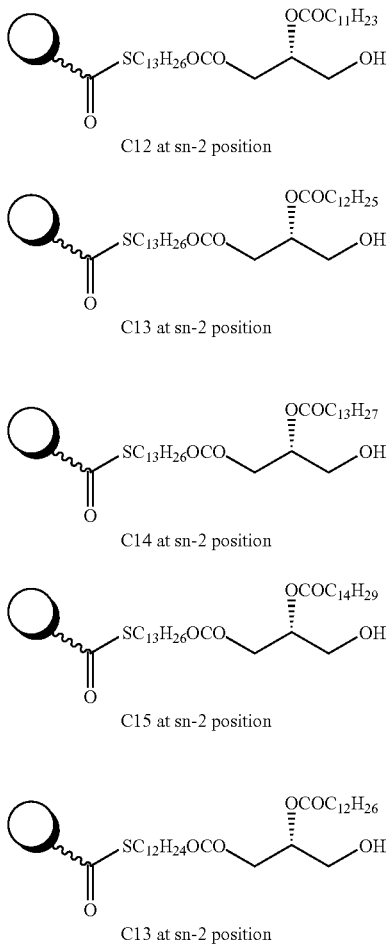
C12 at sn-2 position
C13 at sn-2 position
C14 at sn-2 position
C15 at sn-2 position
C13 at sn-2 position
TABLE 2-continued
Preferred Compounds and Probes of the Invention
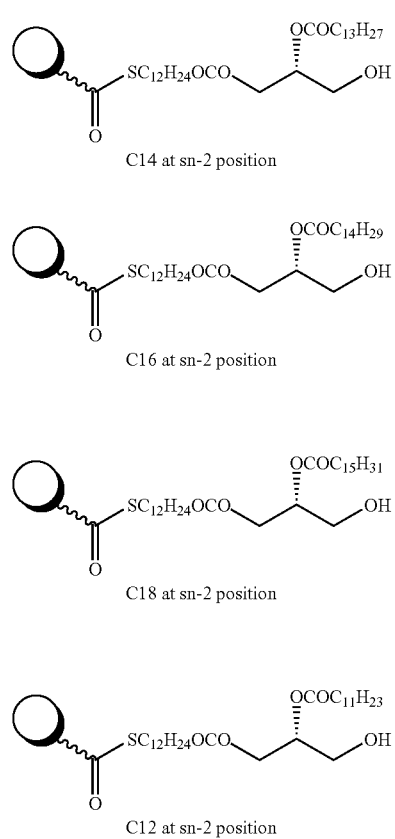
C14 at sn-2 position
C16 at sn-2 position
C18 at sn-2 position
C12 at sn-2 position
TABLE 3
Further preferred compounds and probes of the invention
C8
$C_8H_{16}$
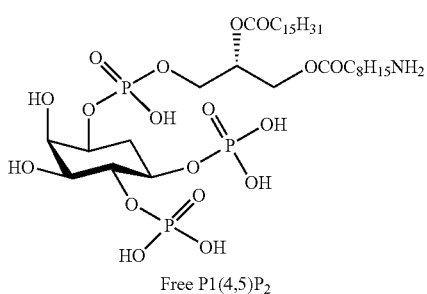
Free P1(4,5)P$_2$ TABLE 3-continued
Further preferred compounds and probes of the invention
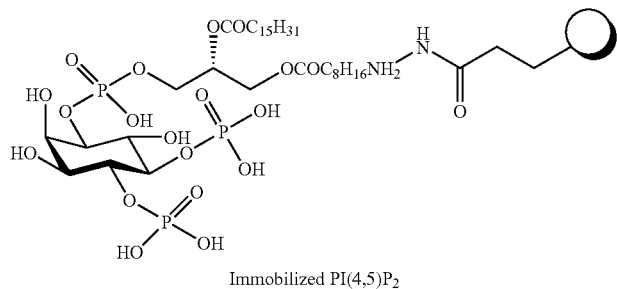
Immobilized PI(4,5)P$_2$
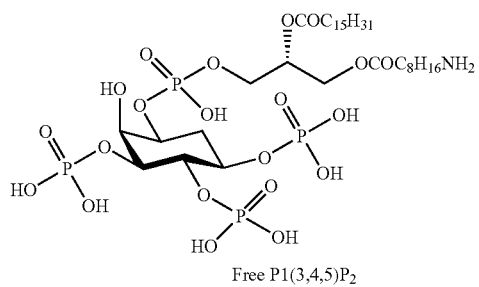
Free PI(3,4,5)P$_2$
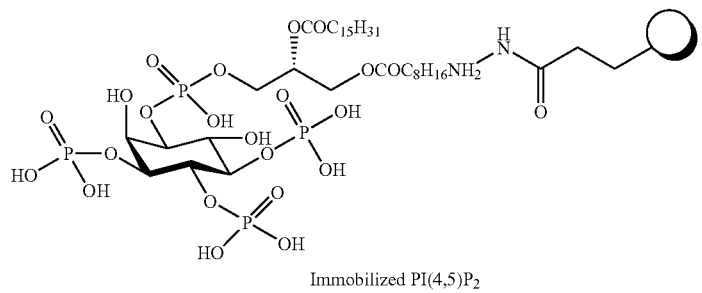
Immobilized PI(4,5)P$_2$
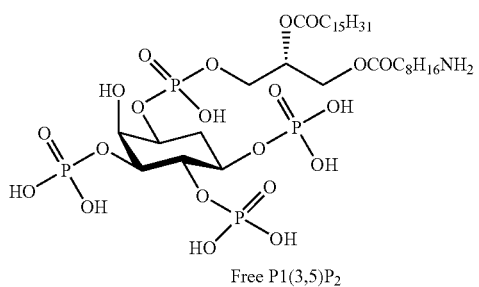
Free PI(3,5)P$_2$
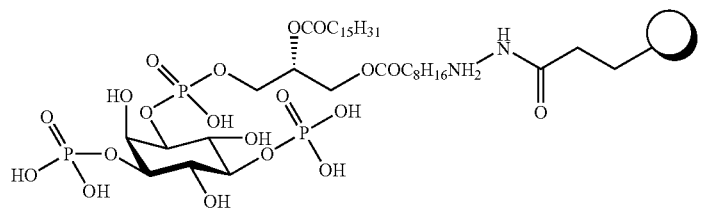
Immobilized PI(3,5)P$_2$ TABLE 3-continued
Further preferred compounds and probes of the invention
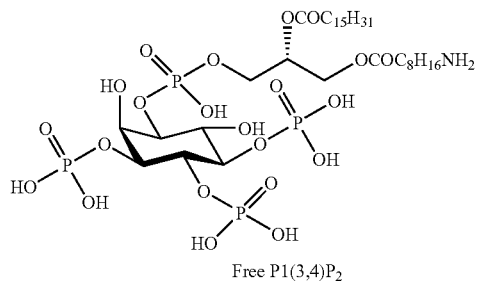
Free PI(3,4)P₂
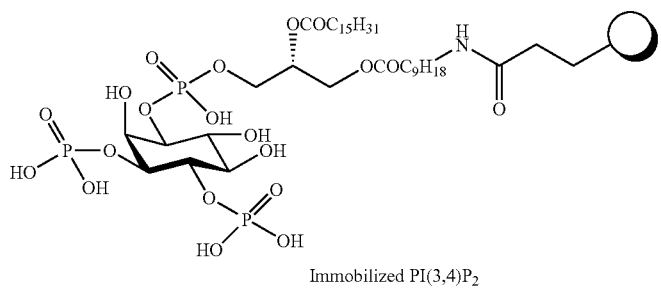
Immobilized PI(3,4)P₂
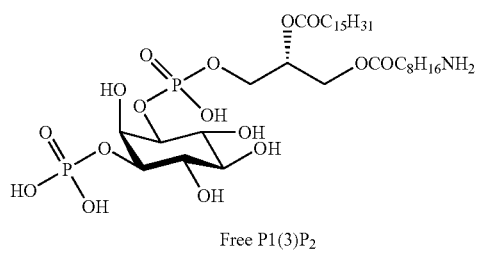
Free PI(3)P₂
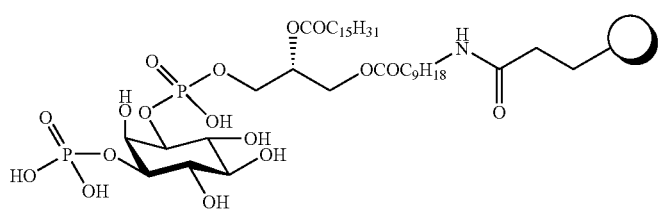
Immobilized PI(3)P₂
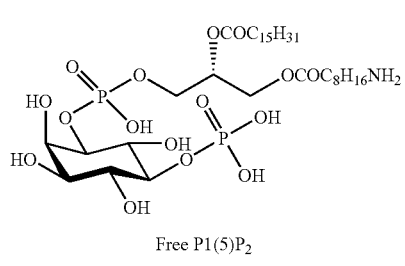
Free PI(5)P₂

TABLE 3-continued
Further preferred compounds and probes of the invention
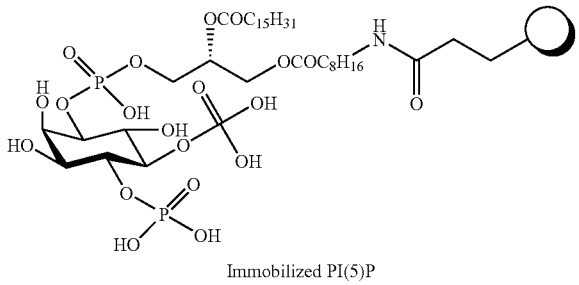
Immobilized PI(5)P
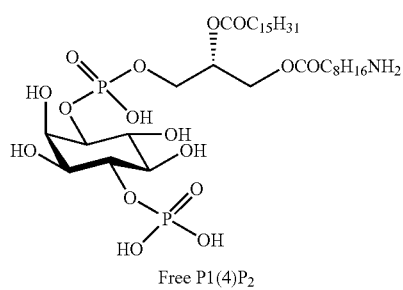
Free PI(4)P$_2$
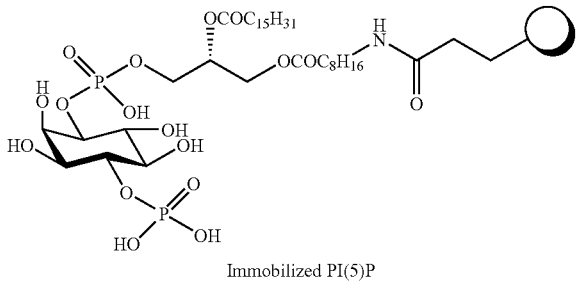
Immobilized PI(5)P
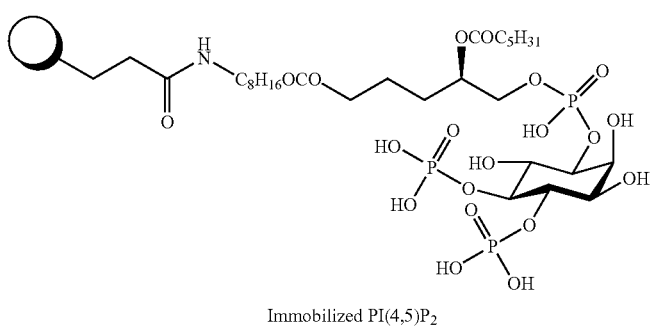
Immobilized PI(4,5)P$_2$
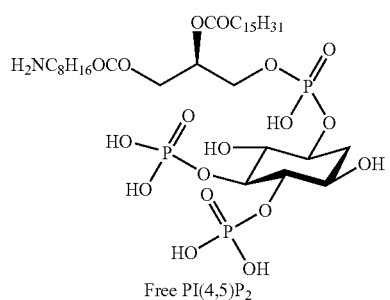
Free PI(4,5)P$_2$ TABLE 3-continued
Further preferred compounds and probes of the invention
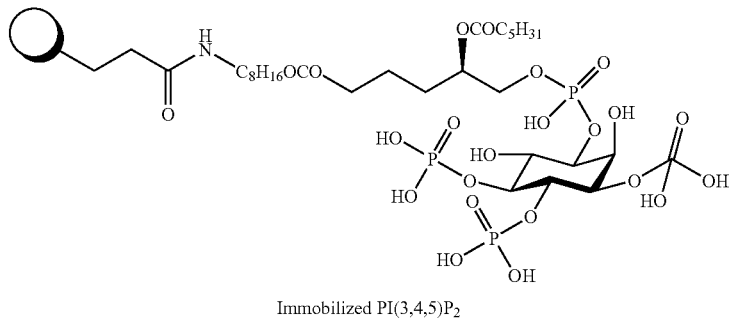
Immobilized PI(3,4,5)P$_2$
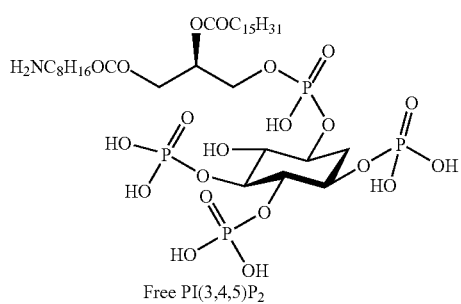
Free PI(3,4,5)P$_2$
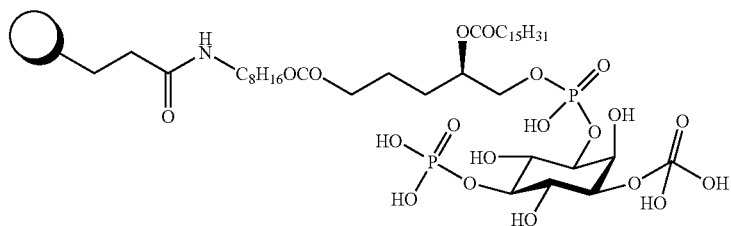
Immobilized PI(3,5)P$_2$
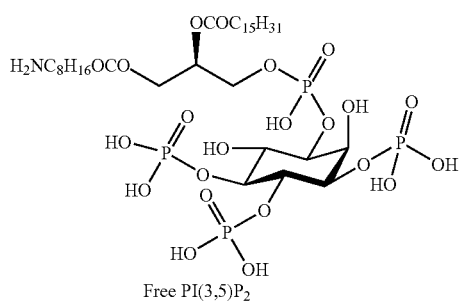
Free PI(3,5)P$_2$
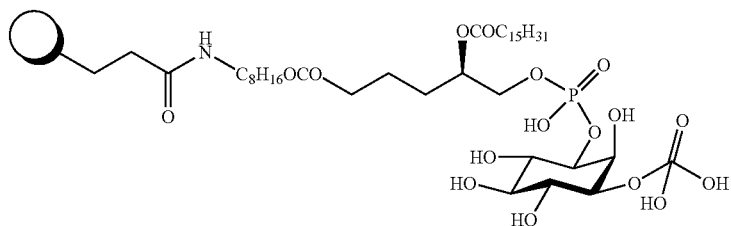
Immobilized PI(3)P TABLE 3-continued
Further preferred compounds and probes of the invention
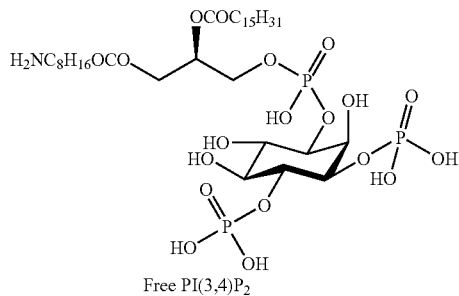
Free PI(3,4)P₂
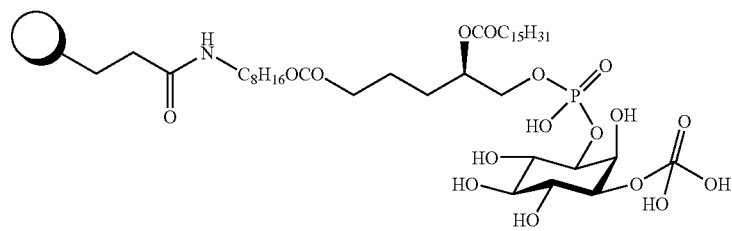
Immobilized PI(3)P
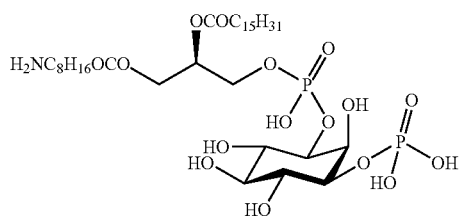
Free PI(3)P
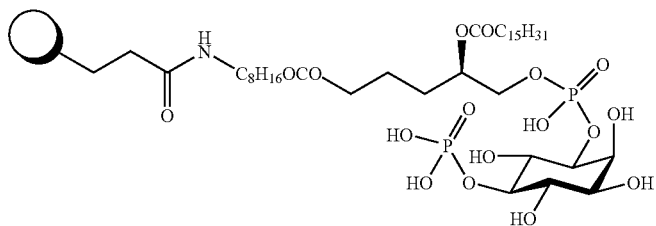
Immobilized PI(5)P
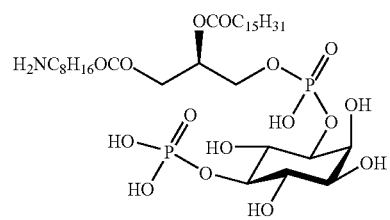
Free PI(5)P₂

TABLE 3-continued
Further preferred compounds and probes of the invention
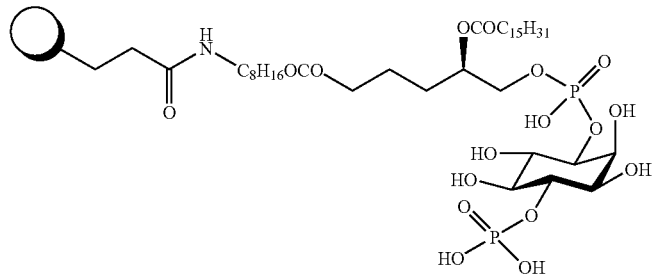
Immobilized PI(4)P
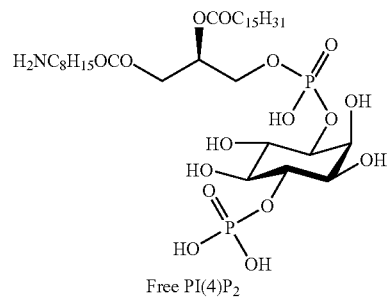
Free PI(4)P₂
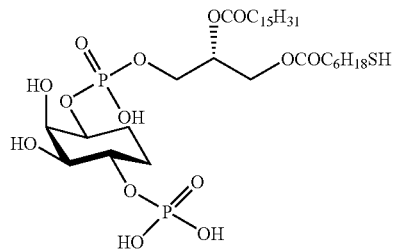
Free PI(4,5)P₂
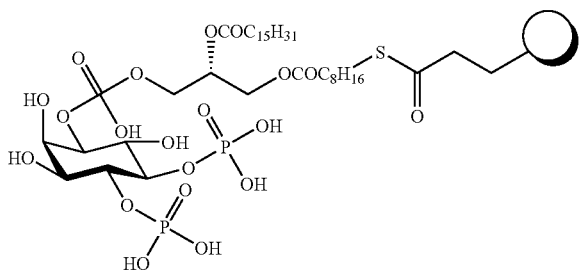
Immobilized PI(4,5)P₂
Free PI(4,5)P₃

TABLE 3-continued
Further preferred compounds and probes of the invention
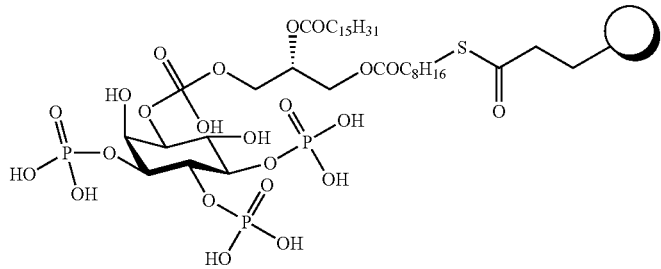
Immobilized PI(3,4)P₃
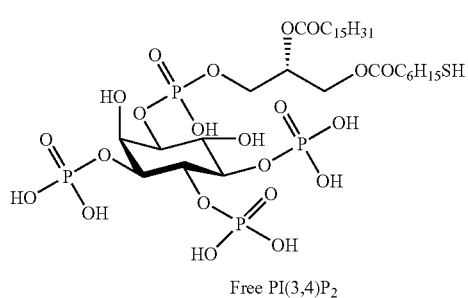
Free PI(3,4)P₂
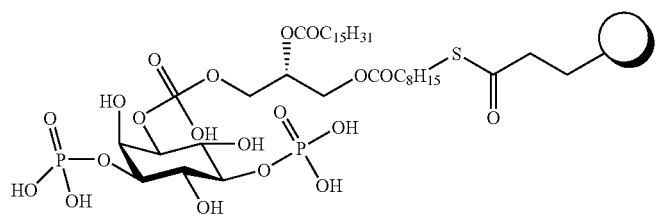
Immobilized PI(3,5)P₂
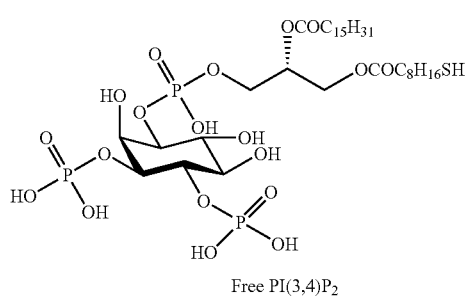
Free PI(3,4)P₂
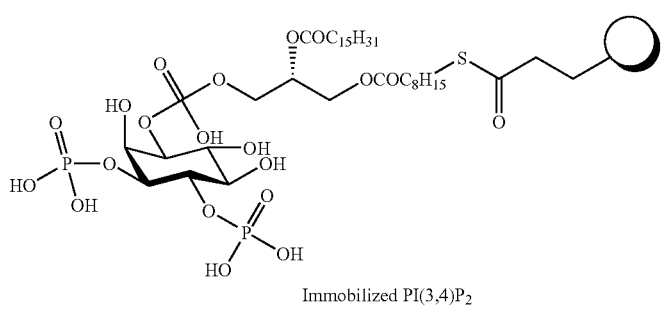
Immobilized PI(3,4)P₂

TABLE 3-continued
Further preferred compounds and probes of the invention
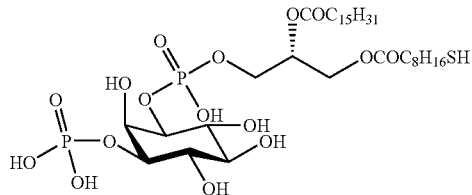
Free PI(3)P$_2$
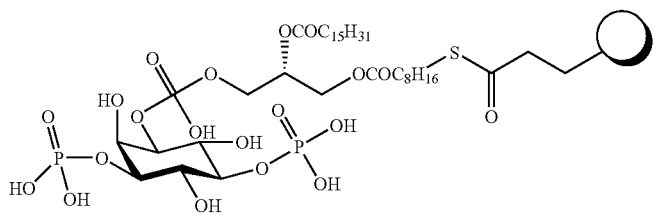
Immobilized PI(5)P$_2$
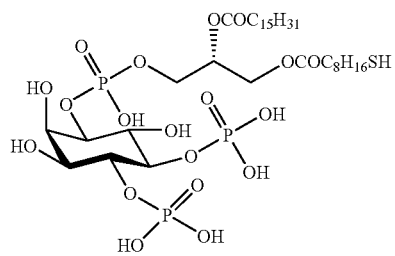
Free PI(5)P$_2$
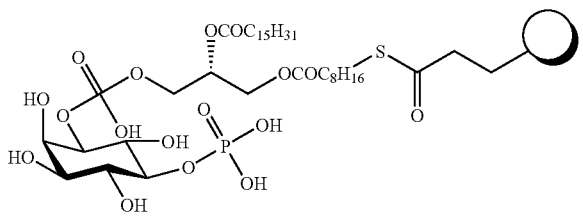
Immobilized PI(5)P$_2$
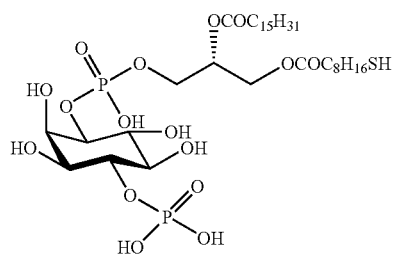
Free PI(4)P TABLE 3-continued
Further preferred compounds and probes of the invention
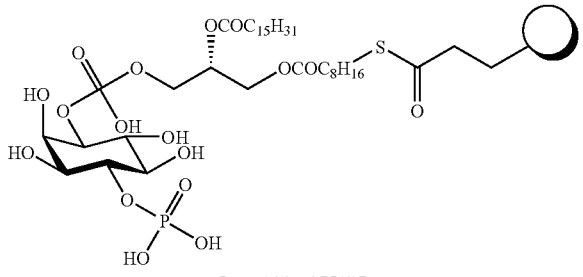
Immobilized PI(4)P$_2$
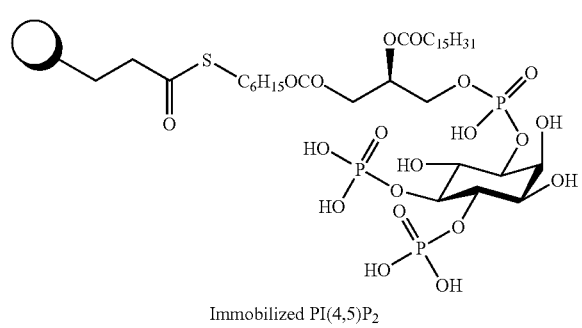
Immobilized PI(4,5)P$_2$
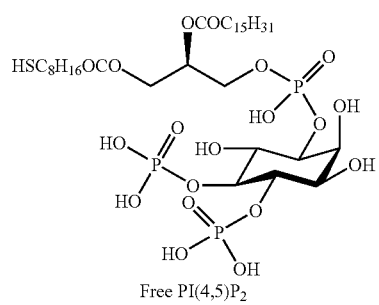
Free PI(4,5)P$_2$
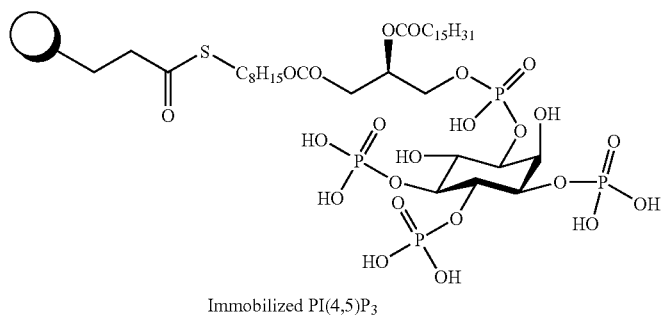
Immobilized PI(4,5)P$_3$
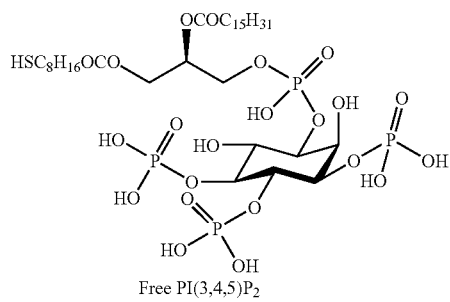
Free PI(3,4,5)P$_2$ TABLE 3-continued
Further preferred compounds and probes of the invention
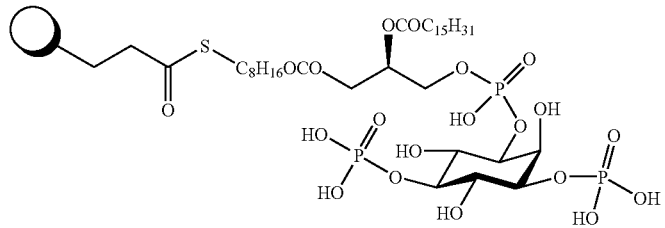
Immobilized PI(3,5)P$_2$
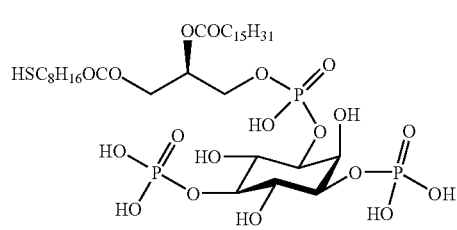
Free PI(3,5)P$_2$
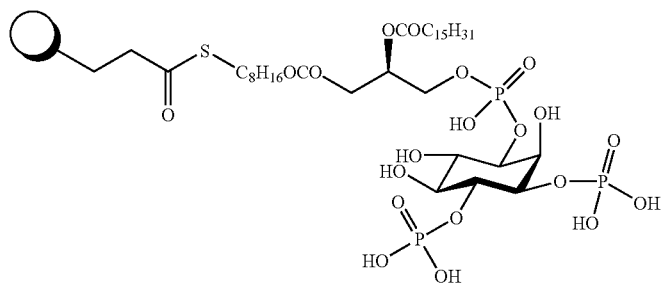
Immobilized PI(3,4)P$_2$
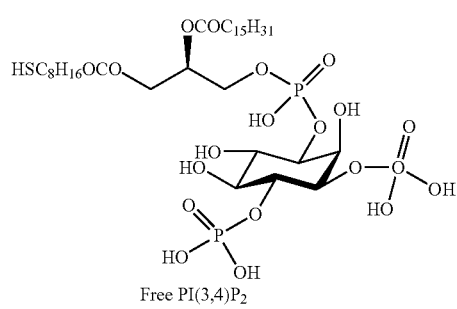
Free PI(3,4)P$_2$
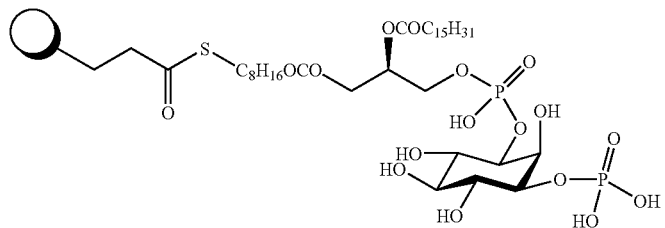
Immobilized PI(3)P TABLE 3-continued
Further preferred compounds and probes of the invention
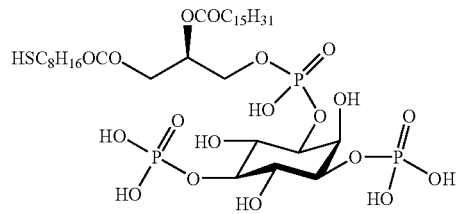
Free PI(3)P
Immobilized PI(5)P
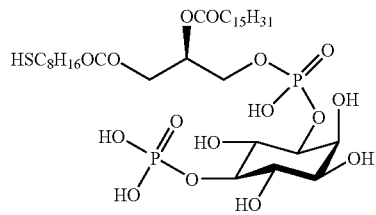
Free PI(5)P
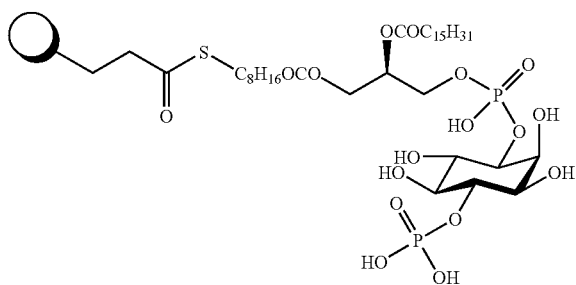
Immobilized PI(4)P
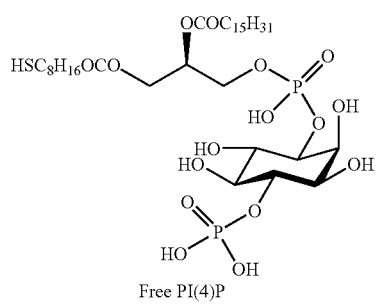
Free PI(4)P TABLE 3-continued
Further preferred compounds and probes of the invention
C9
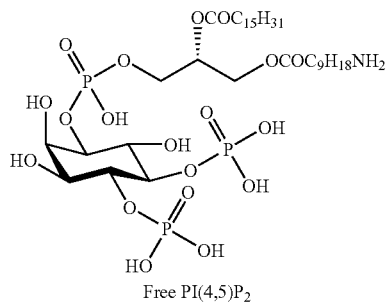
Free PI(4,5)P$_2$
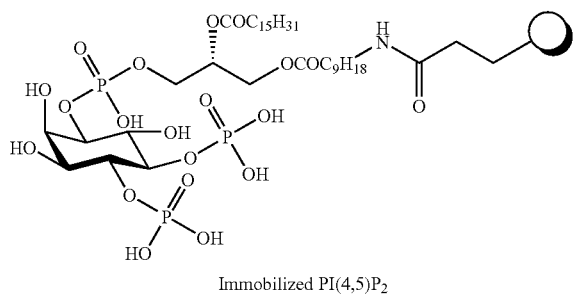
Immobilized PI(4,5)P$_2$
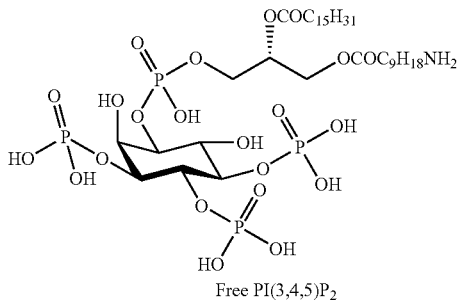
Free PI(3,4,5)P$_2$
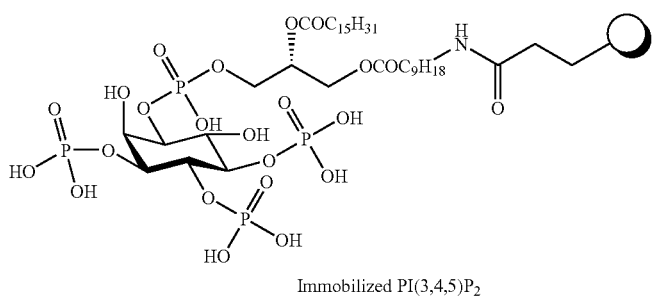
Immobilized PI(3,4,5)P$_2$
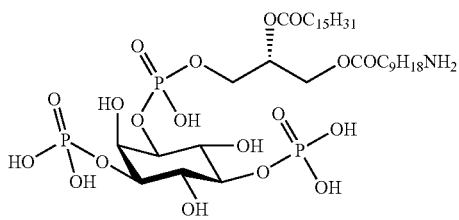
Free PI(3,5)P$_2$ TABLE 3-continued
Further preferred compounds and probes of the invention
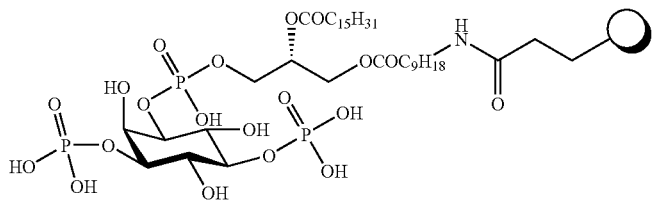
Immobilized PI(3,5)P$_2$
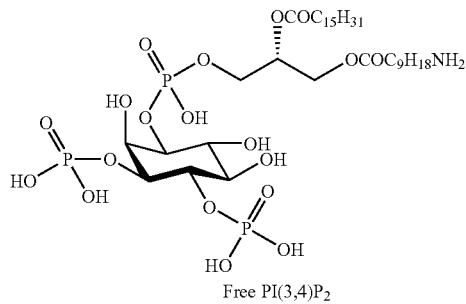
Free PI(3,4)P$_2$
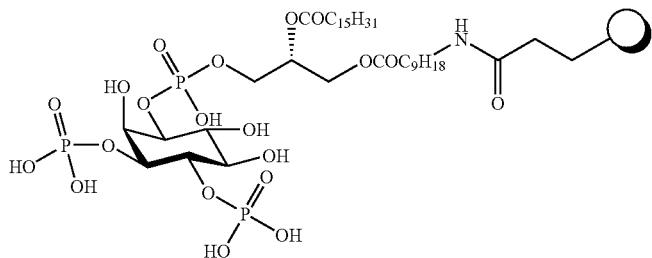
Immobilized PI(3,4)P$_2$
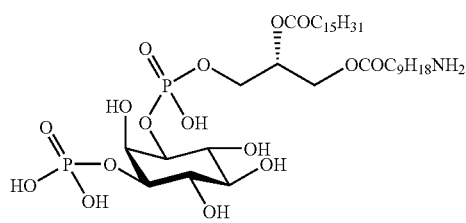
Free PI(3)P$_2$
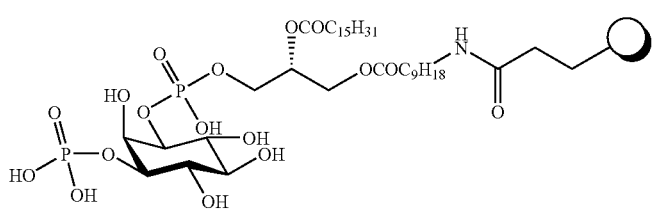
Immobilized PI(3)P$_2$ TABLE 3-continued
Further preferred compounds and probes of the invention
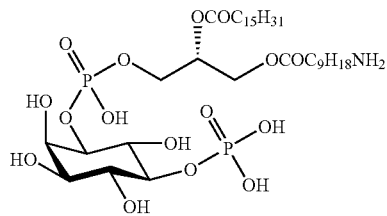
Free PI(5)P$_2$
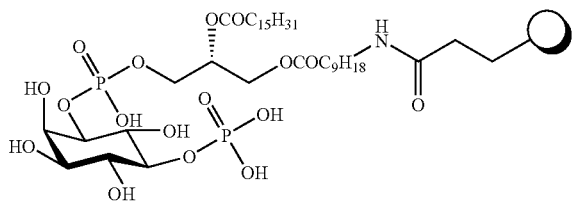
Immobilized PI(5)P$_2$
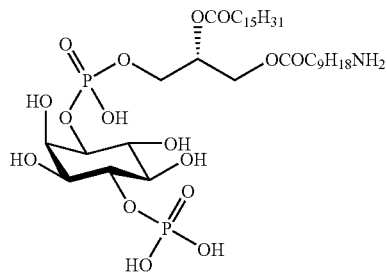
Free PI(4)P$_2$
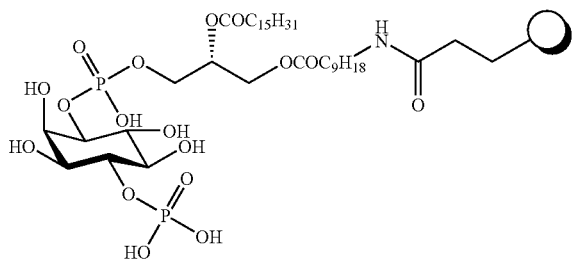
Immobilized PI(4)P$_2$
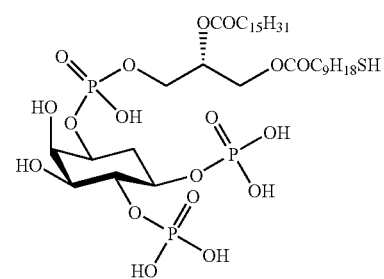
Free PI(4,5)P$_2$ TABLE 3-continued
Further preferred compounds and probes of the invention
Immobilized PI(4,5)P$_2$
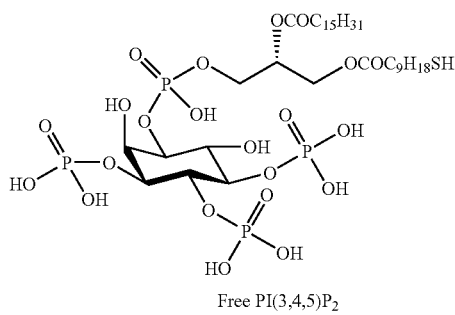
Free PI(3,4,5)P$_2$
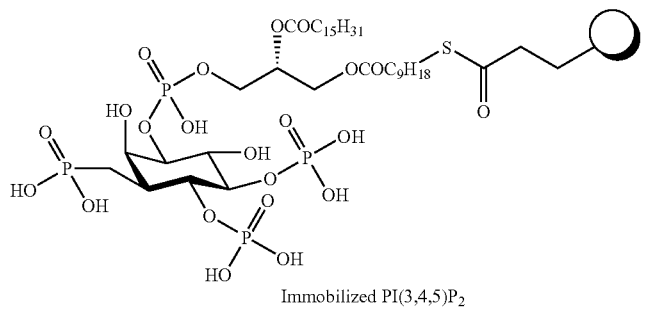
Immobilized PI(3,4,5)P$_2$
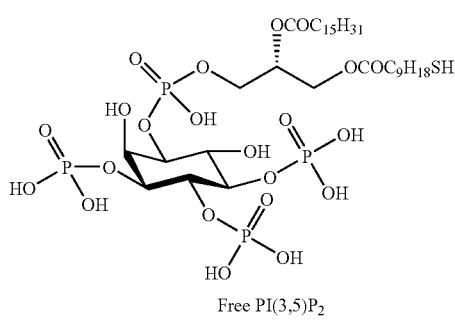
Free PI(3,5)P$_2$
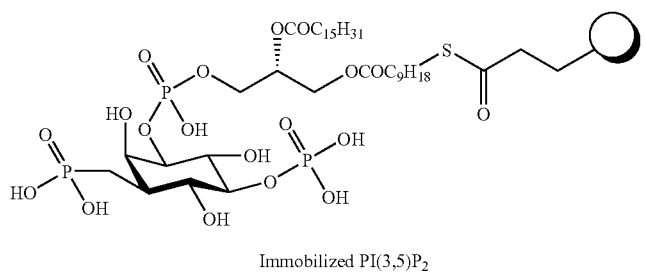
Immobilized PI(3,5)P$_2$ TABLE 3-continued
Further preferred compounds and probes of the invention
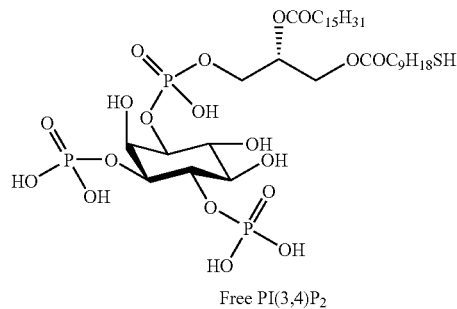
Free PI(3,4)P$_2$
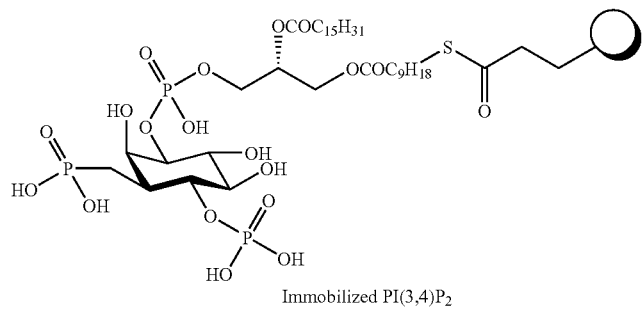
Immobilized PI(3,4)P$_2$
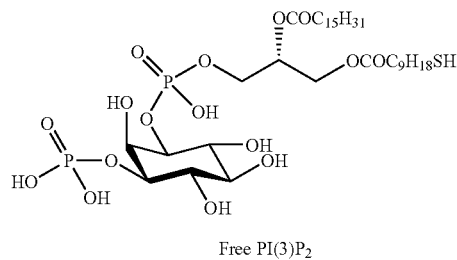
Free PI(3)P$_2$
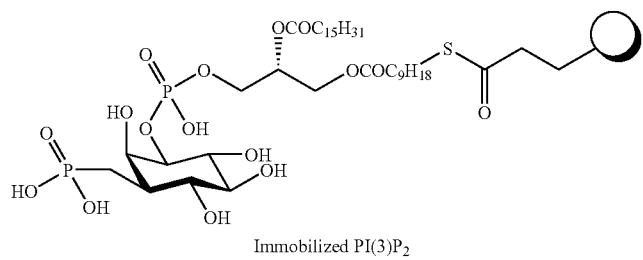
Immobilized PI(3)P$_2$
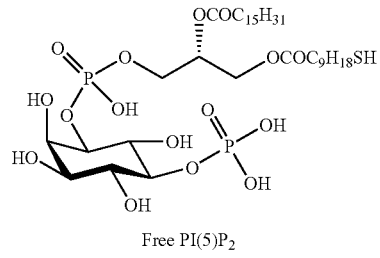
Free PI(5)P$_2$ TABLE 3-continued
Further preferred compounds and probes of the invention
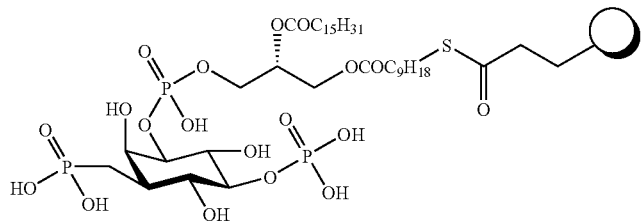
Immobilized PI(5)P
Free PI(4)P$_2$
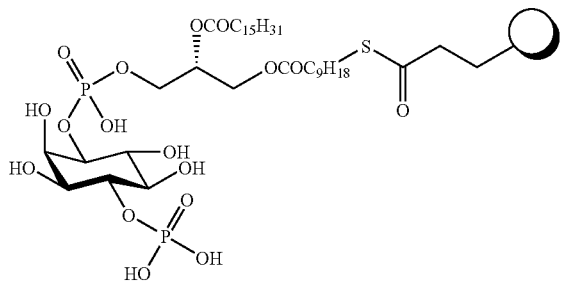
Immobilized PI(4)P
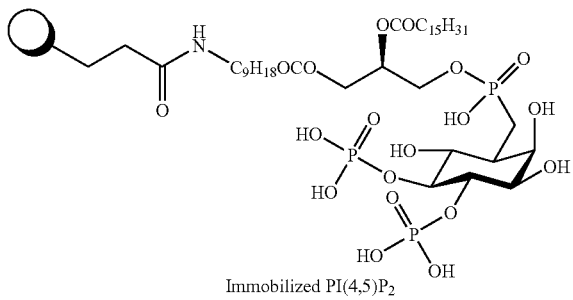
Immobilized PI(4,5)P$_2$
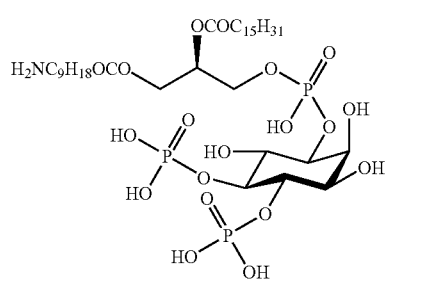
Free PI(4,5)P$_2$ TABLE 3-continued
Further preferred compounds and probes of the invention
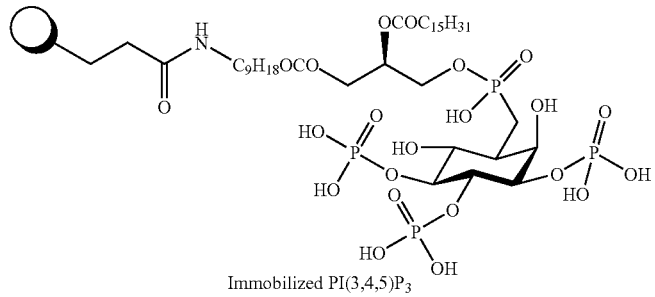
Immobilized PI(3,4,5)P$_3$
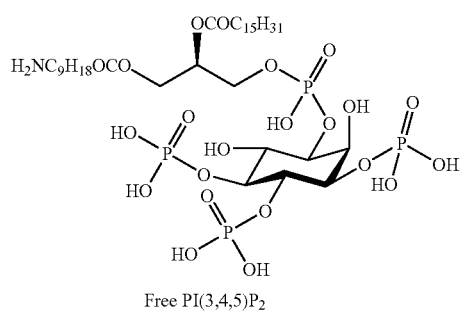
Free PI(3,4,5)P$_2$
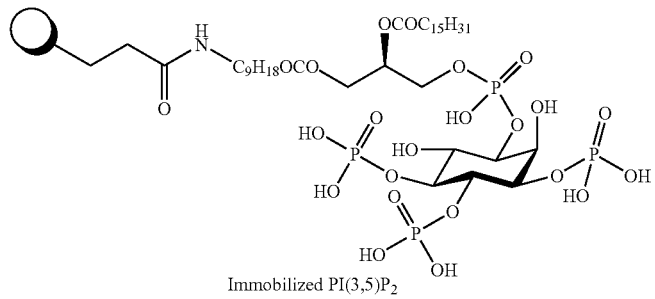
Immobilized PI(3,5)P$_2$
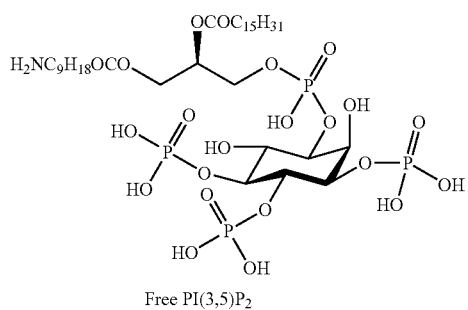
Free PI(3,5)P$_2$
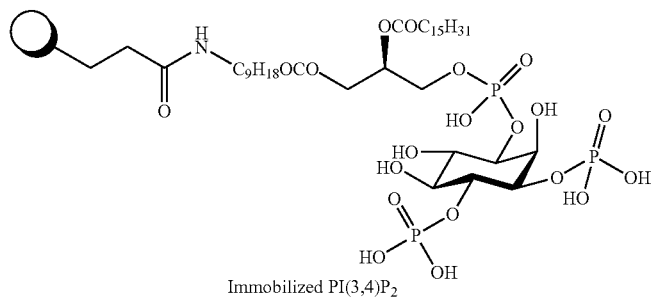
Immobilized PI(3,4)P$_2$ TABLE 3-continued
Further preferred compounds and probes of the invention
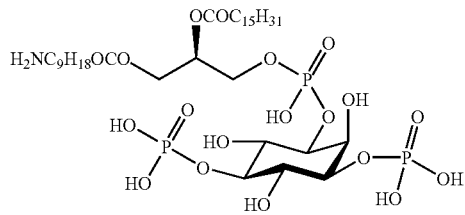
Free PI(3,4)P$_2$
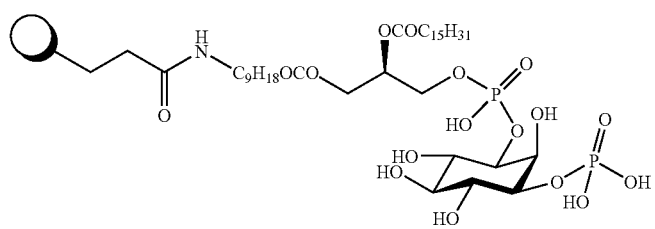
Immobilized PI(3)P
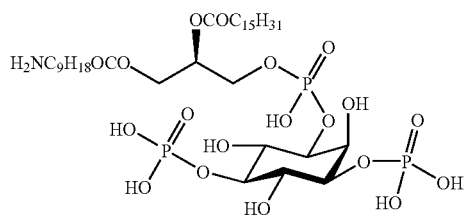
Free PI(5)P$_2$
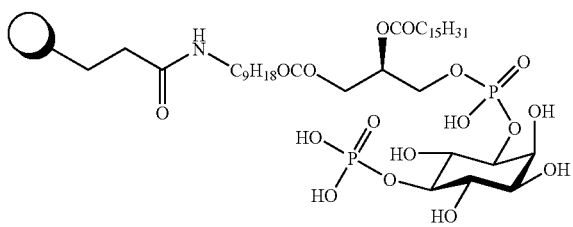
Immobilized PI(5)P
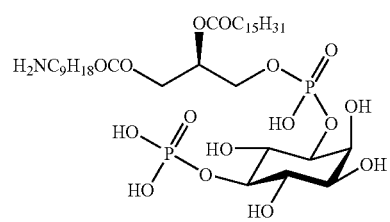
Free PI(5)P$_2$ TABLE 3-continued
Further preferred compounds and probes of the invention
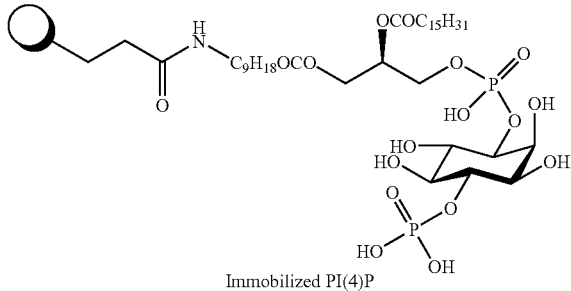
Immobilized PI(4)P
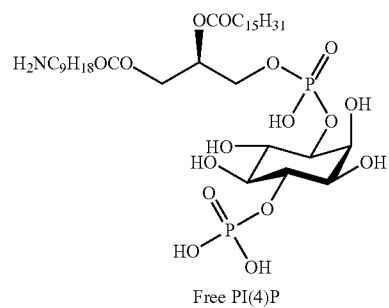
Free PI(4)P
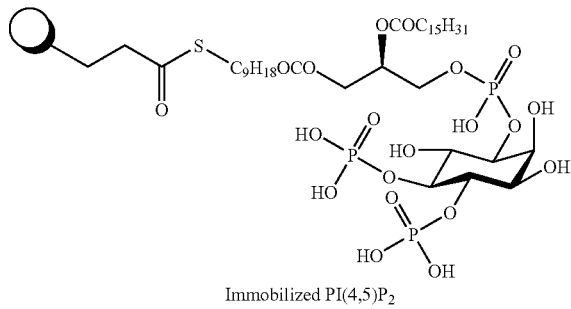
Immobilized PI(4,5)P$_2$
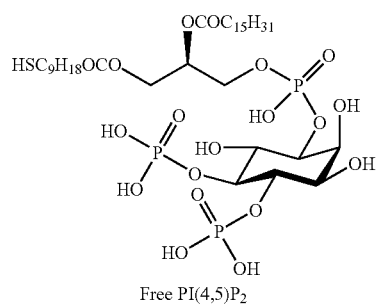
Free PI(4,5)P$_2$
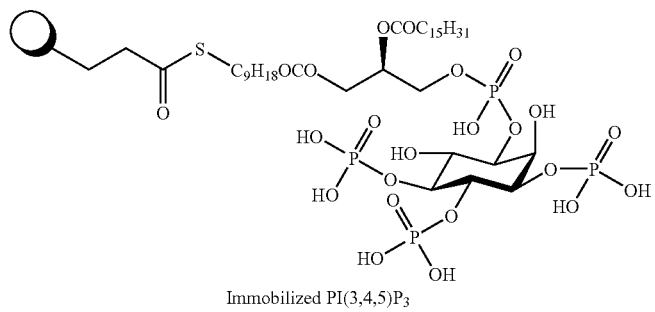
Immobilized PI(3,4,5)P$_3$

TABLE 3-continued
Further preferred compounds and probes of the invention
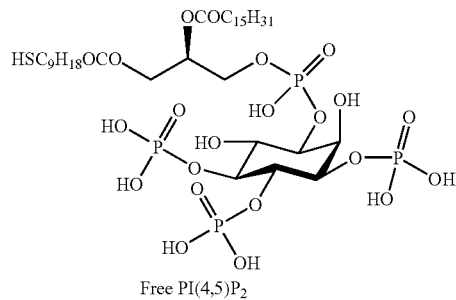
Free PI(4,5)P$_2$
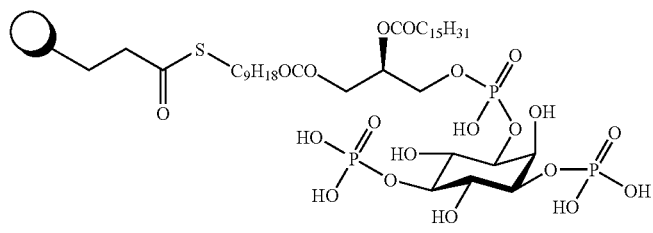
Immobilized PI(3,5)P$_2$
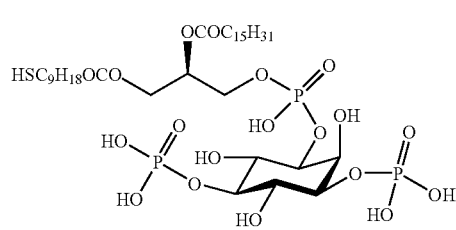
Free PI(3,5)P$_2$
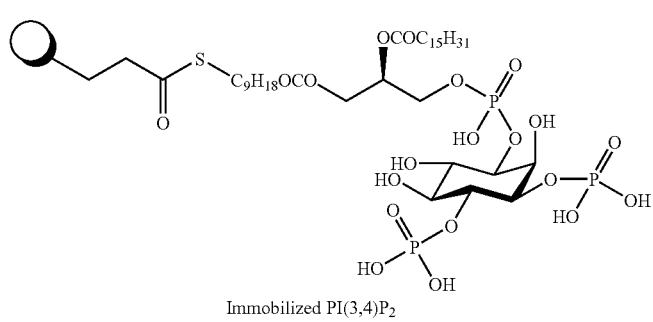
Immobilized PI(3,4)P$_2$
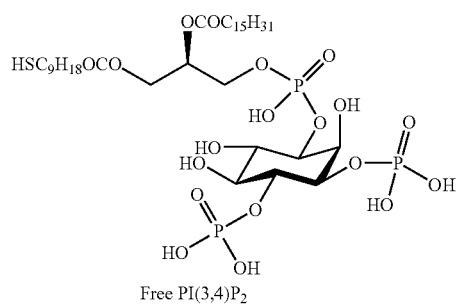
Free PI(3,4)P$_2$ TABLE 3-continued
Further preferred compounds and probes of the invention
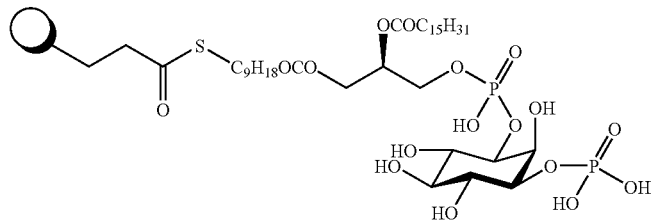
Immobilized PI(3)P
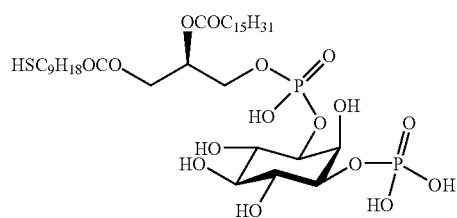
Free PI(3)P
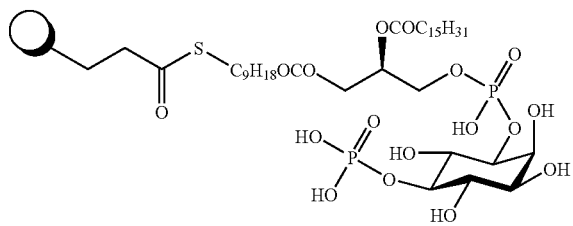
Immobilized PI(5)P
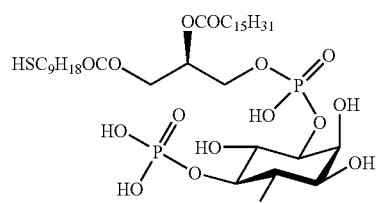
Free PI(5)P
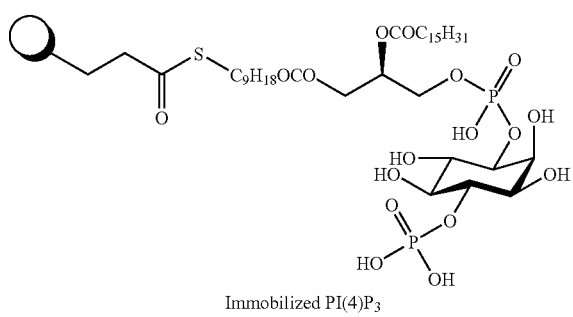
Immobilized PI(4)P$_3$ TABLE 3-continued
Further preferred compounds and probes of the invention
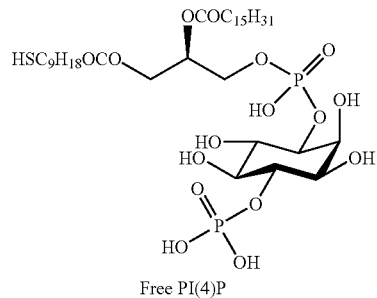
Free PI(4)P
C10
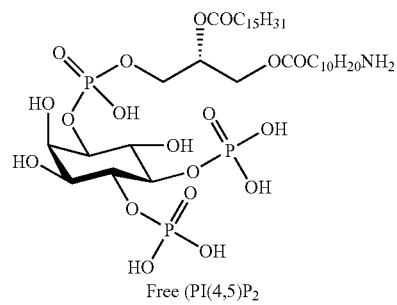
Free (PI(4,5)P$_2$
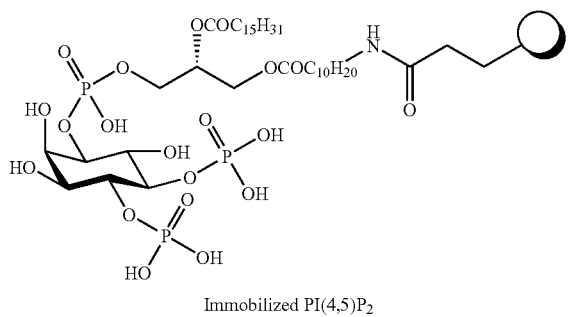
Immobilized PI(4,5)P$_2$
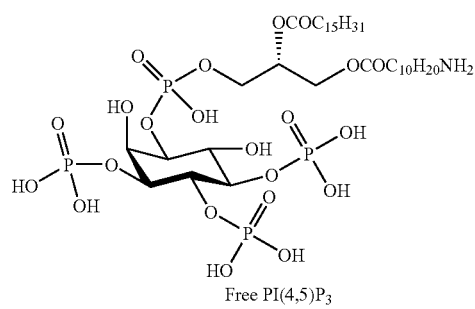
Free PI(4,5)P$_3$ TABLE 3-continued
Further preferred compounds and probes of the invention
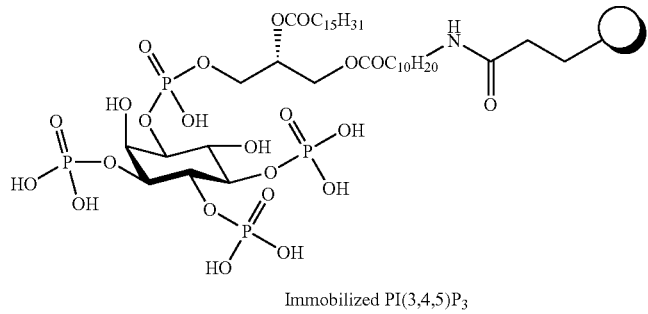
Immobilized PI(3,4,5)P$_3$
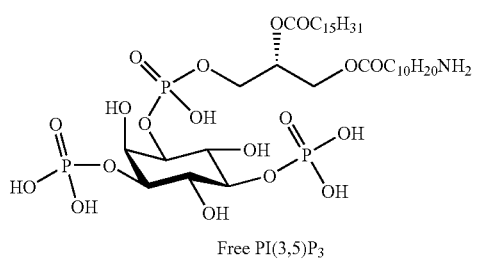
Free PI(3,5)P$_3$
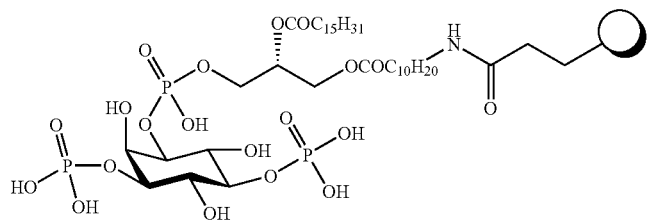
Immobilized PI(3,5)P$_2$
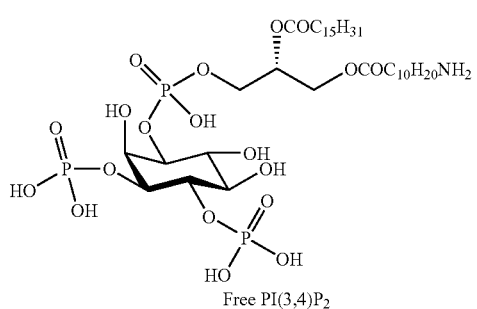
Free PI(3,4)P$_2$
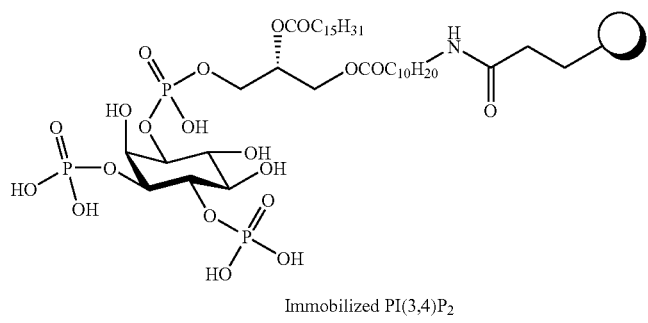
Immobilized PI(3,4)P$_2$ TABLE 3-continued
Further preferred compounds and probes of the invention
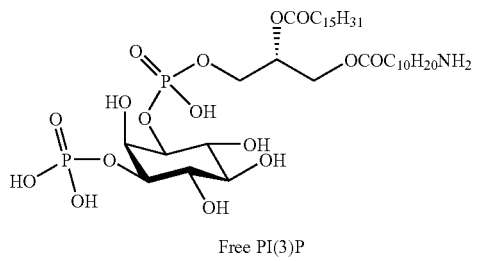
Free PI(3)P
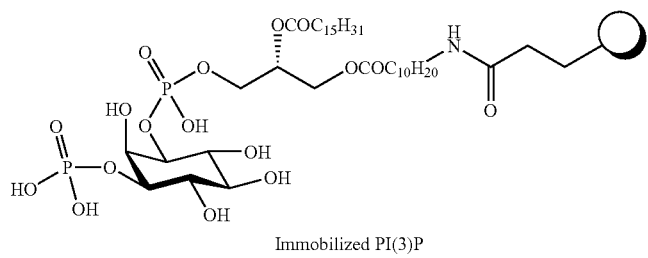
Immobilized PI(3)P
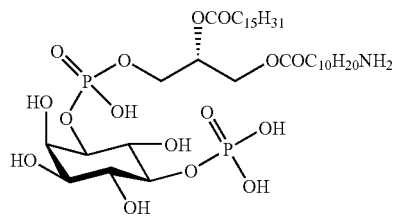
Free PI(5)P
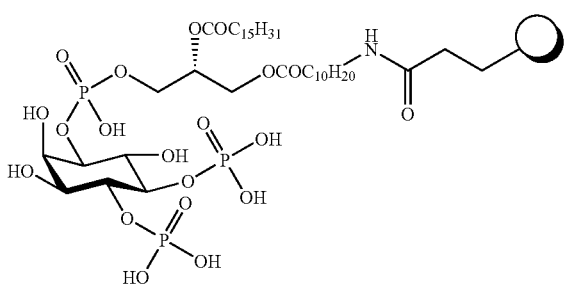
Immobilized PI(5)P
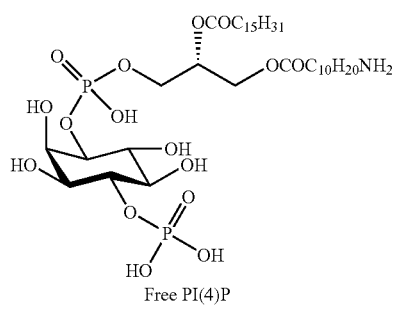
Free PI(4)P TABLE 3-continued
Further preferred compounds and probes of the invention
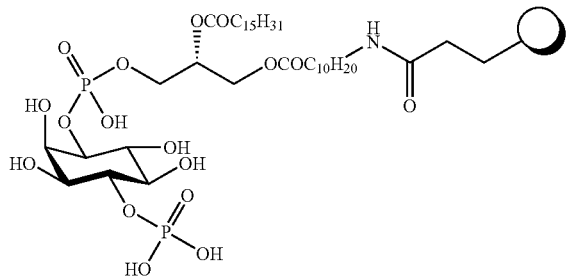
Immobilized PI(4)P
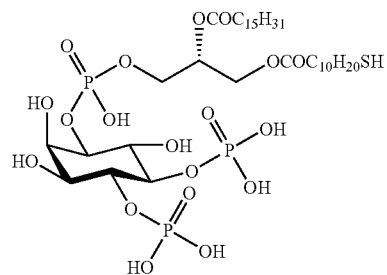
Free PI(4,5)P$_2$
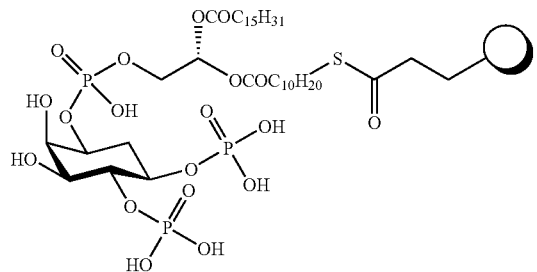
Immobilized PI(4,5)P$_2$
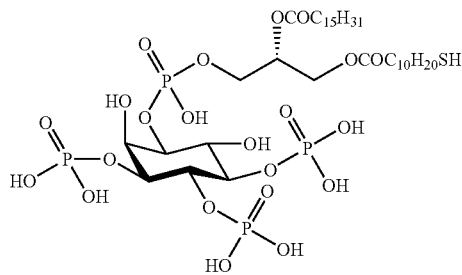
Free PI(3,4,5)P$_3$
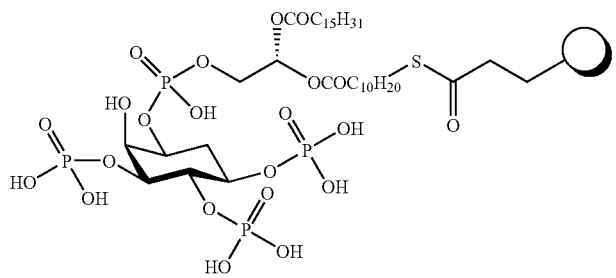
Immobilized PI(3,4,5)P$_3$ TABLE 3-continued
Further preferred compounds and probes of the invention
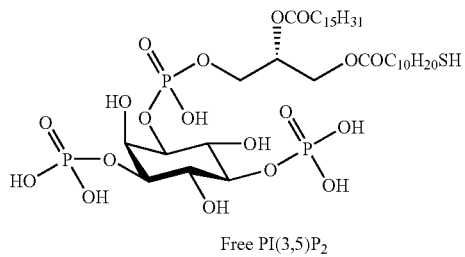
Free PI(3,5)P$_2$
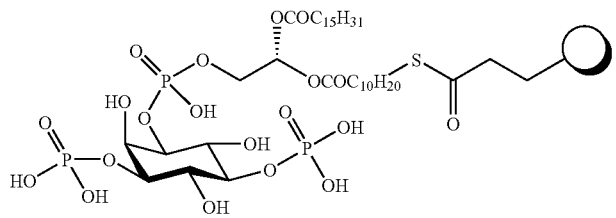
Immobilized PI(3,5)P$_2$
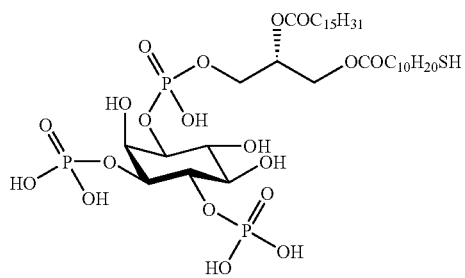
Free PI(3,4)P$_2$
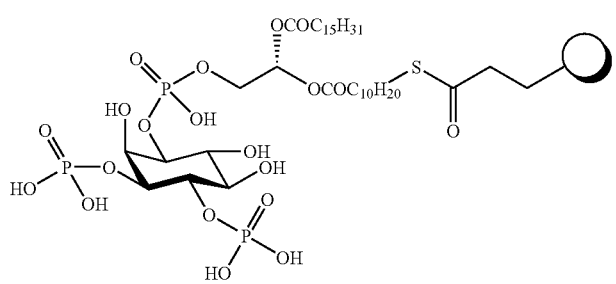
Immobilized PI(3,4)P$_2$
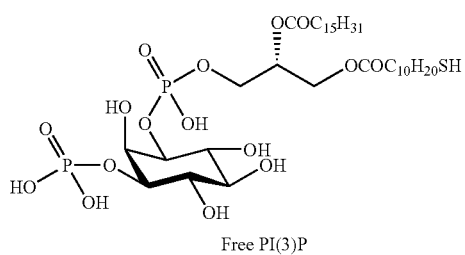
Free PI(3)P

TABLE 3-continued
Further preferred compounds and probes of the invention
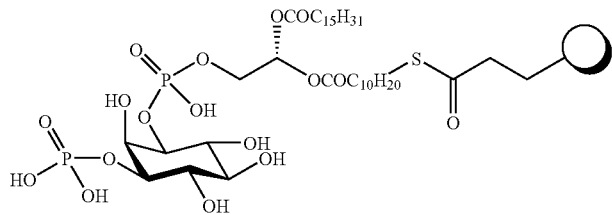
Immobilized PI(3)P
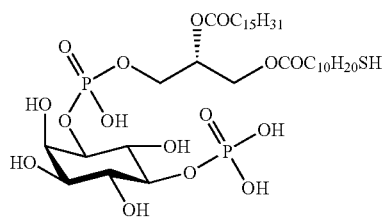
Free PI(5)P
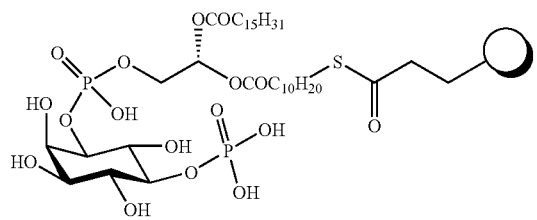
Immobilized PI(5)P
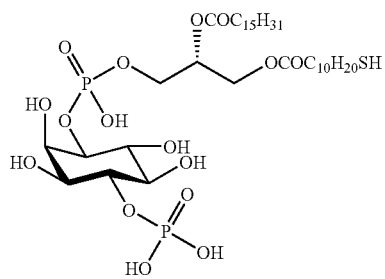
Free PI(4)P
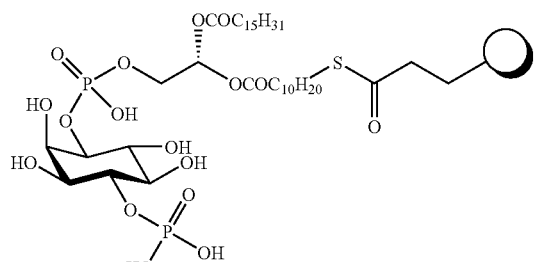
Immobilized PI(4)P TABLE 3-continued
Further preferred compounds and probes of the invention
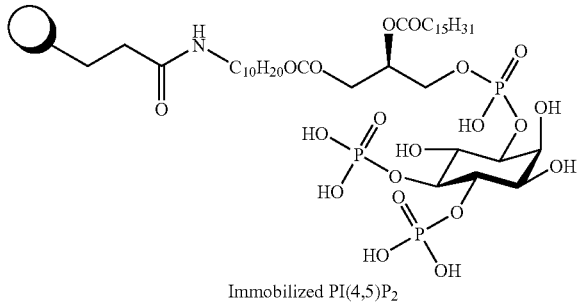
Immobilized PI(4,5)P$_2$
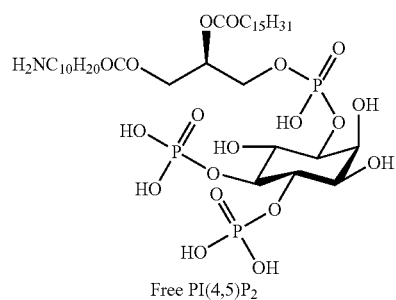
Free PI(4,5)P$_2$
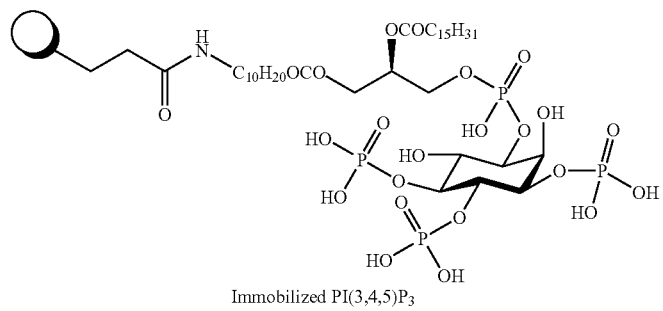
Immobilized PI(3,4,5)P$_3$
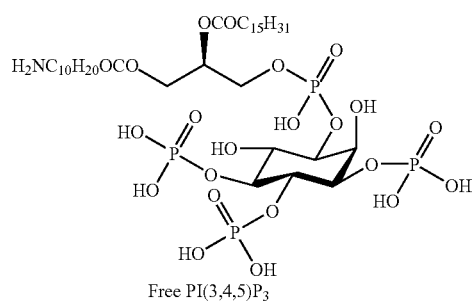
Free PI(3,4,5)P$_3$
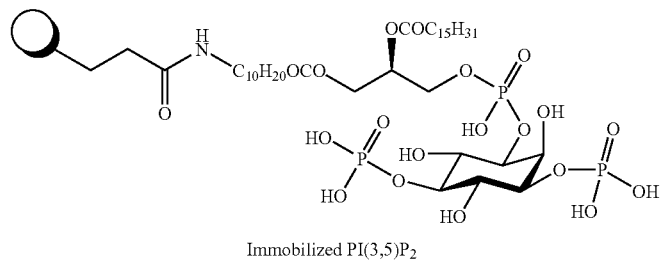
Immobilized PI(3,5)P$_2$ TABLE 3-continued
Further preferred compounds and probes of the invention
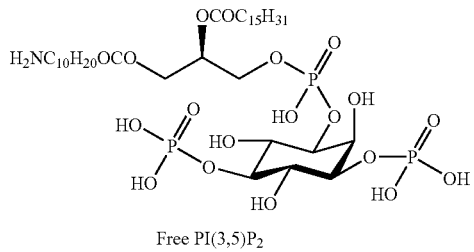
Free PI(3,5)P$_2$
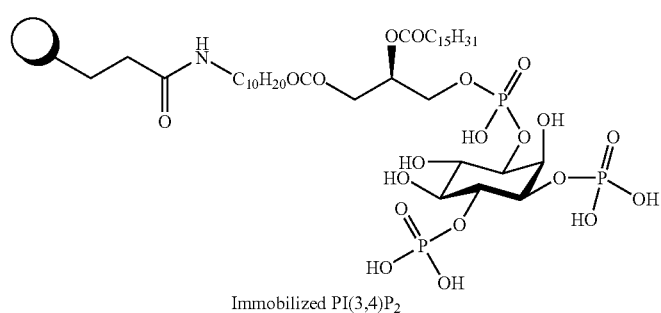
Immobilized PI(3,4)P$_2$
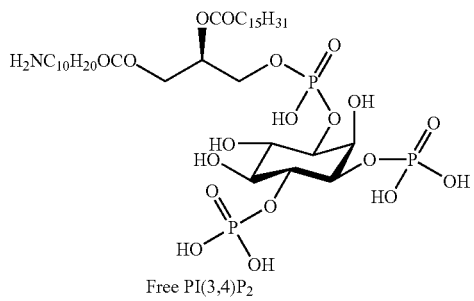
Free PI(3,4)P$_2$
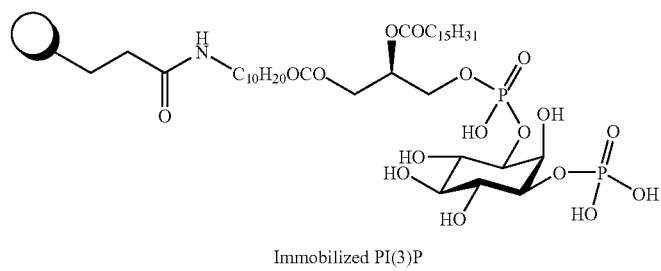
Immobilized PI(3)P
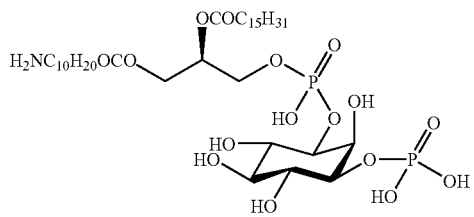
Free PI(3)P TABLE 3-continued
Further preferred compounds and probes of the invention
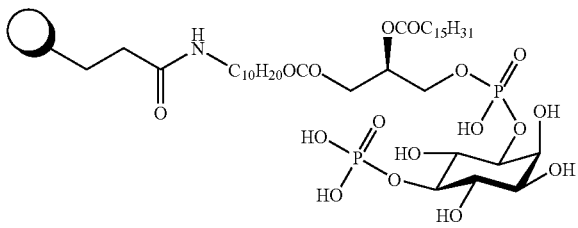
Immobilized PI(5)P
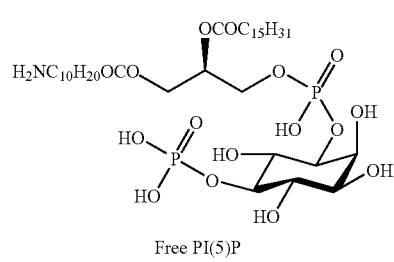
Free PI(5)P
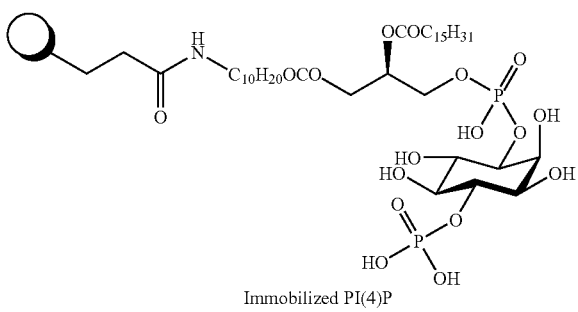
Immobilized PI(4)P
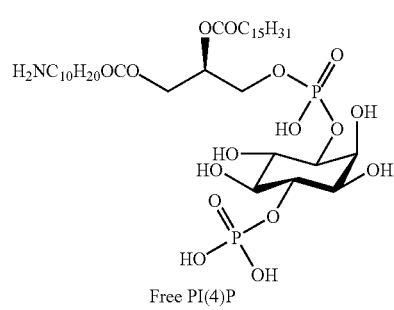
Free PI(4)P
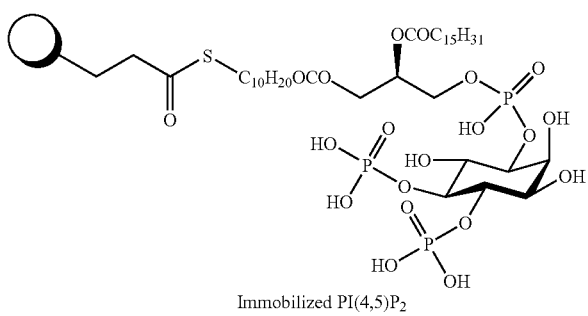
Immobilized PI(4,5)P$_2$ TABLE 3-continued
Further preferred compounds and probes of the invention
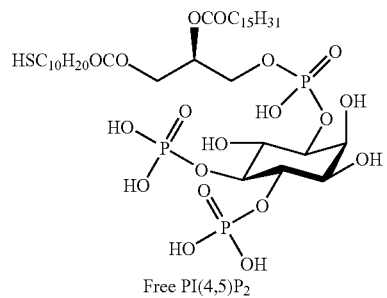
Free PI(4,5)P₂
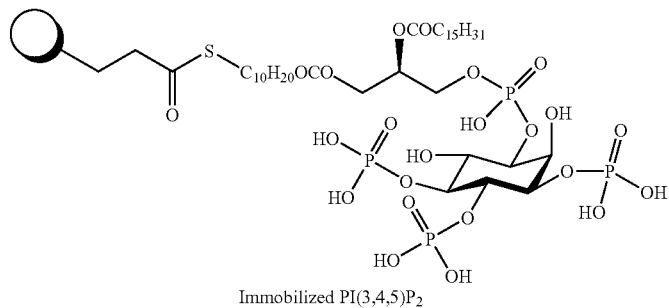
Immobilized PI(3,4,5)P₂
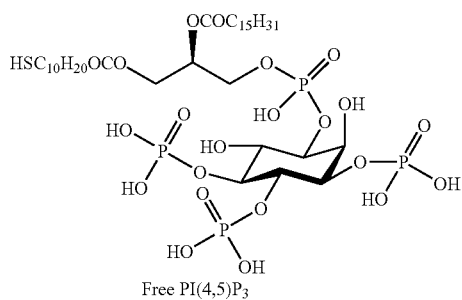
Free PI(4,5)P₃
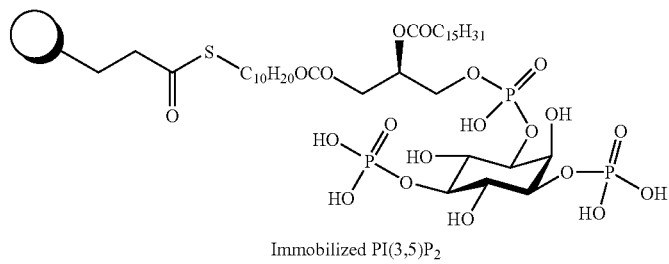
Immobilized PI(3,5)P₂
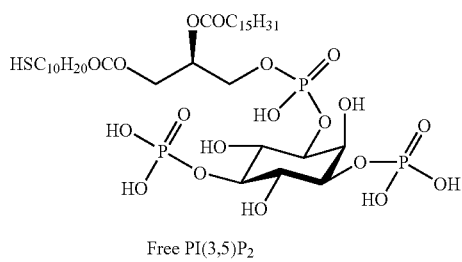
Free PI(3,5)P₂

TABLE 3-continued
Further preferred compounds and probes of the invention
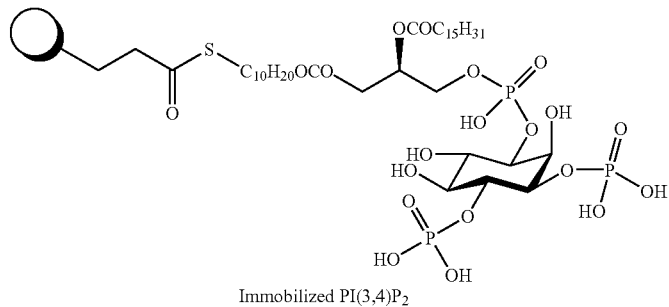
Immobilized PI(3,4)P$_2$
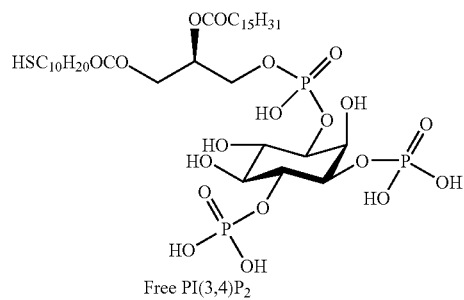
Free PI(3,4)P$_2$
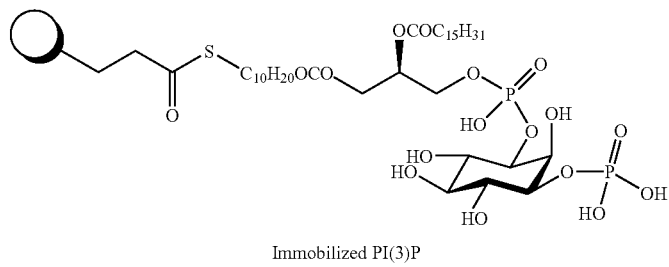
Immobilized PI(3)P
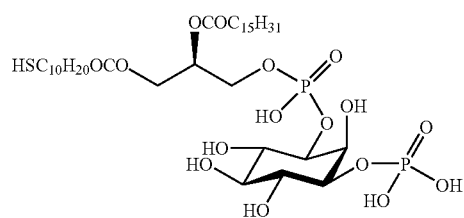
Free PI(3)P
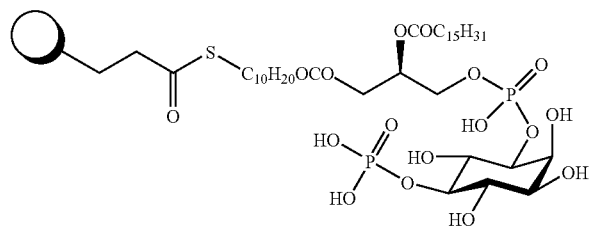
Immobilized PI(5)P TABLE 3-continued
Further preferred compounds and probes of the invention
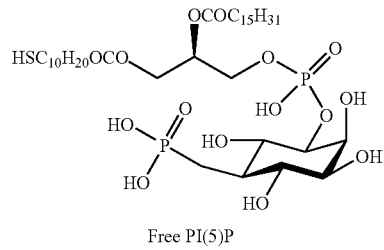
Free PI(5)P
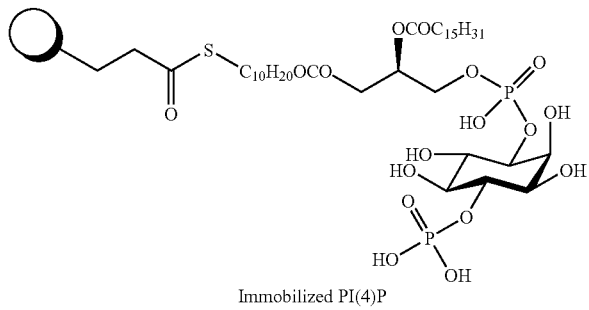
Immobilized PI(4)P
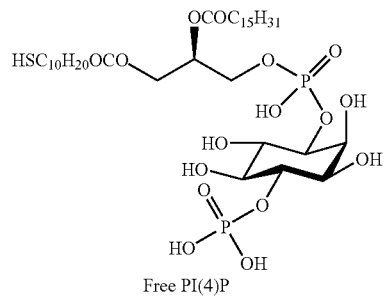
Free PI(4)P
C11
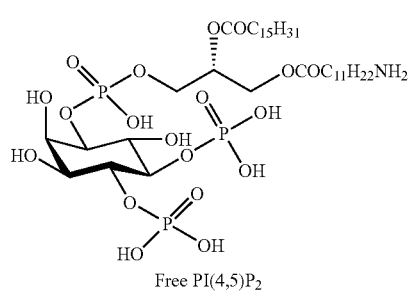
Free PI(4,5)P$_2$
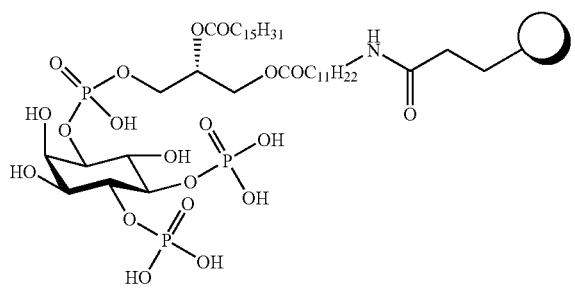
Immobilized PI(4,5)P$_2$ TABLE 3-continued
Further preferred compounds and probes of the invention
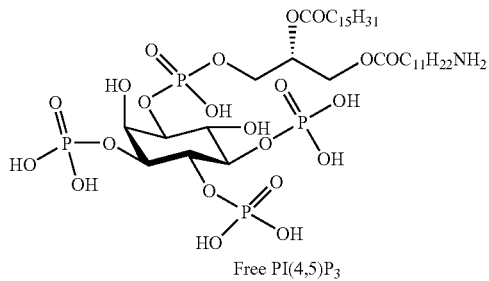
Free PI(4,5)P₃
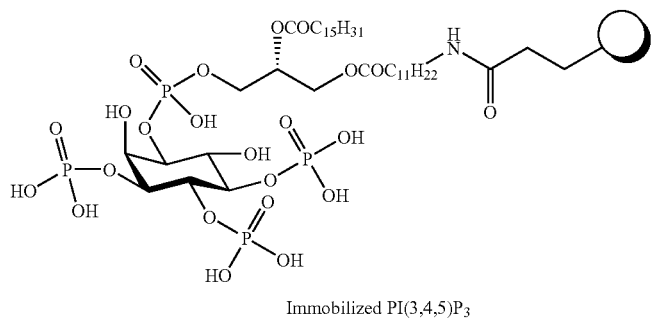
Immobilized PI(3,4,5)P₃
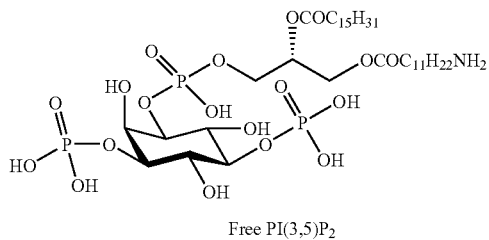
Free PI(3,5)P₂
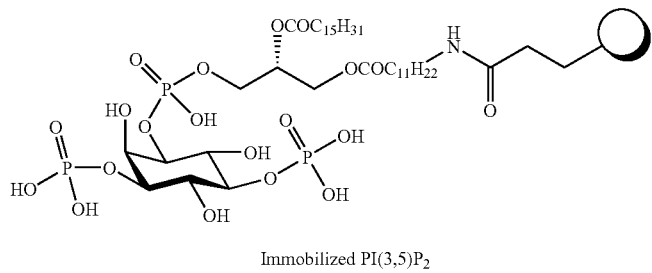
Immobilized PI(3,5)P₂
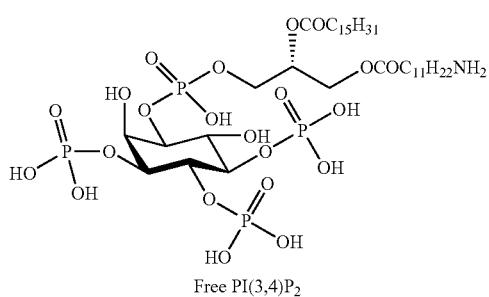
Free PI(3,4)P₂

TABLE 3-continued
Further preferred compounds and probes of the invention
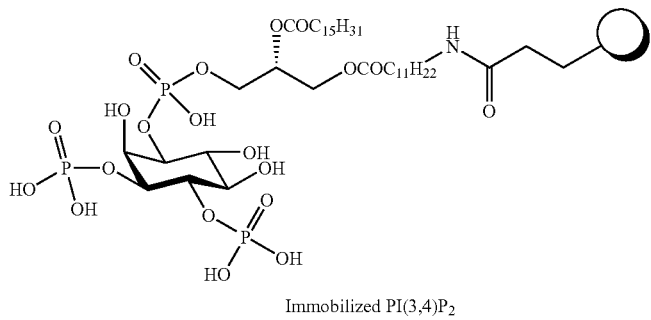
Immobilized PI(3,4)P$_2$
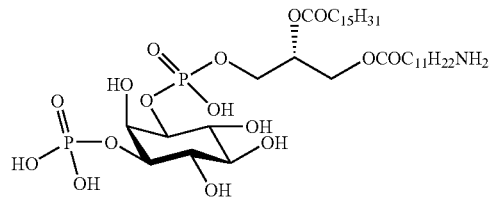
Free PI(3)P
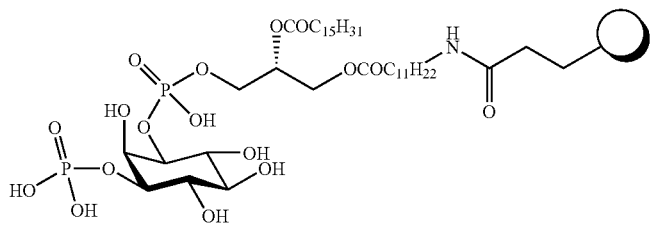
Immobilized PI(3)P
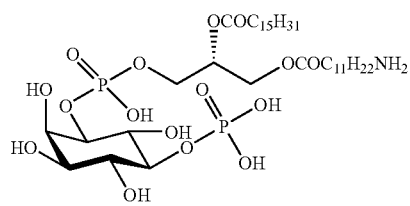
Free PI(5)P
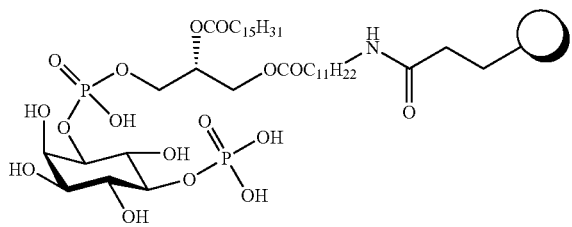
Immobilized PI(5)P TABLE 3-continued
Further preferred compounds and probes of the invention
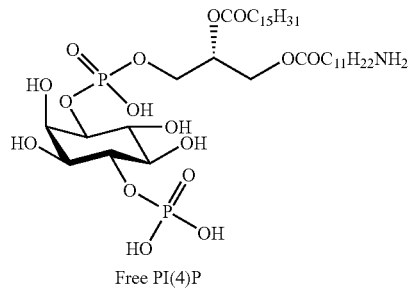
Free PI(4)P
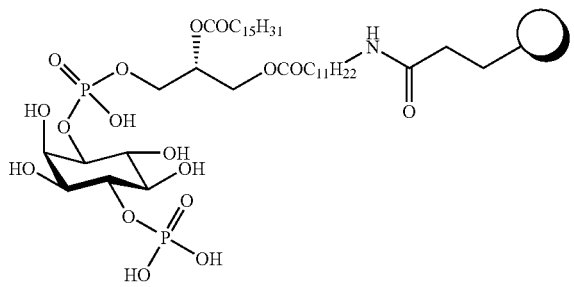
Immobilized PI(4)P
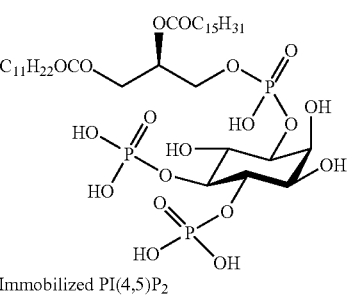
Immobilized PI(4,5)P$_2$
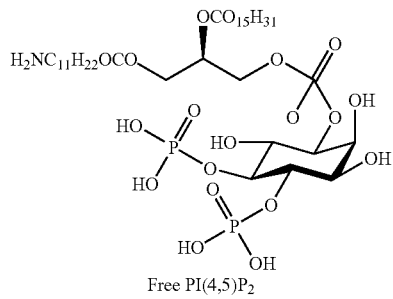
Free PI(4,5)P$_2$
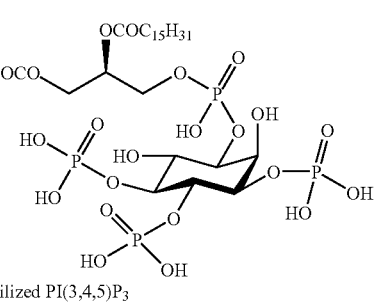
Immobilized PI(3,4,5)P$_3$ TABLE 3-continued
Further preferred compounds and probes of the invention
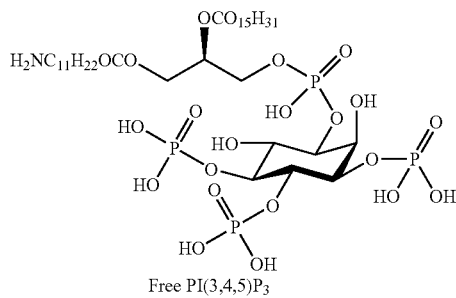
Free PI(3,4,5)P$_3$
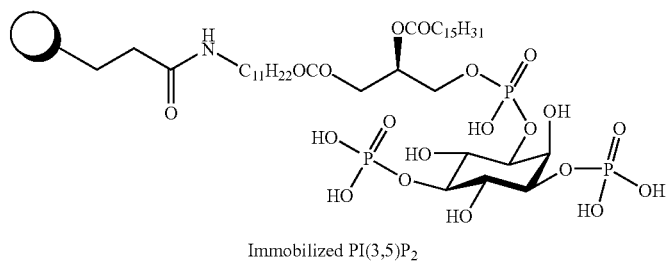
Immobilized PI(3,5)P$_2$
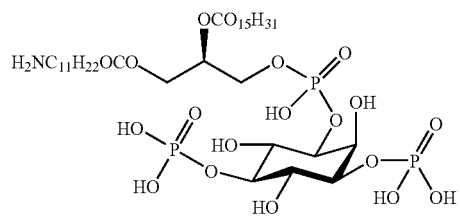
Free PI(3,5)P$_2$
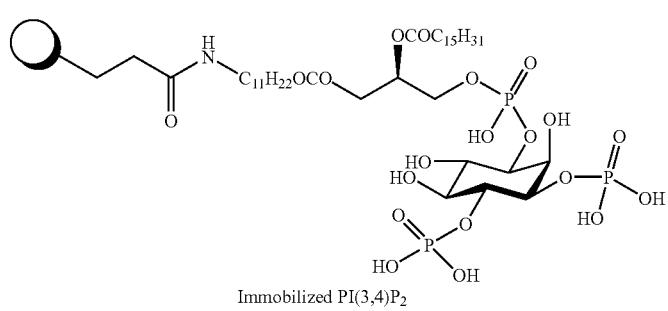
Immobilized PI(3,4)P$_2$
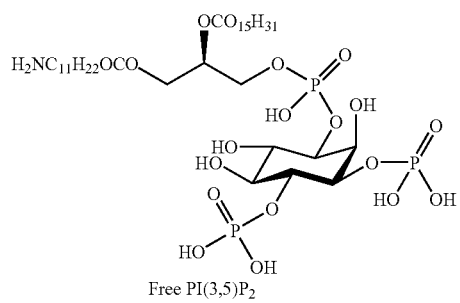
Free PI(3,5)P$_2$ TABLE 3-continued
Further preferred compounds and probes of the invention
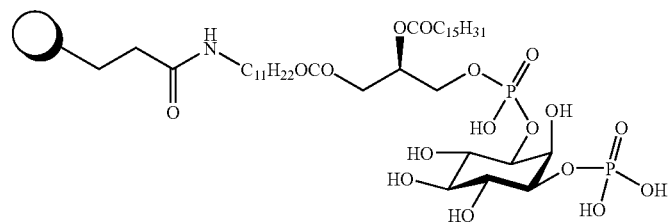
Immobilized PI(3)P
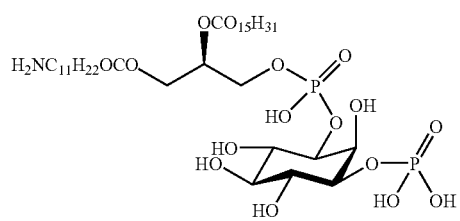
Free PI(3)P
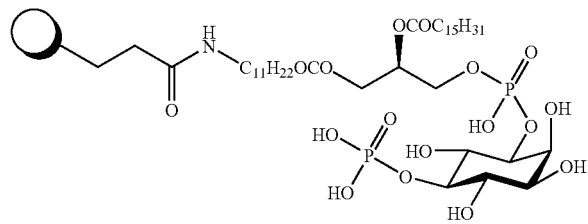
Immobilized PI(5)P₃
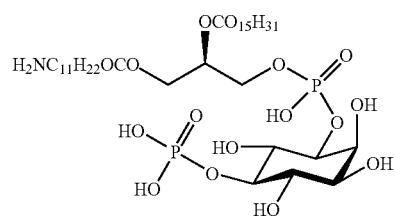
Free PI(5)P
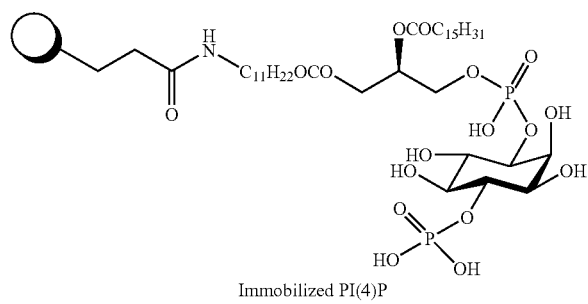
Immobilized PI(4)P TABLE 3-continued
Further preferred compounds and probes of the invention
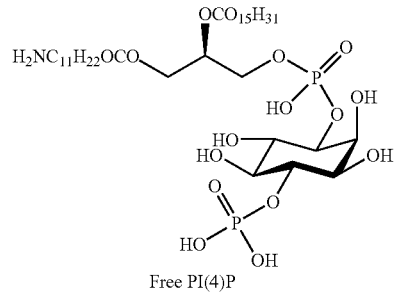
Free PI(4)P
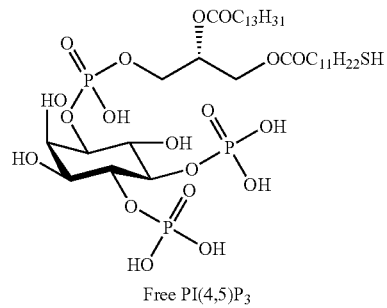
Free PI(4,5)P$_3$
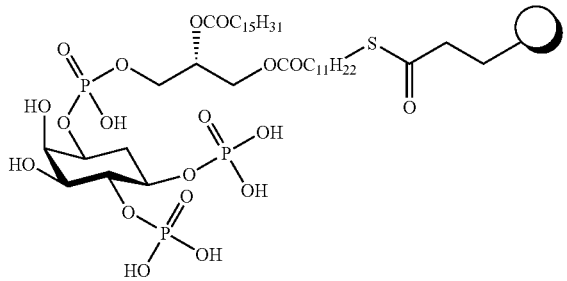
Immobilized PI(4,5)P$_2$
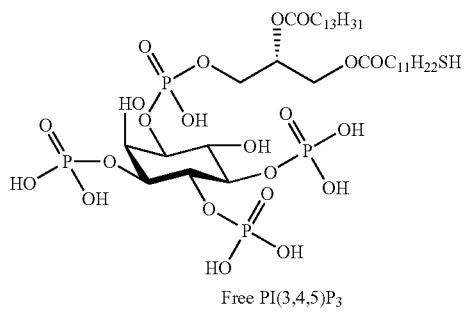
Free PI(3,4,5)P$_3$
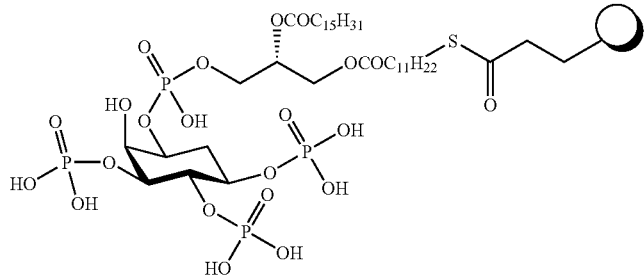
Immobilized PI(3,4,5)P$_3$ TABLE 3-continued
Further preferred compounds and probes of the invention
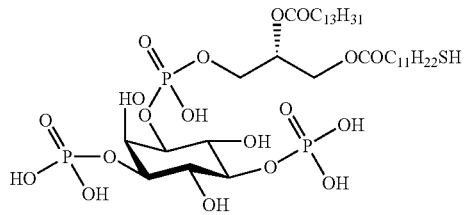
Free PI(3,5)P$_2$
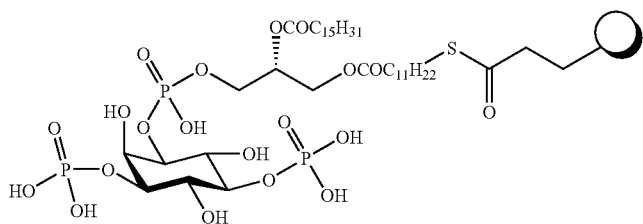
Immobilized PI(3,5)P$_2$
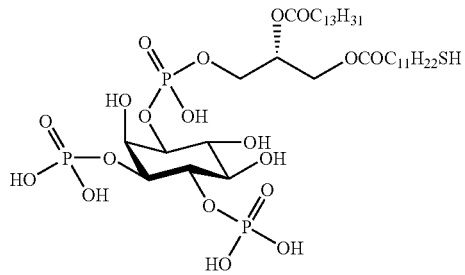
Free PI(3,4)P$_2$
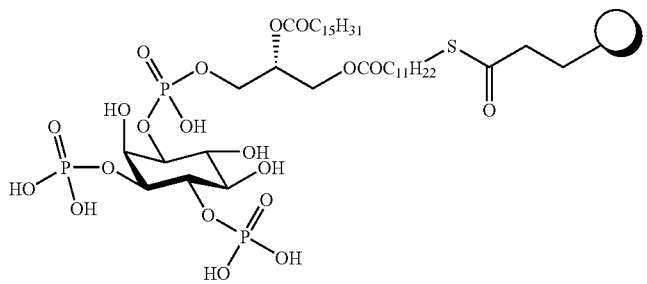
Immobilized PI(3,4)P$_2$
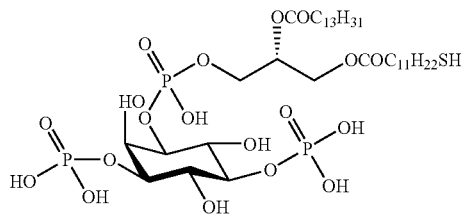
Free PI(3)P

TABLE 3-continued
Further preferred compounds and probes of the invention
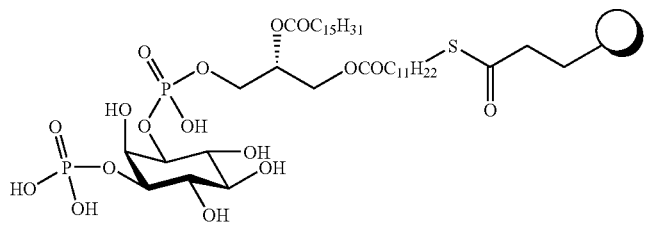
Immobilized PI(5)P
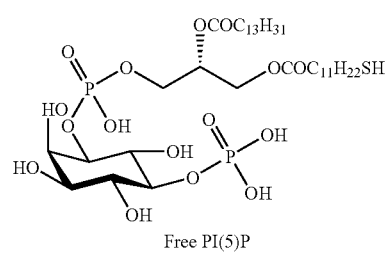
Free PI(5)P
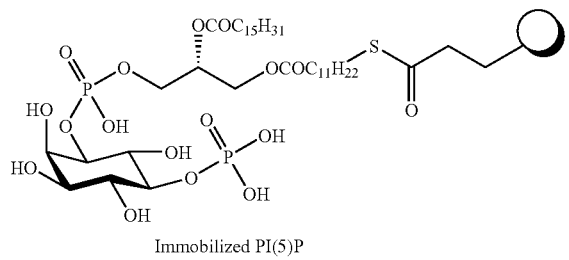
Immobilized PI(5)P
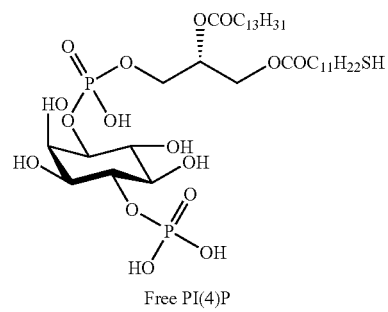
Free PI(4)P
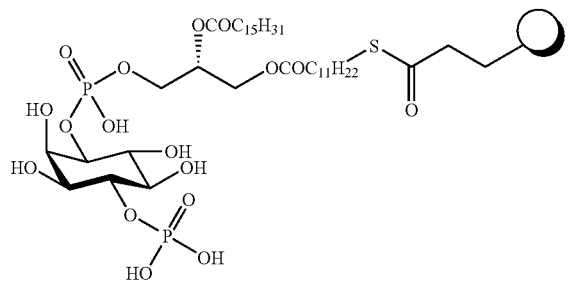
Immobilized PI(4)P TABLE 3-continued
Further preferred compounds and probes of the invention
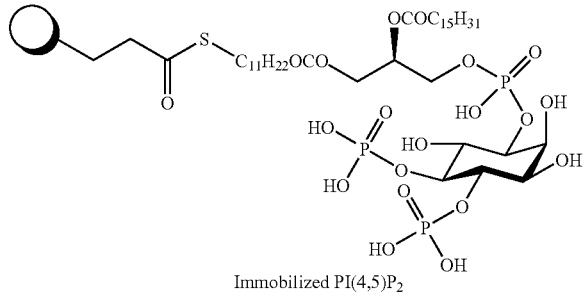
Immobilized PI(4,5)P$_2$
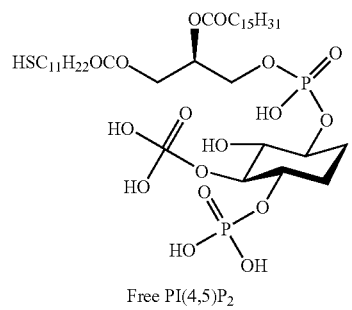
Free PI(4,5)P$_2$
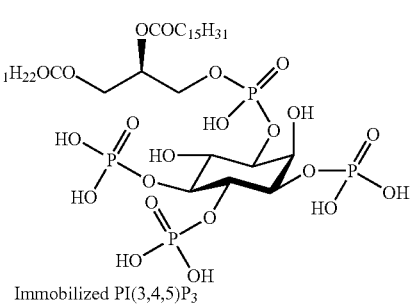
Immobilized PI(3,4,5)P$_3$
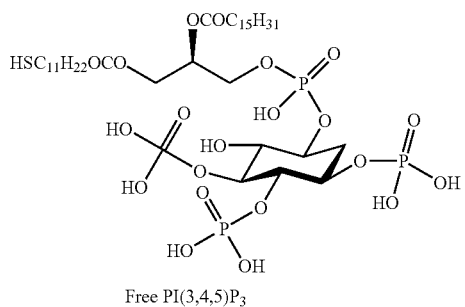
Free PI(3,4,5)P$_3$
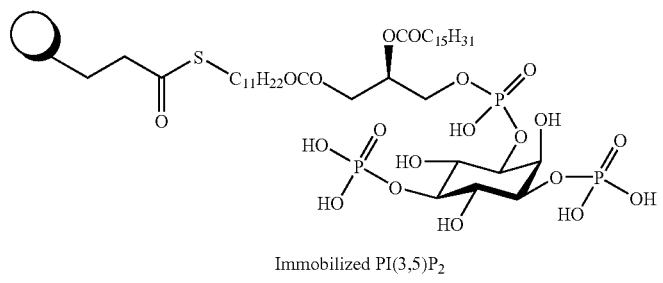
Immobilized PI(3,5)P$_2$ TABLE 3-continued
Further preferred compounds and probes of the invention
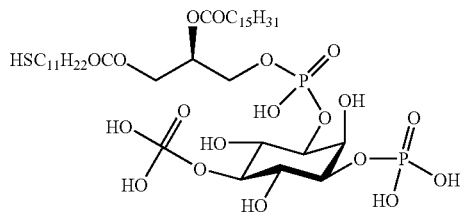
Free PI(3,5)P$_2$
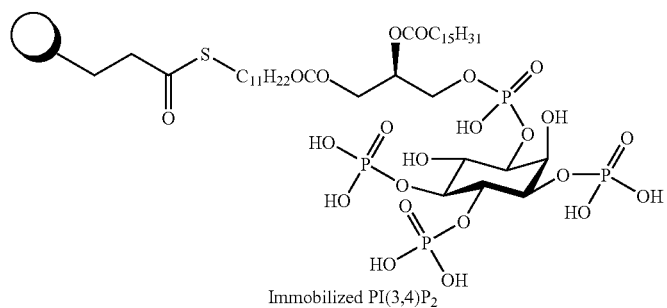
Immobilized PI(3,4)P$_2$
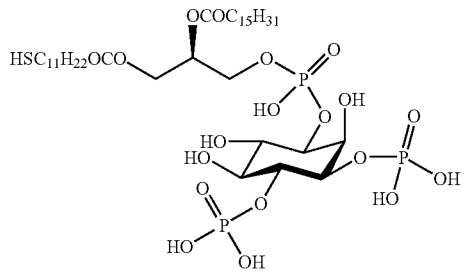
Free PI(3,4)P$_2$
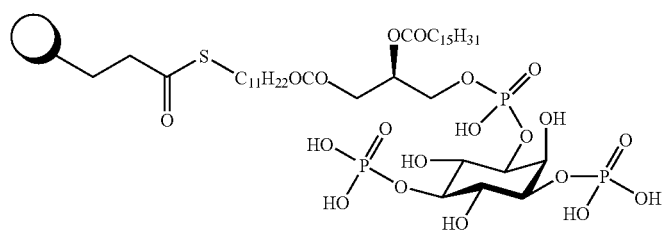
Immobilized PI(3)P
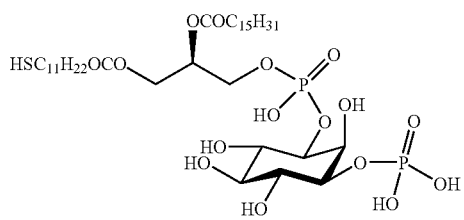
Free PI(3)P TABLE 3-continued
Further preferred compounds and probes of the invention
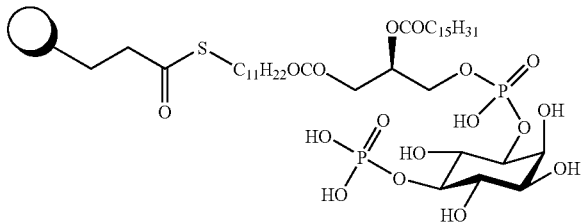
Immobilized PI(5)P
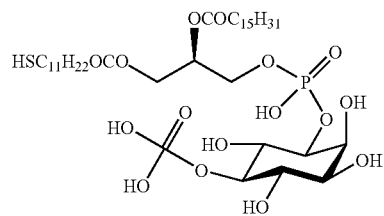
Free PI(5)P
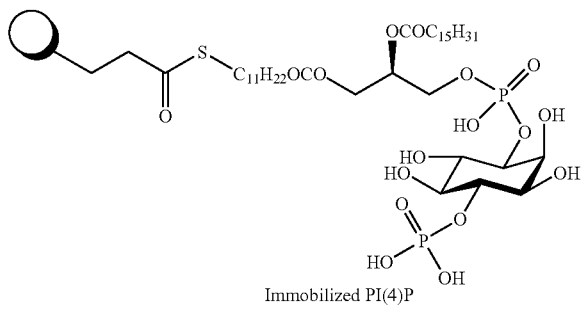
Immobilized PI(4)P
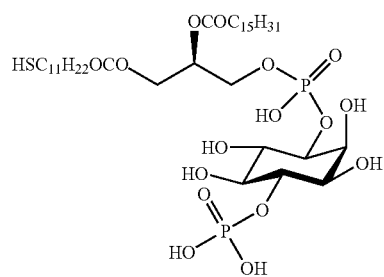
Free PI(4)P
C12
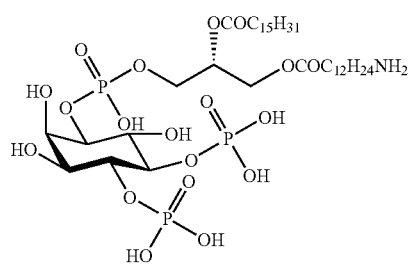
Free PI(4,5)P$_2$ TABLE 3-continued
Further preferred compounds and probes of the invention
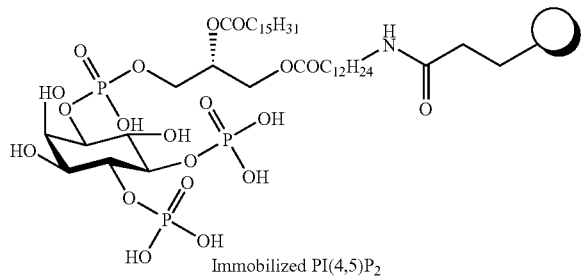
Immobilized PI(4,5)P$_2$
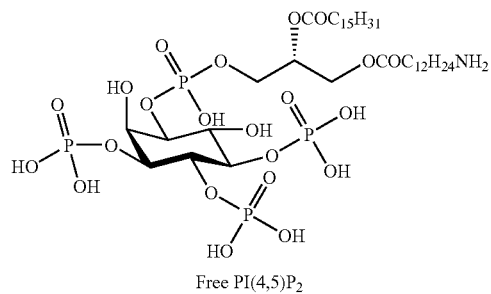
Free PI(4,5)P$_2$
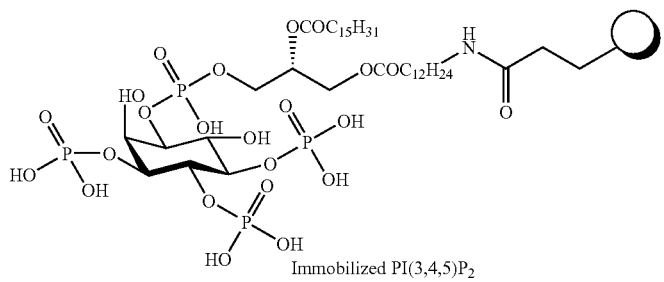
Immobilized PI(3,4,5)P$_2$
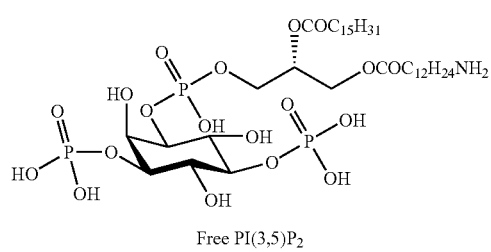
Free PI(3,5)P$_2$
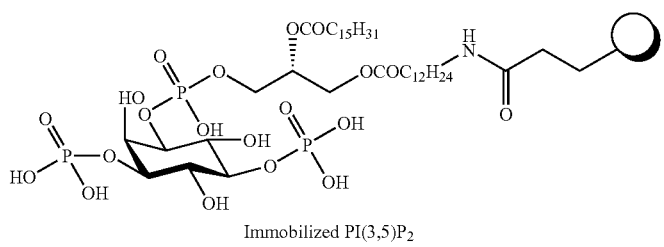
Immobilized PI(3,5)P$_2$ TABLE 3-continued
Further preferred compounds and probes of the invention
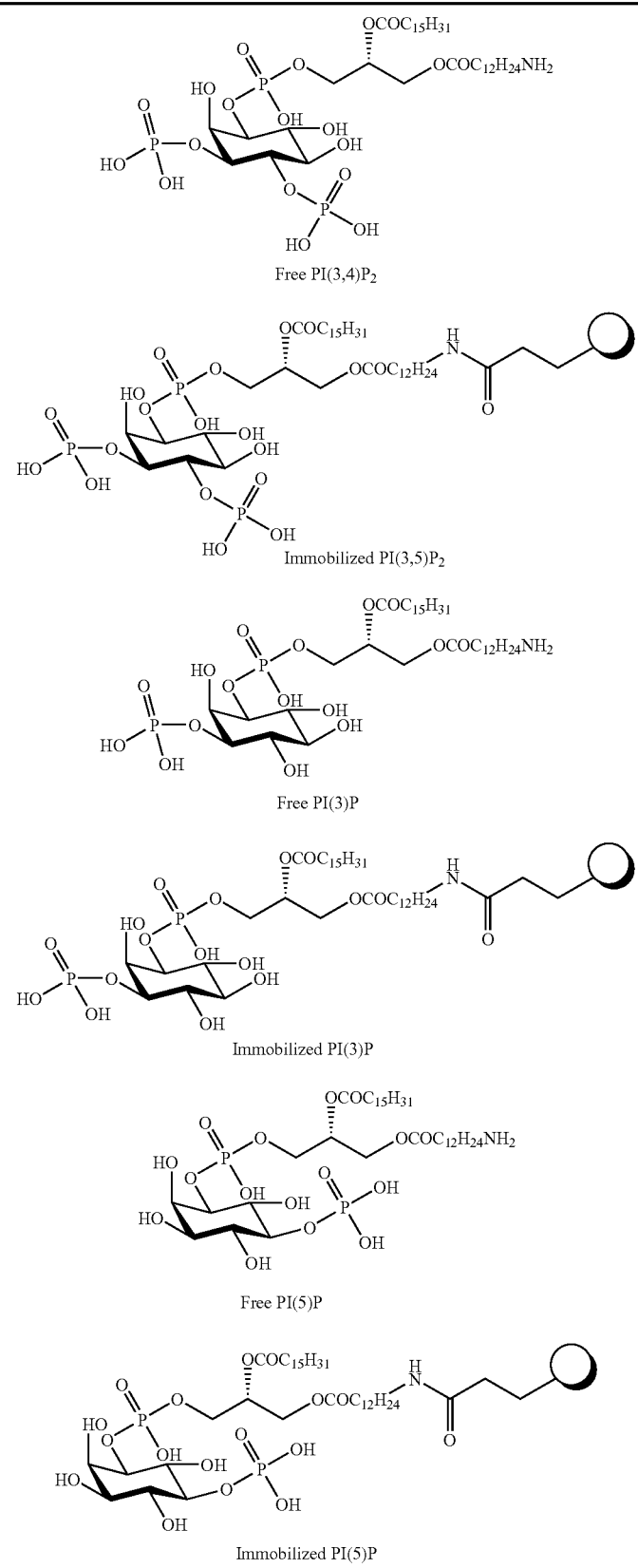
Free PI(3,4)P₂
Immobilized PI(3,5)P₂
Free PI(3)P
Immobilized PI(3)P
Free PI(5)P
Immobilized PI(5)P TABLE 3-continued
Further preferred compounds and probes of the invention
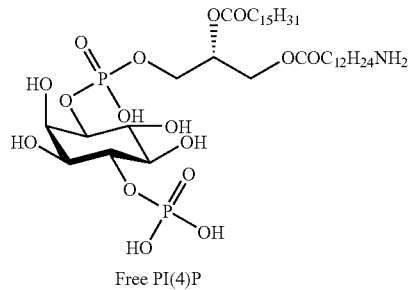
Free PI(4)P
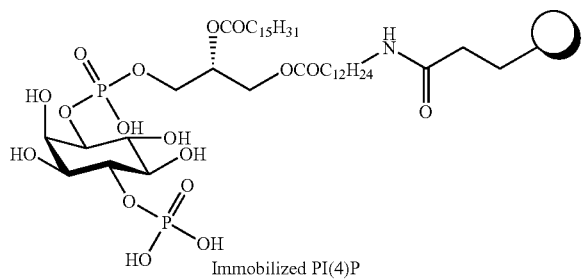
Immobilized PI(4)P
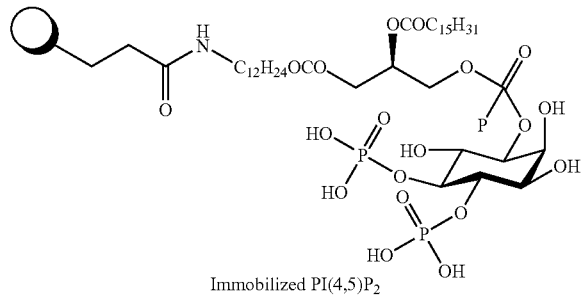
Immobilized PI(4,5)P$_2$
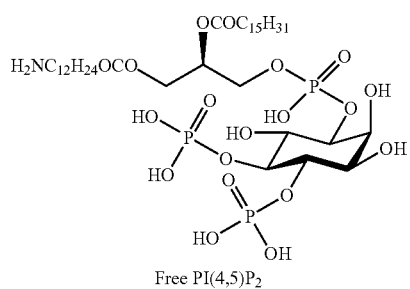
Free PI(4,5)P$_2$
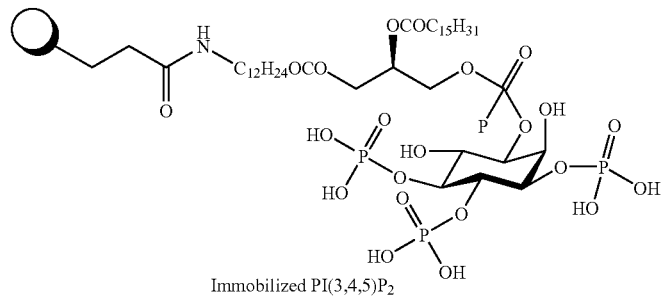
Immobilized PI(3,4,5)P$_2$ TABLE 3-continued
Further preferred compounds and probes of the invention
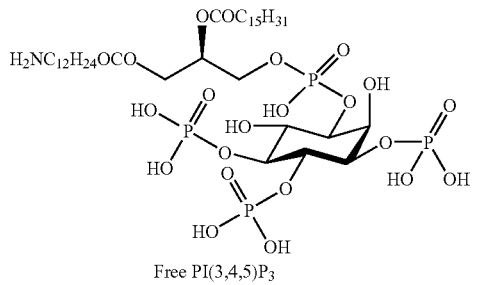
Free PI(3,4,5)P₃
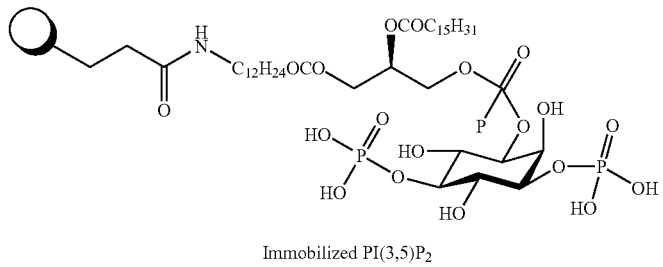
Immobilized PI(3,5)P₂
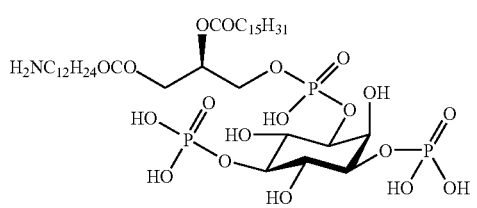
Free PI(3,5)P₂
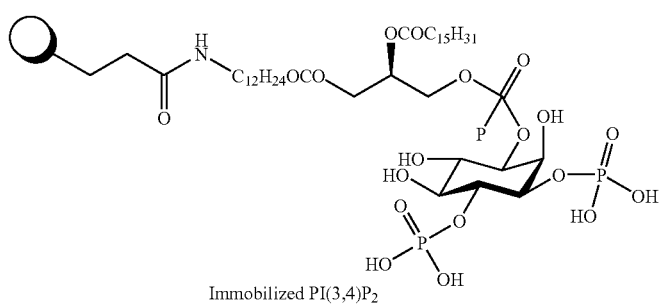
Immobilized PI(3,4)P₂
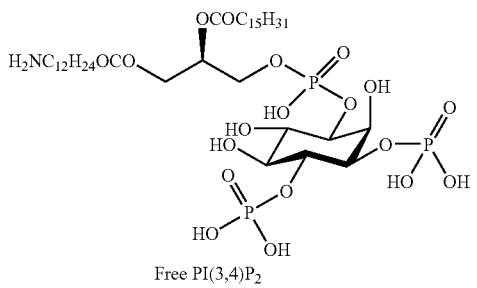
Free PI(3,4)P₂

TABLE 3-continued
Further preferred compounds and probes of the invention
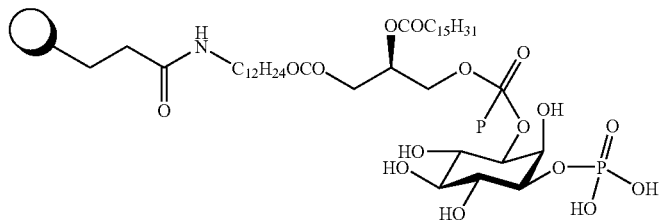
Immobilized PI(3)P
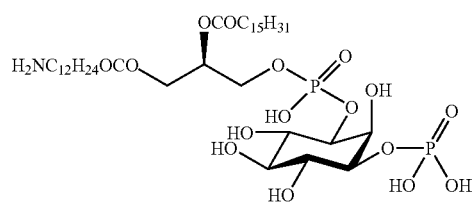
Free PI(3)P
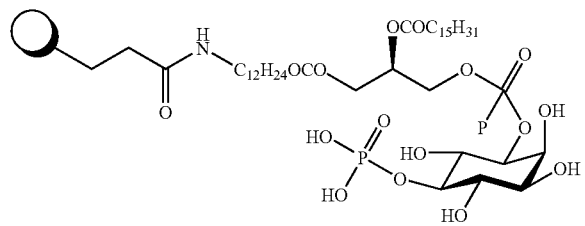
Immobilized PI(5)P
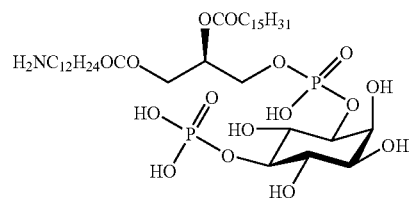
Free PI(5)P
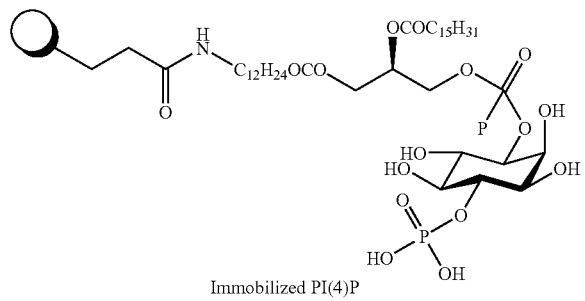
Immobilized PI(4)P TABLE 3-continued
Further preferred compounds and probes of the invention
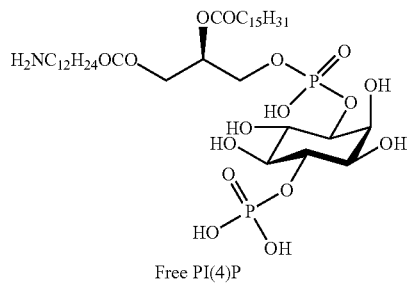
Free PI(4)P
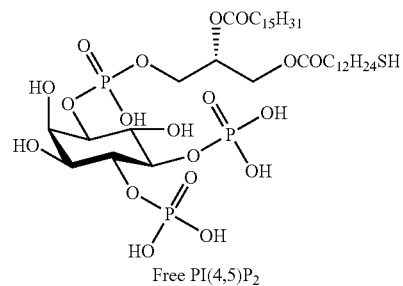
Free PI(4,5)P$_2$
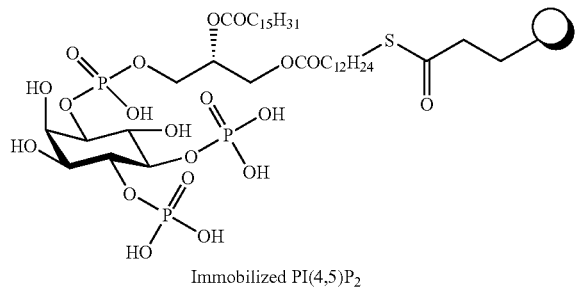
Immobilized PI(4,5)P$_2$
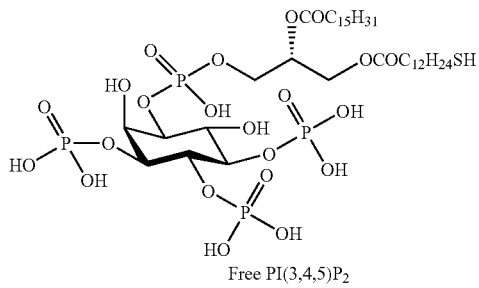
Free PI(3,4,5)P$_2$
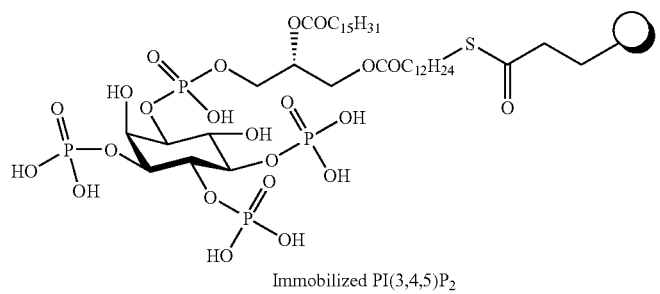
Immobilized PI(3,4,5)P$_2$ TABLE 3-continued
Further preferred compounds and probes of the invention
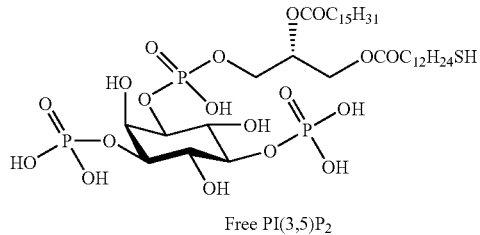
Free PI(3,5)P$_2$
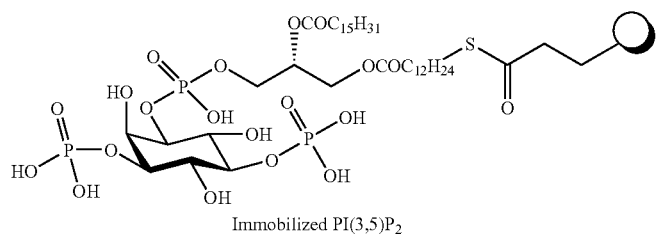
Immobilized PI(3,5)P$_2$
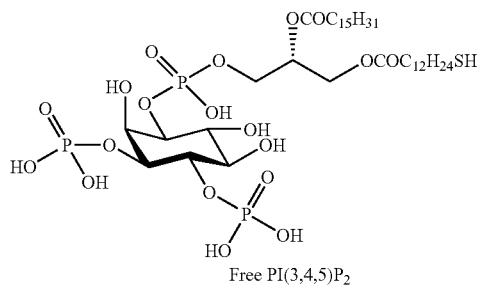
Free PI(3,4,5)P$_2$
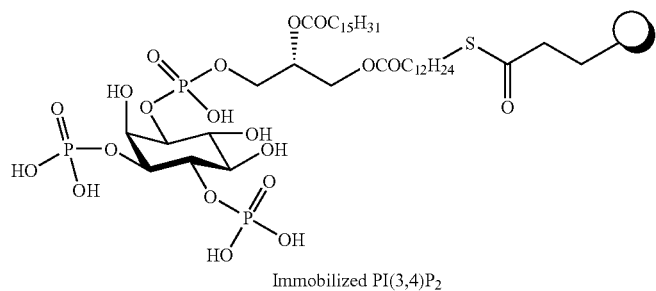
Immobilized PI(3,4)P$_2$
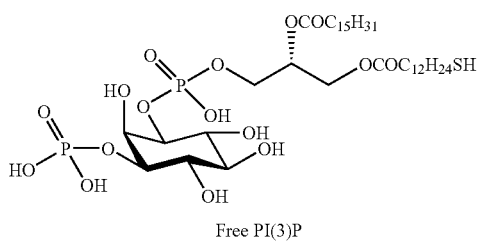
Free PI(3)P TABLE 3-continued
Further preferred compounds and probes of the invention
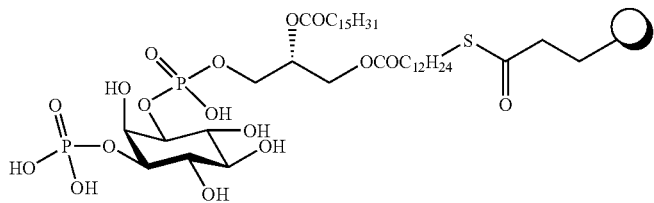
Immobilized P(3)P
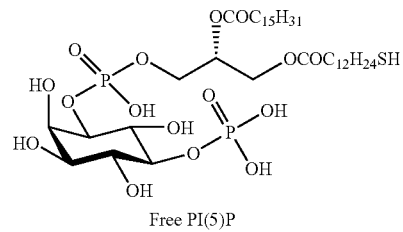
Free PI(5)P
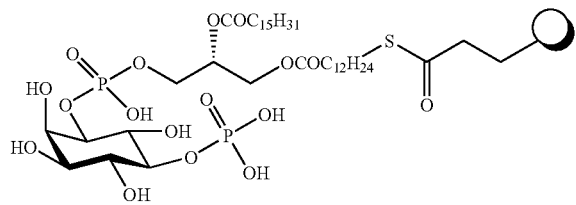
Immobilized PI(5)P
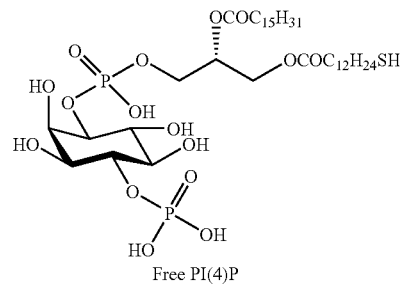
Free PI(4)P
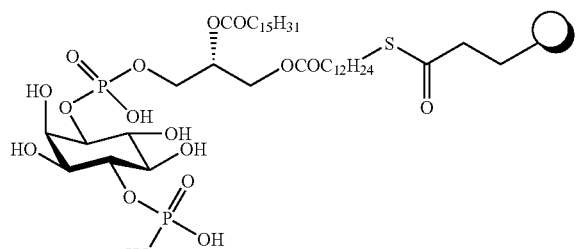
Immobilized PI(4)P TABLE 3-continued
Further preferred compounds and probes of the invention
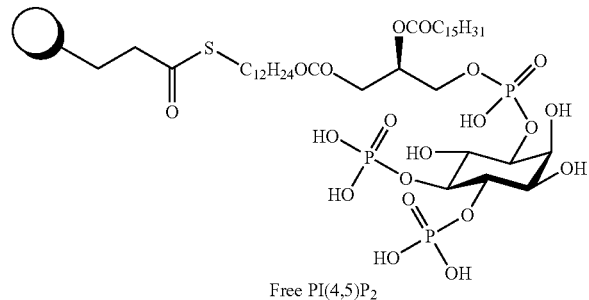
Free PI(4,5)P$_2$
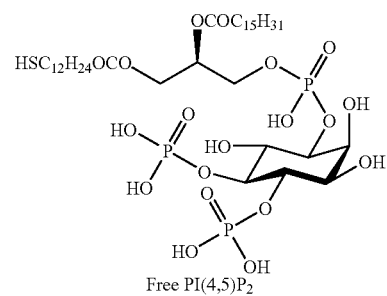
Free PI(4,5)P$_2$
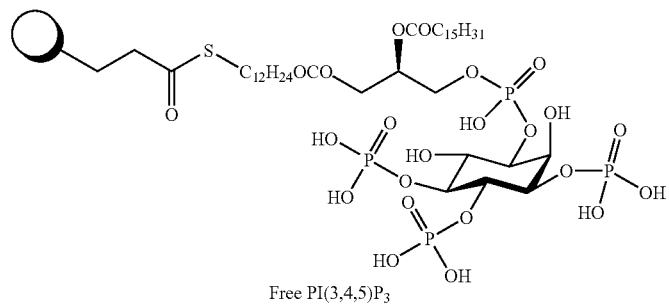
Free PI(3,4,5)P$_3$
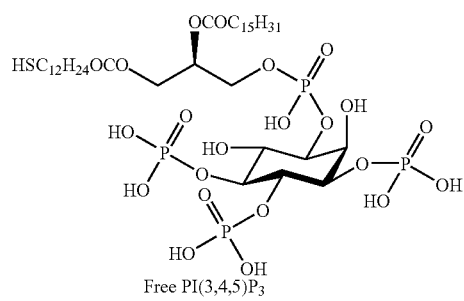
Free PI(3,4,5)P$_3$
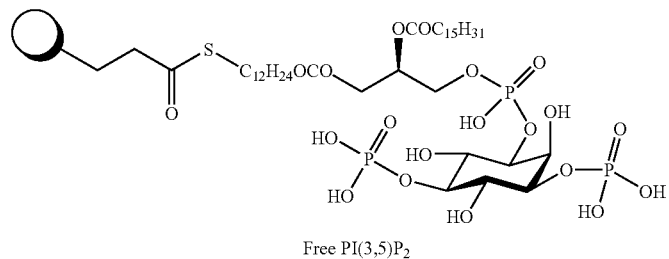
Free PI(3,5)P$_2$ TABLE 3-continued
Further preferred compounds and probes of the invention
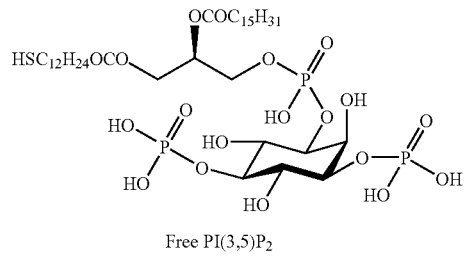
Free PI(3,5)P$_2$
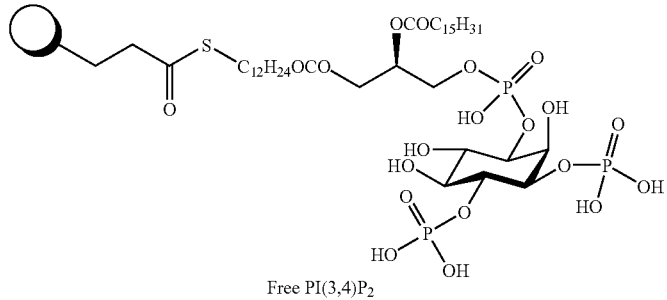
Free PI(3,4)P$_2$
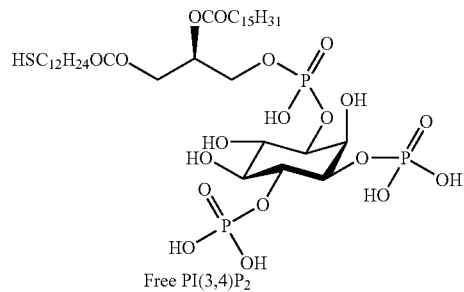
Free PI(3,4)P$_2$
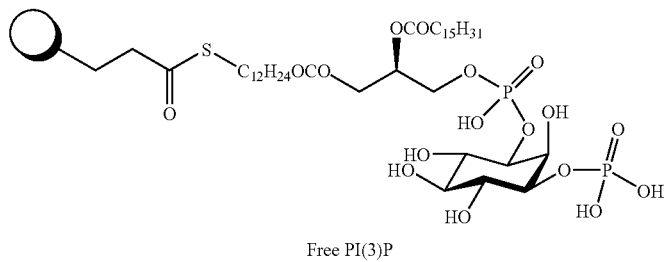
Free PI(3)P
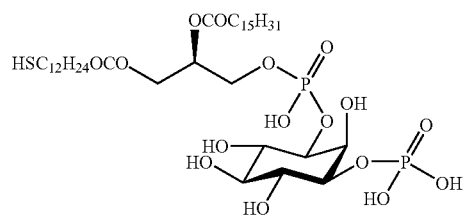
Free PI(3)P TABLE 3-continued
Further preferred compounds and probes of the invention
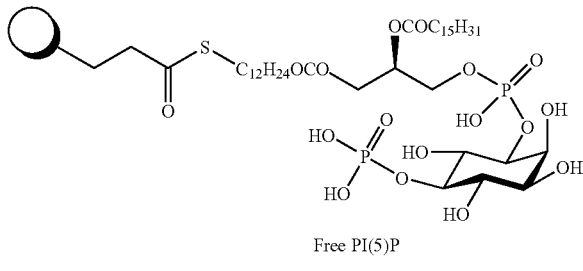
Free PI(5)P
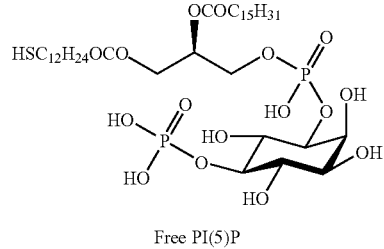
Free PI(5)P
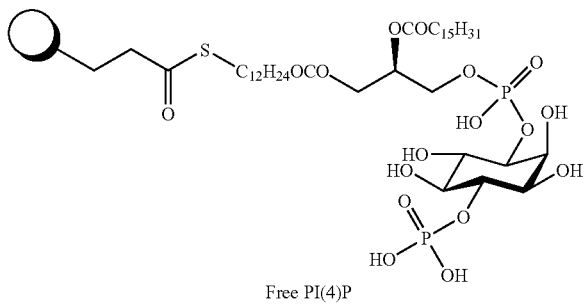
Free PI(4)P
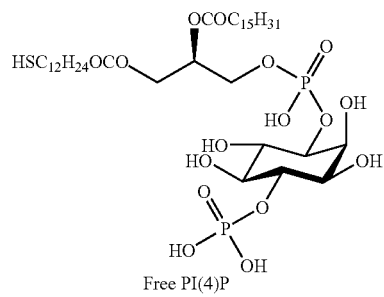
Free PI(4)P
C13
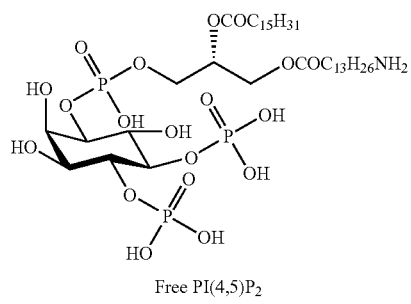
Free PI(4,5)P$_2$ TABLE 3-continued
Further preferred compounds and probes of the invention
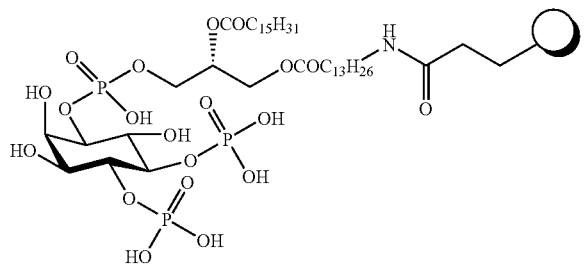
Immobilized PI(4,5)P$_2$
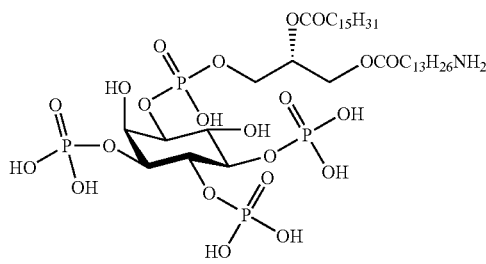
Free PI(3,4,5)P$_3$
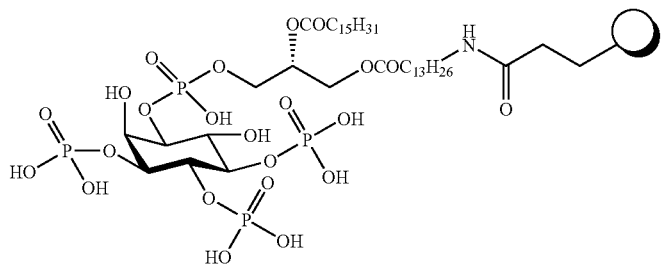
Immobilized PI(3,4,5)P$_3$
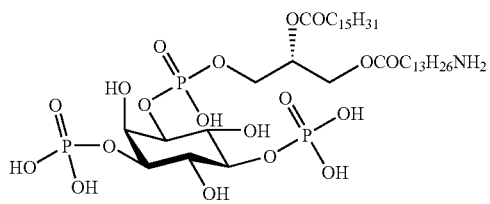
Free PI(3,5)P$_2$
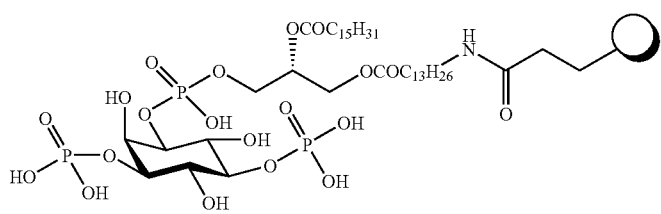
Immobilized PI(3,5)P$_2$ TABLE 3-continued
Further preferred compounds and probes of the invention
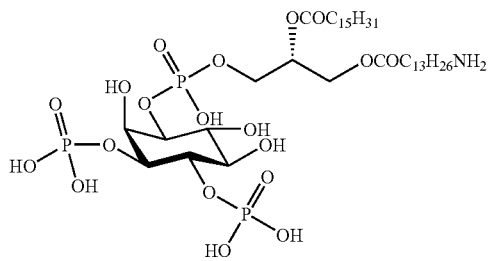
Free PI(3,4)P$_2$
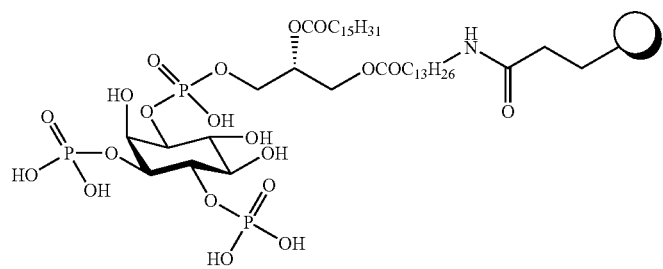
Immobilized PI(3,4)P$_2$
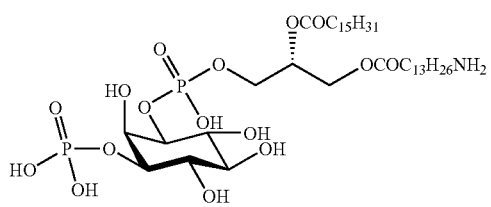
Free PI(3)P
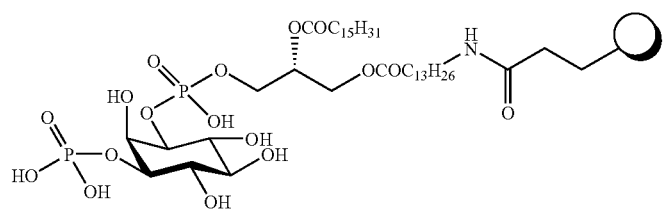
Immobilized PI(3)P
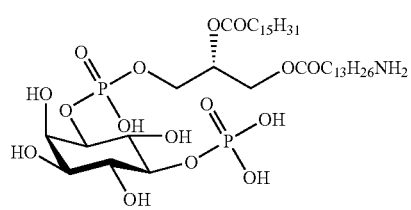
Free PI(5)P TABLE 3-continued
Further preferred compounds and probes of the invention
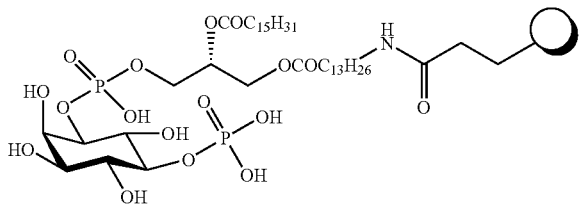
Immobilized PI(5)P
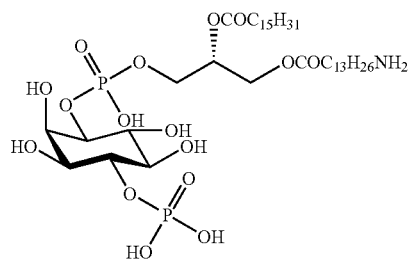
Free PI(4)P
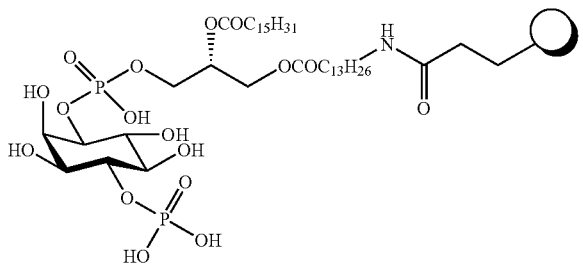
Immobilized PI(4)P
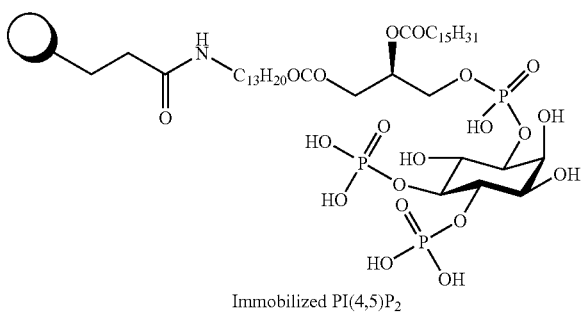
Immobilized PI(4,5)P$_2$
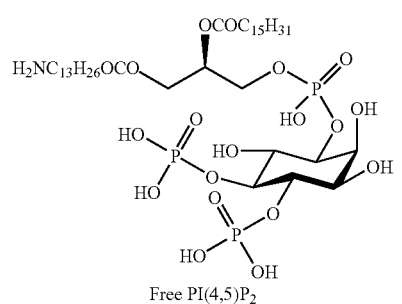
Free PI(4,5)P$_2$ TABLE 3-continued
Further preferred compounds and probes of the invention
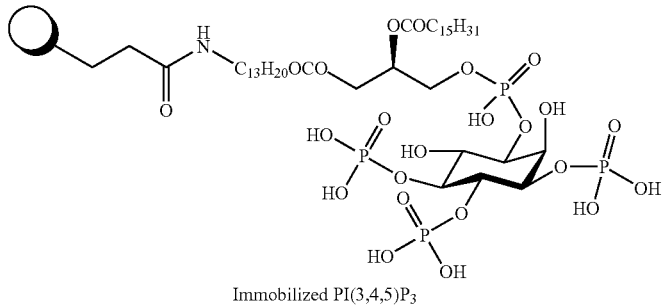
Immobilized PI(3,4,5)P$_3$
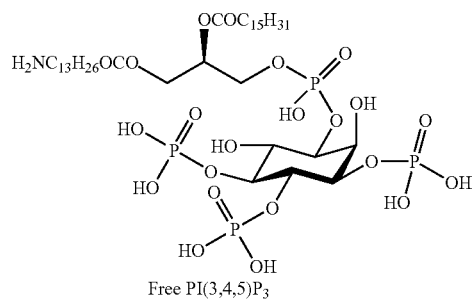
Free PI(3,4,5)P$_3$
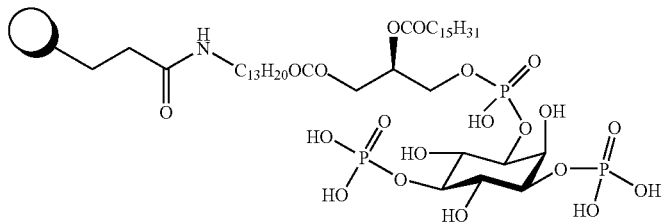
Immobilized PI(3,5)P$_2$
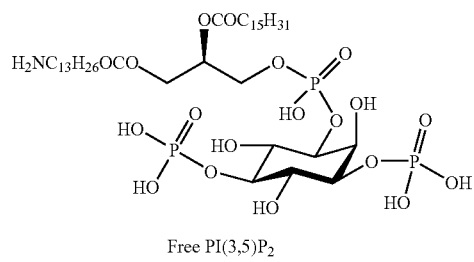
Free PI(3,5)P$_2$
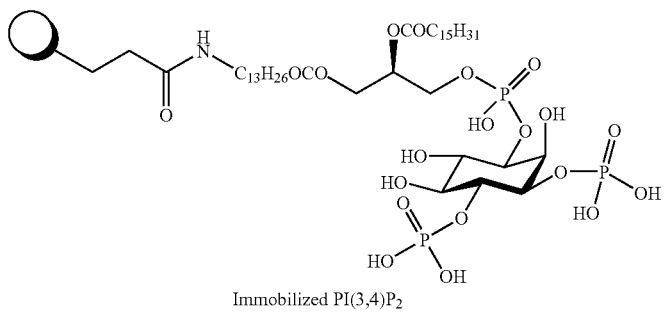
Immobilized PI(3,4)P$_2$ TABLE 3-continued
Further preferred compounds and probes of the invention
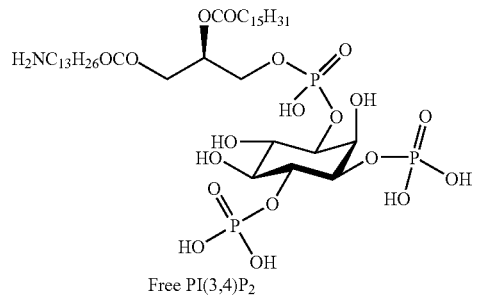
Free PI(3,4)P₂
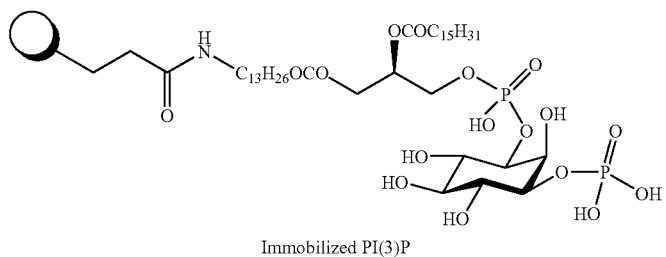
Immobilized PI(3)P
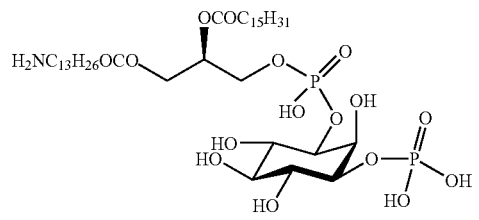
Free PI(3)P
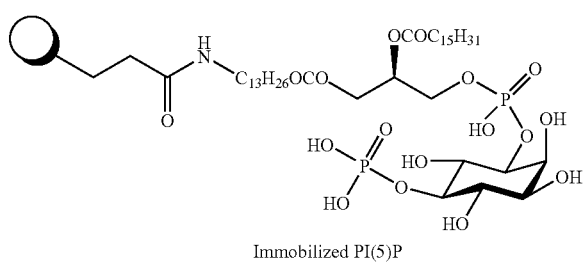
Immobilized PI(5)P
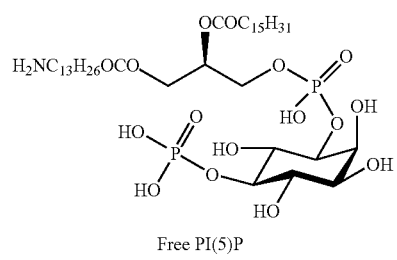
Free PI(5)P TABLE 3-continued
Further preferred compounds and probes of the invention
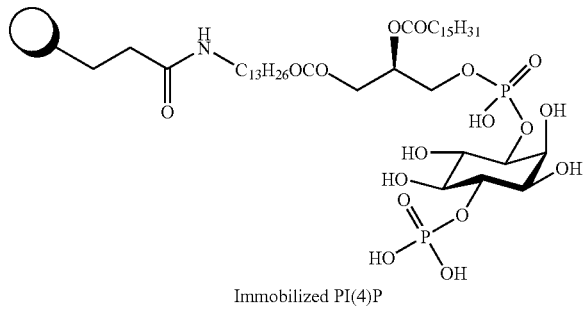
Immobilized PI(4)P
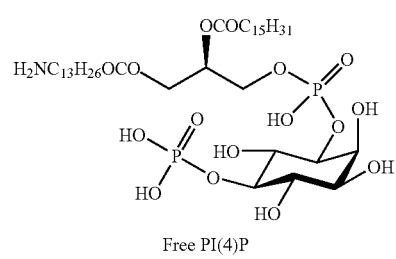
Free PI(4)P
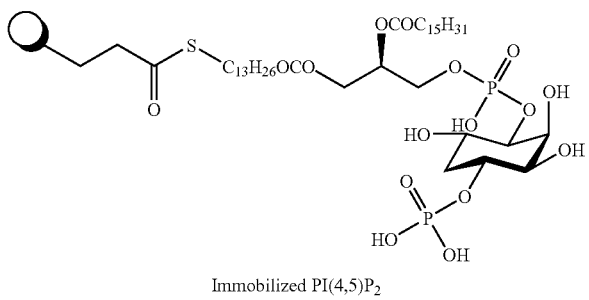
Immobilized PI(4,5)P$_2$
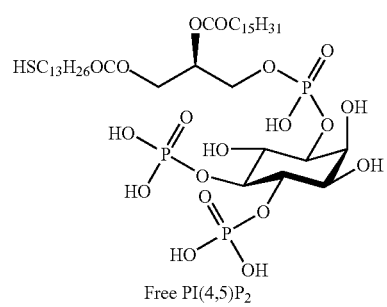
Free PI(4,5)P$_2$
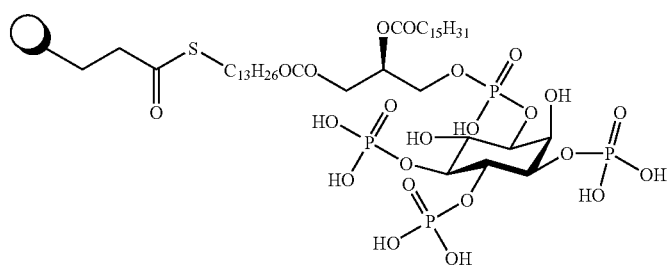
Immobilized PI(3,4,5)P$_3$ TABLE 3-continued
Further preferred compounds and probes of the invention
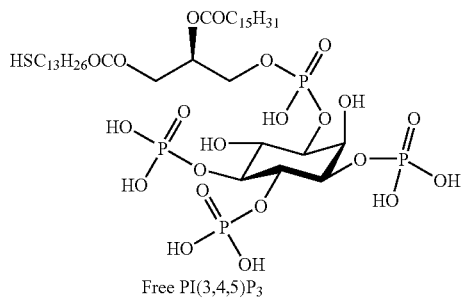
Free PI(3,4,5)P₃
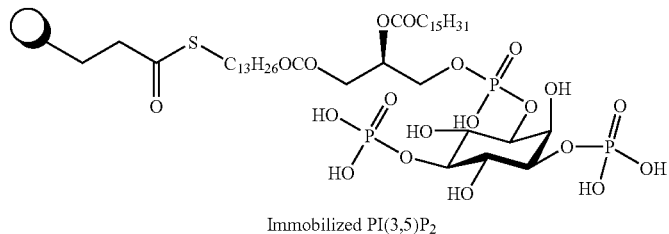
Immobilized PI(3,5)P₂
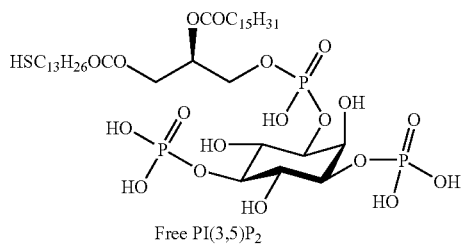
Free PI(3,5)P₂
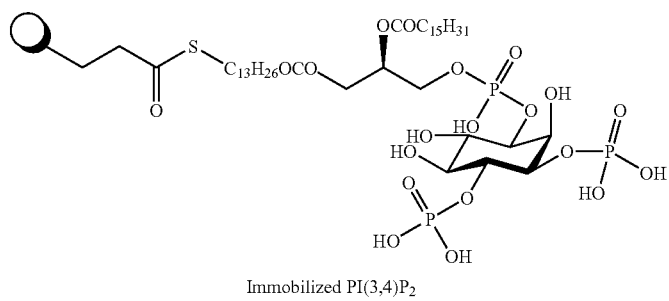
Immobilized PI(3,4)P₂
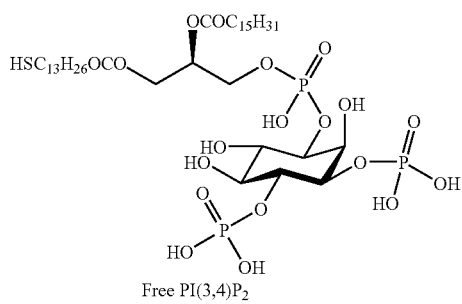
Free PI(3,4)P₂

TABLE 3-continued
Further preferred compounds and probes of the invention
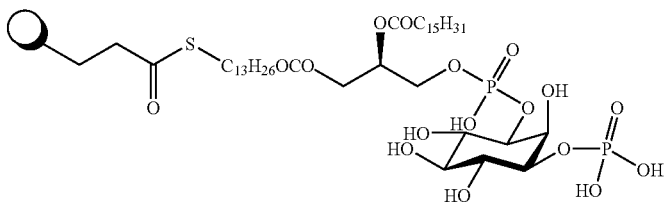
Immobilized PI(3)P
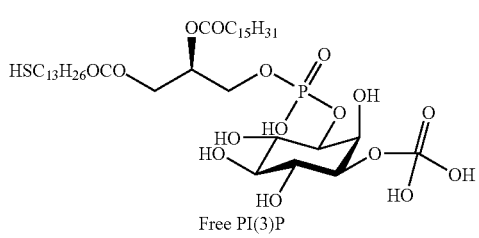
Free PI(3)P
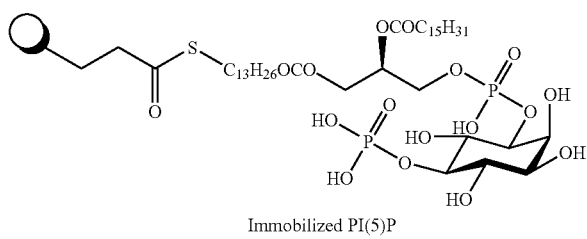
Immobilized PI(5)P
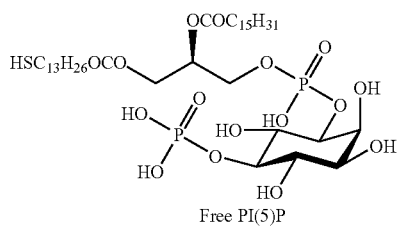
Free PI(5)P
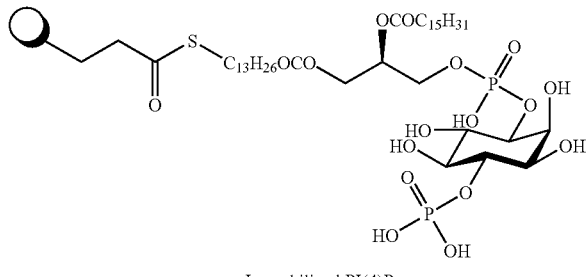
Immobilized PI(4)P
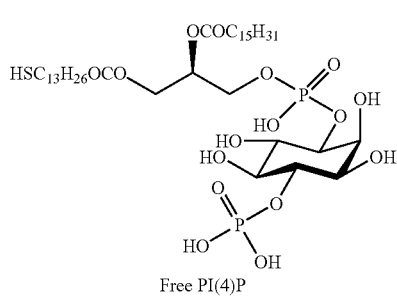
Free PI(4)P TABLE 3-continued
Further preferred compounds and probes of the invention
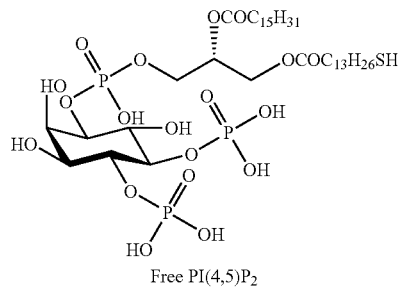
Free PI(4,5)P$_2$
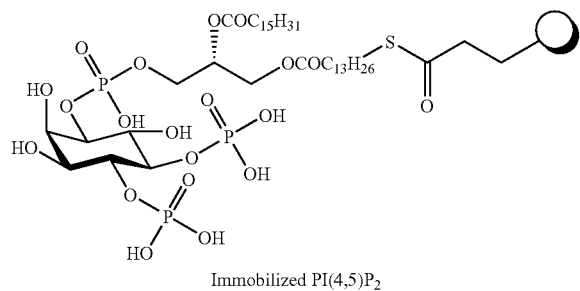
Immobilized PI(4,5)P$_2$
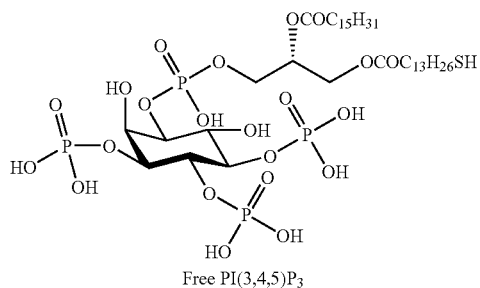
Free PI(3,4,5)P$_3$
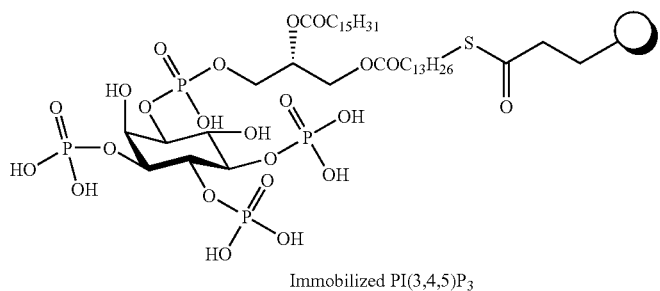
Immobilized PI(3,4,5)P$_3$
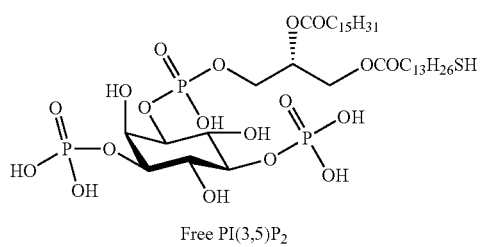
Free PI(3,5)P$_2$ TABLE 3-continued
Further preferred compounds and probes of the invention
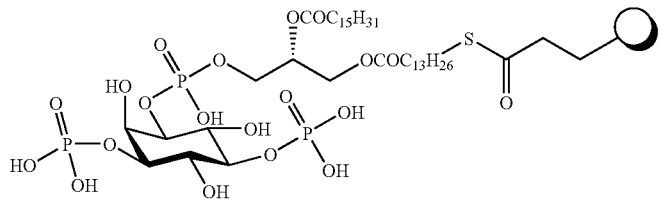
Immobilized PI(3,5)P$_2$
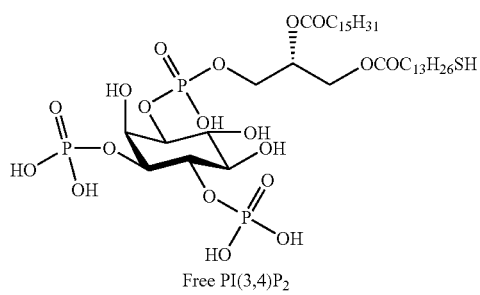
Free PI(3,4)P$_2$
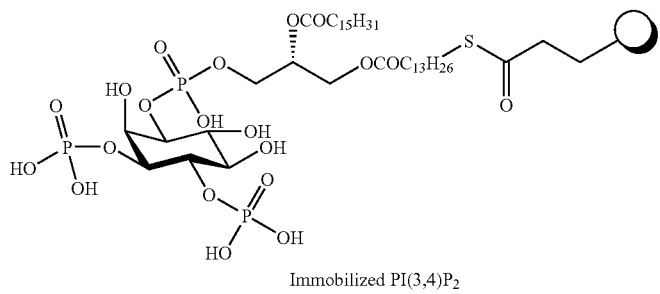
Immobilized PI(3,4)P$_2$
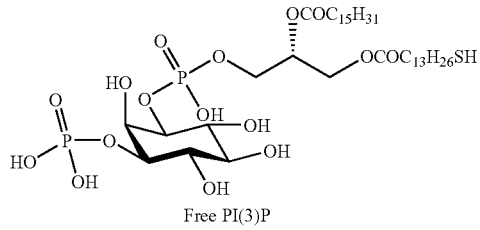
Free PI(3)P
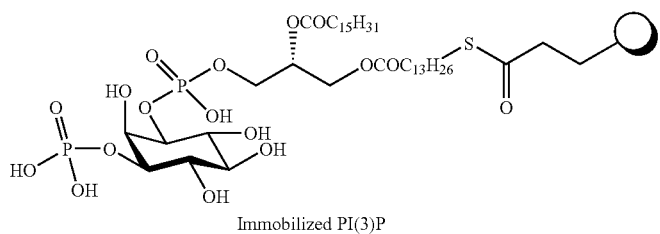
Immobilized PI(3)P
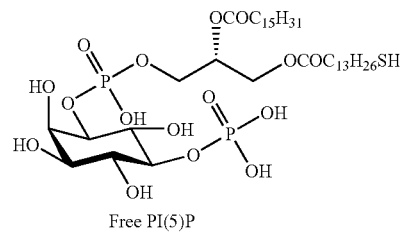
Free PI(5)P TABLE 3-continued
Further preferred compounds and probes of the invention
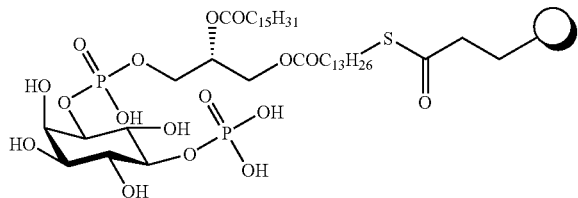
Immobilized PI(5)P
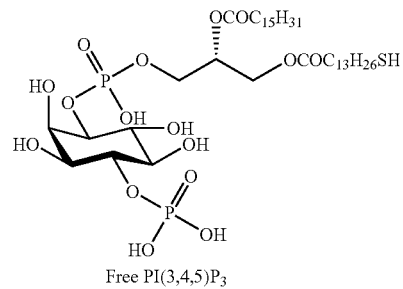
Free PI(3,4,5)P$_3$
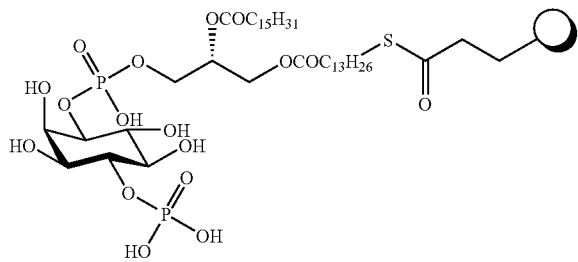
Immobilized PI(4)P
C14
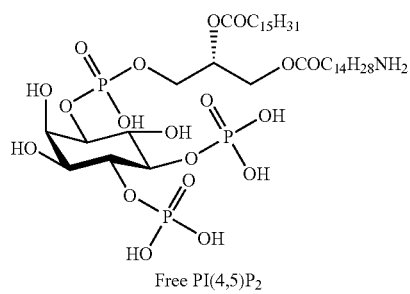
Free PI(4,5)P$_2$
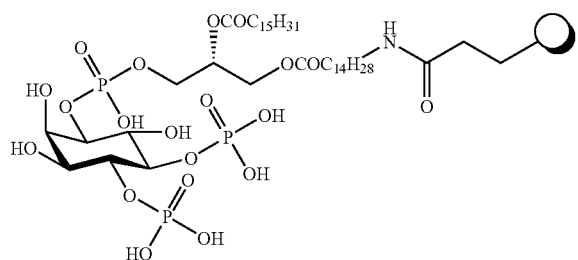
Immobilized PI(4,5)P$_2$ TABLE 3-continued
Further preferred compounds and probes of the invention
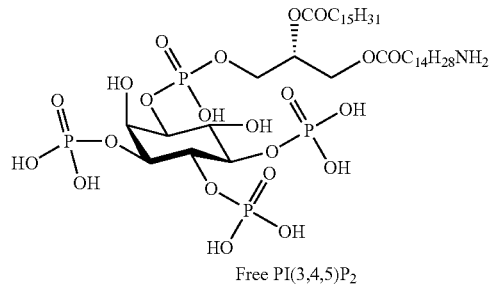
Free PI(3,4,5)P$_2$
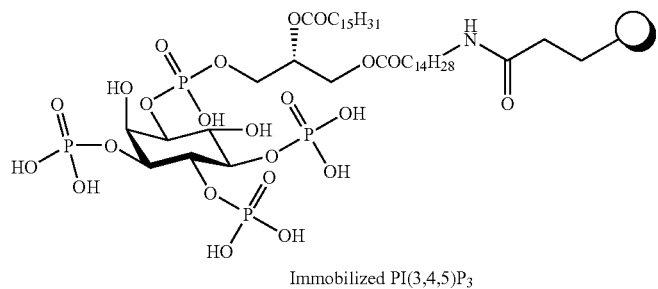
Immobilized PI(3,4,5)P$_3$
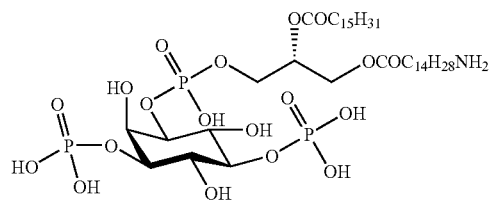
Free PI(3,5)P$_2$
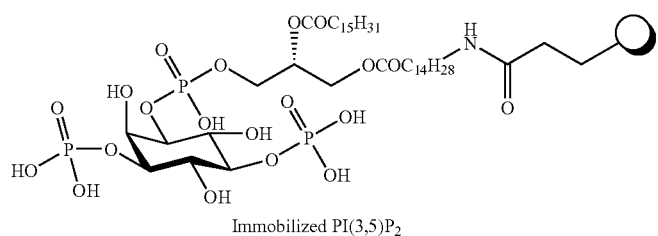
Immobilized PI(3,5)P$_2$
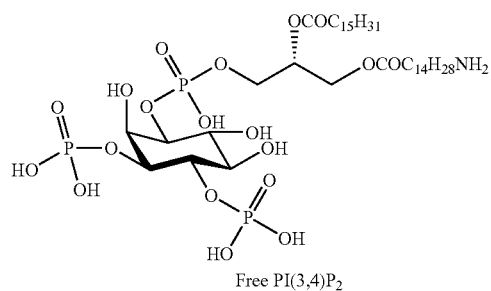
Free PI(3,4)P$_2$ TABLE 3-continued
Further preferred compounds and probes of the invention
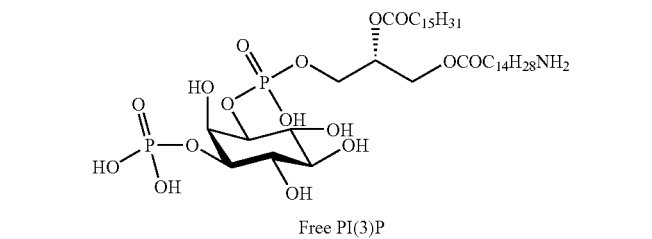
Free PI(3)P
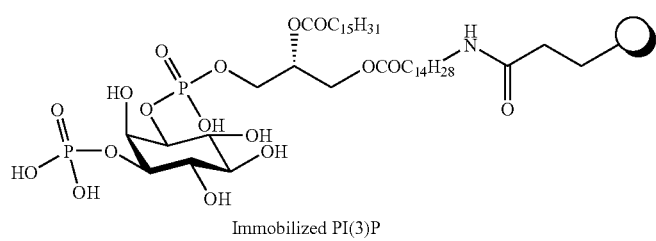
Immobilized PI(3)P
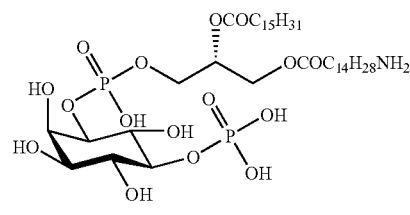
Free PI(5)P
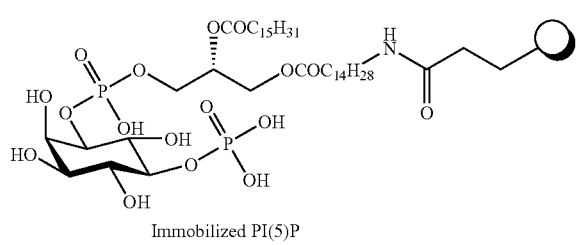
Immobilized PI(5)P
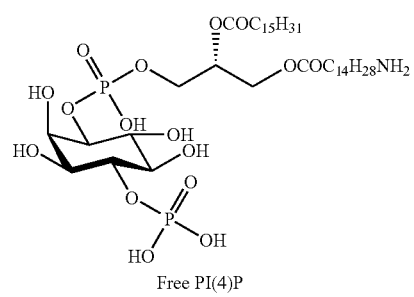
Free PI(4)P
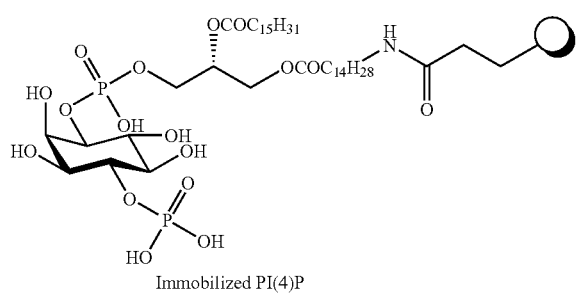
Immobilized PI(4)P TABLE 3-continued
Further preferred compounds and probes of the invention
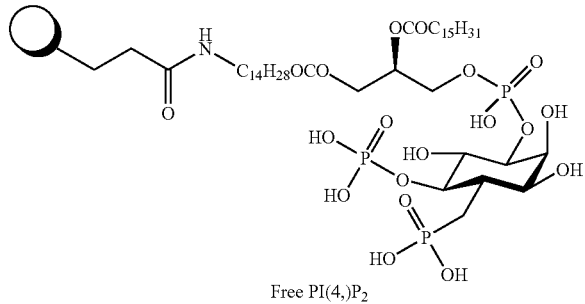
Free PI(4,)P$_2$
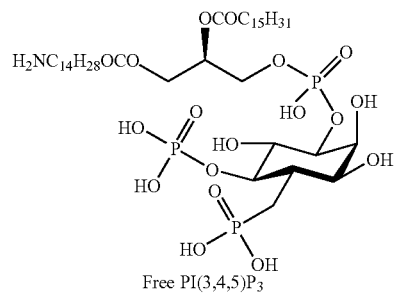
Free PI(3,4,5)P$_3$
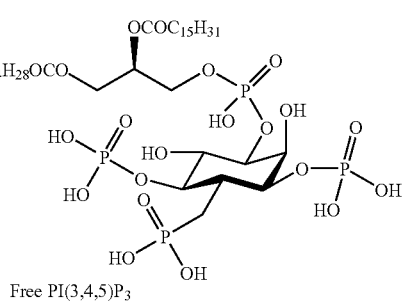
Free PI(3,4,5)P$_3$
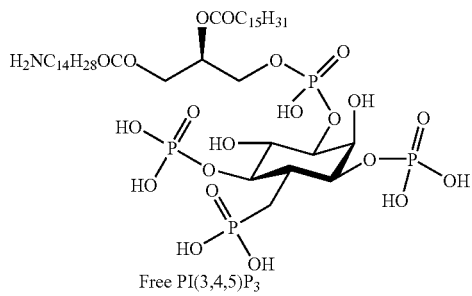
Free PI(3,4,5)P$_3$
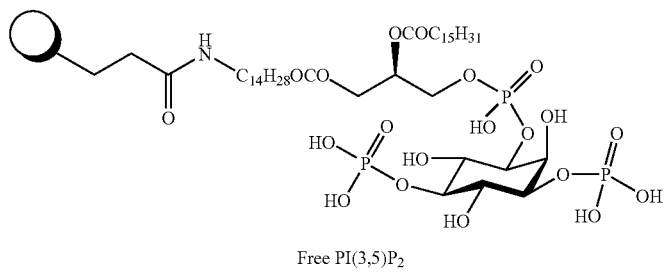
Free PI(3,5)P$_2$ TABLE 3-continued
Further preferred compounds and probes of the invention
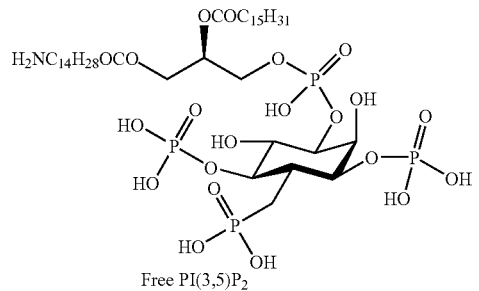
Free PI(3,5)P₂
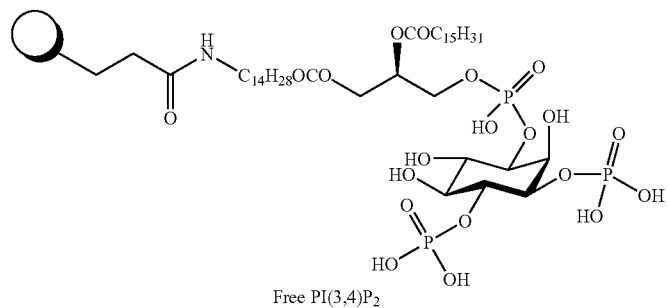
Free PI(3,4)P₂
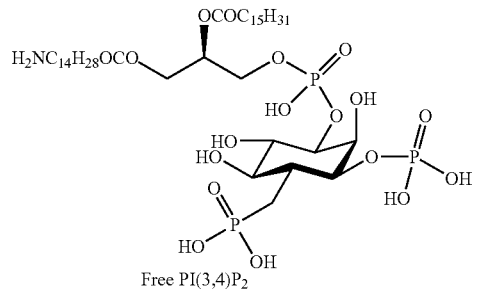
Free PI(3,4)P₂
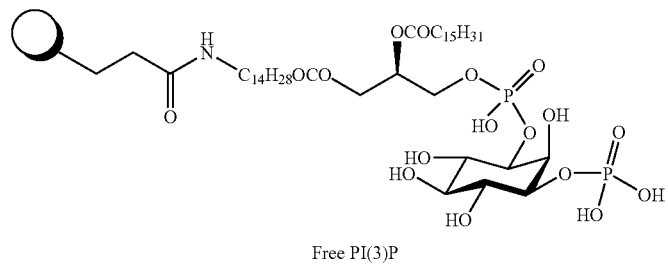
Free PI(3)P
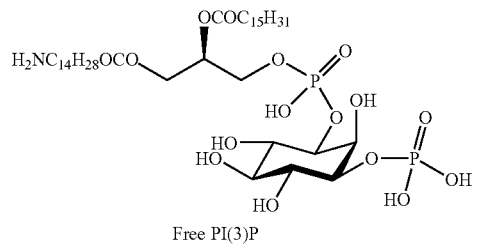
Free PI(3)P TABLE 3-continued
Further preferred compounds and probes of the invention
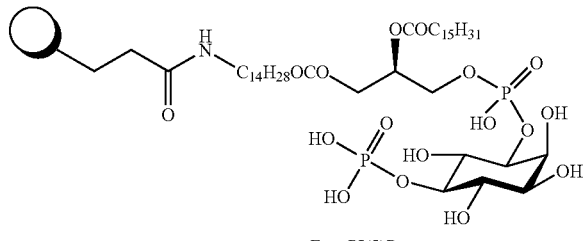
Free PI(5)P
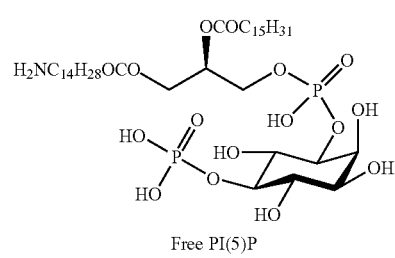
Free PI(5)P
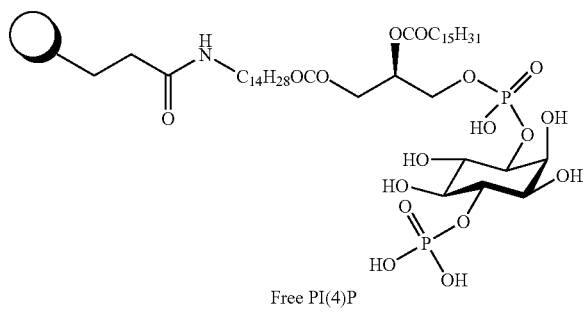
Free PI(4)P
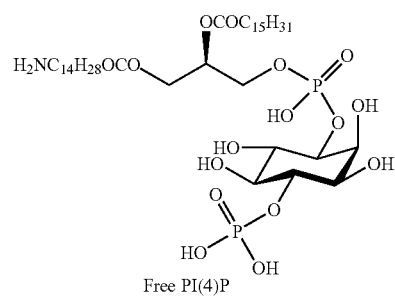
Free PI(4)P
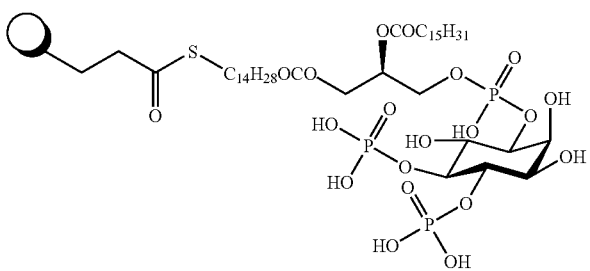
Immobilized PI(4,5)P$_2$ TABLE 3-continued
Further preferred compounds and probes of the invention
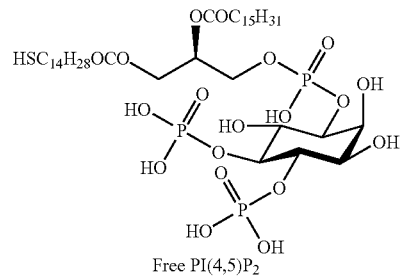
Free PI(4,5)P$_2$
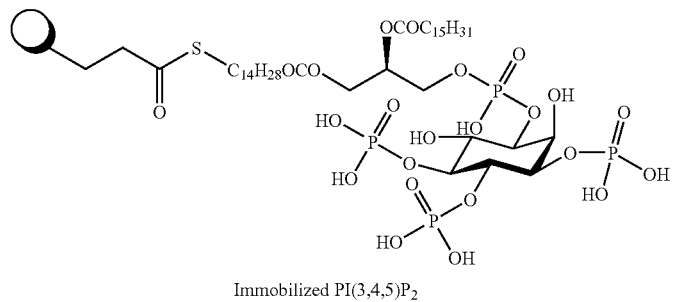
Immobilized PI(3,4,5)P$_2$
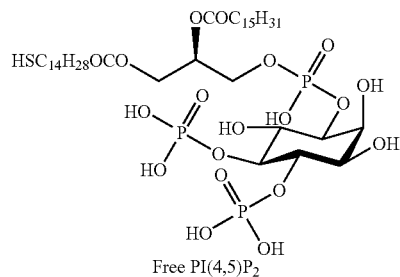
Free PI(4,5)P$_2$
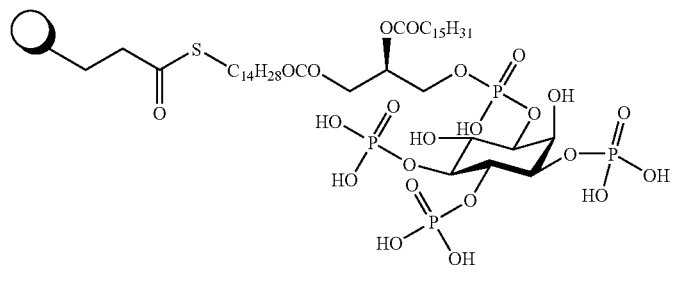
Immobilized PI(3,4,5)P$_2$
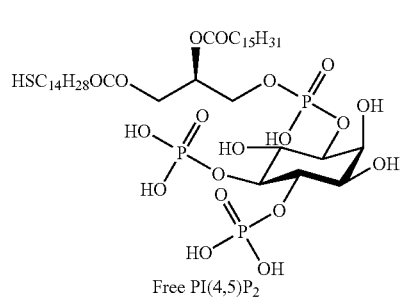
Free PI(4,5)P$_2$ TABLE 3-continued
Further preferred compounds and probes of the invention
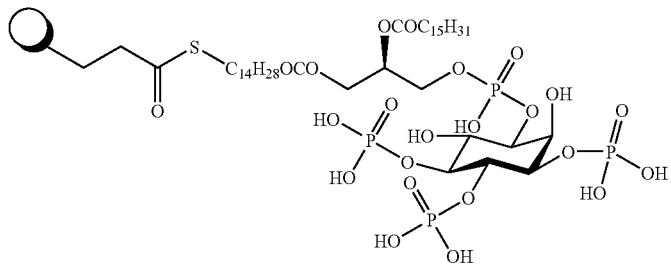
Immobilized PI(3,4,5)P₂
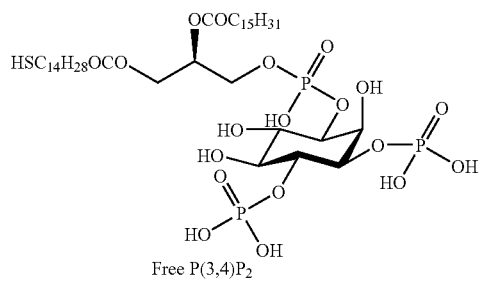
Free P(3,4)P₂
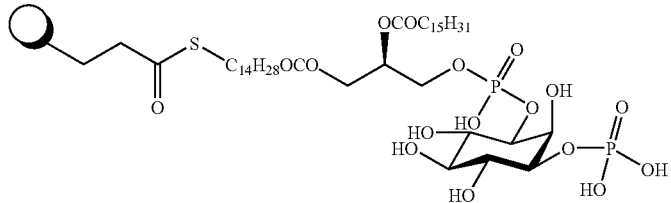
Immobilized PI(3)P
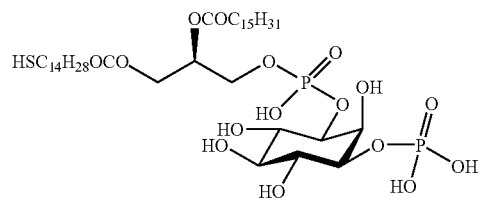
Free PI(3)P
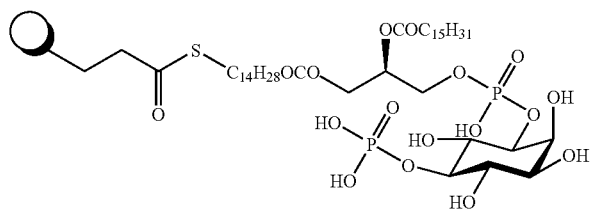
Immobilized PI(5)P
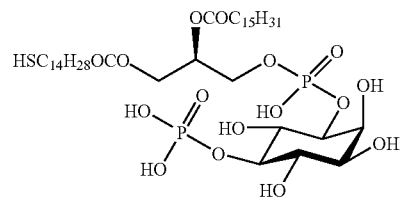
Free PI(5)P TABLE 3-continued
Further preferred compounds and probes of the invention
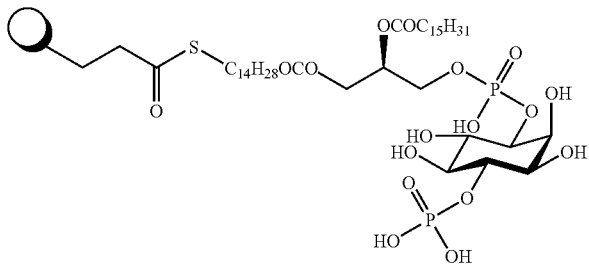
Immobilized PI(4)P
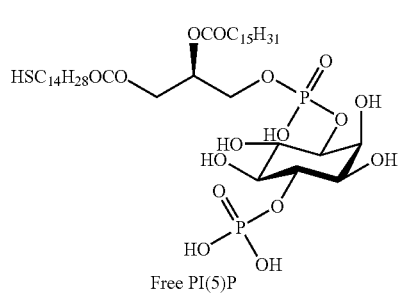
Free PI(5)P
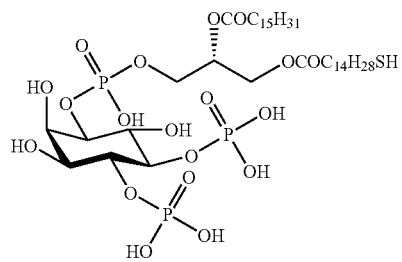
Free PI(4,5)P$_2$
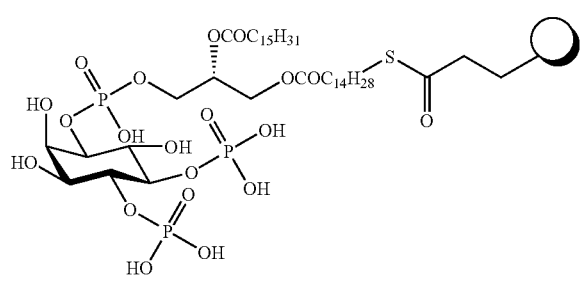
Free PI(4,5)P$_2$
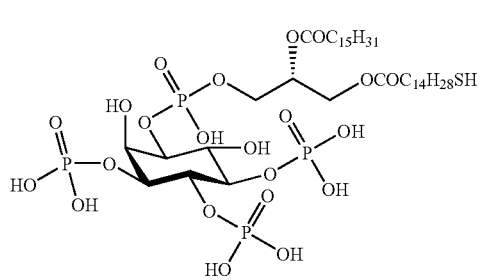
Free PI(3,4,5)P$_3$ TABLE 3-continued
Further preferred compounds and probes of the invention
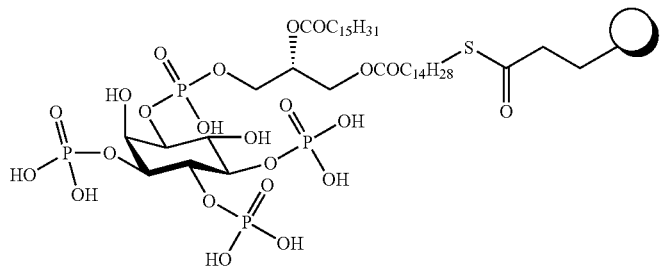
Immobilized PI(3,4,5)P$_3$
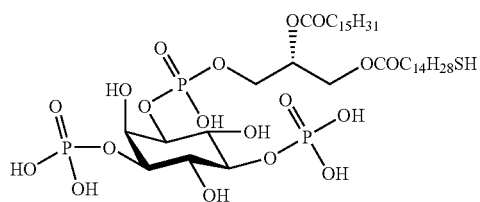
Free PI(3,5)P$_3$
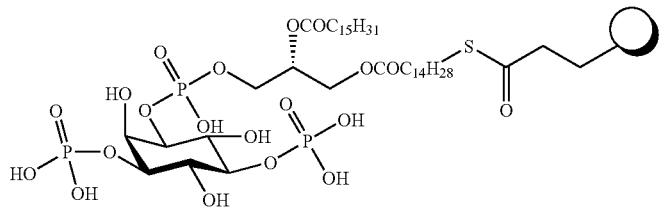
Immobilized PI(3,5)P$_2$
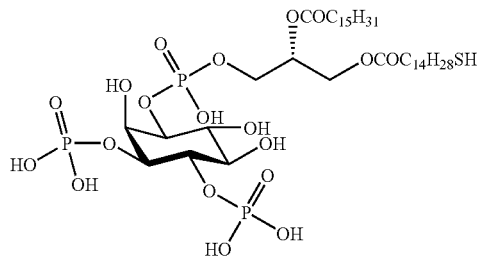
Free PI(3,4)P$_2$
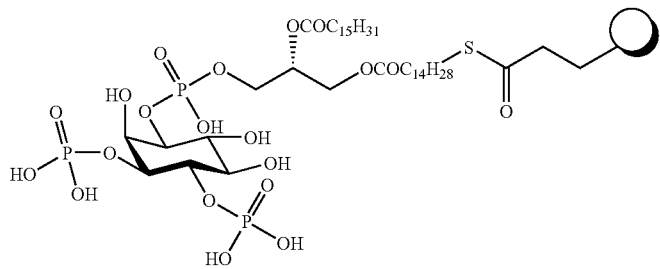
Immobilized PI(3,4)P$_2$

TABLE 3-continued
Further preferred compounds and probes of the invention
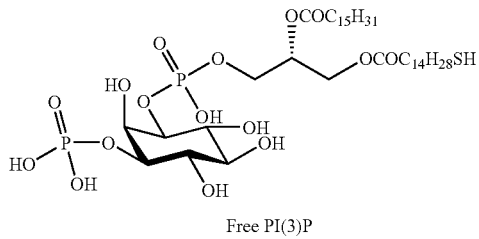
Free PI(3)P
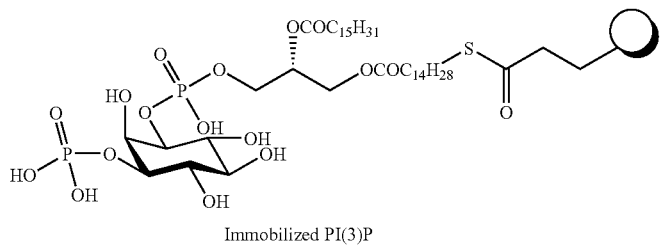
Immobilized PI(3)P
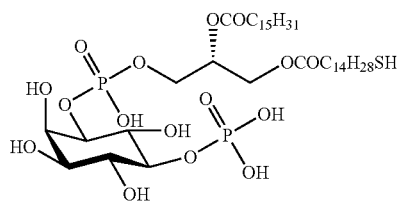
Free PI(5)P
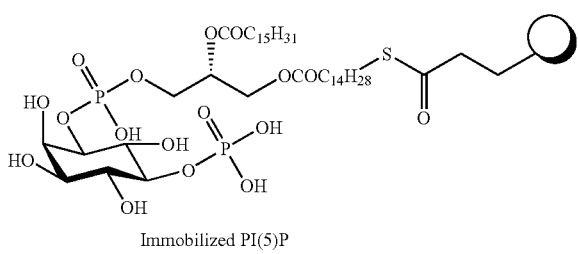
Immobilized PI(5)P
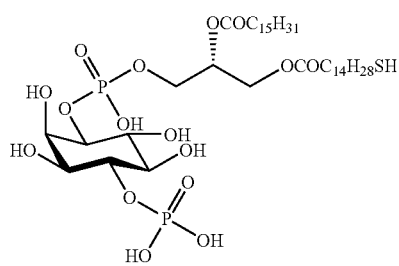
Free PI(5)P TABLE 3-continued
Further preferred compounds and probes of the invention
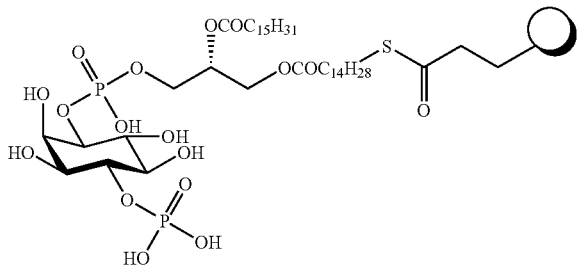
Immobilized PI(4)P
C15
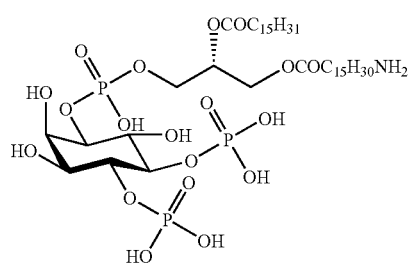
Free PI(4,5)P$_2$
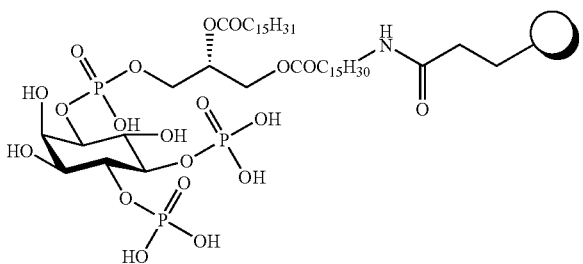
Immobilized PI(4,5)P$_2$
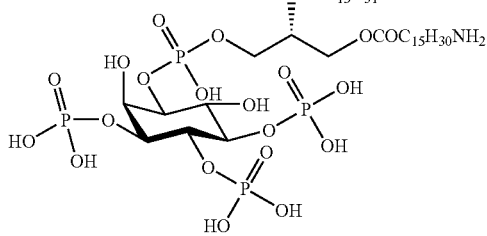
Free PI(4,5)P$_3$
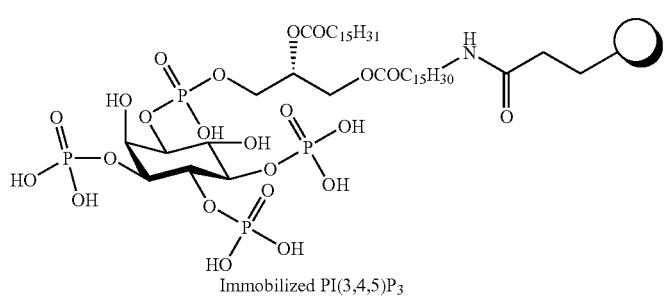
Immobilized PI(3,4,5)P$_3$ TABLE 3-continued
Further preferred compounds and probes of the invention
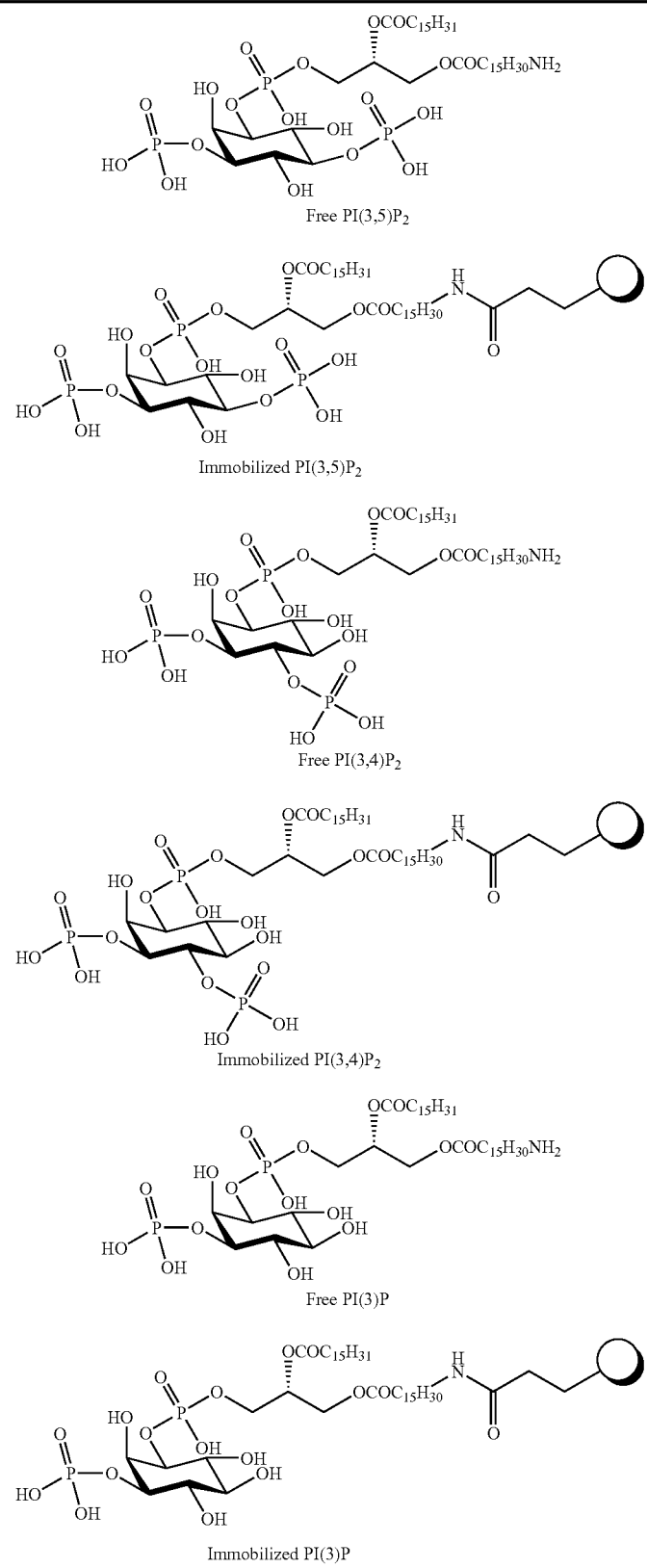

TABLE 3-continued
Further preferred compounds and probes of the invention
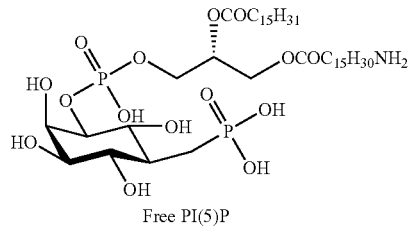
Free PI(5)P
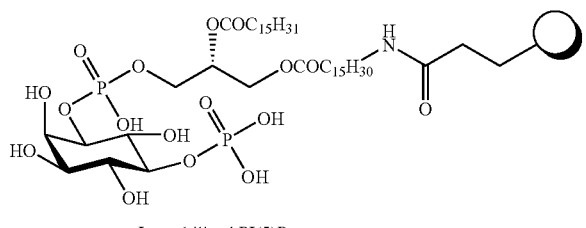
Immobilized PI(5)P
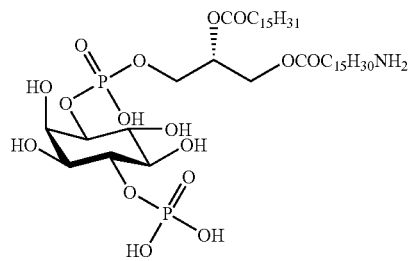
Free PI(4)P
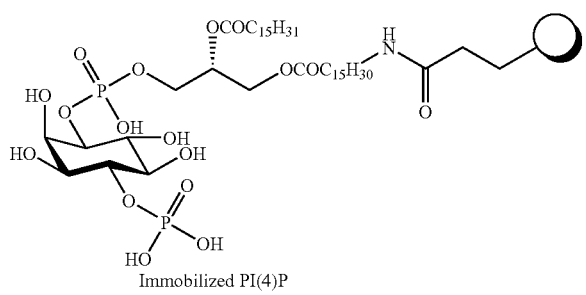
Immobilized PI(4)P
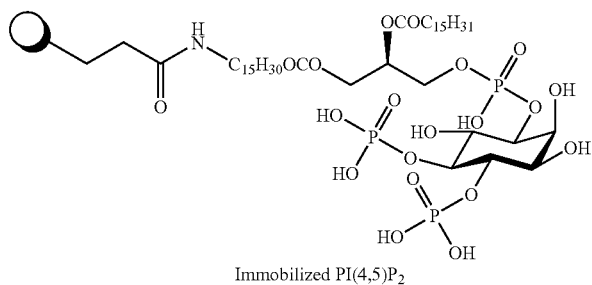
Immobilized PI(4,5)P$_2$ TABLE 3-continued
Further preferred compounds and probes of the invention
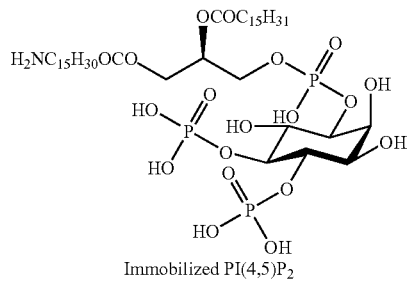
Immobilized PI(4,5)P$_2$
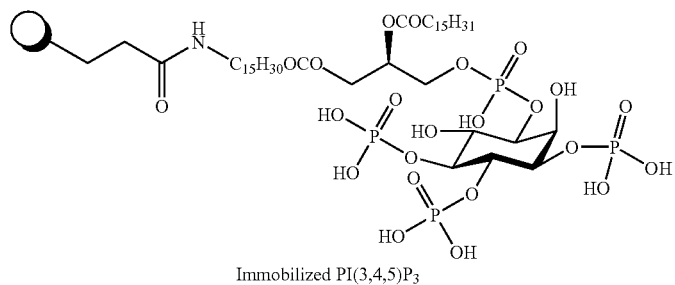
Immobilized PI(3,4,5)P$_3$
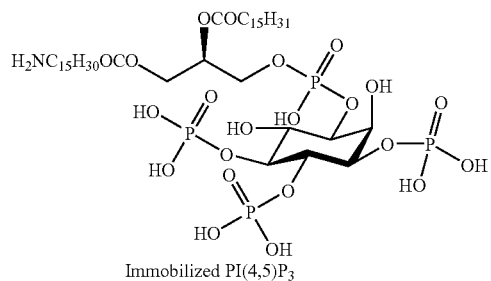
Immobilized PI(4,5)P$_3$
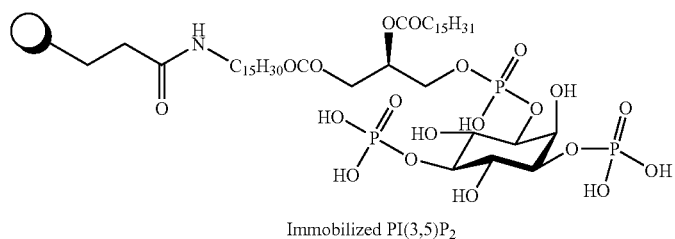
Immobilized PI(3,5)P$_2$
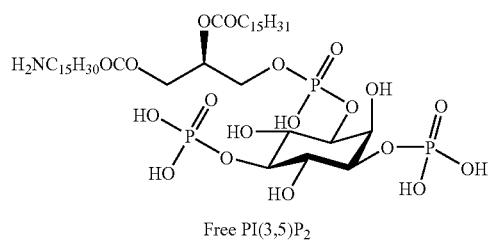
Free PI(3,5)P$_2$ TABLE 3-continued
Further preferred compounds and probes of the invention
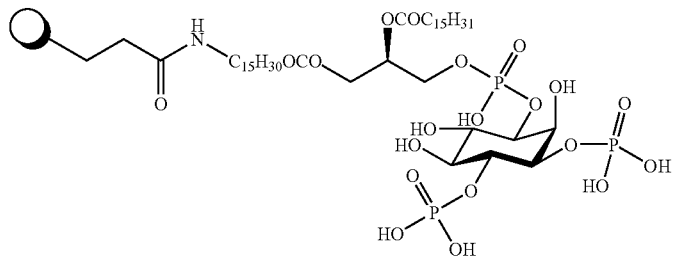
Immobilized PI(3,4)P$_2$
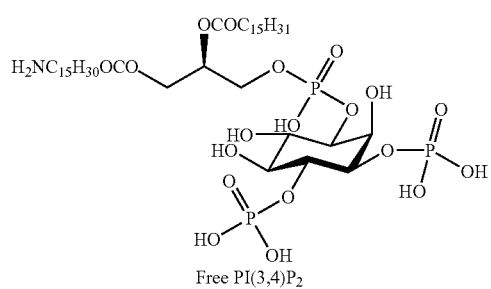
Free PI(3,4)P$_2$
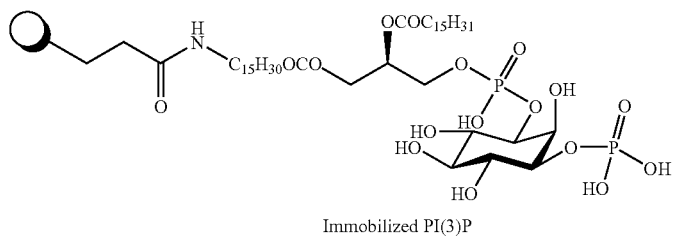
Immobilized PI(3)P
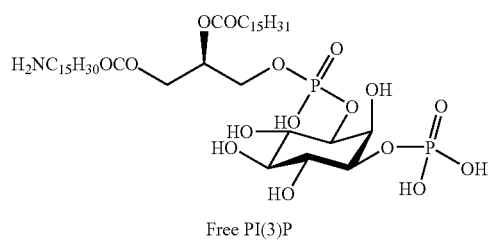
Free PI(3)P
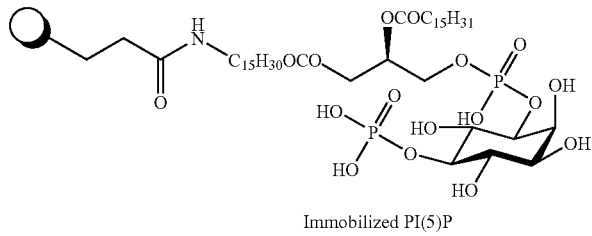
Immobilized PI(5)P
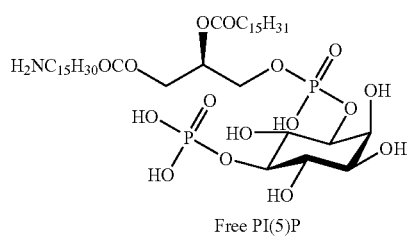
Free PI(5)P

TABLE 3-continued
Further preferred compounds and probes of the invention
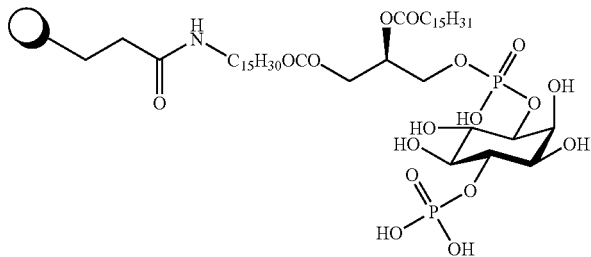
Immobilized PI(4)P
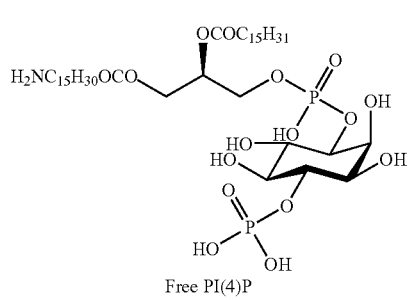
Free PI(4)P
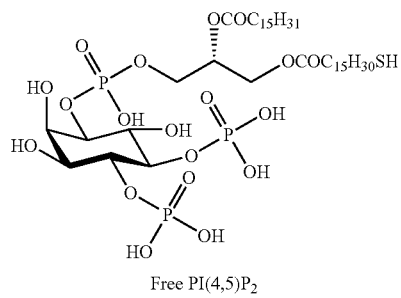
Free PI(4,5)P$_2$
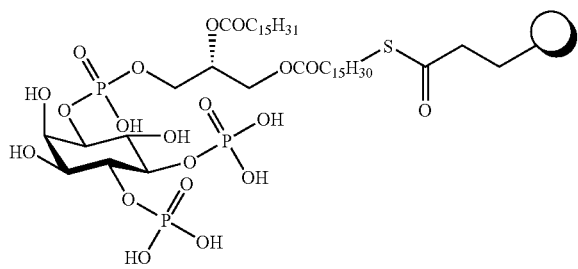
Immobilized PI(4,5)P$_2$
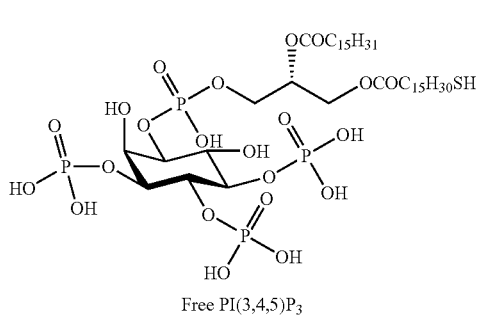
Free PI(3,4,5)P$_3$ TABLE 3-continued
Further preferred compounds and probes of the invention
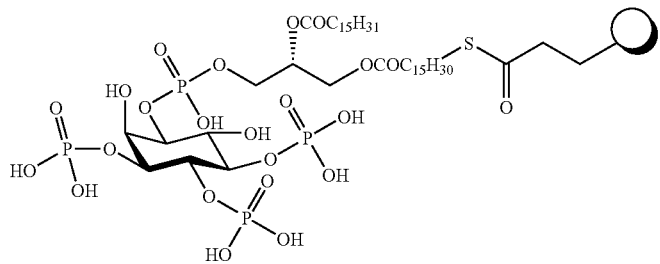
Immobilized PI(3,4,5)P$_3$
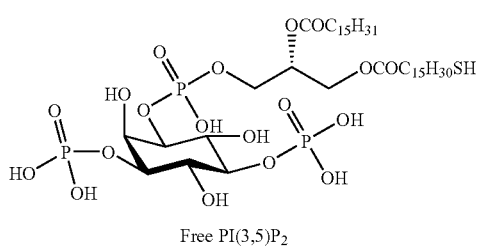
Free PI(3,5)P$_2$
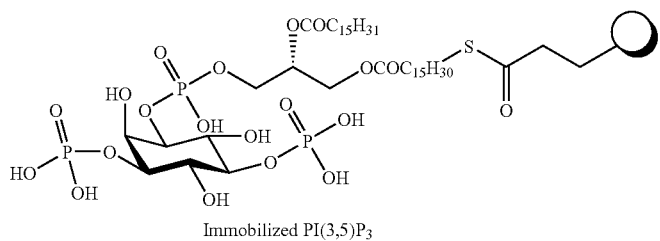
Immobilized PI(3,5)P$_3$
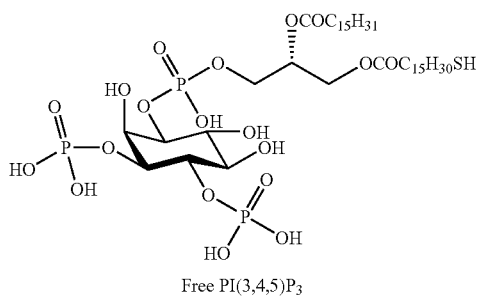
Free PI(3,4,5)P$_3$
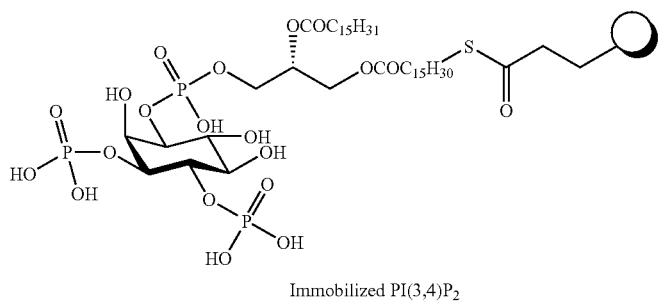
Immobilized PI(3,4)P$_2$ TABLE 3-continued
Further preferred compounds and probes of the invention
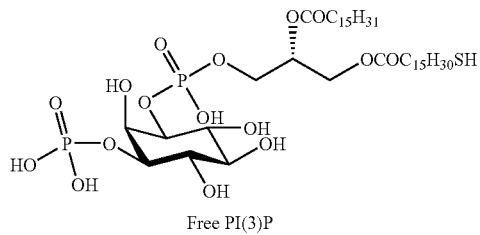
Free PI(3)P
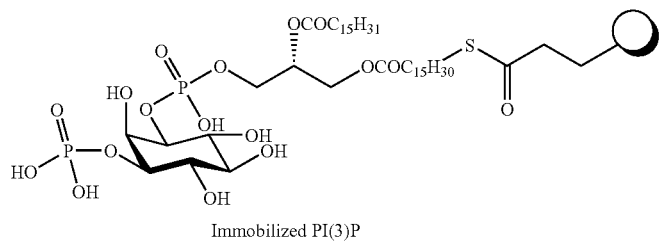
Immobilized PI(3)P
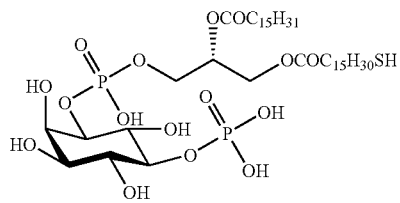
Free PI(5)P
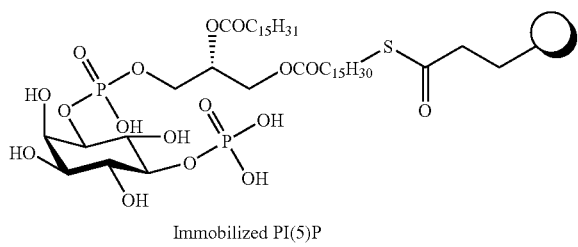
Immobilized PI(5)P
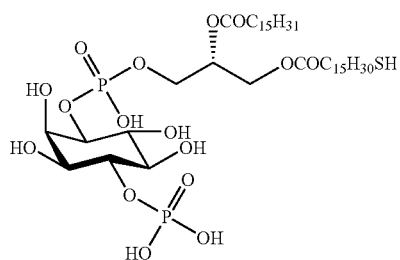
Free PI(4)P TABLE 3-continued
Further preferred compounds and probes of the invention
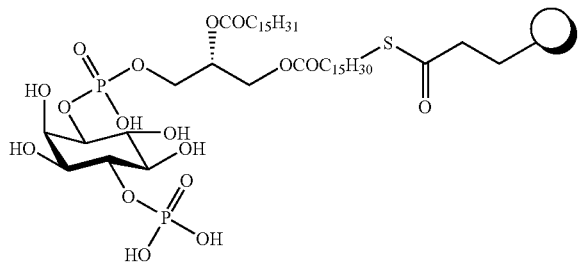
Immobilized PI(4)P
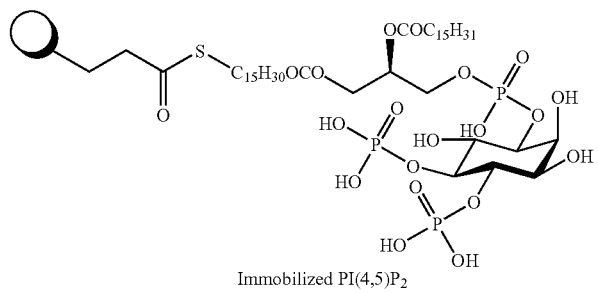
Immobilized PI(4,5)P$_2$
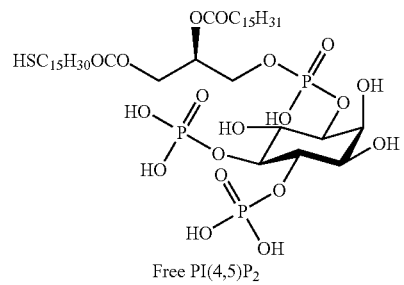
Free PI(4,5)P$_2$
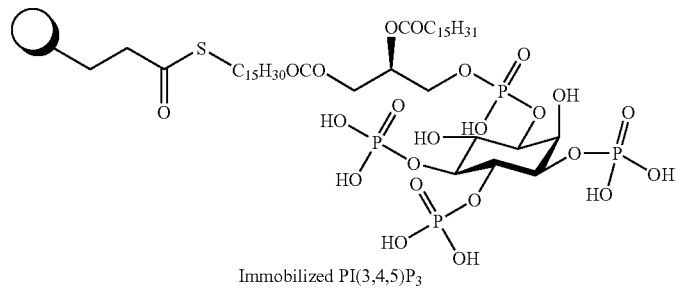
Immobilized PI(3,4,5)P$_3$
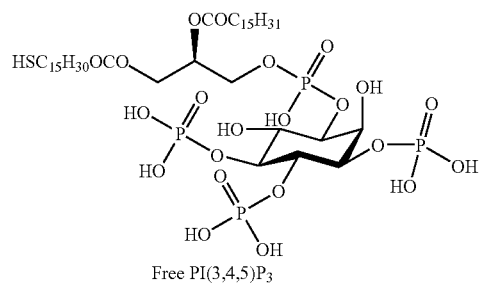
Free PI(3,4,5)P$_3$ TABLE 3-continued
Further preferred compounds and probes of the invention
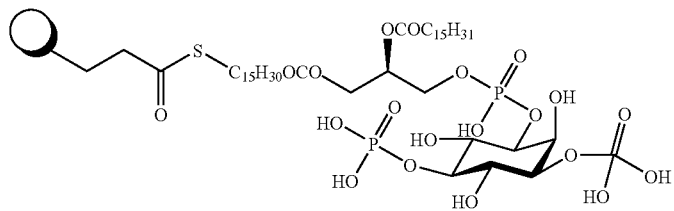
Immobilized PI(3,5)P₂
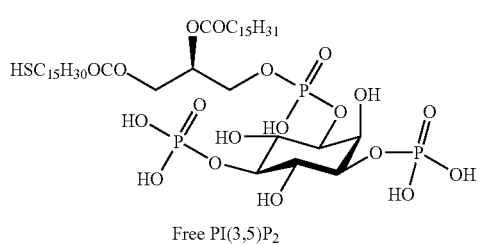
Free PI(3,5)P₂
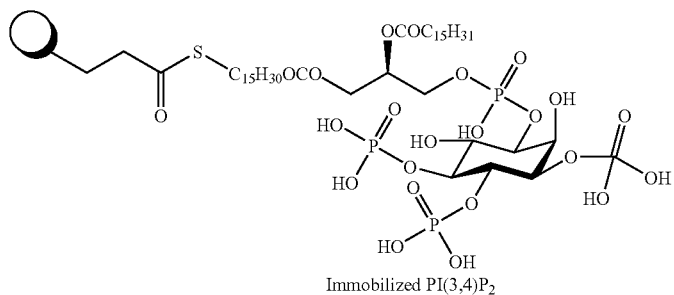
Immobilized PI(3,4)P₂
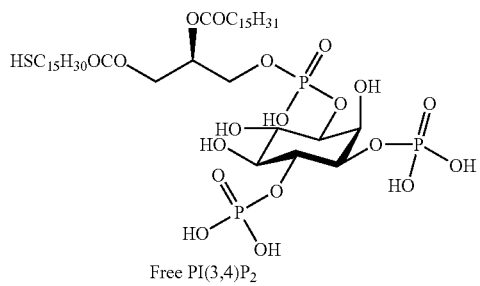
Free PI(3,4)P₂
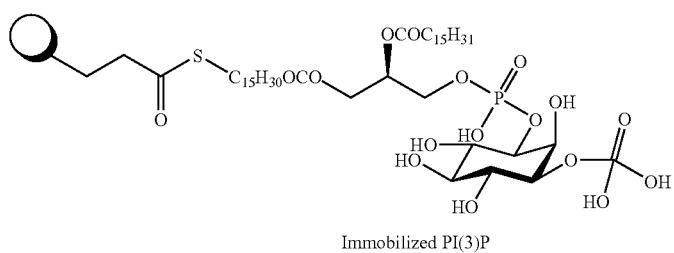
Immobilized PI(3)P TABLE 3-continued
Further preferred compounds and probes of the invention
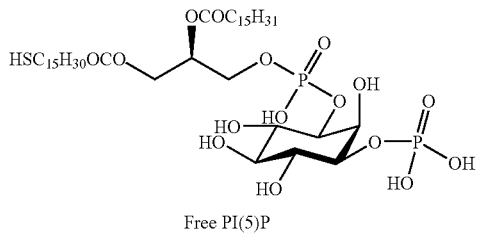
Free PI(5)P
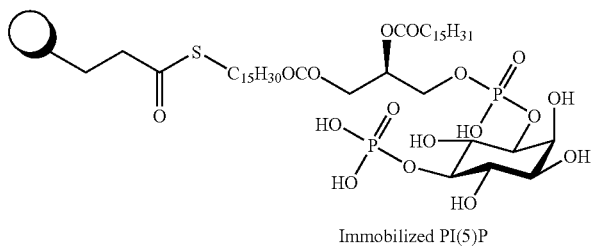
Immobilized PI(5)P
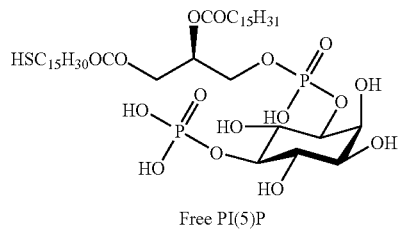
Free PI(5)P
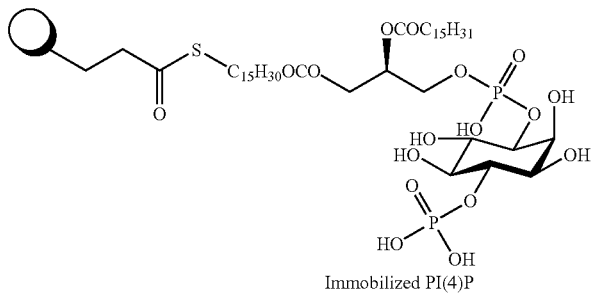
Immobilized PI(4)P
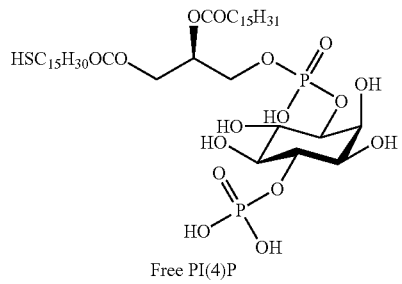
Free PI(4)P
C16

TABLE 3-continued
Further preferred compounds and probes of the invention
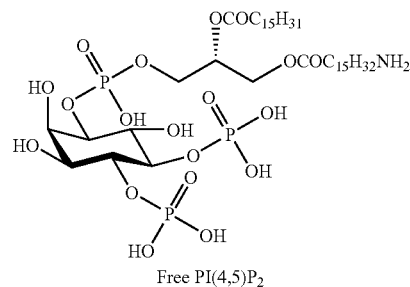
Free PI(4,5)P$_2$
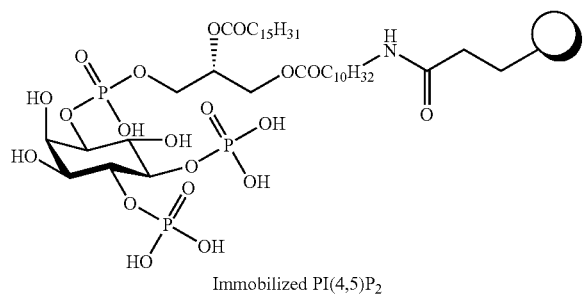
Immobilized PI(4,5)P$_2$
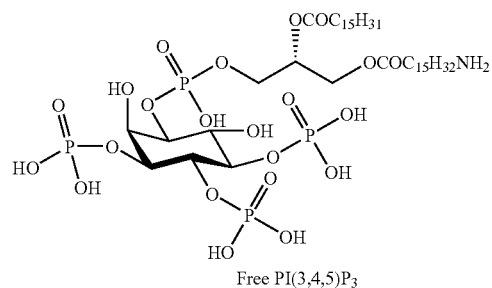
Free PI(3,4,5)P$_3$
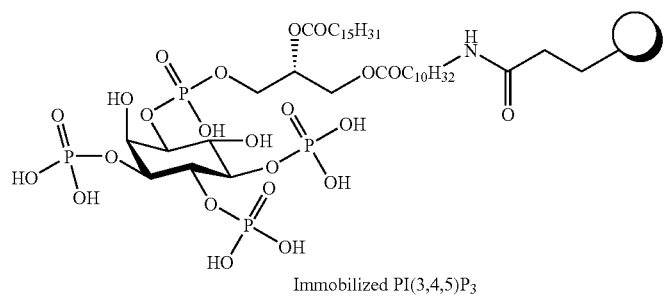
Immobilized PI(3,4,5)P$_3$
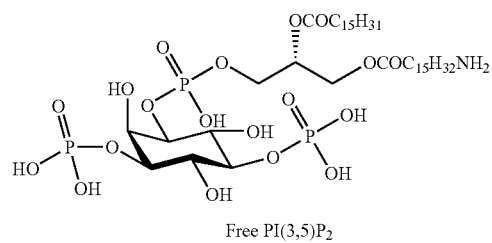
Free PI(3,5)P$_2$

TABLE 3-continued
Further preferred compounds and probes of the invention
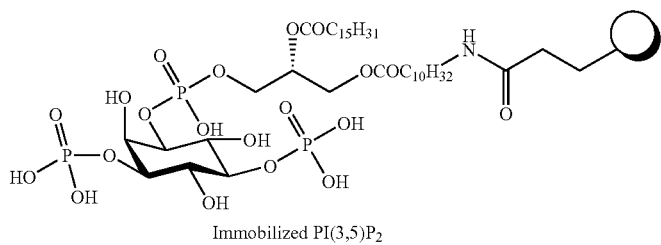
Immobilized PI(3,5)P$_2$
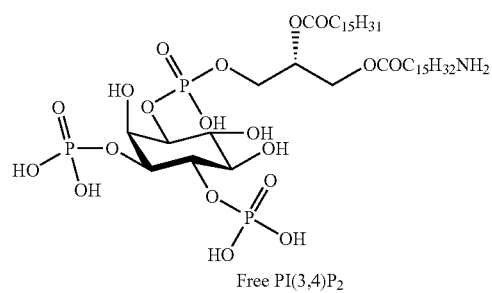
Free PI(3,4)P$_2$
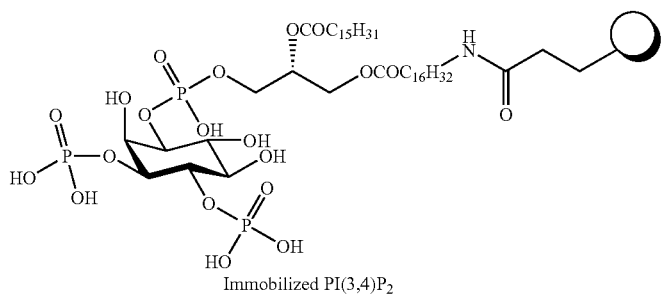
Immobilized PI(3,4)P$_2$
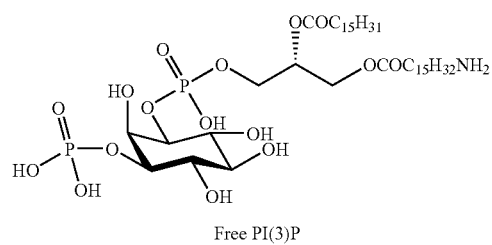
Free PI(3)P
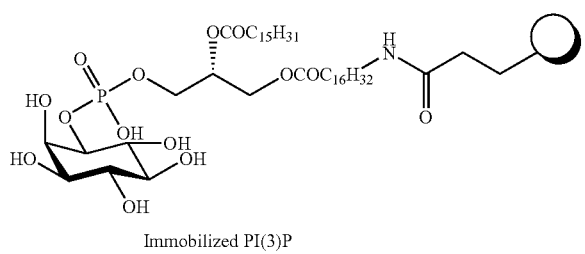
Immobilized PI(3)P TABLE 3-continued
Further preferred compounds and probes of the invention
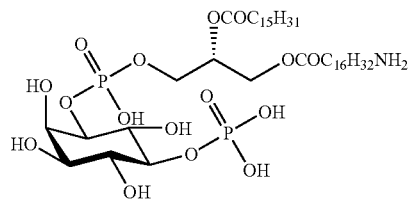
Free PI(5)P
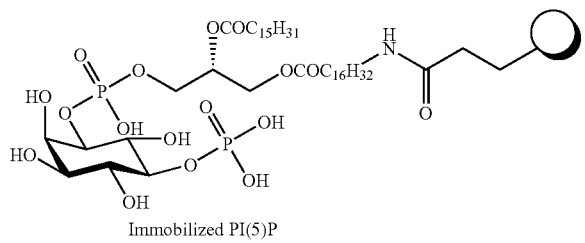
Immobilized PI(5)P
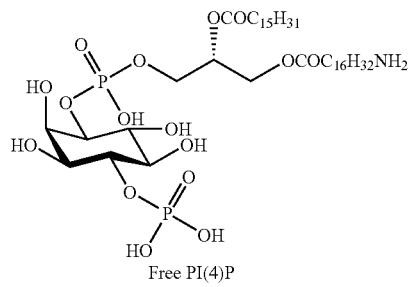
Free PI(4)P
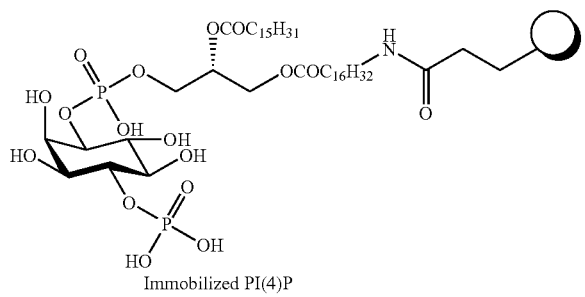
Immobilized PI(4)P
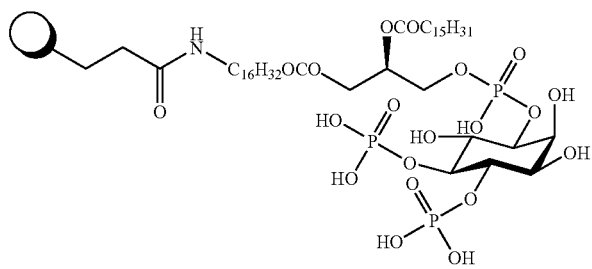
Immobilized PI(4,5)P₂

TABLE 3-continued
Further preferred compounds and probes of the invention
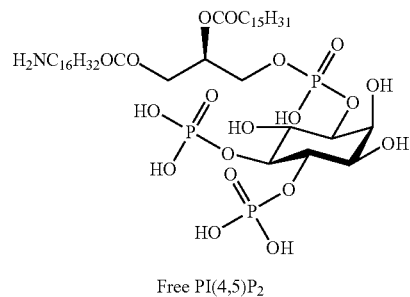
Free PI(4,5)P$_2$
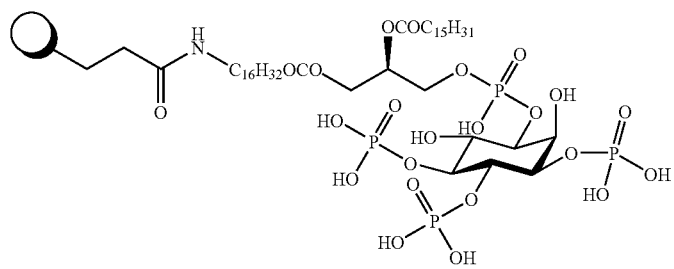
Immobilized PI(3,4,5)P$_3$
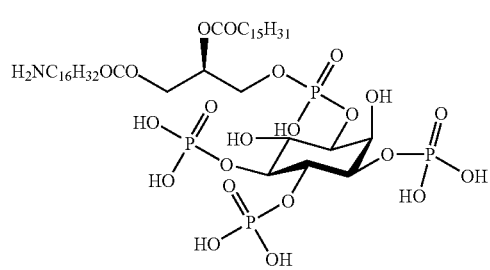
Free PI(3,4,5)P$_2$
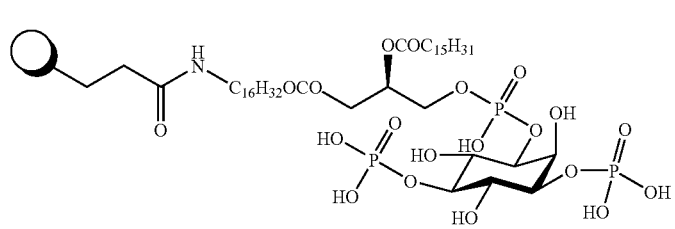
Immobilized PI(3,5)P$_2$
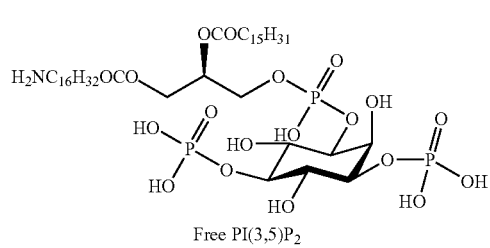
Free PI(3,5)P$_2$ TABLE 3-continued
Further preferred compounds and probes of the invention
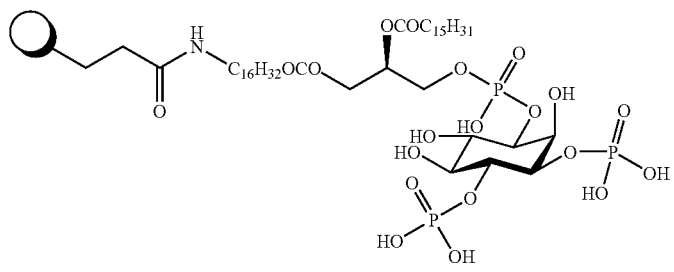
Immobilized PI(3,4)P$_2$
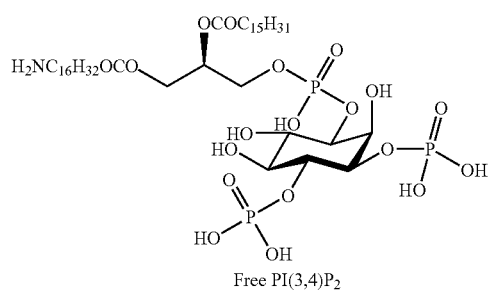
Free PI(3,4)P$_2$
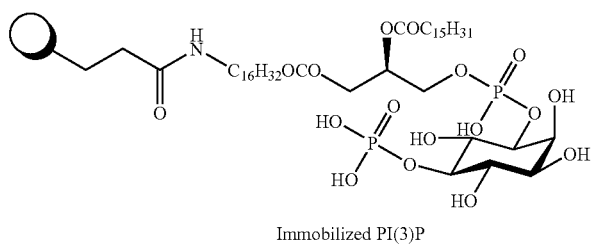
Immobilized PI(3)P
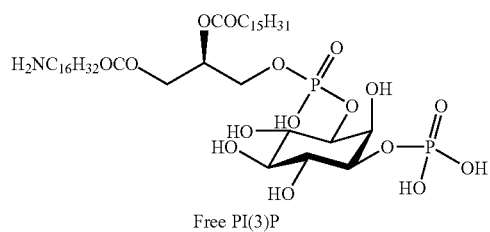
Free PI(3)P
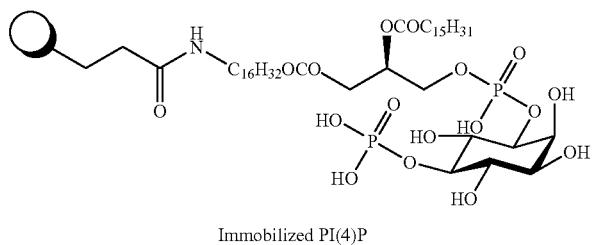
Immobilized PI(4)P
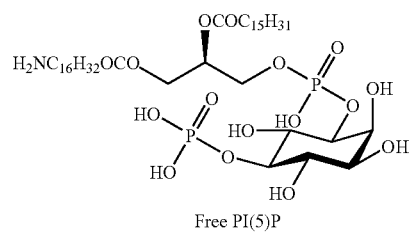
Free PI(5)P TABLE 3-continued
Further preferred compounds and probes of the invention
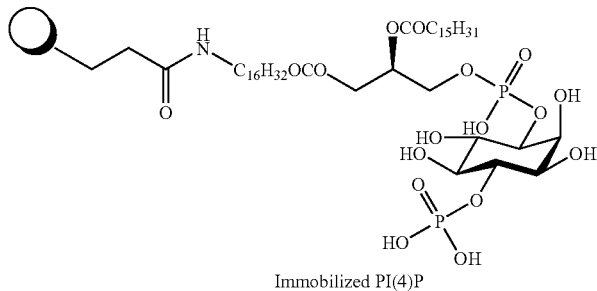
Immobilized PI(4)P
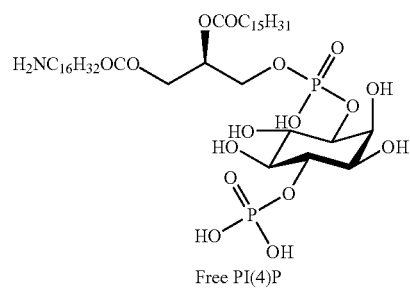
Free PI(4)P
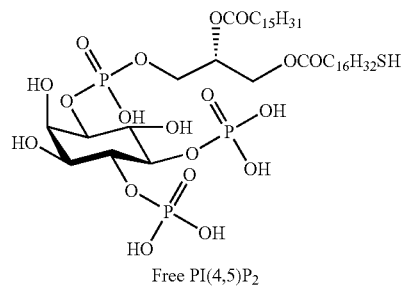
Free PI(4,5)P$_2$
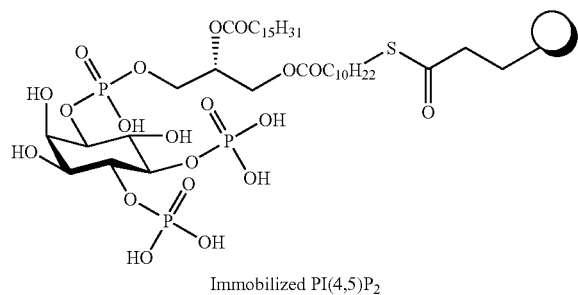
Immobilized PI(4,5)P$_2$
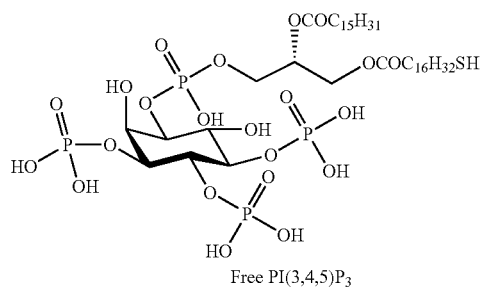
Free PI(3,4,5)P$_3$ TABLE 3-continued
Further preferred compounds and probes of the invention
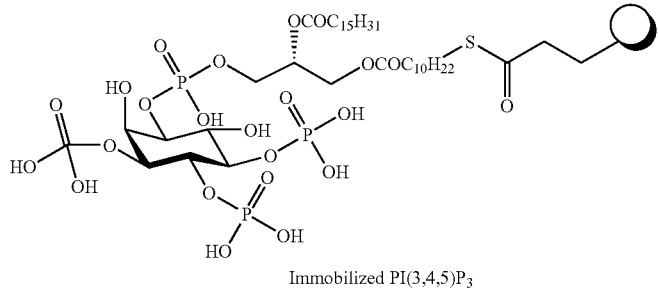
Immobilized PI(3,4,5)P$_3$
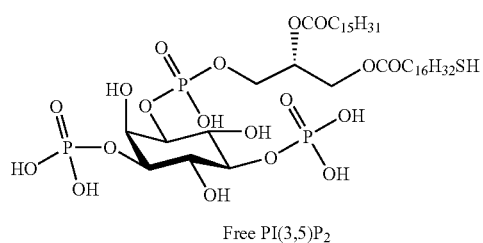
Free PI(3,5)P$_2$
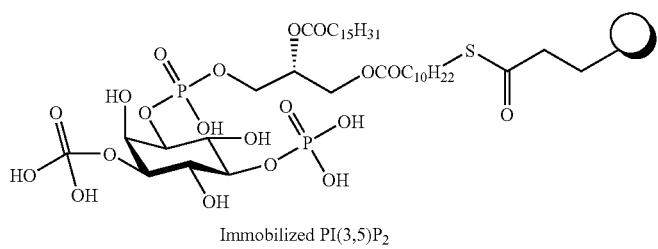
Immobilized PI(3,5)P$_2$
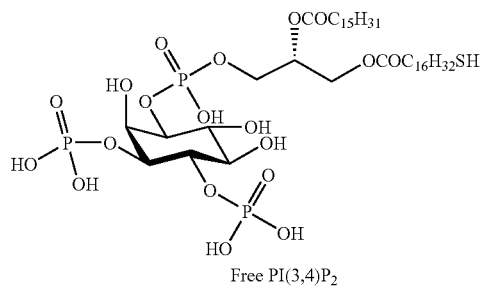
Free PI(3,4)P$_2$
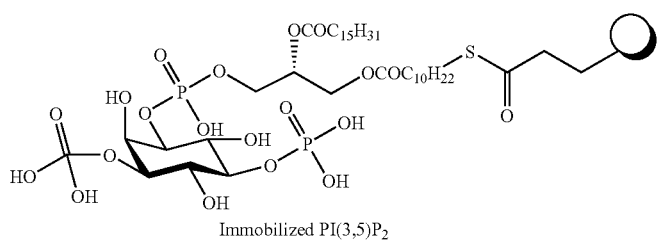
Immobilized PI(3,5)P$_2$
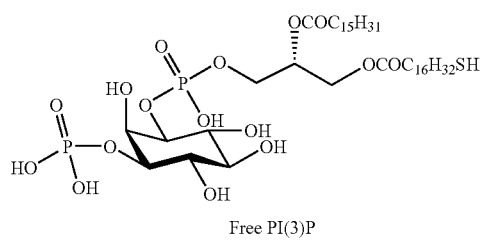
Free PI(3)P TABLE 3-continued
Further preferred compounds and probes of the invention
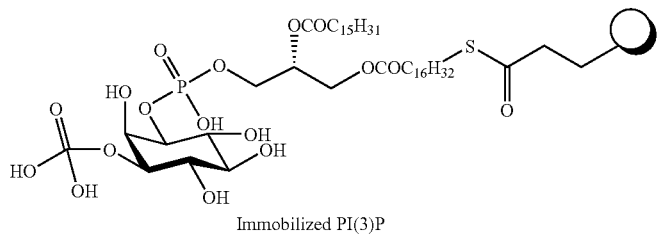
Immobilized PI(3)P
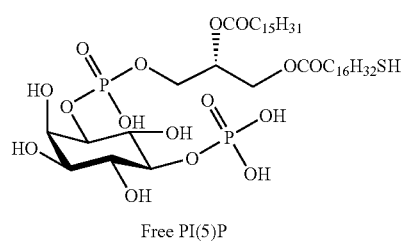
Free PI(5)P
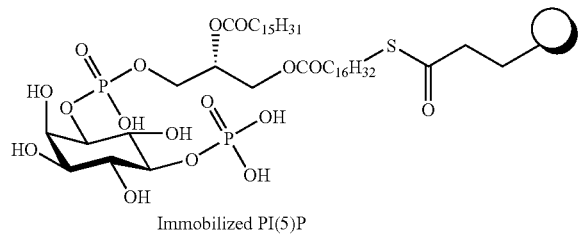
Immobilized PI(5)P
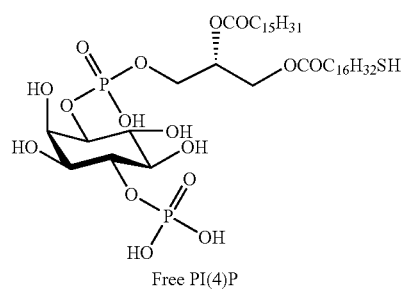
Free PI(4)P
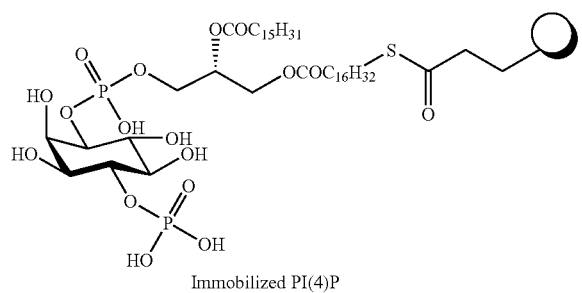
Immobilized PI(4)P TABLE 3-continued
Further preferred compounds and probes of the invention
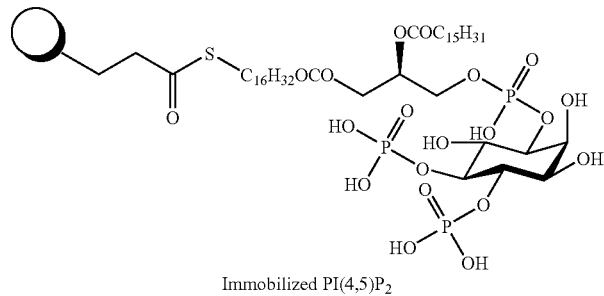
Immobilized PI(4,5)P$_2$
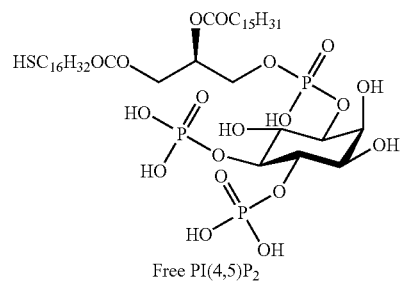
Free PI(4,5)P$_2$
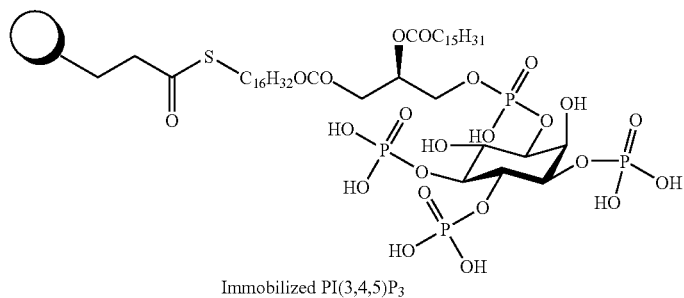
Immobilized PI(3,4,5)P$_3$
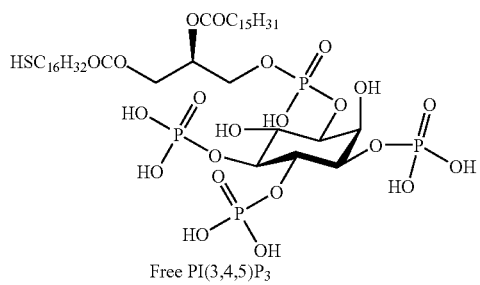
Free PI(3,4,5)P$_3$
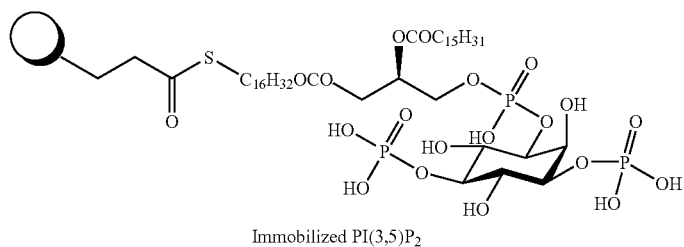
Immobilized PI(3,5)P$_2$ TABLE 3-continued
Further preferred compounds and probes of the invention
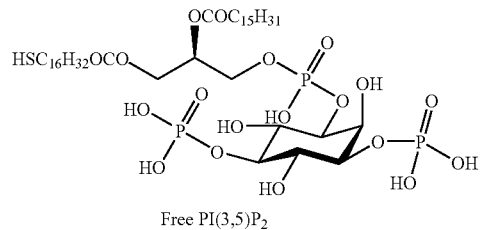
Free PI(3,5)P$_2$
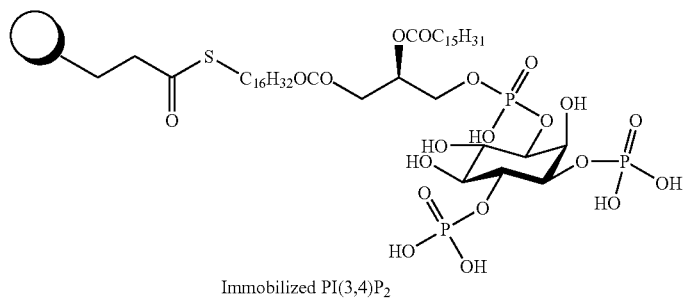
Immobilized PI(3,4)P$_2$
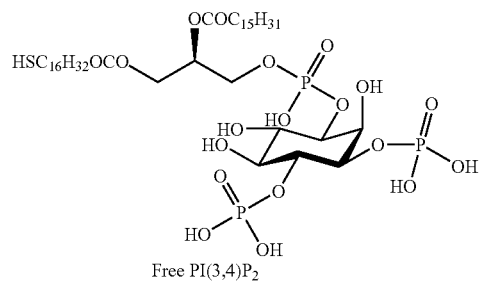
Free PI(3,4)P$_2$
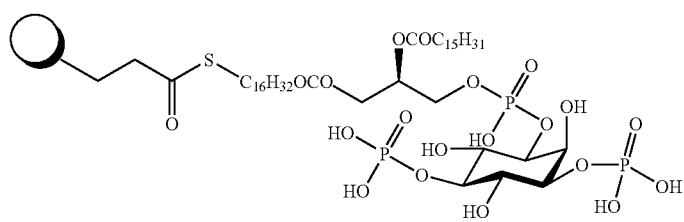
Immobilized PI(3)P
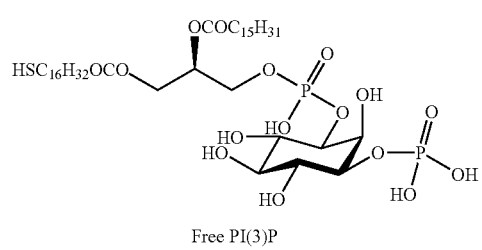
Free PI(3)P

TABLE 3-continued

Further preferred compounds and probes of the invention

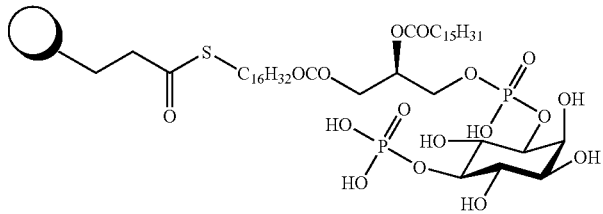

Immobilized PI(5)P

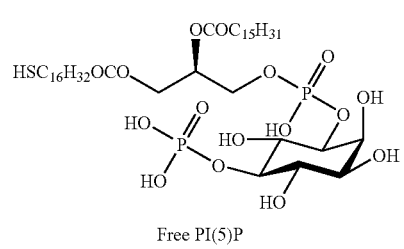

Free PI(5)P

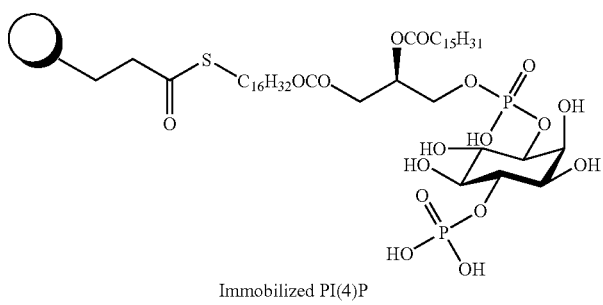

Immobilized PI(4)P

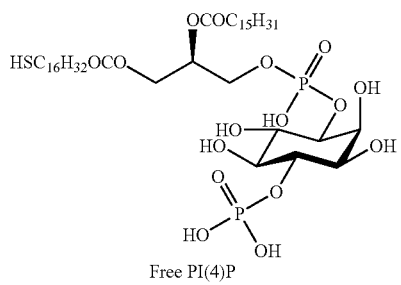

Free PI(4)P

---

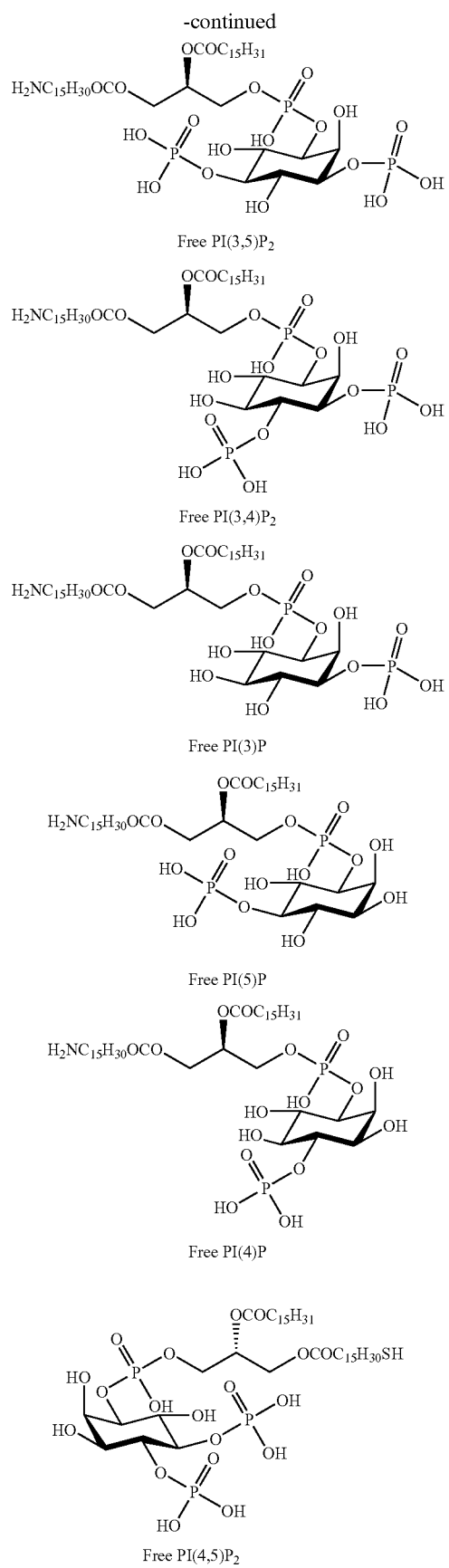

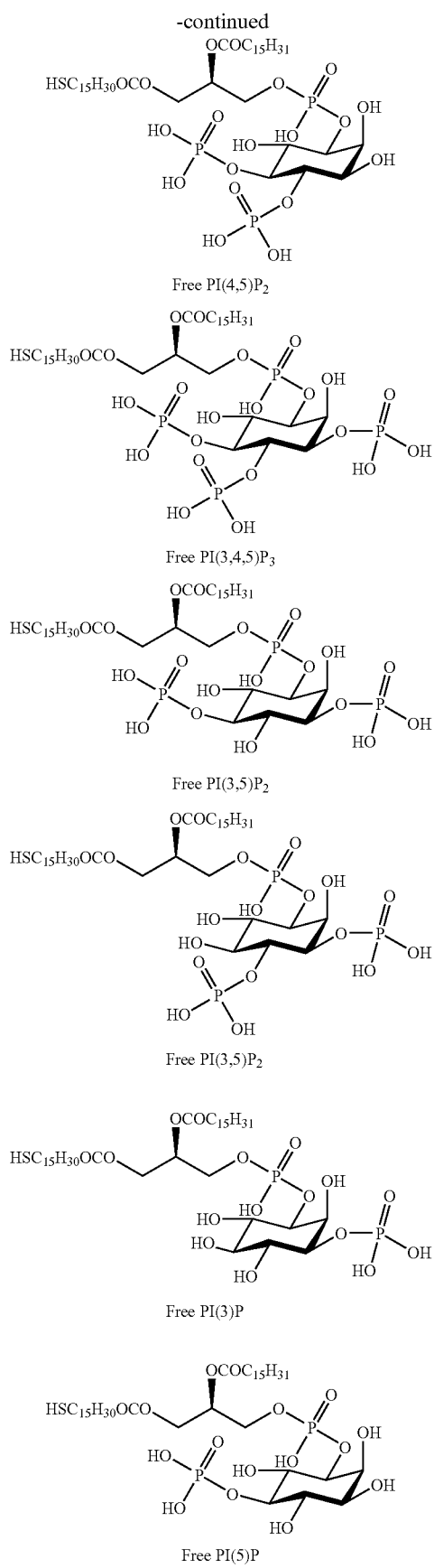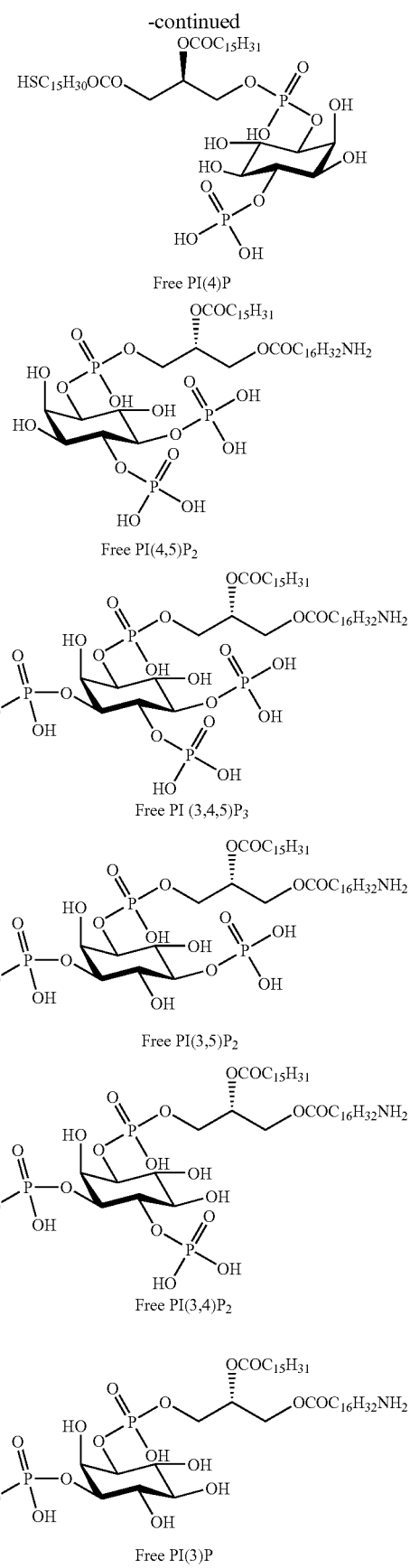

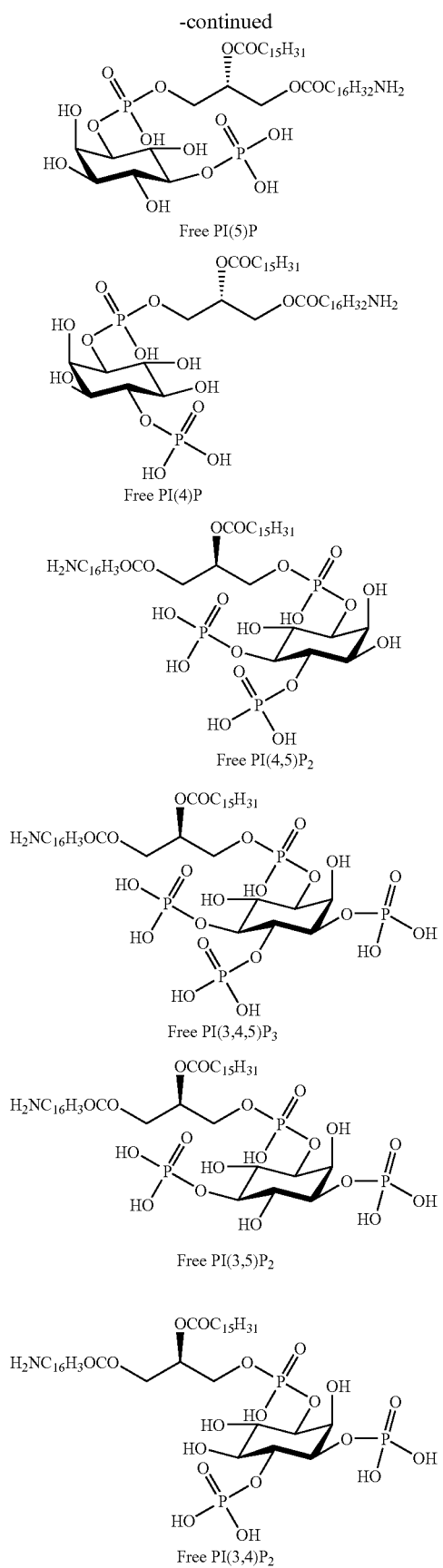
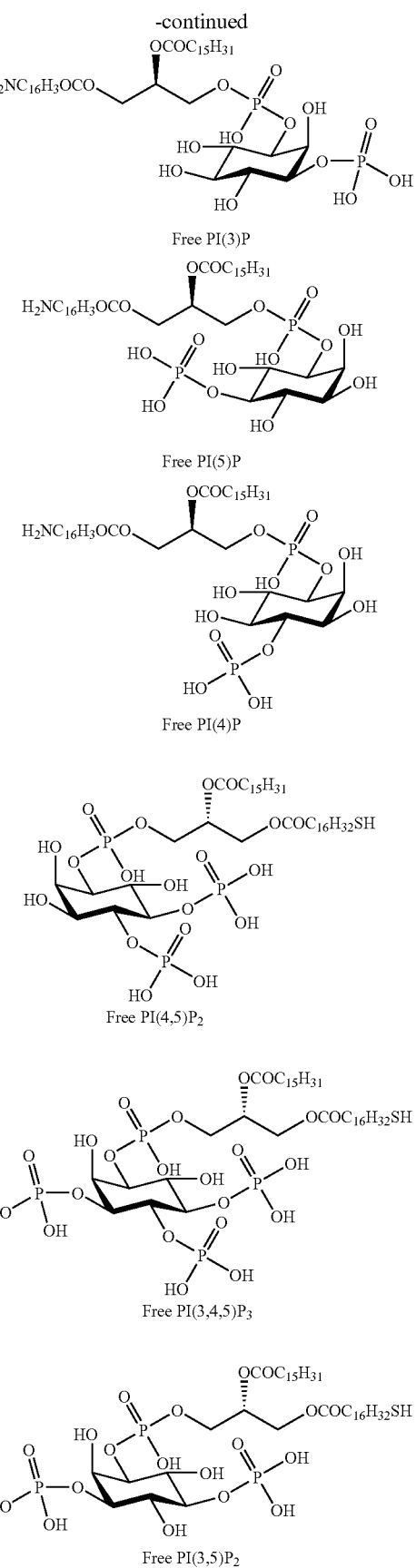

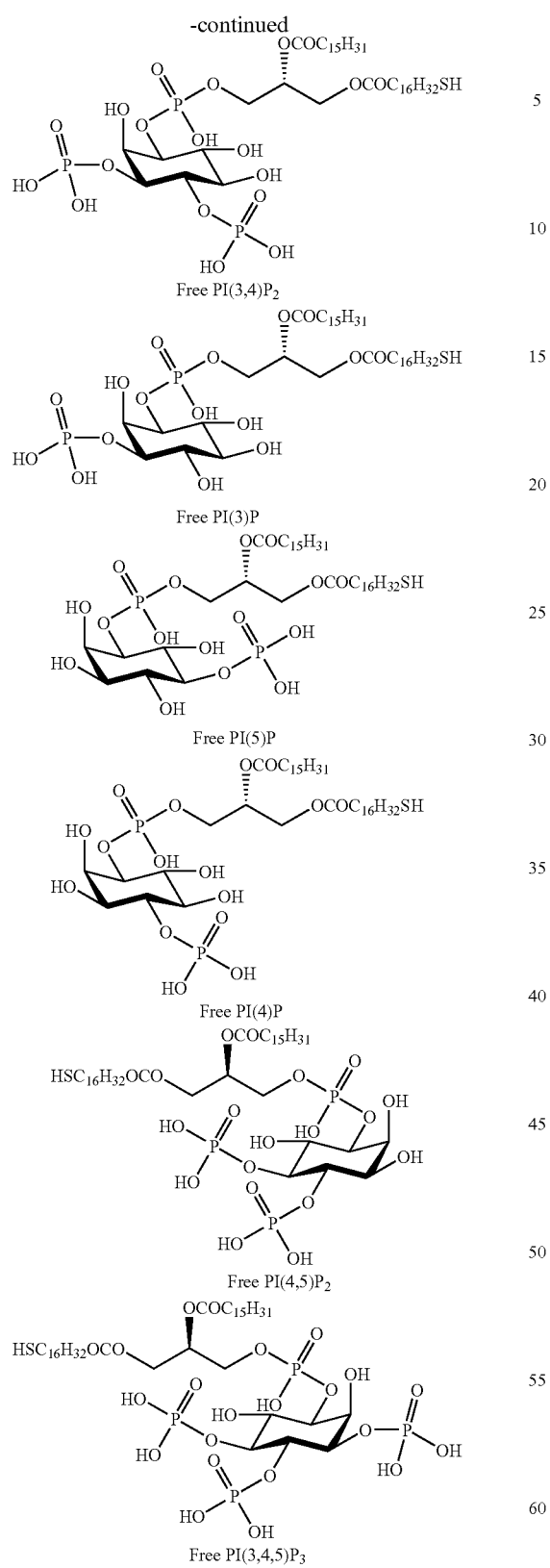
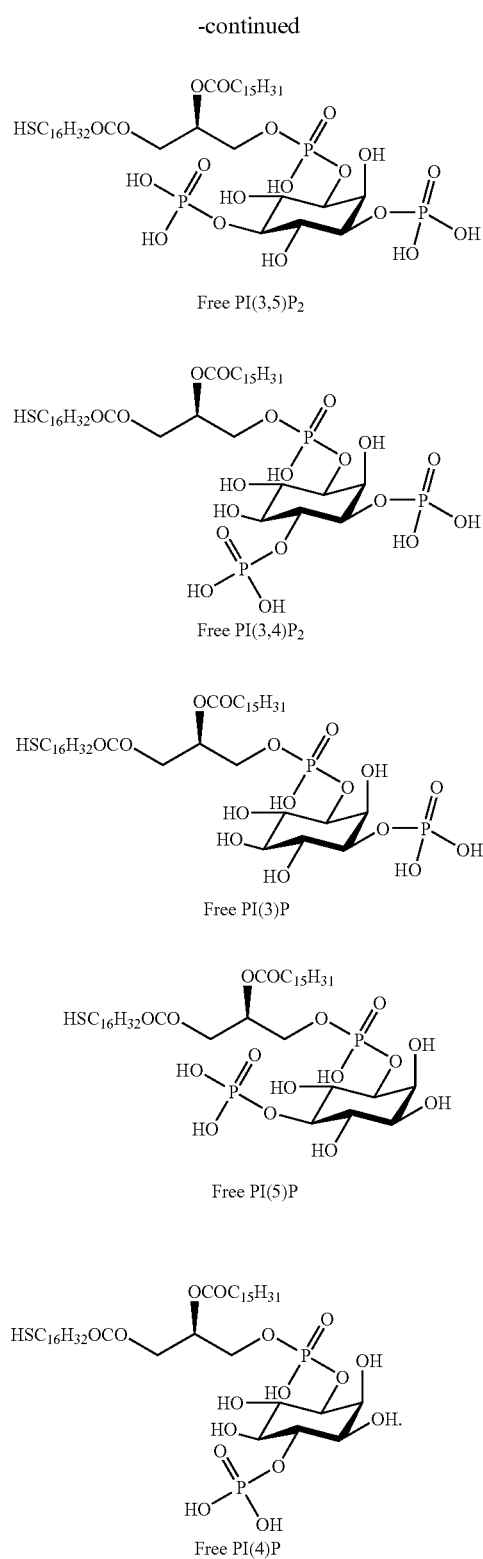

The invention claimed is:

1. A probe having any of the following general formulae:

Formula V

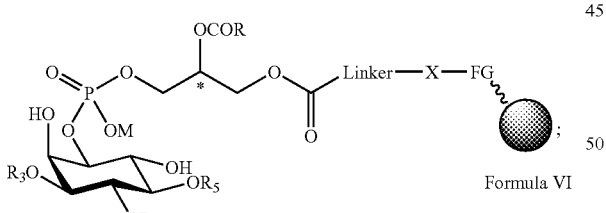

Formula VI

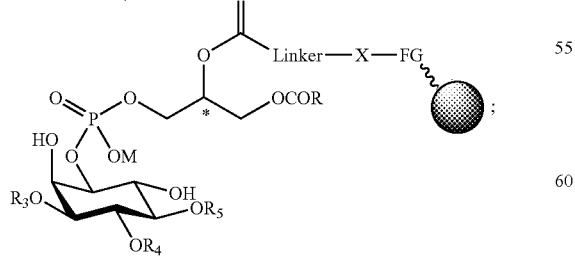

wherein:
R=aryl or alkyl group;
R=$C_mH_{2m+1}$, where m=8-20;
$R_3$=P(O)(OM)$_2$; $R_4$=H; $R_5$=H (PI(3)P);
$R_3$=H; $R_4$=P(O)(OM)$_2$, $R_5$=H (PI(4)P);
$R_3$=H; $R_4$=H; $R_5$=P(O)(OM)$_2$ (PI(5)P);
$R_3$=P(O)(OM)$_2$; $R_4$=P(O)(OM)$_2$; $R_5$=H (PI(3,4)P$_2$);
$R_3$=P(O)(OM)$_2$; $R_4$=H; $R_5$=P(O)(OM)$_2$ (PI(3,5)P$_2$);
$R_3$=H; $R_4$=P(O)(OM)$_2$; $R_5$=P(O)(OM)$_2$ (PI(4,5)P$_2$); or
$R_3$=P(O)(OM)$_2$; $R_4$=P(O)(OM)$_2$; $R_5$=P(O)(OM)$_2$ (PI(3,4,5)P$_3$);
M=any cation including Na$^+$, NH4$^+$;
*Denotes a stereogenic centre;
Linker=(CH$_2$)$_n$ with n=8-20;
X=O, S, or NH;
FG=Carbonyl from a carboxylate, thiolo(ester), or an amide;
unsaturations are allowed, including in an arachidonyl side chain;

=solid support with attachment to functional group;

Formula VII

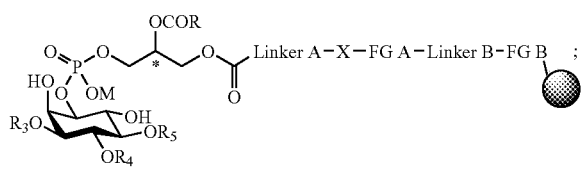

and

Formula VIII

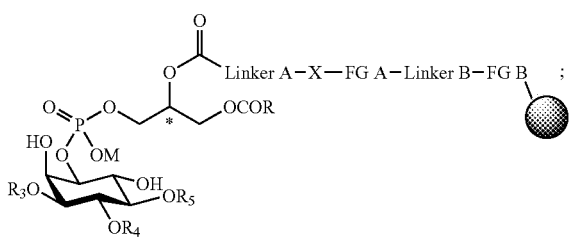

wherein:
R=aryl or alkyl group;
R=$C_mH_{2m+1}$, where m=8-20;
$R_3$=P(O)(OM)$_2$; $R_4$=H; $R_5$=H (PI(3)P);
$R_3$=H; $R_4$=P(O)(OM)$_2$; $R_5$=H (PI(4)P);
$R_3$=H; $R_4$=H; $R_5$=P(O)(OM)$_2$ (PI(5)P);
$R_3$=P(O)(OM)$_2$; $R_4$=P(O)(OM)$_2$; $R_5$=H (PI(3,4)P$_2$);
$R_3$=P(O)(OM)$_2$; $R_4$=H; $R_5$=P(O)(OM)$_2$ (PI(3,5)P$_2$);
$R_3$=H; $R_4$=P(O)(OM)$_2$, $R_5$=P(O)(OM)$_2$ (PI(4,5)P$_2$); or
$R_3$=P(O)(OM)$_2$; $R_4$=P(O)(OM)$_2$, $R_5$=P(O)(OM)$_2$ (PI(3,4,5)P$_3$);
M=any cation including Na$^+$ and NH4$^+$;
*Denotes a stereogenic centre;
X=O, S, or NH;
FG A=Carbonyl from a carboxylate, thiolo(ester), or an amide;
Linker A=(CH$_2$)$_n$ with n=8-20;
Linker B=aryl, heteroaryl, alkyl with possible heteroatoms and/or saturations;
these could be any atoms, including C, N, O, S, or methylene groups linked via amide and ester bonds;
FG B=Amide, thiolo(ester), or ester;
unsaturations are allowed, including in an arachidonyl side chain;

=solid support with attachment to functional group.

2. The probe according to claim 1, wherein the total length of linker A and linker B of formula VII or VIII is 8-60 atoms.

3. The probe according to claim 1, wherein the R group is alkyl.

4. The probe according to claim 1, wherein the probe has a formula of one of the compounds as listed below:

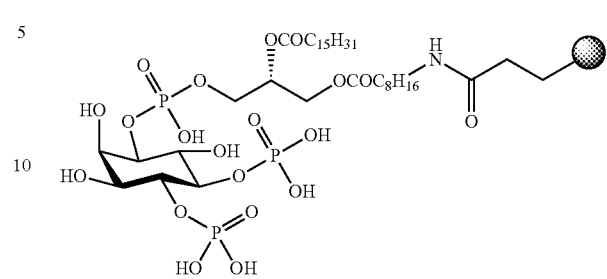

Immobilized PI(4,5)P$_2$

Immobilized PI(3,4,5)P$_3$

Immobilized PI(3,5)P$_2$

Immobilized PI(3,4)P$_2$

Immobilized PI(3)P

Immobilized PI(5)P

-continued
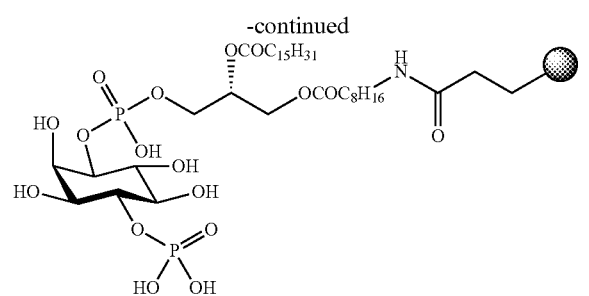
Immobilized PI(4)P
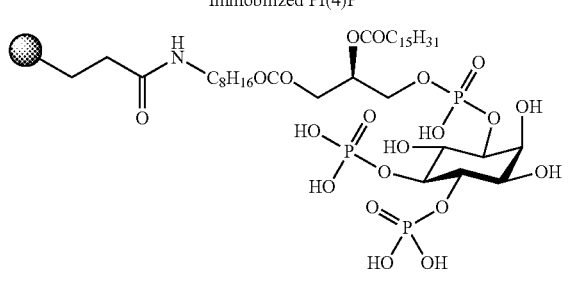
Immobilized PI(4,5)P$_2$
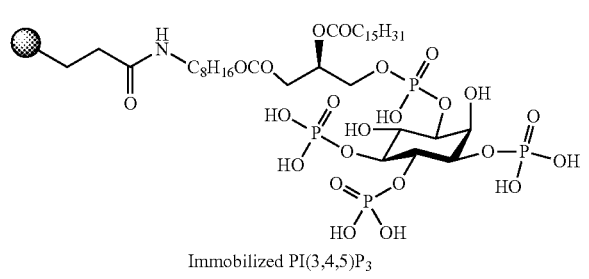
Immobilized PI(3,4,5)P$_3$
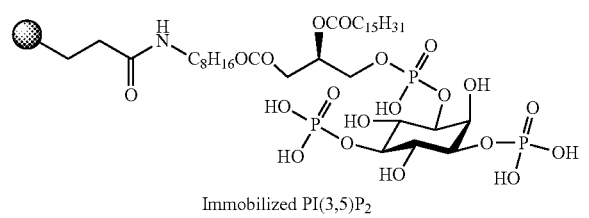
Immobilized PI(3,5)P$_2$
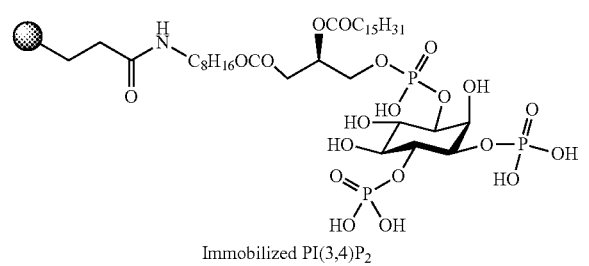
Immobilized PI(3,4)P$_2$
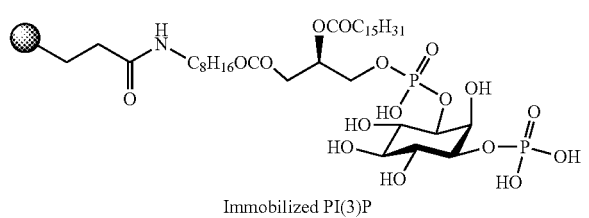
Immobilized PI(3)P
-continued
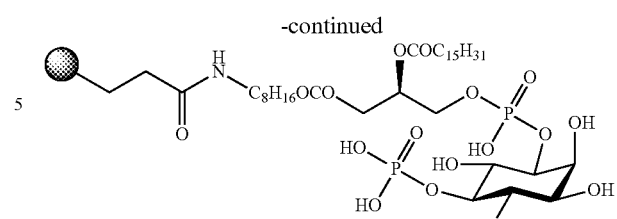
Immobilized PI(5)P
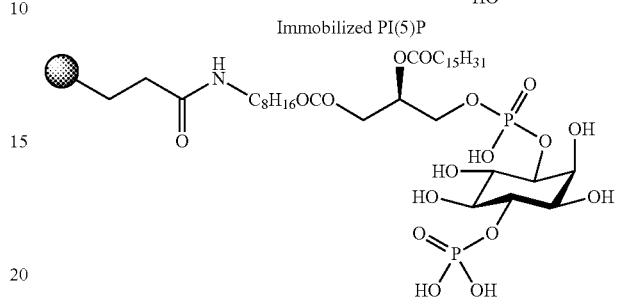
Immobilized PI(4)P
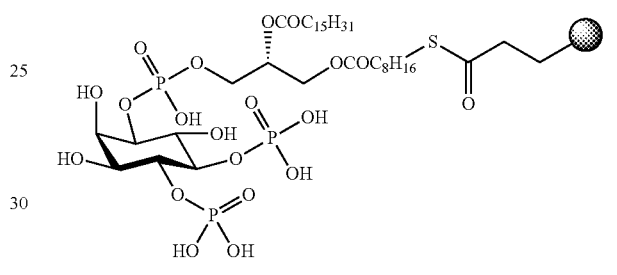
Immobilized PI(4,5)P$_2$
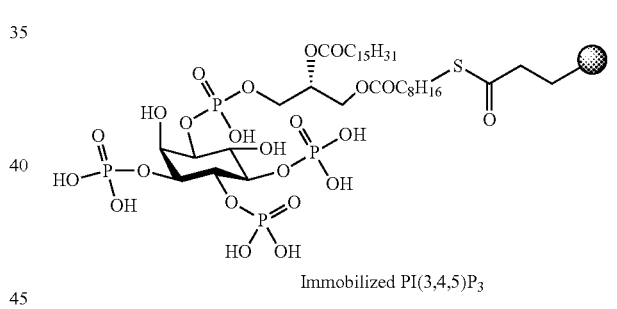
Immobilized PI(3,4,5)P$_3$
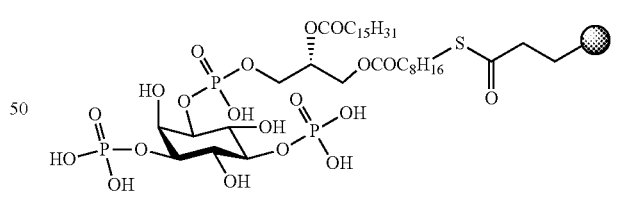
Immobilized PI(3,5)P$_2$
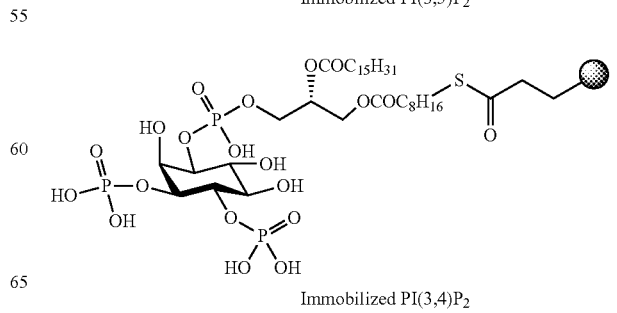
Immobilized PI(3,4)P$_2$ -continued
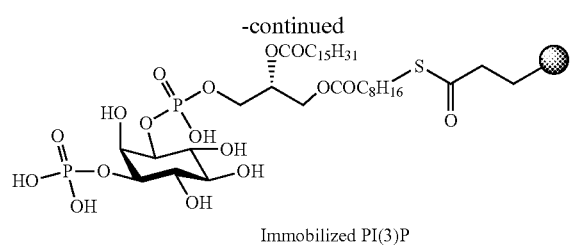
Immobilized PI(3)P
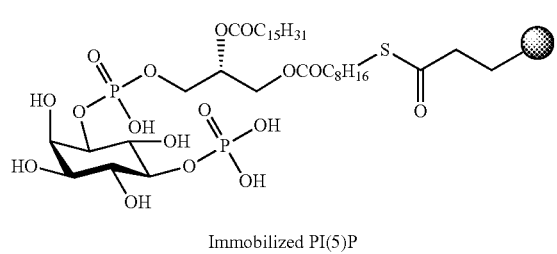
Immobilized PI(5)P
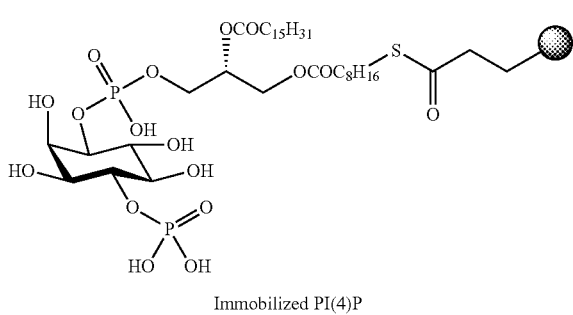
Immobilized PI(4)P
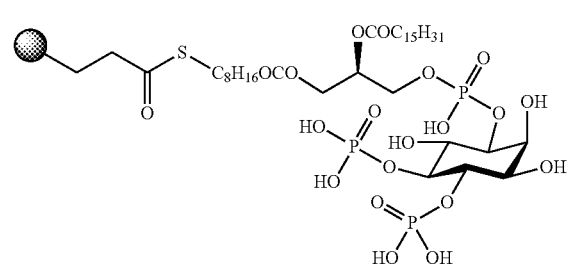
Immobilized PI(4,5)P$_2$
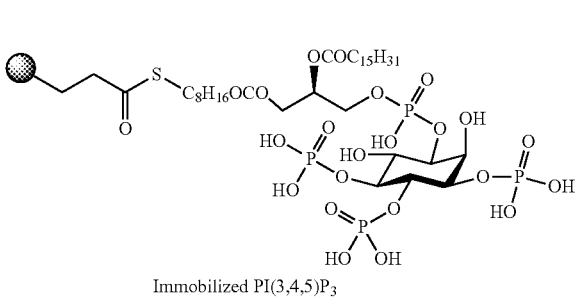
Immobilized PI(3,4,5)P$_3$
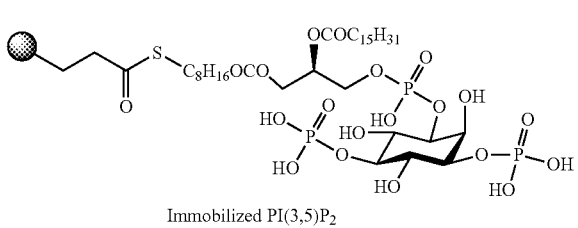
Immobilized PI(3,5)P$_2$
-continued
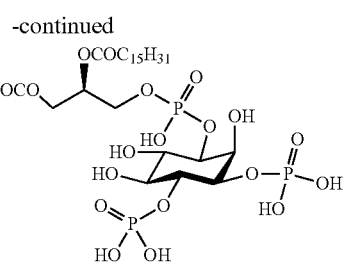
Immobilized PI(3,4)P$_2$
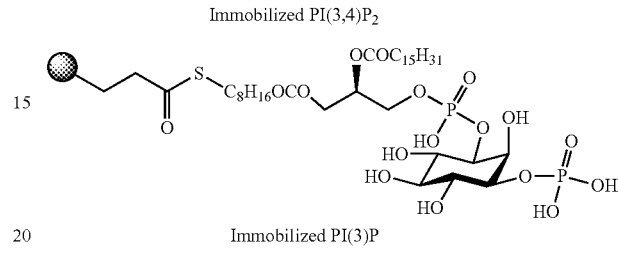
Immobilized PI(3)P
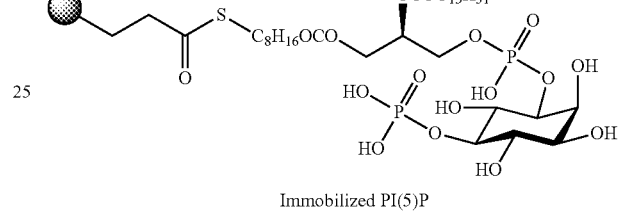
Immobilized PI(5)P
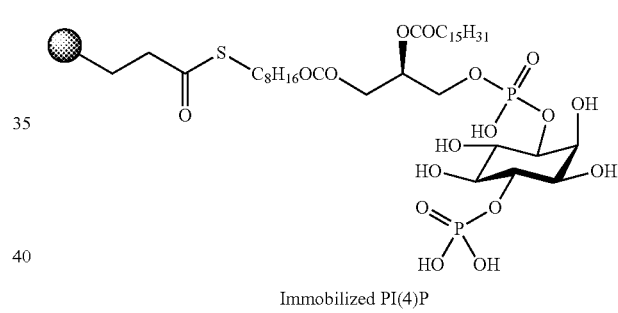
Immobilized PI(4)P
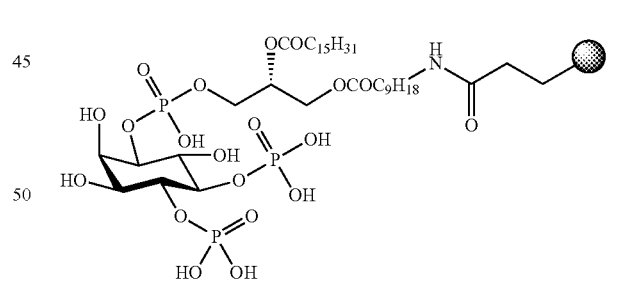
Immobilized PI(4,5)P$_2$
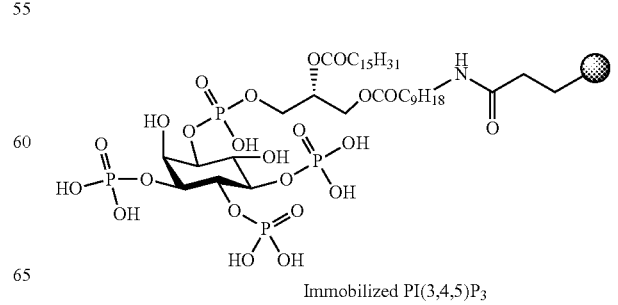
Immobilized PI(3,4,5)P$_3$ -continued
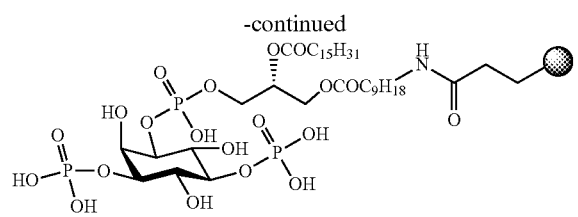
Immobilized PI(3,5)P$_2$
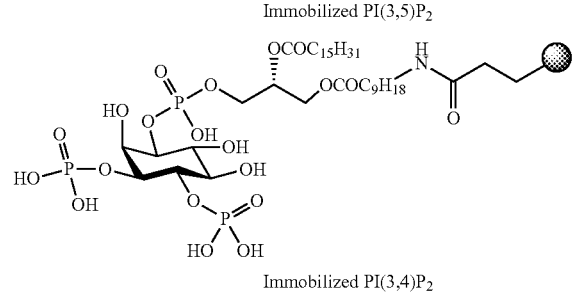
Immobilized PI(3,4)P$_2$
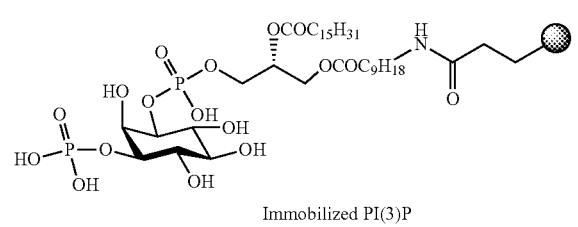
Immobilized PI(3)P
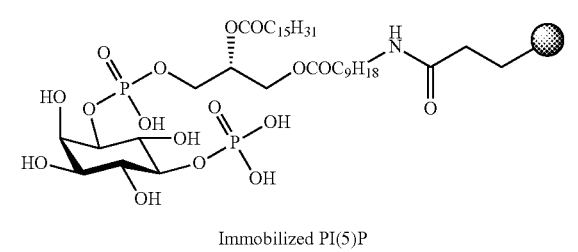
Immobilized PI(5)P
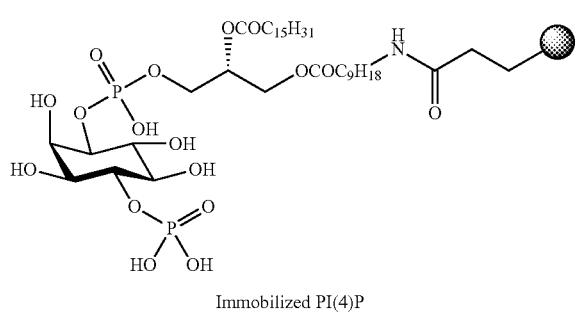
Immobilized PI(4)P
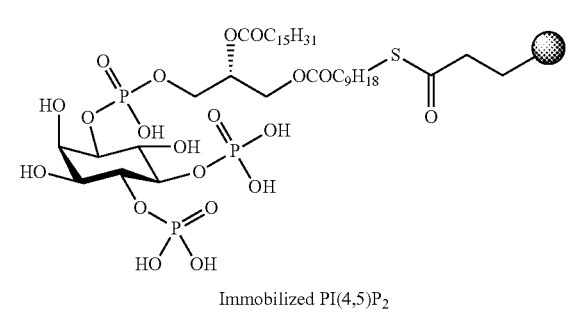
Immobilized PI(4,5)P$_2$
-continued
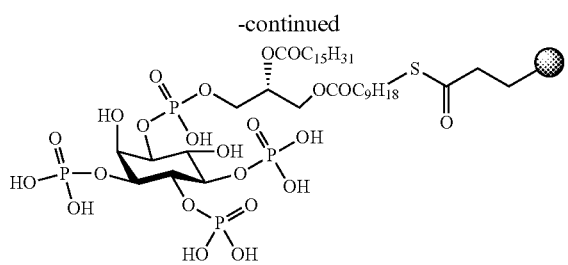
Immobilized PI(3,4,5)P$_3$
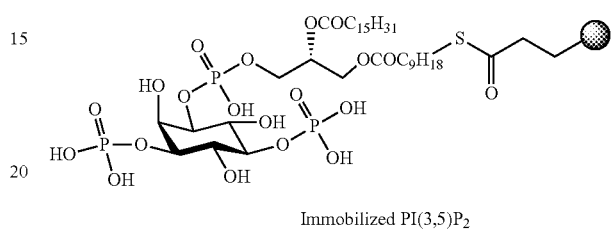
Immobilized PI(3,5)P$_2$
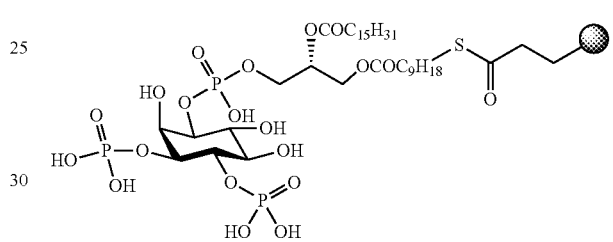
Immobilized PI(3,4)P$_2$
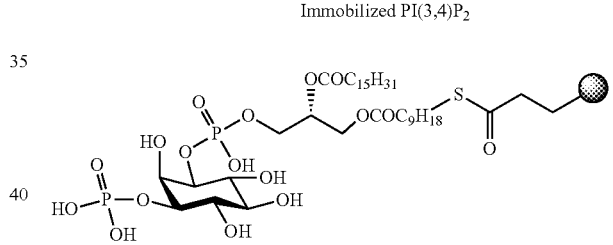
Immobilized PI(3)P
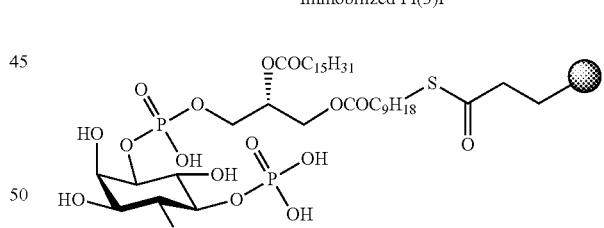
Immobilized PI(5)P
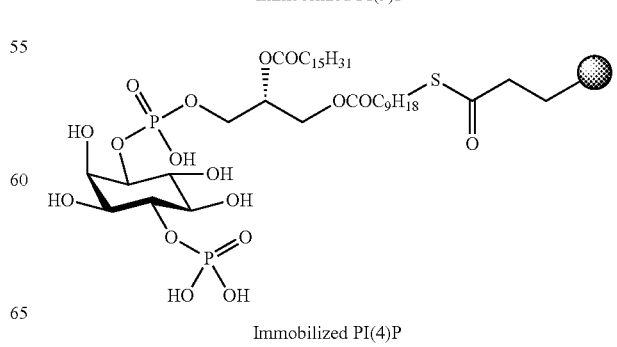
Immobilized PI(4)P -continued
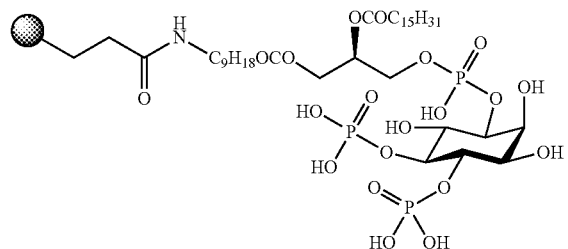
Immobilized PI(4,5)P₂
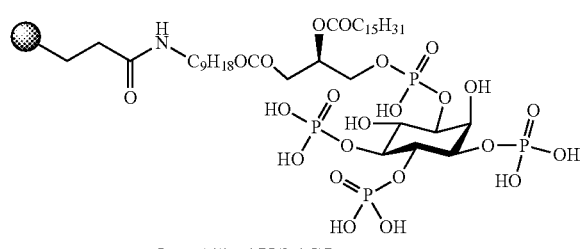
Immobilized PI(3,4,5)P₃
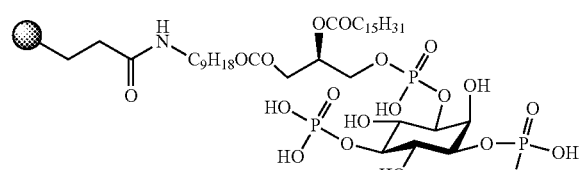
Immobilized PI(3,5)P₂
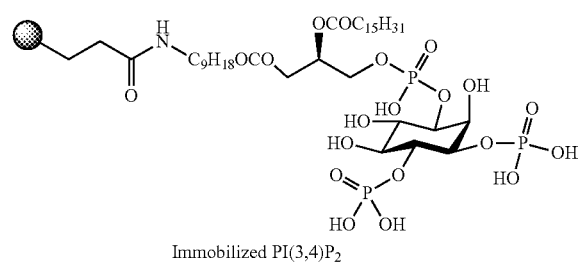
Immobilized PI(3,4)P₂
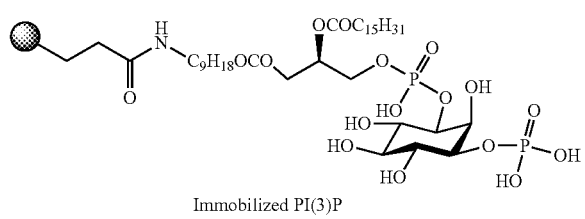
Immobilized PI(3)P
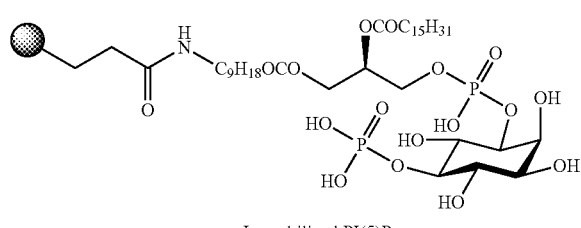
Immobilized PI(5)P
-continued
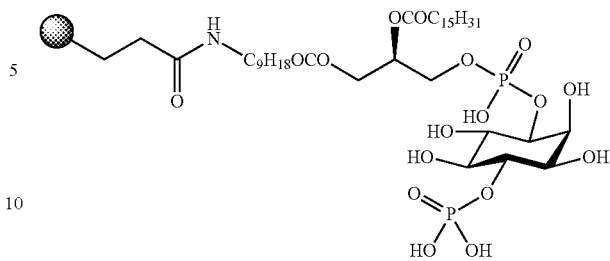
Immobilized PI(4)P
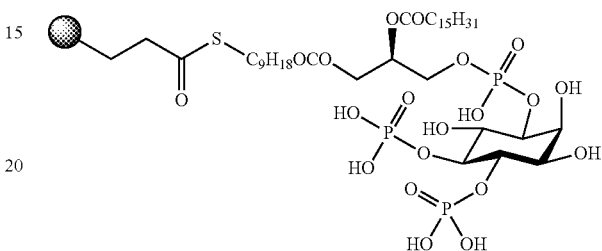
Immobilized PI(4,5)P₂
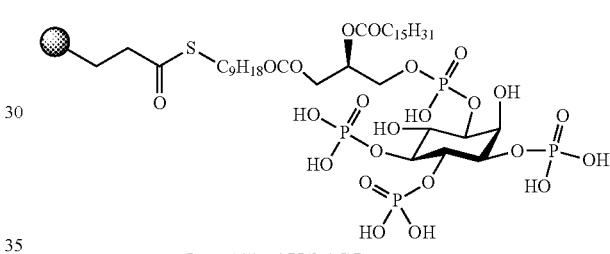
Immobilized PI(3,4,5)P₃
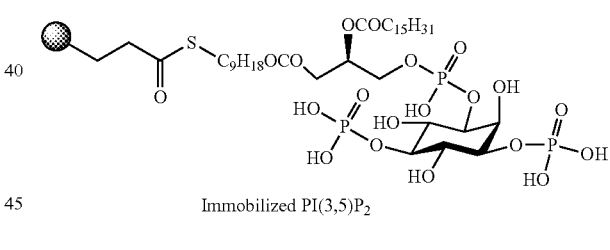
Immobilized PI(3,5)P₂
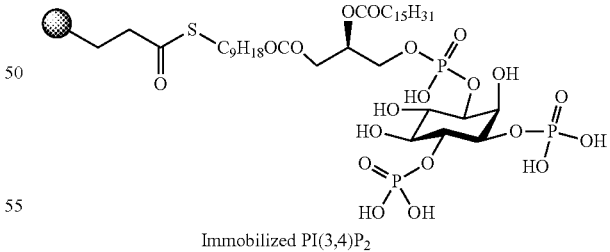
Immobilized PI(3,4)P₂
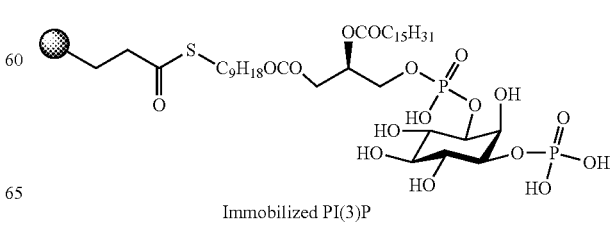
Immobilized PI(3)P -continued
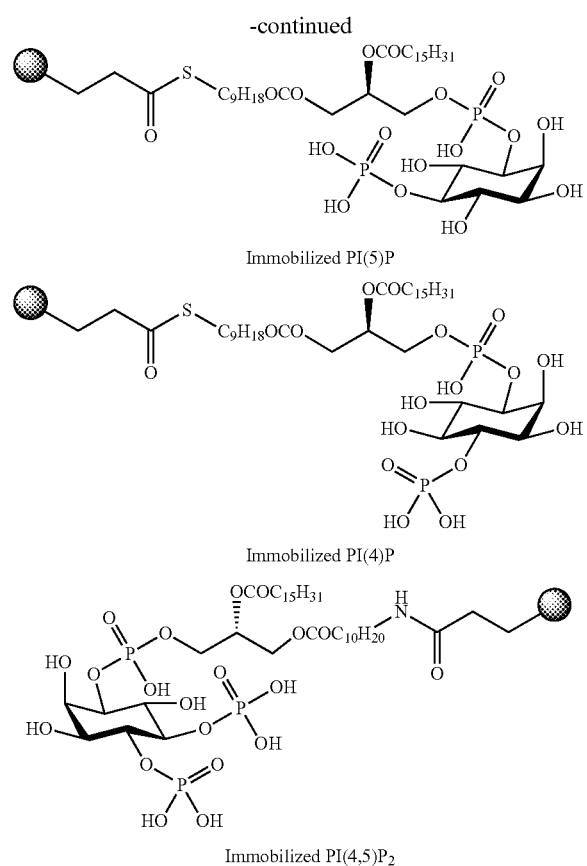
Immobilized PI(5)P
Immobilized PI(4)P
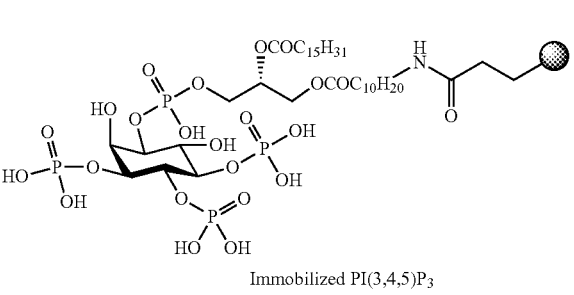
Immobilized PI(4,5)P$_2$
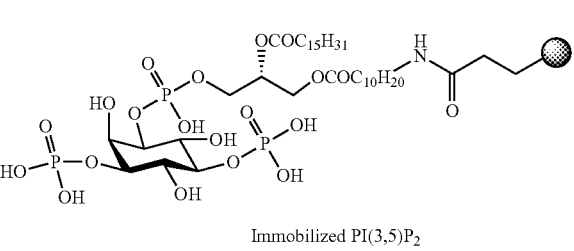
Immobilized PI(3,4,5)P$_3$
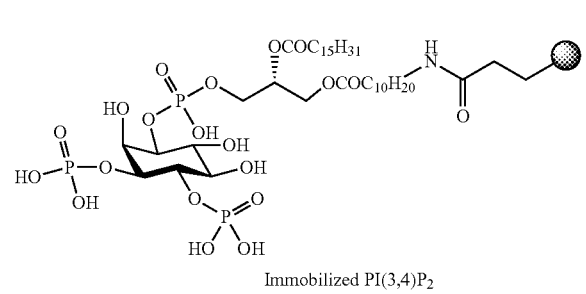
Immobilized PI(3,5)P$_2$
Immobilized PI(3,4)P$_2$
-continued
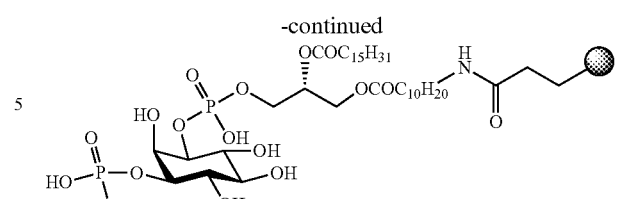
Immobilized PI(3)P
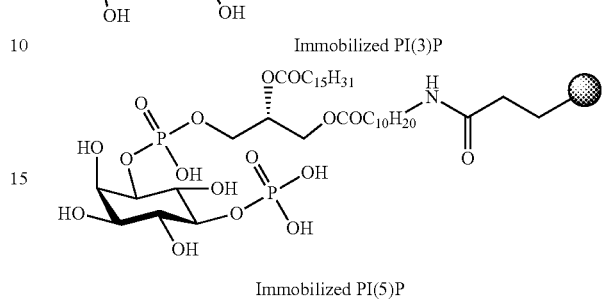
Immobilized PI(5)P
Immobilized PI(4)P
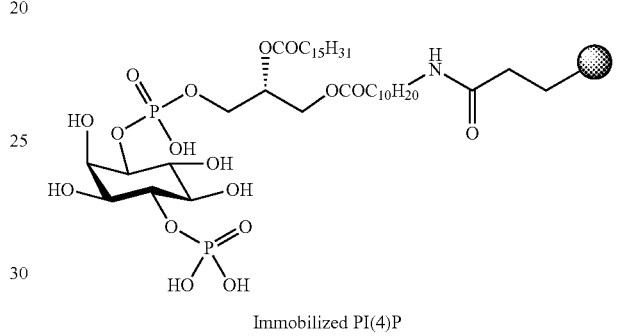
Immobilized PI(4,5)P$_2$
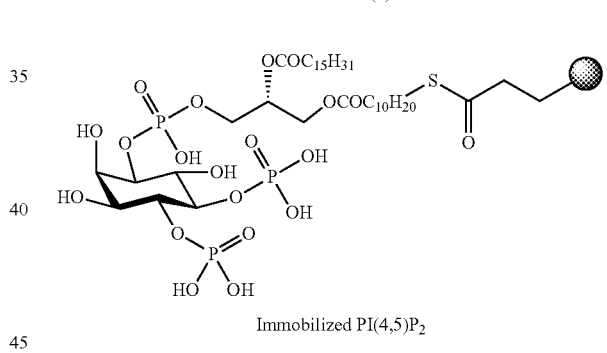
Immobilized PI(3,4,5)P$_3$
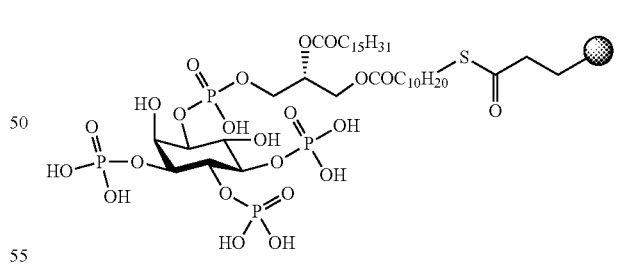
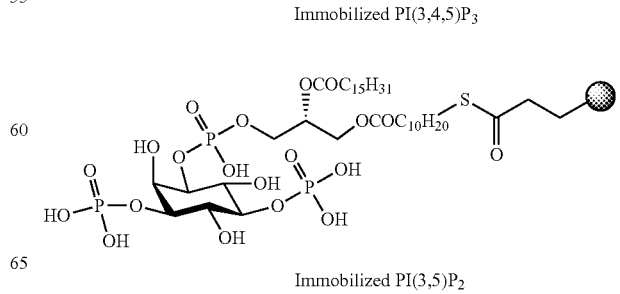
Immobilized PI(3,5)P$_2$

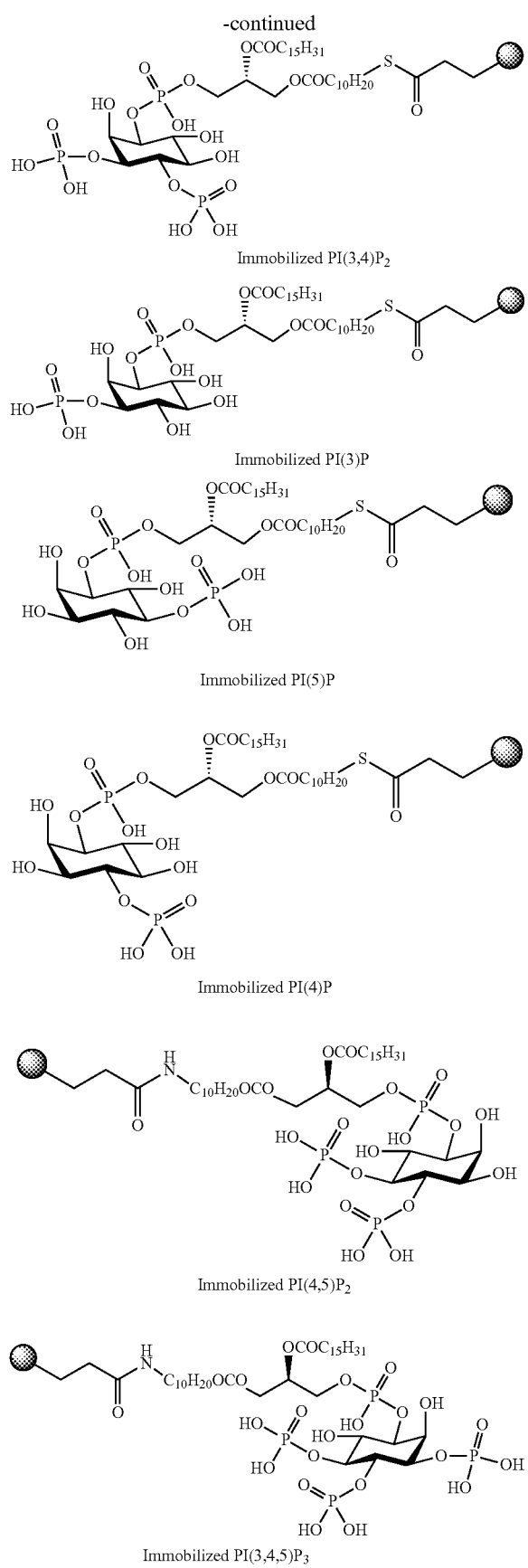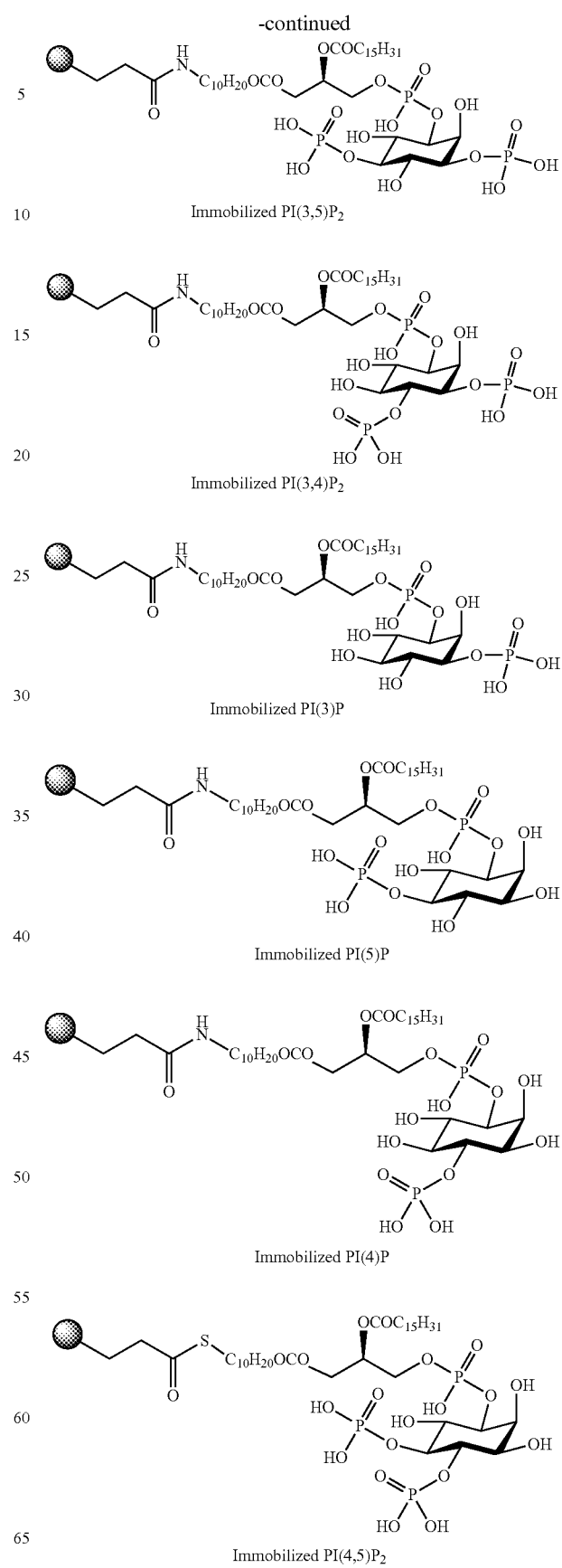

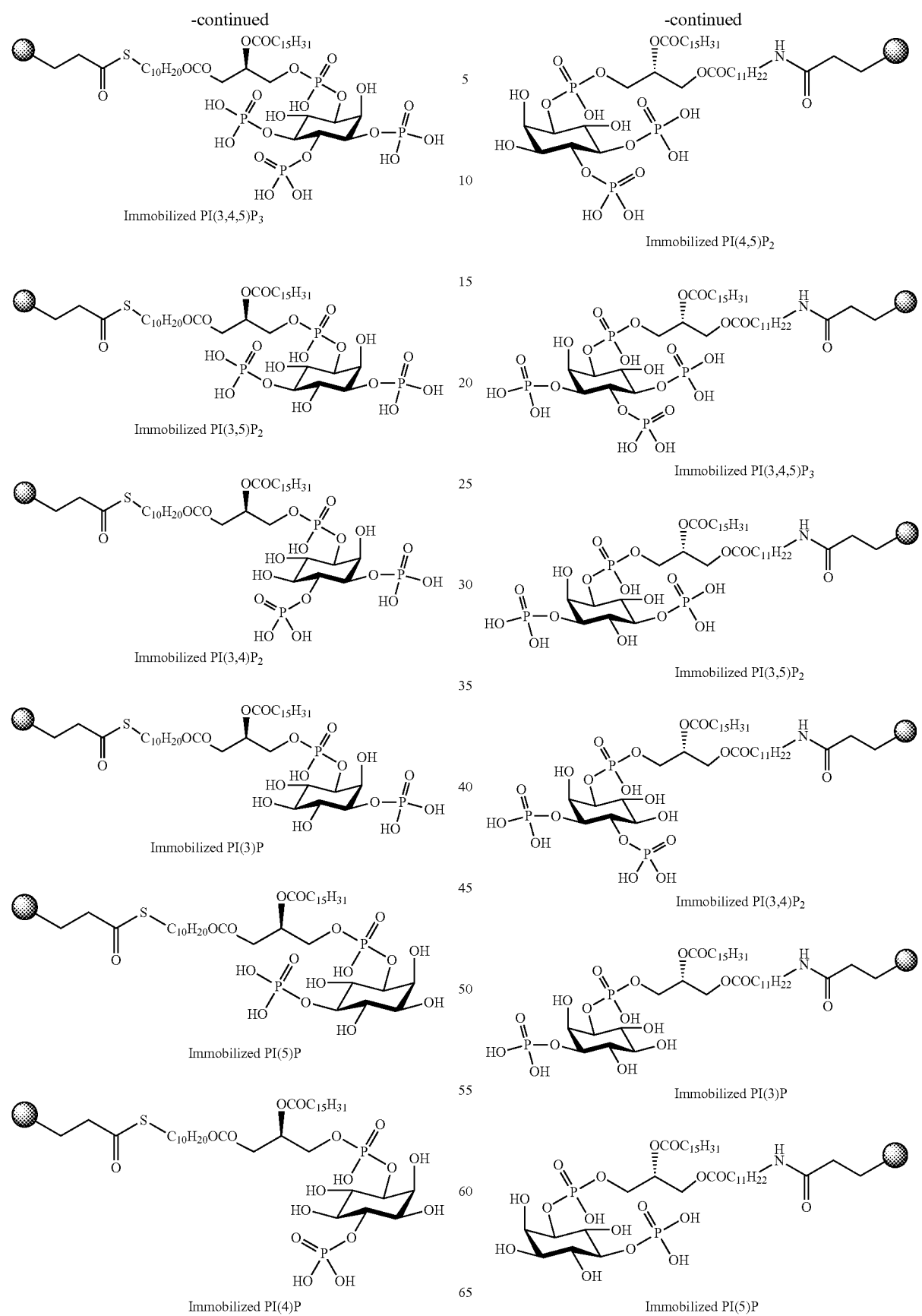

-continued
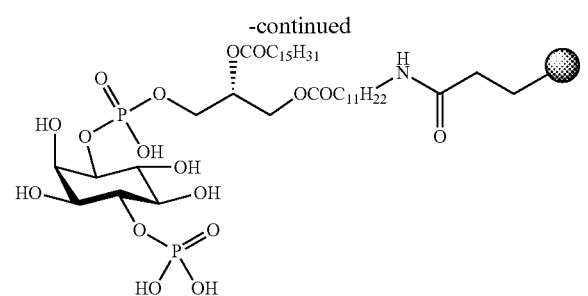
Immobilized PI(4)P
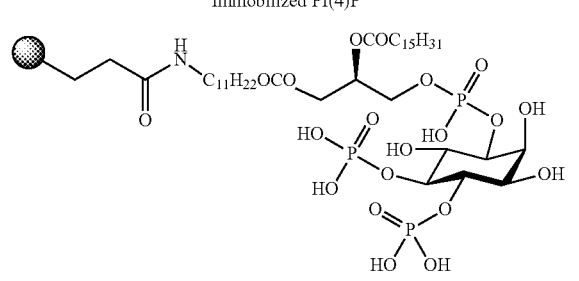
Immobilized PI(4,5)P$_2$
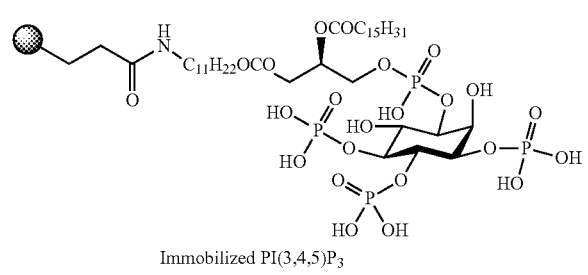
Immobilized PI(3,4,5)P$_3$
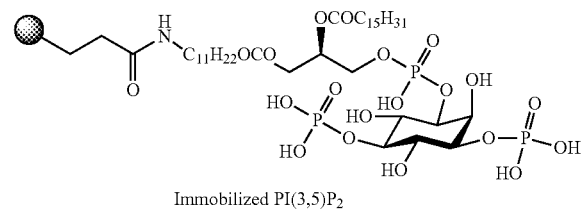
Immobilized PI(3,5)P$_2$
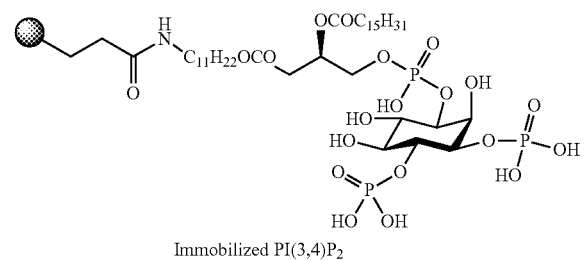
Immobilized PI(3,4)P$_2$
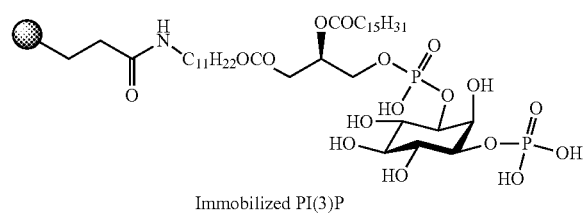
Immobilized PI(3)P
-continued
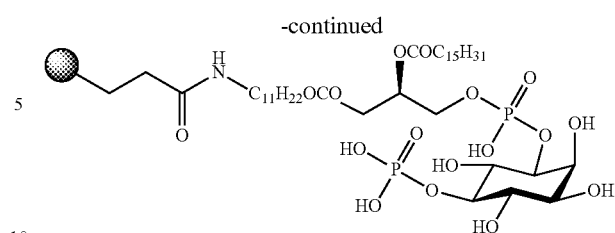
Immobilized PI(5)P
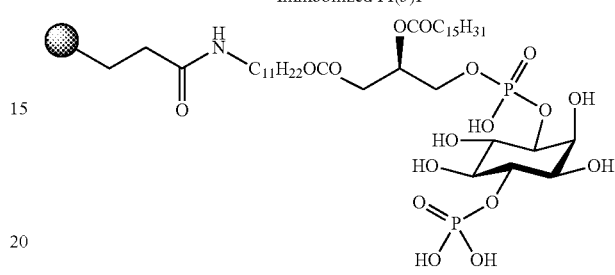
Immobilized PI(4)P
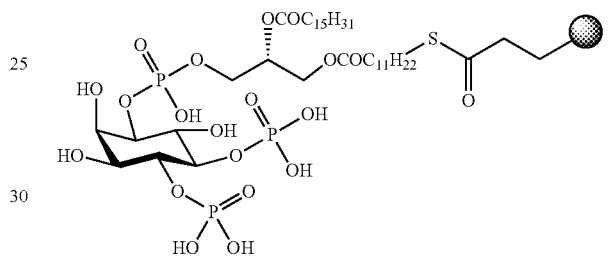
Immobilized PI(4,5)P$_2$
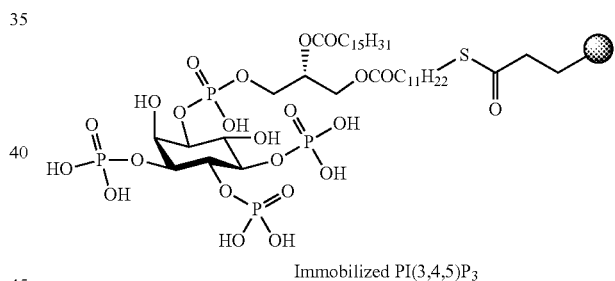
Immobilized PI(3,4,5)P$_3$
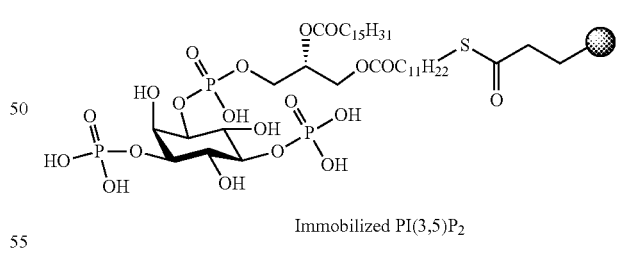
Immobilized PI(3,5)P$_2$
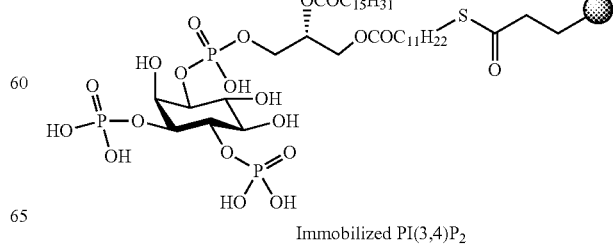
Immobilized PI(3,4)P$_2$ -continued
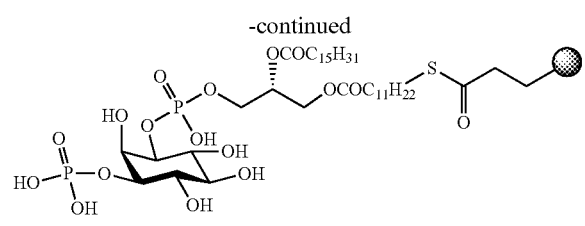
Immobilized PI(3)P
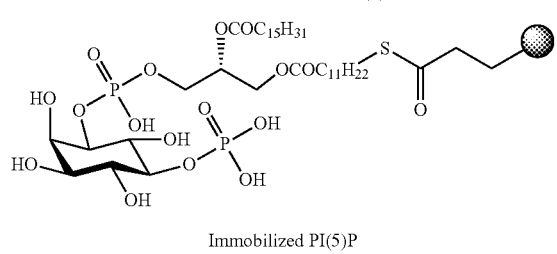
Immobilized PI(5)P
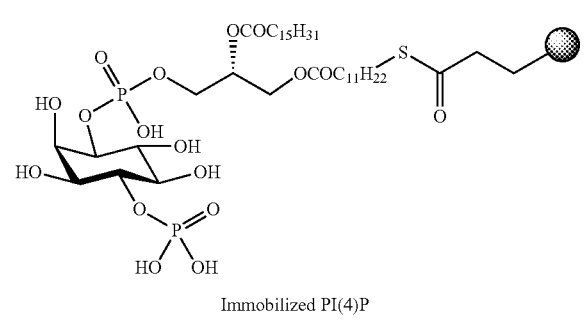
Immobilized PI(4)P
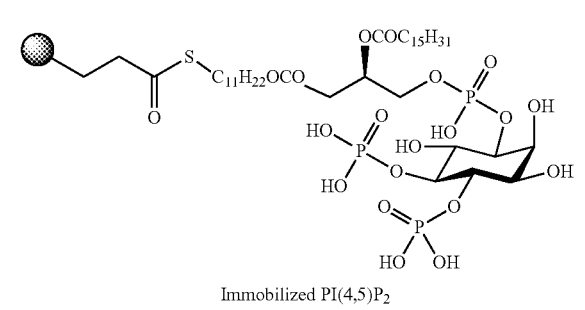
Immobilized PI(4,5)P$_2$
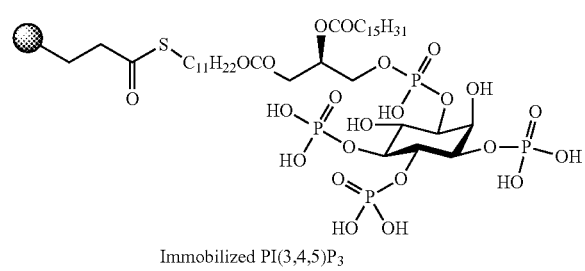
Immobilized PI(3,4,5)P$_3$
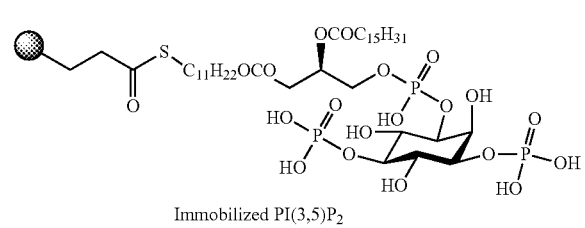
Immobilized PI(3,5)P$_2$
-continued
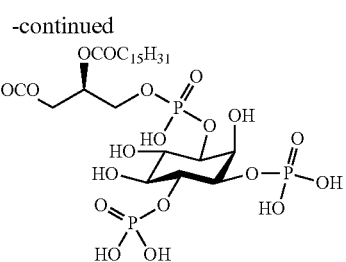
Immobilized PI(3,4)P$_2$
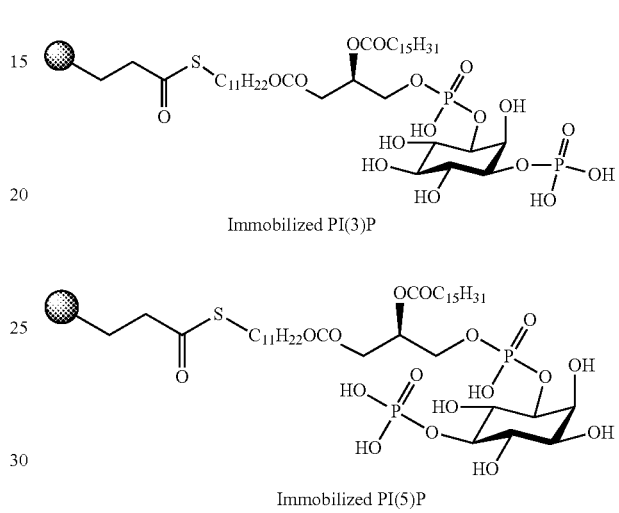
Immobilized PI(3)P
Immobilized PI(5)P
Immobilized PI(4)P
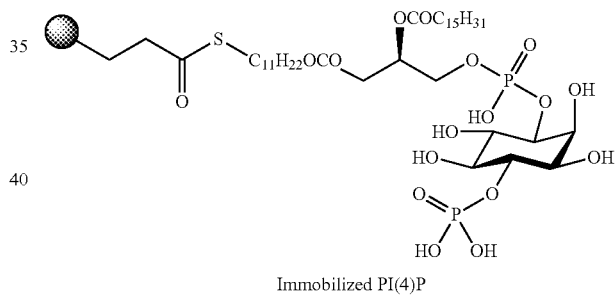
Immobilized PI(4,5)P$_2$
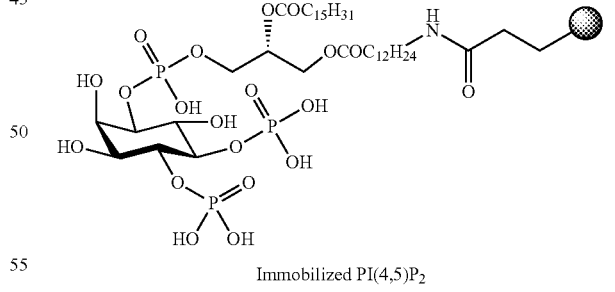
Immobilized PI(3,4,5)P$_3$ -continued
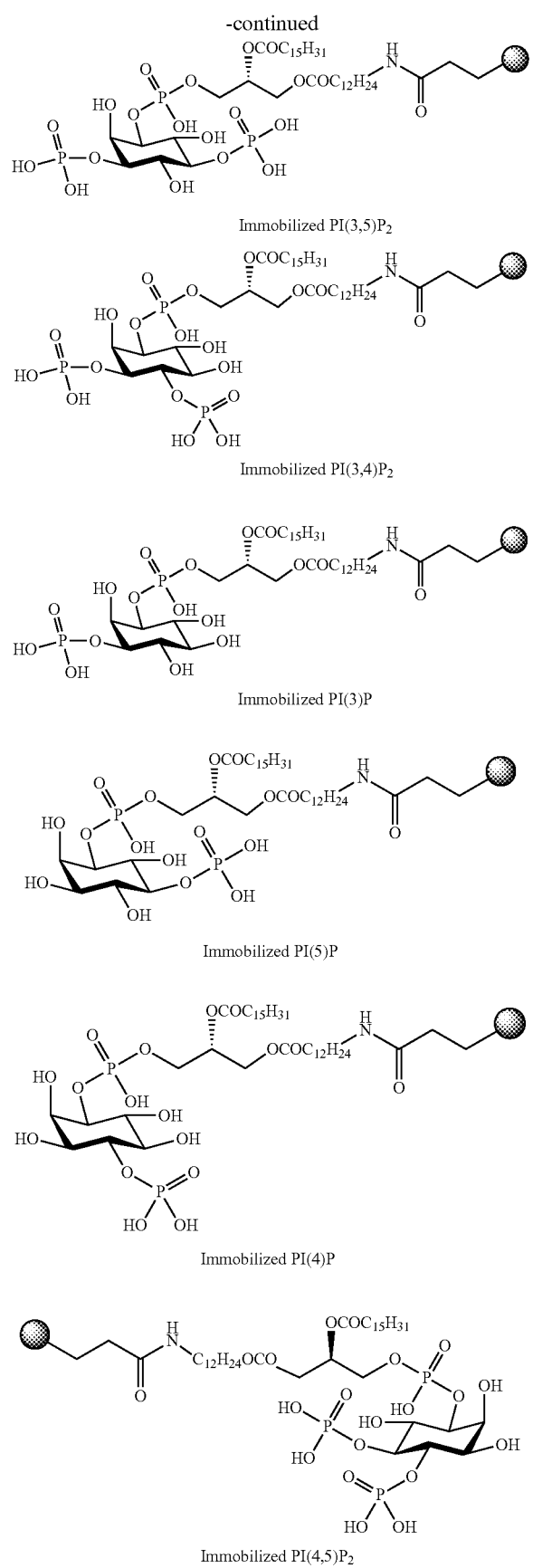
Immobilized PI(3,5)P$_2$
Immobilized PI(3,4)P$_2$
Immobilized PI(3)P
Immobilized PI(5)P
Immobilized PI(4)P
Immobilized PI(4,5)P$_2$
-continued
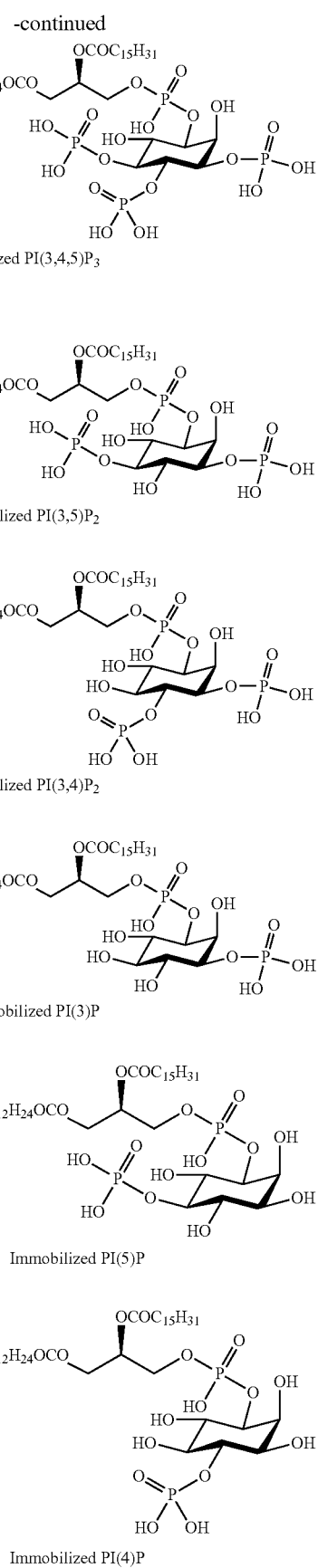
Immobilized PI(3,4,5)P$_3$
Immobilized PI(3,5)P$_2$
Immobilized PI(3,4)P$_2$
Immobilized PI(3)P
Immobilized PI(5)P
Immobilized PI(4)P -continued
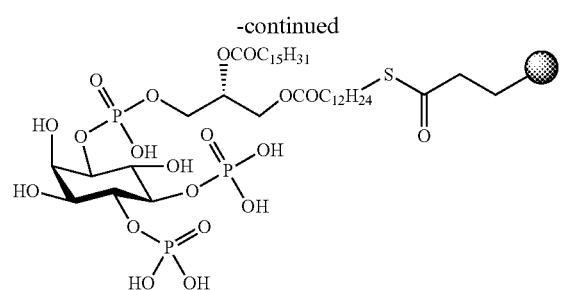
Immobilized PI(4,5)P$_2$
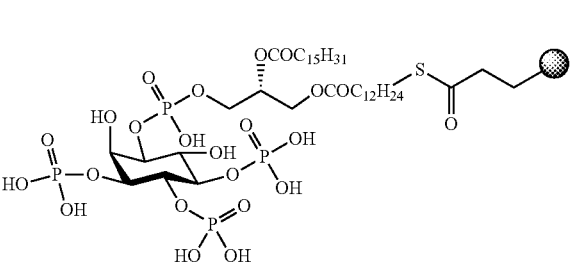
Immobilized PI(3,4,5)P$_3$
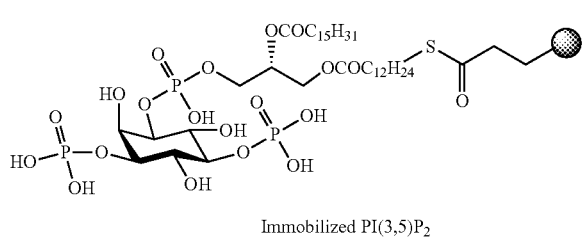
Immobilized PI(3,5)P$_2$
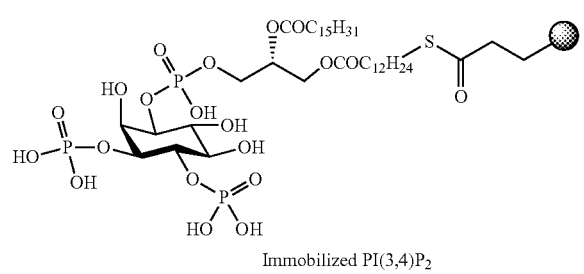
Immobilized PI(3,4)P$_2$
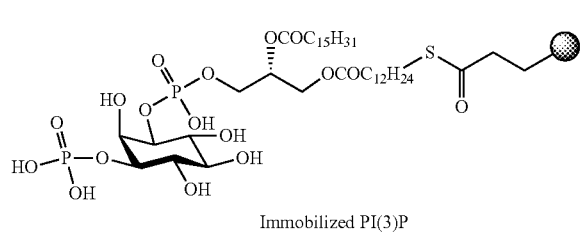
Immobilized PI(3)P
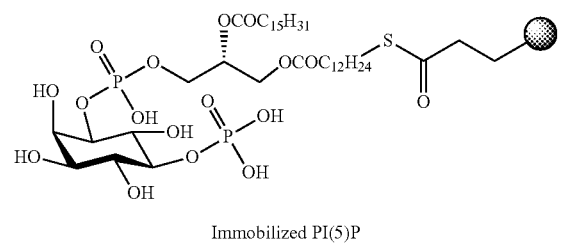
Immobilized PI(5)P
-continued
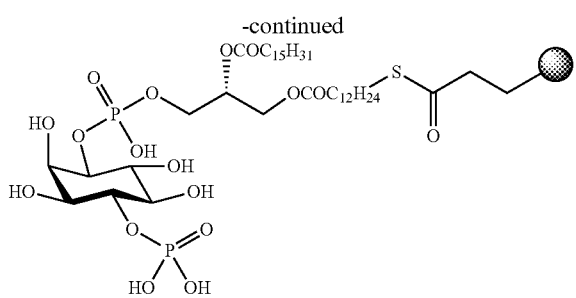
Immobilized PI(4)P
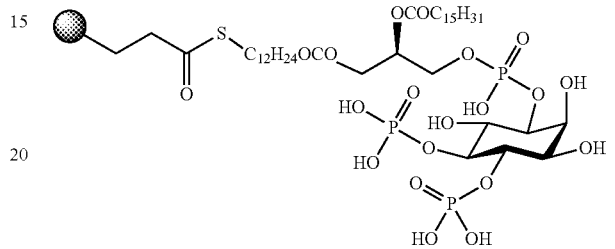
Immobilized PI(4,5)P$_2$
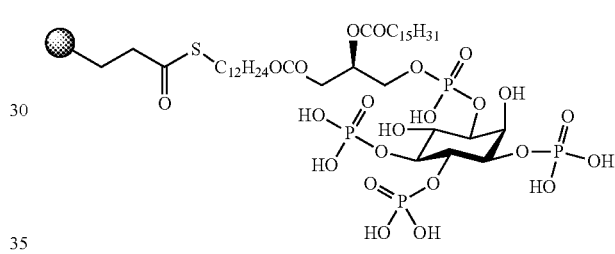
Immobilized PI(3,4,5)P$_3$
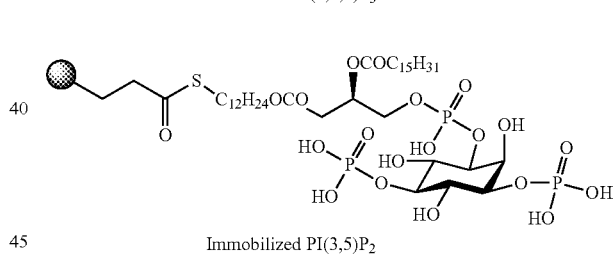
Immobilized PI(3,5)P$_2$
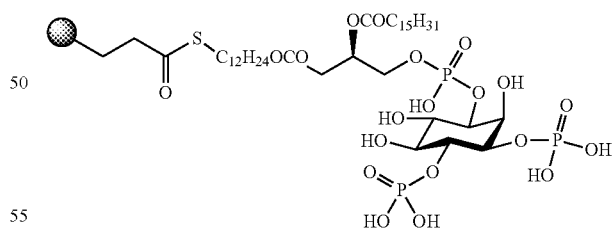
Immobilized PI(3,4)P$_2$
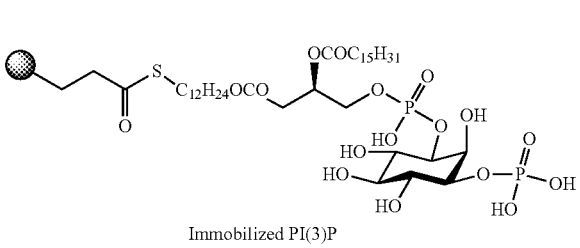
Immobilized PI(3)P -continued
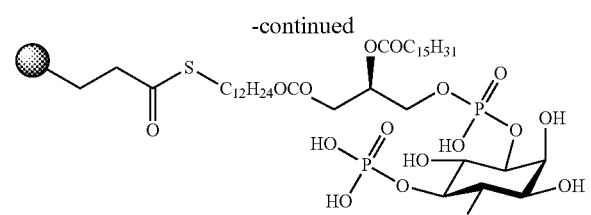
Immobilized PI(5)P
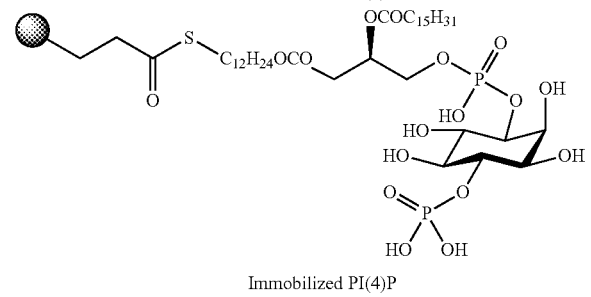
Immobilized PI(4)P
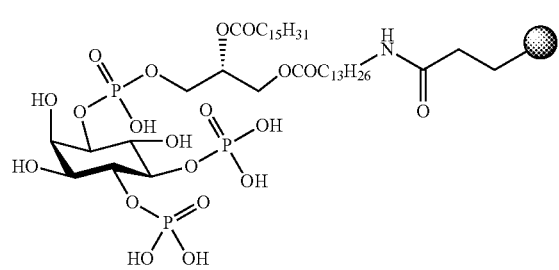
Immobilized PI(4,5)P$_2$
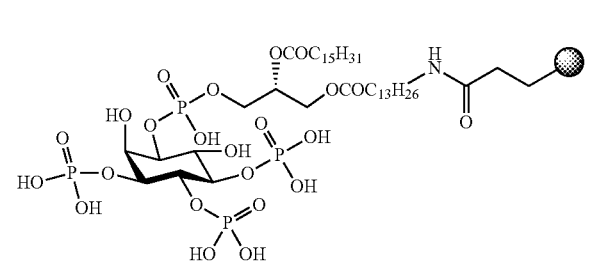
Immobilized PI(3,4,5)P$_3$
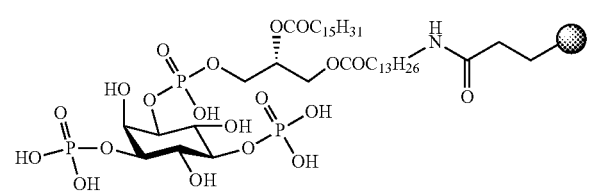
Immobilized PI(3,5)P$_2$
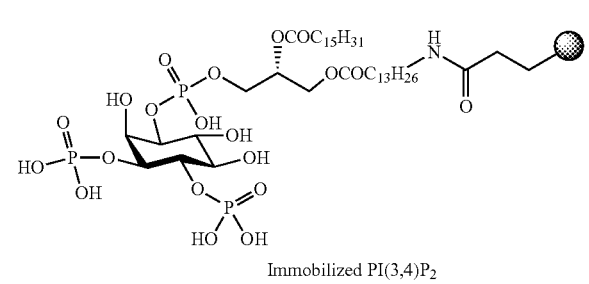
Immobilized PI(3,4)P$_2$
-continued
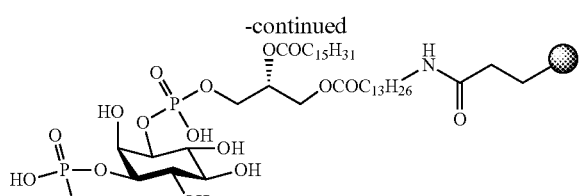
Immobilized PI(3)P
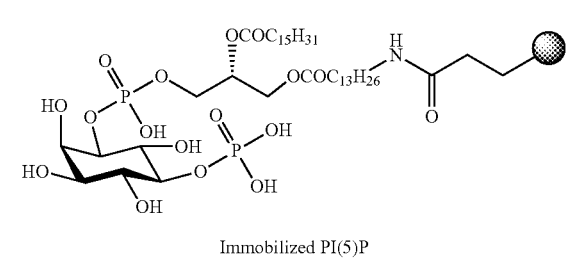
Immobilized PI(5)P
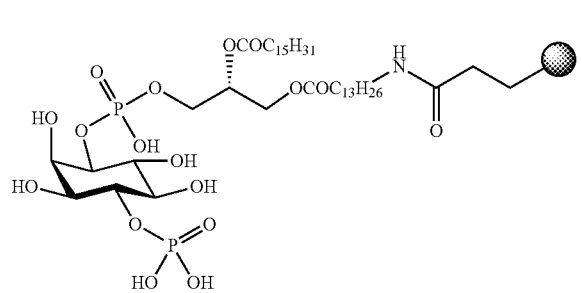
Immobilized PI(4)P
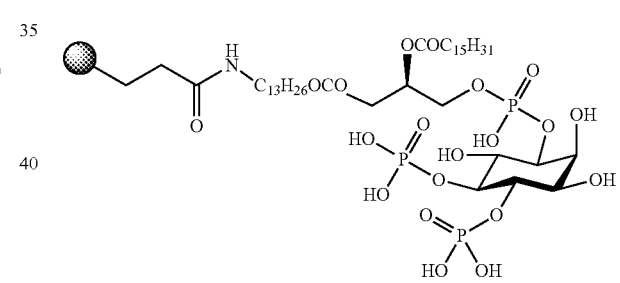
Immobilized PI(4,5)P$_2$
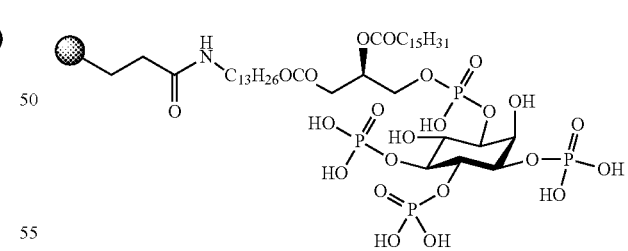
Immobilized PI(3,4,5)P$_3$
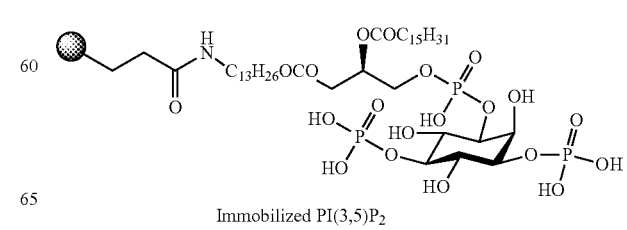
Immobilized PI(3,5)P$_2$ -continued
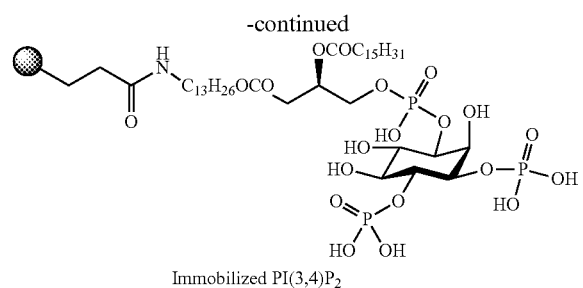
Immobilized PI(3,4)P$_2$
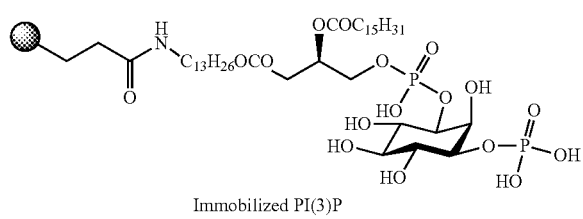
Immobilized PI(3)P
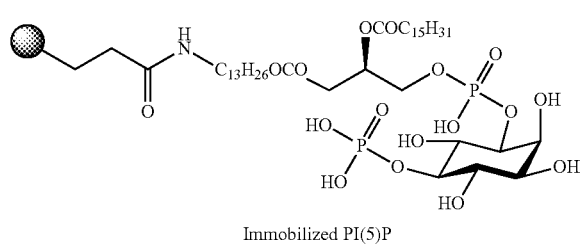
Immobilized PI(5)P
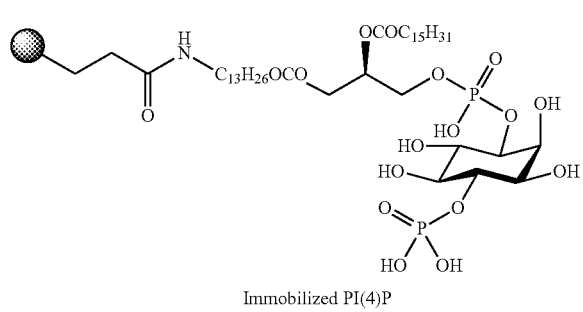
Immobilized PI(4)P
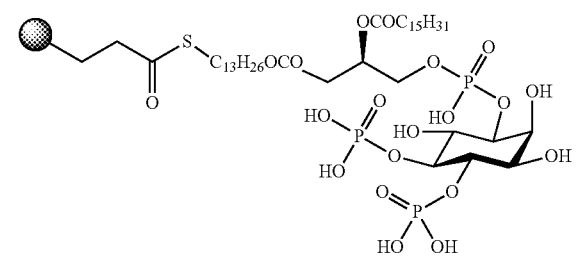
Immobilized PI(4,5)P$_2$
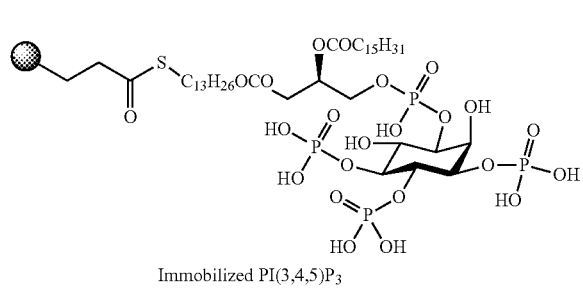
Immobilized PI(3,4,5)P$_3$
-continued
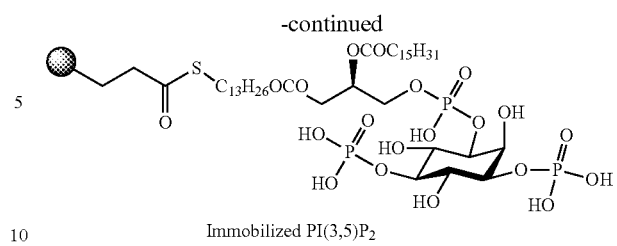
Immobilized PI(3,5)P$_2$
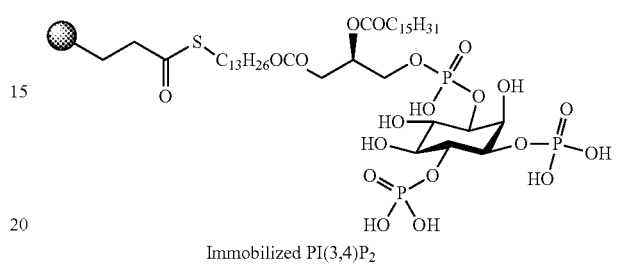
Immobilized PI(3,4)P$_2$
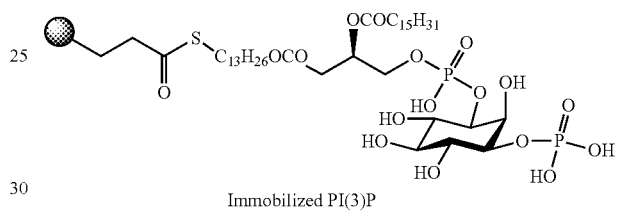
Immobilized PI(3)P
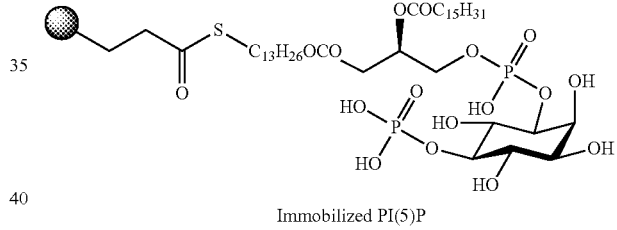
Immobilized PI(5)P
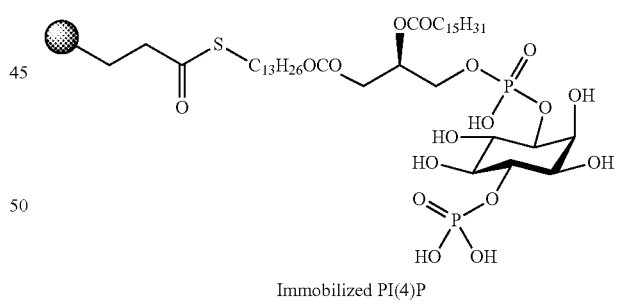
Immobilized PI(4)P
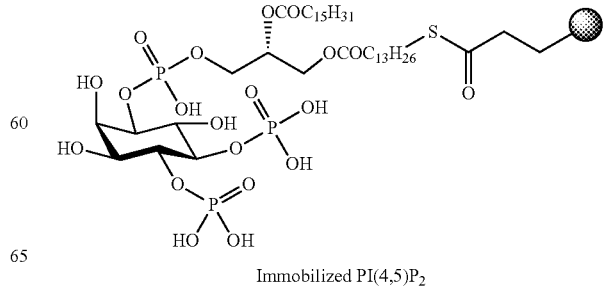
Immobilized PI(4,5)P$_2$ -continued
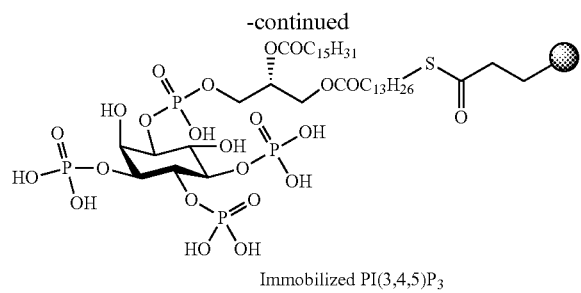
Immobilized PI(3,4,5)P₃
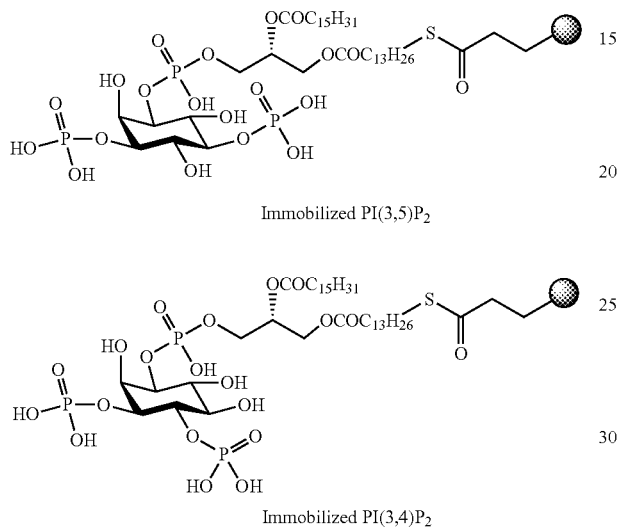
Immobilized PI(3,5)P₂
Immobilized PI(3,4)P₂
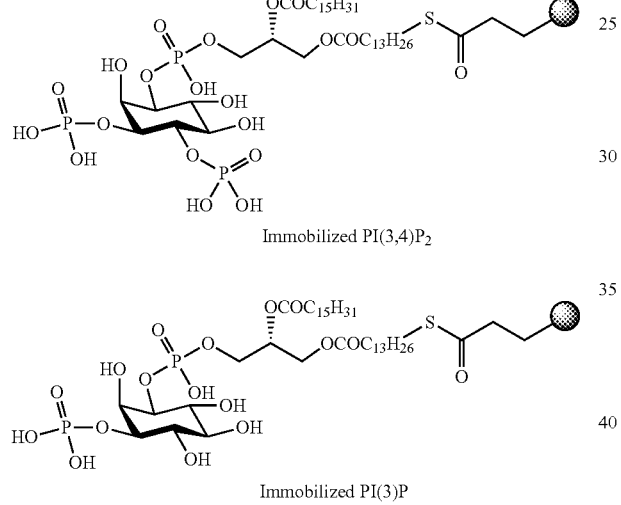
Immobilized PI(3)P
Immobilized PI(5)P
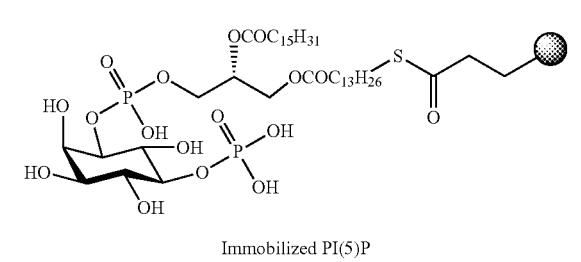
Immobilized PI(4)P
-continued
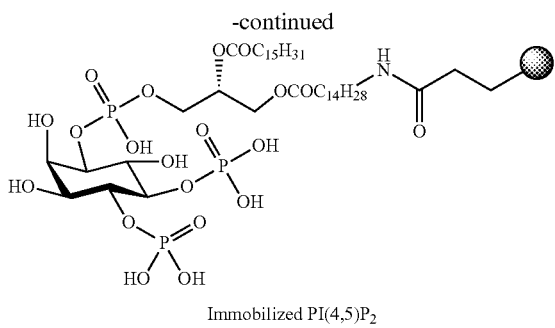
Immobilized PI(4,5)P₂
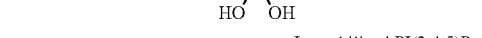
Immobilized PI(3,4,5)P₃
Immobilized PI(3,5)P₂
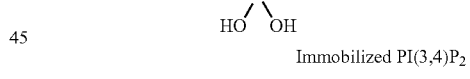
Immobilized PI(3,4)P₂
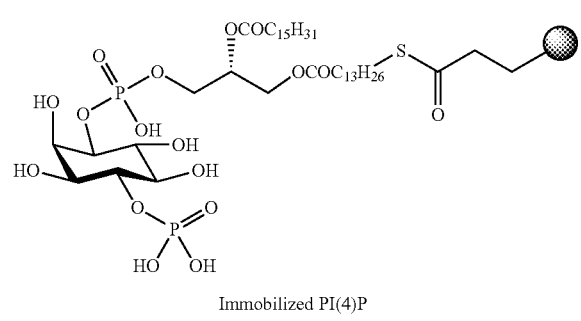
Immobilized PI(3)P
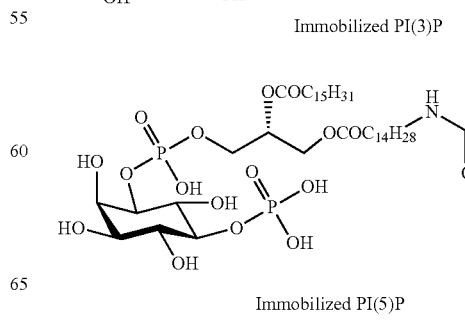
Immobilized PI(5)P -continued
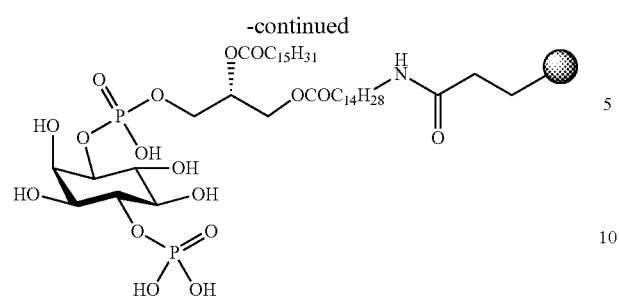
Immobilized PI(4)P
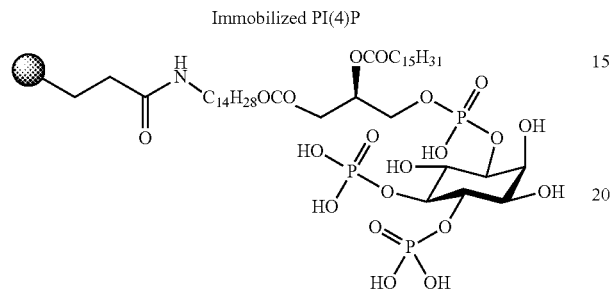
Immobilized PI(4,5)P$_2$
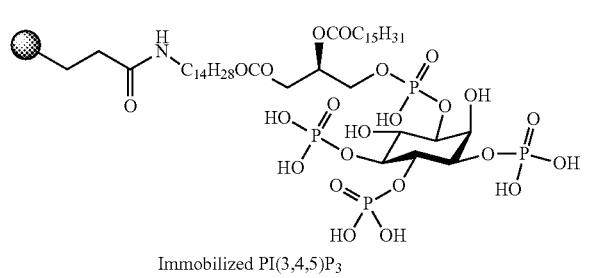
Immobilized PI(3,4,5)P$_3$
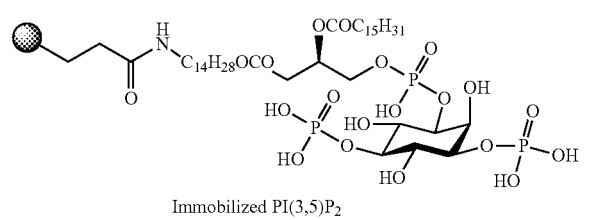
Immobilized PI(3,5)P$_2$
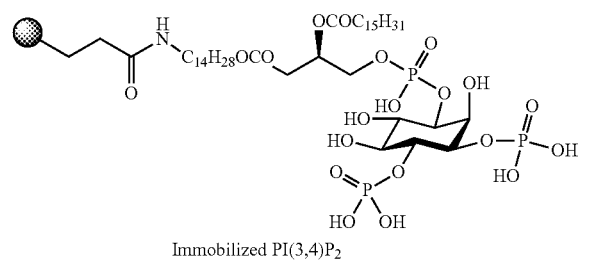
Immobilized PI(3,4)P$_2$
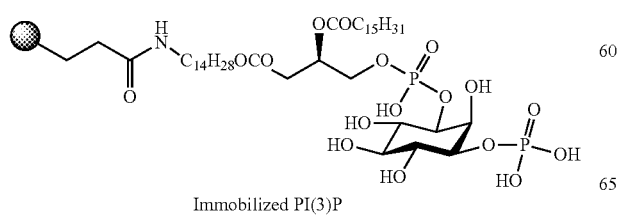
Immobilized PI(3)P
-continued
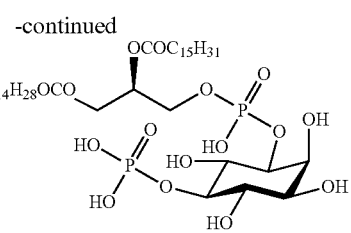
Immobilized PI(5)P
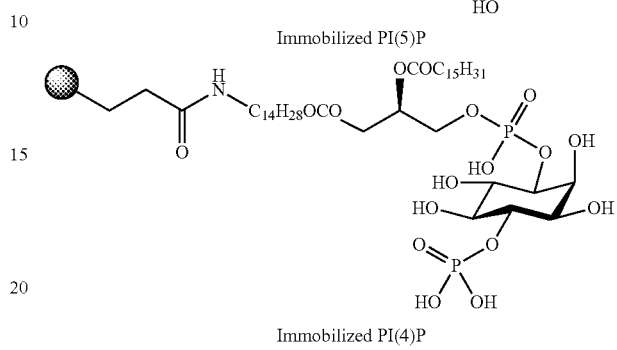
Immobilized PI(4)P
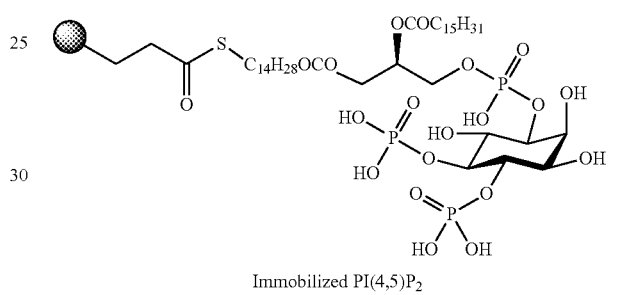
Immobilized PI(4,5)P$_2$
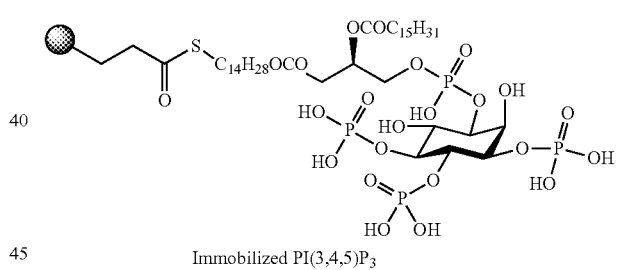
Immobilized PI(3,4,5)P$_3$
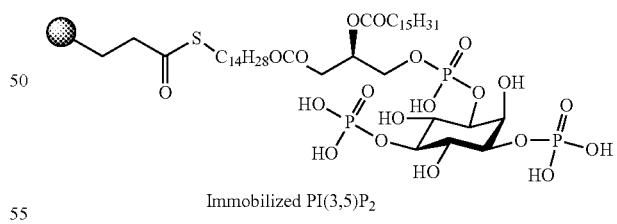
Immobilized PI(3,5)P$_2$
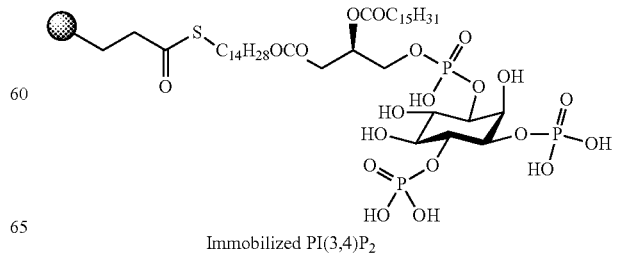
Immobilized PI(3,4)P$_2$ -continued
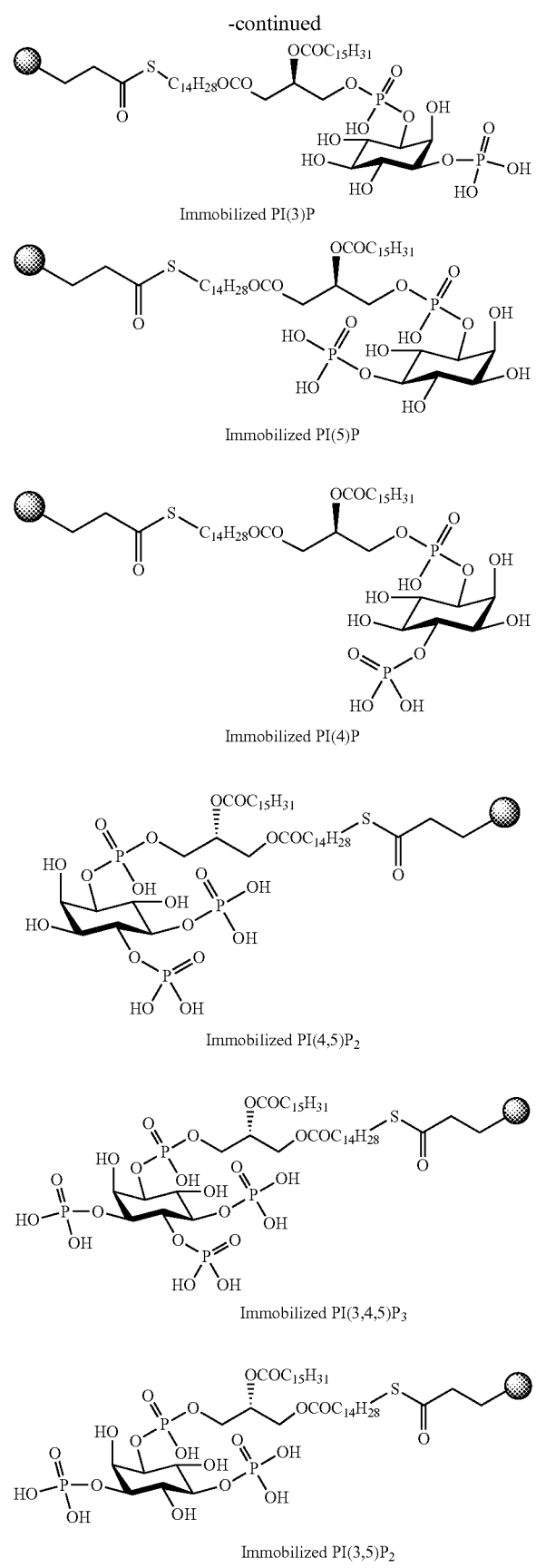
Immobilized PI(3)P
Immobilized PI(5)P
Immobilized PI(4)P
Immobilized PI(4,5)P$_2$
Immobilized PI(3,4,5)P$_3$
Immobilized PI(3,5)P$_2$
-continued
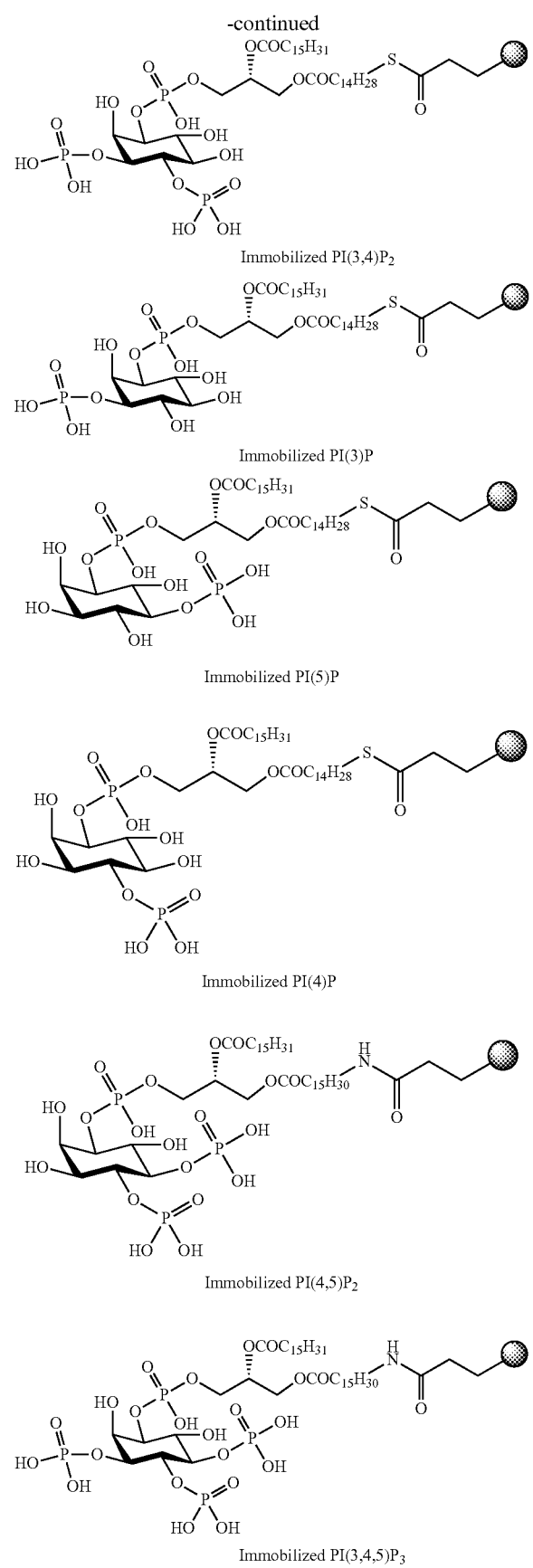
Immobilized PI(3,4)P$_2$
Immobilized PI(3)P
Immobilized PI(5)P
Immobilized PI(4)P
Immobilized PI(4,5)P$_2$
Immobilized PI(3,4,5)P$_3$

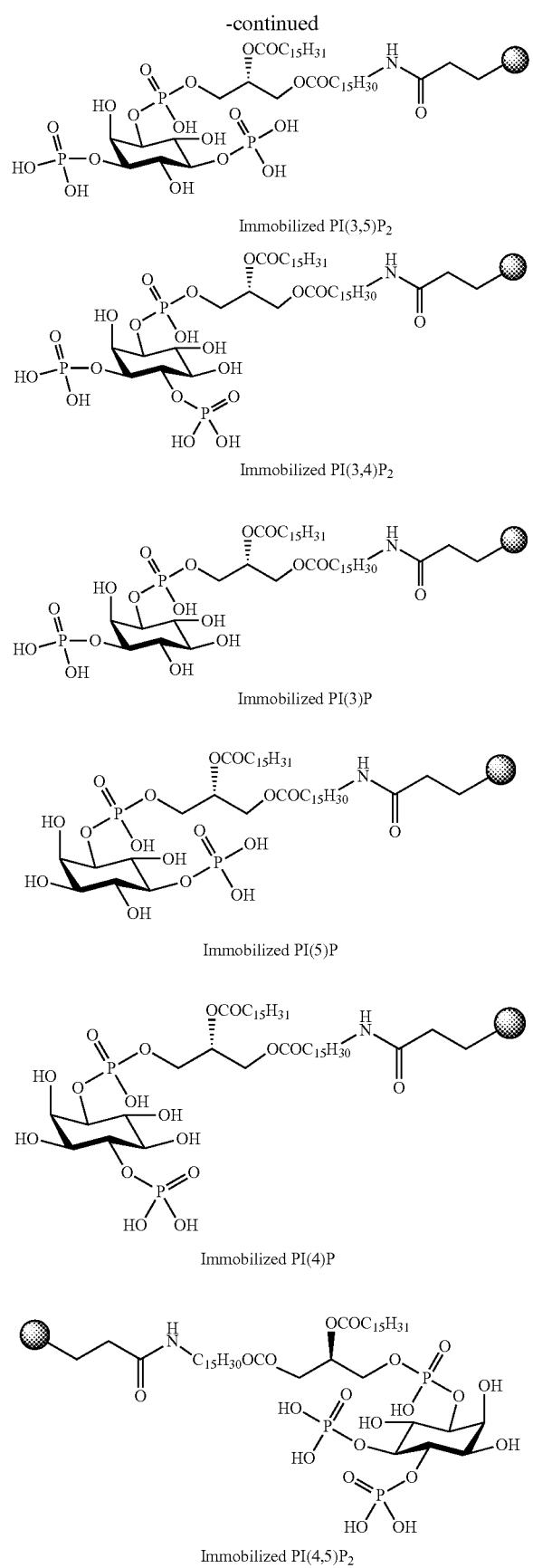
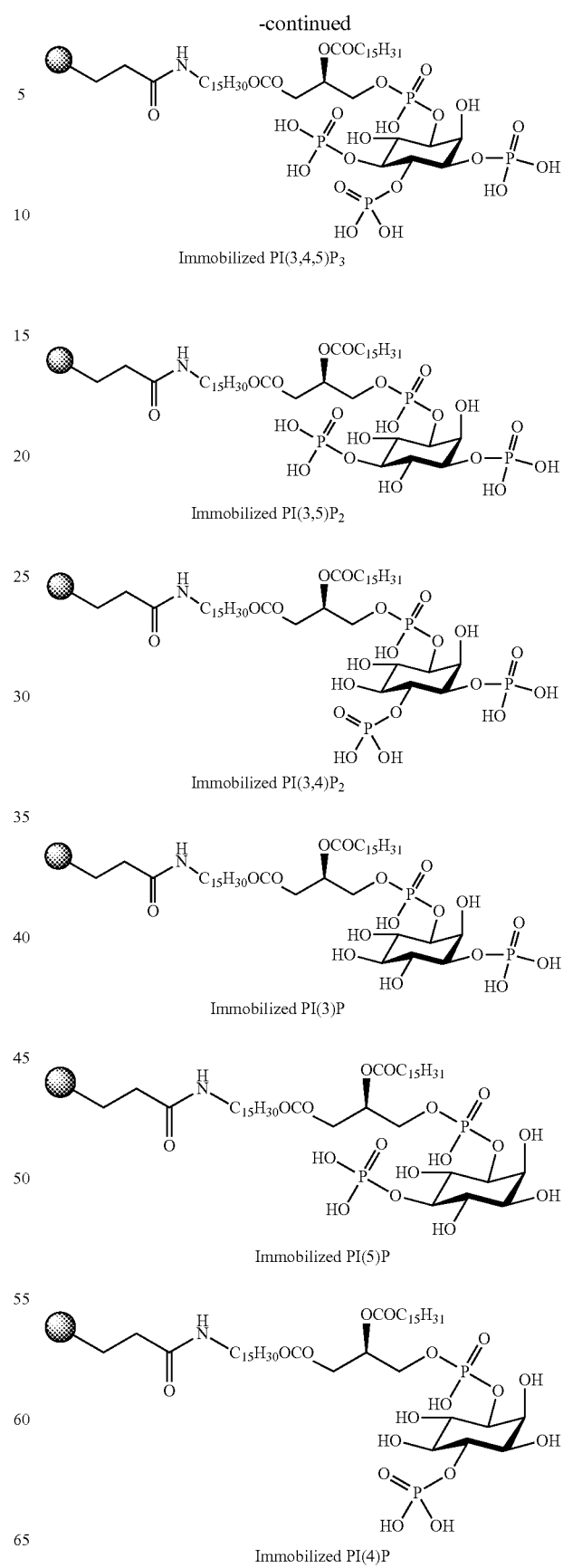

-continued
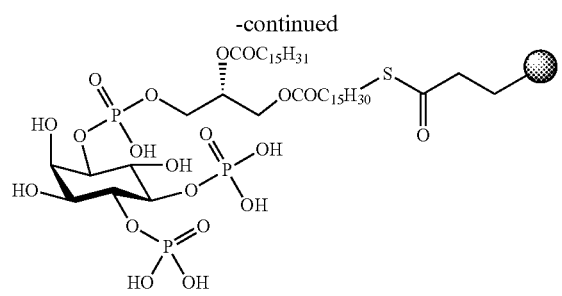
Immobilized PI(4,5)P₂
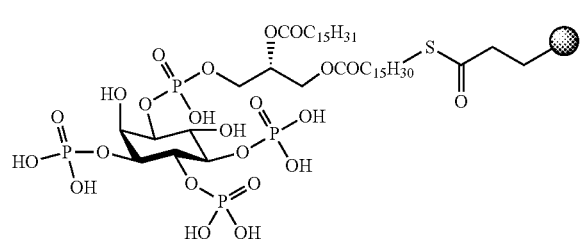
Immobilized PI(3,4,5)P₃
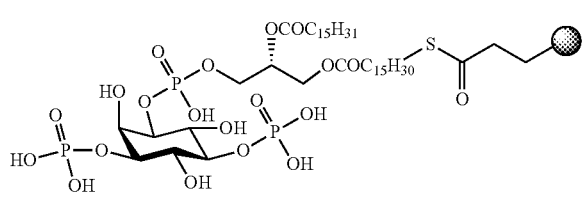
Immobilized PI(3,5)P₂
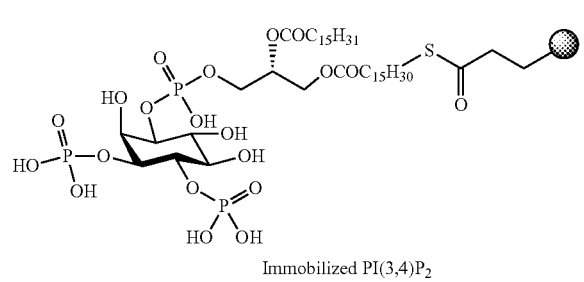
Immobilized PI(3,4)P₂
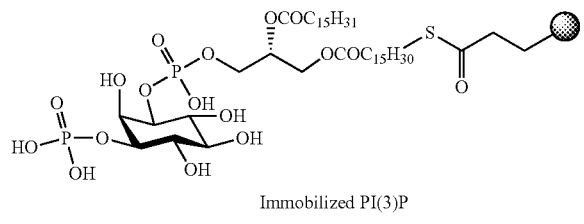
Immobilized PI(3)P
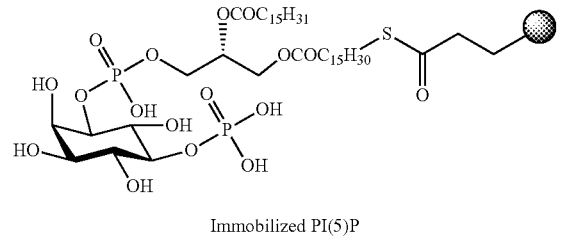
Immobilized PI(5)P
-continued
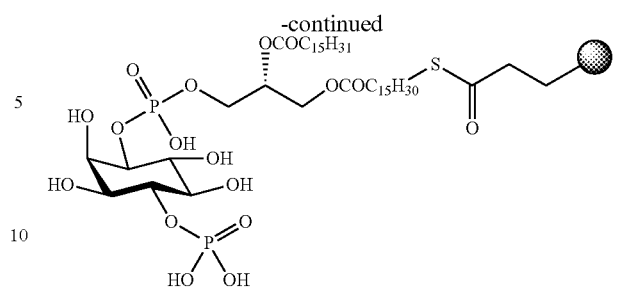
Immobilized PI(4)P
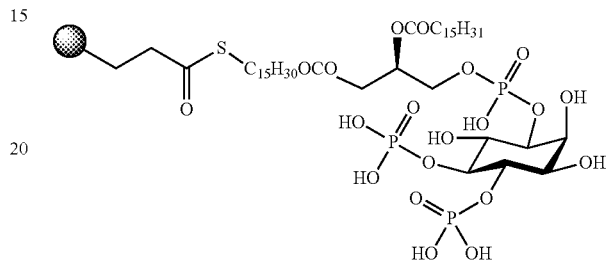
Immobilized PI(4,5)P₂
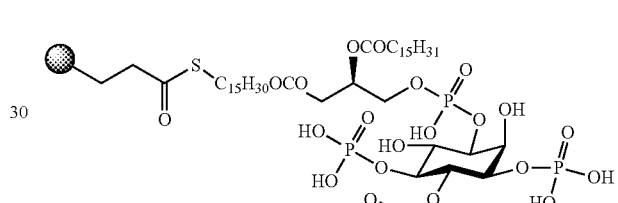
Immobilized PI(3,4,5)P₃
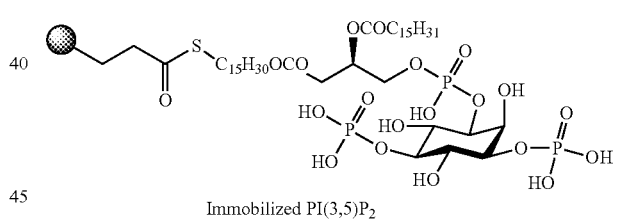
Immobilized PI(3,5)P₂
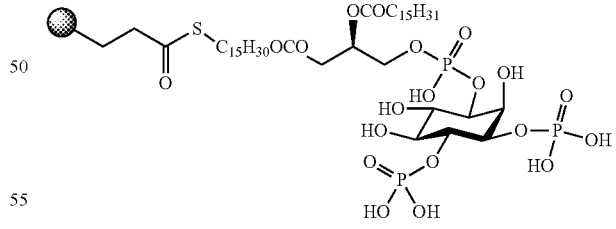
Immobilized PI(3,4)P₂
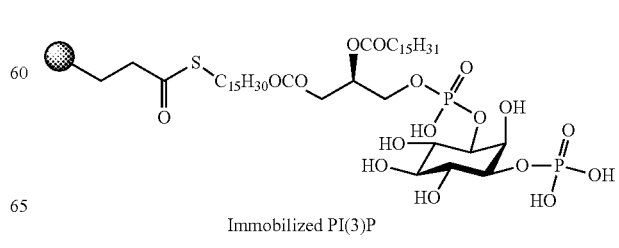
Immobilized PI(3)P -continued
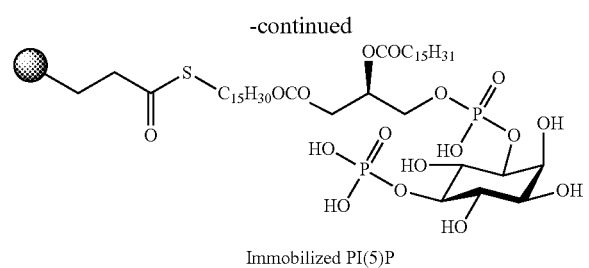
Immobilized PI(5)P
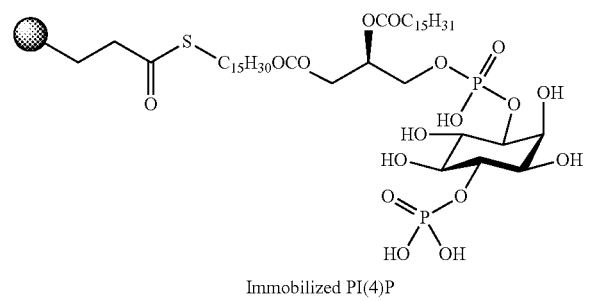
Immobilized PI(4)P
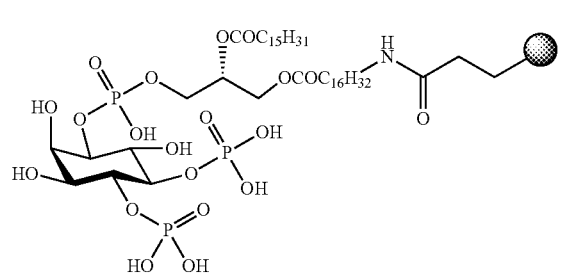
Immobilized PI(4,5)P$_2$
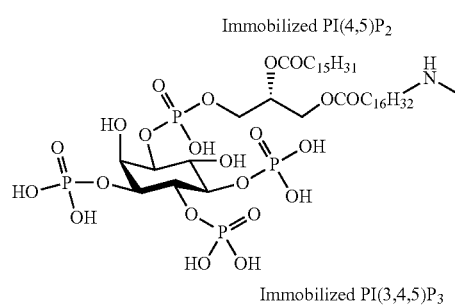
Immobilized PI(3,4,5)P$_3$
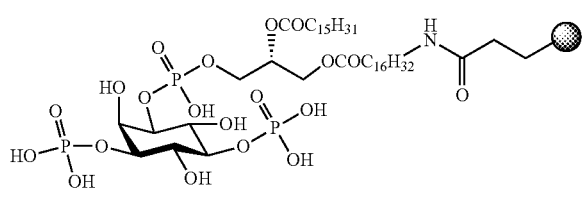
Immobilized PI(3,5)P$_2$
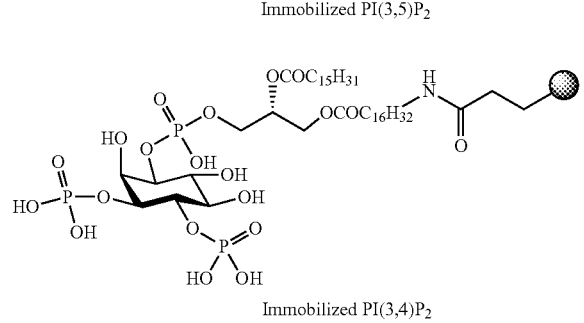
Immobilized PI(3,4)P$_2$
-continued
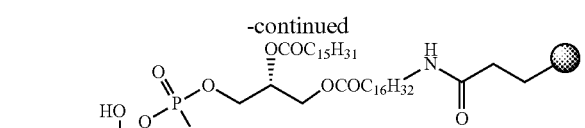
Immobilized PI(3)P
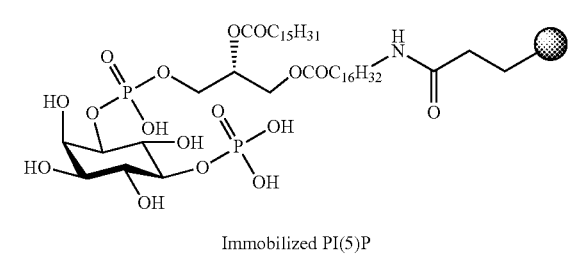
Immobilized PI(5)P
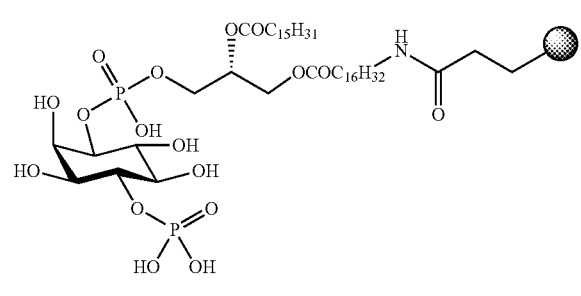
Immobilized PI(4)P
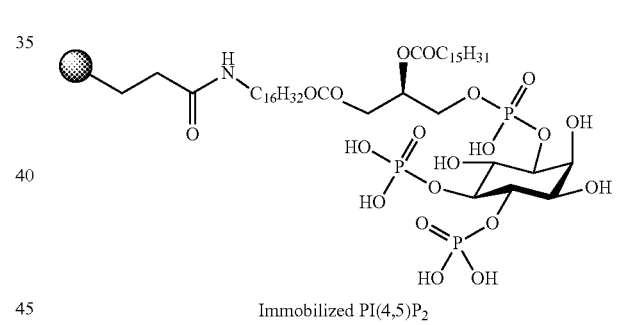
Immobilized PI(4,5)P$_2$
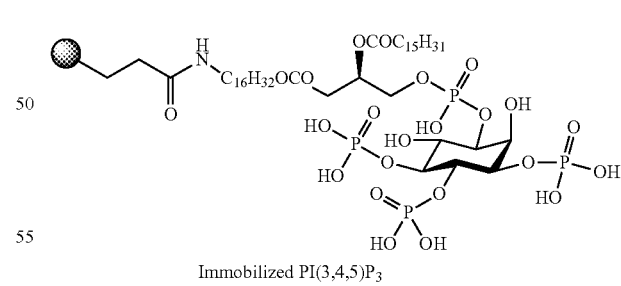
Immobilized PI(3,4,5)P$_3$
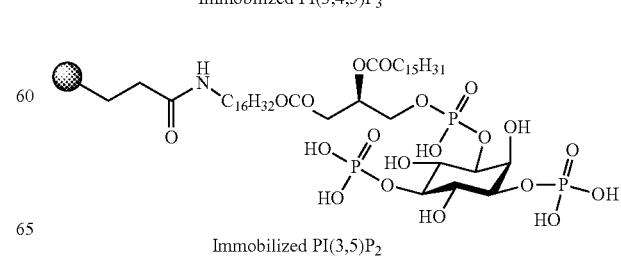
Immobilized PI(3,5)P$_2$

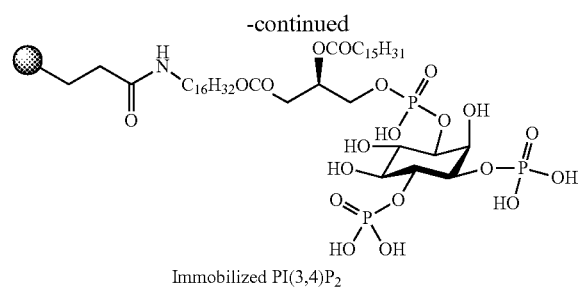
Immobilized PI(3,4)P$_2$
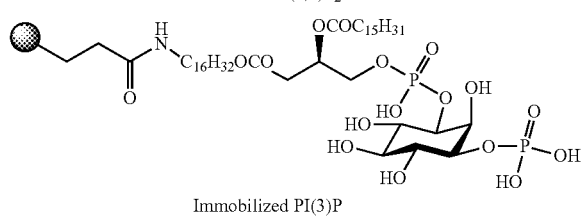
Immobilized PI(3)P
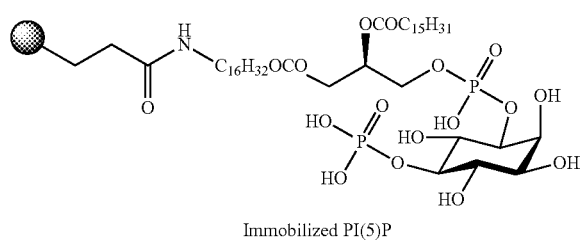
Immobilized PI(5)P
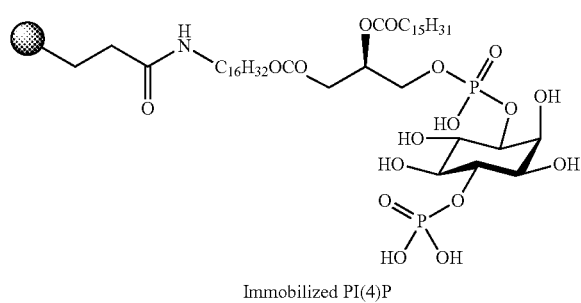
Immobilized PI(4)P
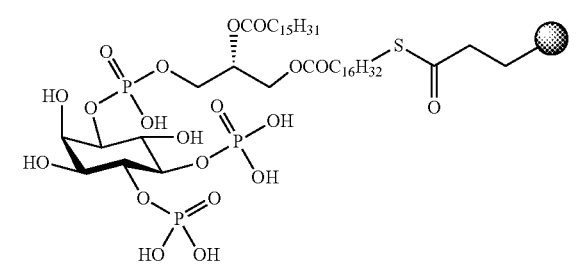
Immobilized PI(4,5)P$_2$
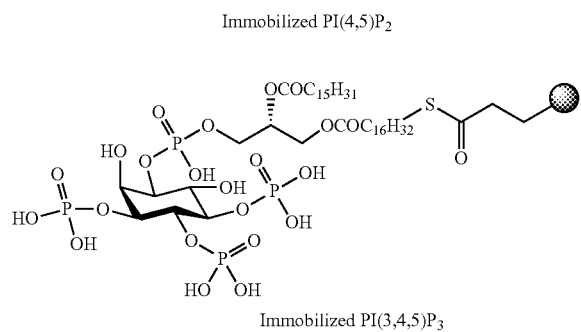
Immobilized PI(3,4,5)P$_3$
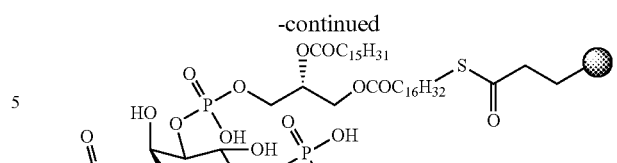
Immobilized PI(3,5)P$_2$
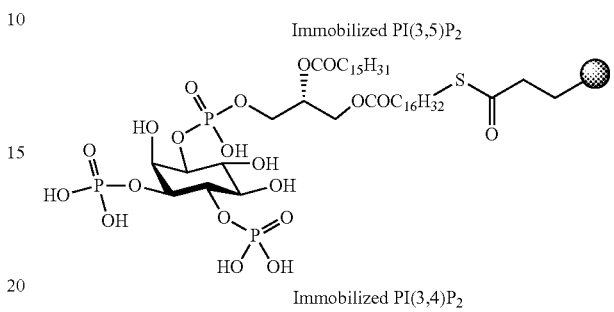
Immobilized PI(3,4)P$_2$
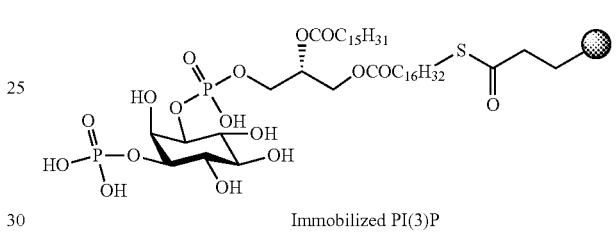
Immobilized PI(3)P
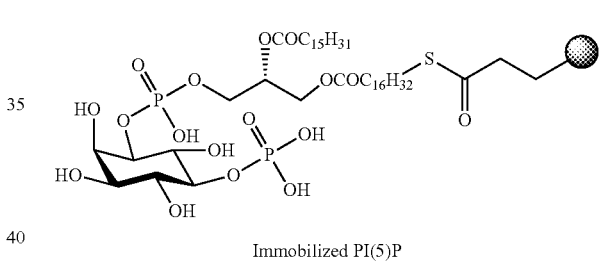
Immobilized PI(5)P
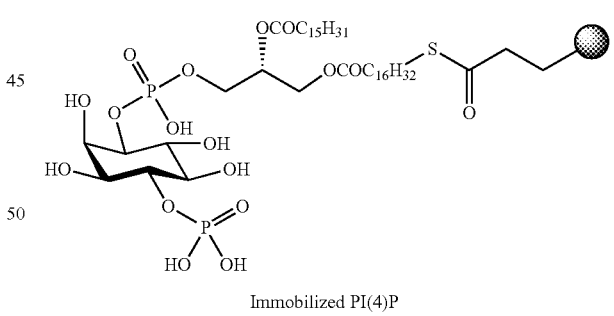
Immobilized PI(4)P
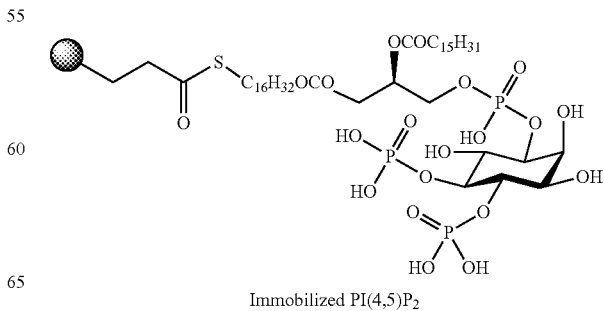
Immobilized PI(4,5)P$_2$

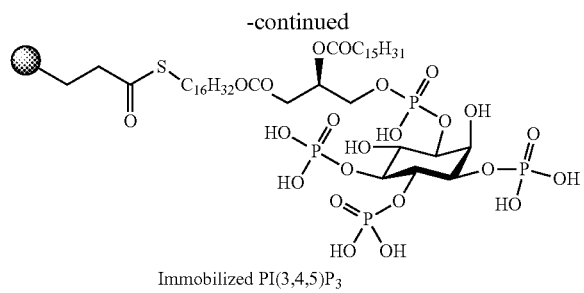

Immobilized PI(3,4,5)P$_3$

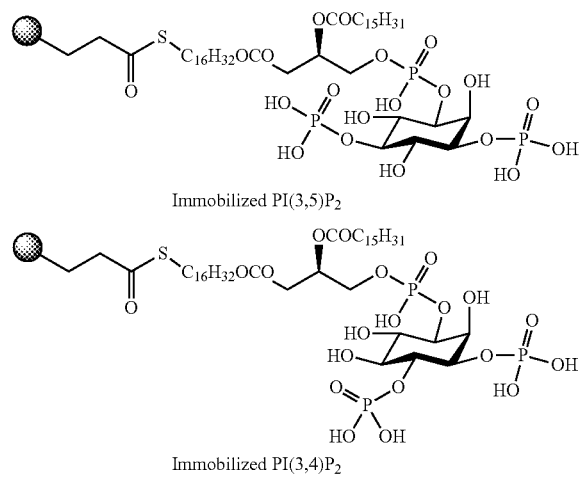

Immobilized PI(3,5)P$_2$

Immobilized PI(3,4)P$_2$

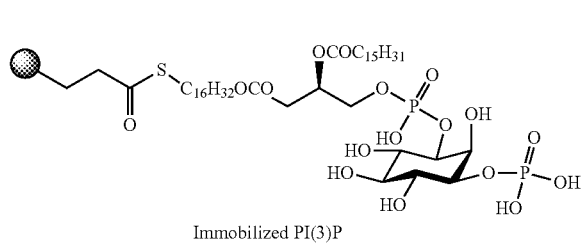

Immobilized PI(3)P

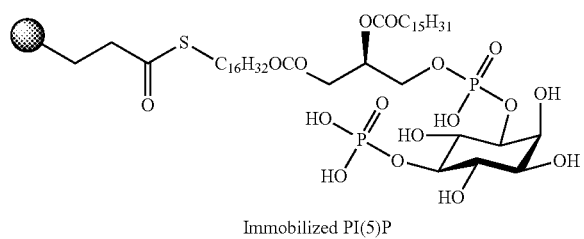

Immobilized PI(5)P

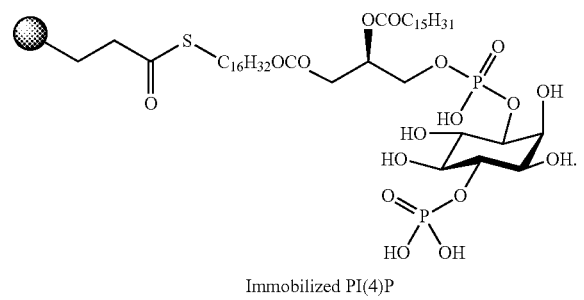

Immobilized PI(4)P

5. A probe consisting of a phosphatidic acid functionalised solid support of the general formula as is depicted in Formulae I, II, III or IV:

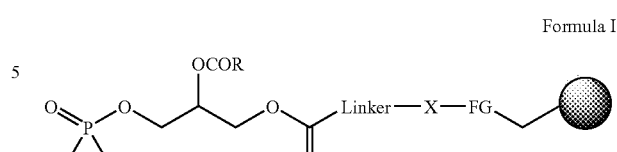
Formula I

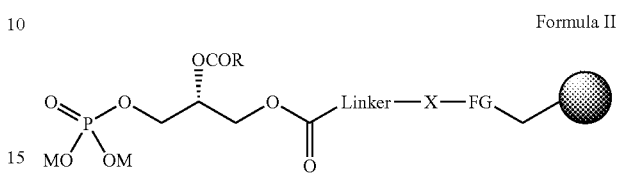
Formula II

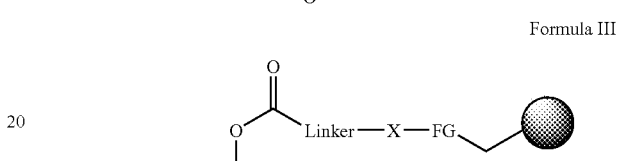
Formula III

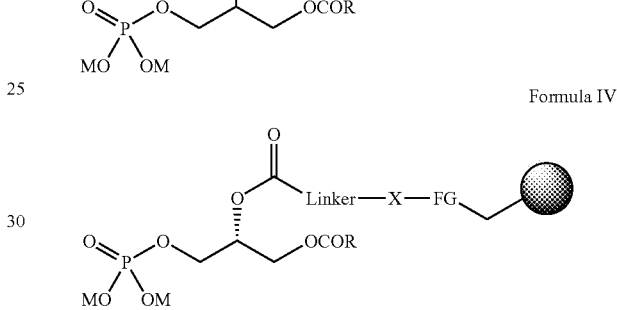
Formula IV (a) the linker consists of (CH$_2$)$_n$, with n=8-20;
(b) the heteroatom X is O, S, or NH;
(c) the functional group (FG) is a carbonyl from a carboxylate (thiolo)ester, or an amide;
(d) the R-substituent carries an aryl or alkyl group; R=C$_m$H$_{2m+1}$, where m=8-20;
(e) the ion M represents any cation, including Na$^+$ and NH4$^+$;
(f) unsaturations are allowed, including in an arachidonyl side chain; and
(g)

=solid support with attachment to functional group.

6. The probe according to claim 5, wherein the diacyl glycerol stereocenter is sn2.

7. The probe according to claim 5, wherein the diacyl glycerol stereocenter is the enantiomeric 2(S)-configuration.

8. The probe according to claim 5, wherein the phosphate head groups are substituted by phosphonic acid or thiono phosphate.

9. The probe according to claim 5 which has a formula of one of the compounds as listed below:

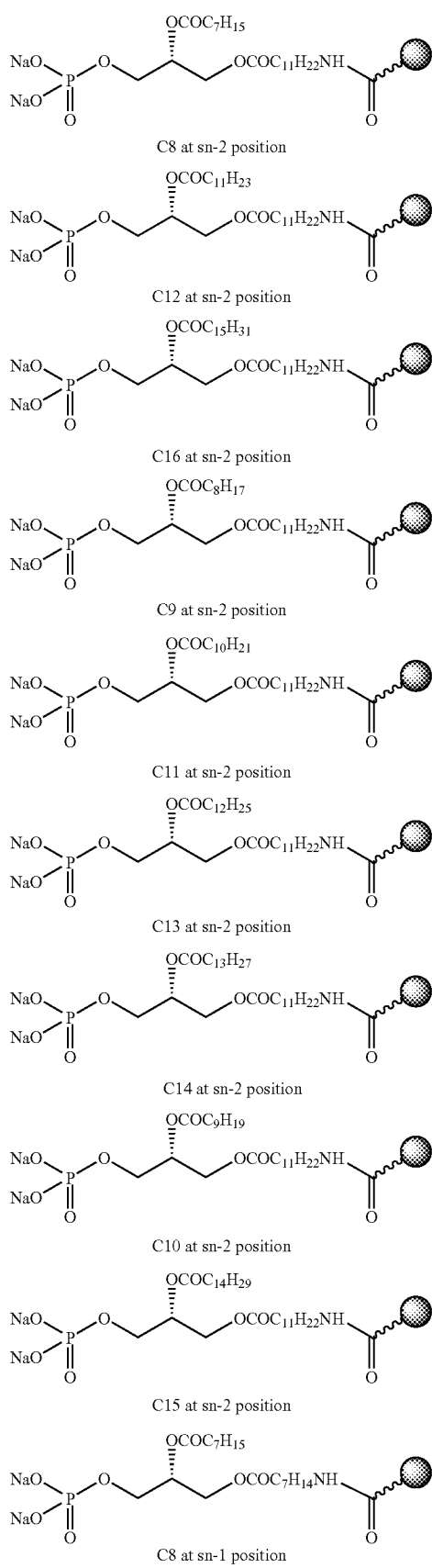
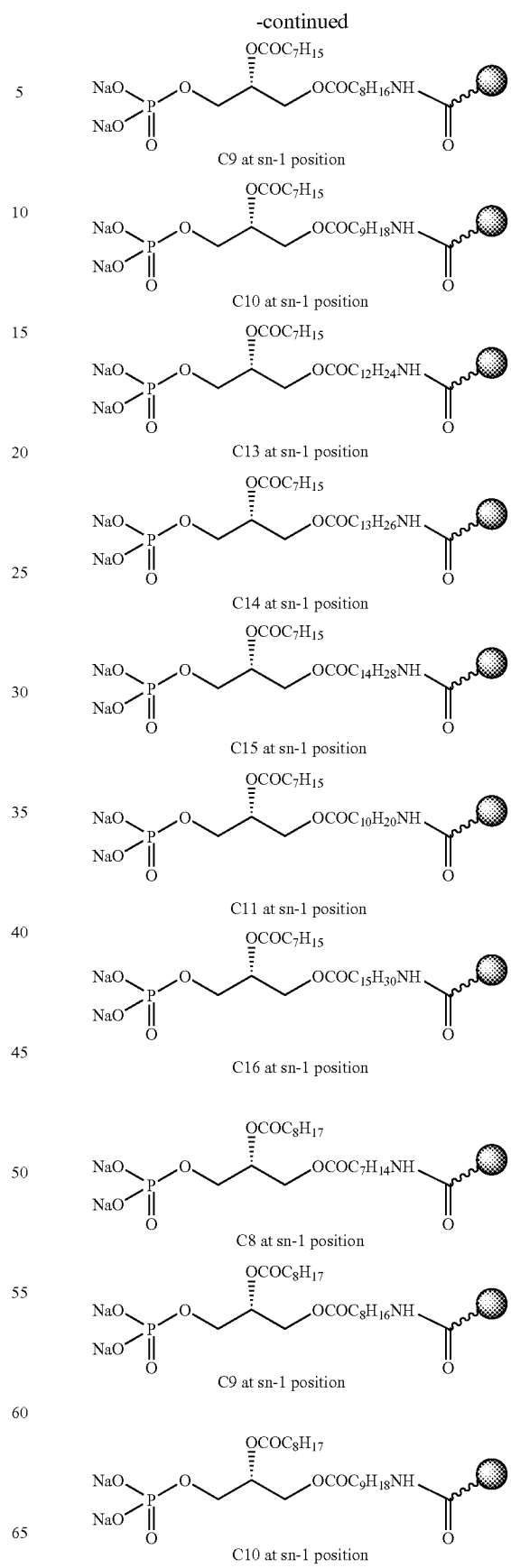

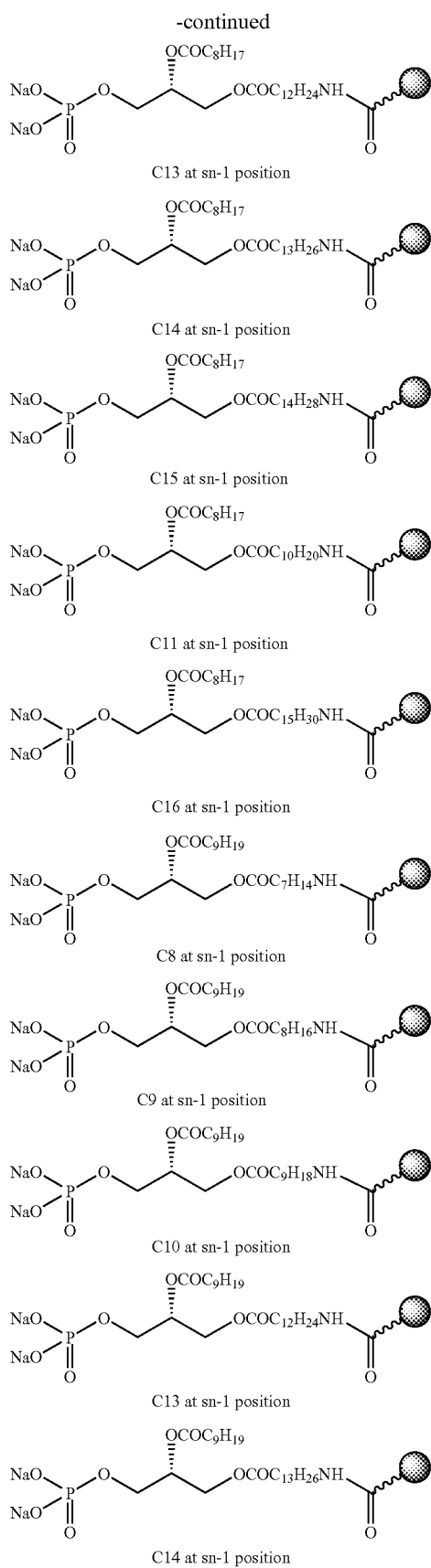
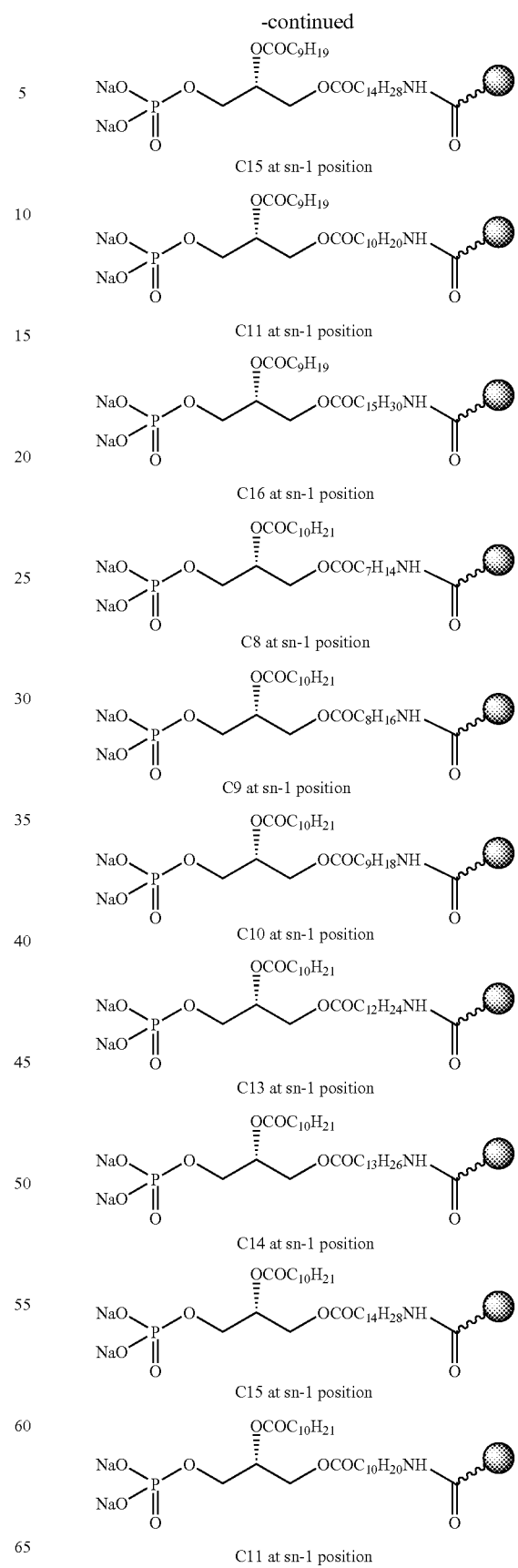

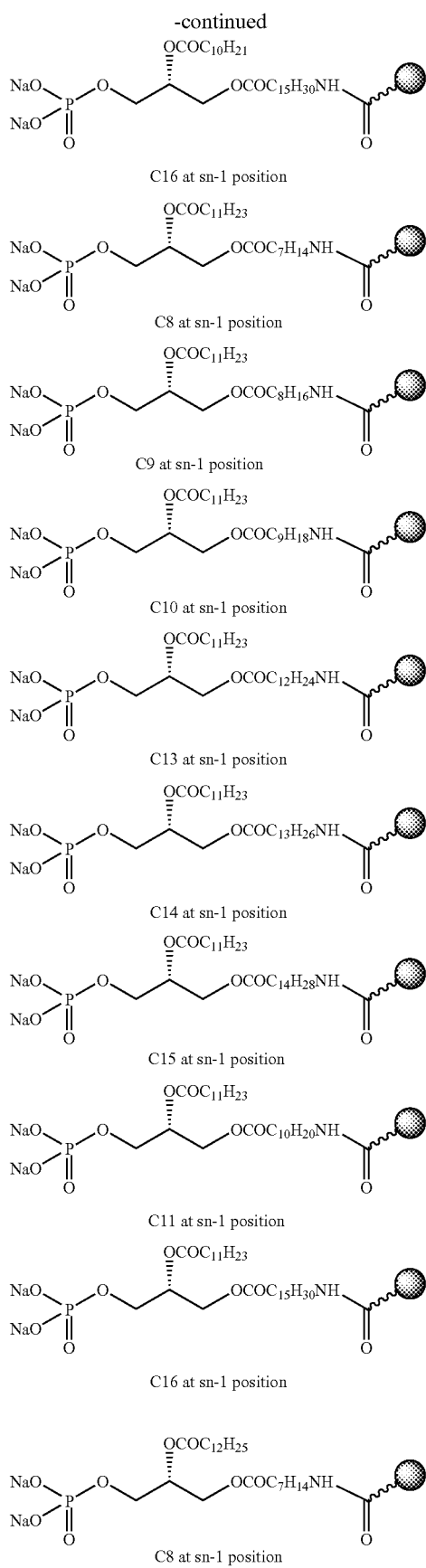
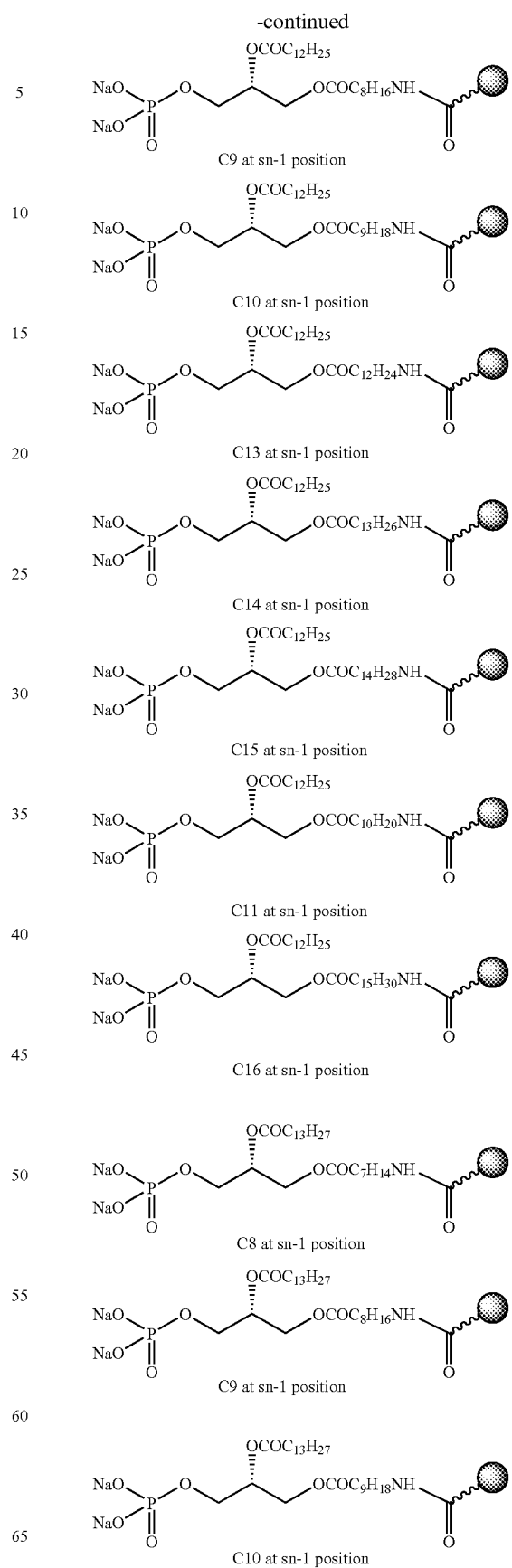

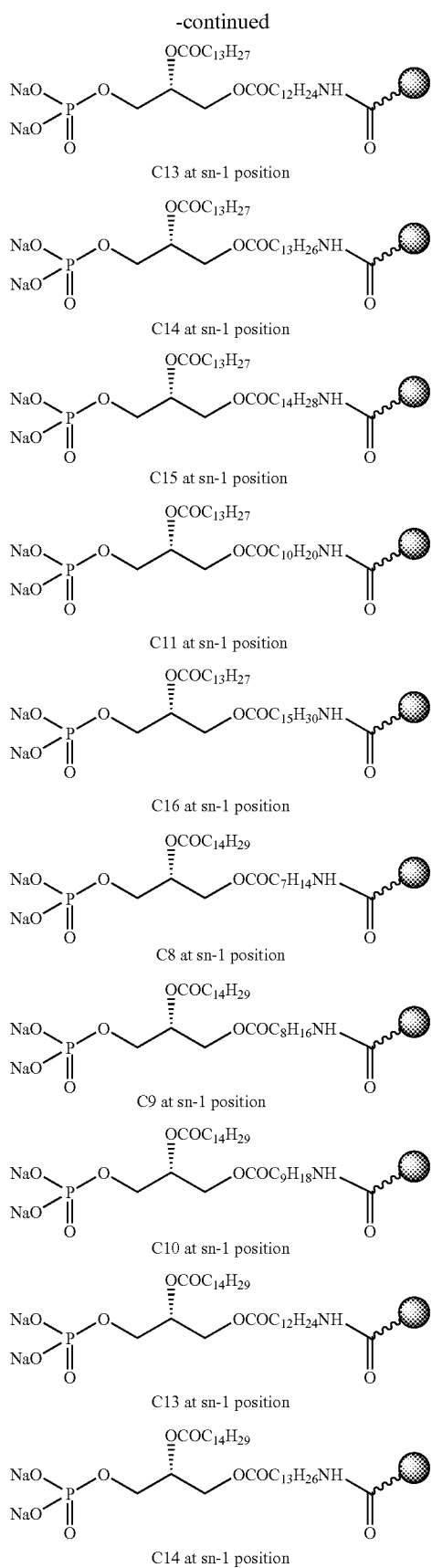
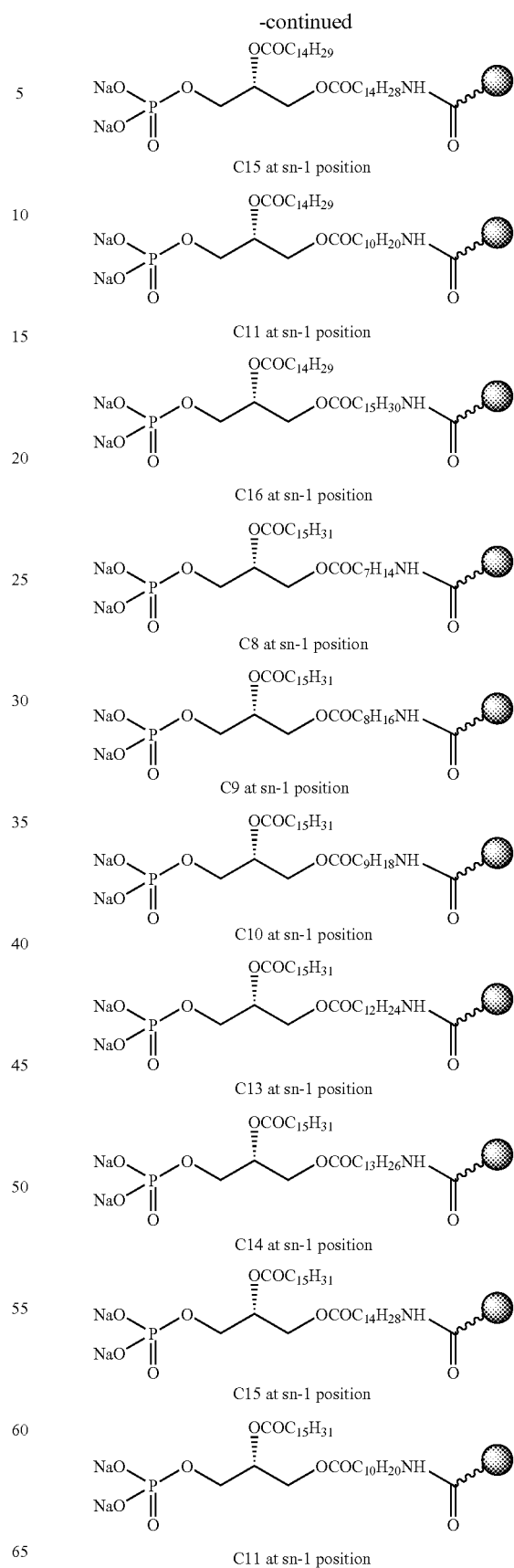

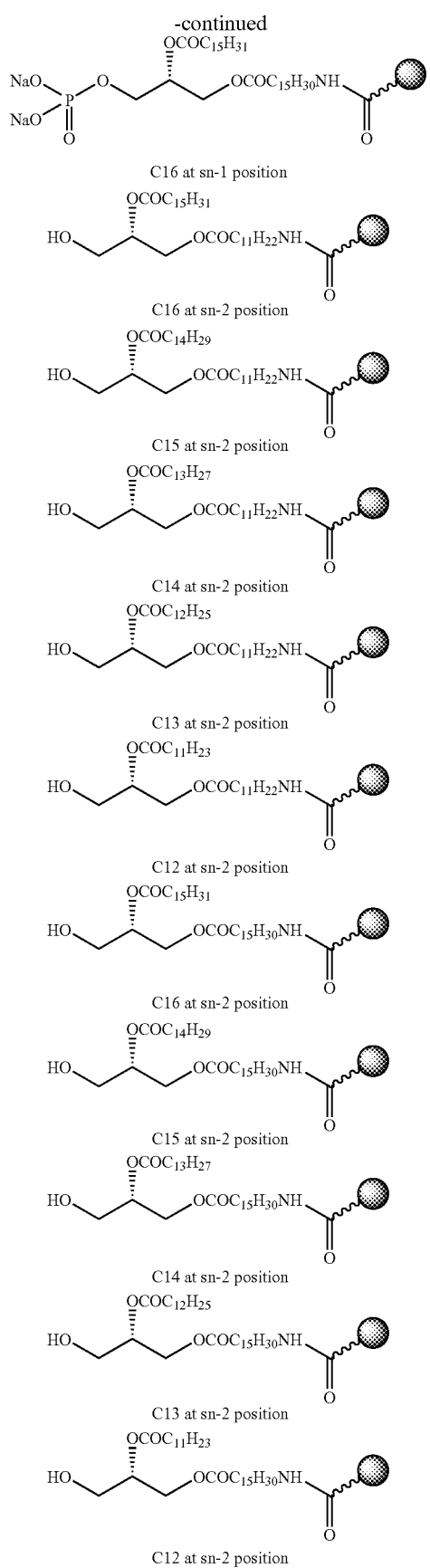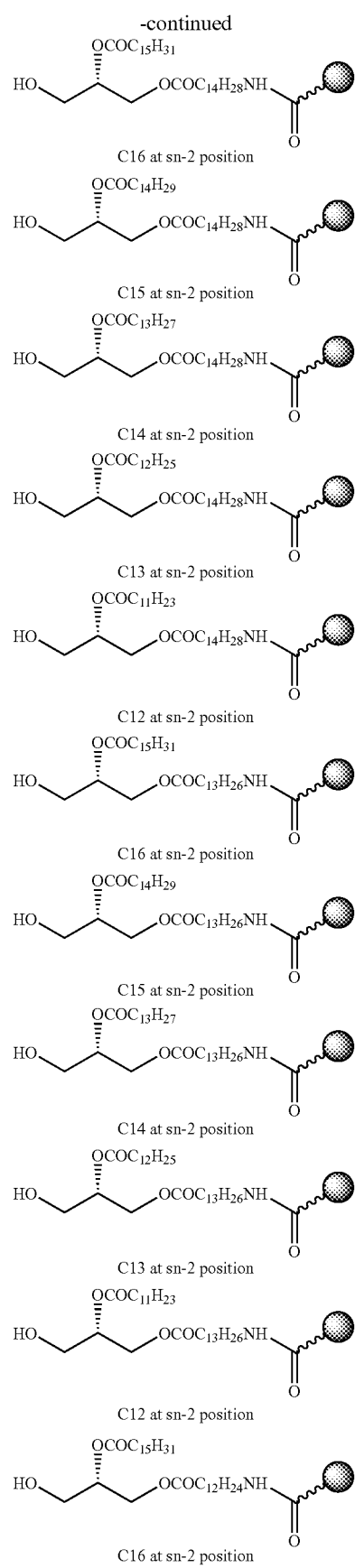

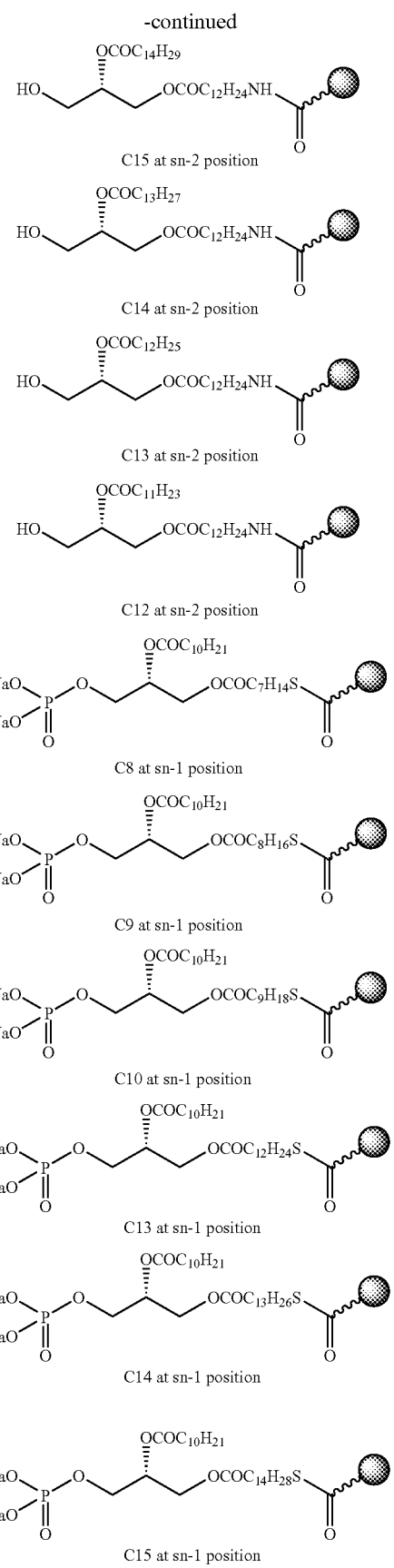
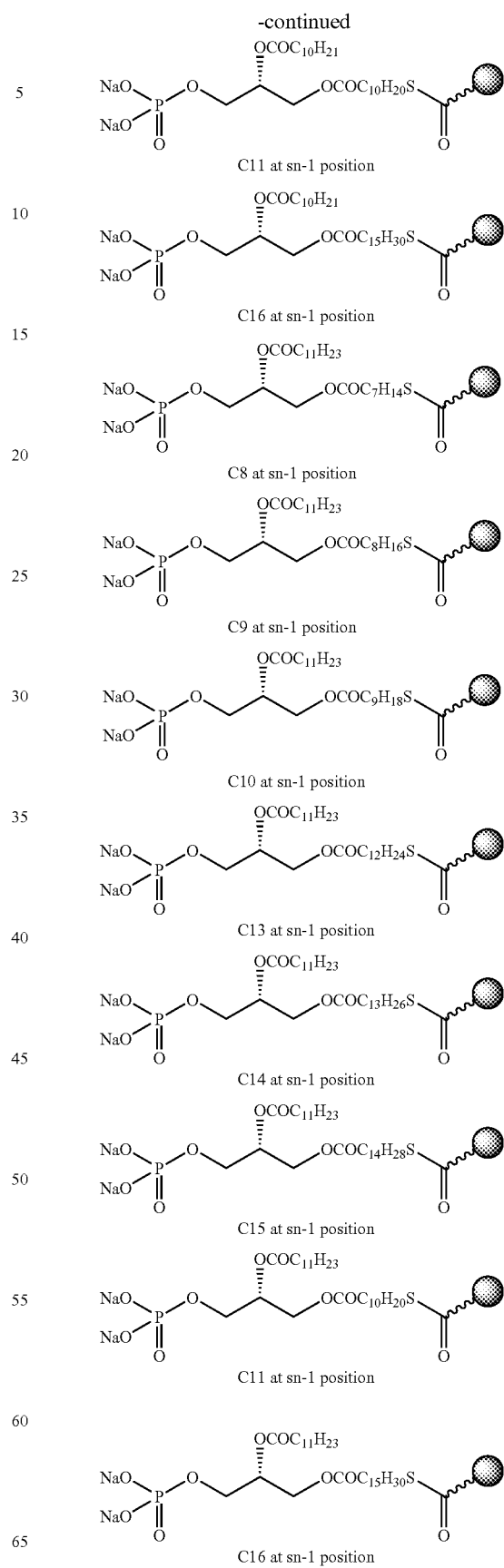

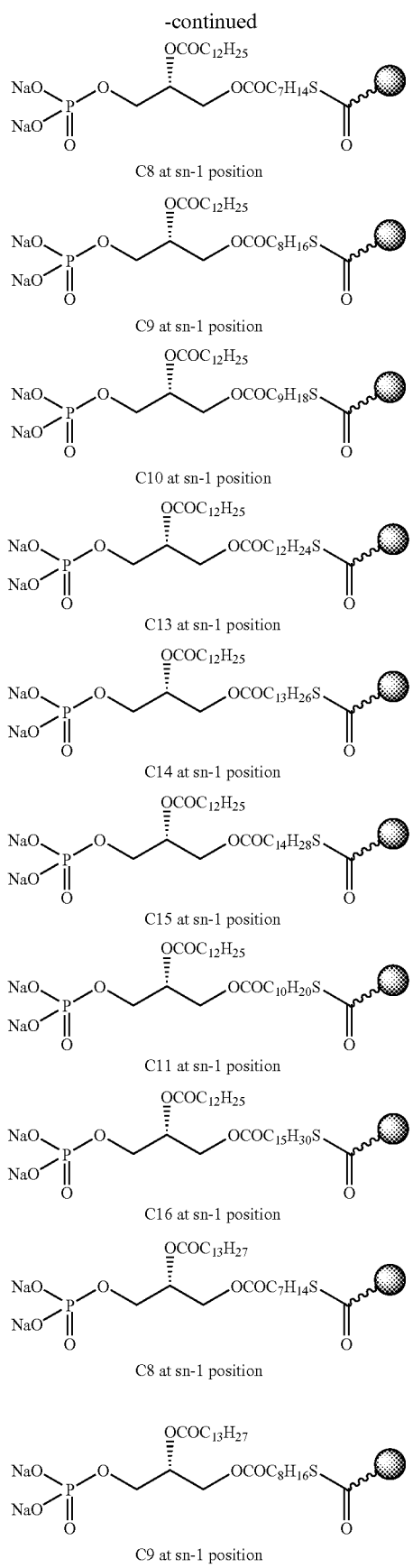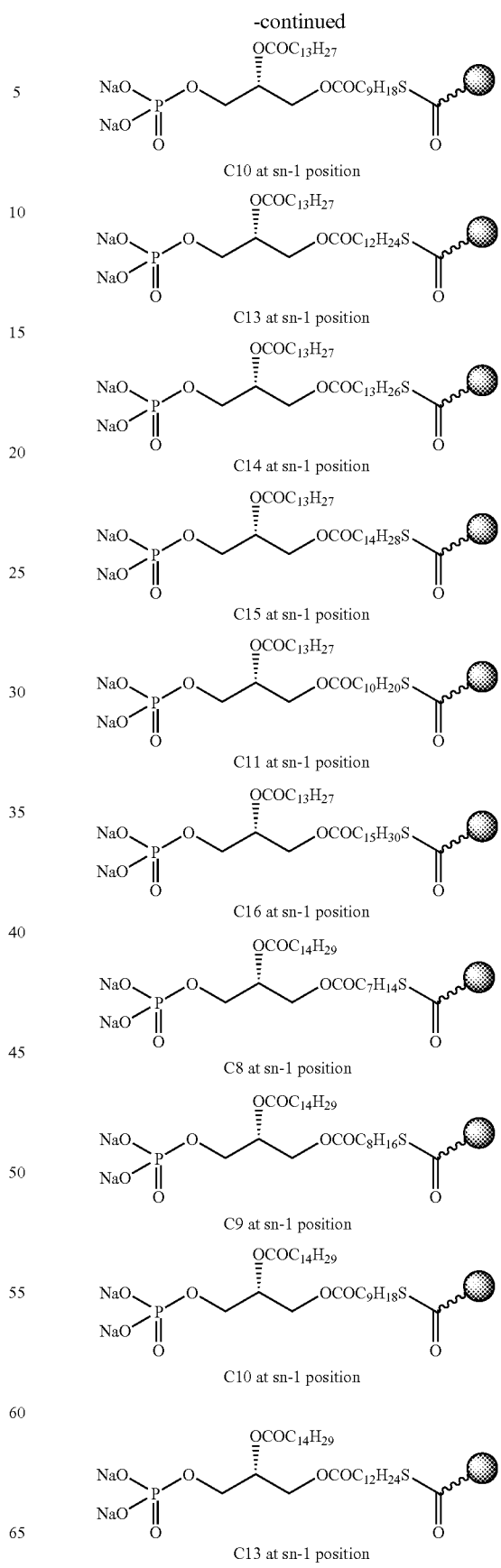

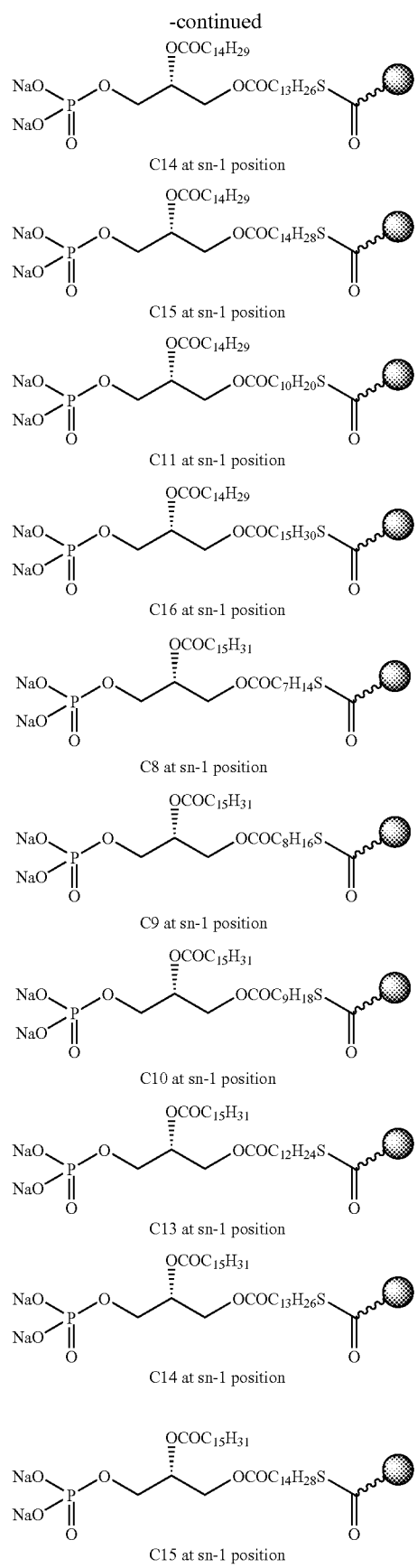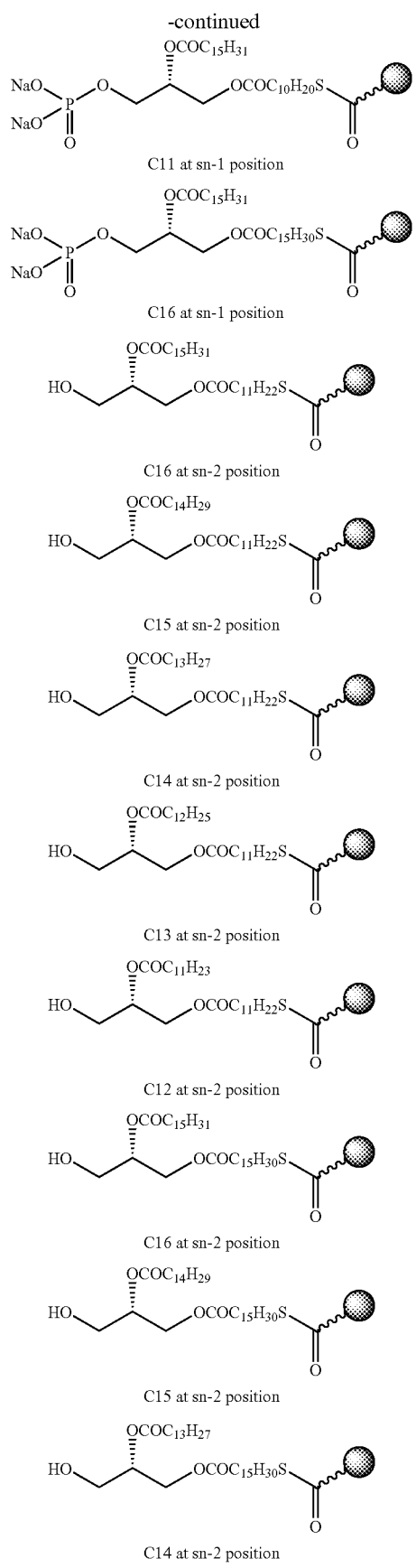

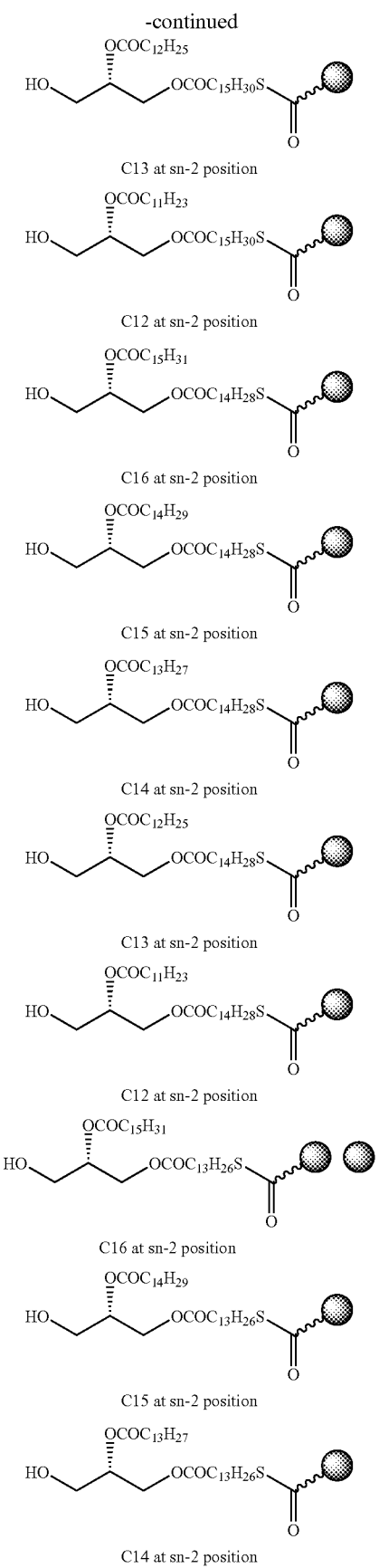
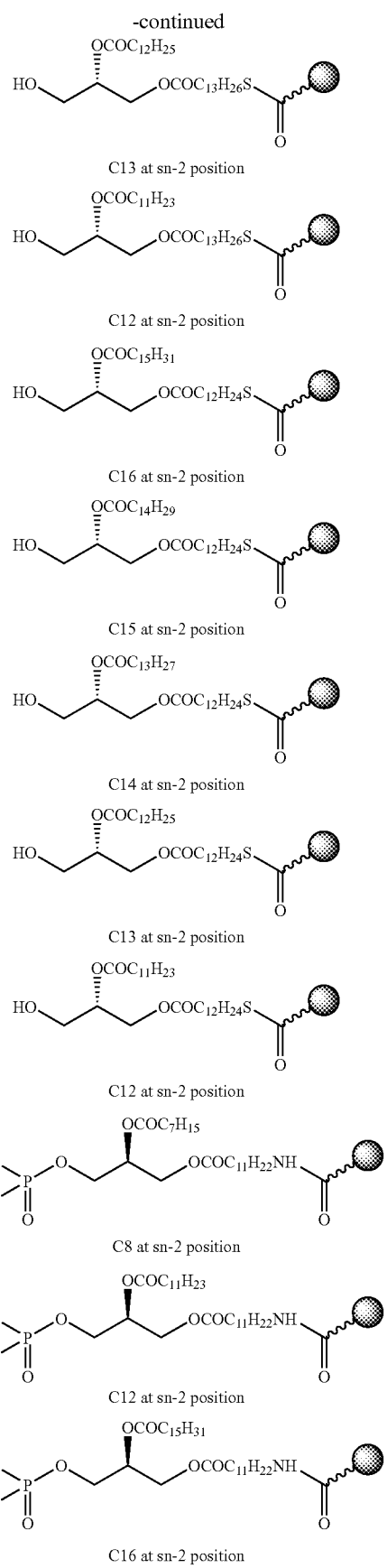

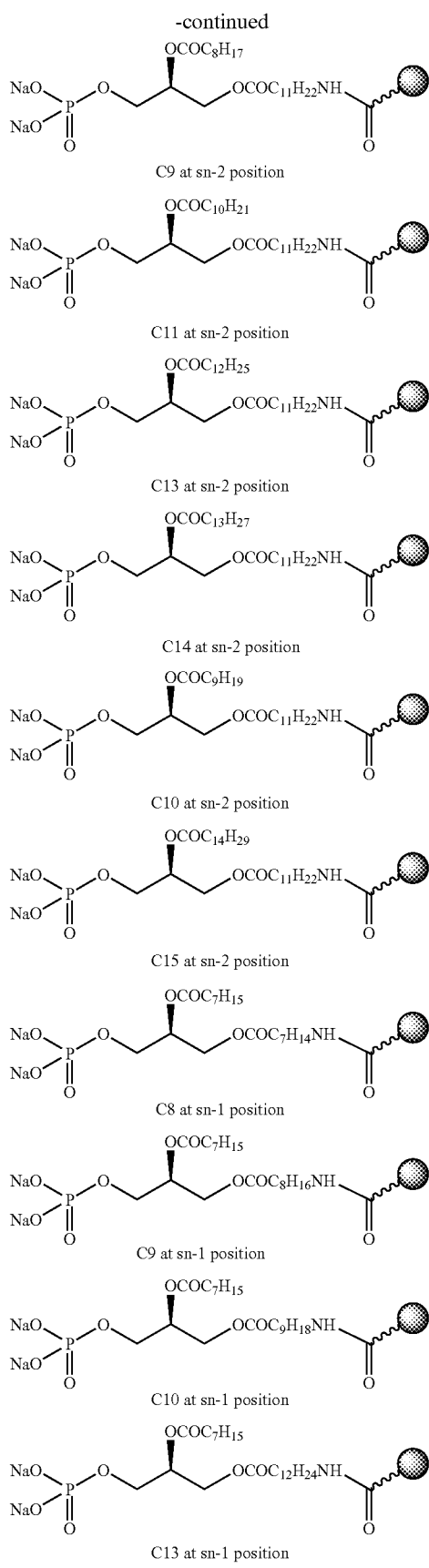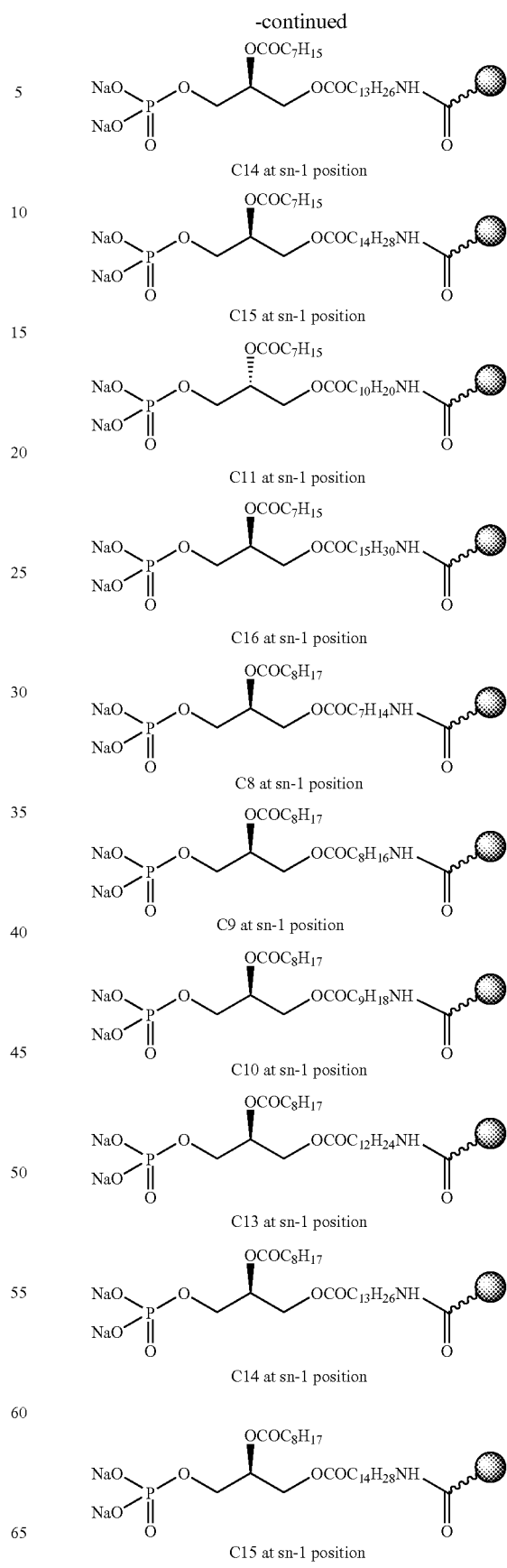

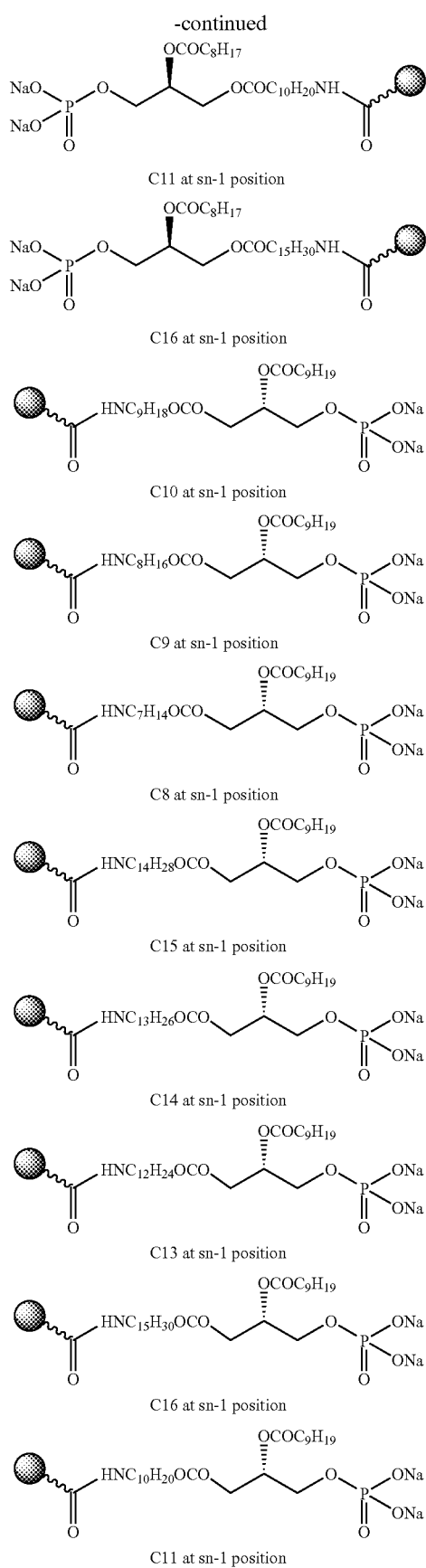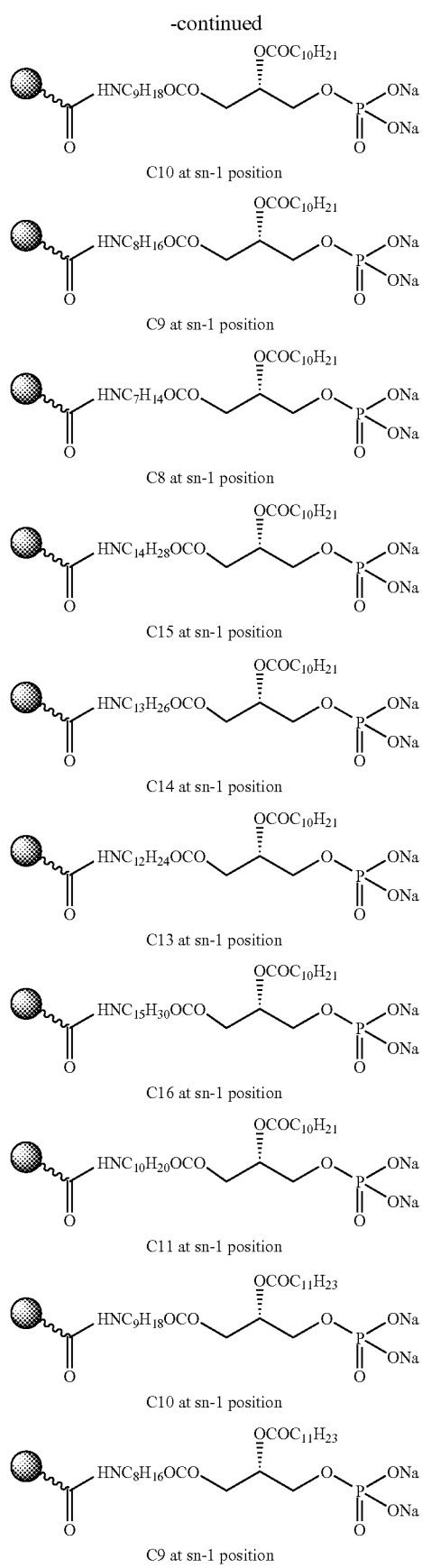

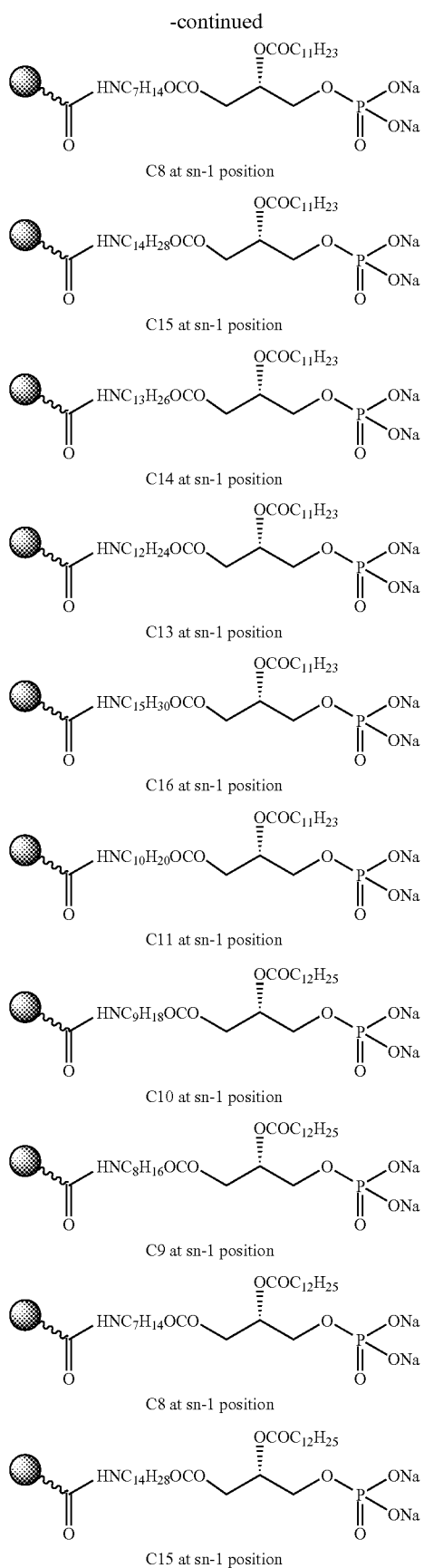
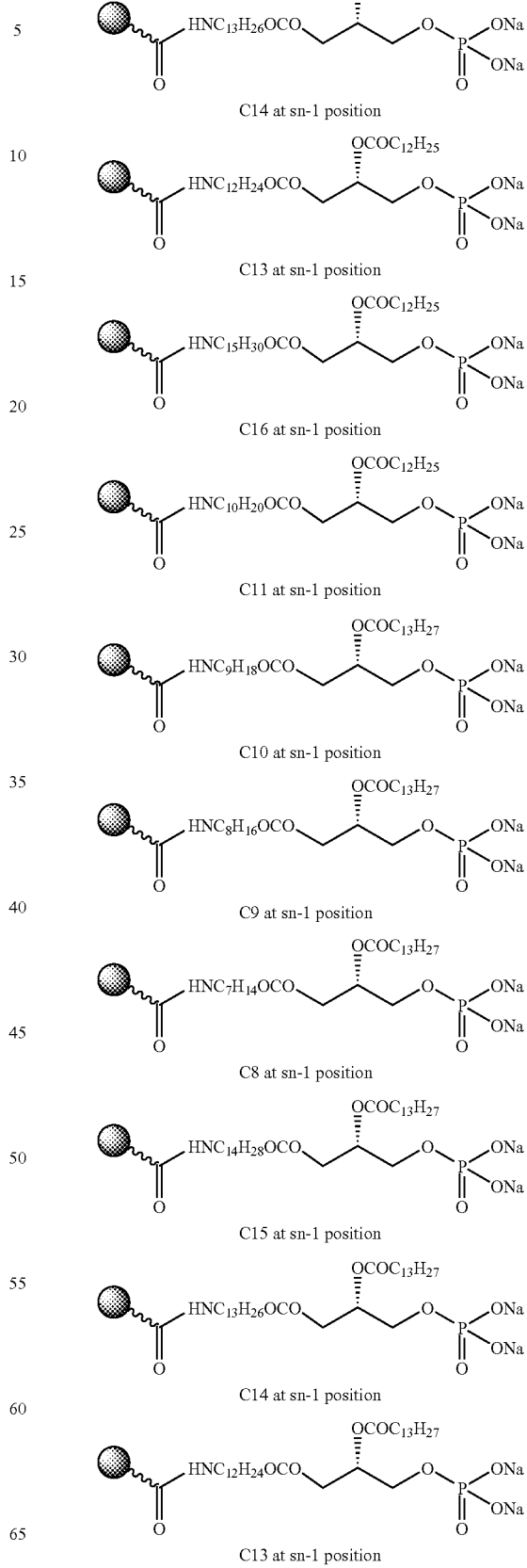

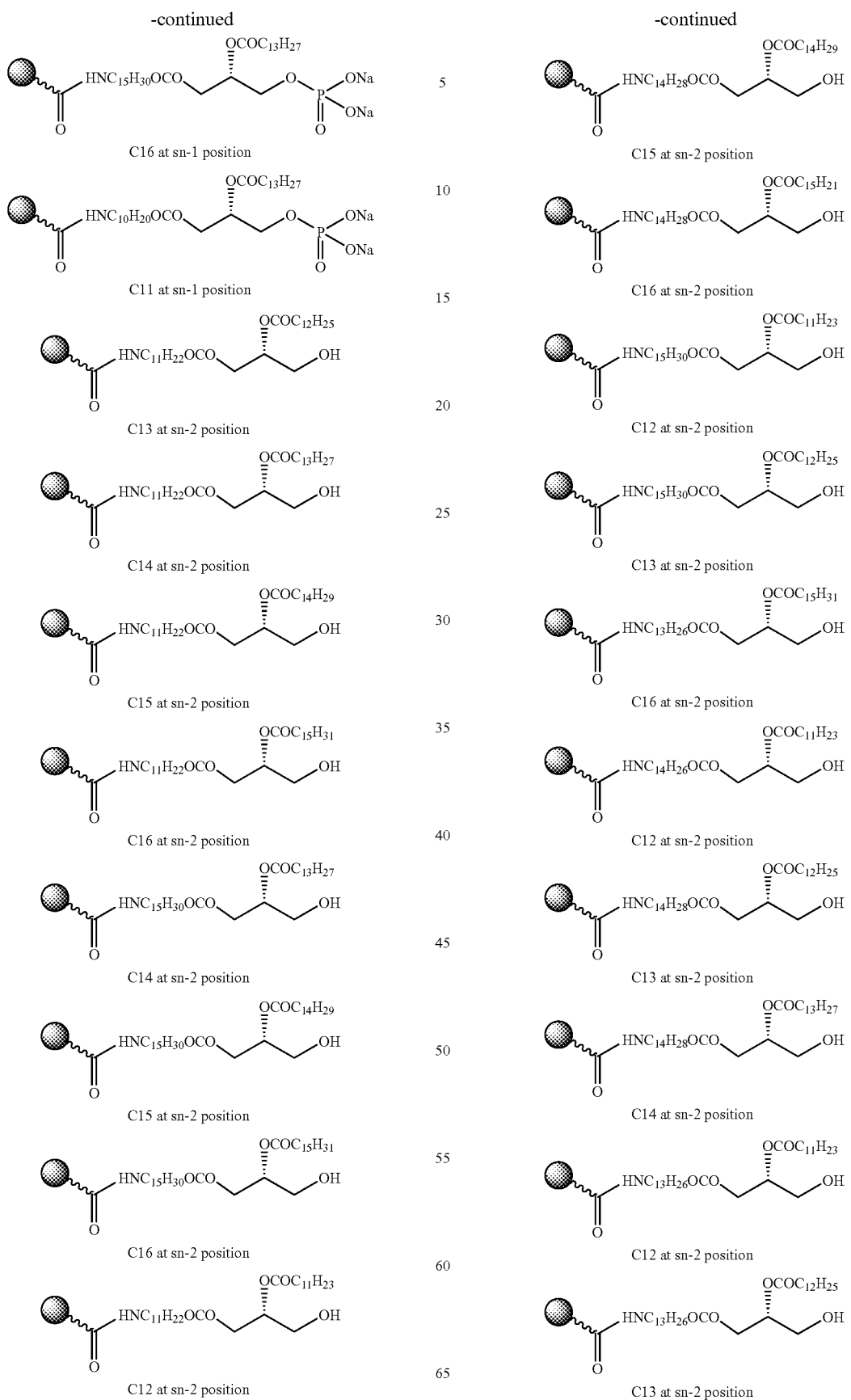

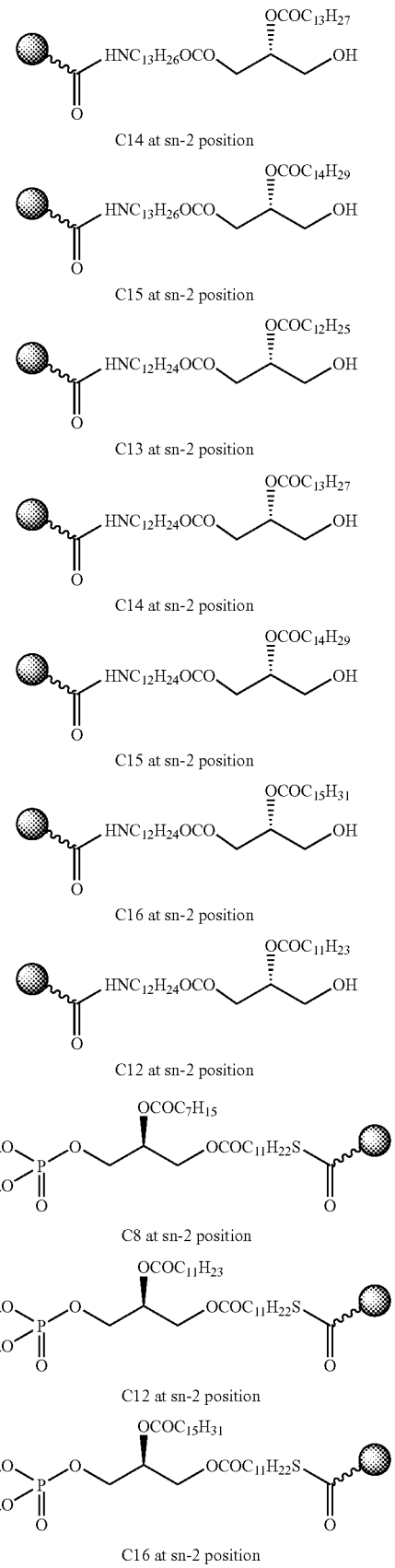
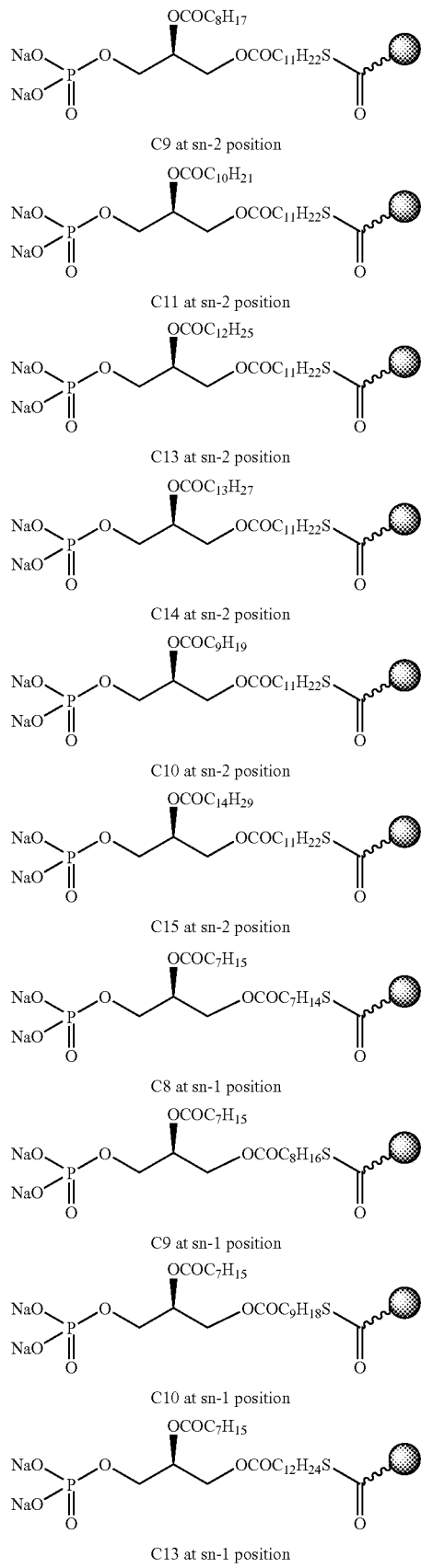

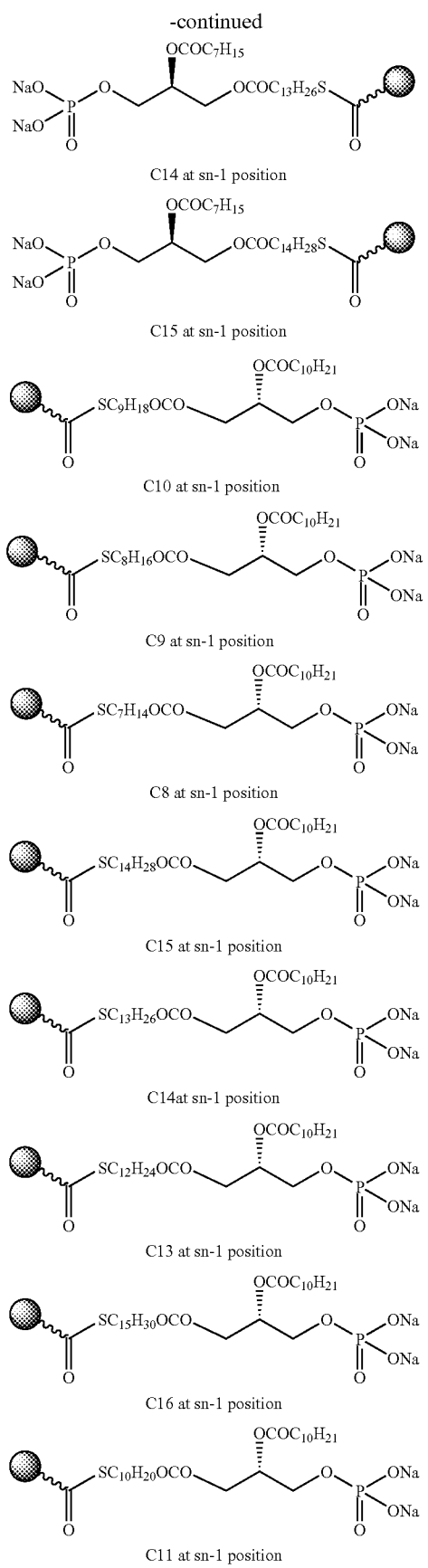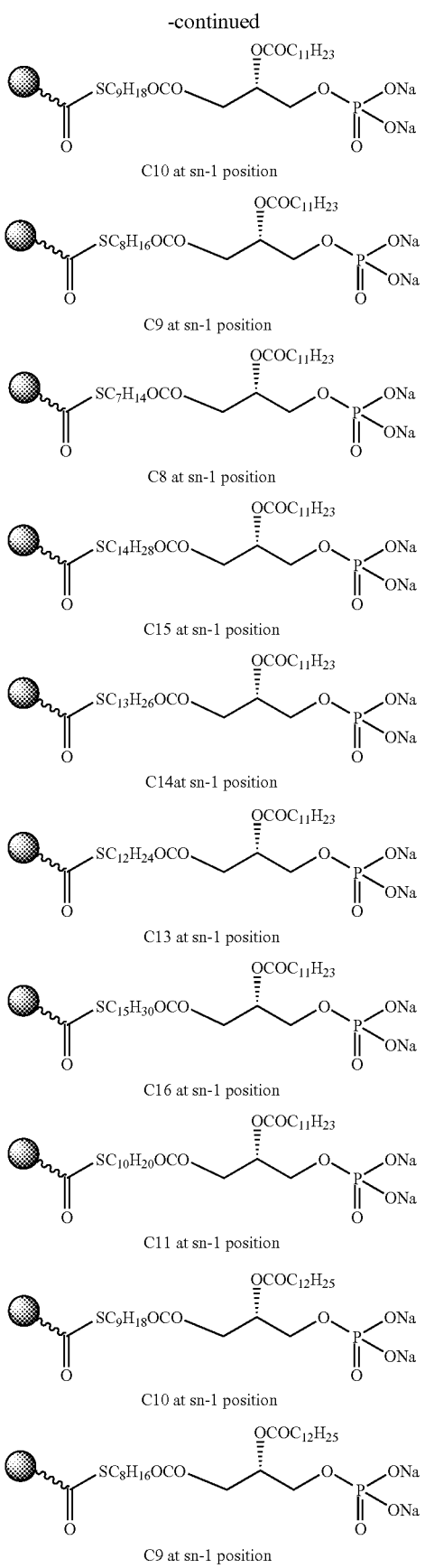

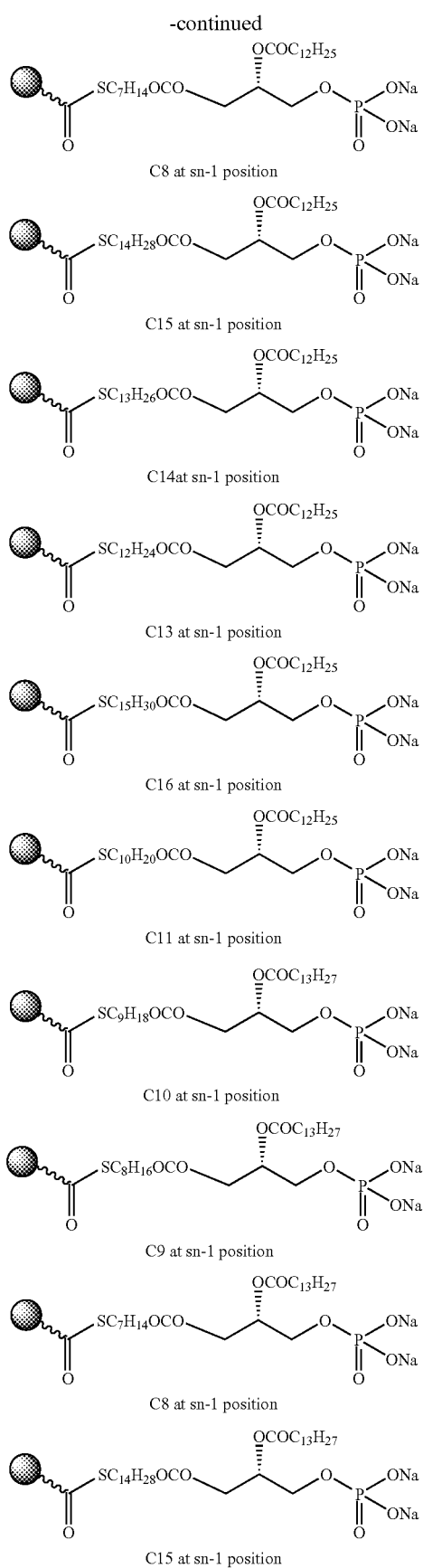
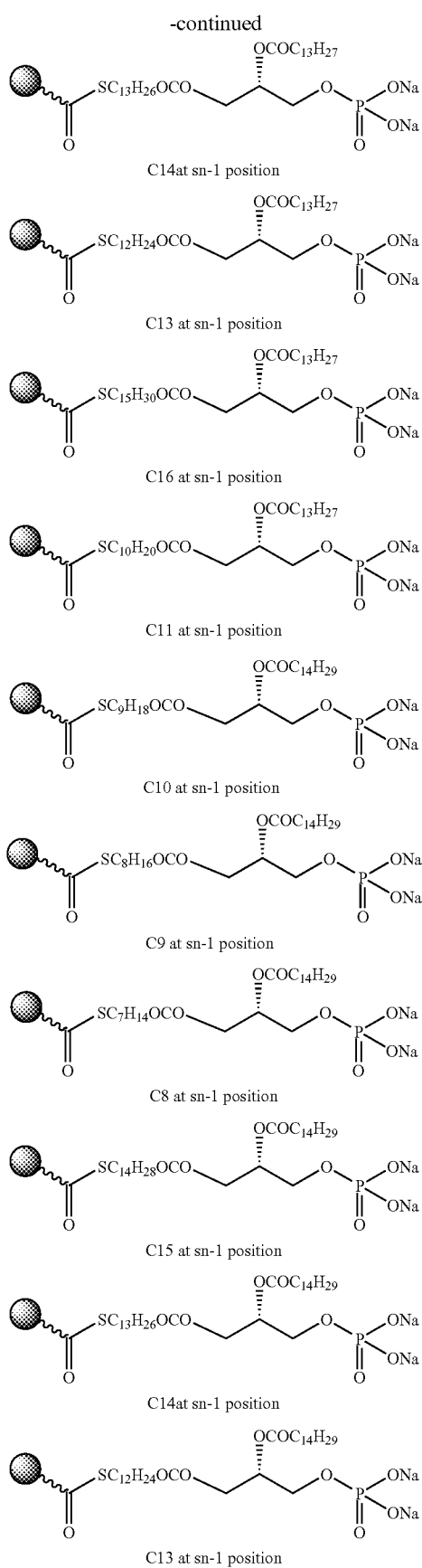

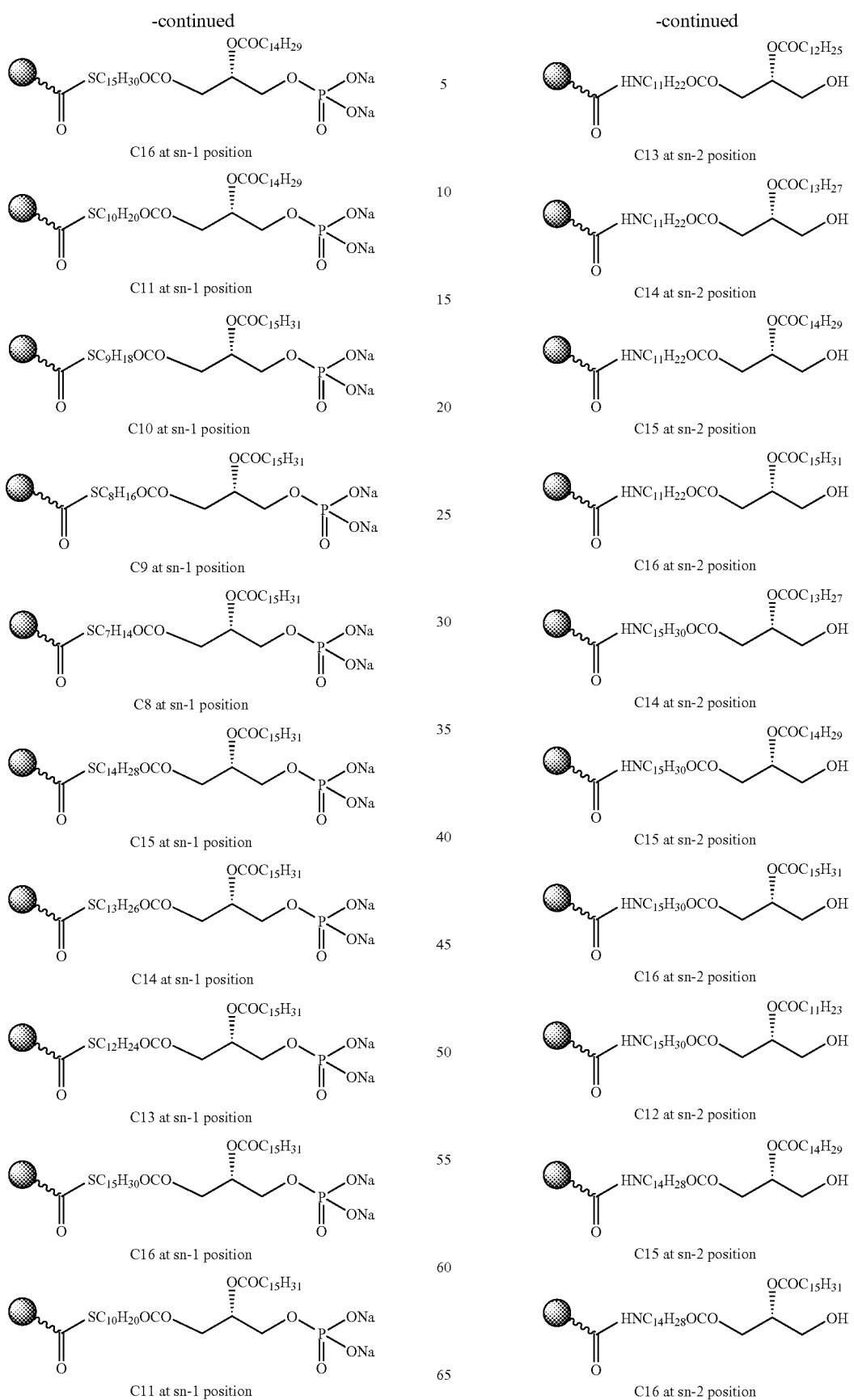

463

-continued

- C12 at sn-2 position
- C13 at sn-2 position
- C16 at sn-2 position
- C12 at sn-2 position
- C13 at sn-2 position
- C14 at sn-2 position
- C15 at sn-2 position
- C12 at sn-2 position
- C13 at sn-2 position
- C14 at sn-2 position

464

-continued

- C13 at sn-2 position
- C14 at sn-2 position
- C15 at sn-2 position
- C16 at sn-2 position
- C12 at sn-2 position
- C8 at sn-2 position
- C12 at sn-2 position
- C16 at sn-2 position
- C9 at sn-2 position
- C11 at sn-2 position

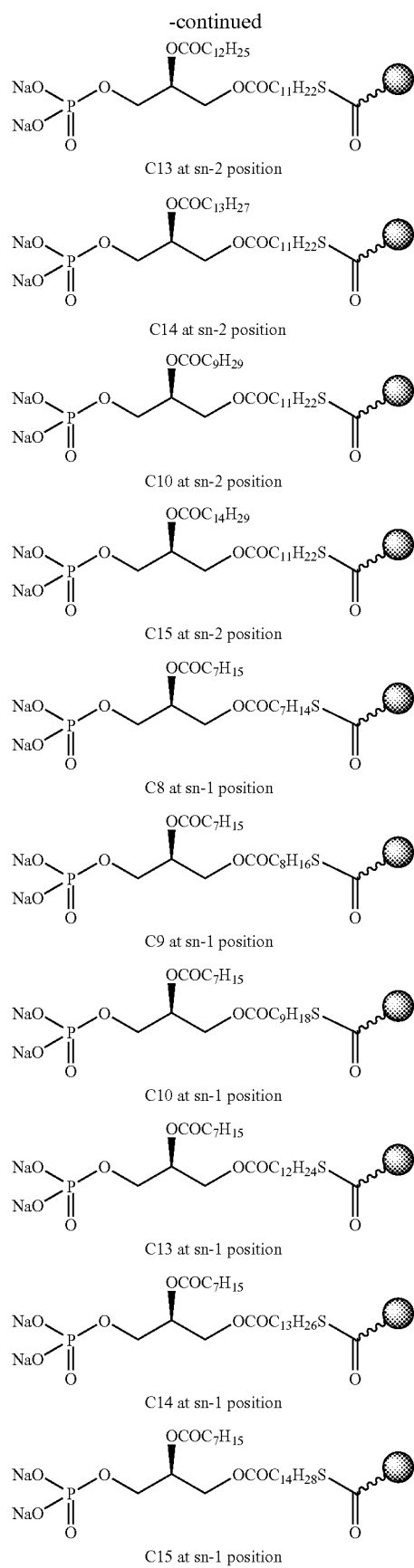
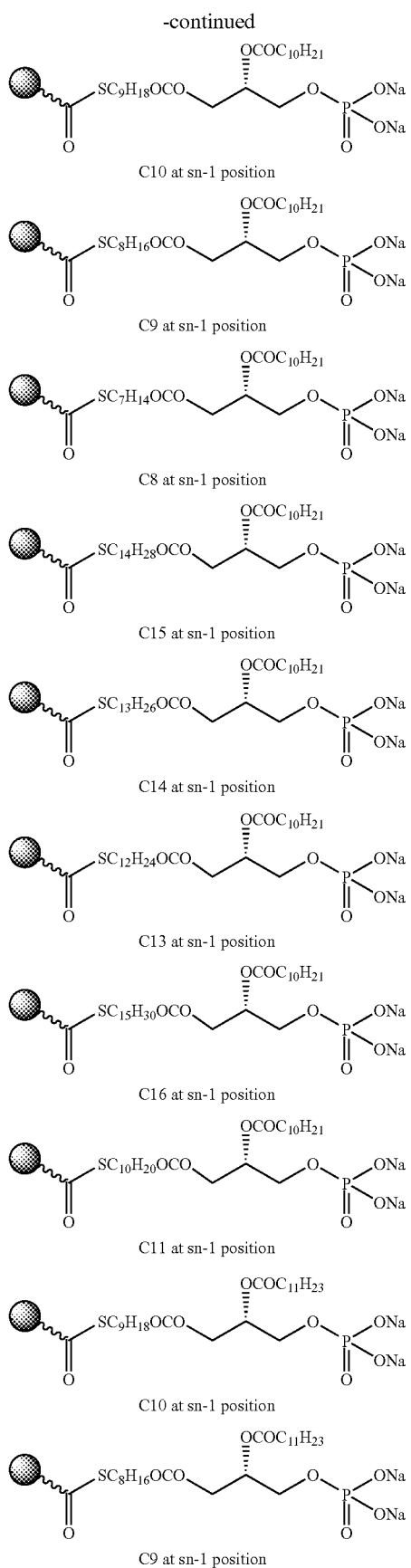

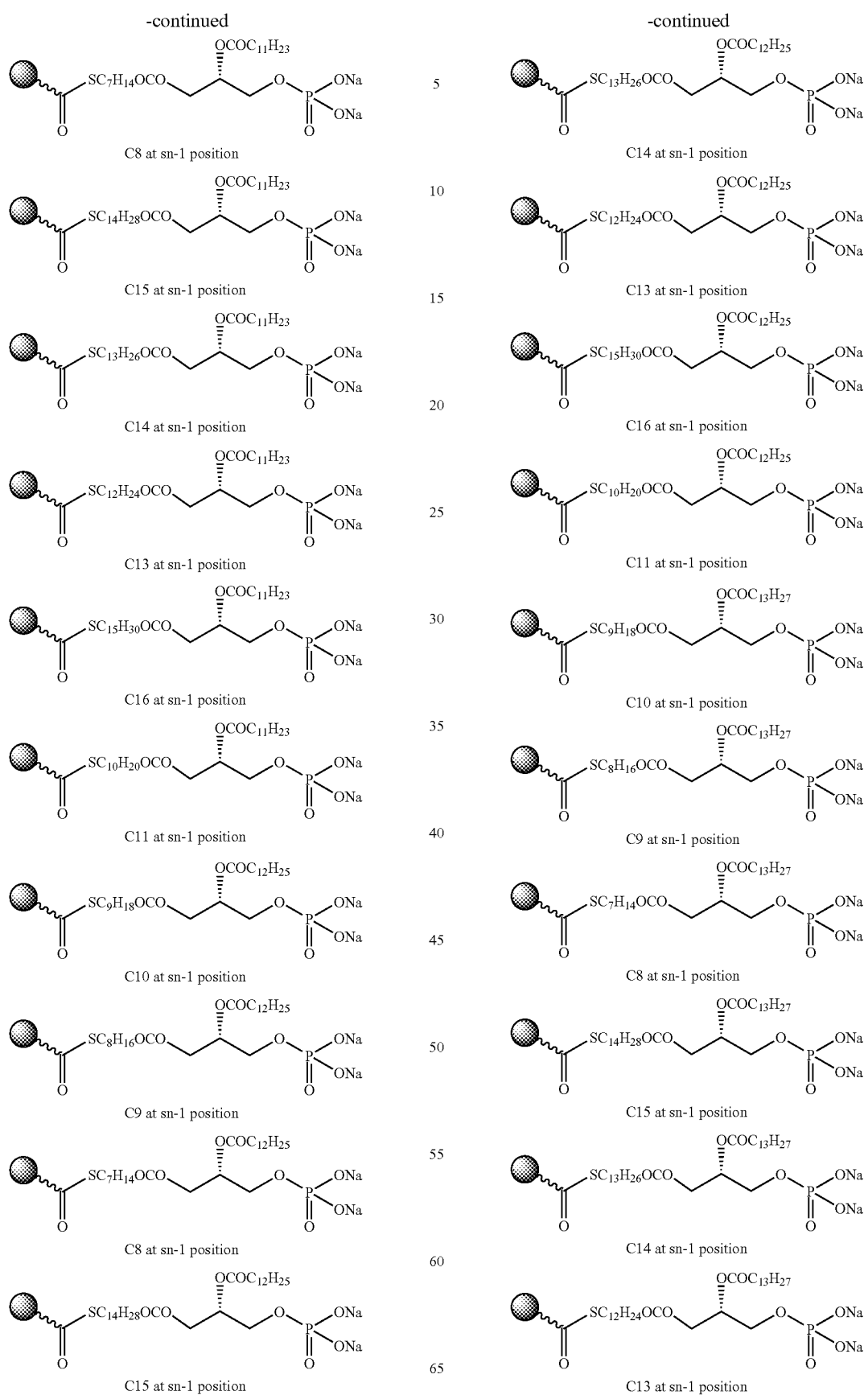

-continued
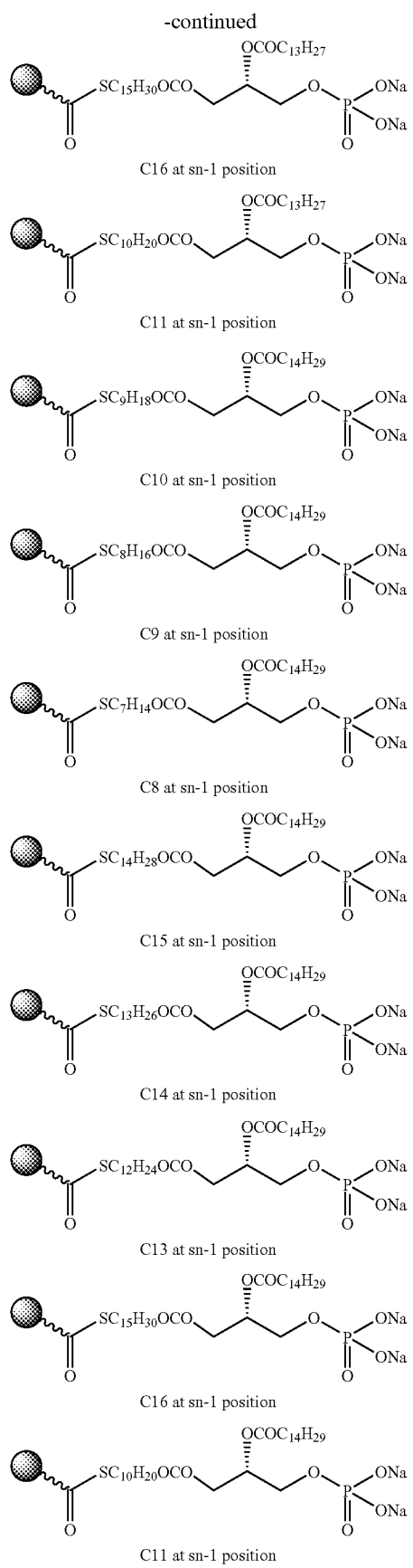
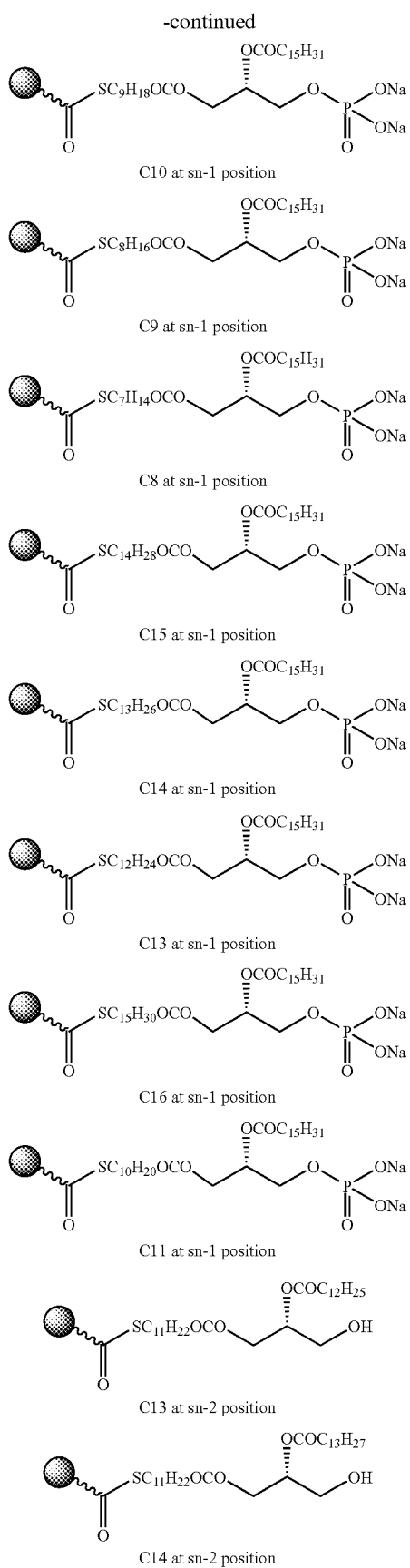

-continued

⬢~~SC₁₁H₂₂OCO~~⟨OCOC₁₄H₂₉⟩~~OH~~
C15 at sn-2 position

⬢~~SC₁₁H₂₂OCO~~⟨OCOC₁₅H₃₁⟩~~OH~~
C16 at sn-2 position

⬢~~SC₁₅H₃₀OCO~~⟨OCOC₁₃H₂₇⟩~~OH~~
C14 at sn-2 position

⬢~~SC₁₅H₃₀OCO~~⟨OCOC₁₄H₂₉⟩~~OH~~
C15 at sn-2 position

⬢~~SC₁₅H₃₀OCO~~⟨OCOC₁₅H₃₁⟩~~OH~~
C16 at sn-2 position

⬢~~SC₁₁H₂₂OCO~~⟨OCOC₁₁H₂₃⟩~~OH~~
C12 at sn-2 position

⬢~~SC₁₄H₂₈OCO~~⟨OCOC₁₄H₂₉⟩~~OH~~
C15 at sn-2 position

⬢~~SC₁₄H₂₈OCO~~⟨OCOC₁₅H₃₁⟩~~OH~~
C16 at sn-2 position

⬢~~SC₁₅H₃₀OCO~~⟨OCOC₁₁H₂₃⟩~~OH~~
C12 at sn-2 position

⬢~~SC₁₅H₃₀OCO~~⟨OCOC₁₂H₂₅⟩~~OH~~
C13 at sn-2 position

⬢~~SC₁₃H₂₆OCO~~⟨OCOC₁₅H₃₁⟩~~OH~~
C16 at sn-2 position

⬢~~SC₁₄H₂₈OCO~~⟨OCOC₁₁H₂₃⟩~~OH~~
C12 at sn-2 position

⬢~~SC₁₄H₂₈OCO~~⟨OCOC₁₂H₂₅⟩~~OH~~
C13 at sn-2 position

⬢~~SC₁₄H₂₈OCO~~⟨OCOC₁₃H₂₇⟩~~OH~~
C14 at sn-2 position

⬢~~SC₁₃H₂₆OCO~~⟨OCOC₁₁H₂₃⟩~~OH~~
C12 at sn-2 position

⬢~~SC₁₃H₂₆OCO~~⟨OCOC₁₂H₂₅⟩~~OH~~
C13 at sn-2 position

⬢~~SC₁₃₅H₂₆OCO~~⟨OCOC₁₃H₂₇⟩~~OH~~
C14 at sn-2 position

⬢~~SC₁₃H₂₆OCO~~⟨OCOC₁₄H₂₉⟩~~OH~~
C15 at sn-2 position

⬢~~SC₁₂H₂₄OCO~~⟨OCOC₁₂H₂₅⟩~~OH~~
C13 at sn-2 position

⬢~~SC₁₂H₂₄OCO~~⟨OCOC₁₃H₂₇⟩~~OH~~
C14 at sn-2 position

-continued

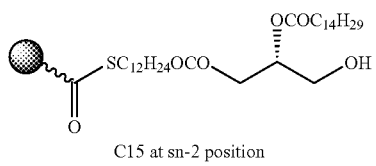

C15 at sn-2 position

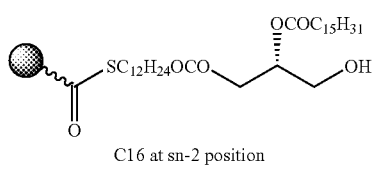

C16 at sn-2 position

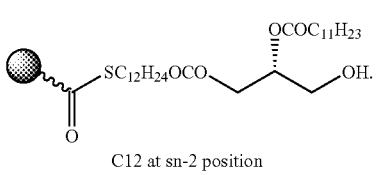

C12 at sn-2 position

10. The probe according to claim 5 which includes attachment of a fluorescent reporter group in the carboxyl side chain ester attached to the sn2-alkoxy substituent of the sn-glycerol-3-phosphate derivative, of formulae I, II, IV, VI, or to the sn1-alkoxy substituent of the sn-glycerol-3-phosphate derivative of formulae III, IV, VII, VIII.

11. The probe according to claim 5 which is capable of binding a protein which itself binds PA, wherein the probe has the following formulae:

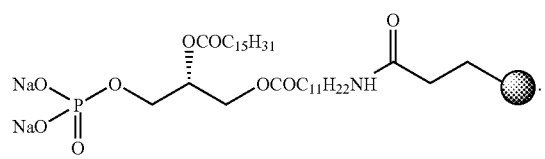

12. A probe which is capable of binding a protein which itself binds PI(3,4,5)P$_3$, wherein the probe has the following formulae:

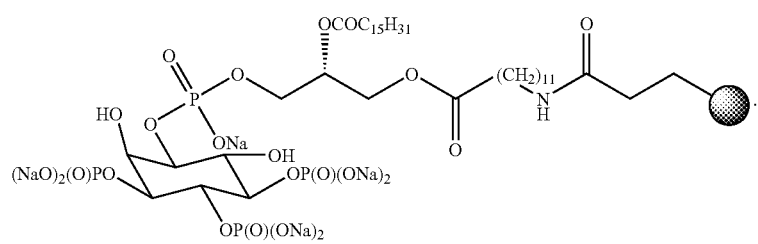

13. A probe which is capable of binding a protein which itself binds PI(4,5)P$_2$, wherein the probe has the following formulae:

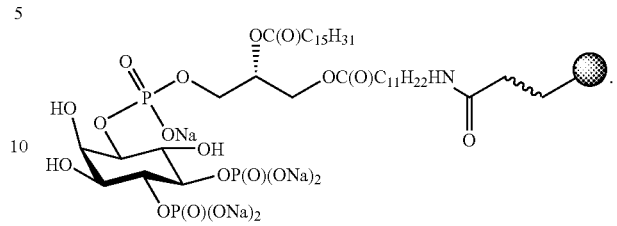

14. The probe according to claim 5 which is capable of binding a PA-binding protein with protein molecular weight in the range 60-250 kD, or 60-160 kD.

15. A probe which comprises a phosphoinositide attached onto a solid support by non-covalent binding, wherein the strength of the non-covalent attachment is such that it is not disrupted under conditions in which a protein is bound specifically to the probe with a binding energy greater than about 200 KJ/mole so that the non-covalent attachment is not disrupted under conditions in which a protein is bound specifically to the probe, and wherein the phosphoinositide is PI(3)P, PI(4)P, PI(5)P, PI(3,4)P$_2$, PI(3,5)P$_2$, PI(4,5)P$_2$, or PI(3,4,5)P$_3$.

16. A method of making a probe according to claim 1 which comprises reacting a compound of formula V' or VI':

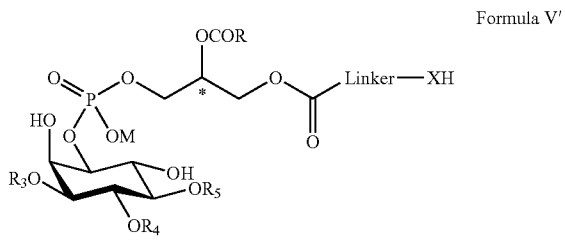

Formula V'

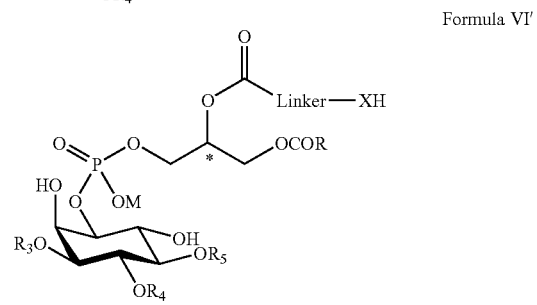

Formula VI' wherein:
R=aryl or alkyl group;
R=$C_mH_{2m+1}$, where m=8-20;
$R_3$=P(O)(OM)$_2$; $R_4$=H; $R_5$=H (PI(3)P);
$R_3$=H; $R_4$=P(O)(OM)$_2$; $R_5$=H (PI(4)P);
$R_3$=H; $R_4$=H; $R_5$=P(O)(OM)$_2$ (PI(5)P);
$R_3$=P(O)(OM)$_2$; $R_4$=P(O)(OM)$_2$; $R_5$=H (PI(3,4)P$_2$);
$R_3$=P(O)(OM)$_2$; $R_4$=H; $R_5$=P(O)(OM)$_2$ (PI(3,5)P$_2$);
$R_3$=H; $R_4$=P(O)(OM)$_2$; $R_5$=P(O)(OM)$_2$ (PI(4,5)P$_2$); or
$R_3$=P(O)(OM)$_2$; $R_4$=P(O)(OM)$_2$; $R_5$=P(O)(OM)$_2$ (PI(3,4,5)P$_3$);
M=any cation, including Na$^+$, NH4$^+$;
*Denotes a stereogenic centre;
Linker=$(CH_2)_n$ with n=8-20;
X=NH, O, or S;
unsaturations are allowed, including in an arachidonyl side chain;
with

where:

=solid support with attachment to RG$_2$; and
RG$_2$=a reactive group capable of reaction with XH, including N-hydroxy-succinimide-activated carboxylate.

17. A method of making a probe according to claim 1 which comprises reacting a compound of formula VII' or VIII':

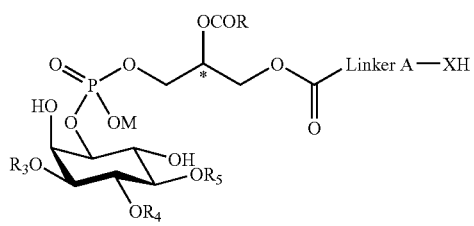

Formula VII'

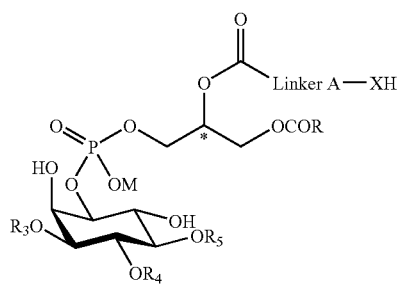

Formula VIII' where:
R=aryl or alkyl group;
R=$C_mH_{2m+1}$, where m=8-20;
$R_3$=P(O)(OM)$_2$; $R_4$=H; $R_5$=H (PI(3)P);
$R_3$=H; $R_4$=P(O)(OM)$_2$; $R_5$=H (PI(4)P);
$R_3$=H; $R_4$=H; $R_5$=P(O)(OM)$_2$ (PI(5)P);
$R_3$=P(O)(OM)$_2$; $R_4$=P(O)(OM)$_2$; $R_5$=H (PI(3,4)P$_2$);
$R_3$=P(O)(OM)$_2$; $R_4$=H; $R_5$=P(O)(OM)$_2$ (PI(3,5)P$_2$),
$R_3$=H; $R_4$=P(O)(OM)$_2$; $R_5$=P(O)(OM)$_2$ (PI(4,5)P$_2$); or
$R_3$=P(O)(OM)$_2$, $R_4$=P(O)(OM)$_2$; $R_5$=P(O)(OM)$_2$ (PI(3,4,5)P$_3$);
M=any cation, including Na$^+$ and NH4$^+$;
*Denotes a stereogenic centre;
Linker A=$(CH_2)_n$ with n=8-20;
X=NH, O, or S;
unsaturations are allowed, including in an arachidonyl side chain;
with

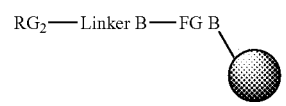

Linker B=aryl, heteroaryl, alkyl with possible heteroatoms and/or saturations;
these could be any atoms, including C, N, O, S, or methylene groups linked via amide and ester bonds;
the total length of linker A and linker B is 8-60 atoms;
FG B=Amide, thiolo(ester), or ester

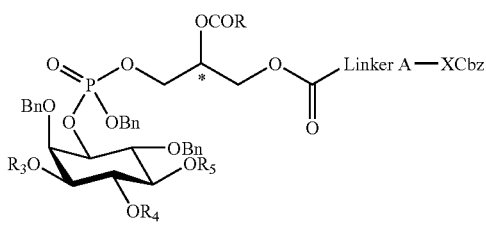

Formula VII''

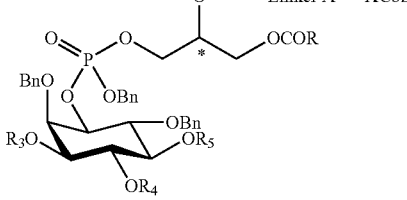

Formula VIII''

=solid support with attachment to FG B; and
RG$_2$=a reactive group capable of reaction with XH, including N-hydroxy-succinimide-activated carboxylate.

18. The method according to claim 16 further comprising deprotecting a compound of formula V'', VI'', VII'', or VIII'' to form a compound of formula V', VI', VII' or VIII':

Formula V″

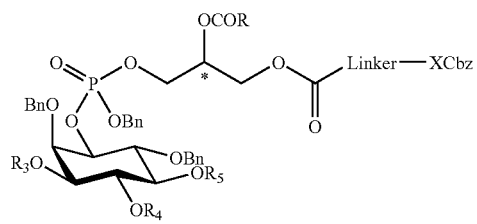

Formula VI″

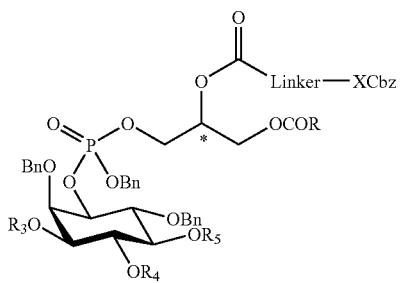

wherein,
R=aryl or alkyl group;
R is $C_mH_{2m+1}$, where m is 8-20;
$R_3$ is $P(O)(OBn)_2$; $R_4$=H; $R_5$ is H (PI(3)P),
$R_3$ is H; $R_4$ is $P(O)(OBn)_2$; $R_5$ is H (PI(4)P);
$R_3$ is H; $R_4$ is H; $R_5$ is $P(O)(OBn)_2$ (PI(5)P);
$R_3$ is $P(O)(OBn)_2$; $R_4$ is $P(O)(OBn)_2$; $R_5$ is H (PI(3,4)$P_2$);
$R_3$ is $P(O)(OBn)_2$; $R_4$ is H; $R_5$ is $P(O)(OBn)_2$ (PI(3,5)$P_2$);
$R_3$ is H; $R_4$ is $P(O)(OBn)_2$; $R_5$ is $P(O)(OBn)_2$ (PI(4,5)$P_2$);
or
$R_3$ is $P(O)(OBn)_2$; $R_4$ is $P(O)(OBn)_2$; $R_5$ is $P(O)(OBn)_2$ (PI(3,4,5)$P_3$);
*Denotes a stereogenic centre;
Linker is $(CH_2)_n$ wherein n=8-20;
X is O, S, or, NH;
unsaturations are allowed, including in an arachidonyl side chain;

Formula VII″

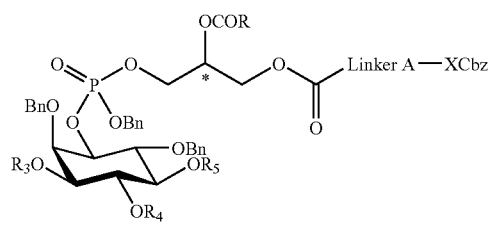

Formula VIII″

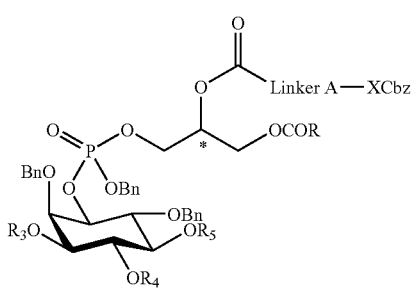

wherein,
R is aryl or alkyl group;
R is $C_mH_{2m+1}$; where m is 8-20;
$R_3$ is $P(O)(OBn)_2$; $R_4$ is H; $R_5$ is H (PI(3)P);
$R_3$ is H; $R_4$ is $P(O)(OBn)_2$, $R_5$ is H (PI(4)P);
$R_3$ is H; $R_4$ is H; $R_5$ is $P(O)(OBn)_2$ (PI(5)P);
$R_3$ is $P(O)(OBn)_2$; $R_4$ is $P(O)(OBn)_2$; $R_5$ is H (PI(3,4)$P_2$);
$R_3$ is $P(O)(OBn)_2$; $R_4$ is H; $R_5$ is $P(O)(OBn)_2$ (PI(3,5)$P_2$);
$R_3$ is H; $R_4$ is $P(O)(OBn)_2$; $R_5$ is $P(O)(OBn)_2$ (PI(4,5)$P_2$);
or
$R_3$ is $P(O)(OBn)_2$; $R_4$ is $P(O)(OBn)_2$; $R_5$ is $P(O)(OBn)_2$ (PI(3,4,5)$P_3$);
*Denotes a stereogenic centre;
Linker A is $(CH_2)_n$ wherein n=8-20;
X is O, S, or NH;
unsaturations are allowed, including in an arachidonyl side chain.

19. The method of claim 16 wherein the R group is alkyl.

20. The method of claim 16, wherein the compound of formula V′, VI′, VII′, or VIII′ is of one of the compounds as listed below:

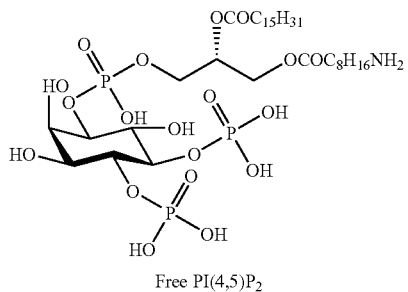

Free PI(4,5)$P_2$

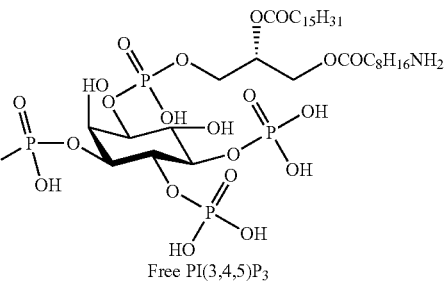

Free PI(3,4,5)$P_3$

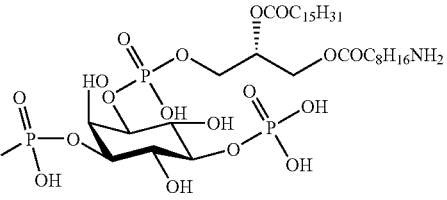

Free PI(3,5)$P_2$

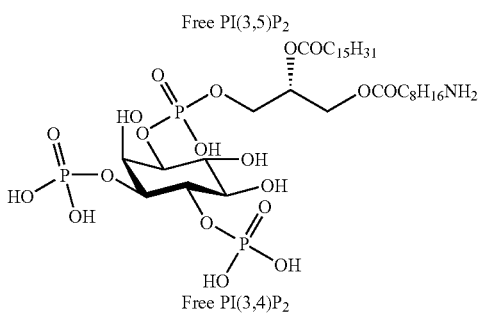

Free PI(3,4)$P_2$

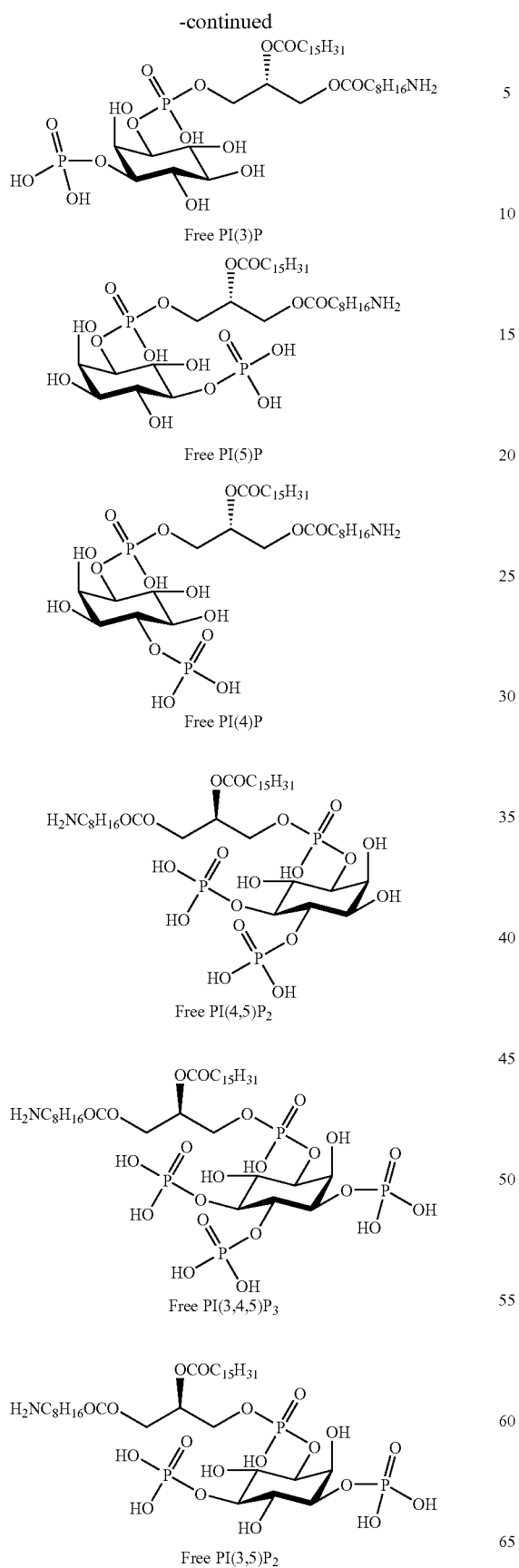
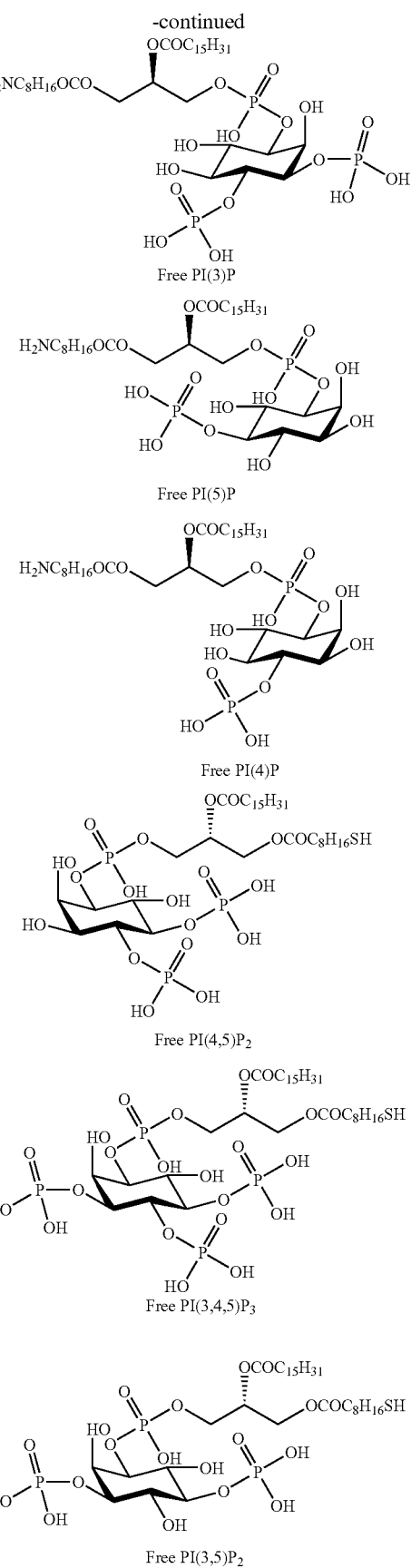

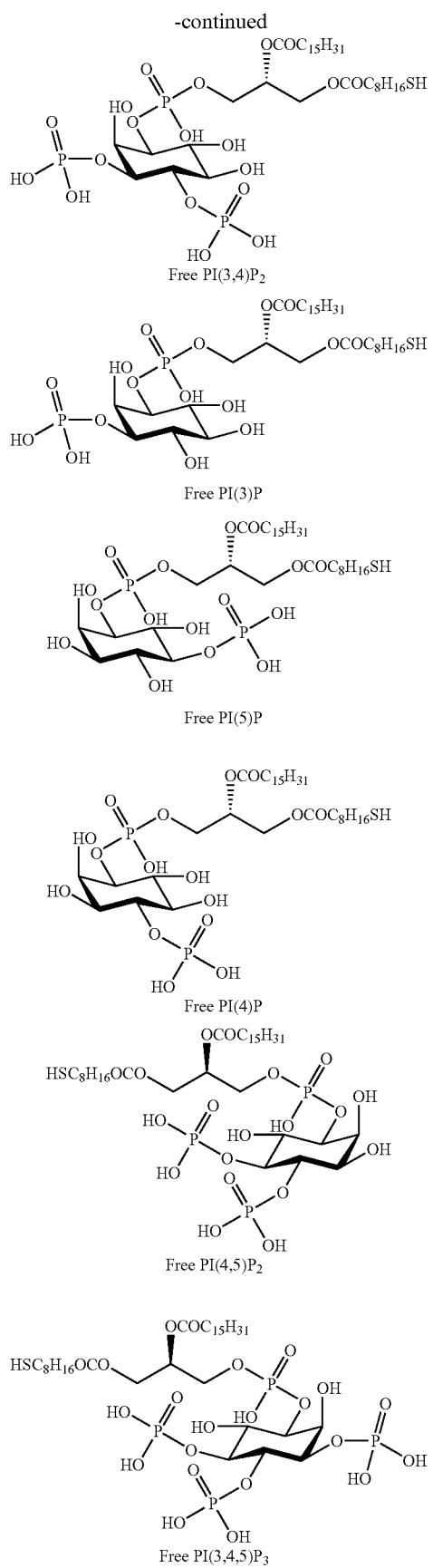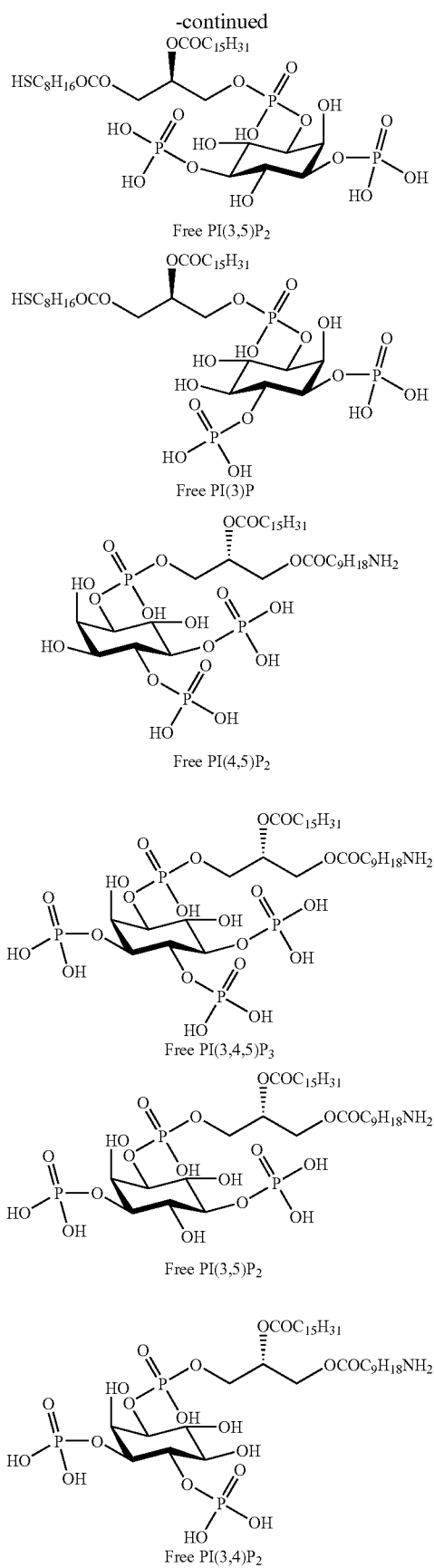

-continued
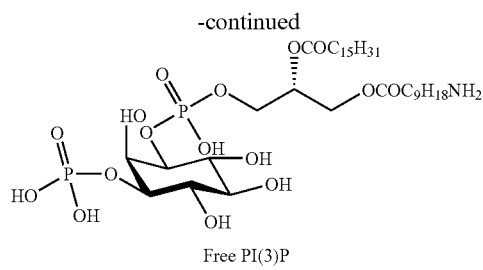
Free PI(3)P
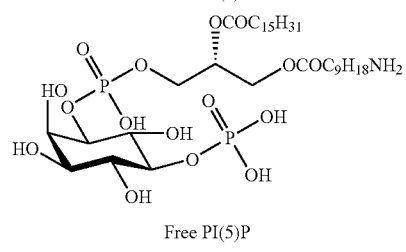
Free PI(5)P
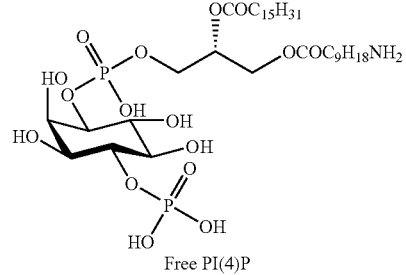
Free PI(4)P
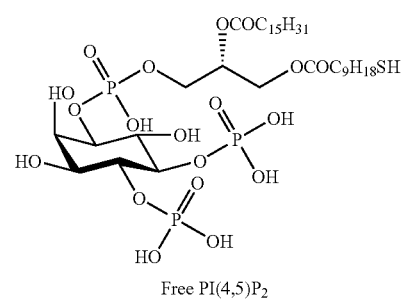
Free PI(4,5)P$_2$
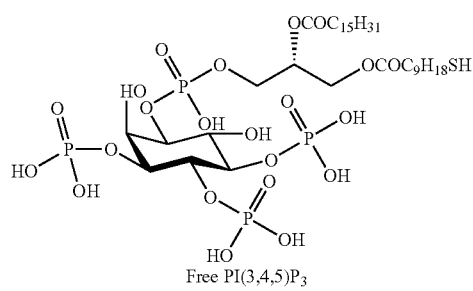
Free PI(3,4,5)P$_3$
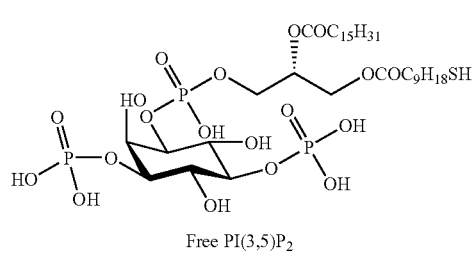
Free PI(3,5)P$_2$
-continued
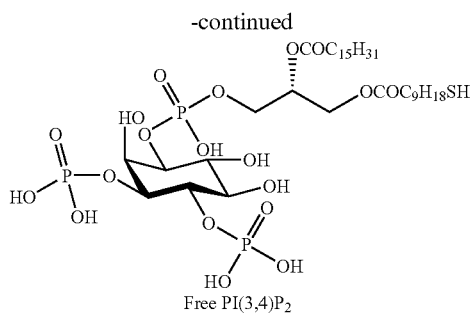
Free PI(3,4)P$_2$
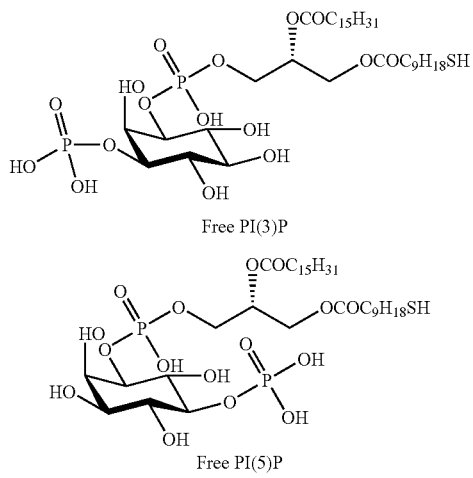
Free PI(3)P
Free PI(5)P
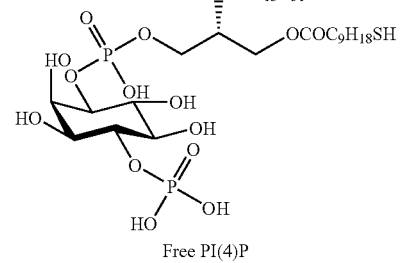
Free PI(4)P
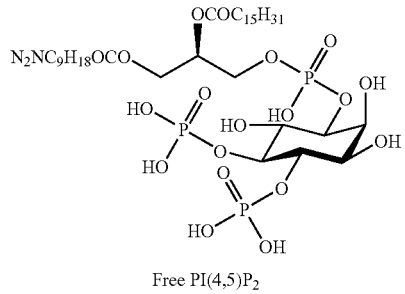
Free PI(4,5)P$_2$
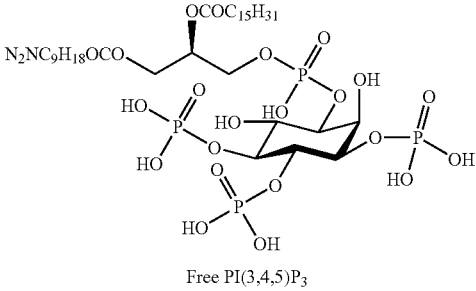
Free PI(3,4,5)P$_3$

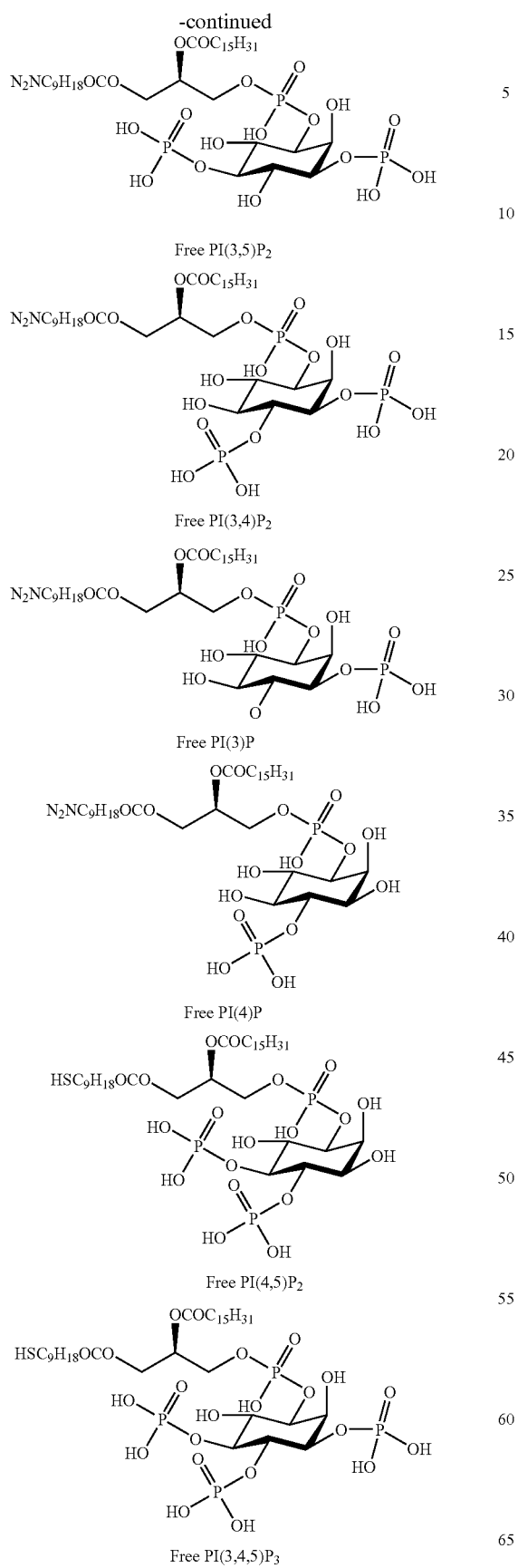
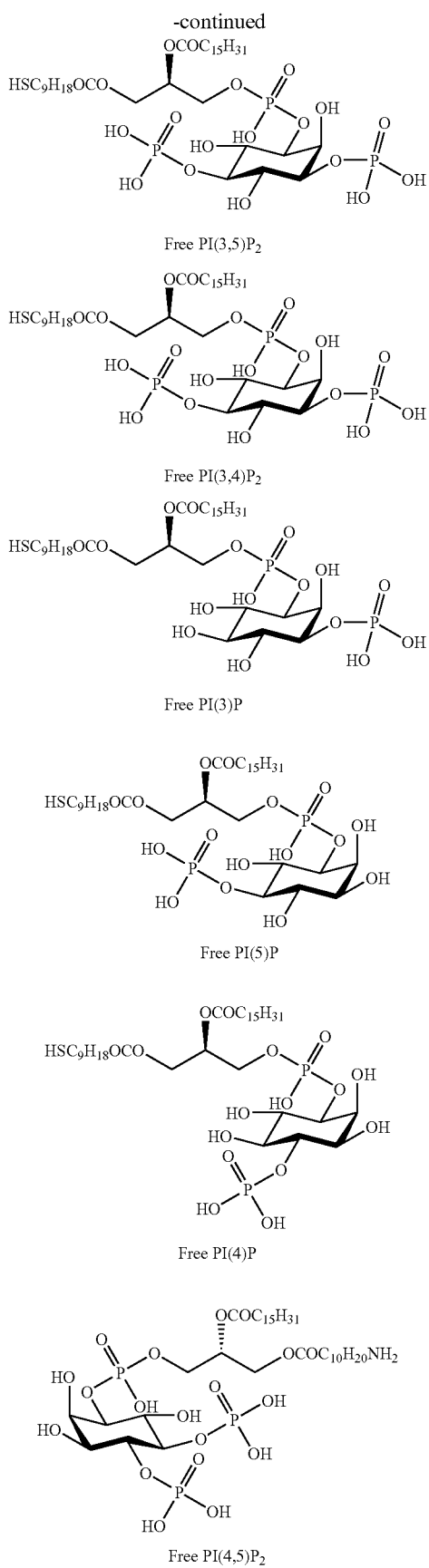

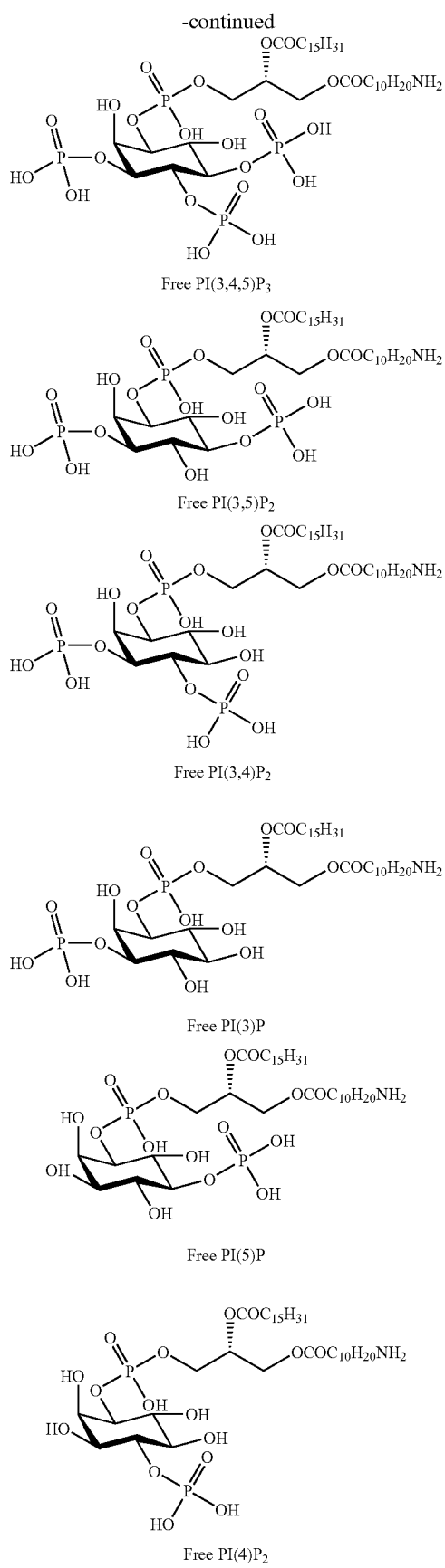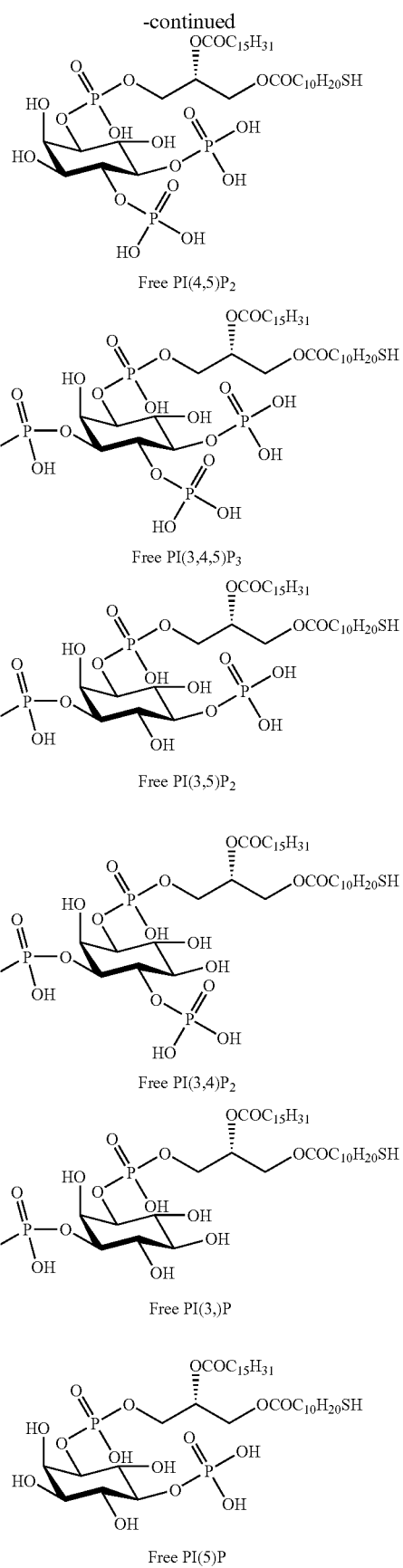

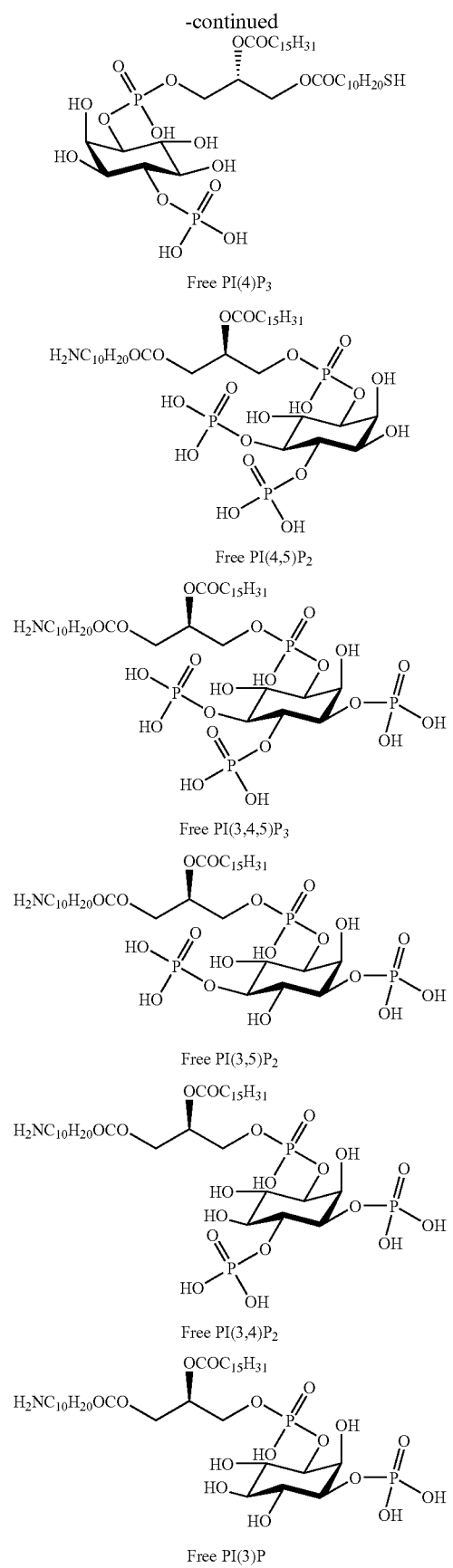
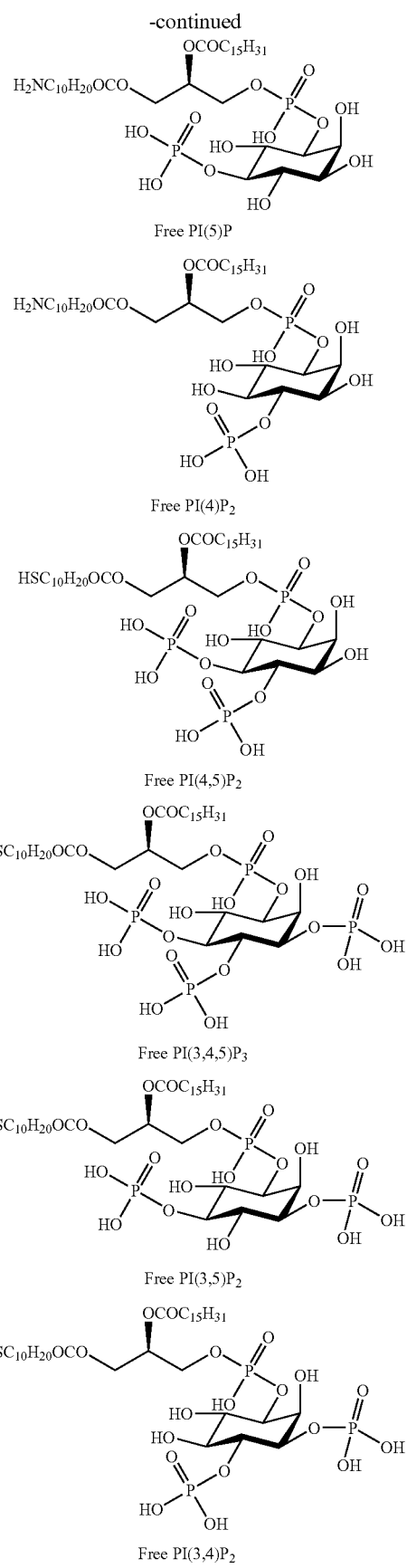

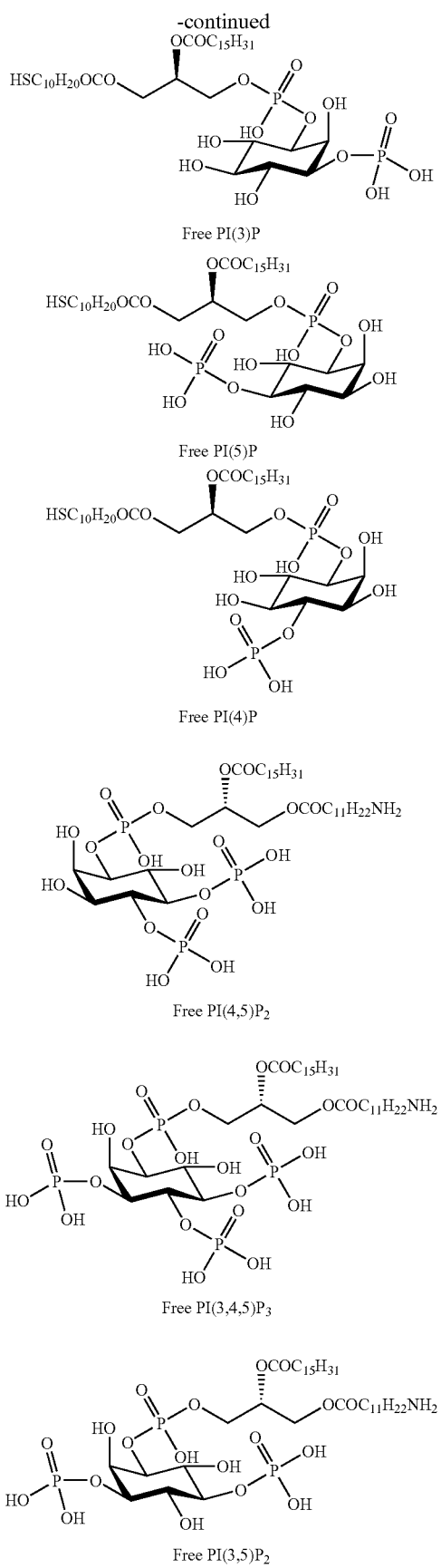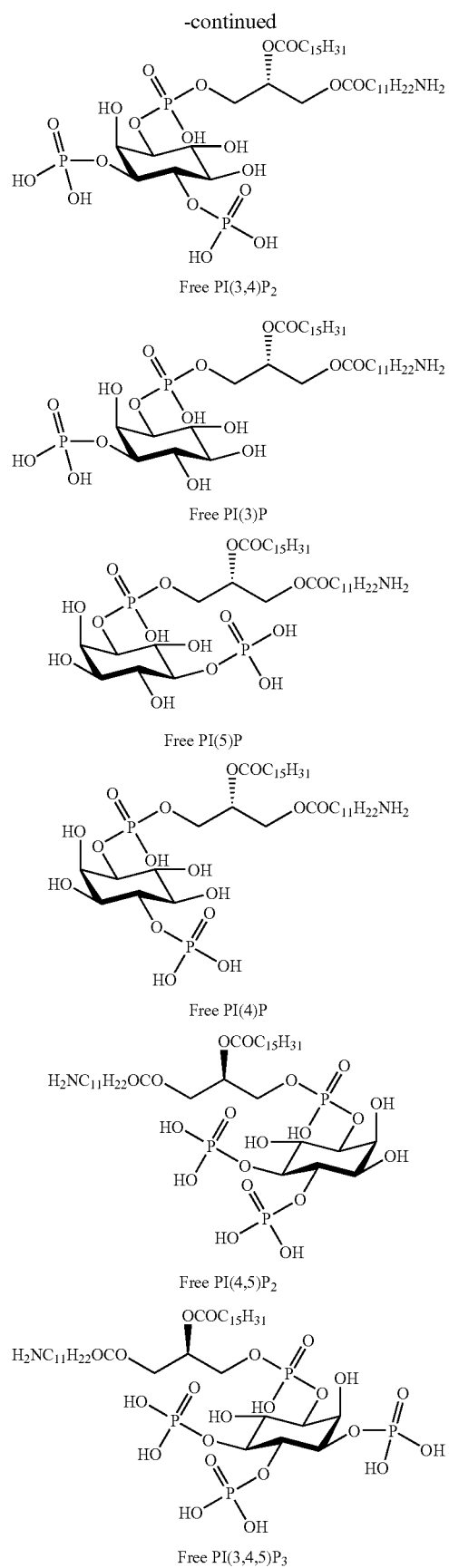

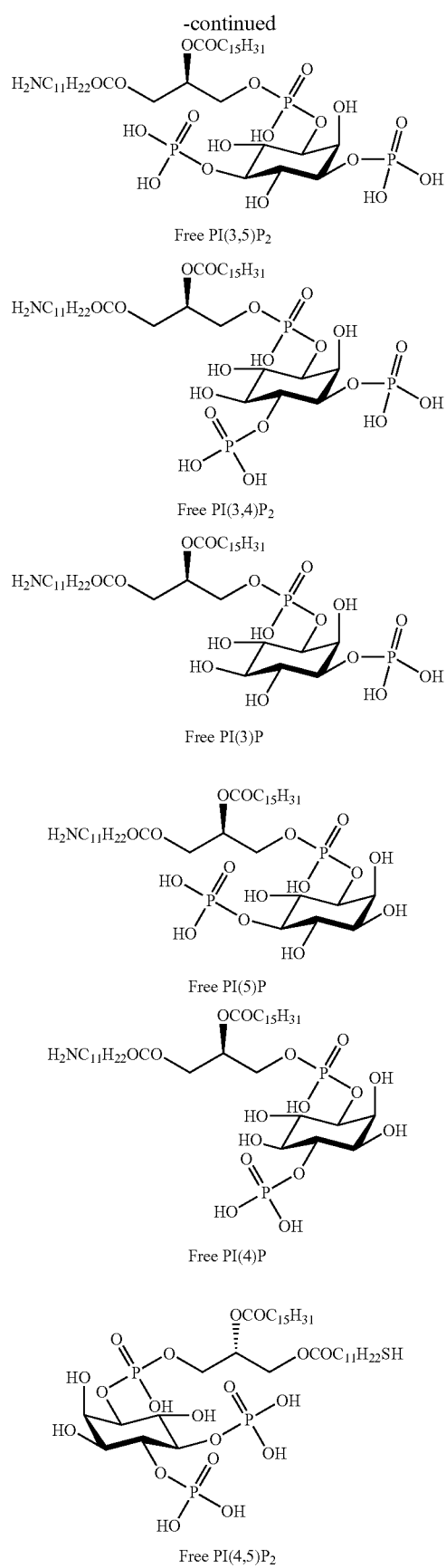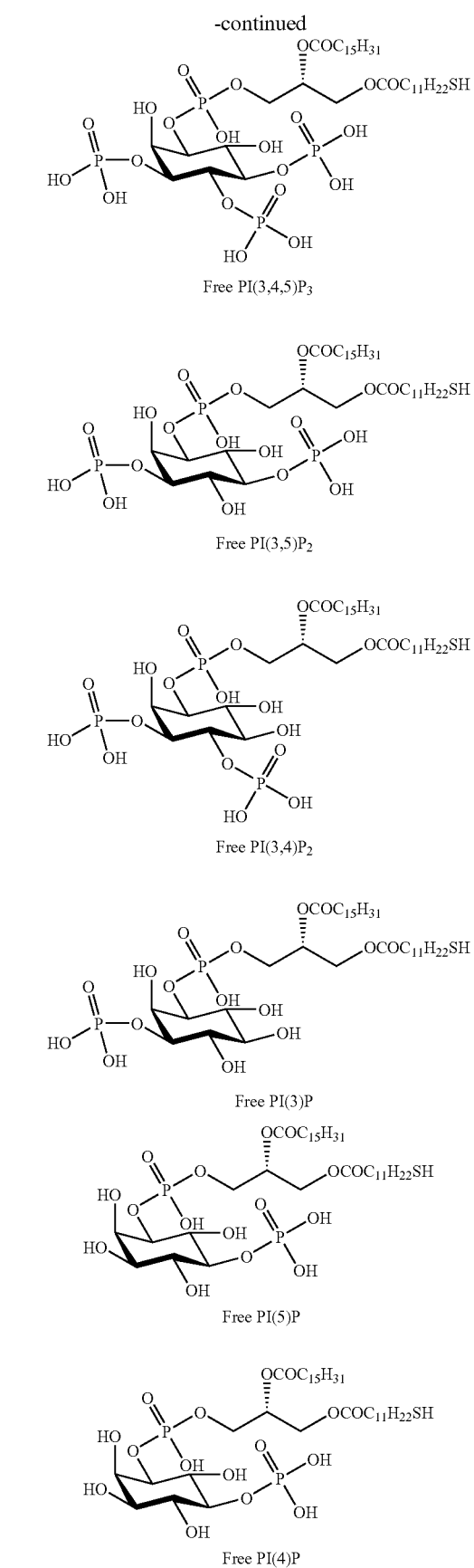

-continued
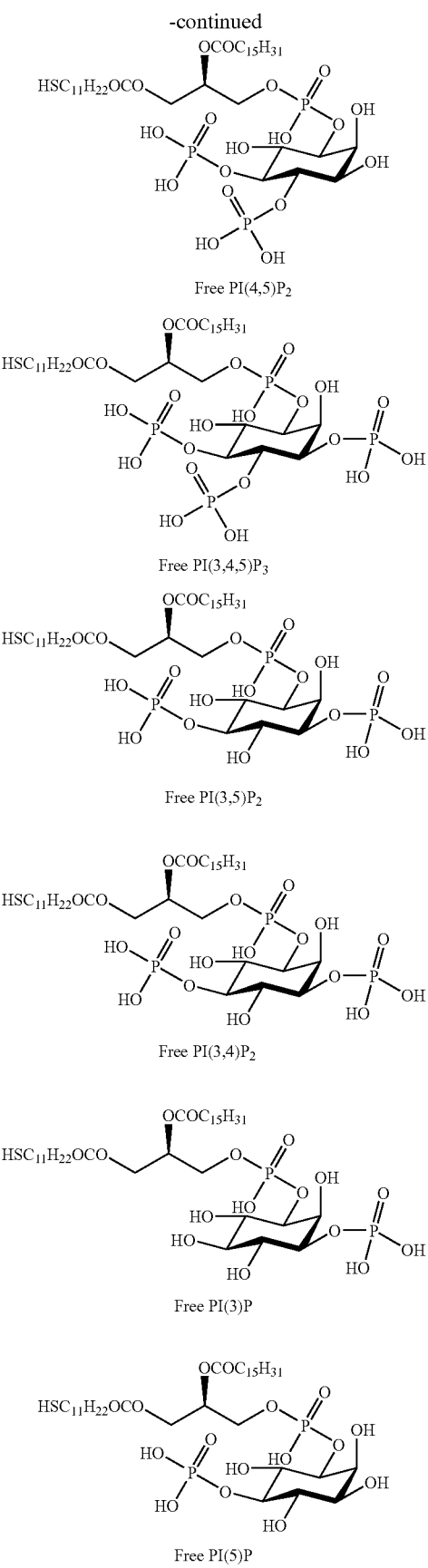
Free PI(4,5)P$_2$
Free PI(3,4,5)P$_3$
Free PI(3,5)P$_2$
Free PI(3,4)P$_2$
Free PI(3)P
Free PI(5)P
-continued
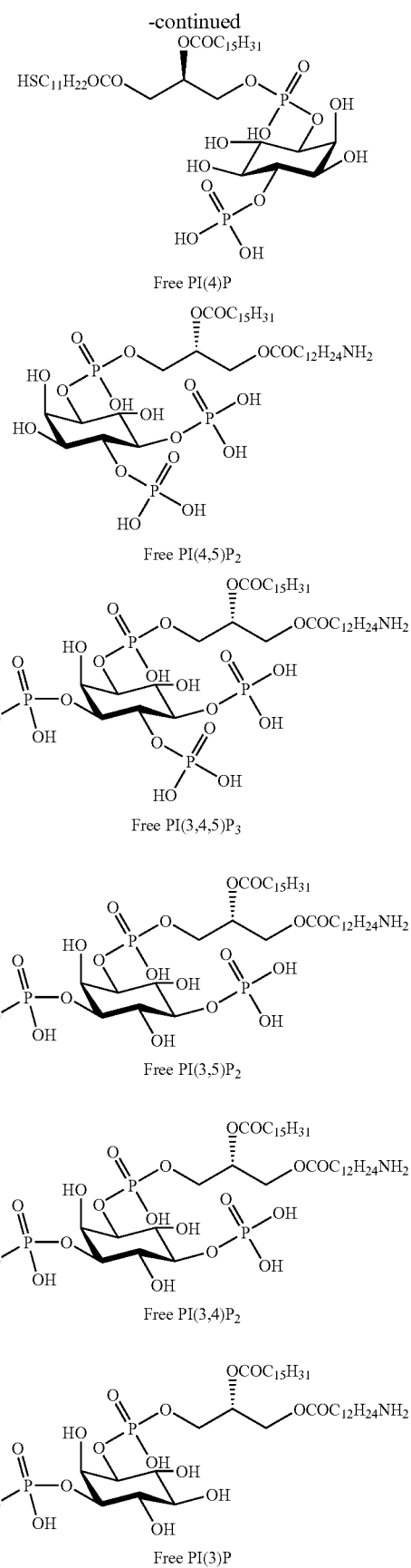
Free PI(4)P
Free PI(4,5)P$_2$
Free PI(3,4,5)P$_3$
Free PI(3,5)P$_2$
Free PI(3,4)P$_2$
Free PI(3)P

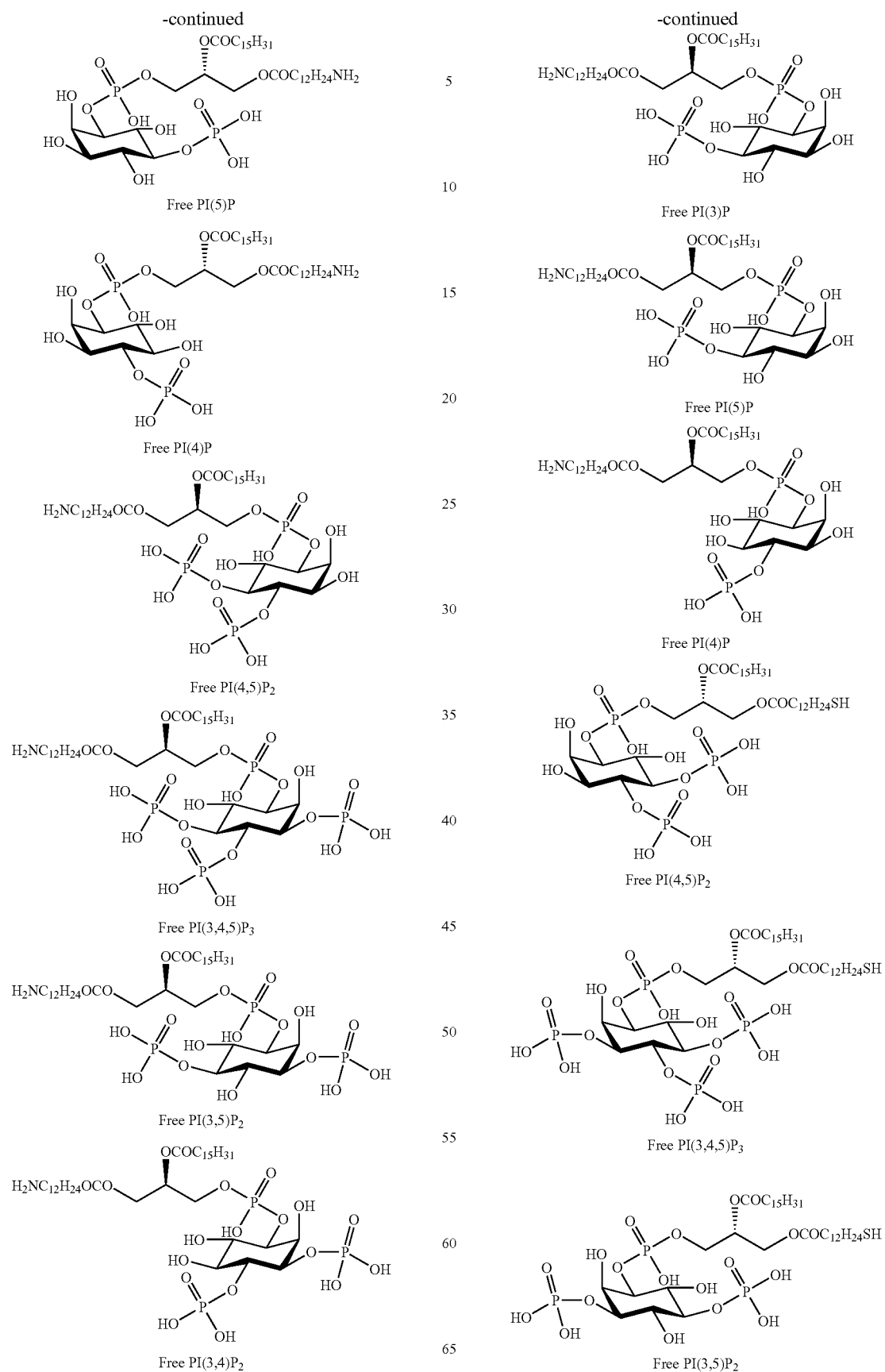

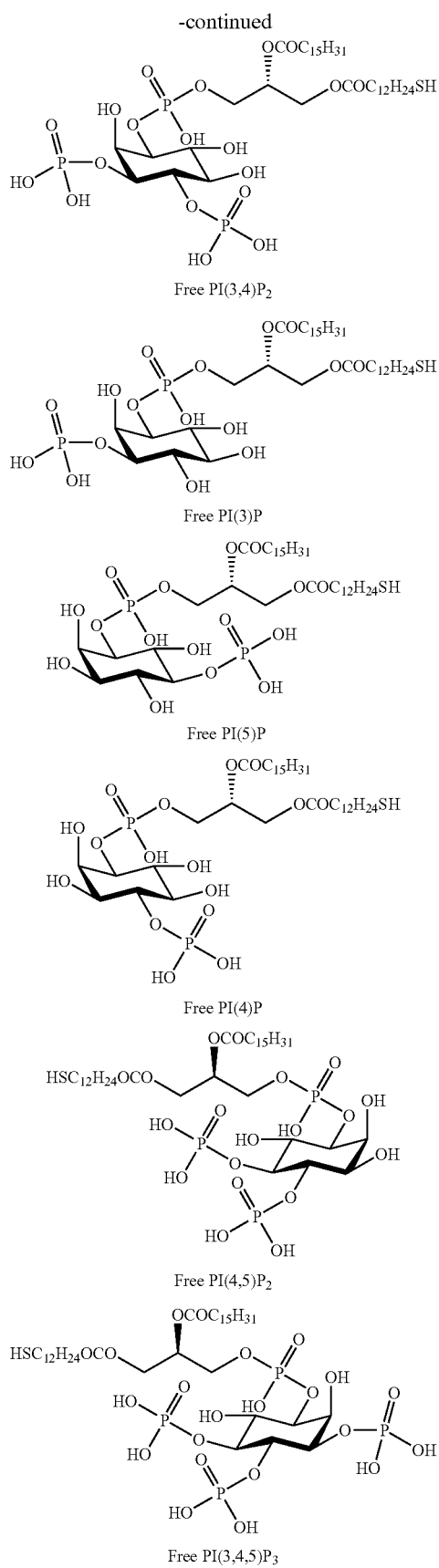
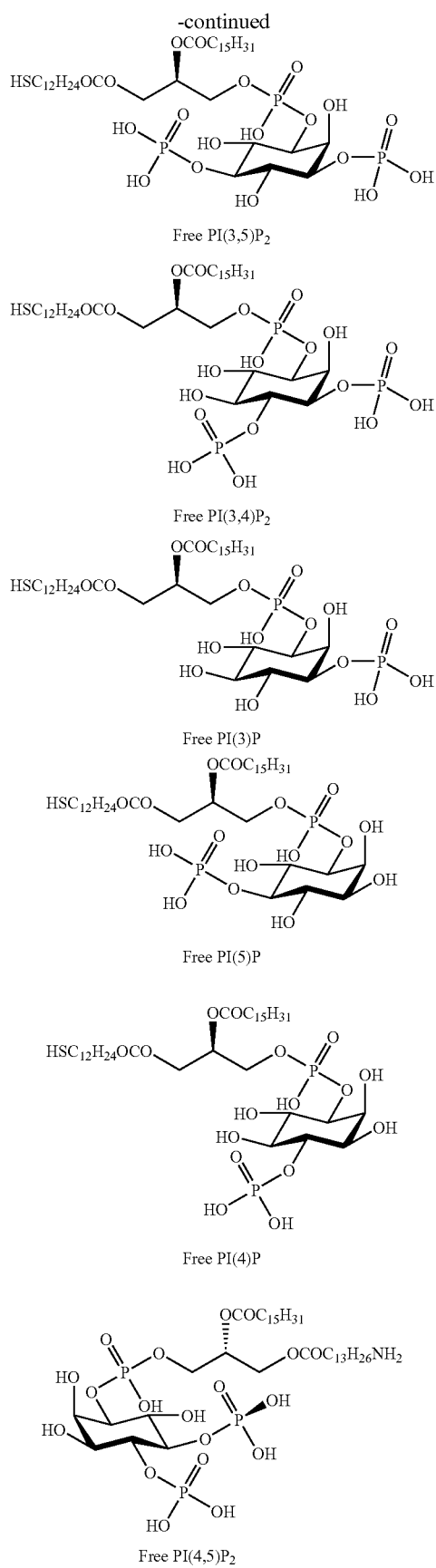

501
-continued
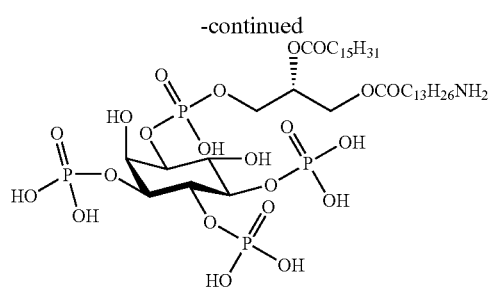
Free PI(3,4,5)P$_3$
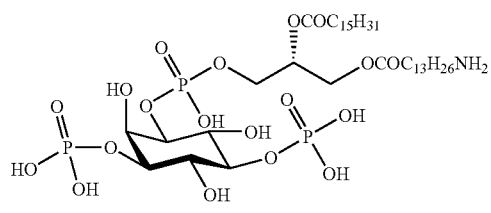
Free PI(3,5)P$_2$
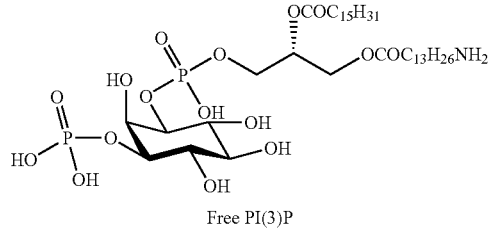
Free PI(3)P
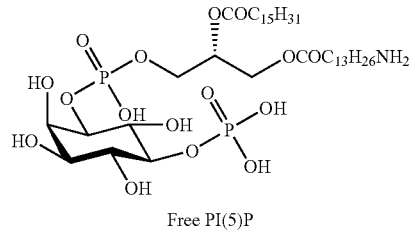
Free PI(5)P
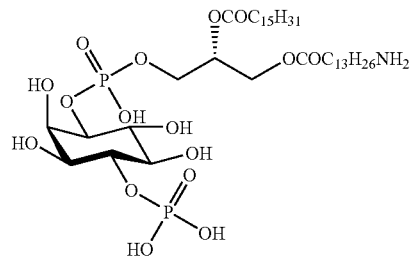
Free PI(4)P$_3$
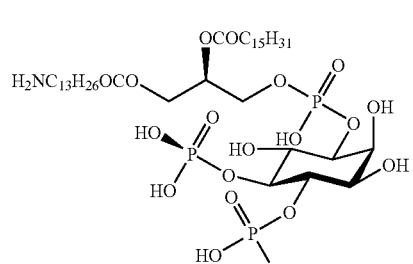
Free PI(4,5)P$_2$
502
-continued
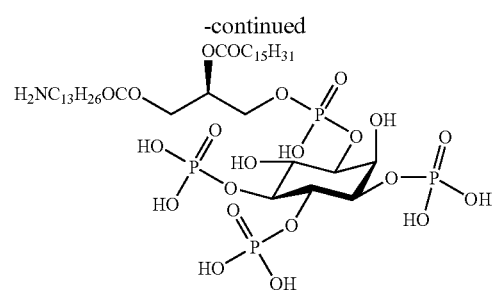
Free PI(3,4,5)P$_3$
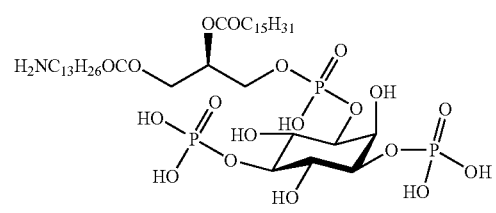
Free PI(3,5)P$_2$
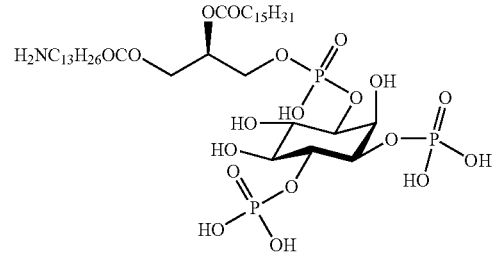
Free PI(3,4)P$_2$
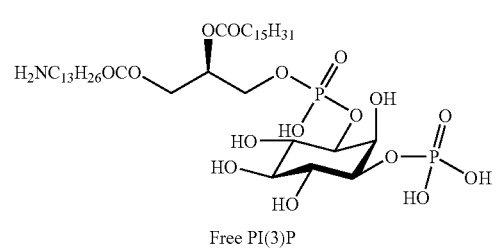
Free PI(3)P
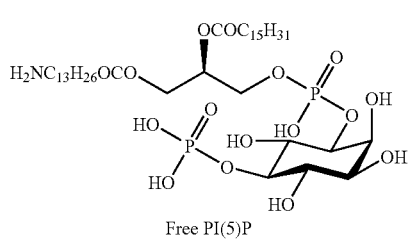
Free PI(5)P
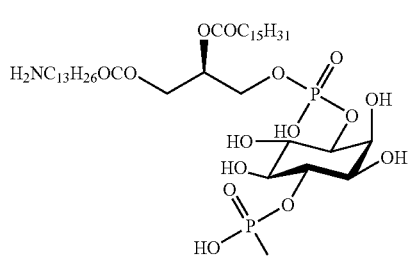
Free PI(4)P

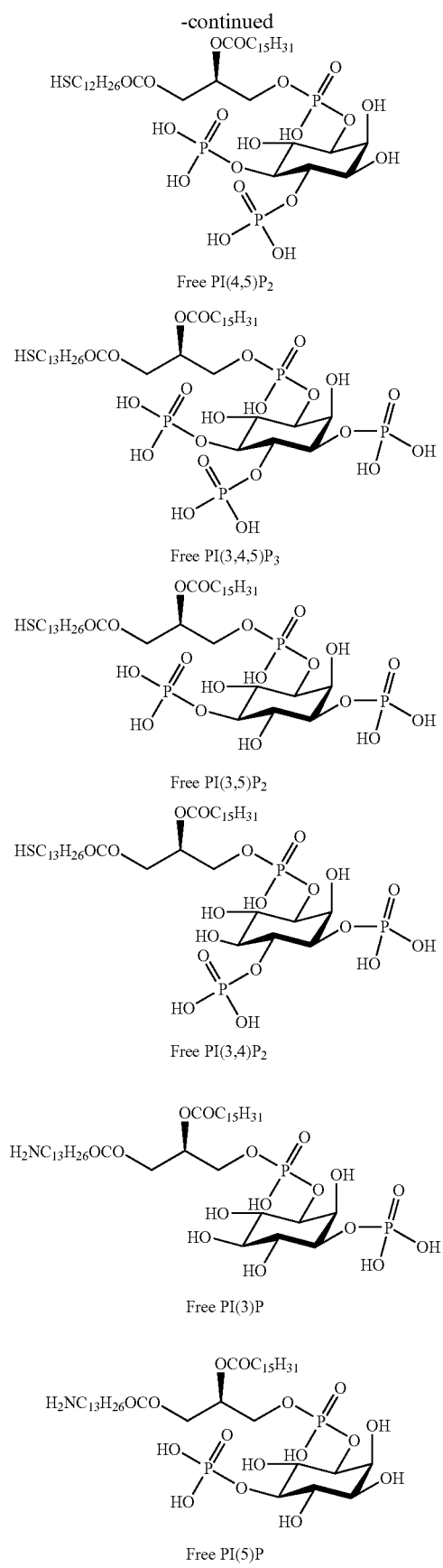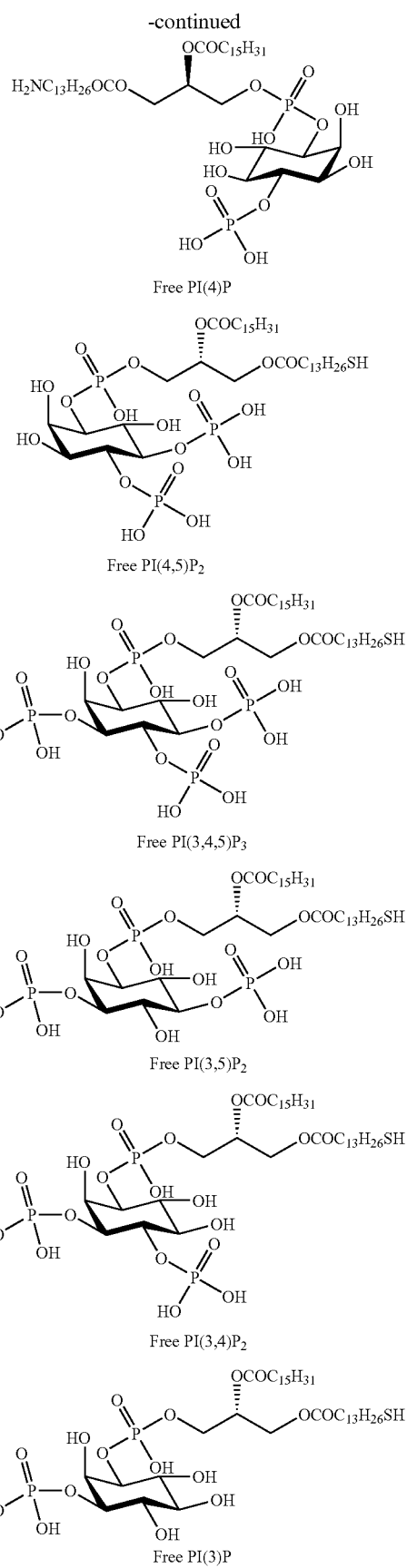

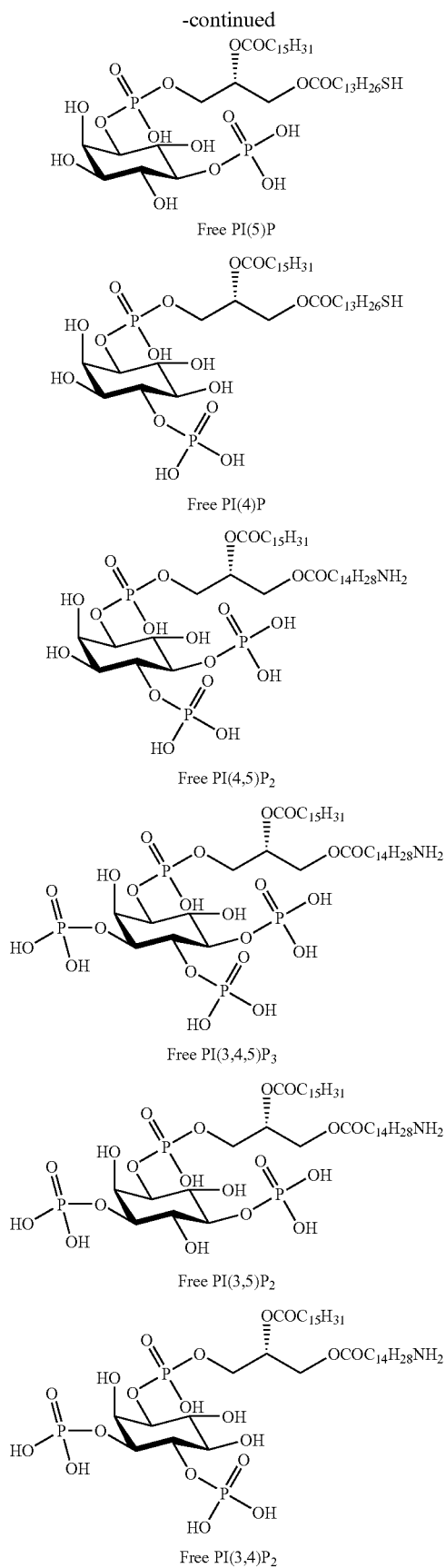
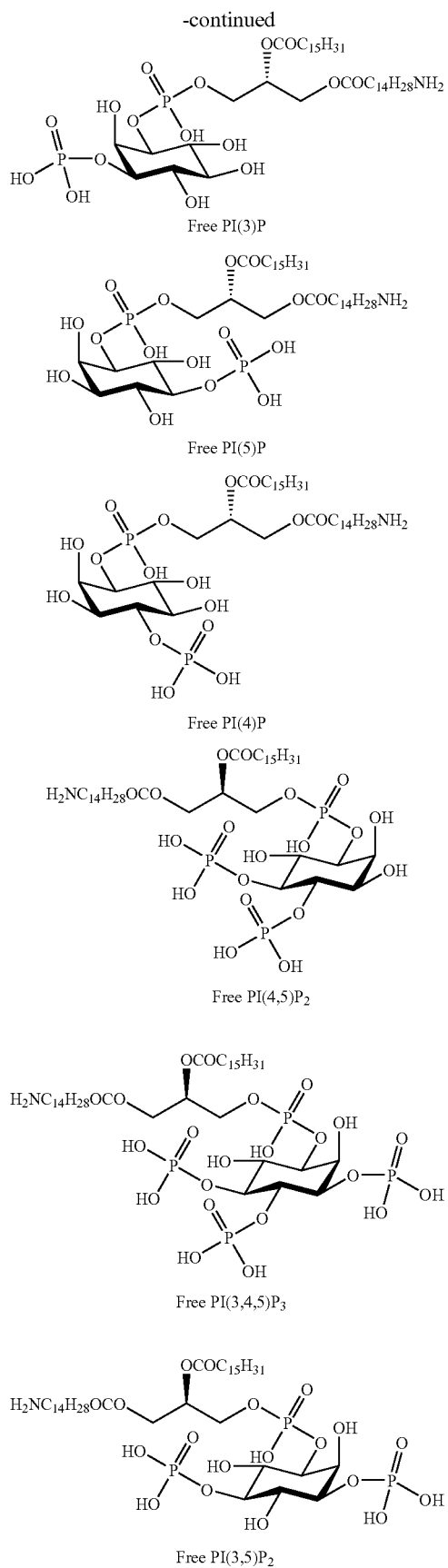

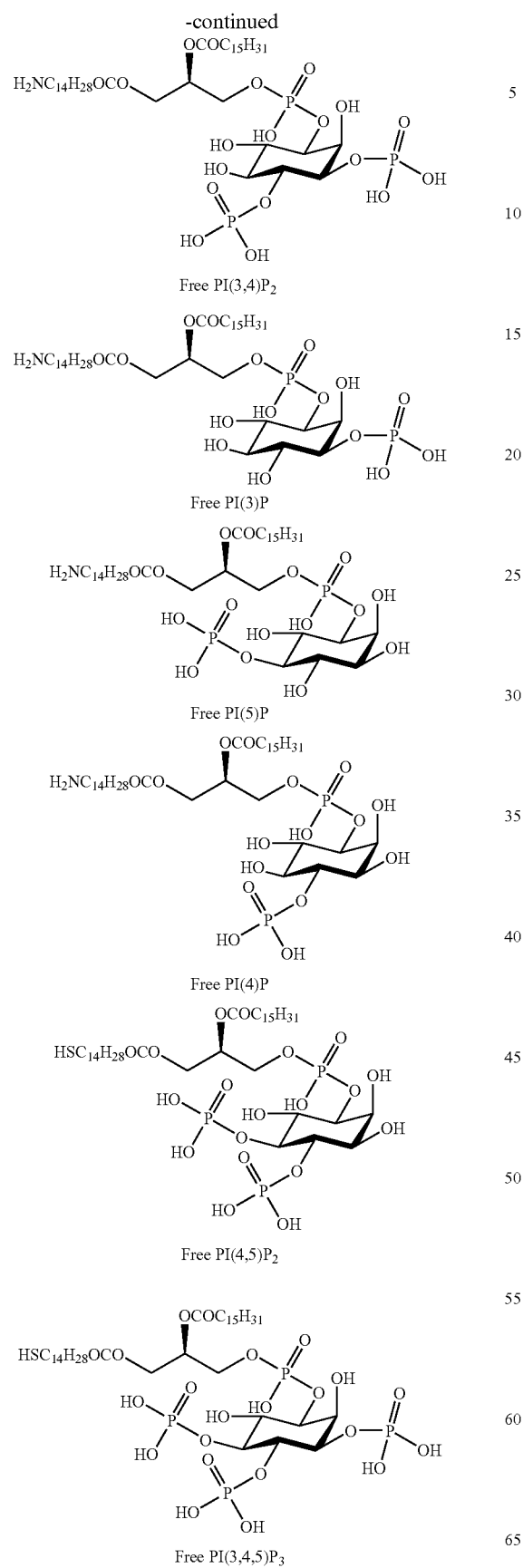
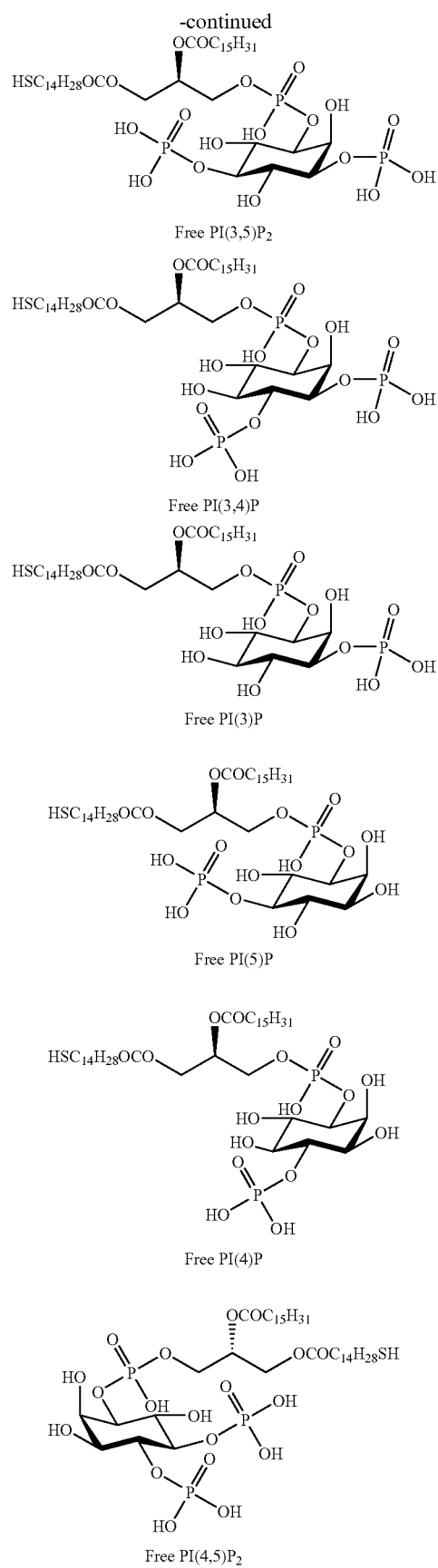

-continued
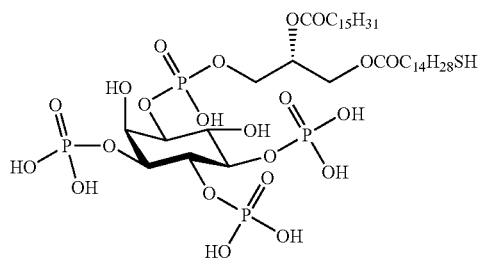
Free PI(3,4,5)P₃
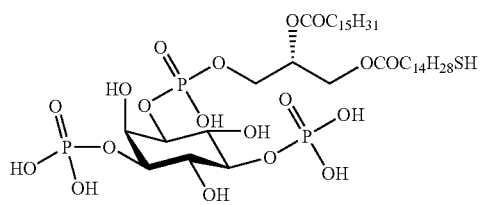
Free PI(3,5)P₂
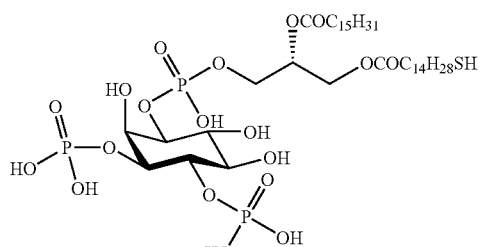
Free PI(3,4)P₂
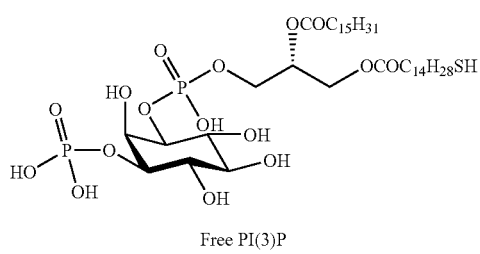
Free PI(3)P
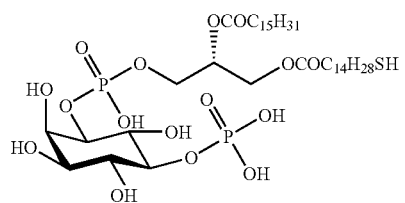
Free PI(5)P
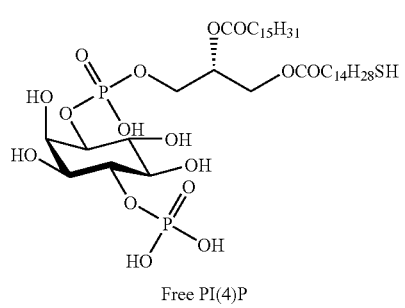
Free PI(4)P
-continued
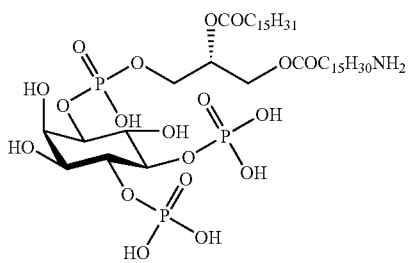
Free PI(4,5)P₂
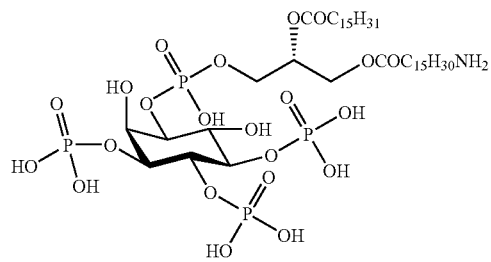
Free PI(3,4,5)P₃
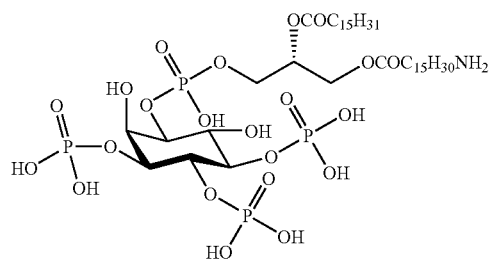
Free PI(3,5)P₂
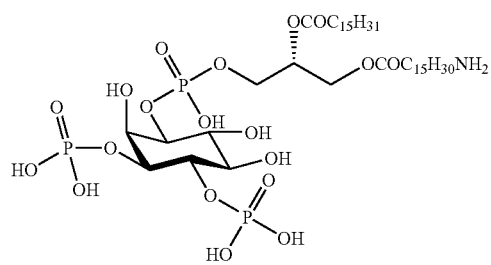
Free PI(3,4)P₂
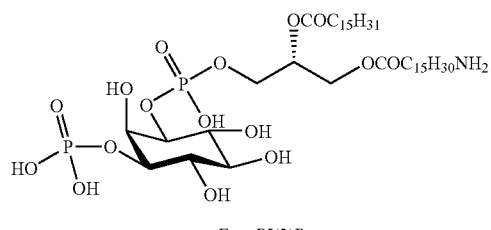
Free PI(3)P
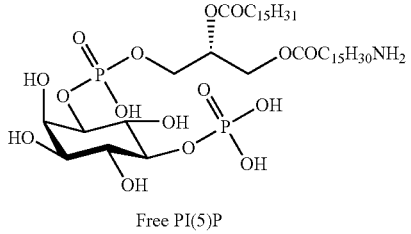
Free PI(5)P

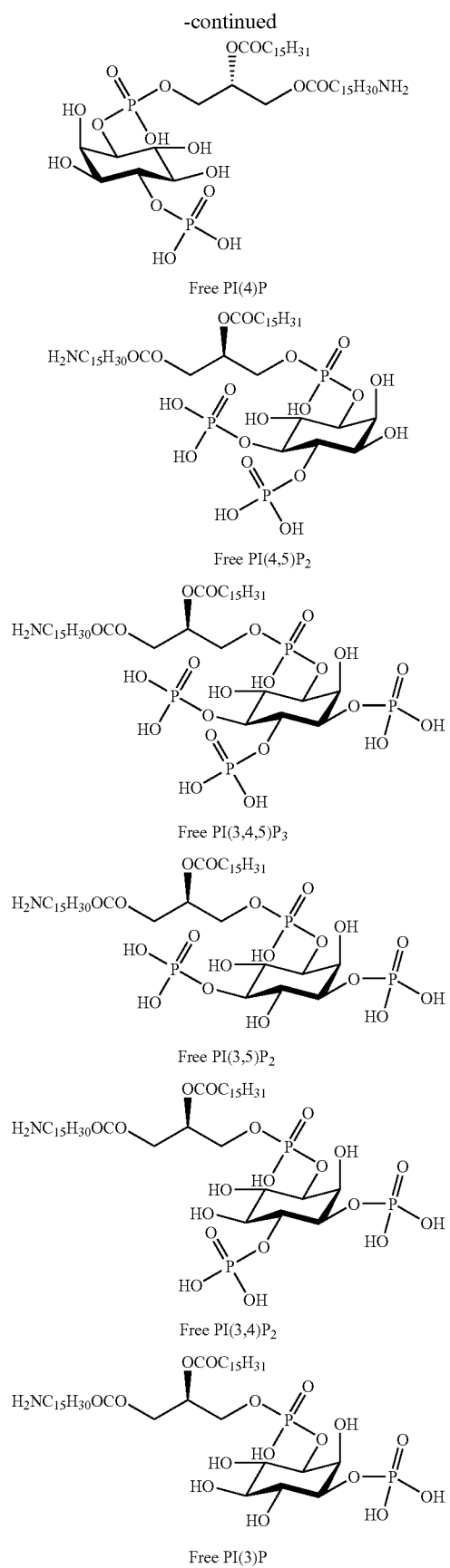
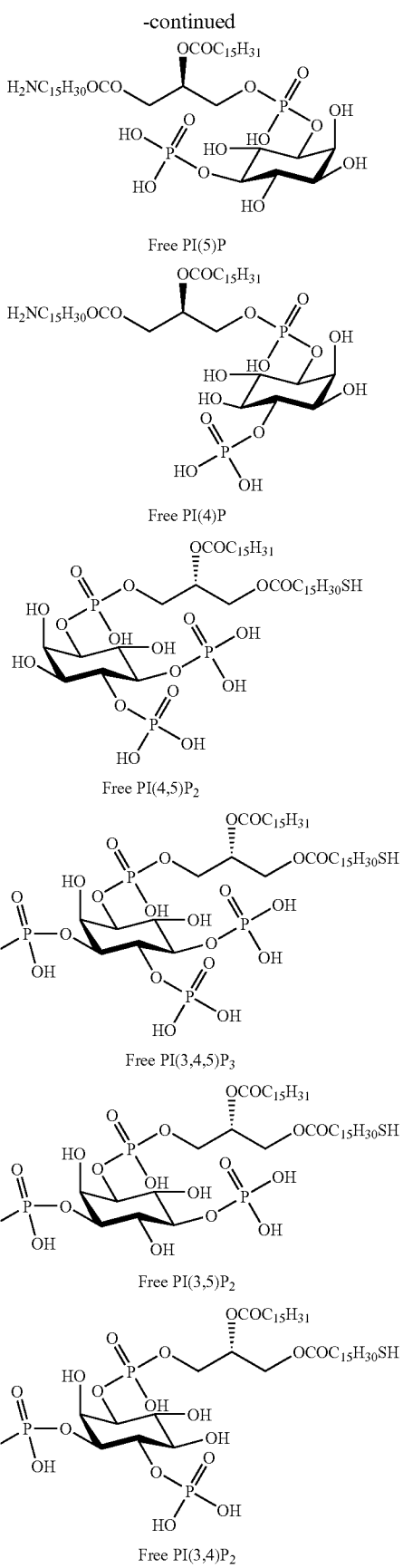

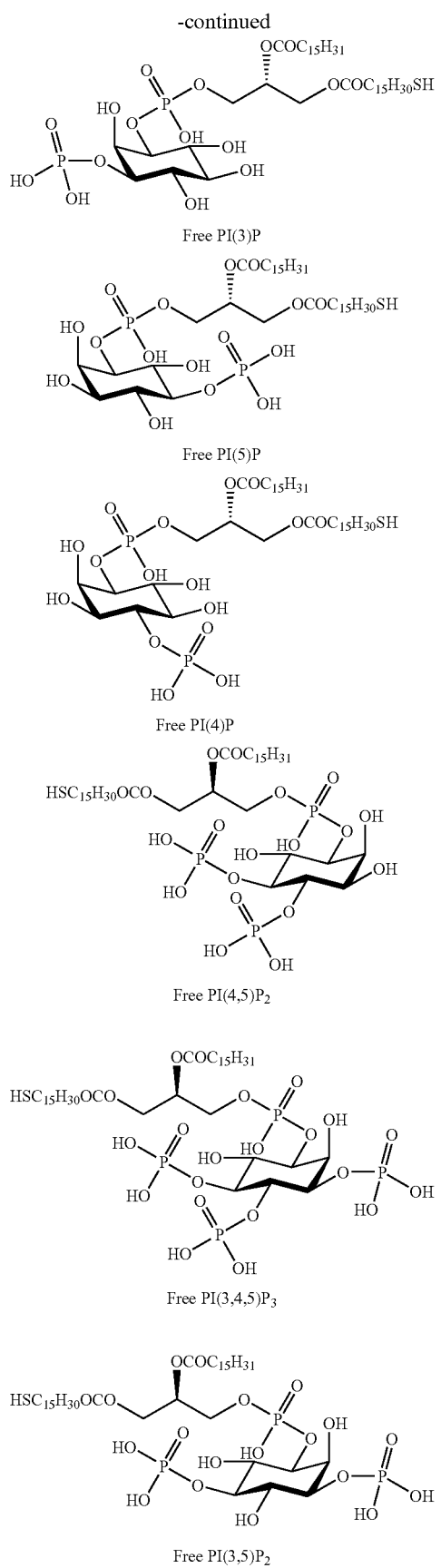
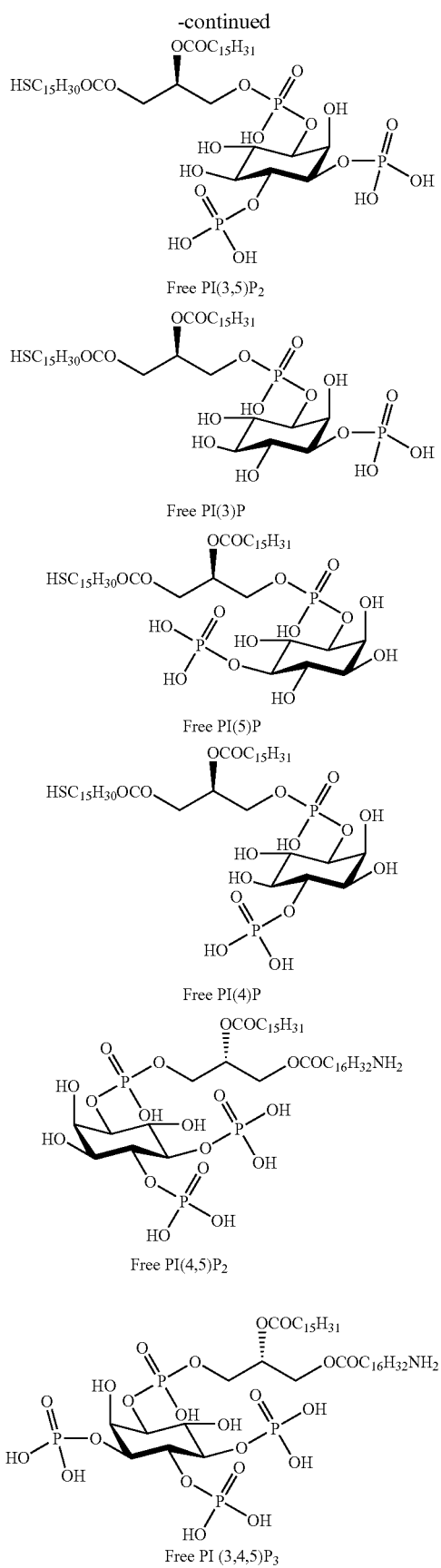

-continued
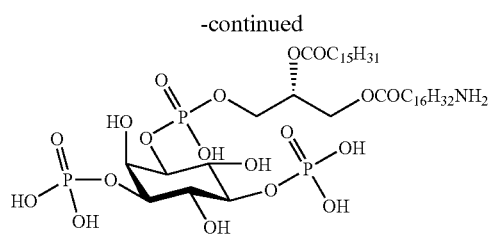
Free PI(3,5)P₂
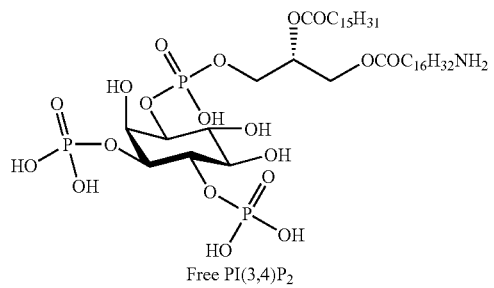
Free PI(3,4)P₂
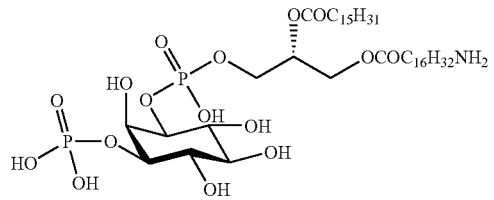
Free PI(3)P
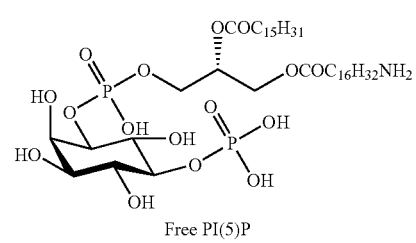
Free PI(5)P
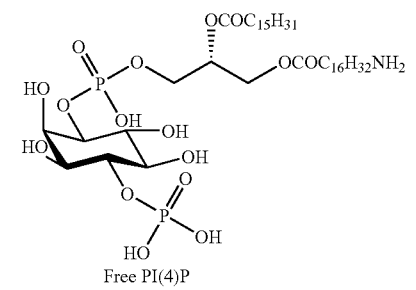
Free PI(4)P
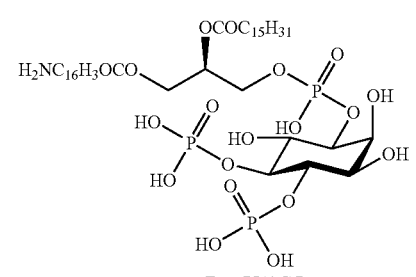
Free PI(4,5)P₂
-continued
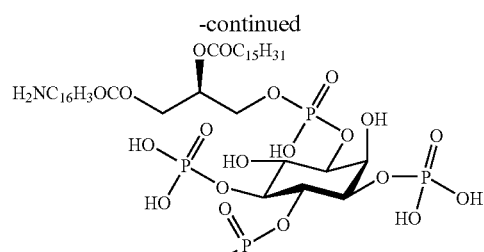
Free PI(3,4,5)P₃
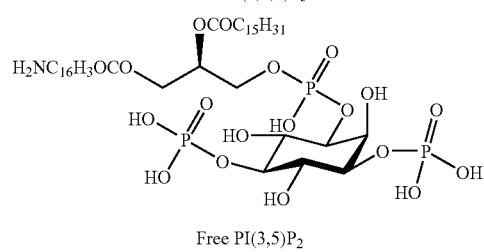
Free PI(3,5)P₂
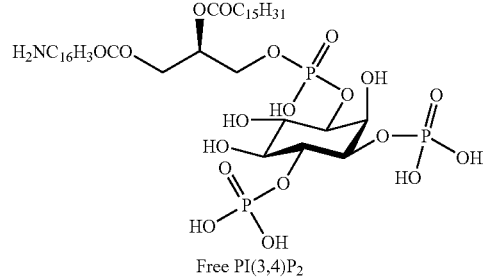
Free PI(3,4)P₂
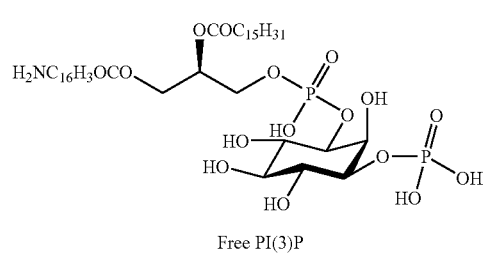
Free PI(3)P
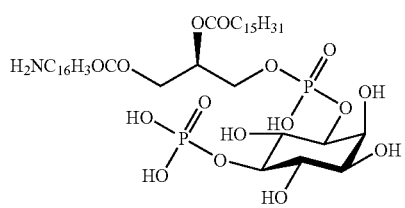
Free PI(5)P
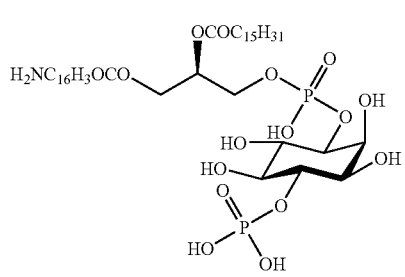
Free PI(4)P -continued
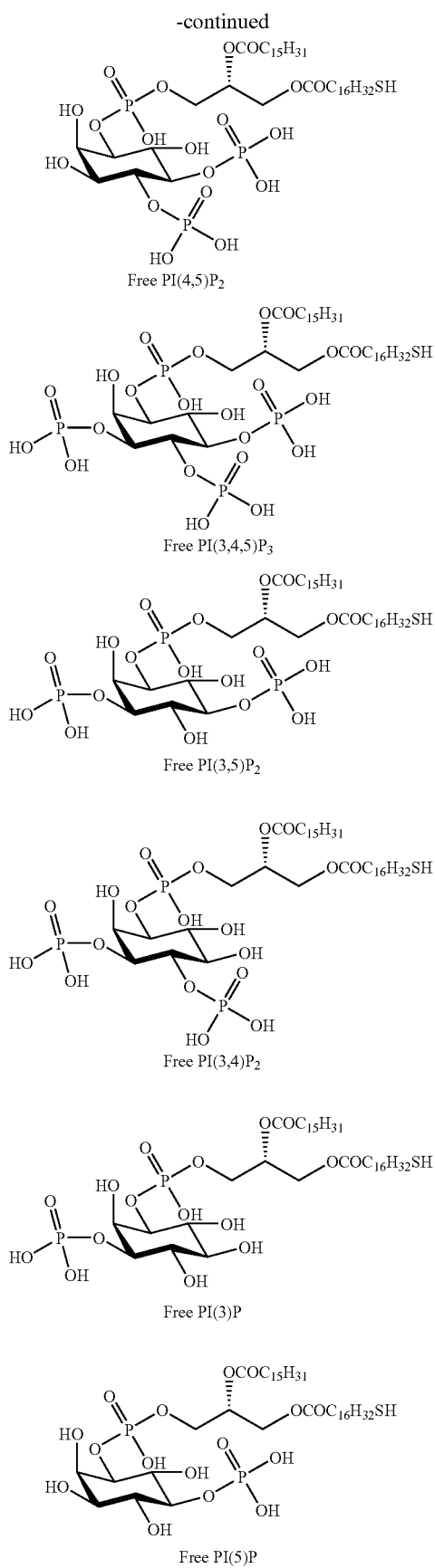
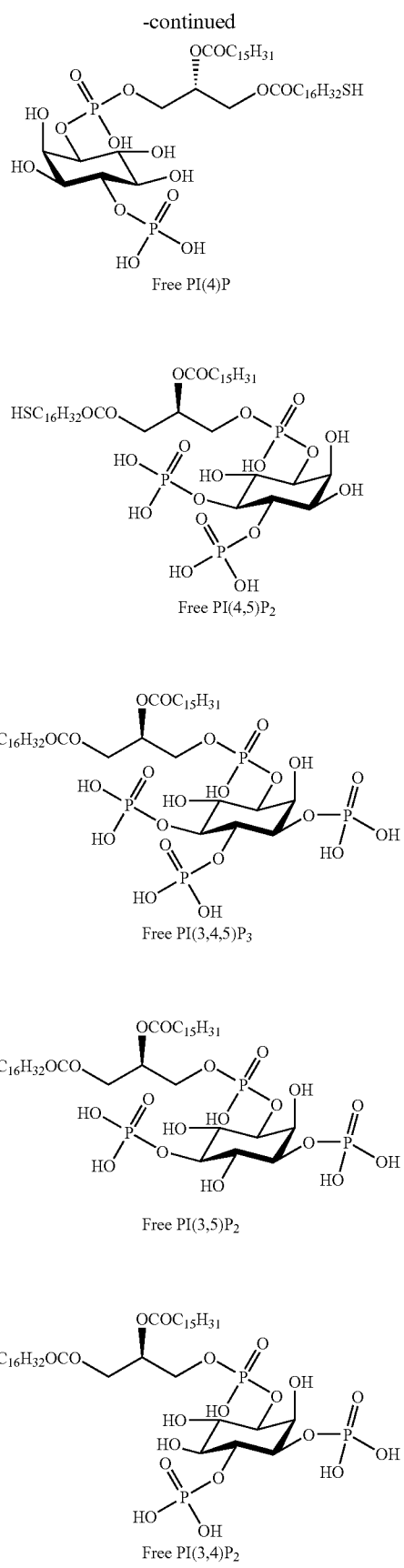

-continued

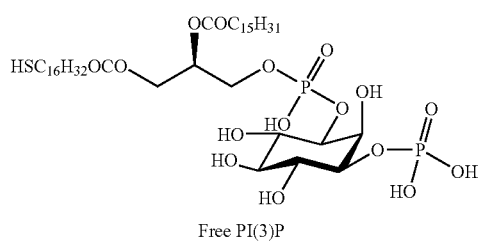

Free PI(3)P

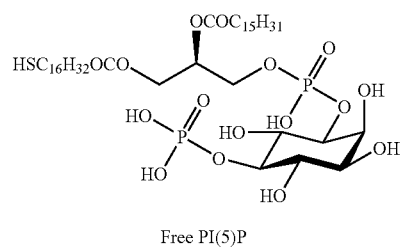

Free PI(5)P

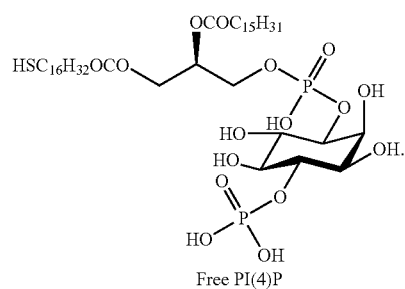

Free PI(4)P

21. A method of making a probe according to claim 5 comprising reacting a compound of formula I', II', III', or IV:

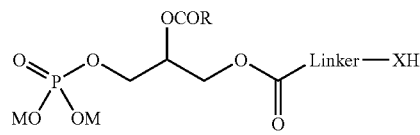
Formula I'

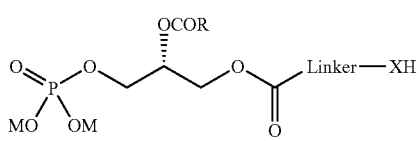
Formula II'

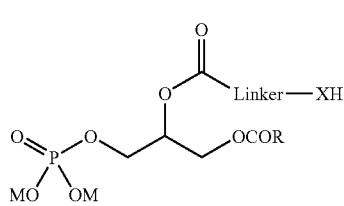
Formula III'

-continued

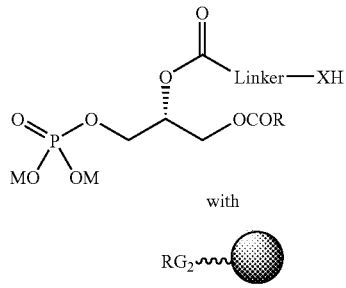
Formula IV' with

wherein,
(a) the linker consists of $(CH_2)_n$, wherein n is 8-20;
(b) the R-substituent carries an aryl or alkyl group;
R is $C_mH_{2m+1}$, where m is 8-20;
(c) the ion M represents any cation, including $Na^+$, $NH4^+$;
(d) unsaturations are allowed, including in an arachidonyl side chain;
X is NH, O, or S
$RG_2$ is a reactive group capable of reaction with XH;

is a solid support with attachment to $RG_2$.

22. The method of claim 21 further comprising deprotecting a compound of formula I″, II″, III″, or IV″ to form the compound of formula I', II', III', or IV':

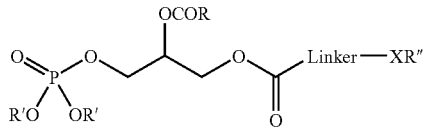
Formula I″

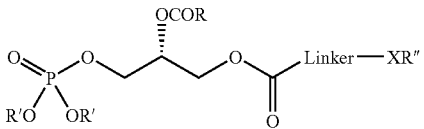
Formula II″

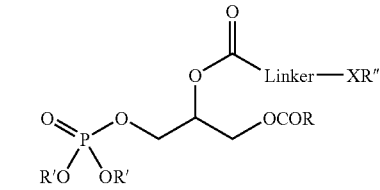
Formula III″

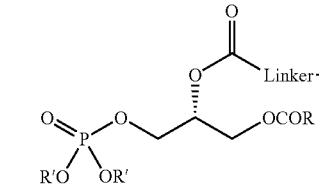
Formula IV″ wherein,
(a) the linker consists of $(CH_2)_n$, wherein n is 8-20;
(b) the heteroatom X is O, S, or NH;

(c) the R-substituent carries an aryl or alkyl group;

R is $C_mH_{2m+1}$, where m is 8-20;

(d) unsaturations are allowed, including in an arachidonyl side chain;

(e) R' is any suitable protecting group, including Bn; trialkyl silyl; and $CNCH_2CH_2$—;

(f) R" is any suitable protecting group, including Fmoc; CBz, when X is NH.

23. The method according to claim 21, wherein the compound of formula I' or II' is of one of the compounds as listed below:

Novel compounds

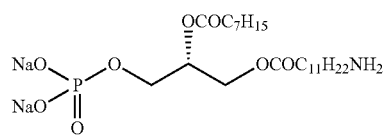

C8 at sn-2 position

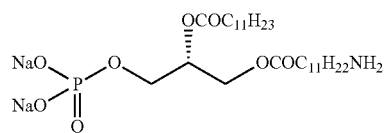

C12 at sn-2 position

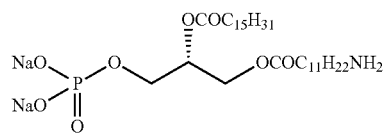

C16 at sn-2 position

Speculative
Changes in chain length at the sn-2 position

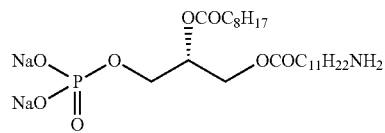

C9 at sn-2 position

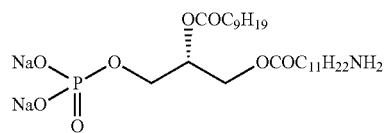

C10 at sn-2 position

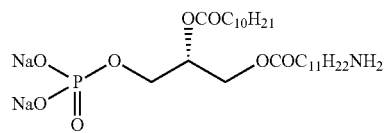

C11 at sn-2 position

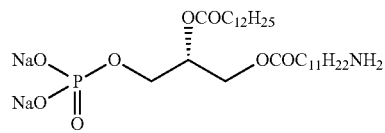

C13 at sn-2 position

-continued

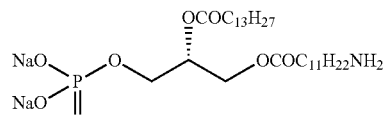

C14 at sn-2 position

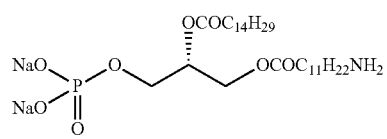

C15 at sn-2 position

Changes in chain length at the sn-1 position
C8 at sn-2 position

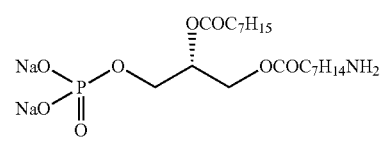

C8 at sn-1 position

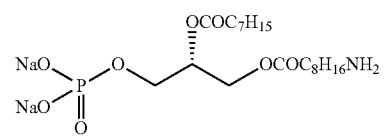

C9 at sn-1 position

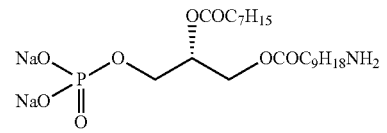

C10 at sn-1 position

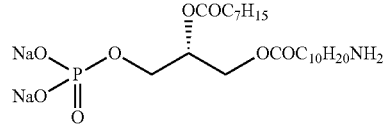

C11 at sn-1 position

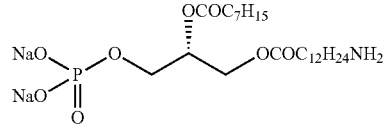

C13 at sn-1 position

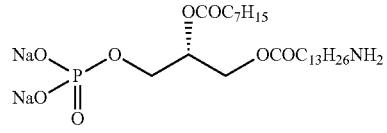

C14 at sn-1 position

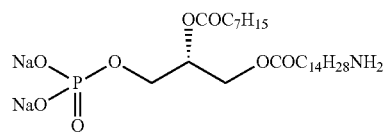

C15 at sn-1 position

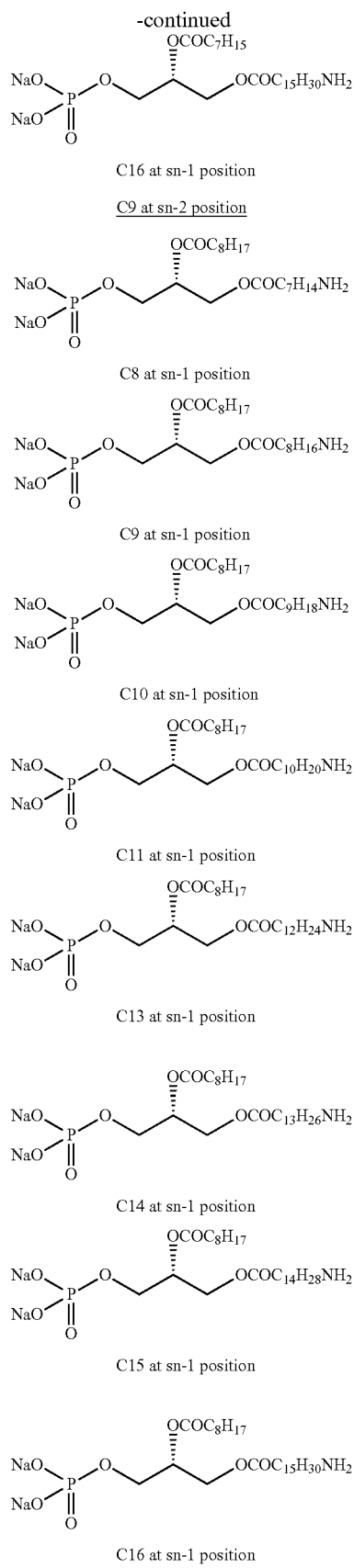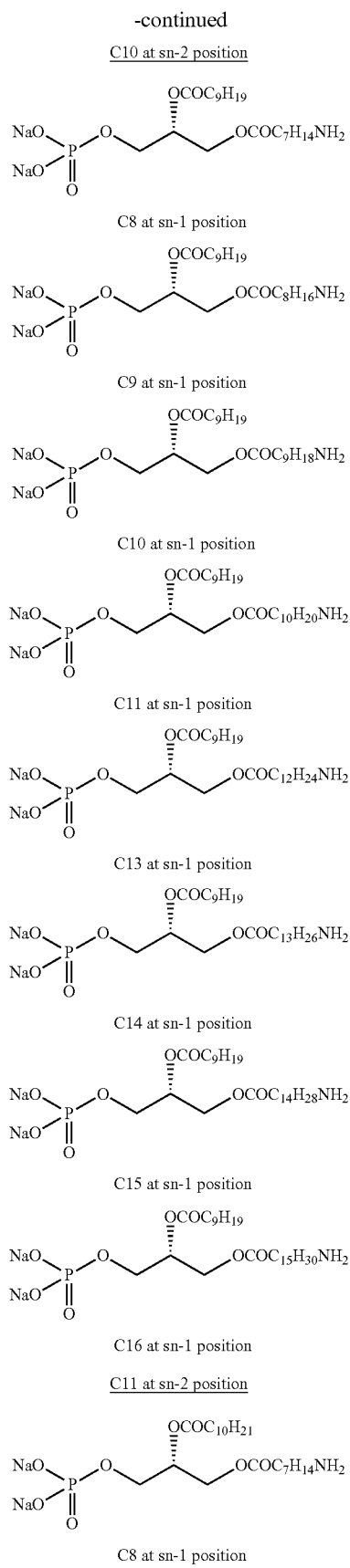

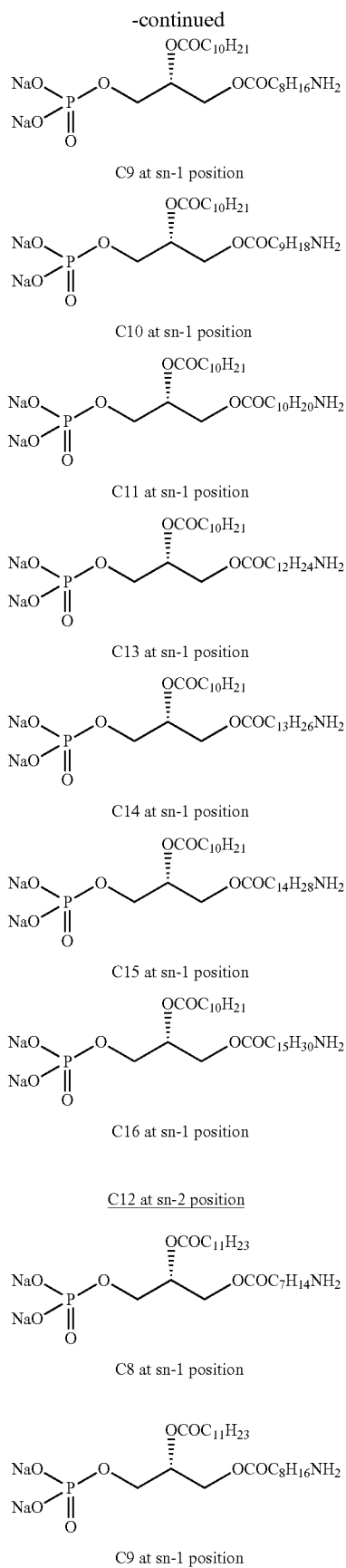
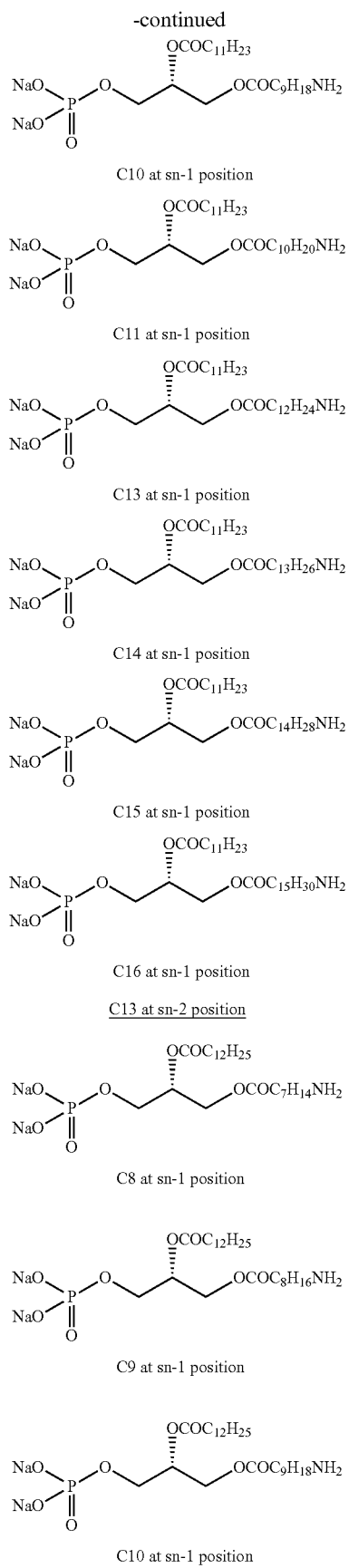

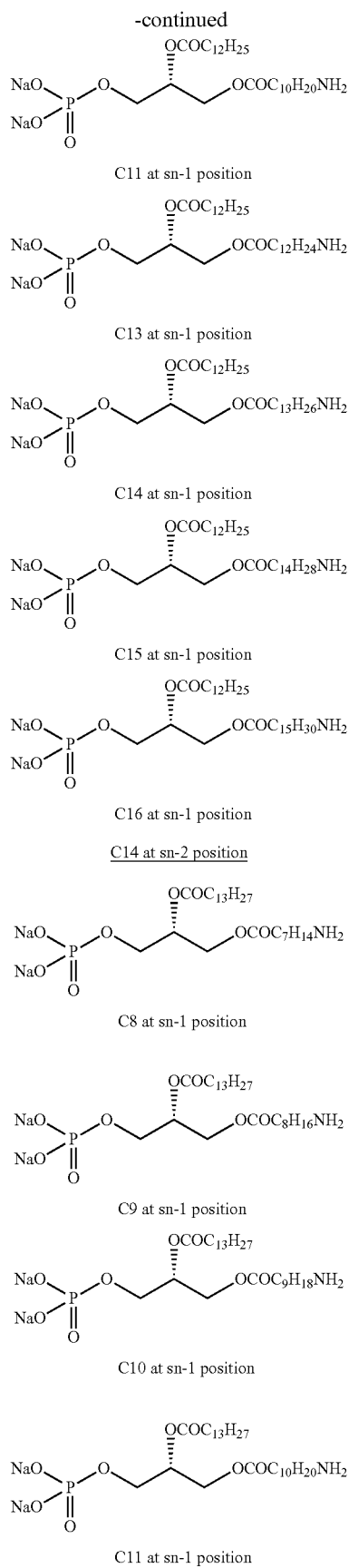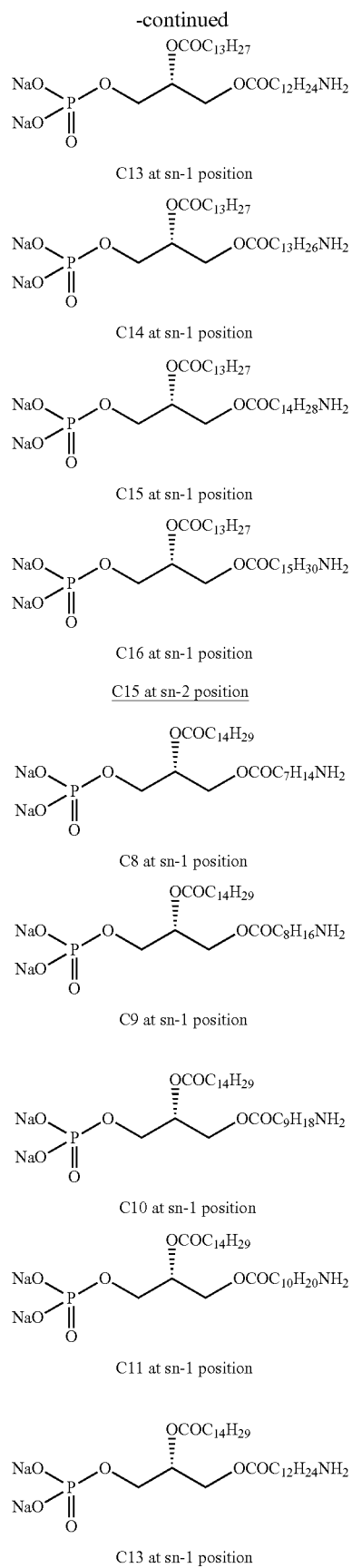

-continued
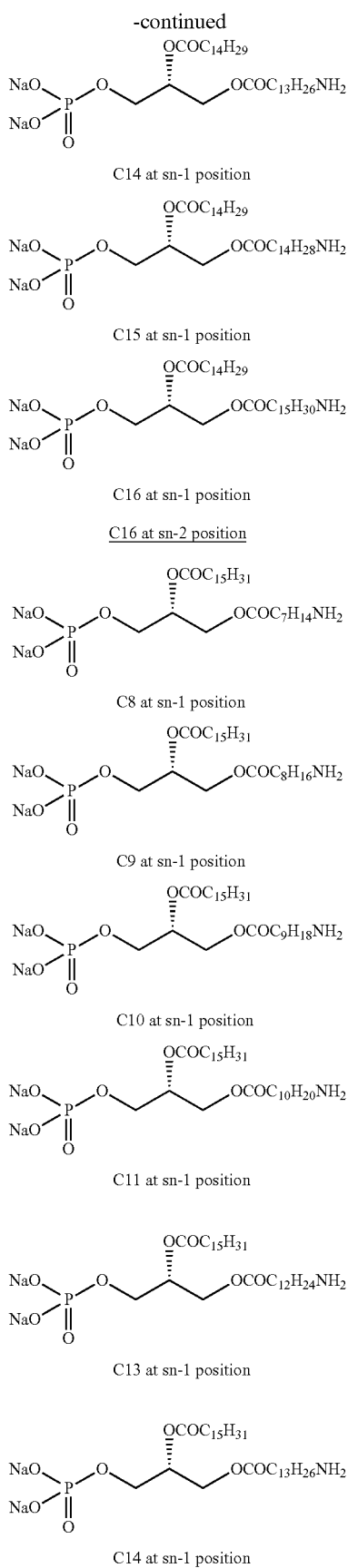
C14 at sn-1 position
C15 at sn-1 position
C16 at sn-1 position
C16 at sn-2 position
C8 at sn-1 position
C9 at sn-1 position
C10 at sn-1 position
C11 at sn-1 position
C13 at sn-1 position
C14 at sn-1 position
-continued
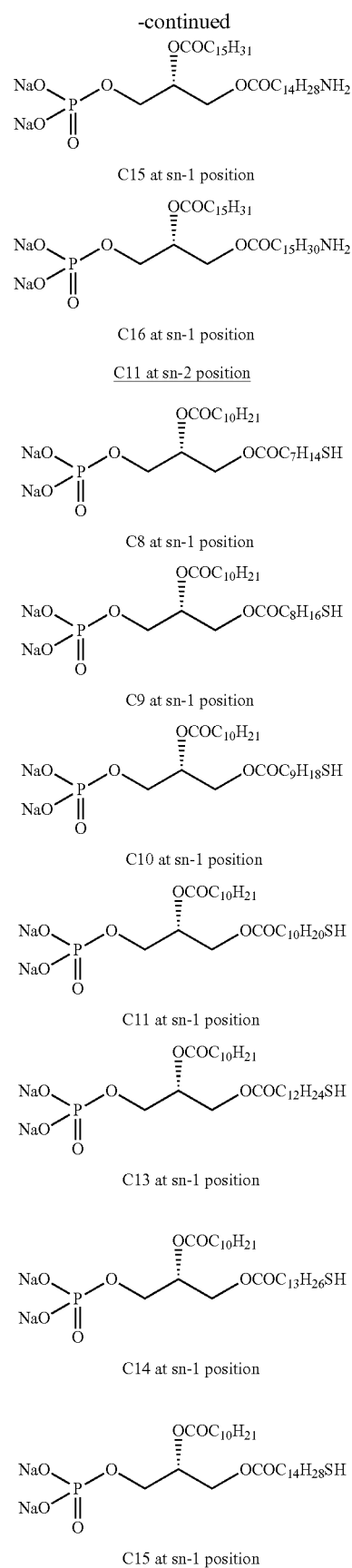
C15 at sn-1 position
C16 at sn-1 position
C11 at sn-2 position
C8 at sn-1 position
C9 at sn-1 position
C10 at sn-1 position
C11 at sn-1 position
C13 at sn-1 position
C14 at sn-1 position
C15 at sn-1 position

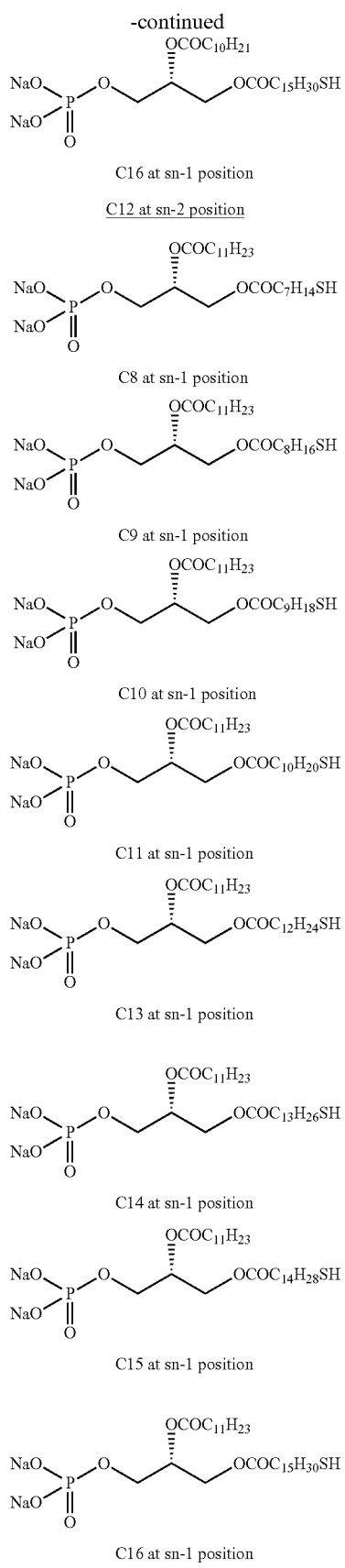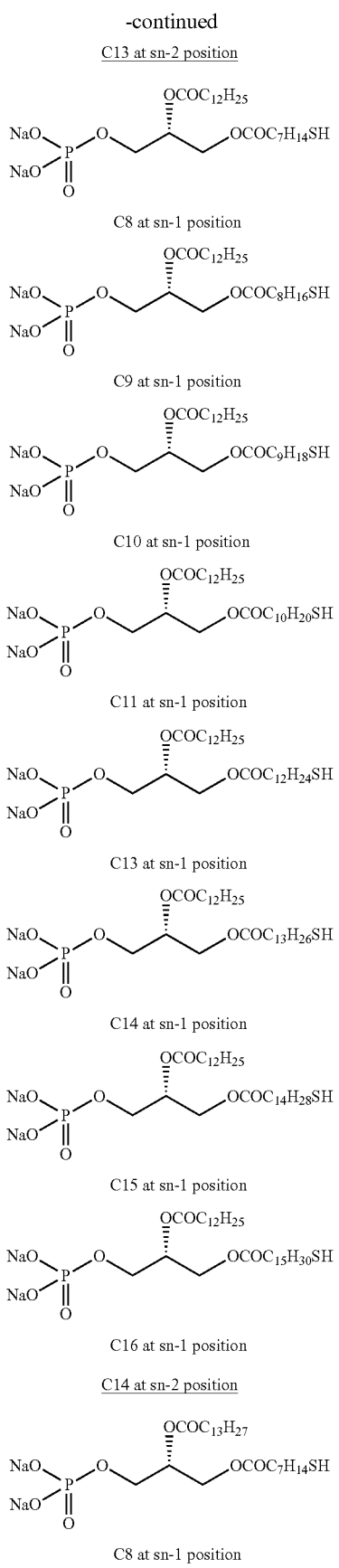

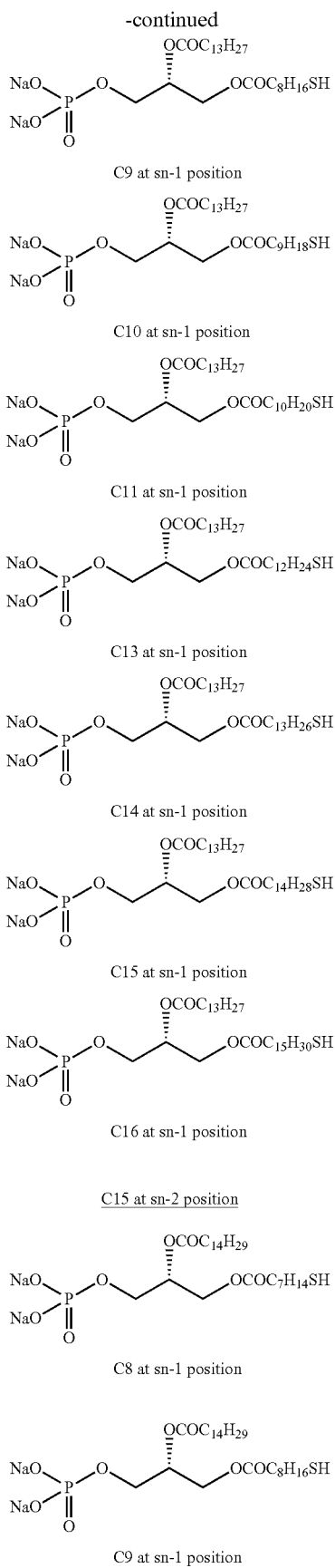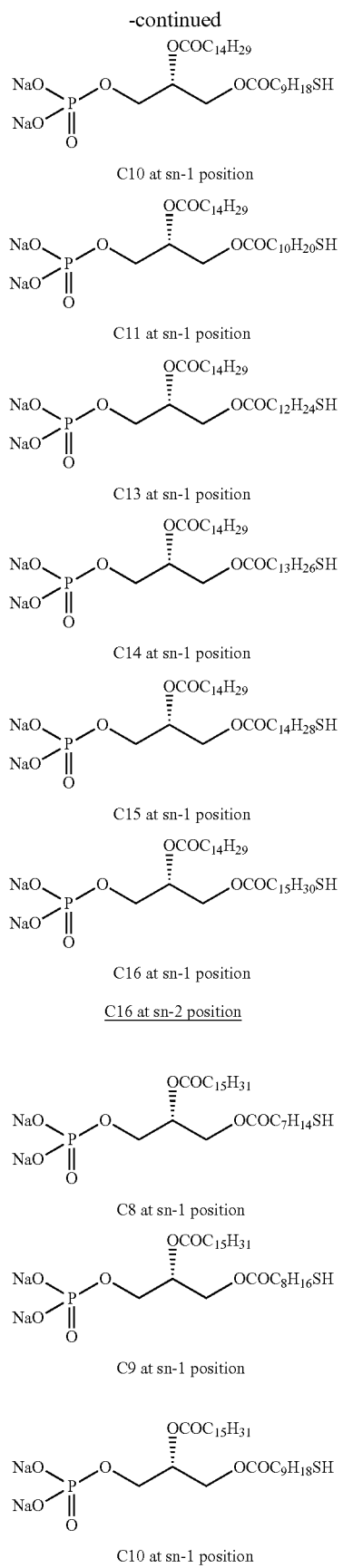

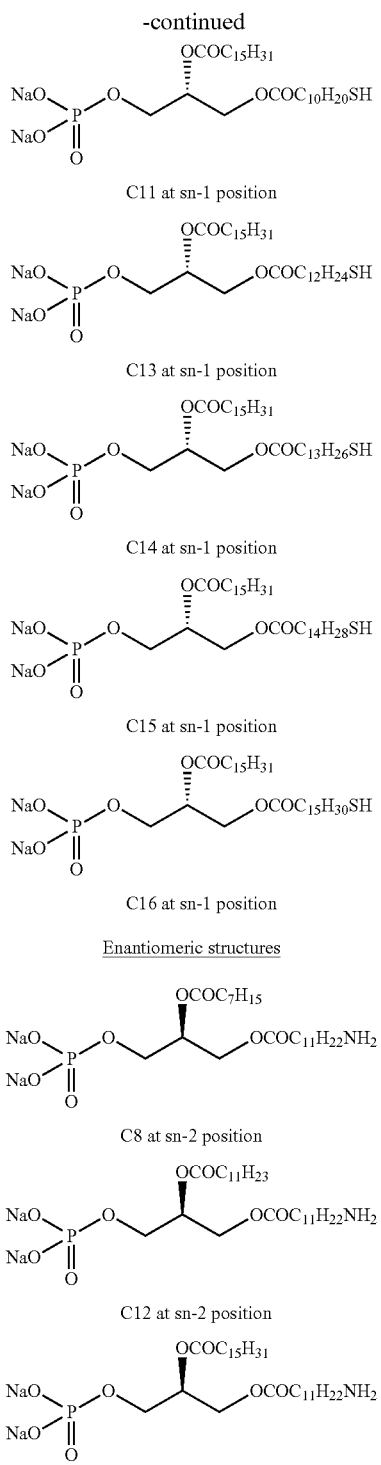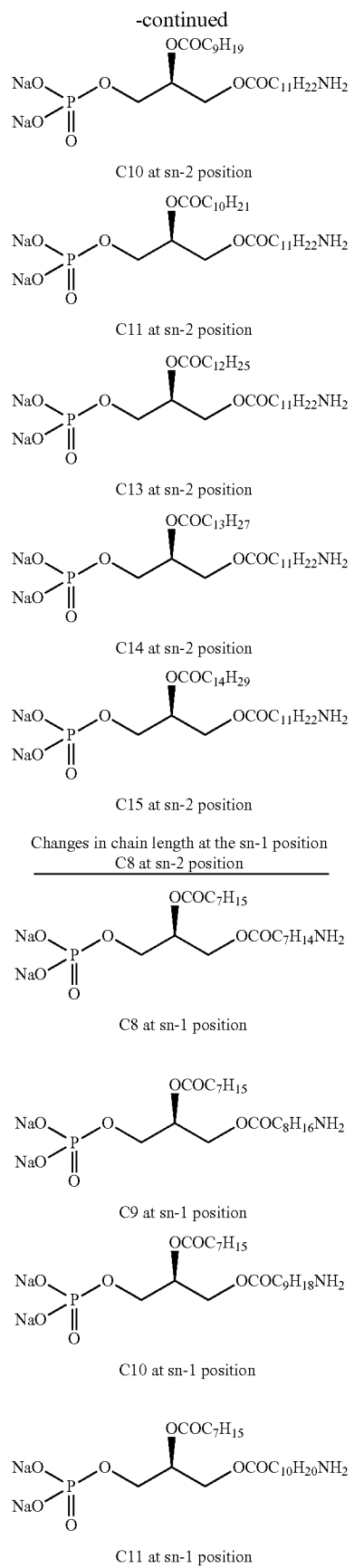

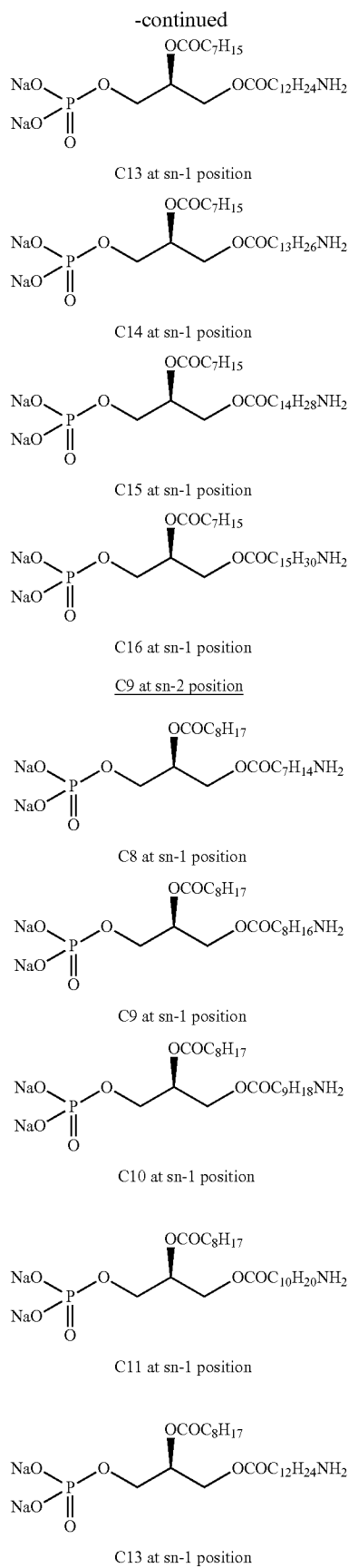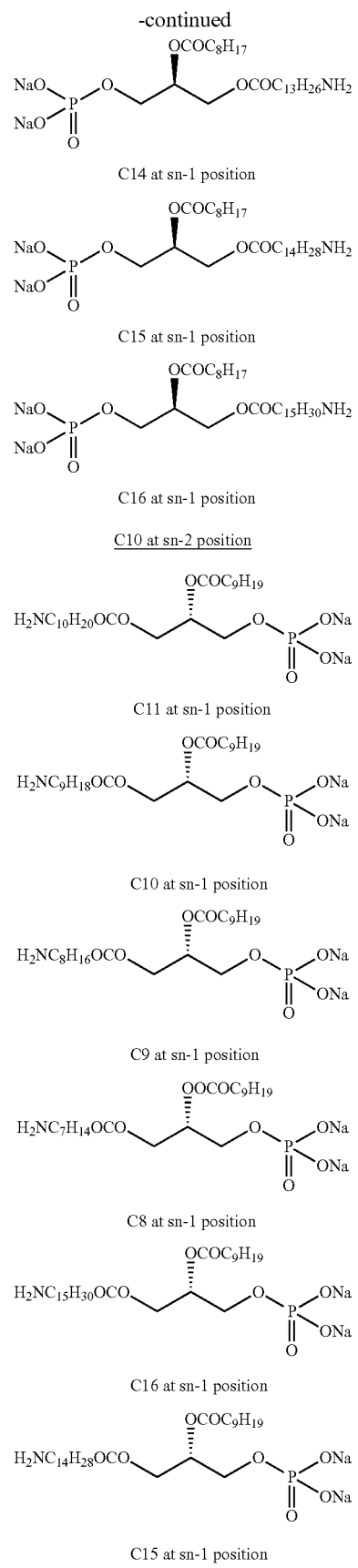

-continued
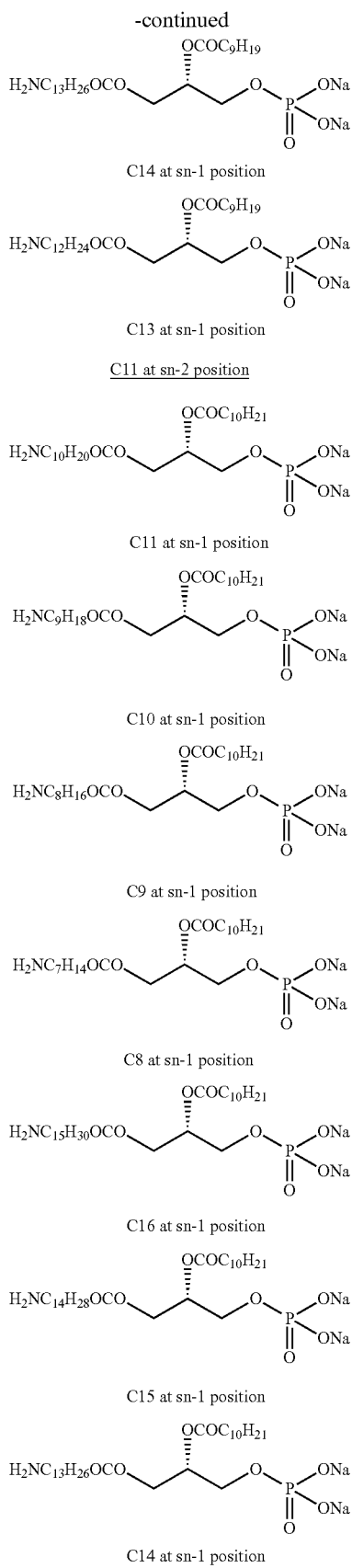
C14 at sn-1 position
C13 at sn-1 position
C11 at sn-2 position
C11 at sn-1 position
C10 at sn-1 position
C9 at sn-1 position
C8 at sn-1 position
C16 at sn-1 position
C15 at sn-1 position
C14 at sn-1 position
-continued
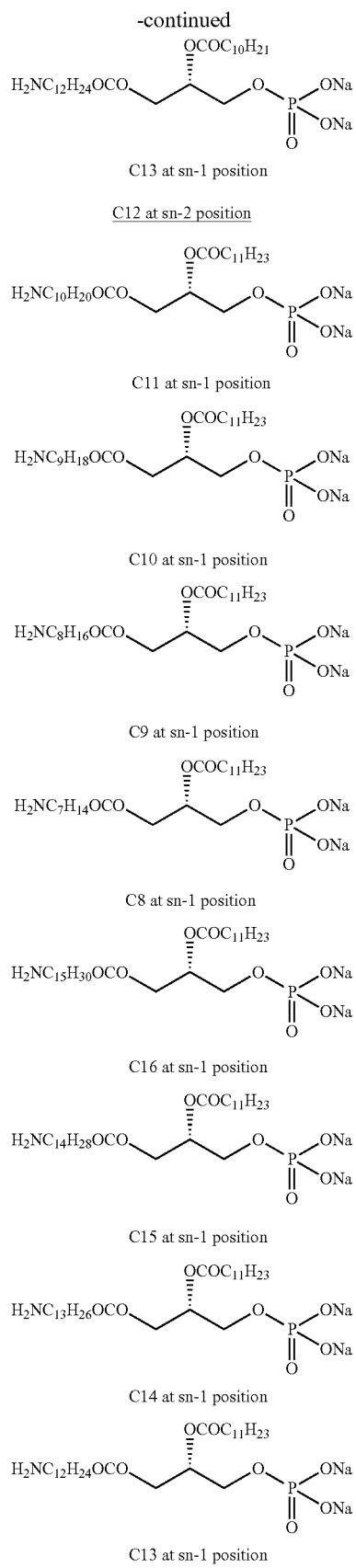
C13 at sn-1 position
C12 at sn-2 position
C11 at sn-1 position
C10 at sn-1 position
C9 at sn-1 position
C8 at sn-1 position
C16 at sn-1 position
C15 at sn-1 position
C14 at sn-1 position
C13 at sn-1 position

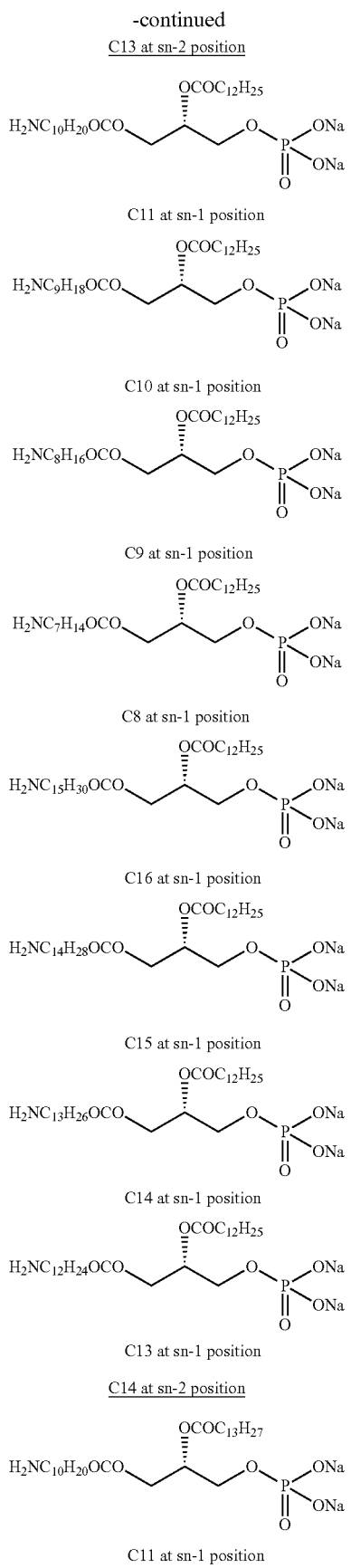
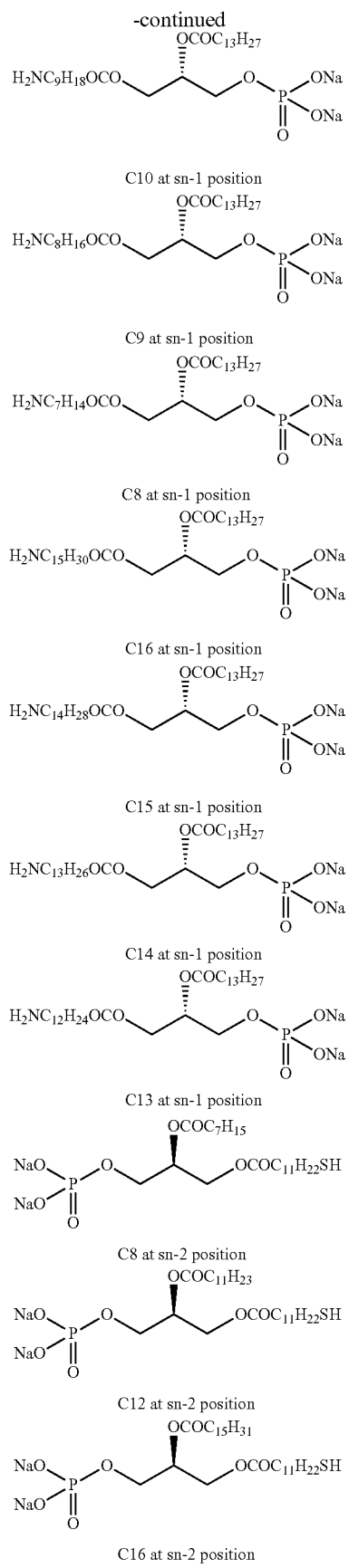

-continued

Changes in chain length at the sn-2 position

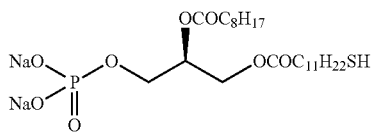

C9 at sn-2 position

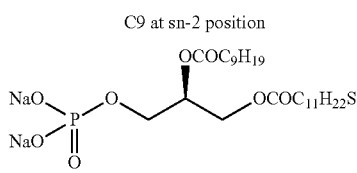

C10 at sn-2 position

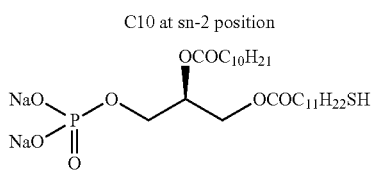

C11 at sn-2 position

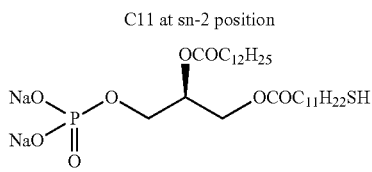

C13 at sn-2 position

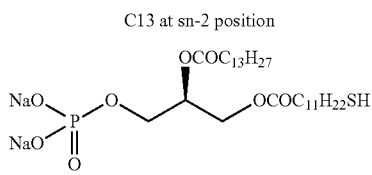

C14 at sn-2 position

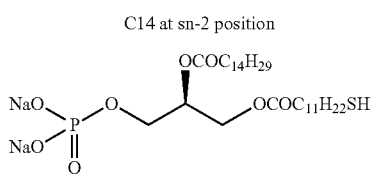

C15 at sn-2 position

Changes in chain length at the sn-1 position
C8 at sn-2 position

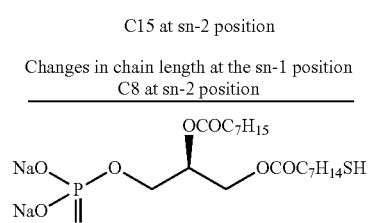

C8 at sn-1 position

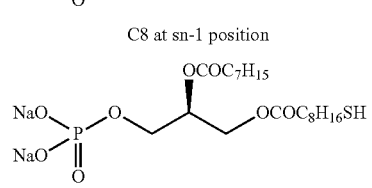

C9 at sn-1 position

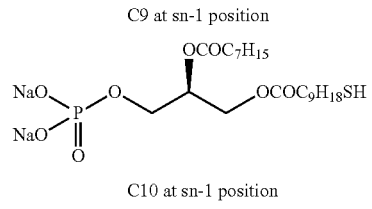

C10 at sn-1 position

-continued

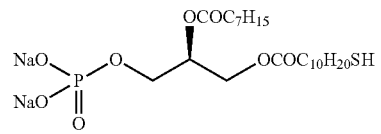

C11 at sn-1 position

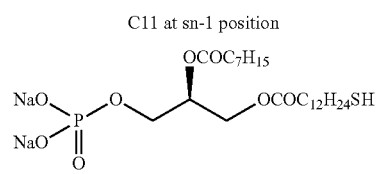

C13 at sn-1 position

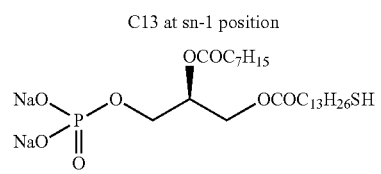

C14 at sn-1 position

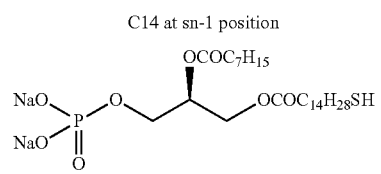

C15 at sn-1 position

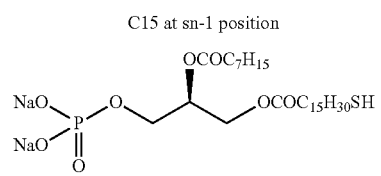

C16 at sn-1 position

C11 at sn-2 position

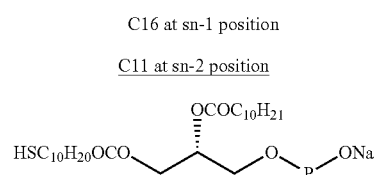

C11 at sn-1 position

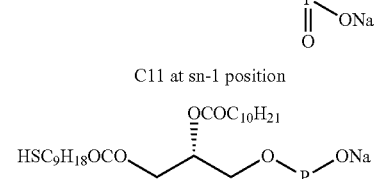

C10 at sn-1 position

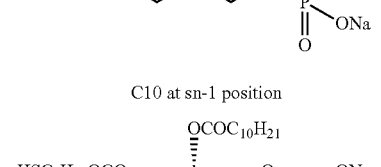

C9 at sn-1 position

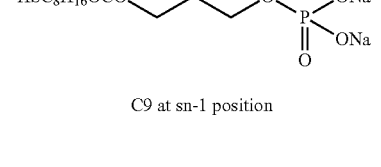

C8 at sn-1 position

-continued
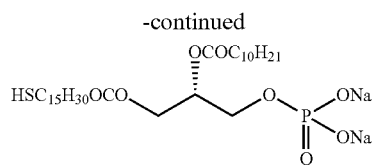
C16 at sn-1 position
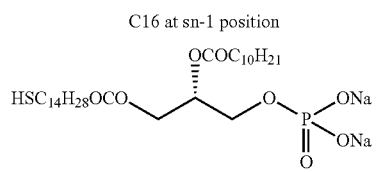
C15 at sn-1 position
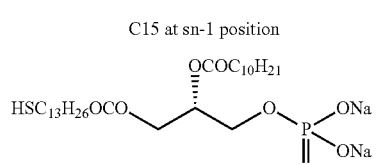
C14 at sn-1 position
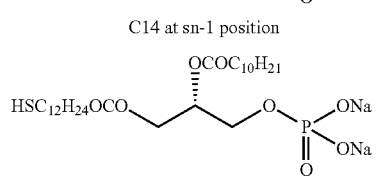
C13 at sn-1 position
C12 at sn-2 position
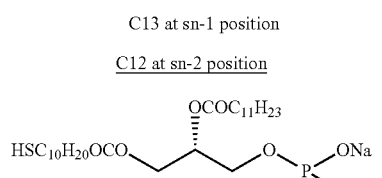
C11 at sn-1 position
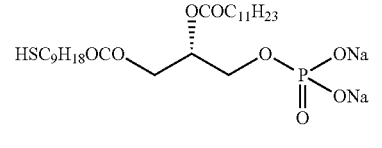
C10 at sn-1 position
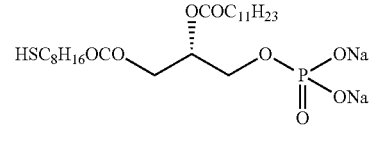
C9 at sn-1 position
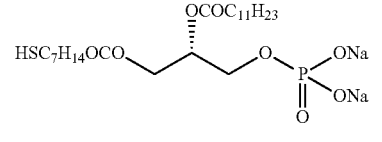
C8 at sn-1 position
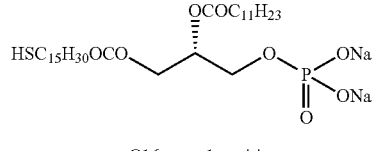
C16 at sn-1 position
-continued
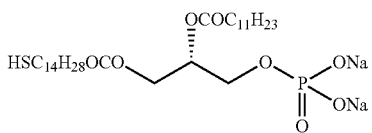
C15 at sn-1 position
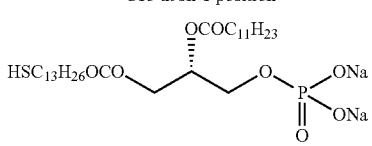
C14 at sn-1 position
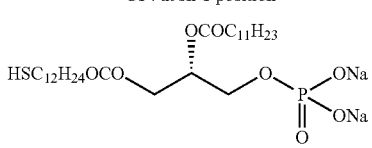
C13 at sn-1 position
C13 at sn-2 position
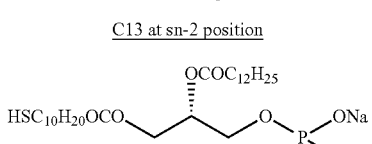
C11 at sn-1 position
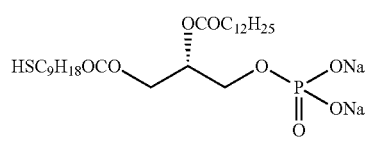
C10 at sn-1 position
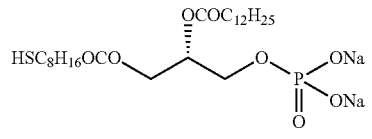
C9 at sn-1 position
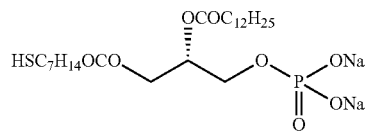
C8 at sn-1 position
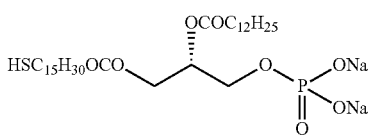
C16 at sn-1 position
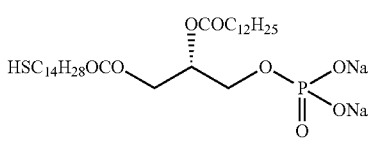
C15 at sn-1 position

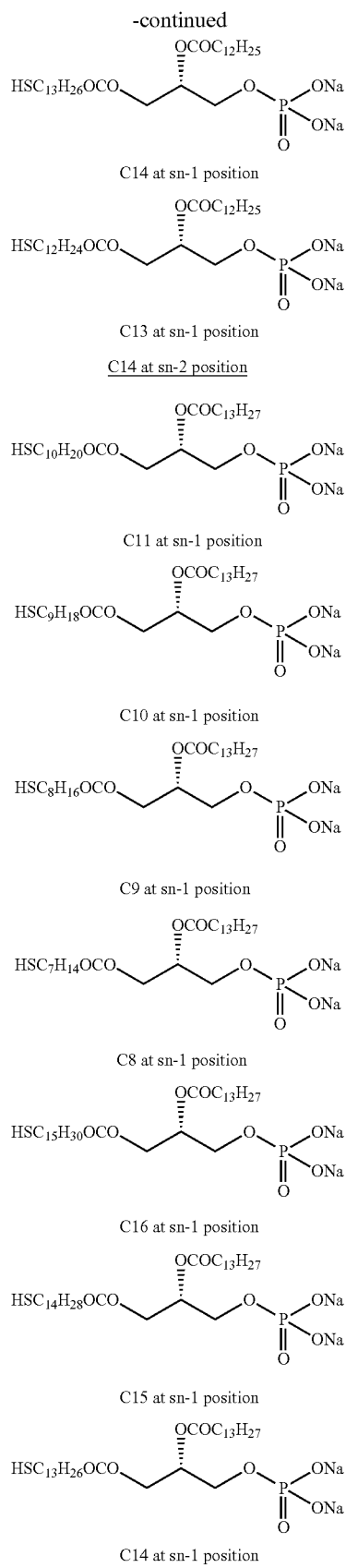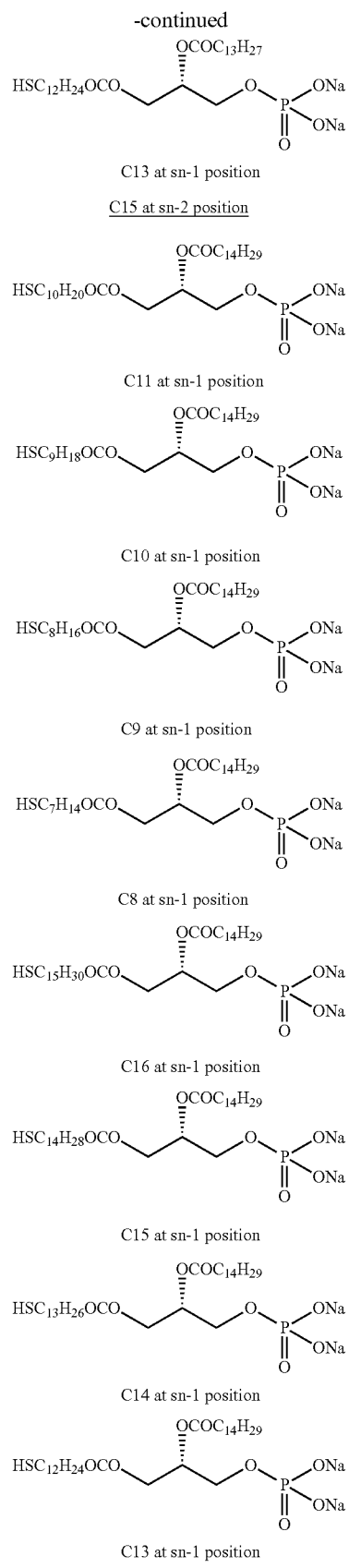

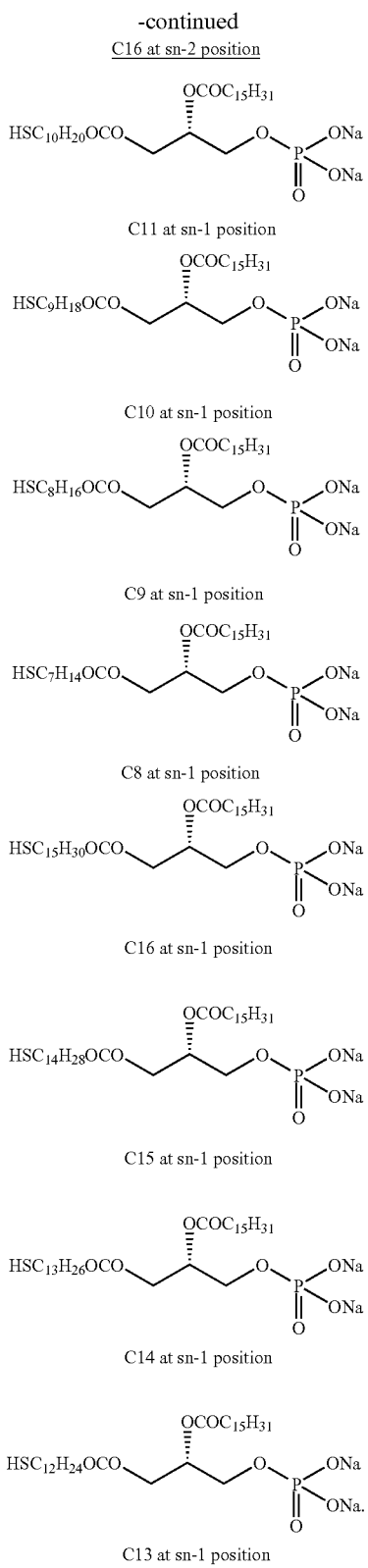

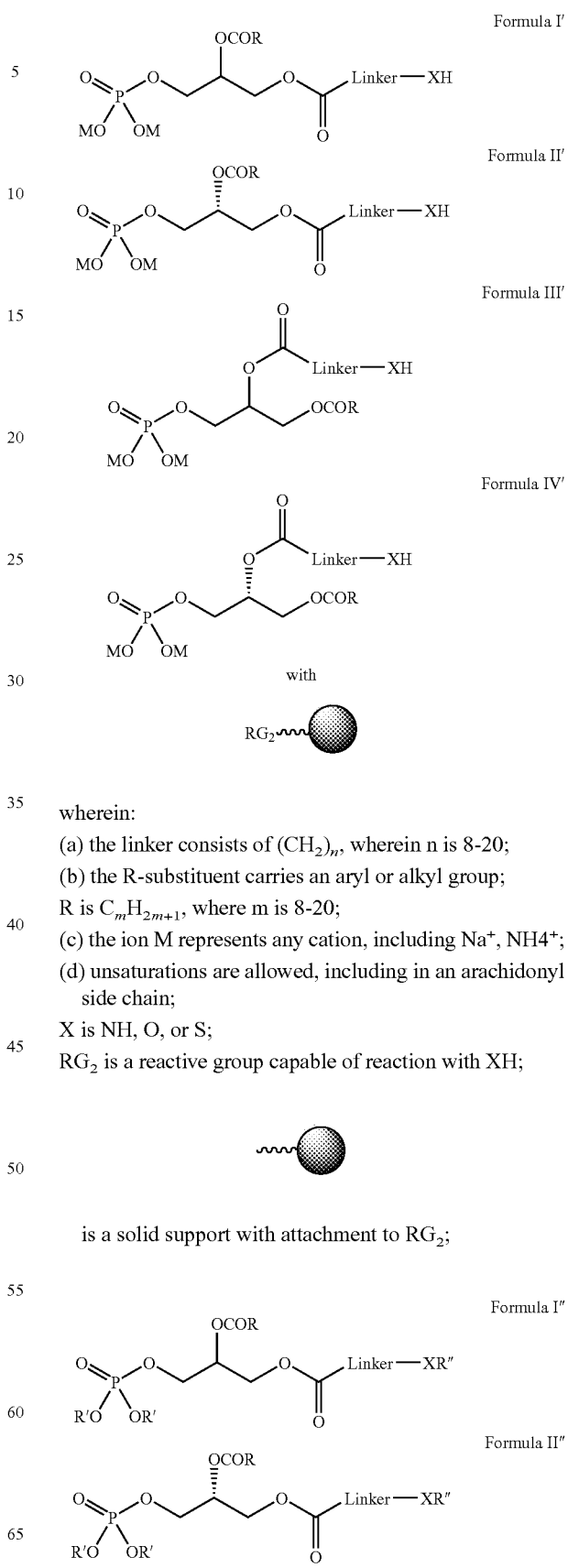

wherein:
(a) the linker consists of $(CH_2)_n$, wherein n is 8-20;
(b) the R-substituent carries an aryl or alkyl group;
R is $C_mH_{2m+1}$, where m is 8-20;
(c) the ion M represents any cation, including $Na^+$, $NH4^+$;
(d) unsaturations are allowed, including in an arachidonyl side chain;
X is NH, O, or S;
$RG_2$ is a reactive group capable of reaction with XH;

is a solid support with attachment to $RG_2$;

24. A method of making a compound of Formula I', II', III', or IV' which method comprises removal of the protecting groups of a compound of Formula I'', II'', III'', or IV'', respectively, including by reductive debenzylation -continued

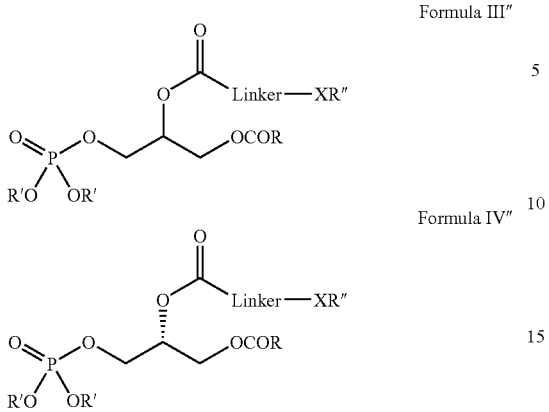

wherein,
(a) the linker consists of $(CH_2)_n$, wherein n is 8-20;
(b) the heteroatom X is O, S, or NH;
(c) the R-substituent carries an aryl or alkyl group;
R is $C_mH_{2m+1}$, where m is 8-20;
(d) unsaturations are allowed, including in an arachidonyl side chain;
(e) R' is any suitable protecting group, including Bn; trialkyl silyl; and $CNCH_2CH_2$—;
(f) R" is any suitable protecting group, including Fmoc; CBz, when X is NH.

25. A method of making a compound of Formula V', VI', VII', or VIII' which method includes reductive debenzylation of a compound of Formula V''', VI''', VII''', or VIII''', respectively

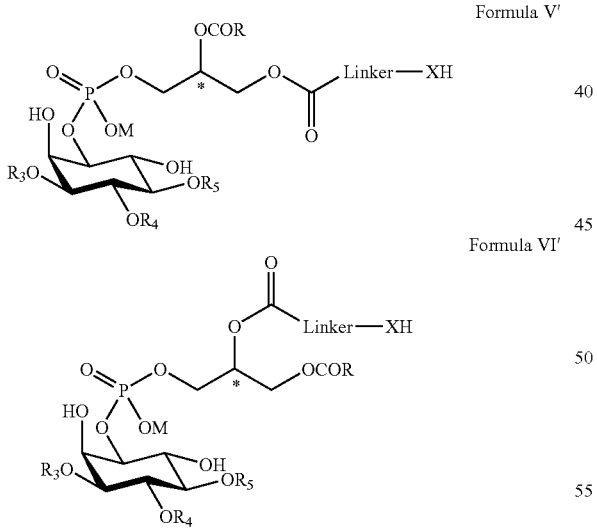

wherein:
R=aryl or alkyl group;
R=$C_mH_{2m+1}$, where m=8-20;
$R_3$=P(O)(OM)$_2$; $R_4$=H; $R_5$=H (PI(3)P);
$R_3$=H; $R_4$=P(O)(OM)$_2$; $R_5$=H (PI(4)P);
$R_3$=H; $R_4$=H; $R_5$=P(O)(OM)$_2$ (PI(5)P);
$R_3$=P(O)(OM)$_2$; $R_4$=P(O)(ONA)$_2$, $R_5$=H (PI(3,4)P$_2$);
$R_3$=P(O)(OM)$_2$; $R_4$=H; $R_5$=P(O)(OM)$_2$ (PI(3,5)P$_2$);
$R_3$=H; $R_4$=P(O)(OM)$_2$; $R_5$=P(O)(OM)$_2$ (PI(4,5)P$_2$); or
$R_3$=P(O)(OM)$_2$; $R_4$=P(O)(OM)$_2$; $R_5$=P(O)(OM)$_2$ (PI(3,4,5)P$_3$);
M=any cation, including Na$^+$, NH4$^+$;
*Denotes a stereogenic centre;
Linker=$(CH_2)_n$ with n=8-20;
X=NH, O, or S
unsaturations are allowed, including in an arachidonyl side chain;
with

where:

=solid support with attachment to RG$_2$; and
RG$_2$=a reactive group capable of reaction with XH, including N-hydroxy-succinimide-activated carboxylate;

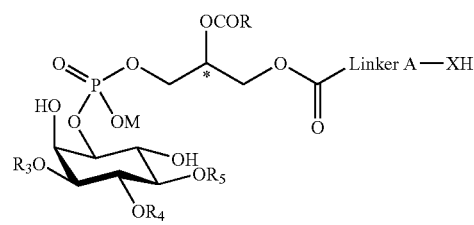

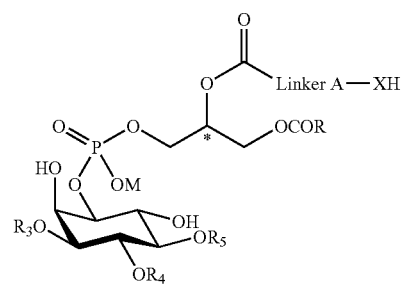

wherein:
R=aryl or alkyl group;
R=$C_mH_{2m+}$, where m=8-20;
$R_3$=P(O)(OM)$_2$; $R_4$=H; $R_5$=H (PI(3)P);
$R_3$=H; $R_4$=P(O)(OM)$_2$; $R_5$=H (PI(4)P);
$R_3$=H; $R_4$=H; $R_5$=P(O)(OM)$_2$ (PI(5)P);
$R_3$=P(O)(OM)$_2$; $R_4$=P(O)(OM)$_2$; $R_5$=H (PI(3,4)P$_2$);
$R_3$=P(O)(OM)$_2$; $R_4$=H; $R_5$=P(O)(OM)$_2$ (PI(3,5)P$_2$);
$R_3$=H; $R_4$=P(O)(OM)$_2$; $R_5$=P(O)(OM)$_2$ (PI(4,5)P$_2$); or
$R_3$=P(O)(OM)$_2$; $R_4$=P(O)(OM)$_2$; $R_5$=P(O)(OM)$_2$ (PI(3,4,5)P$_3$);
M=any cation, including Na$^+$, NH4$^+$;
*Denotes a stereogenic centre;
Linker A=$(CH_2)_n$ with n=8-20;
X=NH, O, or S;
unsaturations are allowed, including in an arachidonyl side chain;

with

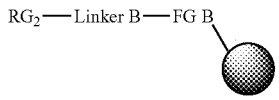

Linker B=aryl, heteroaryl, alkyl with possible heteroatoms and/or saturations: these could be any atoms, including C, N, O, S, or methylene groups linked via amide and ester bonds;
the total length of linker A and linker B is 8-60 atoms
FG B=Amide, thiolo(ester), or ester

=solid support with attachment to FG B; and
$RG_2$=a reactive group capable of reaction with XH, including N-hydroxy-succinimide-activated carboxylate;

Formula V″

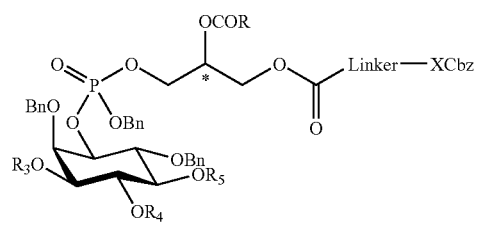

Formula VI″

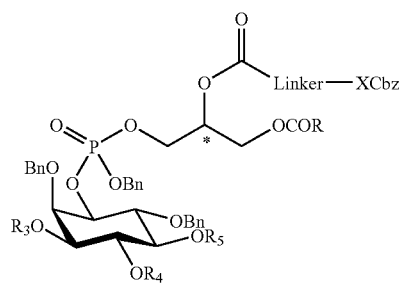

wherein:
R is an aryl or alkyl group;
R is $C_mH_{2m+1}$, where m is 8-20;
$R_3$ is $P(O)(OBn)_2$; $R_4$ is H; $R_5$ is H (PI(3)P);
$R_3$ is H; $R_4$ is $P(O)(OBn)_2$; $R_5$ is H (PI(4)P);
$R_3$ is H; $R_4$ is H; $R_5$ is $P(O)(OBn)_2$ (PI(5)P);
$R_3$ is $P(O)(OBn)_2$; $R_4$ is $P(O)(OBn)_2$; $R_5$ is H (PI(3,4)$P_2$);
$R_3$ is $P(O)(OBn)_2$; $R_4$ is H; $R_5$ is $P(O)(OBn)_2$ (PI(3,5)$P_2$);
$R_3$ is H; $R_4$ is $P(O)(OBn)_2$; $R_5$ is $P(O)(OBn)_2$ (PI(4,5)$P_2$); or
$R_3$ is $P(O)(OBn)_2$; $R_4$ is $P(O)(OBn)_2$; $R_5$ is $P(O)(OBn)_2$ (PI(3,4,5)$P_3$);
*Denotes a stereogenic centre;
Linker is $(CH_2)_n$ wherein n is 8-20;
X is O, S, or NH;
unsaturations are allowed, including in an arachidonyl side chain;

Formula VII′

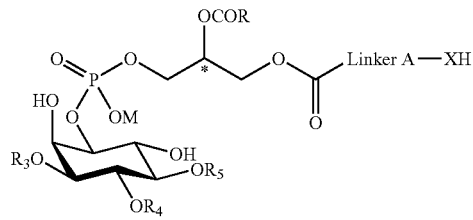

Formula VIII′

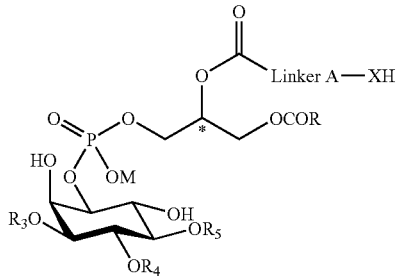

wherein:
R is an aryl or alkyl group;
R is $C_mH_{2m+1}$, where m is 8-20;
$R_3$ is $P(O)(OBn)_2$; $R_4$ is H; $R_5$ is H (PI(3)P);
$R_3$ is H; $R_4$ is $P(O)(OBn)_2$; $R_5$ is H (PI(4)P);
$R_3$ is H; $R_4$ is H; $R_5$ is $P(O)(OBn)_2$ (PI(5)P);
$R_3$ is $P(O)(OBn)_2$; $R_4$ is $P(O)(OBn)_2$; $R_5$ is H (PI(3,4)$P_2$);
$R_3$ is $P(O)(OBn)_2$; $R_4$ is H; $R_5$ is $P(O)(OBn)_2$ (PI(3,5)$P_2$);
$R_3$ is H; $R_4$ is $P(O)(OBn)_2$; $R_5$ is $P(O)(OBn)_2$ (PI(4,5)$P_2$); or
$R_3$ is $P(O)(OBn)_2$; $R_4$ is $P(O)(OBn)_2$; $R_5$ is $P(O)(OBn)_2$ (PI(3,4,5)$P_3$);
*Denotes a stereogenic centre;
Linker A is $(CH_2)_n$ wherein n is 8-20;
X is O, S, or NH;
unsaturations are allowed, including in an arachidonyl side chain.

26. A method of making a compound of Formula I″, II″, III″, or IV″;

Formula I″

Formula II″

Formula III″

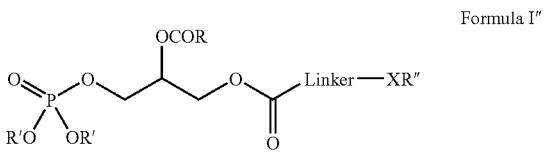

-continued

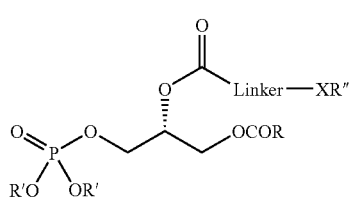

Formula IV″ wherein,
(a) the linker consists of $(CH_2)_m$, wherein n is 8-20;
(b) the heteroatom X is O, S, or NH;
(c) the R-substituent carries an aryl or alkyl group;
R is $C_mH_{2m+1}$, where m is 8-20;
(d) unsaturations are allowed, including in an arachidonyl side chain;
(e) R′ is any suitable protecting group, including Bn; trialkyl silyl; and $CNCH_2CH_2$—;
(f) R″ is any suitable protecting group, including Fmoc; CBz, when X is NH.

By phosphitylation of alcohol:

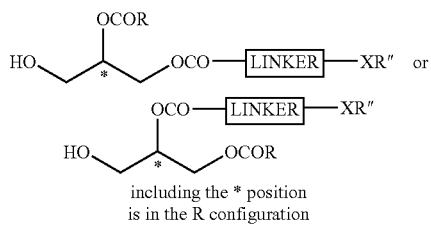

including the * position is in the R configuration with $(R'''O)_2 PNP_{r2}$ and oxidation of the phosphitylated product, where R″=Bn;
$CNCH_2CH_2$—; trialkyl silyl.

27. A method of making a compound of Formula V″, VI″, VII″, or VIII″;

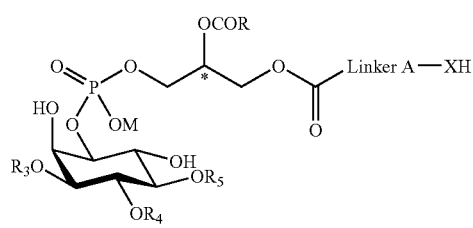

Formula V″

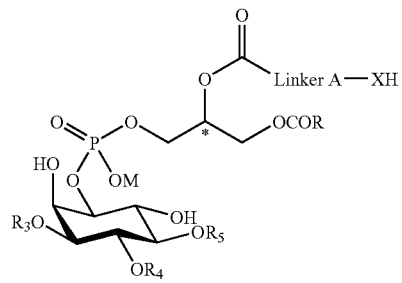

Formula VI″ wherein:
R is an aryl or alkyl group;
R is $C_mH_{2m+1}$, where m is 8-20;
$R_3$ is $P(O)(OBn)_2$; $R_4$ is H; $R_5$ is H (PI(3)P);
$R_3$ is H; $R_4$ is $P(O)(OBn)_2$; $R_5$ is H (PI(4)P);
$R_3$ is H; $R_4$ is H; $R_5$ is $P(O)(OBn)_2$ (PI(5)P);
$R_3$ is $P(O)(OBn)_2$; $R_4$ is $P(O)(OBn)_2$; $R_5$ is H (PI(3,4)$P_2$);
$R_3$ is $P(O)(OBn)_2$; $R_4$ is H; $R_5$ is $P(O)(OBn)_2$ (PI(3,5)$P_2$);
$R_3$ is H; $R_4$ is $P(O)(OBn)_2$; $R_5$ is $P(O)(OBn)_2$ (PI(4,5)$P_2$); or
$R_3$ is $P(O)(OBn)_2$; $R_4$ is $P(O)(OBn)_2$; $R_5$ is $P(O)(OBn)_2$ (PI(3,4,5)$P_3$);
*Denotes a stereogenic centre;
Linker is $(CH_2)_n$ wherein n is 8-20;
X is O, S, or NH;
unsaturations are allowed, including in an arachidonyl side chain;

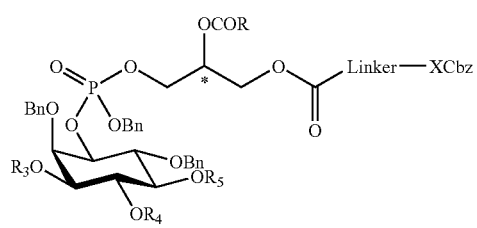

Formula VII′

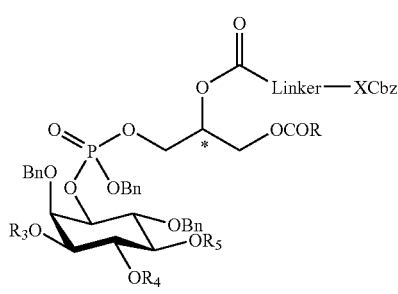

Formula VIII′ wherein:
R is an aryl or alkyl group;
R is $C_mH_{2m+1}$, where m is 8-20;
$R_3$ is $P(O)(OBn)_2$; $R_4$ is H; $R_5$ is H (PI(3)P);
$R_3$ is H; $R_4$ is $P(O)(OBn)_2$; $R_5$ is H (PI(4)P);
$R_3$ is H; $R_4$ is H; $R_5$ is $P(O)(OBn)_2$ (PI(5)P);
$R_3$ is $P(O)(OBn)_2$; $R_4$ is $P(O)(OBn)_2$; $R_5$ is H (PI(3,4)$P_2$);
$R_3$ is $P(O)(OBn)_2$; $R_4$ is H; $R_5$ is $P(O)(OBn)_2$ (PI(3,5)$P_2$);
$R_3$ is H; $R_4$ is $P(O)(OBn)_2$; $R_5$ is $P(O)(OBn)_2$ (PI(4,5)$P_2$); or
$R_3$ is $P(O)(OBn)_2$; $R_4$ is $P(O)(OBn)_2$; $R_5$ is $P(O)(OBn)_2$ (PI(3,4,5)$P_3$);
*Denotes a stereogenic centre;
Linker is $(CH_2)_n$ wherein n is 8-20;
X is O, S, or NH;
unsaturations are allowed, including in an arachidonyl side chain;
by coupling a first alcohol of formula:

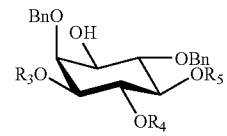

with a second alcohol of formula:

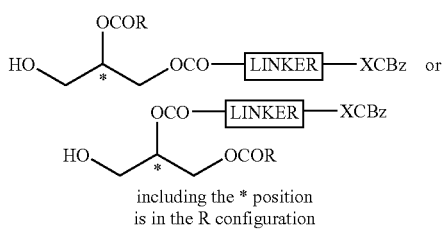

including the * position
is in the R configuration through a phosphodiester linkage.

28. The method according to claim 27, in which the second alcohol is phosphitylated with $BnOP(N^1Pr_2)_2$ to produce a phosphoramidite of formula:

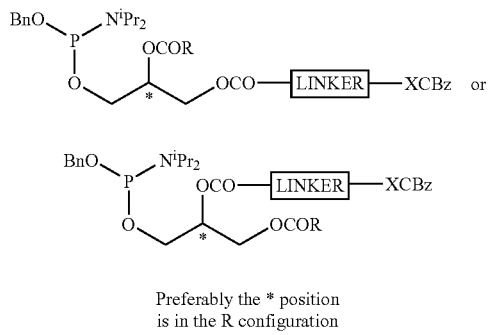

Preferably the * position
is in the R configuration which is then coupled to the first alcohol of claim 27 to make the compound of Formula V", VI", VII", or VIII".

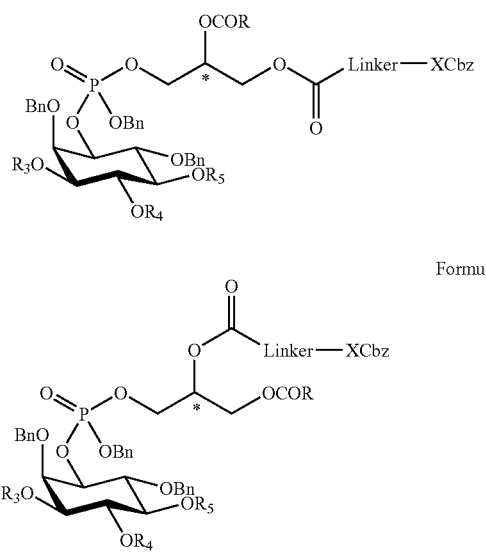

Formula V"

Formula VI"

wherein:
R is an aryl or alkyl group;
R is $C_mH_{2m+1}$, where m is 8-20;
$R_3$ is $P(O)(OBn)_2$; $R_4$ is H; $R_5$ is H (PI(3)P);
$R_3$ is H; $R_4$ is $P(O)(OBn)_2$, $R_5$ is H (PI(4)P);
$R_3$ is $R_4$ is H; $R_5$ is $P(O)(OBn)_2$ (PI(5)P);
$R_3$ is $P(O)(OBn)_2$; $R_4$ is $P(O)(OBn)_2$; $R_5$ is H (PI(3,4)$P_2$);
$R_3$ is $P(O)(OBn)_2$; $R_4$ is H; $R_5$ is $P(O)(OBn)_2$ (PI(3,5)$P_2$);
$R_3$ is H; $R_4$ is $P(O)(OBn)_2$; $R_5$ is $P(O)(OBn)_2$ (PI(4,5)$P_2$);
or
$R_3$ is $P(O)(OBn)_2$; $R_4$ is $P(O)(OBn)_2$; $R_5$ is $P(O)(OBn)_2$ (PI(3,4,5)$P_3$);
*Denotes a stereogenic centre;
Linker is $(CH_2)_n$ wherein n is 8-20,
X is O, S, or NH;
unsaturations are allowed, including in an arachidonyl side chain;

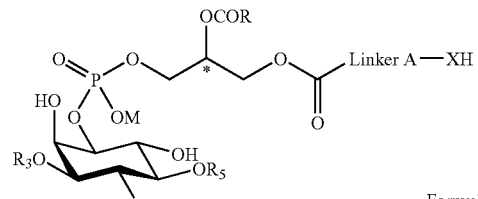

Formula VII'

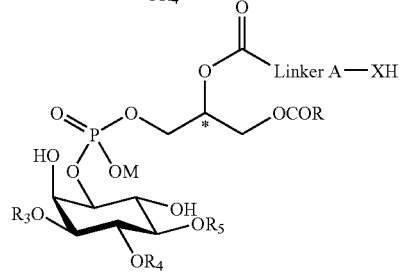

Formula VIII' wherein:
R is an aryl or alkyl group;
R is $C_mH_{2m+1}$, where m is 8-20;
$R_3$ is $P(O)(OBn)_2$; $R_4$ is H; $R_5$ is H (PI(3)P);
$R_3$ is H; $R_4$ is $P(O)(OBn)_2$; $R_5$ is H (PI(4)P);
$R_3$ is H; $R_4$ is H; $R_5$ is $P(O)(OBn)_2$ (PI(5)P);
$R_3$ is $P(O)(OBn)_2$; $R_4$ is $P(O)(OBn)_2$; $R_5$ is H (PI(3,4)$P_2$);
$R_3$ is $P(O)(OBn)_2$; $R_4$ is H; $R_5$ is $P(O)(OBn)_2$ (PI(3,5)$P_2$);
$R_3$ is H; $R_4$ is $P(O)(OBn)_2$; $R_5$ is $P(O)(OBn)_2$ (PI(4,5)$P_2$);
or
$R_3$ is $P(O)(OBn)_2$; $R_4$ is $P(O)(OBn)_2$; $R_5$ is $P(O)(OBn)_2$ (PI(3,4,5)$P_3$);
*Denotes a stereogenic centre;
Linker is $(CH_2)_n$ wherein n is 8-20;
X is O, S, or NH;
unsaturations are allowed, including in an arachidonyl side chain.

29. A method of making a compound of Formula I', II', III', or IV' which comprises making a compound of Formula I", II", III" or IV" by a method of claim 26 followed by removal of the protecting groups of the compound of Formula I", II", III", or IV", including by reductive debenzylation

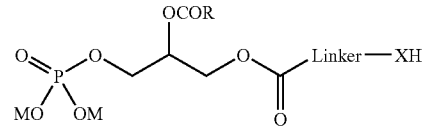

Formula I'

-continued

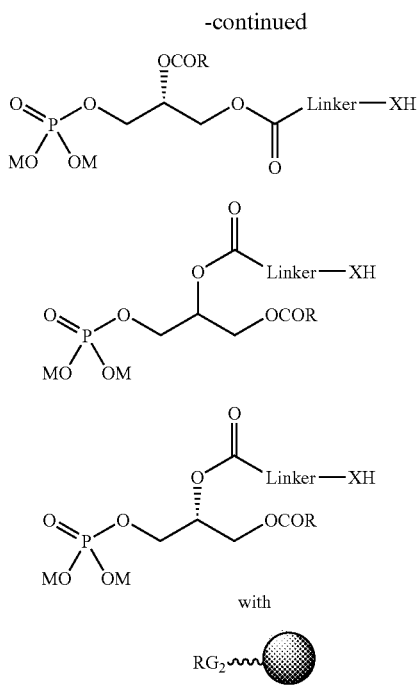

wherein:
(a) the linker consists of $(CH_2)_n$, wherein n is 8-20;
(b) the R-substituent carries an aryl or alkyl group;
R is $C_mH_{2m+1}$, where m is 8-20;
(c) the ion M represents any cation, including $Na^+$, $NH4^+$;
(d) unsaturations are allowed, including in an arachidonyl side chain;
X is NH, O, or S;
$RG_2$ is a reactive group capable of reaction with XH;

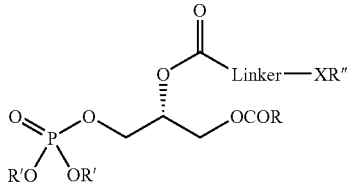

is a solid support with attachment to $RG_2$;

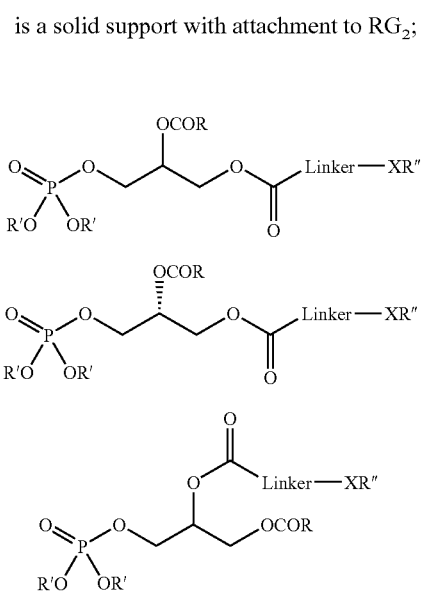

-continued

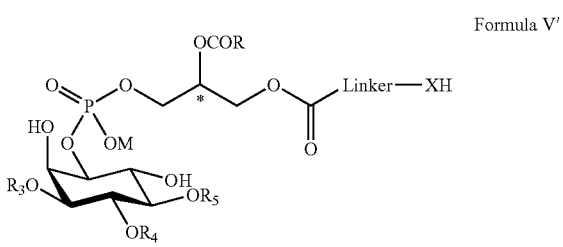

wherein,
(a) the linker consists of $(CH_2)_n$, wherein n is 8-20;
(b) the heteroatom X is O, S, or NH;
(c) the R-substituent carries an aryl or alkyl group;
R is $C_mH_{2m+1}$, where m is 8-20;
(d) unsaturations are allowed, including in an arachidonyl side chain;
(e) R' is any suitable protecting group, including Bn; trialkyl silyl; and $CNCH_2CH_2$—;
(f) R" is any suitable protecting group, including Fmoc; CBz, when X is NH.

30. A method of making a compound of Formula V', VI', VII', or VIII', which comprises making a compound of Formula V", VI", VII", or VIII" by a method of claim 27 followed by reductive debenzylation of the compound of Formula V", VI", VII", VIII":

Formula V'

Formula VI' wherein:
R=aryl or alkyl group;
R=$C_mH_{2m+1}$, where m=8-20;
$R_3$=$P(O)(OM)_2$; $R_4$=H; $R_5$=H (PI(3)P);
$R_3$=H; $R_4$=$P(O)(OM)_2$; $R_5$=H (PI(4)P);
$R_3$=H; $R_4$=H; $R_5$=$P(O)(OM)_2$ (PI(5)P);
$R_3$=$P(O)(OM)_2$; $R_4$=$P(O)(OM)_2$; $R_5$=H (PI(3,4)$P_2$);
$R_3$=$P(O)(OM)_2$; $R_4$=H; $R_5$=$P(O)(OM)_2$ (PI(3,5)$P_2$);
$R_3$=H; $R_4$=$P(O)(OM)_2$; $R_5$=$P(O)(OM)_2$ (PI(4,5)$P_2$); or
$R_3$=$P(O)(OM)_2$; $R_4$=$P(O)(OM)_2$; $R_5$=$P(O)(OM)_2$ (PI(3,4,5)$P_3$);
M=any cation, including $Na^+$, $NH4^+$;
*Denotes a stereogenic centre;
Linker=$(CH_2)_n$ with n=8-20;
X=NH, O, or S unsaturations are allowed, including in an arachidonyl side chain;

with

where:

= solid support with attachment to $RG_2$; and
$RG_2$ = a reactive group capable of reaction with XH, including N-hydroxy-succinimide-activated carboxylate;

Formula VII'

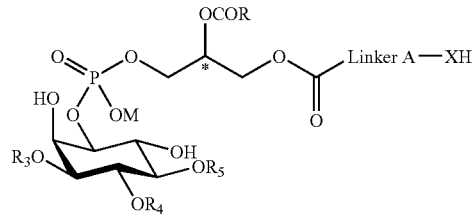

Formula VIII'

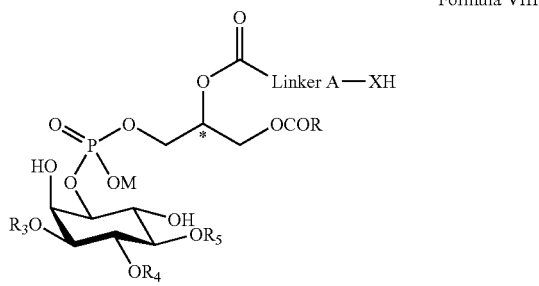

wherein:
R = aryl or alkyl group;
R = $C_mH_{2m+1}$, where m=8-20;
$R_3$ = P(O)(OM)$_2$; $R_4$ = H; $R_5$ = H (PI(3)P);
$R_3$ = H; $R_4$ = P(O)(OM)$_2$; $R_5$ = H (PI(4)P);
$R_3$ = H; $R_4$ = H; $R_5$ = P(O)(OM)$_2$ (PI(5)P),
$R_3$ = P(O)(OM)$_2$; $R_4$ = P(O)(OM)$_2$; $R_5$ = H (PI(3,4)P$_2$);
$R_3$ = P(O)(OM)$_2$; $R_4$ = H; $R_5$ = P(O)(OM)$_2$ (PI(3,5)P$_2$);
$R_3$ = H; $R_4$ P(O)(OM)$_2$; $R_5$ = P(O)(OM)$_2$ (PI(4,5)P$_2$); or
$R_3$ = P(O)(OM)$_2$; $R_4$ = P(O)(OM)$_2$; $R_5$ = P(O)(OM)$_2$ (PI(3,4,5)P$_3$);
M = any cation, including Na$^+$, NH4$^+$;
*Denotes a stereogenic centre;
Linker A = $(CH_2)_n$ with n=8-20;
X = NH, O, or S;
unsaturations are allowed, including in an arachidonyl side chain;

with

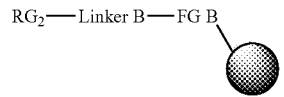

Linker B = aryl, heteroaryl, alkyl with possible heteroatoms and/or saturations.:these could be any atoms, including C, N, O, S, or methylene groups linked via amide and ester bonds;
the total length of linker A and linker B is 8-60 atoms
FG B = Amide, thiolo(ester), or ester

= solid support with attachment to FG B; and
$RG_2$ = a reactive group capable of reaction with XH, including N-hydroxy-succinimide-activated carboxylate;

Formula V"

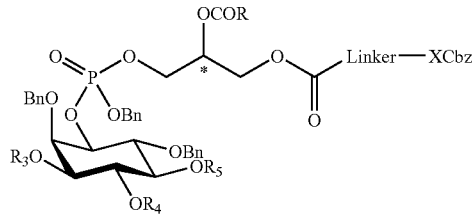

Formula VI"

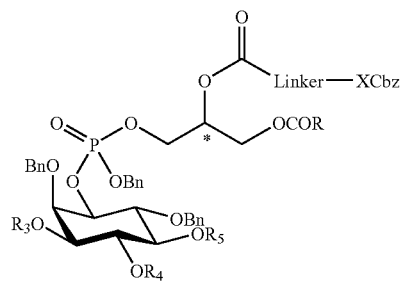

wherein:
R is an aryl or alkyl group;
R is where m is 8-20;
$R_3$ is P(O)(OBn)$_2$; $R_4$ is H; $R_5$ is H (PI(3)P);
$R_3$ is H; $R_4$ is P(O)(OBn)$_2$; $R_5$ is H (PI(4)P);
$R_3$ is H; $R_4$ is H; $R_5$ is P(O)(OBn)$_2$ (PI(5)P);
$R_3$ is P(O)(OBn)$_2$; $R_4$ is P(O)(OBn)$_2$, $R_5$ is H (PI(3,4)P$_2$),
$R_3$ is P(O)(OBn)$_2$, $R_4$ is H; $R_5$ is P(O)(OBn)$_2$ (PI(3,5)P$_2$);
$R_3$ is H; $R_4$ is P(O)(OBn)$_2$; $R_5$ is P(O)(OBn)$_2$ (PI(4,5)P$_2$); or
$R_3$ is P(O)(OBn)$_2$; $R_4$ is P(O)(OBn)$_2$; $R_5$ is P(O)(OBn)$_2$ (PI(3,4,5)P$_3$);
*Denotes a stereogenic centre;
Linker is $(CH_2)_n$ wherein n is 8-20;
X is O, S, or NH;
unsaturations are allowed, including in an arachidonyl side chain;

Formula VII'

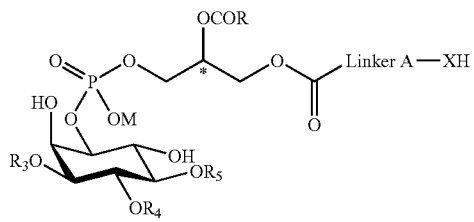

Formula VIII'

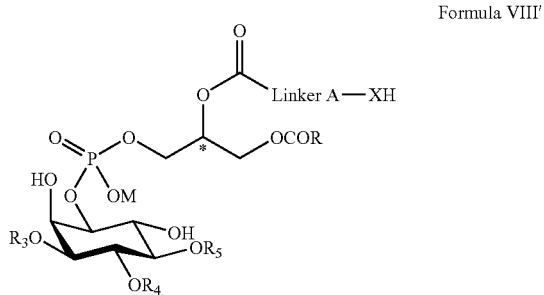

wherein:

R is an aryl or alkyl group;

R is $C_mH_{2m+1}$, where m is 8-20;

$R_3$ is $P(O)(OBn)_2$; $R_4$ is H; $R_5$ is H (PI(3)P);

$R_3$ is H; $R_4$ is $P(O)(OBn)_2$; $R_5$ is H (PI(4)P);

$R_3$ is H; $R_4$ is H; $R_5$ is $P(O)(OBn)_2$ (PI(5)P);

$R_3$ is $P(O)(OBn)_2$; $R_4$ is $P(O)(OBn)_2$; $R_5$ is H (PI(3,4)$P_2$);

$R_3$ is $P(O)(OBn)_2$; $R_4$ is H; $R_5$ is $P(O)(OBn)_2$ (PI(3,5)$P_2$);

$R_3$ is H; $R_4$ is $P(O)(OBn)_2$; $R_5$ is $P(O)(OBn)_2$ (PI(4,5)$P_2$); or $R_3$ is $P(O)(OBn)_2$; $R_4$ is $P(O)(OBn)_2$; $R_5$ is $P(O)(OBn)_2$ (PI(3,4,5)$P_3$);

*Denotes a stereogenic centre;

Linker A is $(CH_2)_n$ wherein n is 8-20;

X is O, S, or NH;

unsaturations are allowed, including in an arachidonyl side chain.

31. A method of making a probe consisting of a phosphatidic acid functionalised solid support of the general formula as is depicted in Formula I, II, III or IV comprising coupling a compound of Formula I', II', III' or IV' made by a method of claim 24 to the solid support Formula I

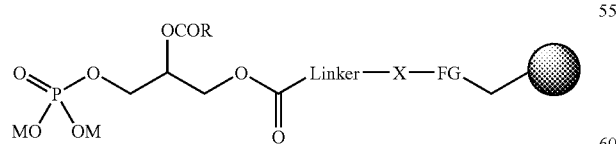

Formula II

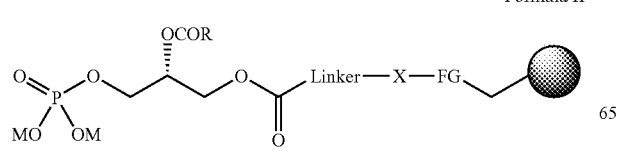

-continued

Formula III

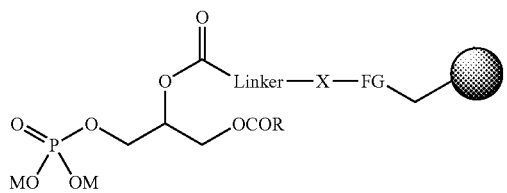

Formula IV

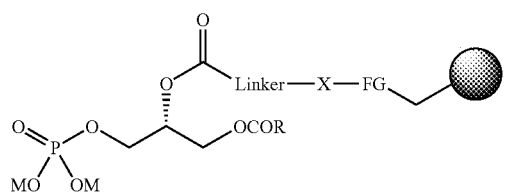

(a) the linker consists of $(CH_2)_n$, with n=8-20;

(b) the heteroatom X is O, S, or NH;

(c) the functional group (FG) is a carbonyl from a carboxylate (thiolo)ester, or an amide;

(d) the R-substituent carries an aryl or alkyl group; $R=C_mH_{2m+1}$, where m=8-20

(e) the ion M represents any cation, including $Na^+$, $NH4^+$;

(f) unsaturations are allowed, including in an arachidonyl side chain; and (g)

=solid support with attachment to functional group;

Formula I'

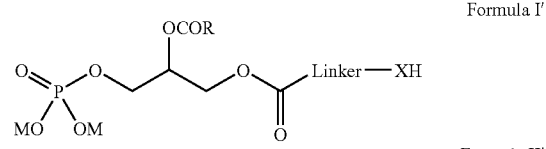

Formula II'

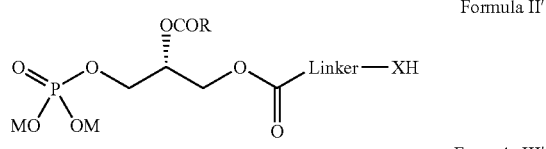

Formula III'

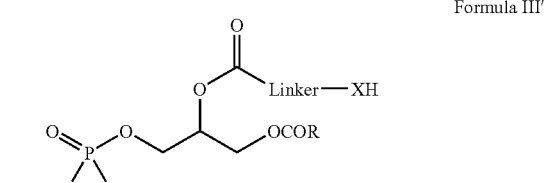

Formula IV'

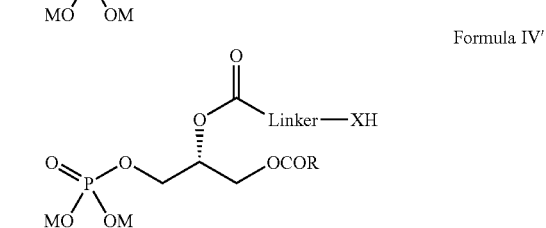

-continued with

wherein:
(a) the linker consists of $(CH_2)_n$, wherein n is 8-20
(b) the R-substituent carries an aryl or alkyl group; R is $C_mH_{2m+1}$, where m is 8-20;
(c) the ion M represents any cation, including $Na^+$, $NH_4^+$;
(d) unsaturations are allowed, including in an arachidonyl side chain;
X is NH, O, or S;
$RG_2$ is a reactive group capable of reaction with XH;

is a solid support with attachment to $RG_2$.

32. A method of making a probe having any of the general Formulae V, VI, VII or VIII comprising coupling a compound of Formula V', VI', VII' or VIII' made by a method of claim 25 to the solid support Formula I'

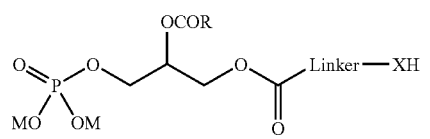

Formula II'

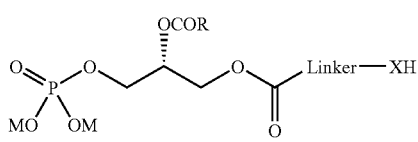

Formula III'

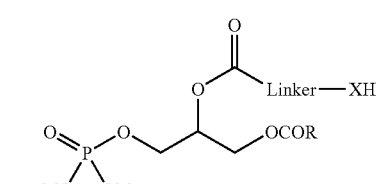

Formula IV'

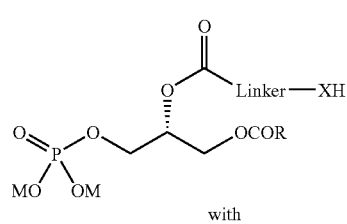

with

wherein:
R=aryl or alkyl group;
R=$C_mH_{2m+1}$, where m=8-20;
$R_3$=$P(O)(OM)_2$; $R_4$=H; $R_5$=H (PI(3)P);
$R_3$=H; $R_4$=$P(O)(OM)_2$; $R_5$=H (PI(4)P);
$R_3$=H; $R_4$=H; $R_5$=$P(O)(OM)_2$ (PI(5)P),
$R_3$=$P(O)(OM)_2$; $R_4$=$P(O)(OM)_2$; $R_5$=H (PI(3,4)$P_2$);
$R_3$=$P(O)(OM)_2$; $R_4$=H; $R_5$=$P(O)(OM)_2$ (PI(3,5)$P_2$);
$R_3$=H; $R_4$=$P(O)(OM)_2$; $R_5$=$P(O)(OM)_2$ (PI(4,5)$P_2$); or
$R_3$=$P(O)(OM)_2$; $R_4$=$P(O)(OM)_2$; $R_5$=$P(O)(OM)_2$ (PI(3,4,5)$P_3$);
M=any cation, including $Na^+$, $NH4^+$;
*Denotes a stereogenic centre;
Linker=$(CH_2)_n$ with n=8-20;
X=O, S, or NH;
FG=Carbonyl from a carboxylate, thiolo(ester), or an amide;
unsaturations are allowed, including in an arachidonyl side chain;

=solid support with attachment to functional group;

Formula VII

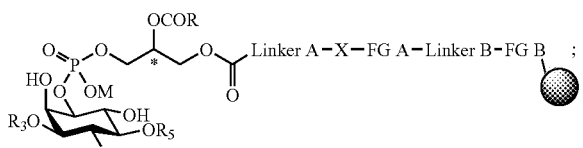

and

Formula VIII

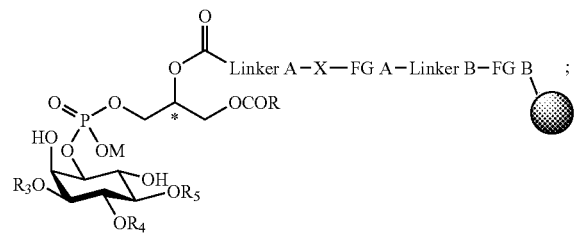

wherein:
R=aryl or alkyl group;
R=$C_mH_{2m+1}$, where m=8-20;
$R_3$=$P(O)(OM)_2$; $R_4$=H; $R_5$=H (PI(3)P);
$R_3$=H; $R_4$=$P(O)(OM)_2$; $R_5$=H (PI(4)P);
$R_3$=H; $R_4$=H; $R_5$=$P(O)(OM)_2$ (PI(5)P);
$R_3$=$P(O)(OM)_2$; $R_4$=$P(O)(OM)_2$; $R_5$=H (PI(3,4)$P_2$);
$R_3$=$P(O)(OM)_2$; $R_4$=H; $R_5$=$P(O)(OM)_2$ (PI(3,5)$P_2$);
$R_3$=H; $R_4$=$P(O)(OM)_2$; $R_5$=$P(O)(OM)_2$ (PI(4,5)$P_2$); or
$R_3$=$P(O)(OM)_2$; $R_4$=$P(O)(OM)_2$; $R_5$=$P(O)(OM)_2$ (PI(3,4,5)$P_3$);
M=any cation, including $Na^+$, $NH4^+$;
*Denotes a stereogenic centre;
X=O, S, or NH
FG A=Carbonyl from a carboxylate, thiolo(ester), or an amide;
Linker A=$(CH_2)_n$ with n=8-20;
Linker B=aryl, heteroaryl, alkyl with possible heteroatoms and/or saturations:
these could be any atoms, including C, N, O, S, or methylene groups linked via amide and ester bonds;
FG B=Amide, thiolo(ester), or ester;
unsaturations are allowed, including in an arachidonyl side chain;

=solid support with attachment to functional group.

Formula V'

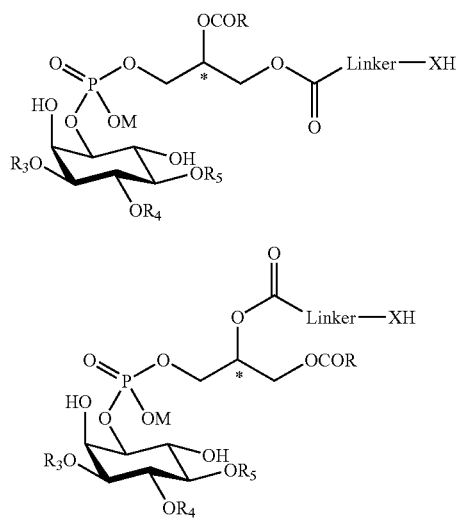

wherein:
R=aryl or alkyl group;
R=$C_mH_{2m+1}$, where m=8-20;
$R_3$=P(O)(OM)$_2$; $R_4$=H; $R_5$=H (PI(3)P);
$R_3$=H; $R_4$=P(O)(OM)$_2$; $R_5$=H (PI(4)P);
$R_3$=H; $R_4$=H; $R_5$=P(O)(OM)$_2$ (PI(5)P);
$R_3$=P(O)(OM)$_2$; $R_4$=P(O)(OM)$_2$, $R_5$=H (PI(3,4)P$_2$),
$R_3$=P(O)(OM)$_2$; $R_4$=H; $R_5$=P(O)(OM)$_2$ (31(3,5)P$_2$);
$R_3$=H; $R_4$=P(O)(OM)$_2$; $R_5$=P(O)(OM)$_2$ (PI(4,5)P$_2$); or
$R_3$=P(O)(OM)$_2$; $R_4$=P(O)(OM)$_2$; $R_5$=P(O)(OM)$_2$ (PI(3,4,5)P$_3$);
M=any cation, including Na$^+$, NH4$^+$;
*Denotes a stereogenic centre;
Linker=(CH$_2$)$_n$ with n=8-20;
X=NH, O, or S
unsaturations are allowed, including in an arachidonyl side chain;
with

where:

=solid support with attachment to RG$_2$; and
RG$_2$=a reactive group capable of reaction with XH, including N-hydroxy-succinimide-activated carboxylate;

Formula VII'

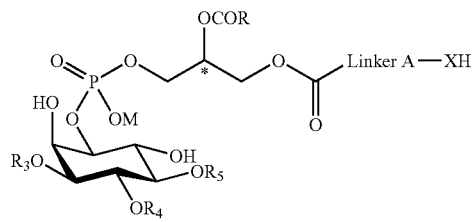

Formula VIII'

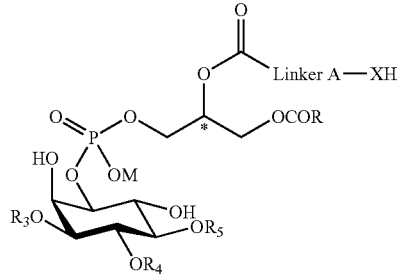

wherein:
R=aryl or alkyl group;
R=$C_mH_{2m+1}$, where m=8-20;
$R_3$=P(O)(OM)$_2$; $R_4$=H; $R_5$=H (PI(3)P);
$R_3$=H; $R_4$=P(O)(OM)$_2$; $R_5$=H (PI(4)P);
$R_3$=H; $R_4$=H; $R_5$=P(O)(OM)$_2$ (PI(5)P);
$R_3$=P(O)(OM)$_2$; $R_4$=P(O)(OM)$_2$; $R_5$=H (PI(3,4)P$_2$);
$R_3$=P(O)(OM)$_2$; $R_4$=H; $R_5$=P(O)(OM)$_2$ (PI(3,5)P$_2$);
$R_3$=H; $R_4$=P(O)(OM)$_2$; $R_5$=P(O)(OM)$_2$ (PI(4,5)P$_2$); or
$R_3$=P(O)(OM)$_2$; $R_4$=P(O)(OM)$_2$; $R_5$=P(O)(OM)$_2$ (PI(3,4,5)P$_3$);
M=any cation, including Na$^+$, NH$^{4+}$;
*Denotes a stereogenic centre;
Linker A=(CH$_2$)$_n$ with n=8-20;
X=NH, O, or S;
unsaturations are allowed, including in an arachidonyl side chain;
with

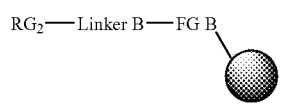

Linker B=aryl, heteroaryl, alkyl with possible heteroatoms and/or saturations:
these could be any atoms, including C, N, O, S, or methylene groups linked via amide and ester bonds;
the total length of linker A and linker B is 8-60 atoms;
FG B=Amide, thiolo(ester), or ester

=solid support with attachment to FG B; and
RG$_2$=a reactive group capable of reaction with XH, including N-hydroxy-succinimide-activated carboxylate.

33. A method according to claim 31 in which the compound is coupled to a carboxylic acid group of the solid support.

34. A method according to claim 27 in which the alcohol of Formula:

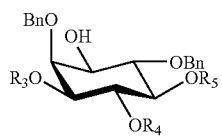

is made from a compound of Formula 44:

Formula 44

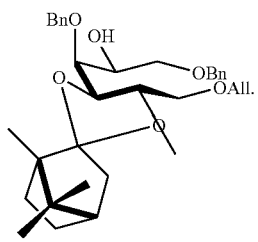

35. The probe according to claim 1 is coupled to a scintillant or a fluorophore.

36. The method of claim 17 further comprising de-protecting a compound of the formula VII" or VIII" to form a compound of formula VII' or VIII'.

37. The method according to claim 17, wherein the R group is an alkyl.

38. The method according to claim 17, wherein the compound of formula VII' or VIII' is one of the compounds as listed below:

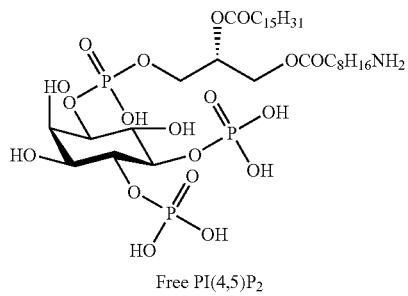

Free PI(4,5)P$_2$

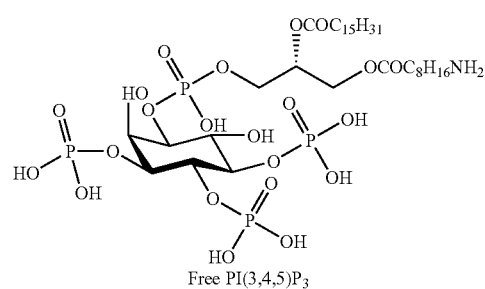

Free PI(3,4,5)P$_3$

-continued

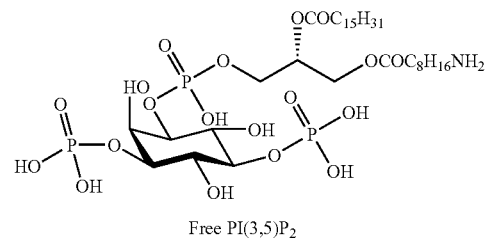

Free PI(3,5)P$_2$

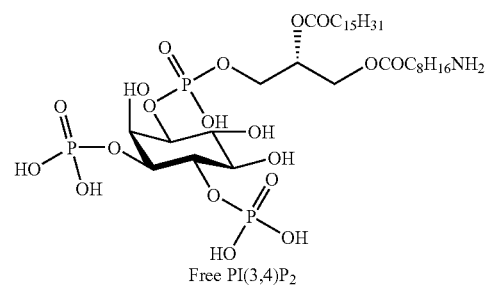

Free PI(3,4)P$_2$

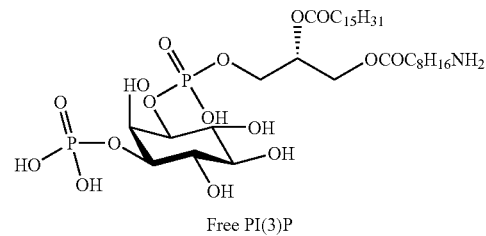

Free PI(3)P

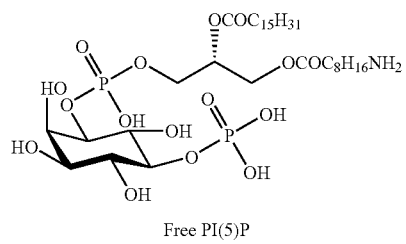

Free PI(5)P

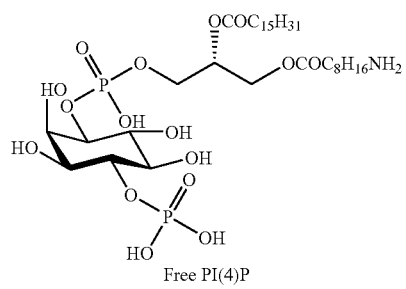

Free PI(4)P

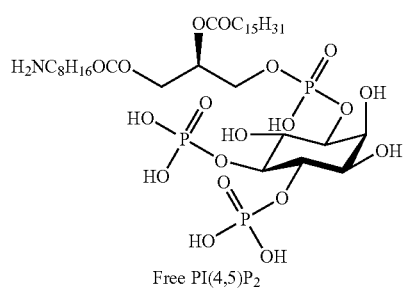

Free PI(4,5)P$_2$

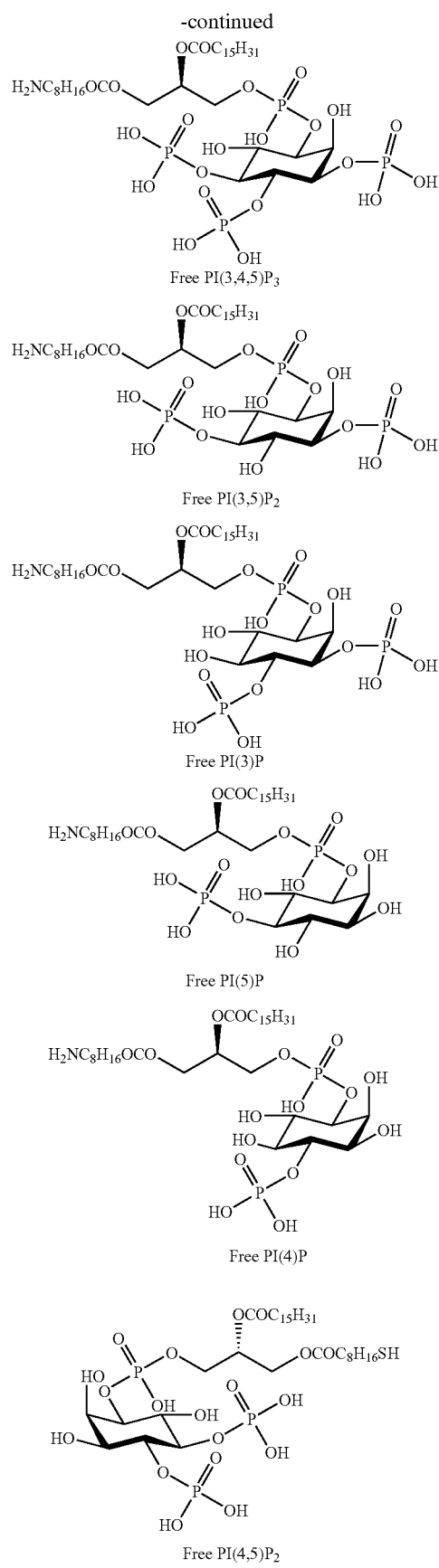
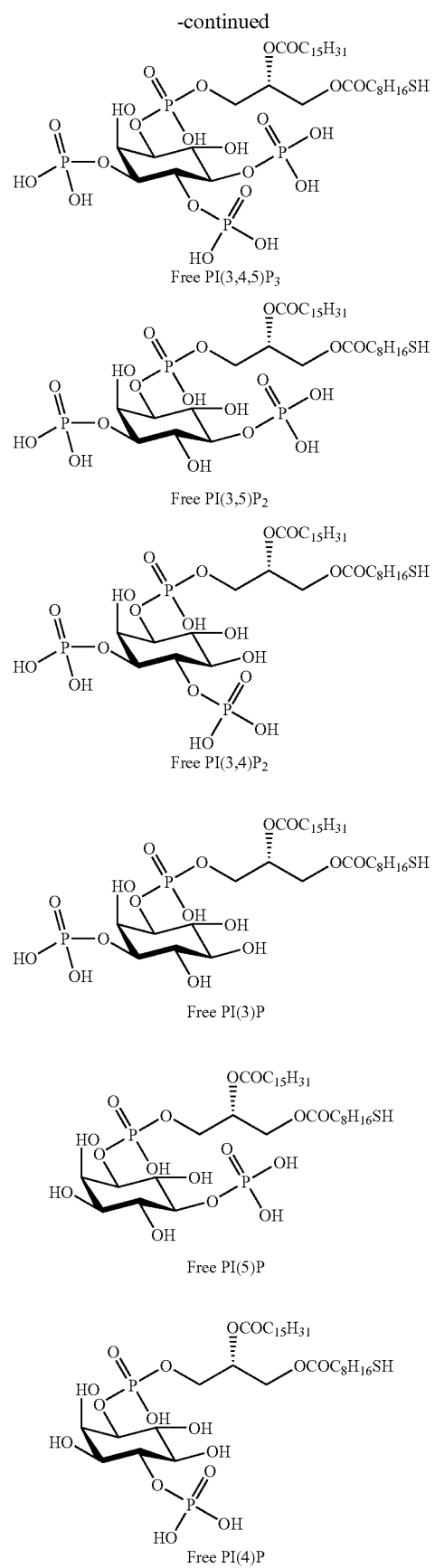

-continued
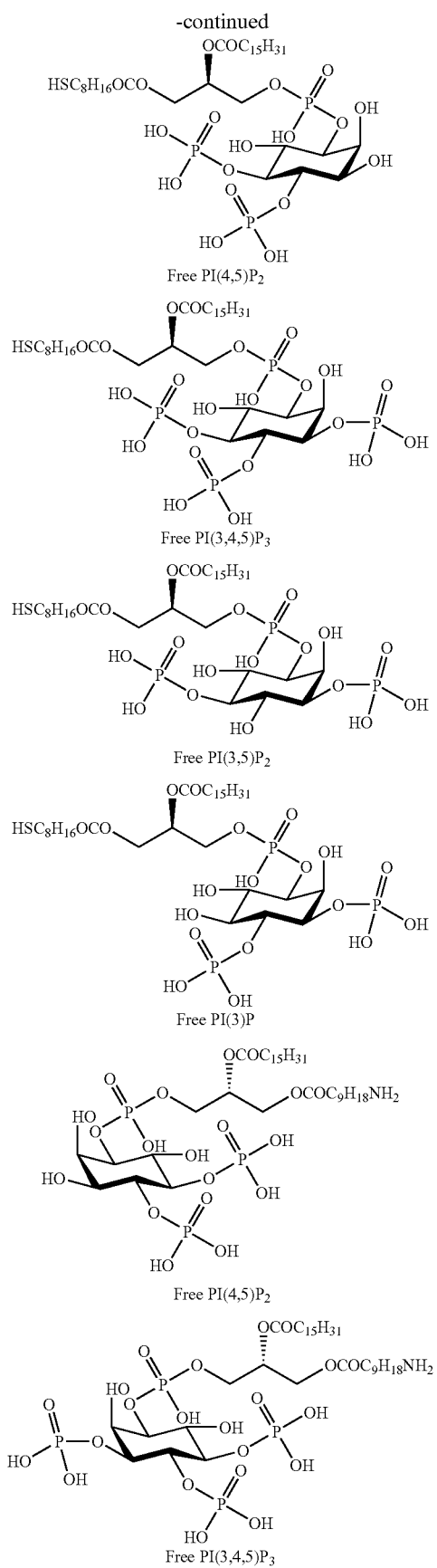
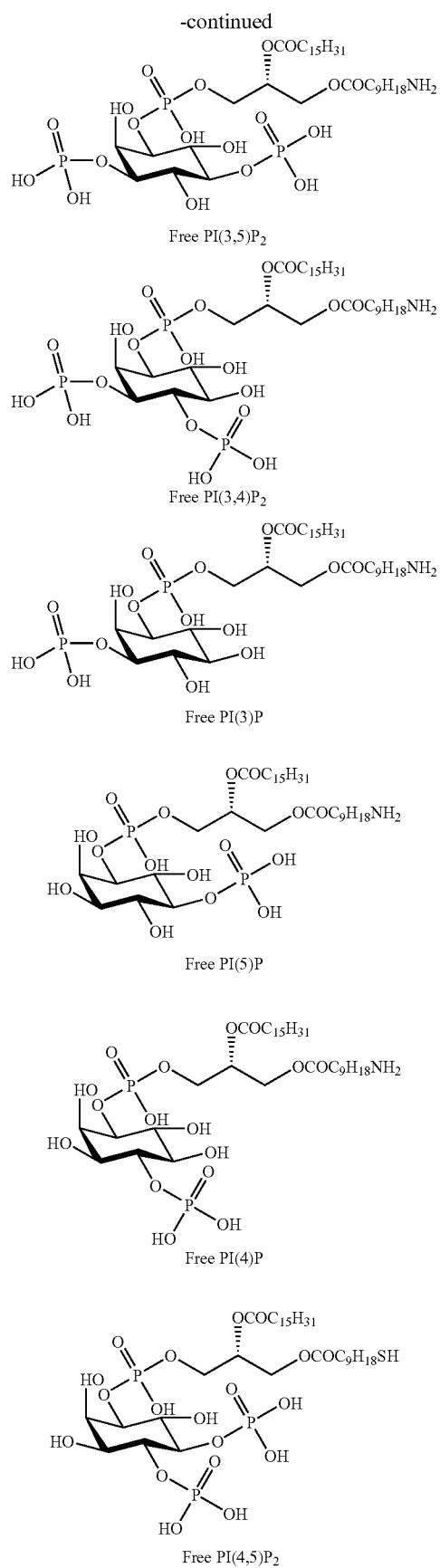

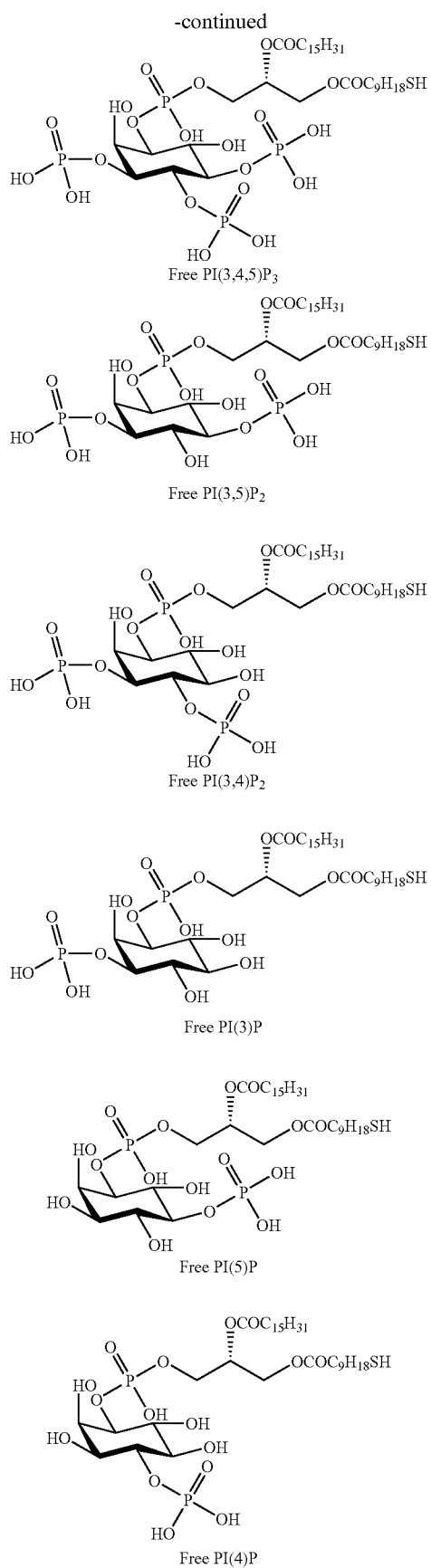
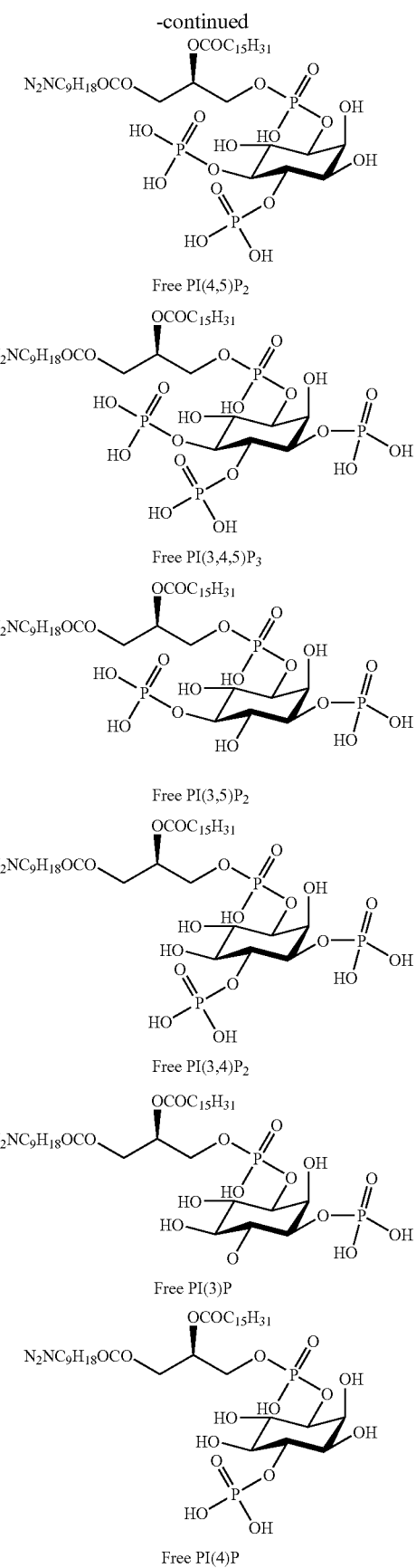

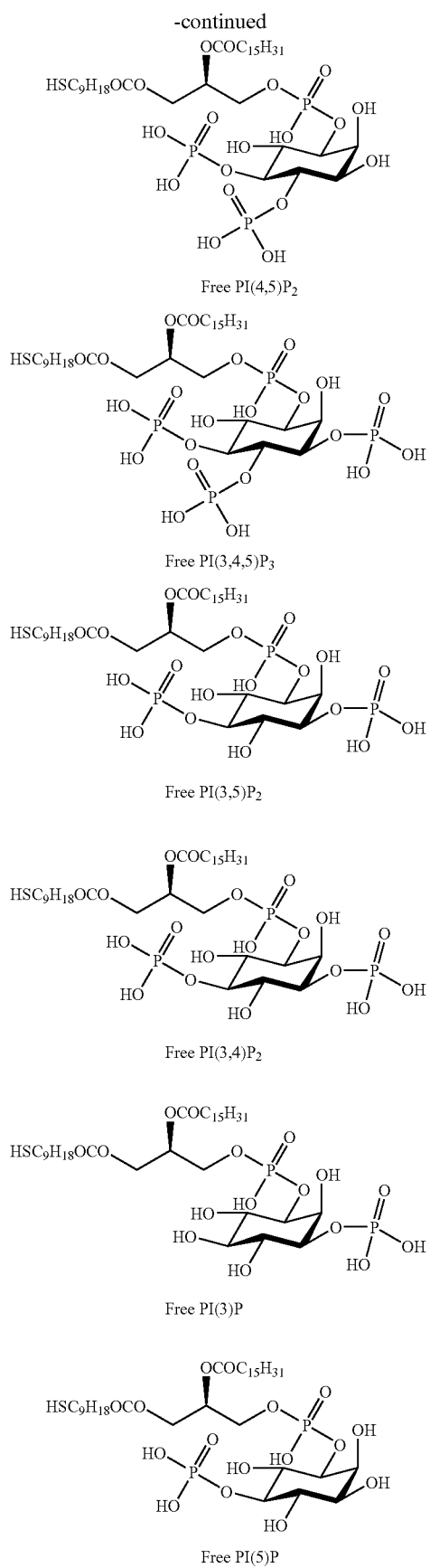
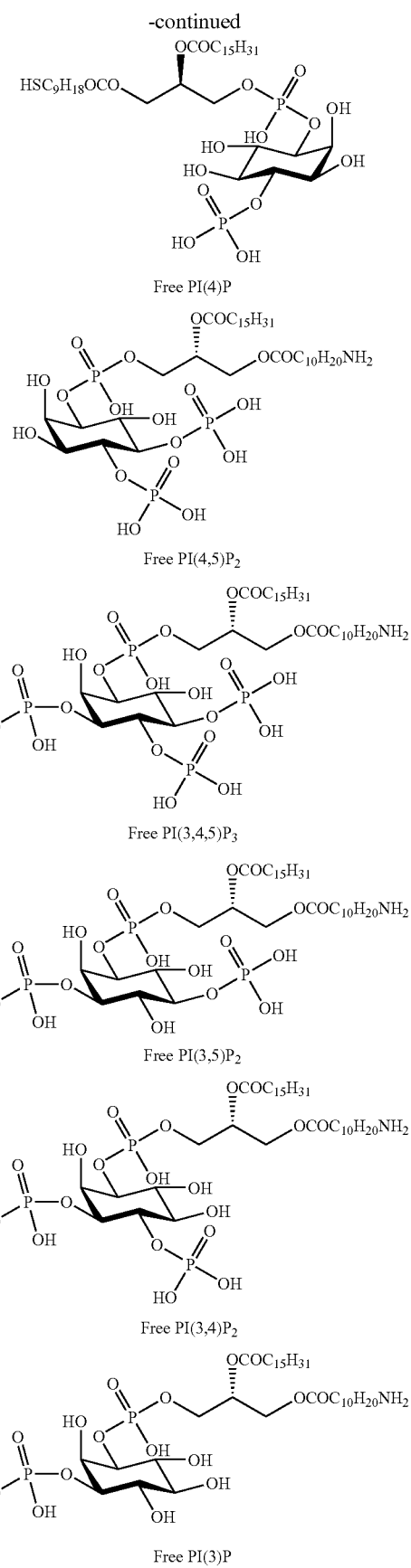

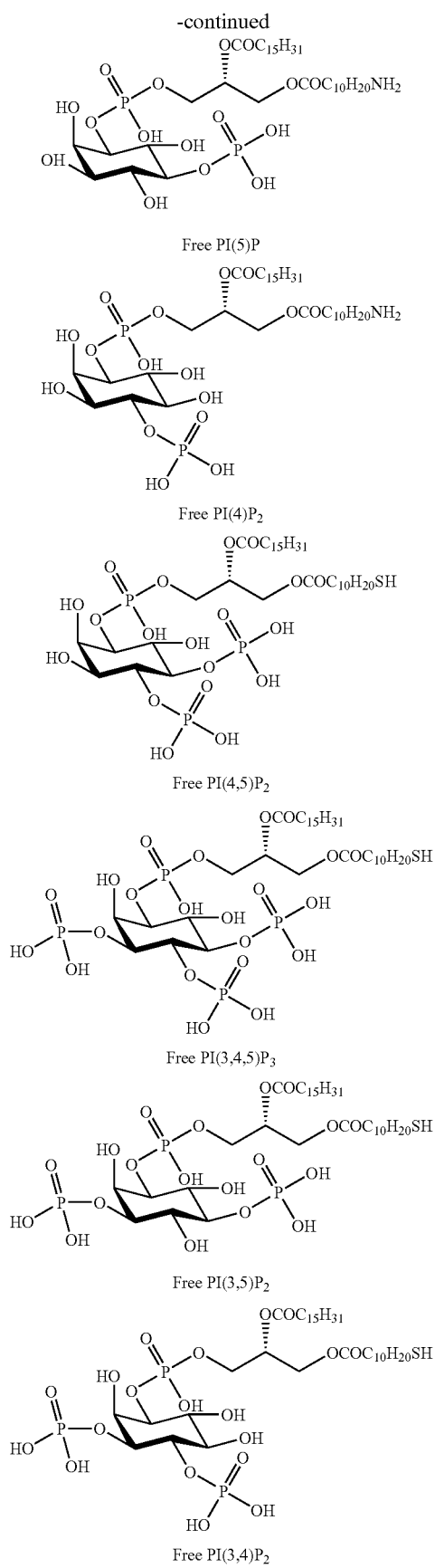
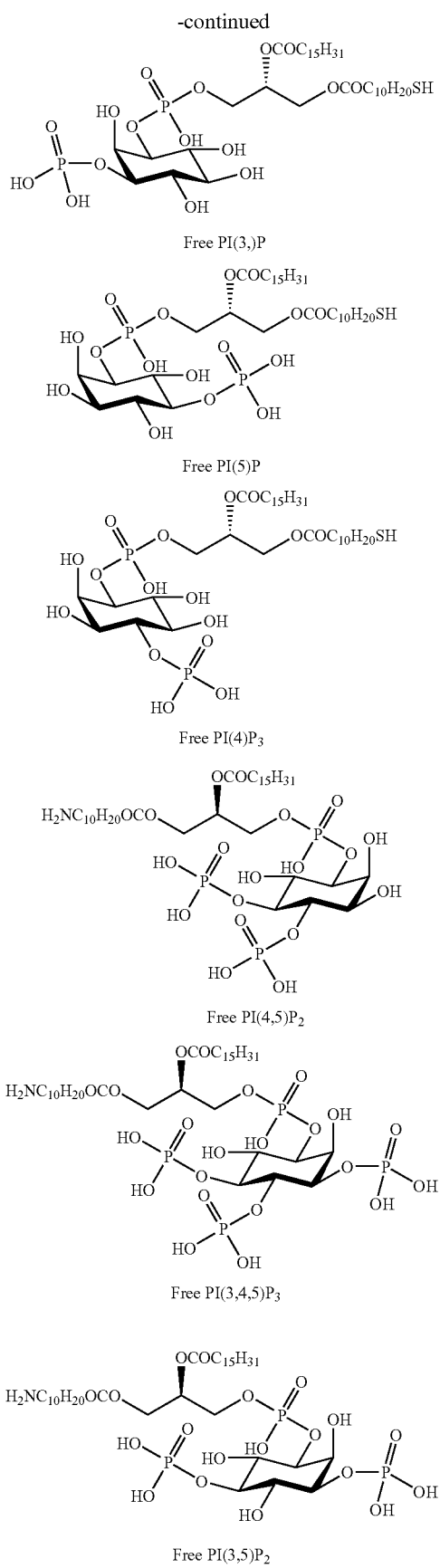

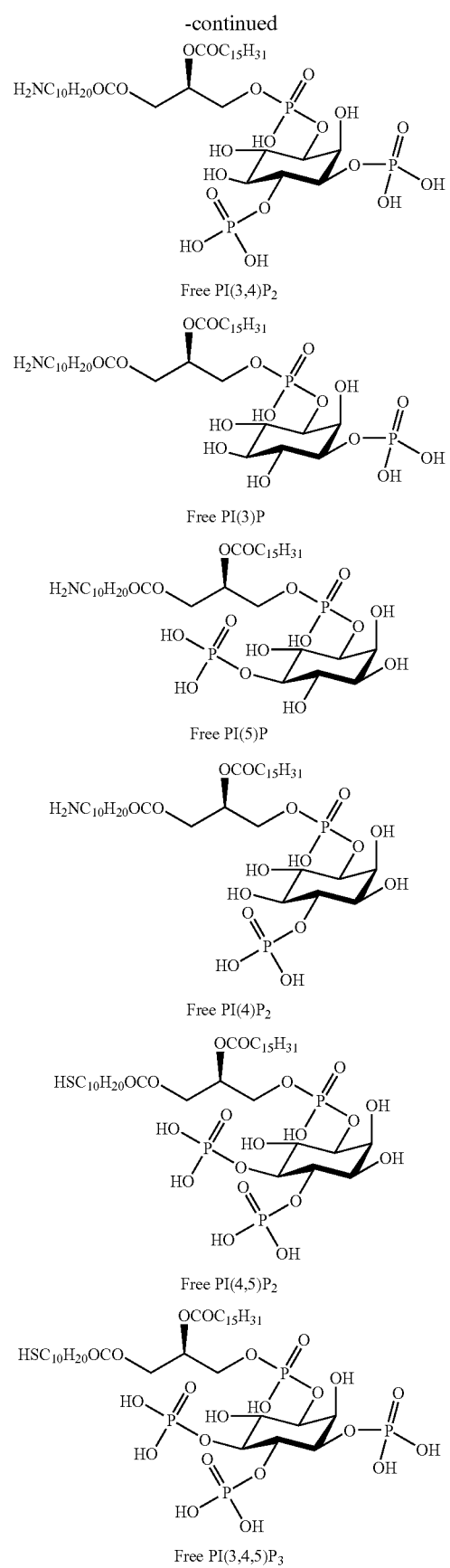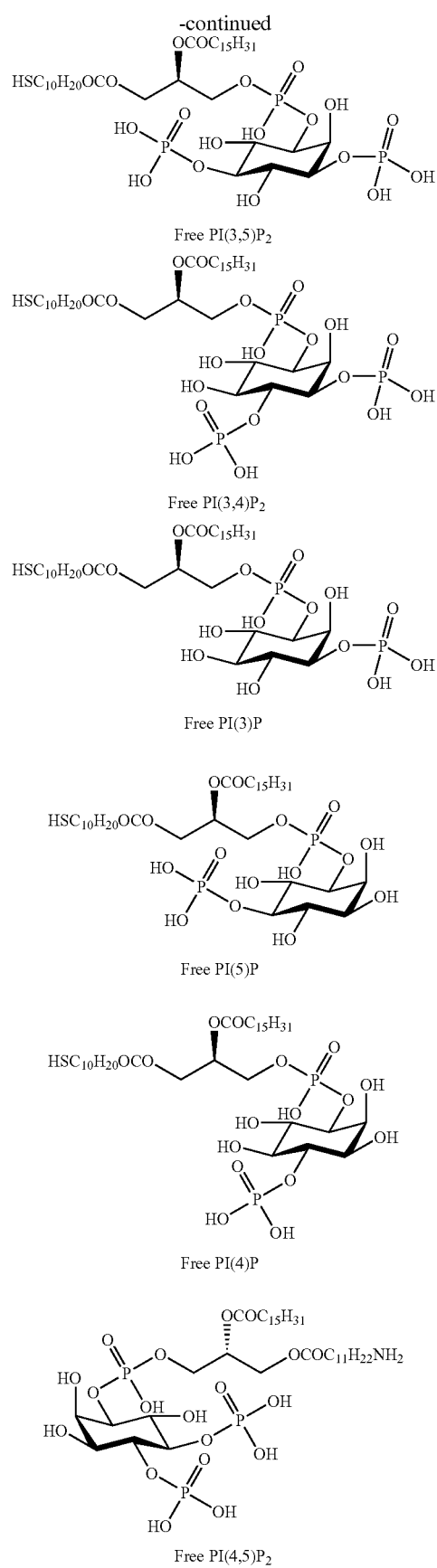

-continued
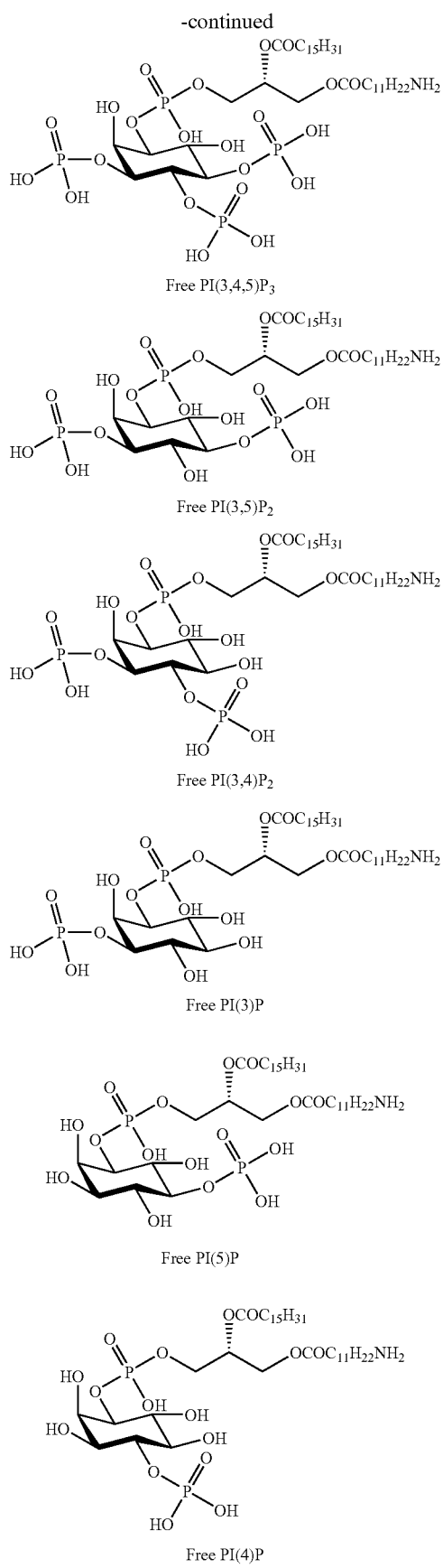
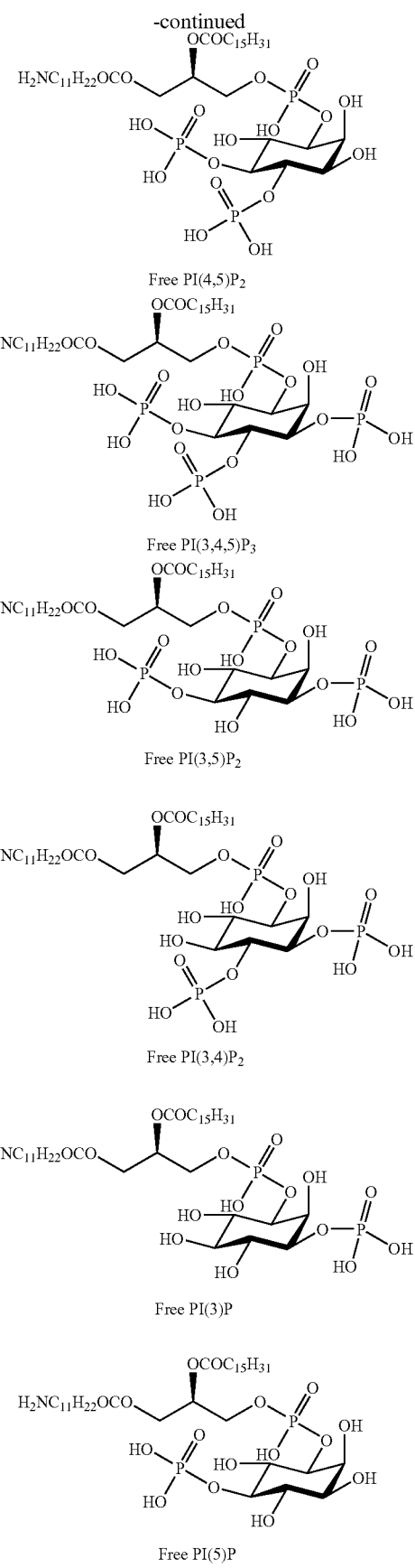

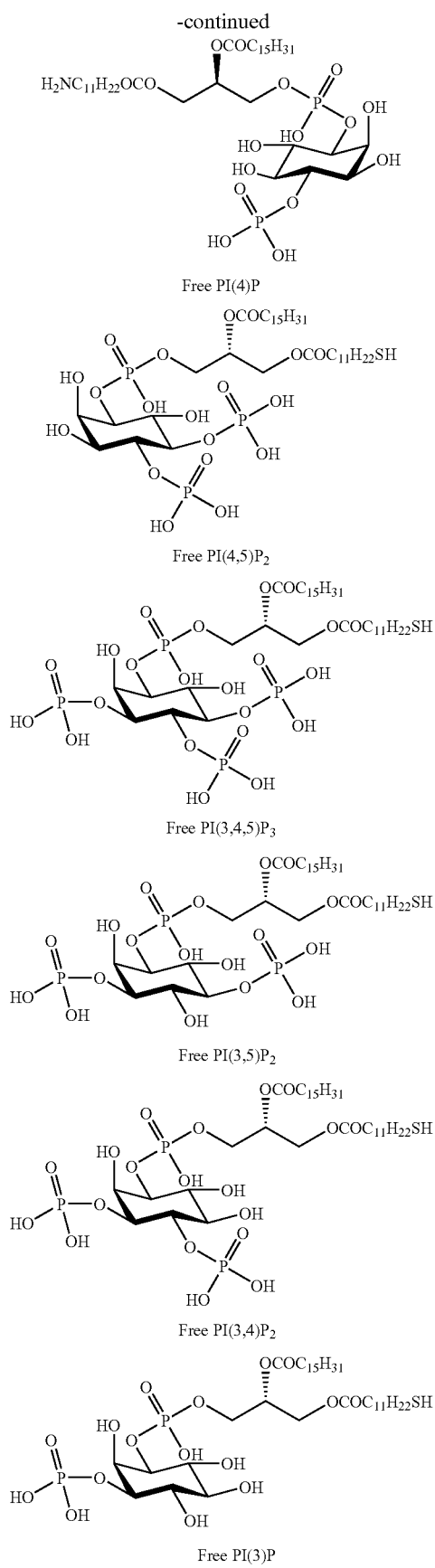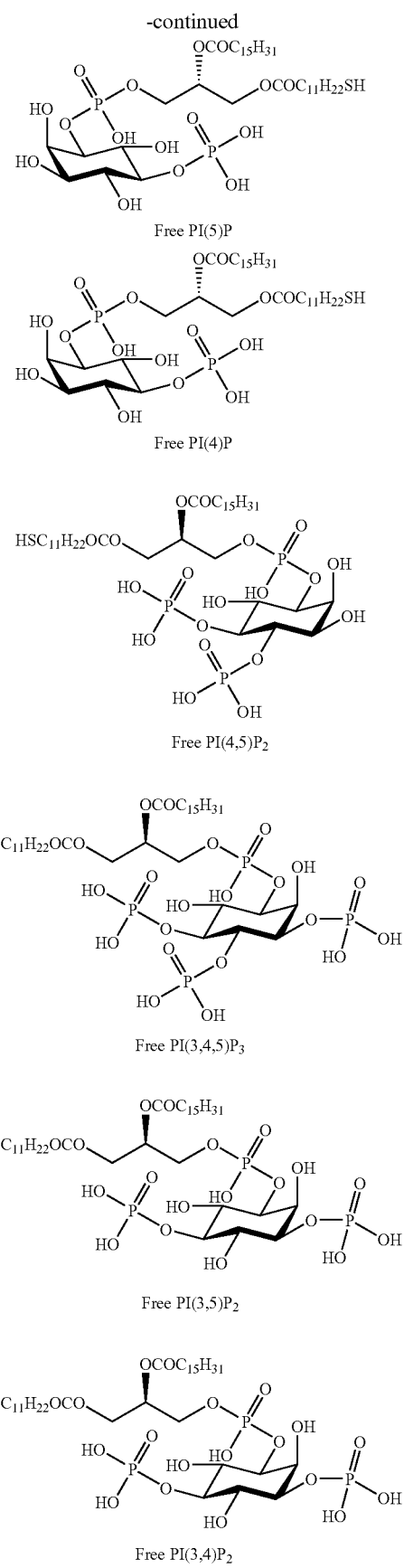

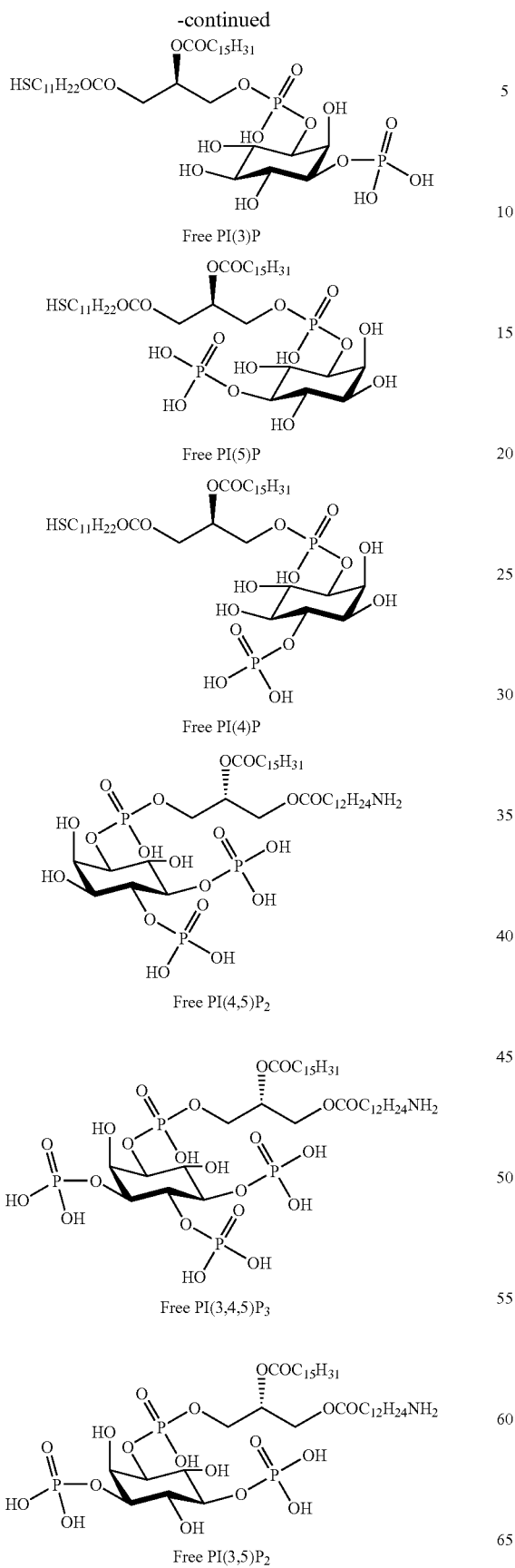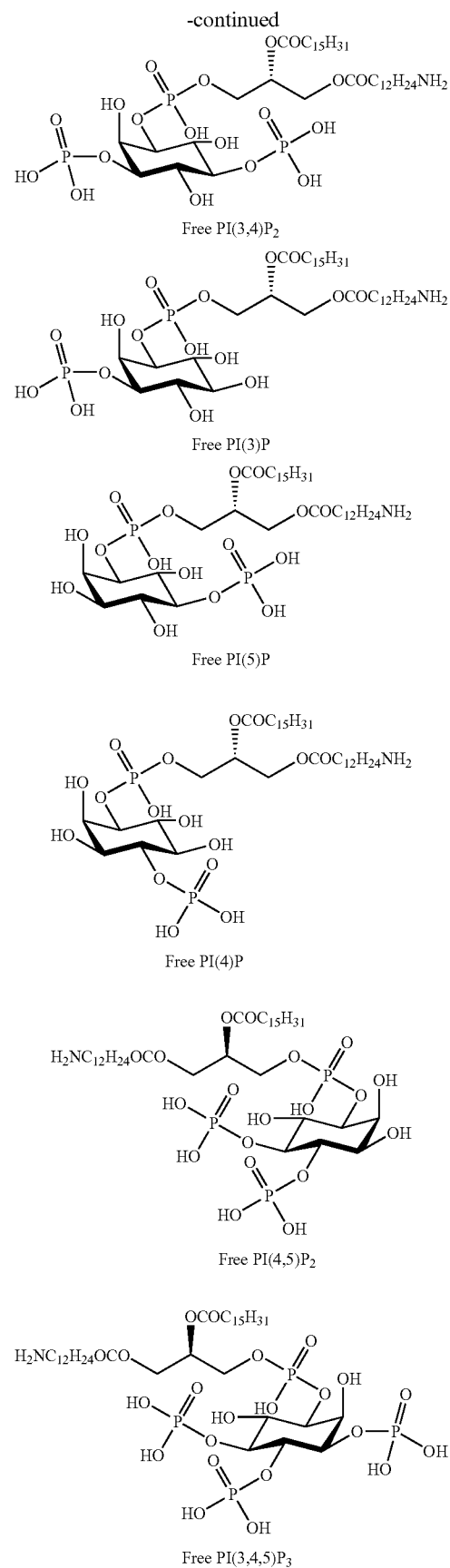

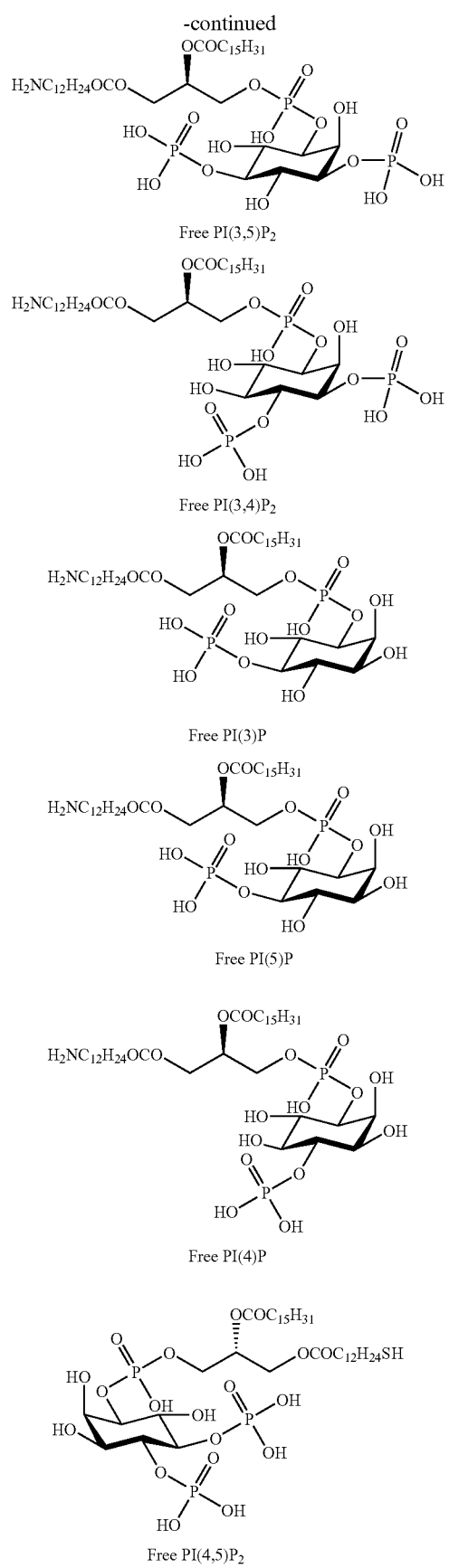
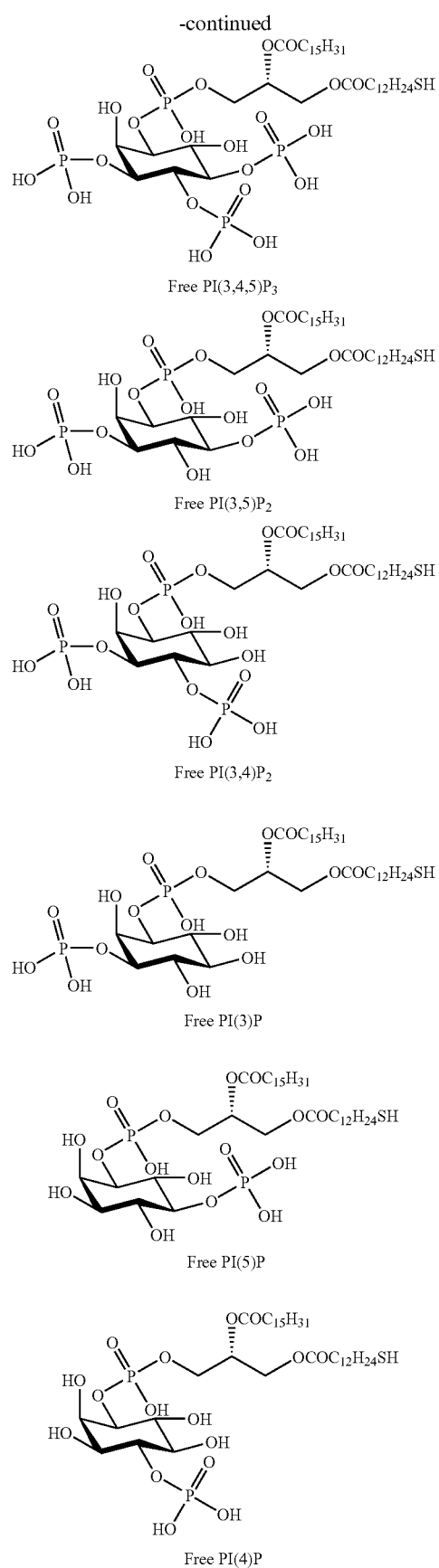

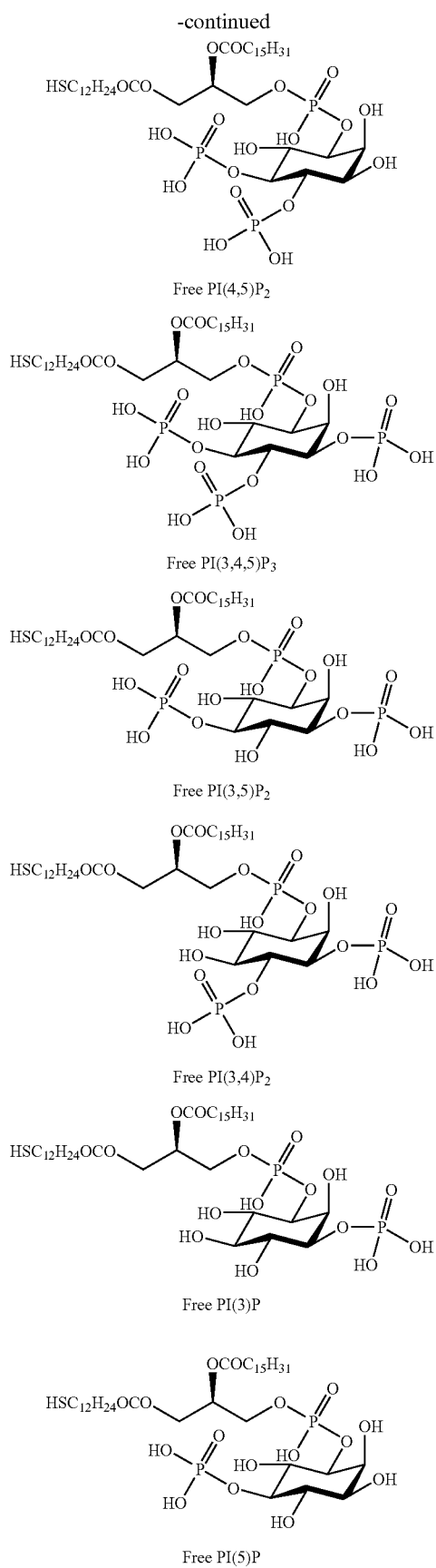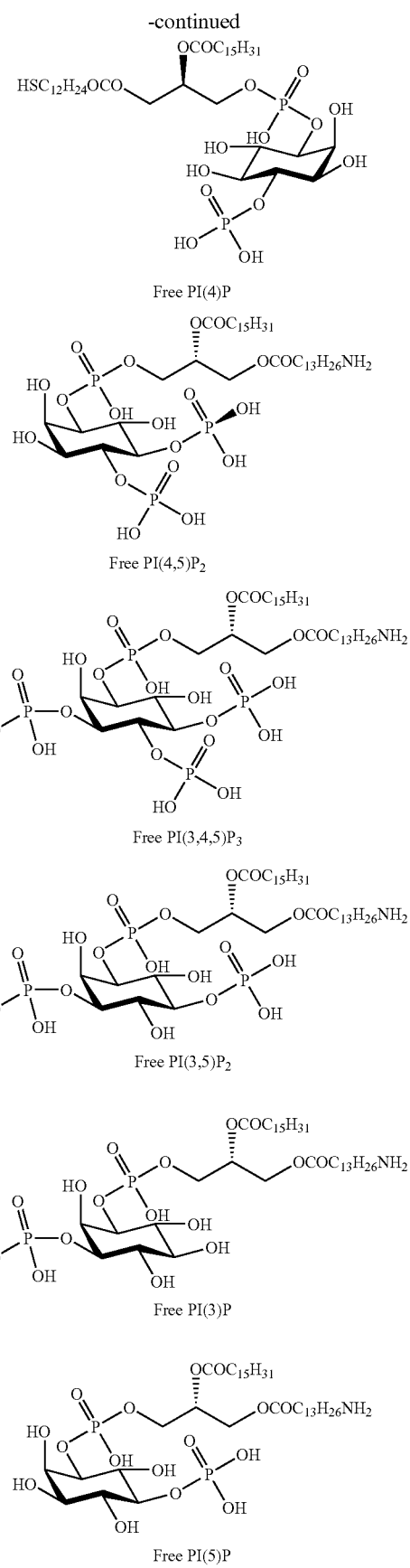

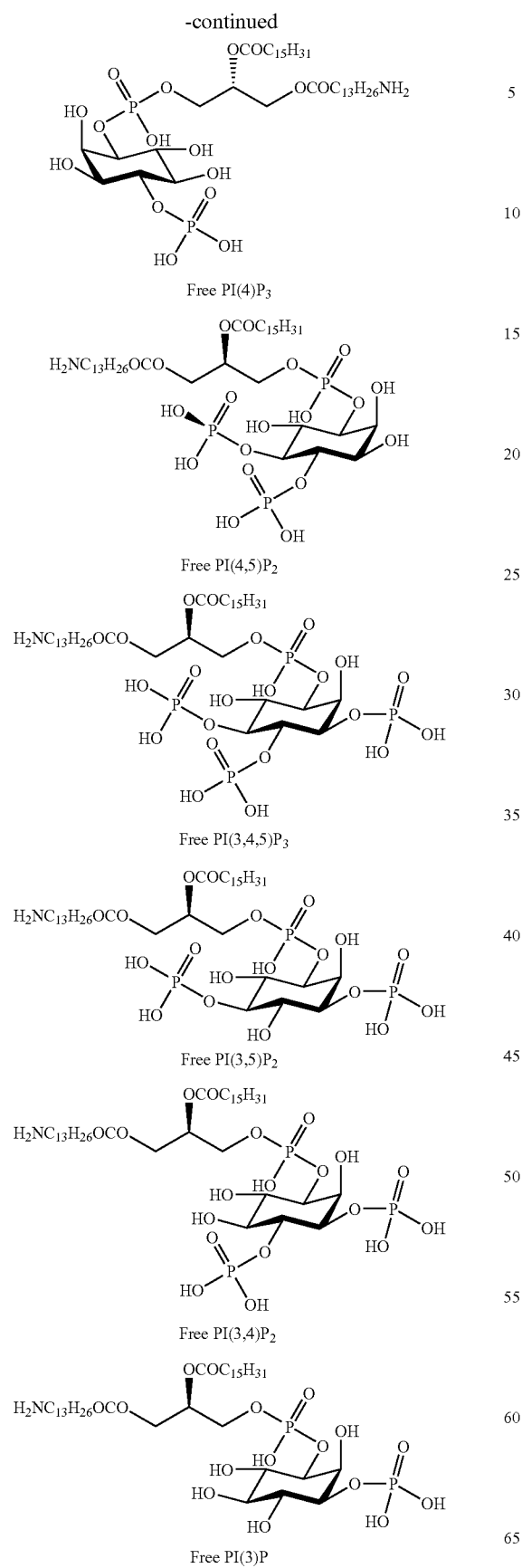
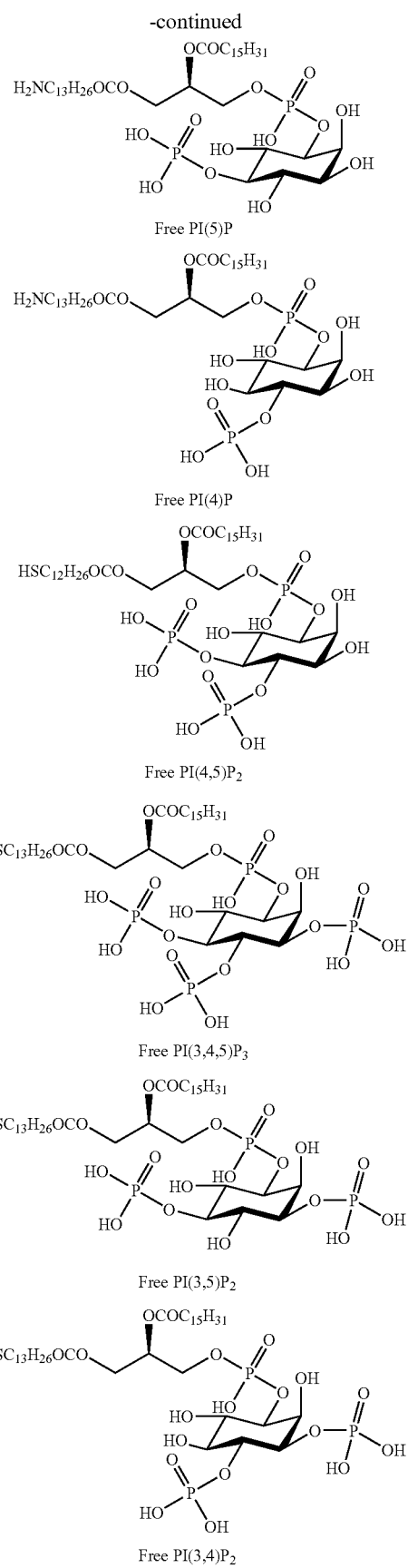

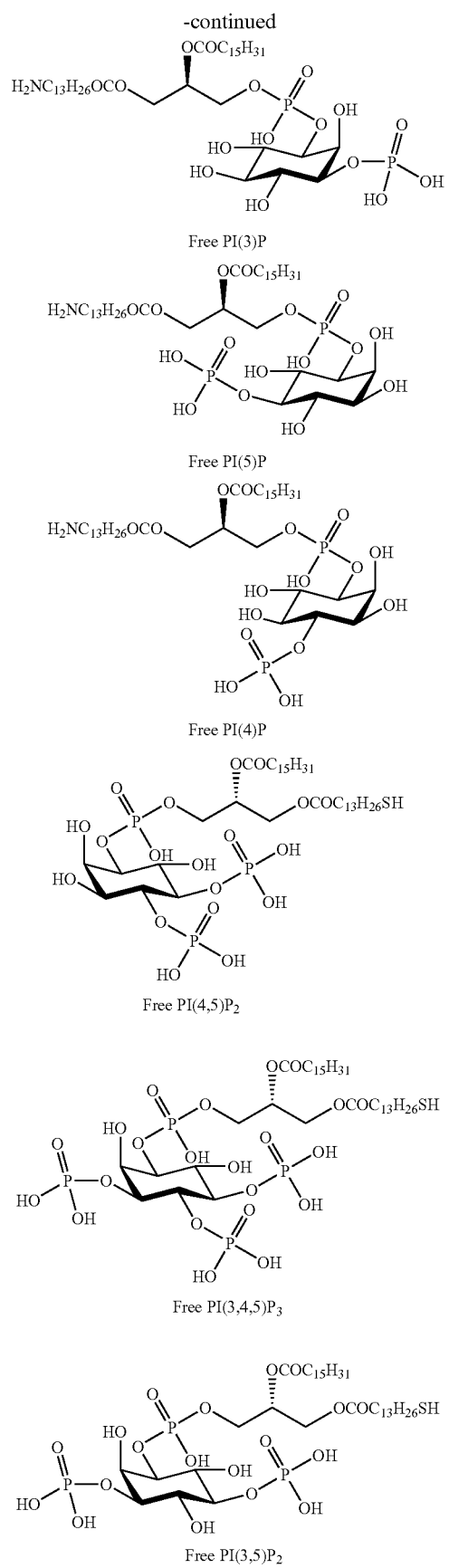
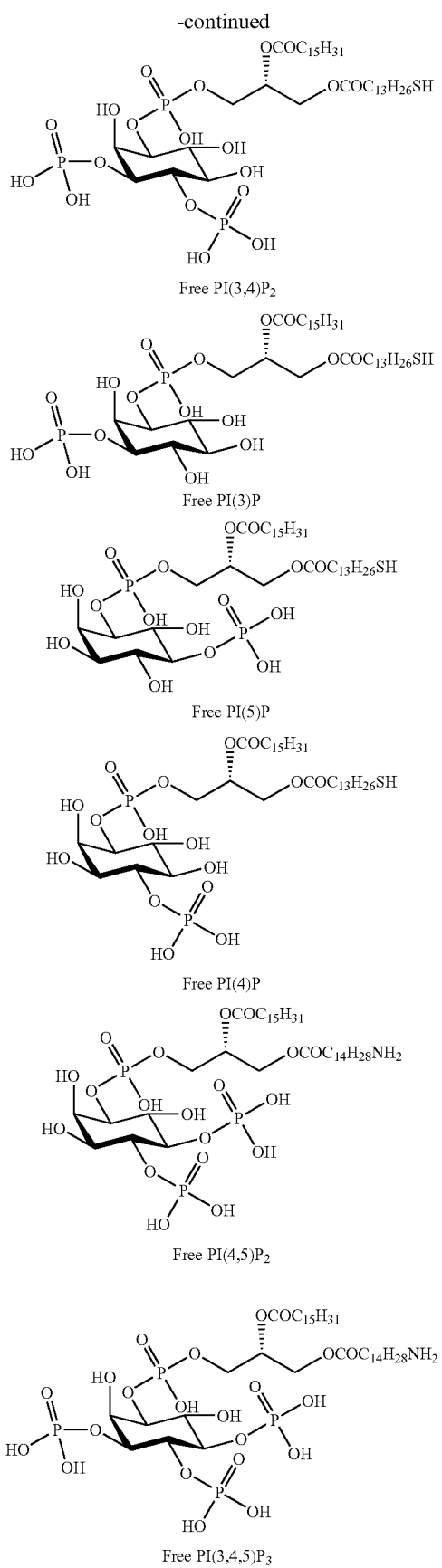

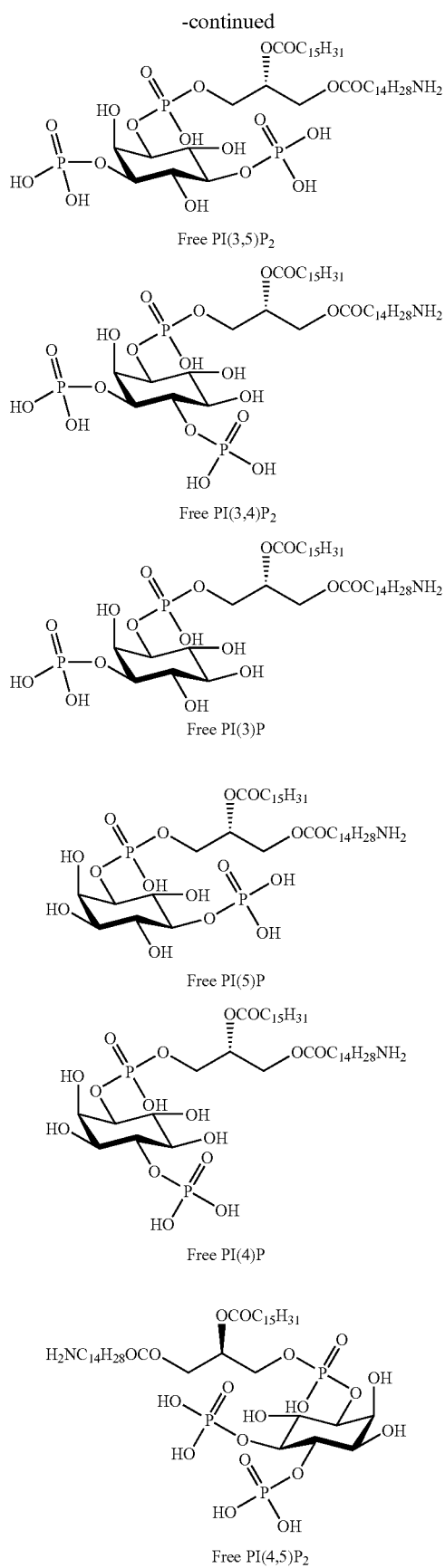
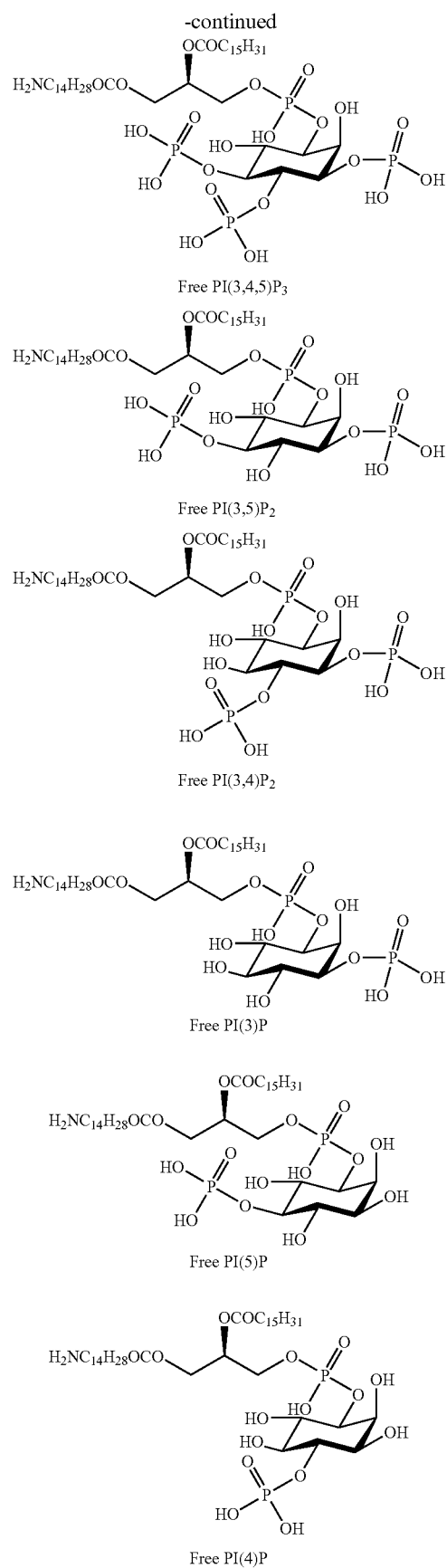

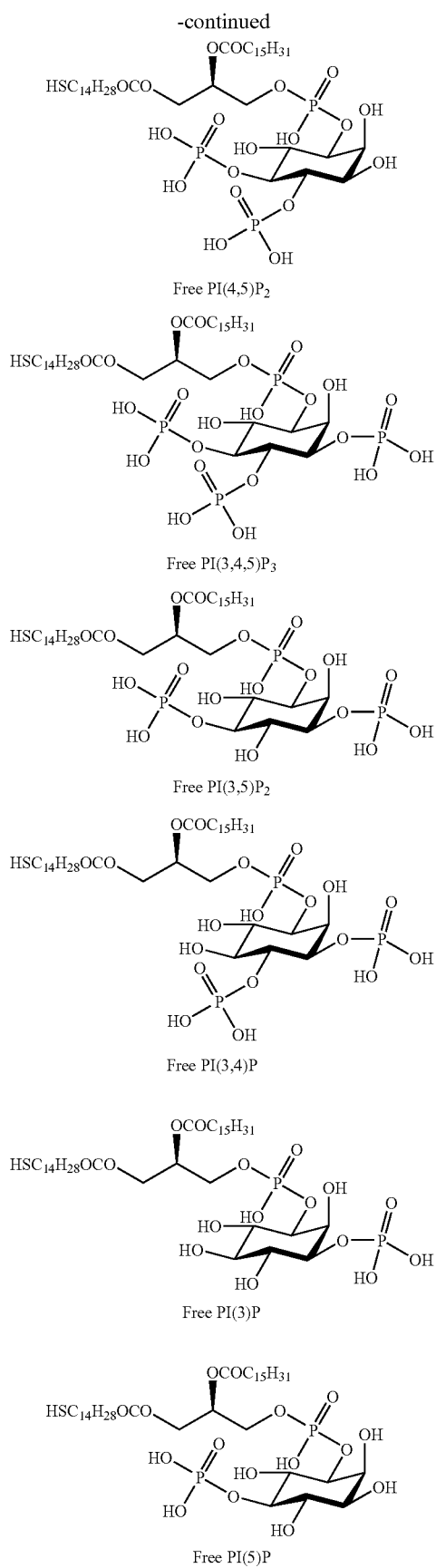
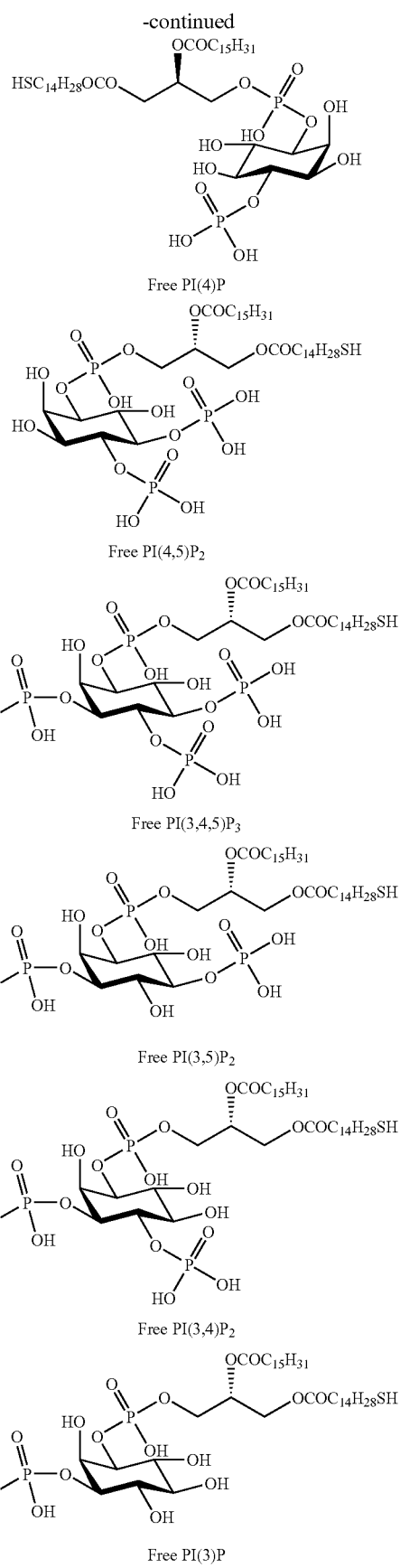

601
-continued
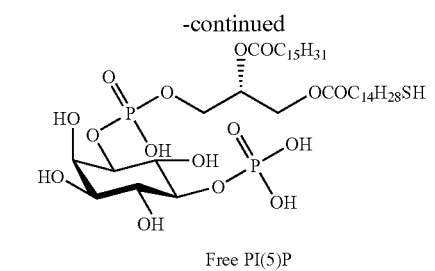
Free PI(5)P
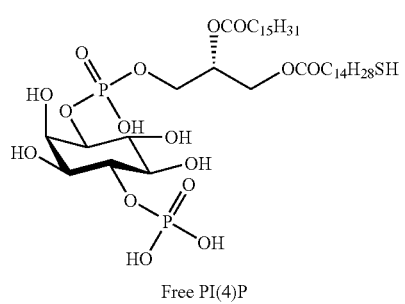
Free PI(4)P
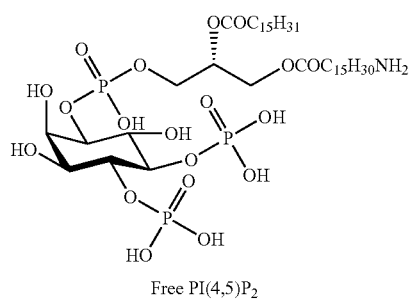
Free PI(4,5)P₂
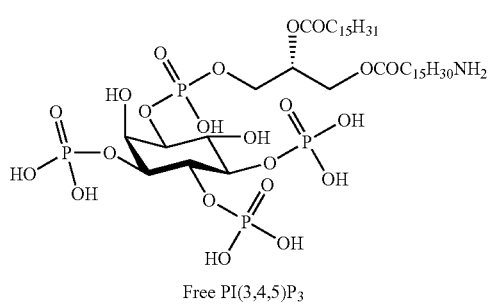
Free PI(3,4,5)P₃
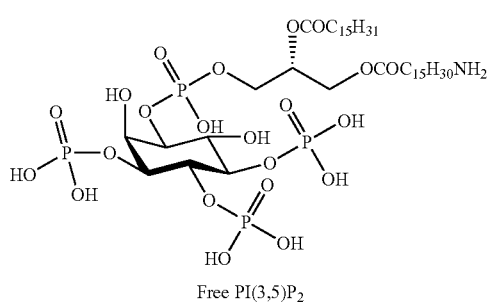
Free PI(3,5)P₂
602
-continued
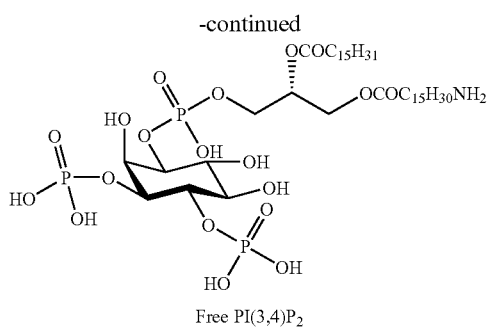
Free PI(3,4)P₂
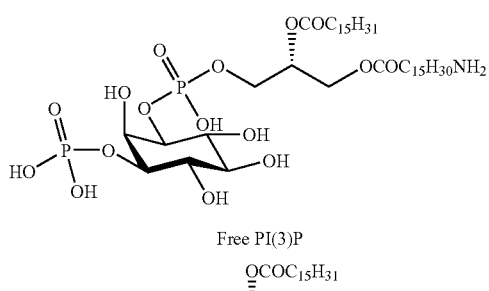
Free PI(3)P
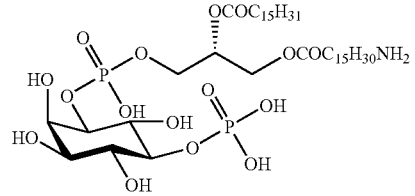
Free PI(5)P
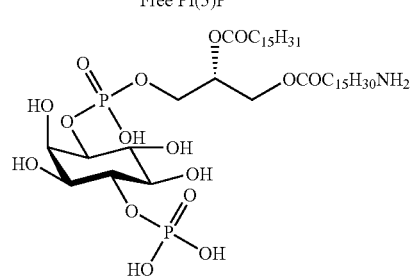
Free PI(4)P
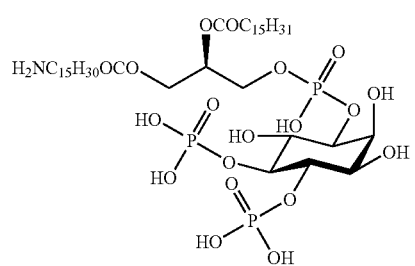
Free PI(4,5)P₂
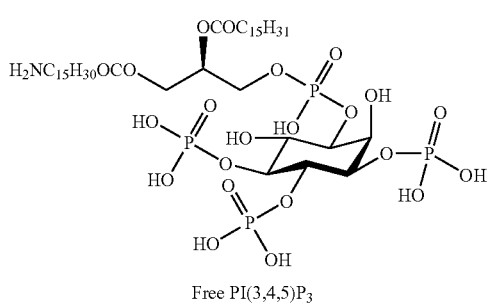
Free PI(3,4,5)P₃